US011578335B2

(12) United States Patent
Mayfield et al.

(10) Patent No.: US 11,578,335 B2
(45) Date of Patent: Feb. 14, 2023

(54) SYNTHETIC ALGAL PROMOTERS

(71) Applicant: The Regents of the University of California, Oakland, CA (US)

(72) Inventors: Stephen P. Mayfield, Cardiff, CA (US); Melissa Scranton, La Jolla, CA (US); David Ryan Georgianna, San Diego, CA (US); Joseph Ostrand, San Diego, CA (US); Anthony Jason Erich Berndt, Calgary (CA)

(73) Assignee: The Regents of the University of California, Oakland, CA (US)

( * ) Notice: Subject to any disclaimer, the term of this patent is extended or adjusted under 35 U.S.C. 154(b) by 434 days.

(21) Appl. No.: 16/077,693

(22) PCT Filed: Feb. 16, 2017

(86) PCT No.: PCT/US2017/018196
§ 371 (c)(1),
(2) Date: Aug. 13, 2018

(87) PCT Pub. No.: WO2017/143080
PCT Pub. Date: Aug. 24, 2017

(65) Prior Publication Data

US 2019/0382779 A1 Dec. 19, 2019

Related U.S. Application Data

(60) Provisional application No. 62/295,997, filed on Feb. 16, 2016.

(51) Int. Cl.
*C12N 15/82* (2006.01)

(52) U.S. Cl.
CPC ................................ *C12N 15/8216* (2013.01)

(58) Field of Classification Search
None
See application file for complete search history.

(56) References Cited

PUBLICATIONS

Schroda et al (The Plant Journal, 2001, 21(2): 121-131).*
Jameel et al (Int. J. Mol. Sci., 2020, 21(4): 1357).*
Lu et al (Critical Reviews in Biotechnology, 2021, 41(8): 1233-1256).*
Jin et al (Microbial Biotechnology, 2019, 12(6): 1476-1486).*
PCT Non-Establishment of International Search Report and Written Opinion dated May 30, 2017 issued in PCT/US2017/018196.
Bailey et al. (2012) "Inferring direct DNA binding from ChIP-seq." *Nucleic Acids Res* 40(17): e128 [10 pages].
Bernard et al. (2010) "TC-motifs at the TATA-box expected position in plant genes: a novel class of motifs involved in the transcription regulation." *BMC Genomics* 11: 166 [15 pages].
Blazeck et al. (2013) "Promoter engineering: recent advances in controlling transcription at the most fundamental level." *Biotechnology Journal* 8: 46-58.
Calistri et al. (2011) "Evolutionary trends of GC/AT distribution patterns in promoters." *Molecular Phylogenetics and Evolution* 60: 228-235.
Davis et al. (2012) "POWRS: position-sensitive motif discovery." *PLoS One*. 7(7): e40373 [10 pages].
Fang et al. (2012) "Transcriptome-wide changes in *Chlamydomonas reinhardtii* gene expression regulated by carbon dioxide and the CO2-concentrating mechanism regulator CIA5/CCM1." *Plant Cell* 24: 1876-1893.
Fujimori et al. (2005) "GC-compositional strand bias around transcription start sites in plants and fungi." *BMC Genomics* 6: 26 [11 pages]. doi:10.1186/1471-2164-6-26.
Gabrielian et al. (1999) "Curved DNA in promoter sequences." *In Silico Biol* 1: 183-196 [MS # 8G/0672—26 pages].
Gupta et al. (2007) "Quantifying similarity between motifs." *Genome Biol*. 8(2): R24 [9 pages].
Kanhere et al. (2005) "Structural properties of promoters: similarities and differences between prokaryotes and eukaryotes." *Nucleic Acids Res* 33(10): 3165-3175.
Koschmann et al. (2012) "Integration of bioinformatics and synthetic promoters leads to the discovery of novel elicitor-responsive cis-regulatory sequences in Arabidopsis." *Plant Physiology* 160: 178-191.
Kumar et al. (2013) "Evaluating nuclear transgene expression systems in *Chlamydomonas reinhardtii*." *Algal Res* 2: 321-332.
Rasala et al. (2014) "Photosynthetic biomanufacturing in green algae; production of recombinant proteins for industrial, nutritional, and medical uses." *Photosynthesis Research* 123(3): 227-23 9.
Riano-Pachon et al. (2008) "Green transcription factors: a chlamydomonas overview." *Genetics* 179: 31-39.
Scaife et al. (2015) "Establishing *Chlamydomonas reinhardtii* as an industrial biotechnology host." *The Plant Journal* 82: 532-546.
Schroda et al. (2000) "The HSP70A promoter as a tool for the improved expression of transgenes in Chlamydomonas." *The Plant Journal* 21: 121-131.
Schroda et al. (2002) "Sequence elements within an HSP70 promoter counteract transcriptional transgene silencing in Chlamydomonas." *The Plant Journal* 31(4): 445-455.
Venter, M. (2007) "Synthetic promoters: genetic control through cis engineering," *Trends Plant Sci* 12(3): 118-124.
Zones et al. (2015) "High-Resolution Profiling of a Synchronized Diurnal Transcriptome from Chlamydomonas reinhardtii Reveals Continuous Cell and Metabolic Differentiation." *Plant Cell* 27(10): 2743-69.

* cited by examiner

*Primary Examiner* — Stuart F Baum
(74) *Attorney, Agent, or Firm* — Tom Hunter; Weaver Austin Villeneuve & Sampson LLP

(57) ABSTRACT

This invention provides synthetic promoters capable of promoting and/or initiating transcription of a polynucleotide in an algal cell, and methods of designing, producing and using such promoters.

17 Claims, 44 Drawing Sheets
(39 of 44 Drawing Sheet(s) Filed in Color)
Specification includes a Sequence Listing.

(C)
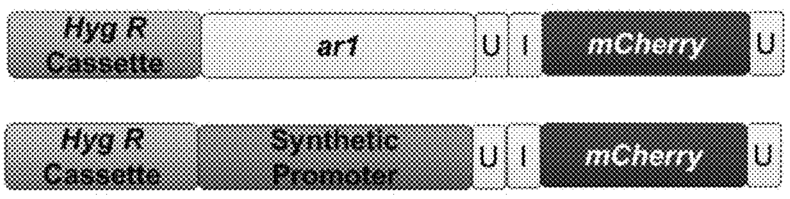
(D)
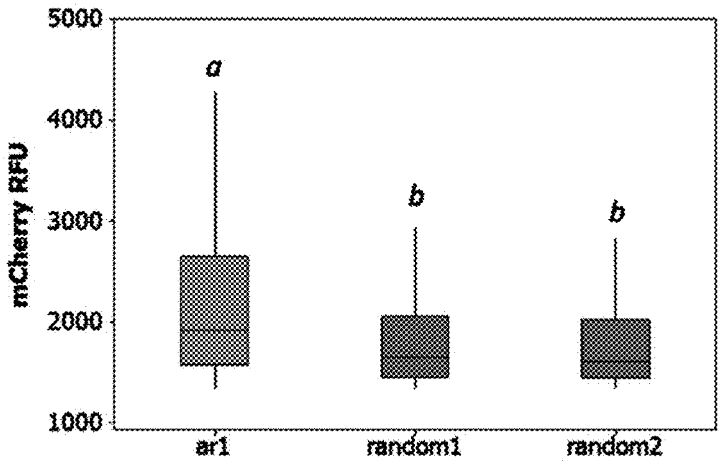
(E)
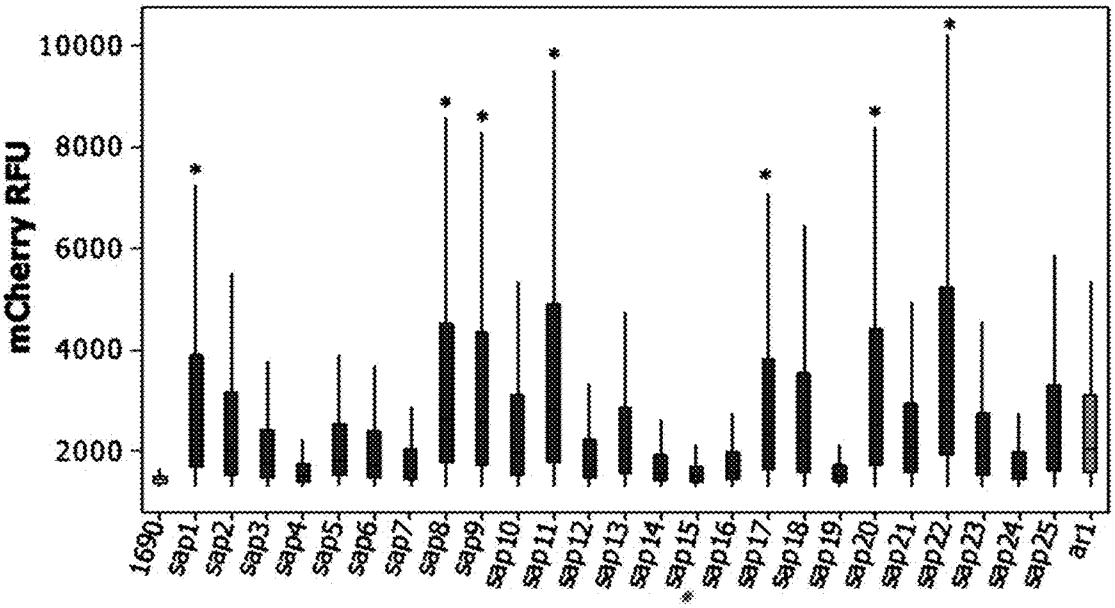
*Fig. 1, cont'd.*

TC RICH MOTIFS
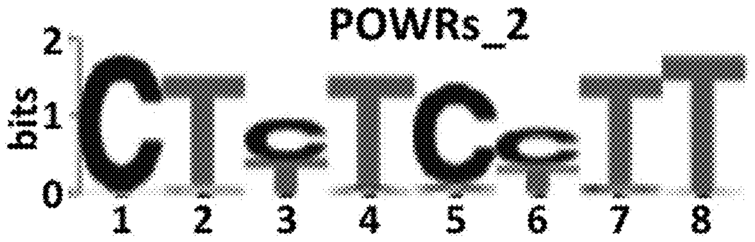
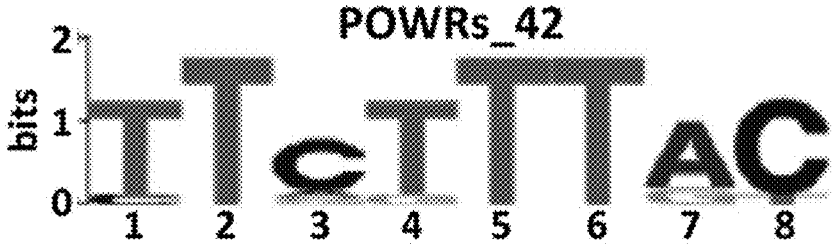
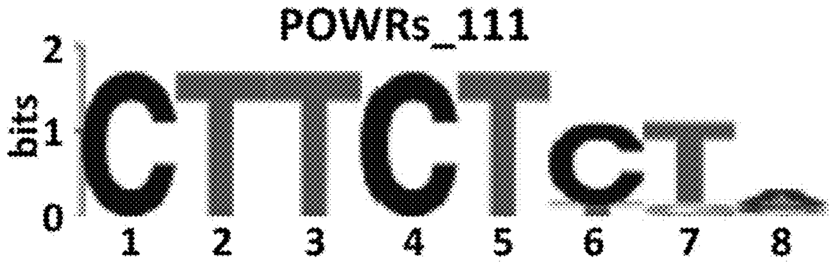
*Fig. 3*

TC RICH MOTIFS
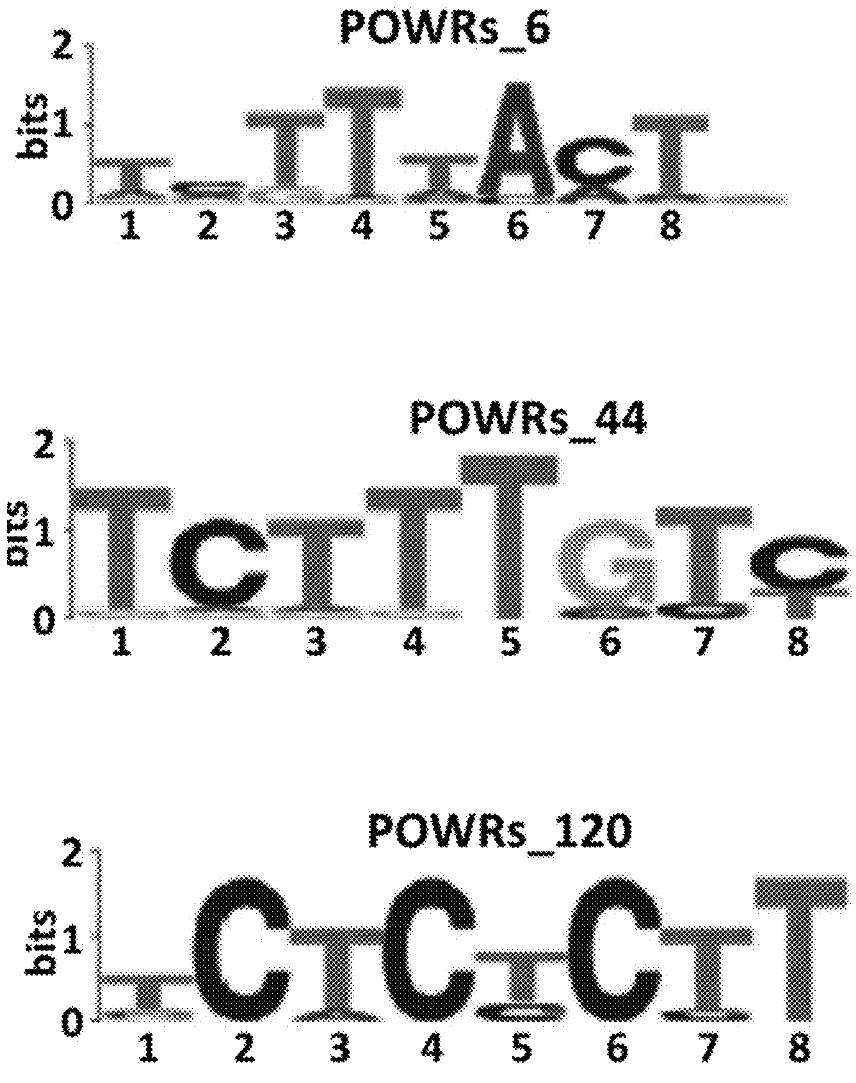
*Fig. 3, cont'd.*

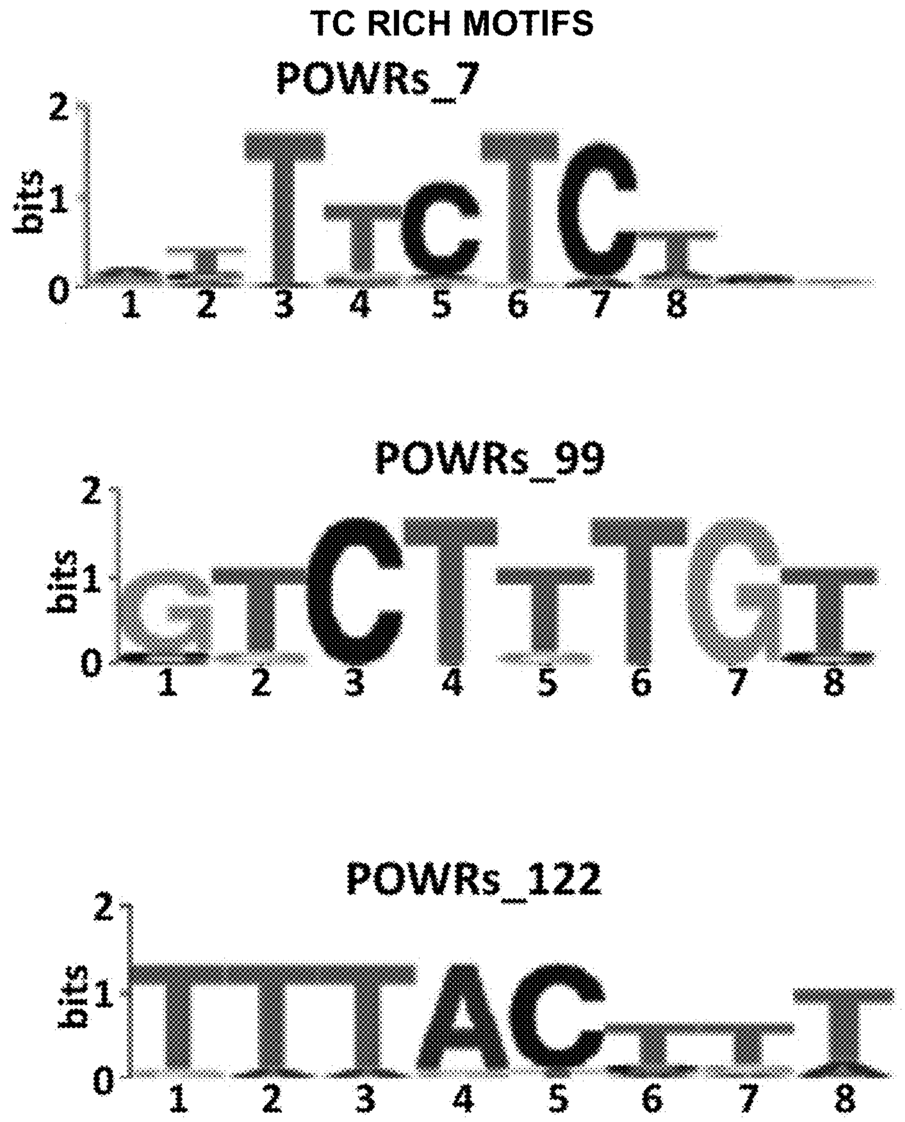
*Fig. 3, cont'd.*

(A)

| Replicate Number | Transformants per plate |
|---|---|
| 1 | ~6000 |
| 2 | ~12000 |

(B)
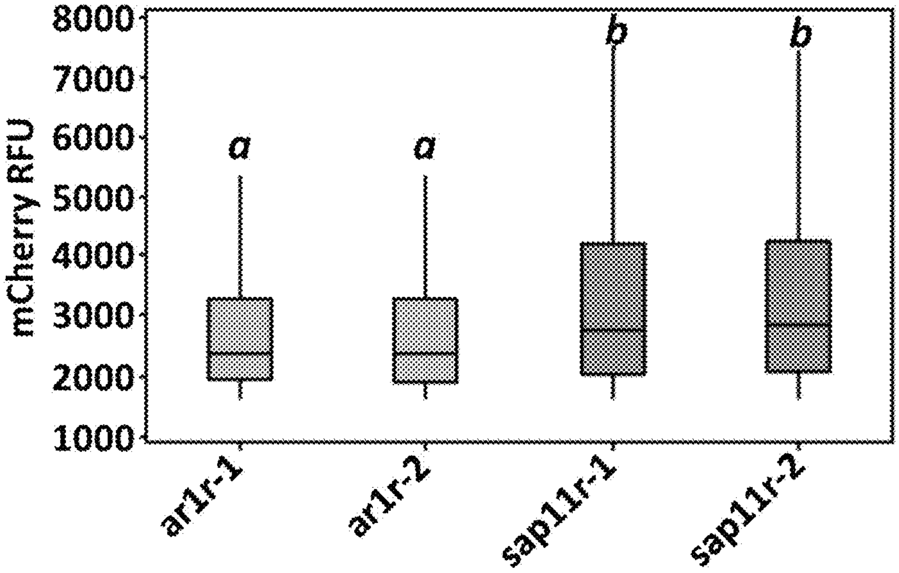
Fig. 4, cont'd.

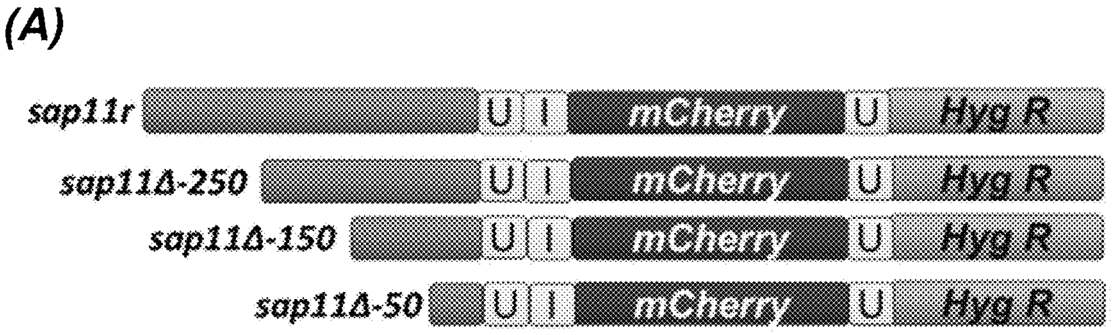
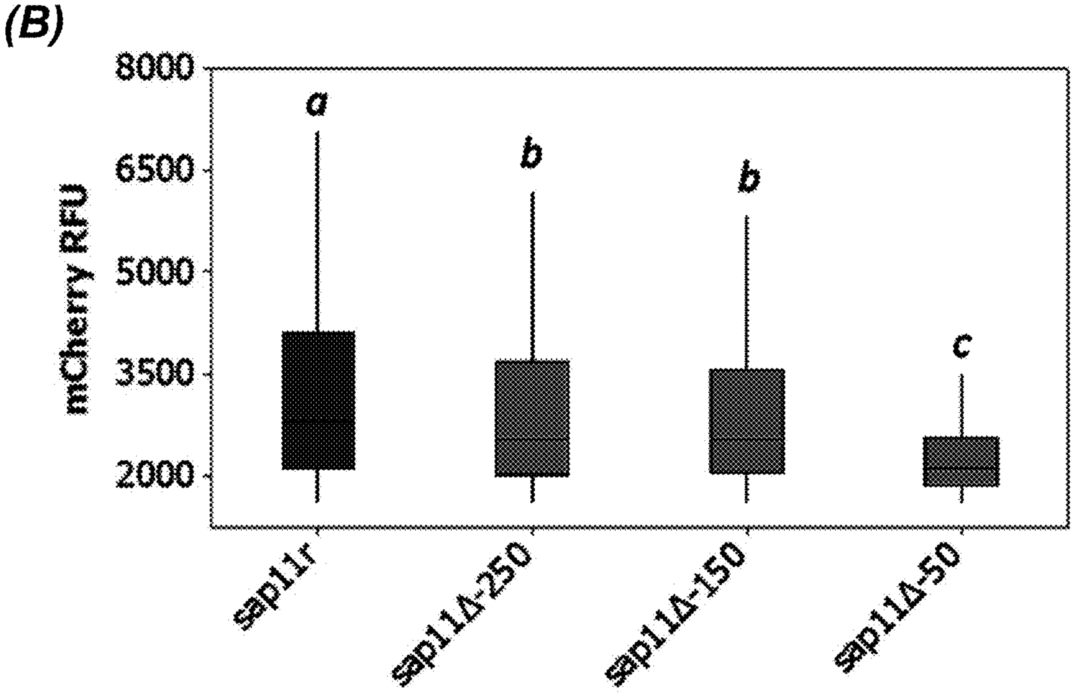
Fig. 5

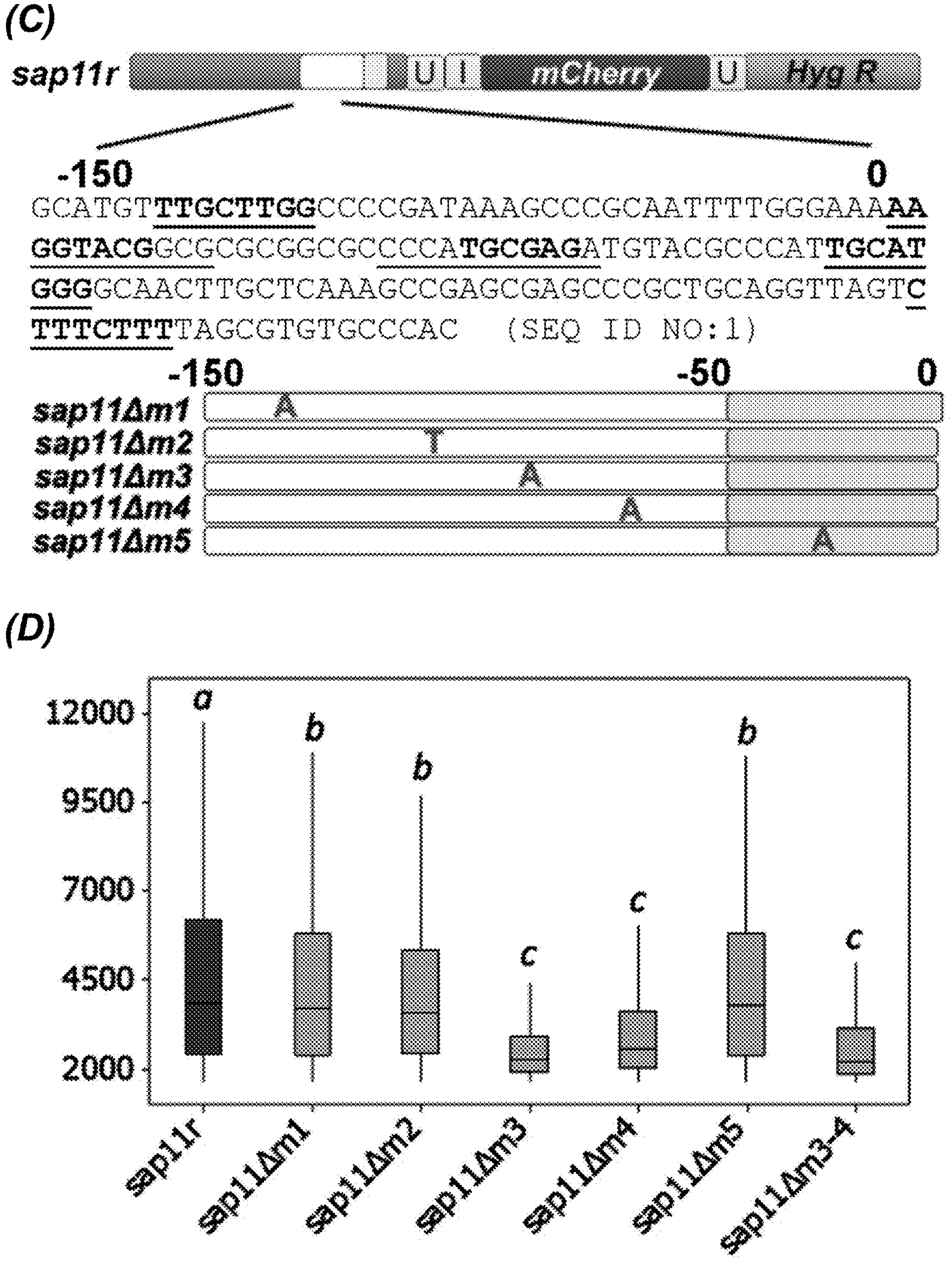
*Fig. 5, cont'd.*

(C)
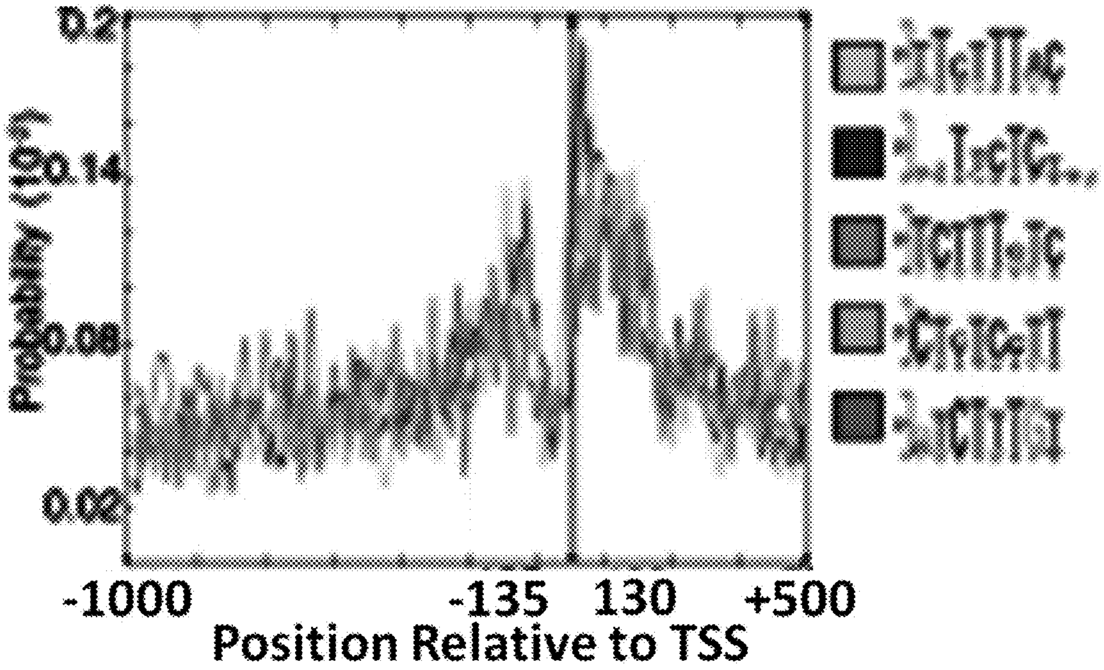
*Fig. 6, cont'd.*

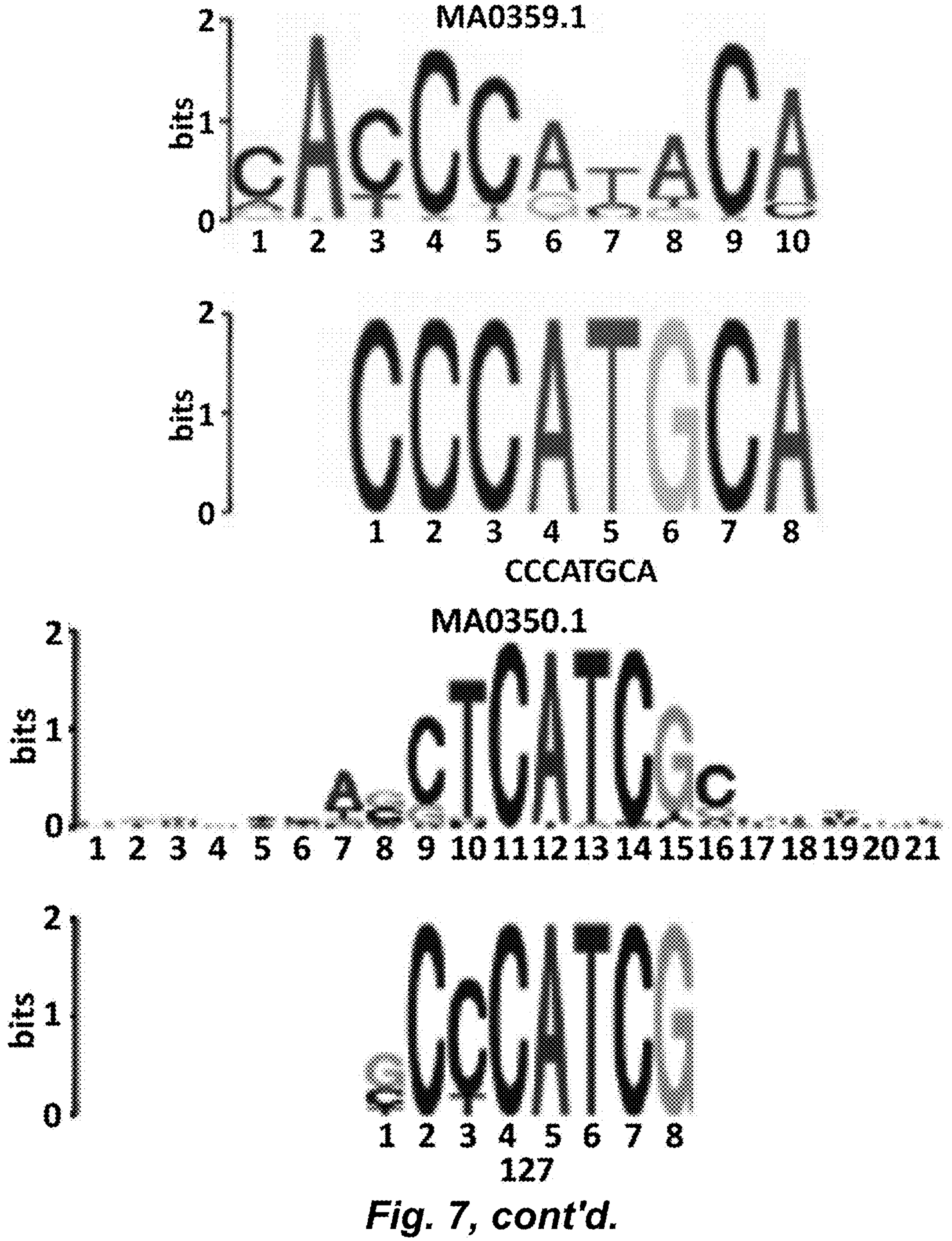
*Fig. 7, cont'd.*

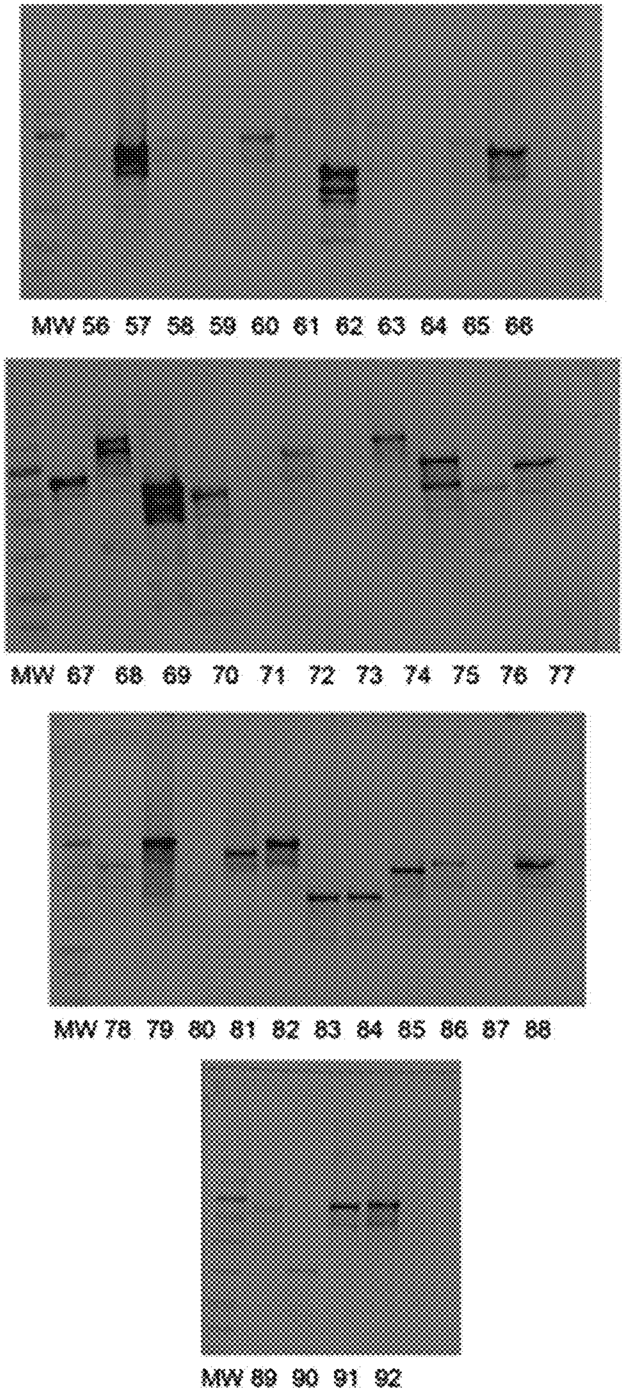
*Fig. 9, cont'd.*

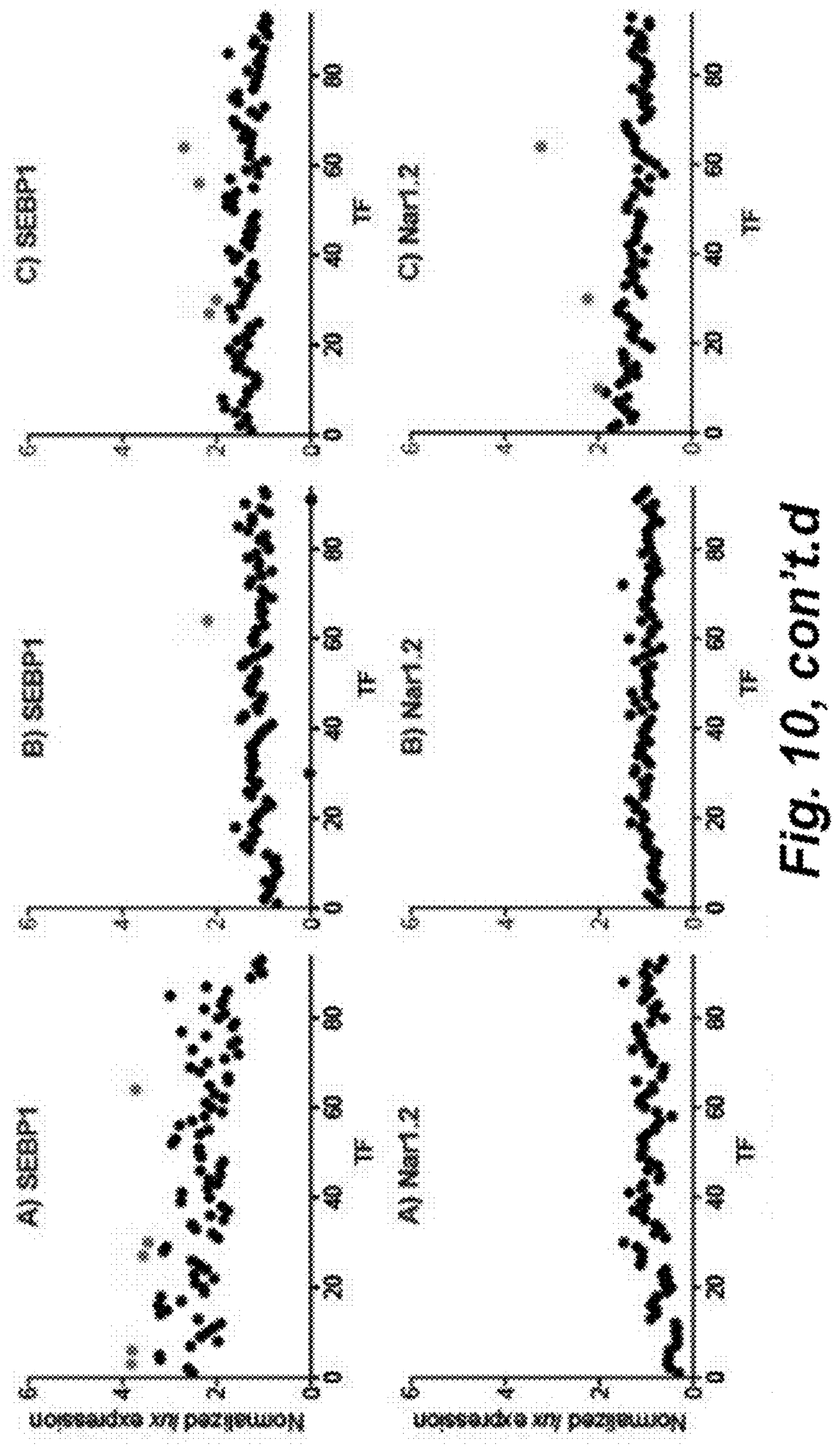
*Fig. 10, con't.d*

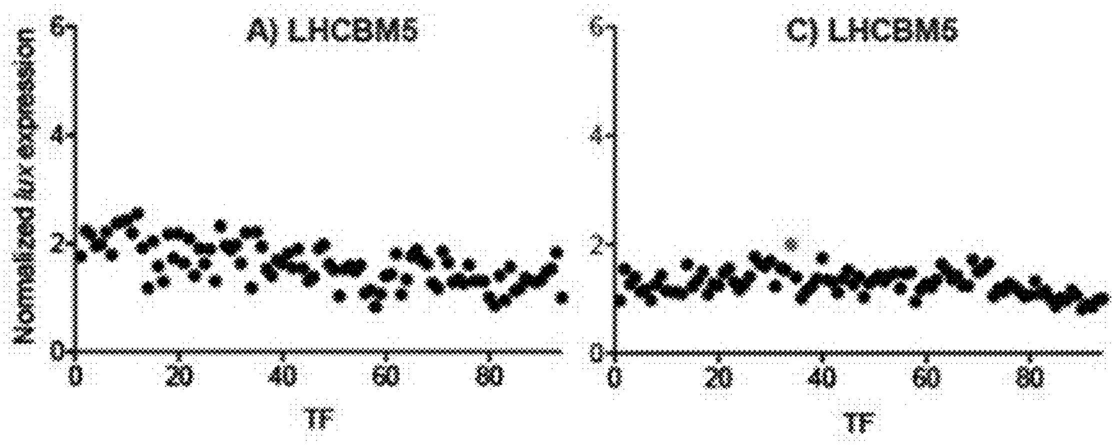
*Fig. 10, cont'd.*

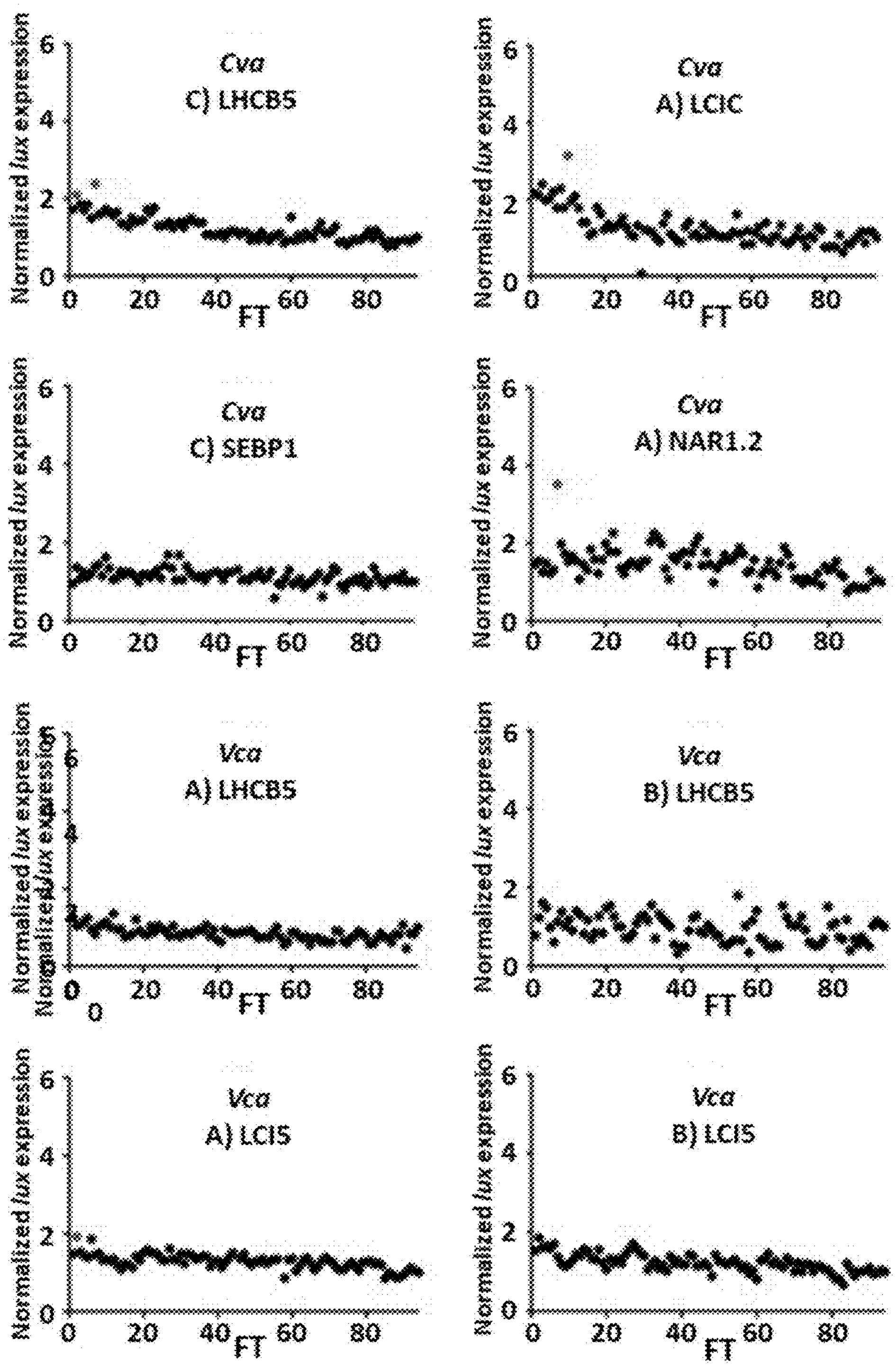
*Fig. 11, cont'd.*

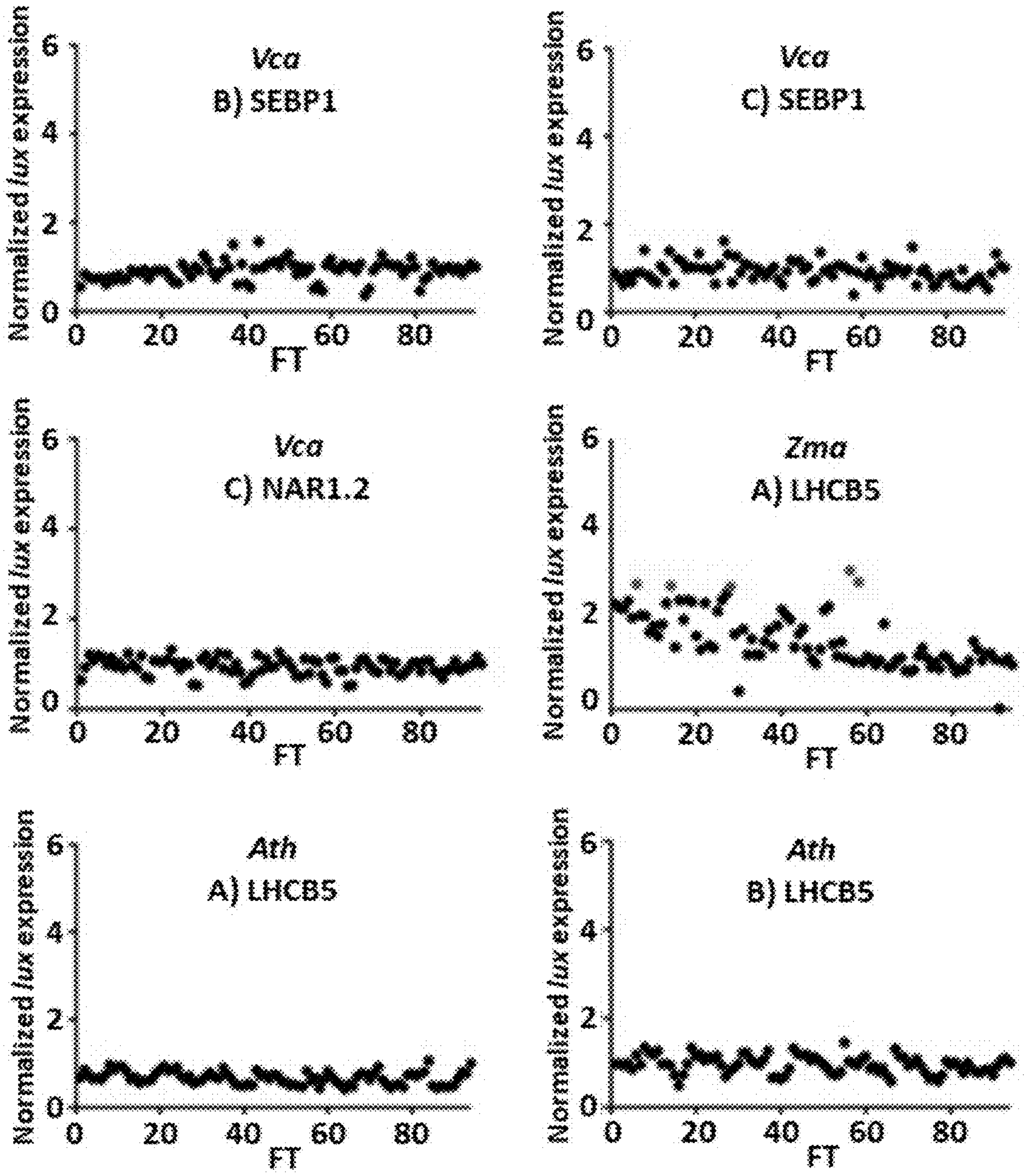
*Fig. 11, cont'd.*

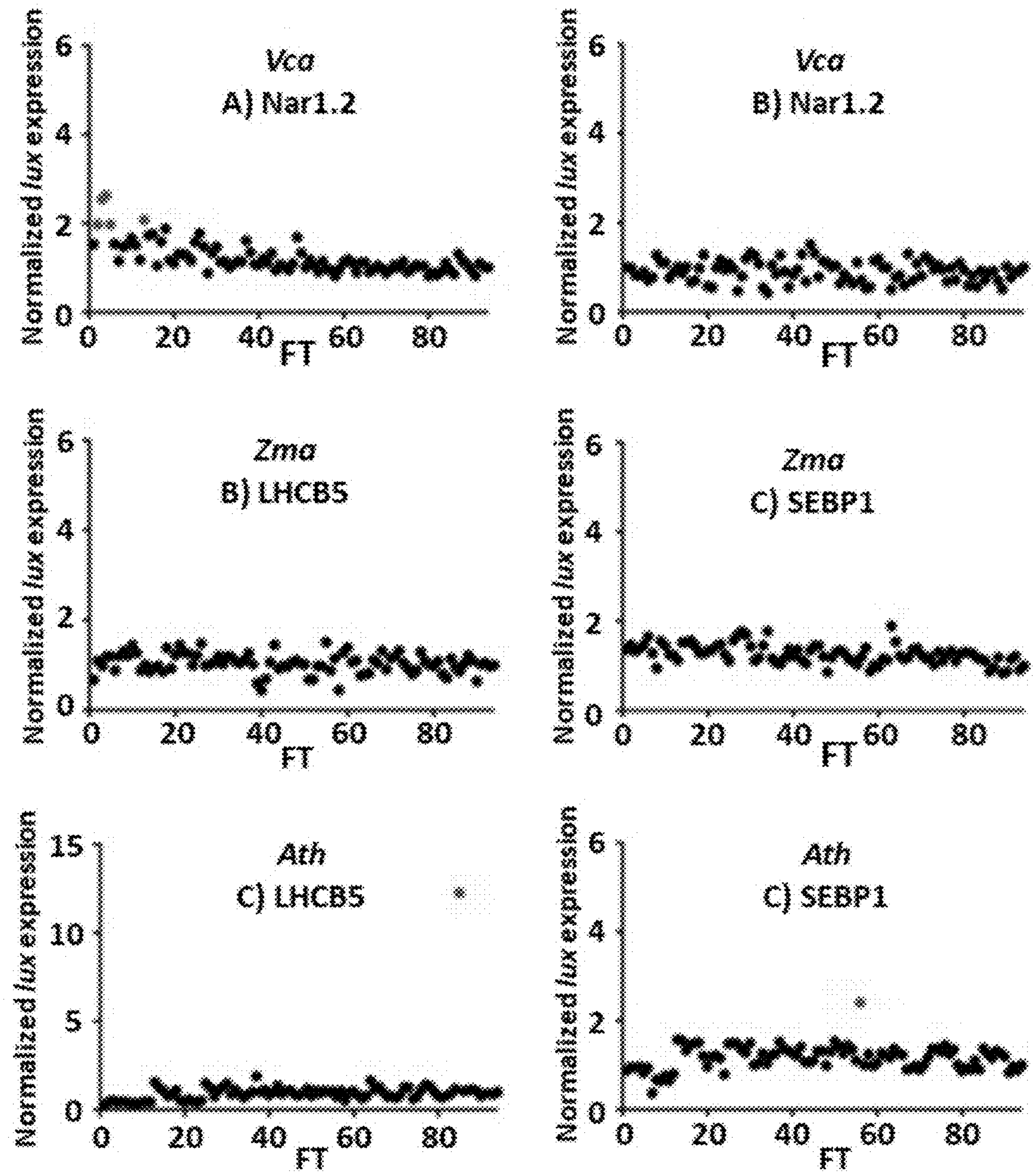
*Fig. 11, cont'd.*

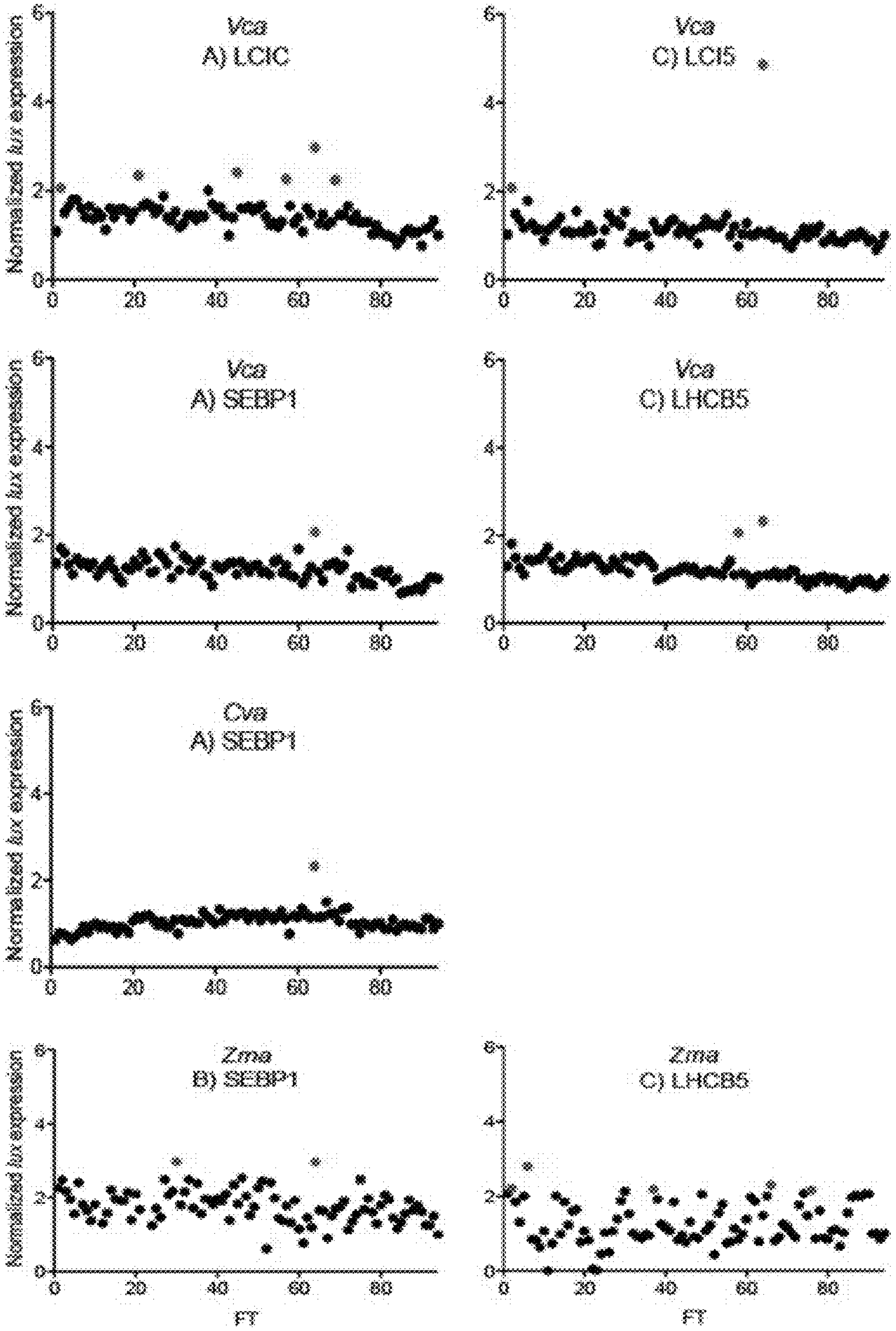
Fig. 11, cont'd.

(B)

| Promoter | Strand | Start | *p*-value | Sequence |
|---|---|---|---|---|
| Cre_Nar1.2_C | + | 209 | 9.72e-7 | CCGCTGTTGG TGTGCAATTTT CAAACATCTG (SEQ ID NO:2) |
| Cre_Nar1.2_C | + | 91 | 9.72e-7 | CTCAATACGA TGTGCAATTTT GCAGCGCATG (SEQ ID NO:3) |
| Cre_LCIC_C | - | 167 | 1.86e-7 | ACCCGGCGCA TGGGCAATTGT AGGAGGGTTG (SEQ ID NO:4) |
| Vca_LCIC_A | - | 79 | 3.30e-7 | CAAGCAGCGC TGCGCAATTTT GACTTGCAGT (SEQ ID NO:5) |
| Vca_SEBP1_A | - | 290 | 1.70e-5 | GCTGCAGTTG TCCGCAAGTGC ACCGATAGCA (SEQ ID NO:6) |
| Zma_SEBP1_B | - | 163 | 1.87e-5 | TGGATCGTTT TCTGAAATTGT TCAGTGTGAT (SEQ ID NO:7) |
| Cre_SEBP1_C | - | 157 | 1.87e-5 | ACCAAACCGG TGTTCAATTGC ATTCAACCCA (SEQ ID NO:8) |
| Vca_LCIC_A | - | 298 | 2.34e-5 | GT TCTGAAAGTGT CCTTCAGGAC (SEQ ID NO:9) |
| CRE_SEBP1_C | - | 60 | 2.34e-5 | AAATGCGACT TGCGCATGTTC AAGCCGGACG (SEQ ID NO:10) |
| Vca_LHCB5_C | - | 259 | 2.78e-5 | AGAGAAGGGC AGCGCAAGTGT CCATACCAGC (SEQ ID NO:11) |
| Vca_LHCB5_C | - | 91 | 3.38e-5 | TTTATAATGA TGGGCAAGTGA AGAGCTCTGA (SEQ ID NO:12) |
| Cre_LCIC_C | - | 123 | 3.72e-5 | GGGCTTGGTT TGTTCATTTGC ACCTCTCCAA (SEQ ID NO:13) |
| CrE_LCIC_C | - | 6 | 4.05e-5 | TTCCTTTCGG TCGGCATGTGC GTGCA (SEQ ID NO:14) |
| Cre_SEBP1_B | - | 295 | 4.40e-5 | ACACT TGGGAATTTGC AATGGGCAAG (SEQ ID NO:15) |
| Cre_LCIC_C | - | 251 | 4.40e-5 | TGTATTTAAC TGTGCACGTTT AACACACAAC (SEQ ID NO:16) |
| Vca_LCI5_C | - | 122 | 4.93e-5 | TTATGCATGG AGCGCATGTGT ATTTAATTTT (SEQ ID NO:17) |

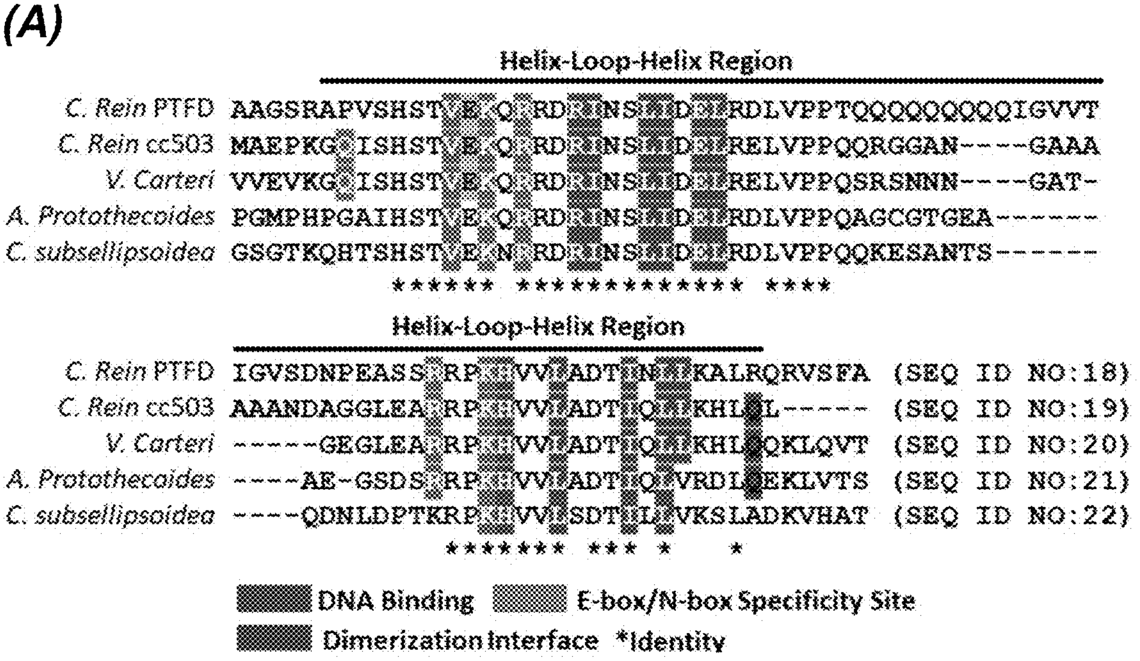

(B)

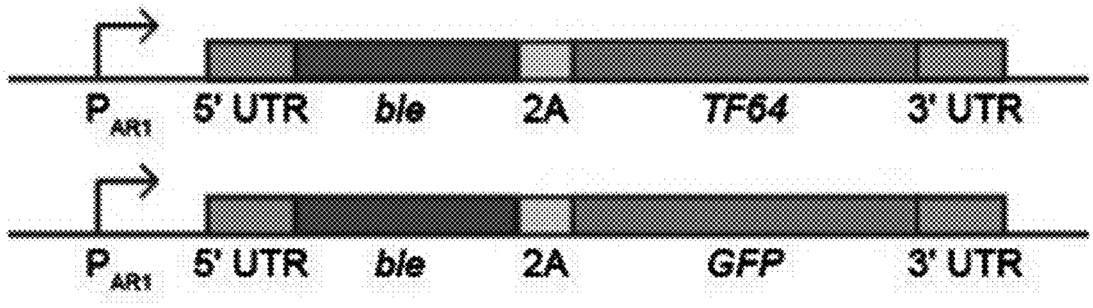

```
                       Helix-Loop-Helix Region
   C. Rein PTFD  AAGSRAPVSHSTVE Q RD  NS  D  RDLVPPTQQQQQQQQQIGVVT
   C. Rein cc503 MAEPKG ISHST E Q RD  NS  D  RELVPPQQRGGAN----GAAA
       V. Carteri VVEVKG ISHST E Q RD  NS  D  RELVPPQSRSNNN----GAT-
  A. Protothecoides PGMPHPGAIHST E Q RD  NS  D  RDLVPPQAGCGTGEA------
  C. subsellipsoidea GSGTKQHTSHST E N RD  NS  D  RDLVPPQQKESANTS------
                    ****** ************** ****

                       Helix-Loop-Helix Region
   C. Rein PTFD  IGVSDNPEASS RP  VV ADT N  KALRQRVSFA  (SEQ ID NO:18)
   C. Rein cc503 AAANDAGGLEA RP  VV ADT Q  KHL L-----  (SEQ ID NO:19)
       V. Carteri -----GEGLEA RP  VV ADT Q  KHL QKLQVT  (SEQ ID NO:20)
  A. Protothecoides ----AE-GSDS RP  VV ADT Q  VRDL EKLVTS  (SEQ ID NO:21)
  C. subsellipsoidea ----QDNLDPTKRP  VV SDT L  VKSLADKVHAT  (SEQ ID NO:22)
                    ******* *** *   *
```

▓ DNA Binding   ▓ E-box/N-box Specificity Site
▓ Dimerization Interface   *Identity (B)

(C)
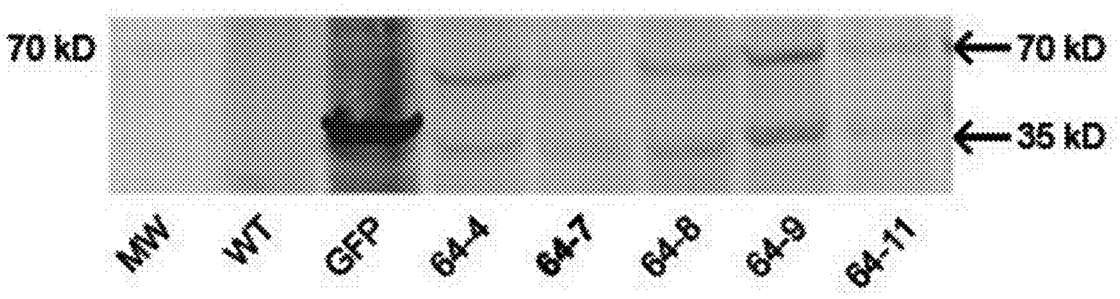
(D)
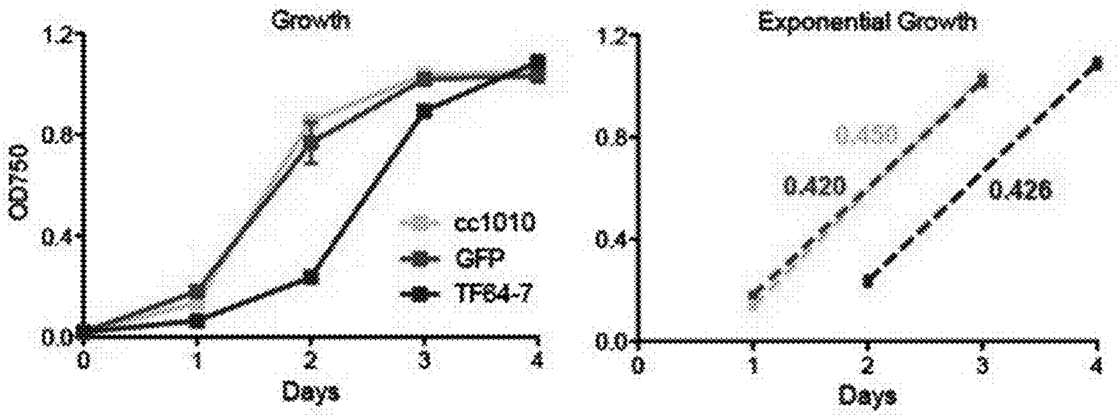
Fig. 13, cont'd.

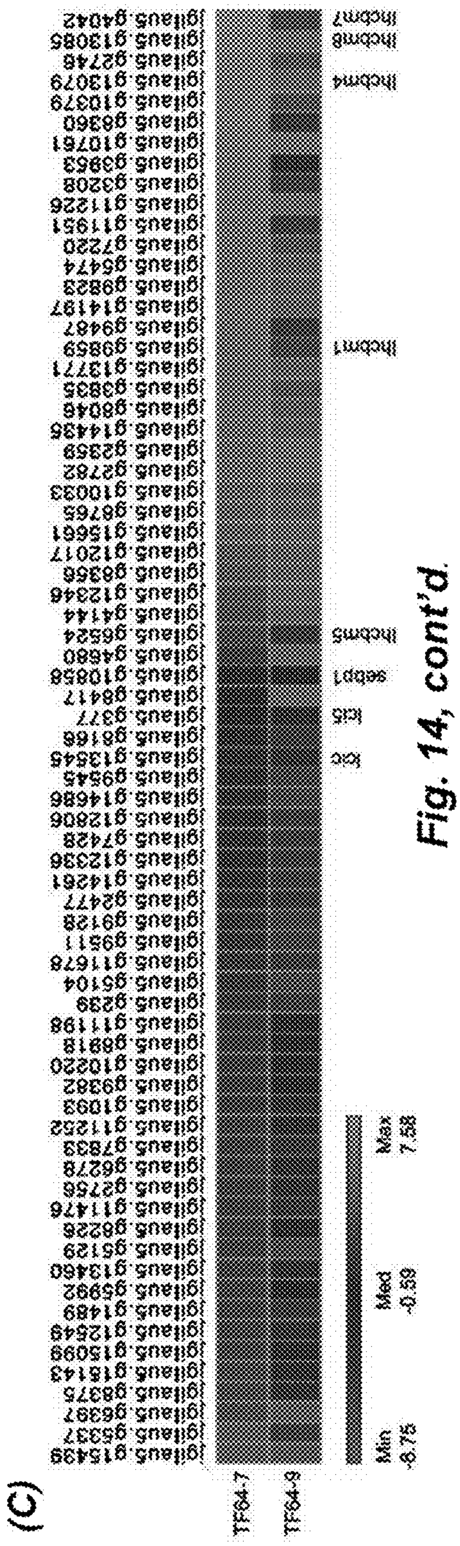
*Fig. 14, cont'd.*

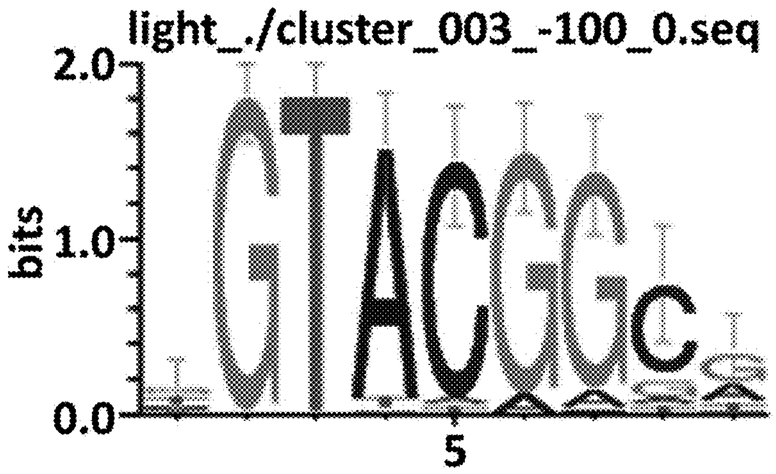
Consensus: NGTACGG[G/C]N
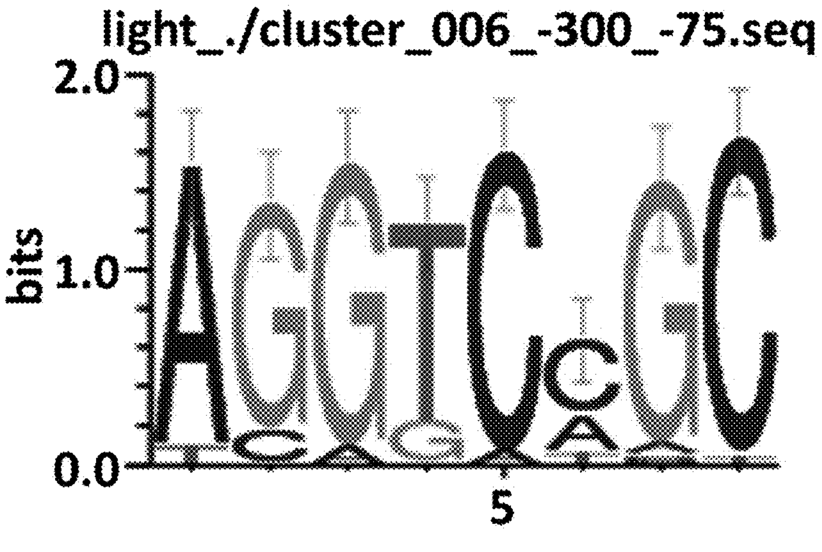
Consensus: A[G/C]GTC[A/C/T]GC
*Fig. 16A*

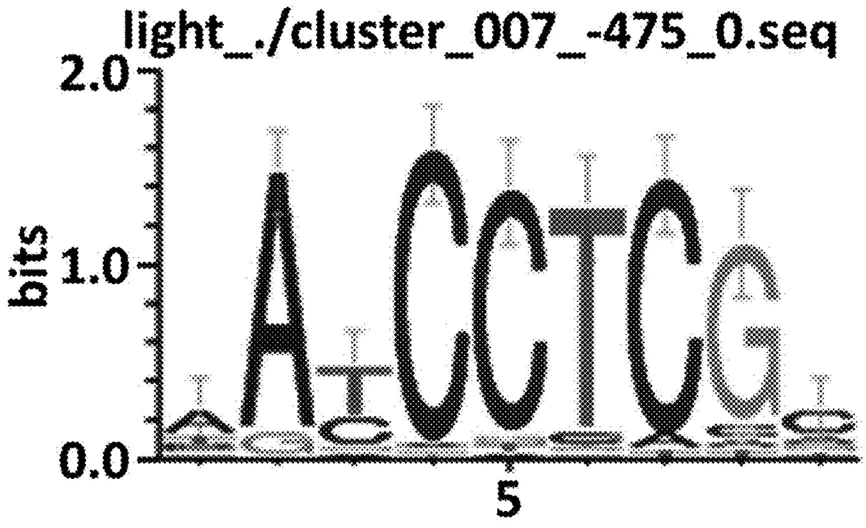
Consensus: NA[A/G][T/C]CCTCGN (SEQ ID NO:229)
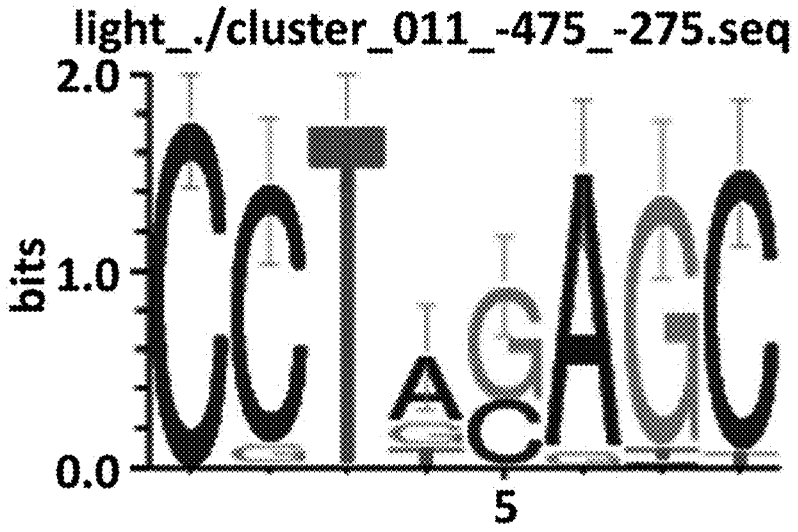
Consensus: CCT[A/G/T][G/C]AGC
*Fig. 16A, cont'd.*

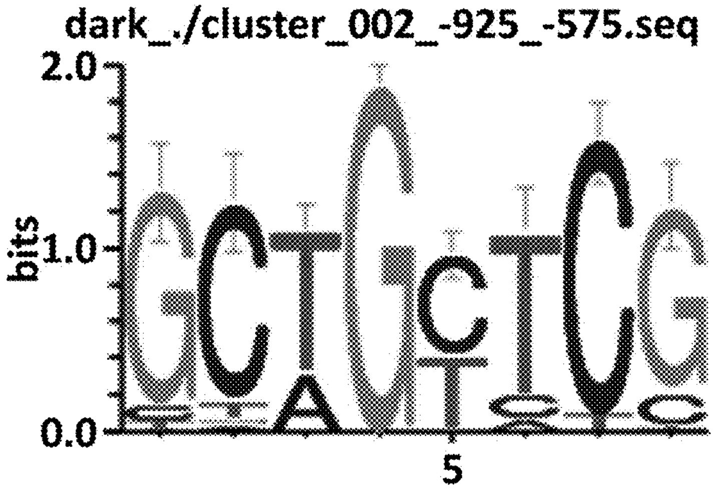
Consensus: GC[A/T]G[C/T][C/T]CG
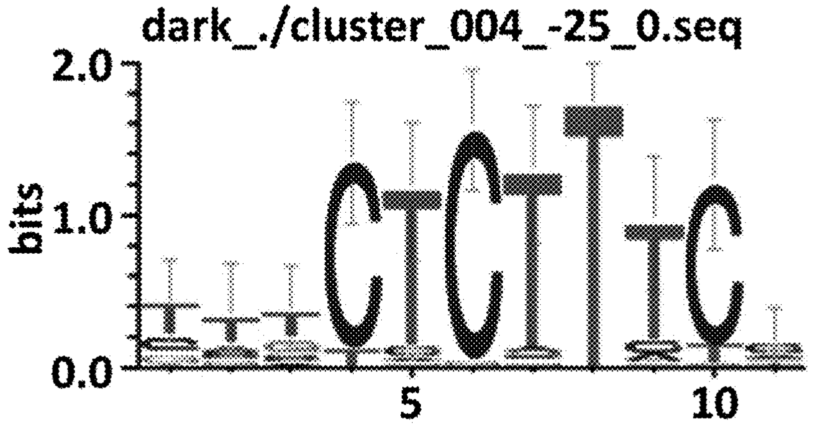
Consensus: [C/G/T]N[C/G/T]CTCTTCN (SEQ ID NO:230)
*Fig. 16B*

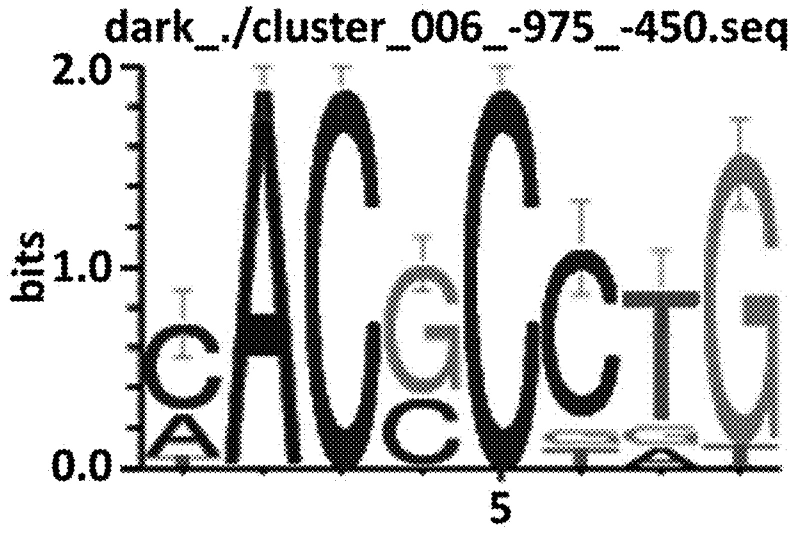
Consensus: [A/C]AC[G/C]CC[A/G/T]G
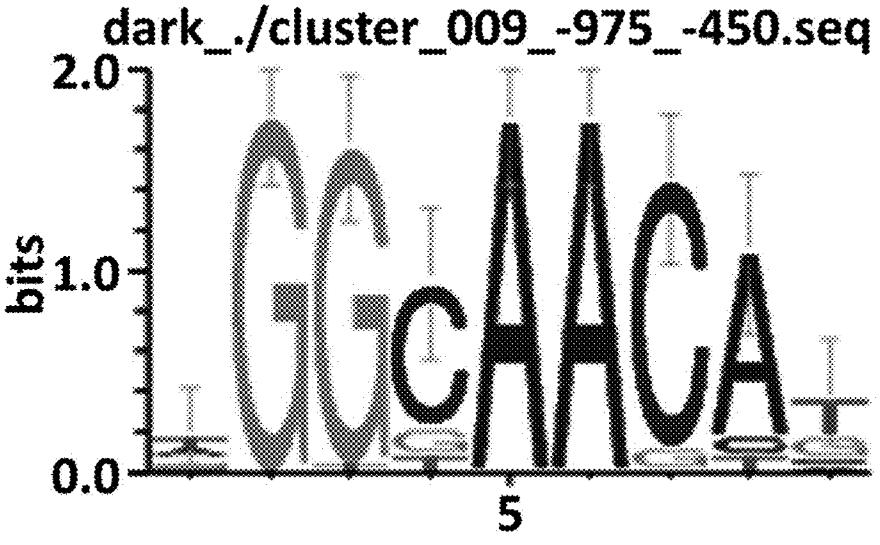
Consensus: NGG[C/G]AACA[C/G/T]
*Fig. 16B cont'd.*

Myb Family
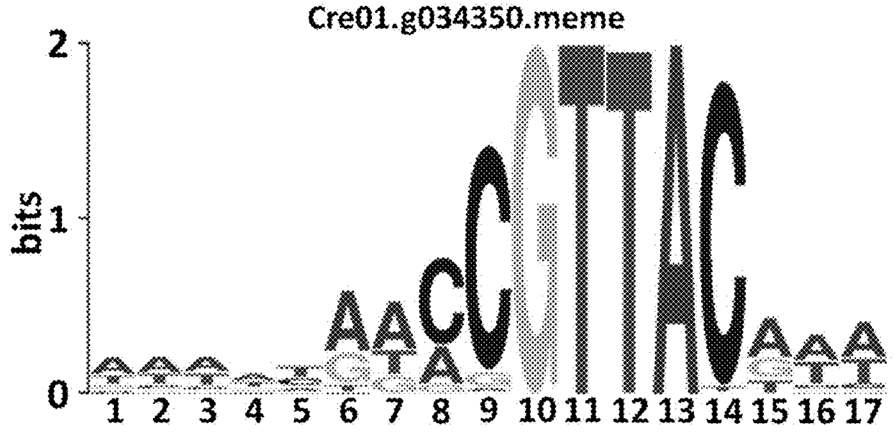
Consensus: N[A/G][A/T][C/A]CGTTAC[A/G][A/T][A/T]
(SEQ ID NO:231)
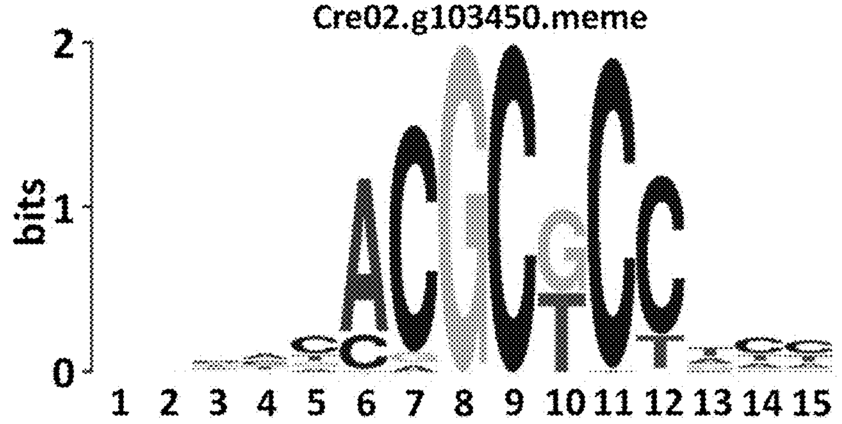
Consensus: N[A/C]CGC[G/T]C[C/T]N
*Fig. 17A*

Myb Family
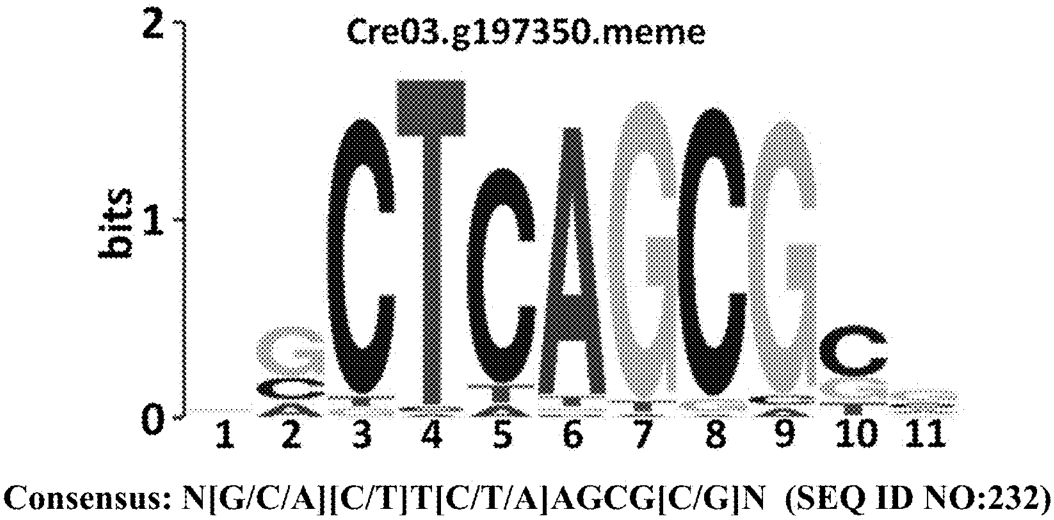
Consensus: N[G/C/A][C/T]T[C/T/A]AGCG[C/G]N (SEQ ID NO:232)
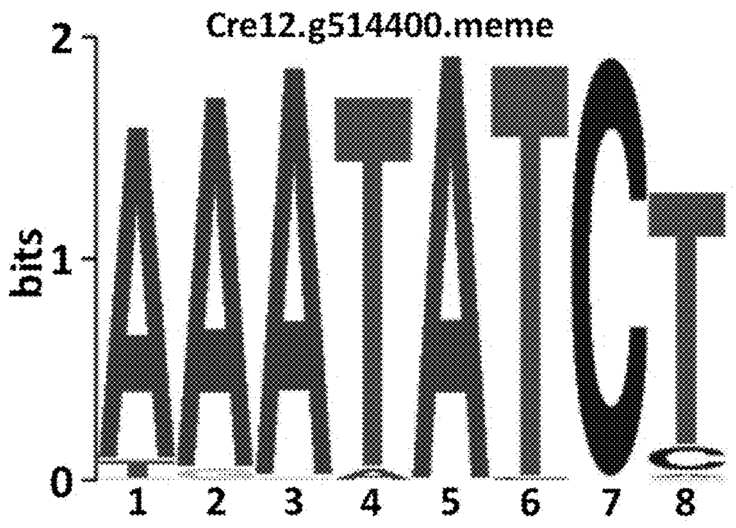
Consensus: AAATATC[T/C]
*Fig. 17A, cont'd.*

SBP family
Cre02.g104700.meme
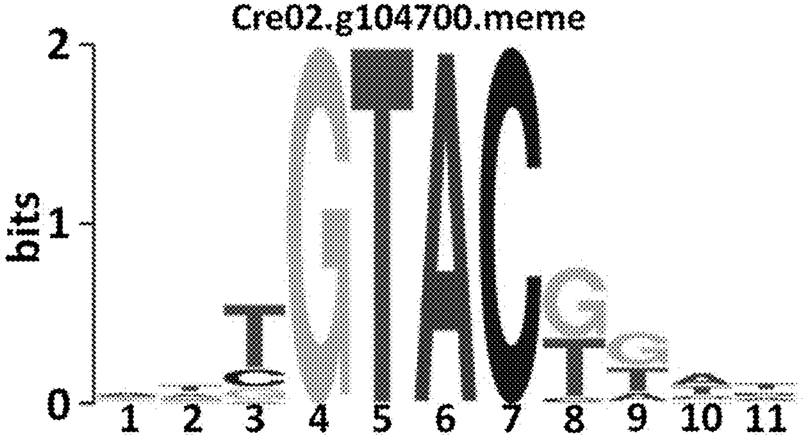
Consensus: N[T/C]GTAC[G/T][G/T]N
bHLH family
Cre14.g620850.meme
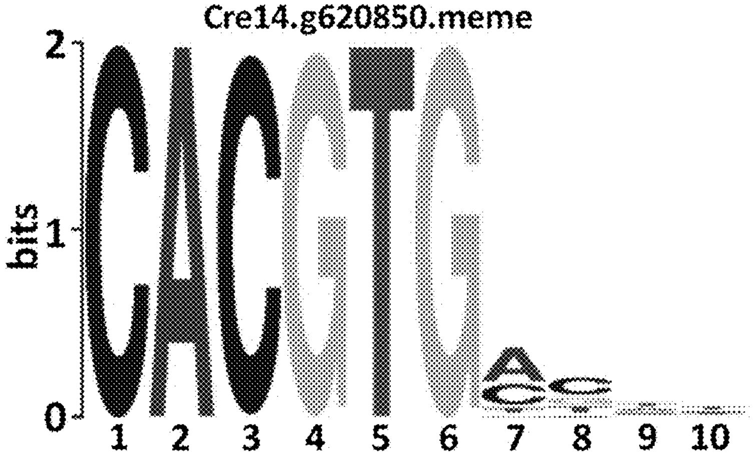
Consensus: CACGTG[A/C]CN
*Fig. 17B*

C2H2 family
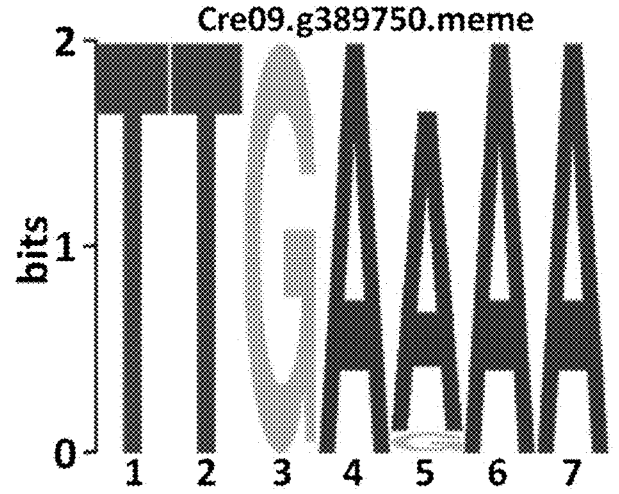
Consensus: TTGAAAA
GATA family
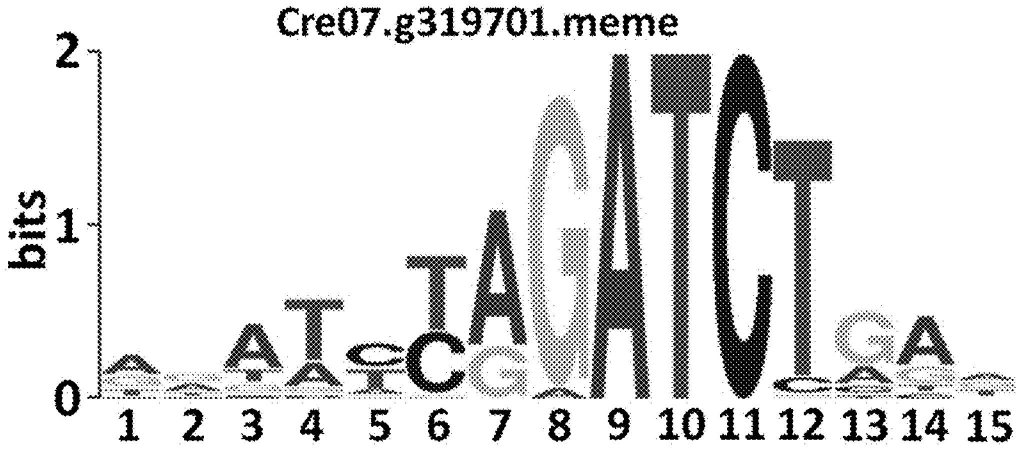
Consensus: N[A/T][A/T][C/T][C/T][A/G]GATCT[G/A]N
(SEQ ID NO:233)
*Fig. 17B, cont'd.* bZIP family
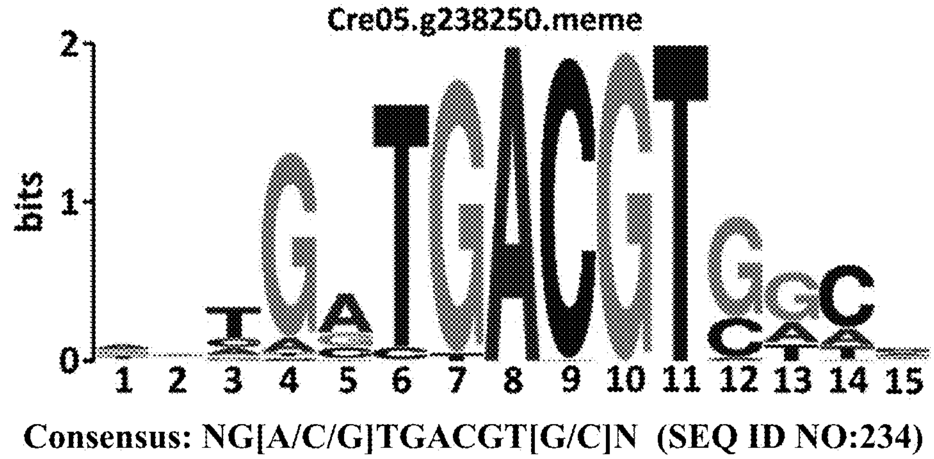
Consensus: NG[A/C/G]TGACGT[G/C]N (SEQ ID NO:234)
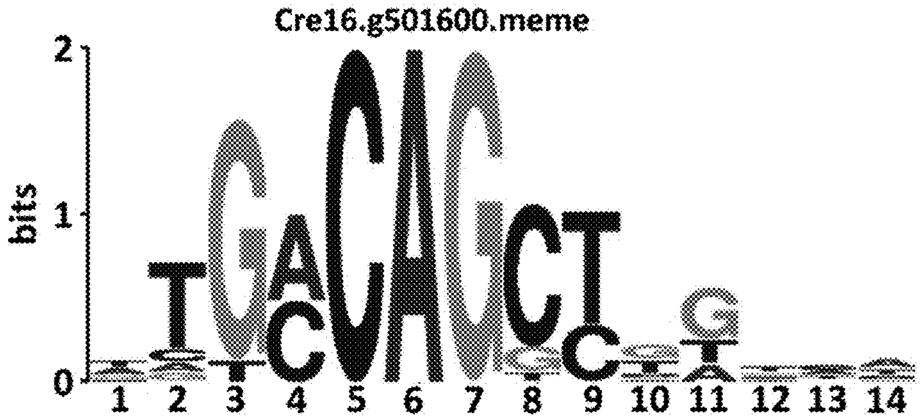
Consensus: N[T/C]G[A/C]CAG[C/G][T/C]N (SEQ ID NO:235)
*Fig. 17C* bZIP family
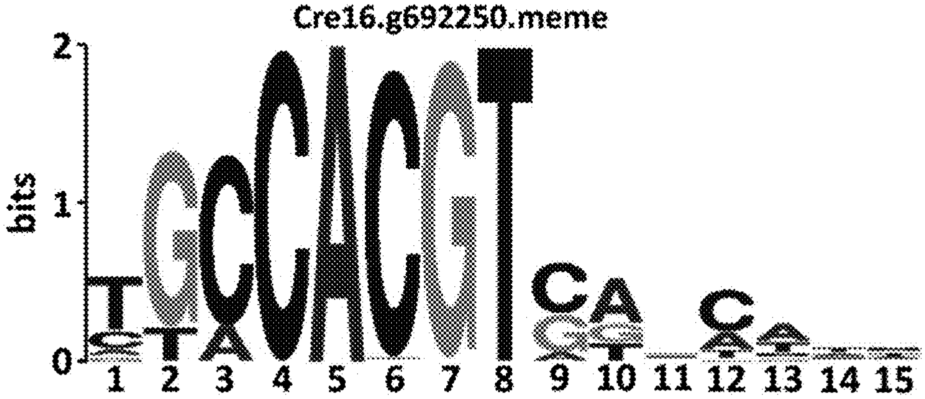
Consensus: N[G/T][A/C]CACGTN
C3H family
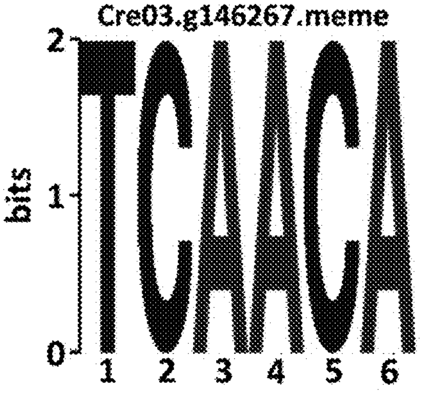
Consensus: TCAACA
*Fig. 17C, cont'd.*

Dof family
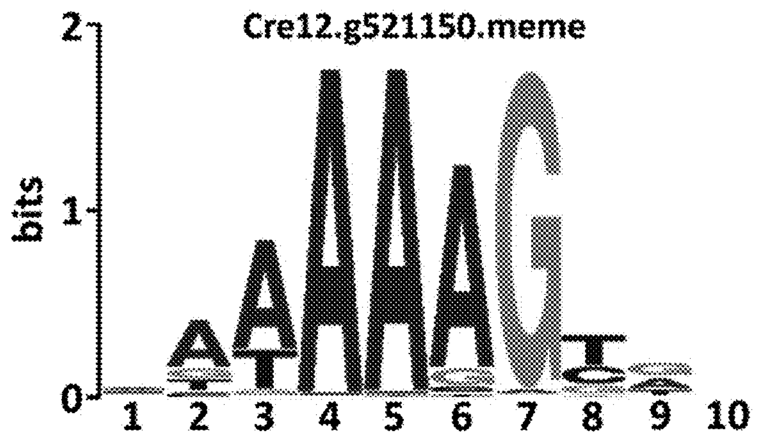
Consensus: N[A/T]AAAGN
G2 family
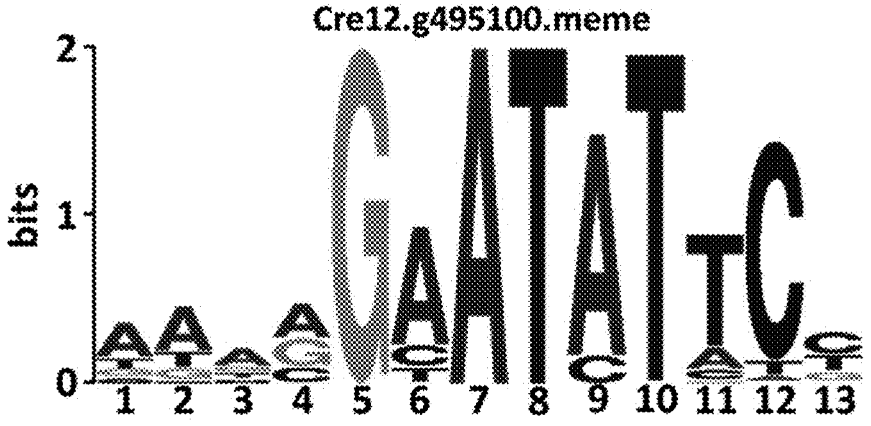
Consensus: NG[A/C/T]AT[A/C]T[A/T]CN (SEQ ID NO:236)
*Fig. 17C, cont'd.* cggcggggagctcgctgaggcttgacatgattggtgcgtatgtttgtatgaag
ctacaggactgatttggcgggctatgagggcgggggaagctctggaagggccg
cgatggggcgcgcggcgtccagaaggcgccatacggcccgctggcggcaccca
tccggtataaaagcccgcgaccccgaacggtgacctccactttcagcgacaaa
cgagcacttatacatacgcgactattctgccgctatacataaccactcagcta
gcttaagatcccatcaagcttgcatgccgggcgcgccagaaggagcgcagcca
aaccaggatgatgtttgatggggtatttgagcacttgcaacccttatccggaa
gccccctggcccacaaaggctaggcgccaatgcaagcagttcgcatgcagccc
ctggagcggtgccctcctgataaaccggccaggggcctatgttctttacttt
tttacaagagaagtcactcaacatcttaaaatggccaggtgagtcgacgagca
agcccggcggatcaggcagcgtgcttgcagatttgacttgcaacgcccgcatt
gtgtcgacgaaggcttttggctcctctgtcgctgtctcaagcagcatctaacc
ctgcgtcgccgtttccatttgcaggatggccatg
(SEQ ID NO:23)

*Fig. 18*

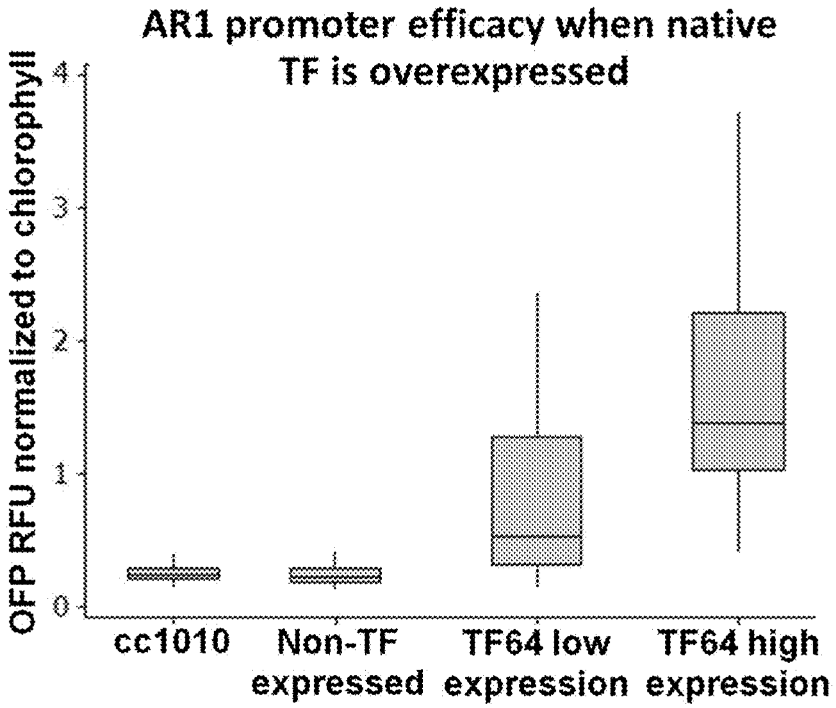

*Fig. 19*

SEQUENCE LISTING

```
<160> NUMBER OF SEQ ID NOS: 236

<210> SEQ ID NO 1
<211> LENGTH: 31
<212> TYPE: DNA
<213> ORGANISM: Chlamydomonas reinhardtii

<400> SEQUENCE: 1

ccgctgttgg tgtgcaattt tcaaacatct g                                   31


<210> SEQ ID NO 2
<211> LENGTH: 31
```

<212> TYPE: DNA
<213> ORGANISM: Chlamydomonas reinhardtii

<400> SEQUENCE: 2
ccgctgttgg tgtgcaattt tcaaacatct g 31

<210> SEQ ID NO 3
<211> LENGTH: 31
<212> TYPE: DNA
<213> ORGANISM: Chlamydomonas reinhardtii

<400> SEQUENCE: 3
ctcaatacga tgtgcaattt tgcagcgcat g 31

<210> SEQ ID NO 4
<211> LENGTH: 31
<212> TYPE: DNA
<213> ORGANISM: Chlamydomonas reinhardtii

<400> SEQUENCE: 4
acccggcgca tgggcaattg taggagggtt g 31

<210> SEQ ID NO 5
<211> LENGTH: 31
<212> TYPE: DNA
<213> ORGANISM: Volvox carteri

<400> SEQUENCE: 5
caagcagcgc tgcgcaattt tgacttgcag t 31

<210> SEQ ID NO 6
<211> LENGTH: 31
<212> TYPE: DNA
<213> ORGANISM: Volvox carteri

<400> SEQUENCE: 6
gctgcagttg tccgcaagtg caccgatagc a 31

<210> SEQ ID NO 7
<211> LENGTH: 31
<212> TYPE: DNA
<213> ORGANISM: Zea mays

<400> SEQUENCE: 7
tggatcgttt tctgaaattg ttcagtgtga t 31

<210> SEQ ID NO 8
<211> LENGTH: 31
<212> TYPE: DNA
<213> ORGANISM: Chlamydomonas reinhardtii

<400> SEQUENCE: 8
accaaaccgg tgttcaattg cattcaaccc a 31

<210> SEQ ID NO 9
<211> LENGTH: 23
<212> TYPE: DNA
<213> ORGANISM: Volvox carteri

<400> SEQUENCE: 9
gttctgaaag tgtccttcag gac 23

<210> SEQ ID NO 10

<211> LENGTH: 31
<212> TYPE: DNA
<213> ORGANISM: Chlamydomonas reinhardtii

<400> SEQUENCE: 10
aaatgcgact tgcgcatgtt caagccggac g 31

<210> SEQ ID NO 11
<211> LENGTH: 31
<212> TYPE: DNA
<213> ORGANISM: Volvox carteri

<400> SEQUENCE: 11
agagaagggc agcgcaagtg tccataccag c 31

<210> SEQ ID NO 12
<211> LENGTH: 31
<212> TYPE: DNA
<213> ORGANISM: Volvox carteri

<400> SEQUENCE: 12
tttataatga tgggcaagtg aagagctctg a 31

<210> SEQ ID NO 13
<211> LENGTH: 31
<212> TYPE: DNA
<213> ORGANISM: Chlamydomonas reinhardtii

<400> SEQUENCE: 13
gggcttggtt tgttcatttg cacctctcca a 31

<210> SEQ ID NO 14
<211> LENGTH: 26
<212> TYPE: DNA
<213> ORGANISM: Chlamydomonas reinhardtii

<400> SEQUENCE: 14
ttcctttcgg tcggcatgtg cgtgca 26

<210> SEQ ID NO 15
<211> LENGTH: 26
<212> TYPE: DNA
<213> ORGANISM: Chlamydomonas reinhardtii

<400> SEQUENCE: 15
acacttggga atttgcaatg ggcaag 26

<210> SEQ ID NO 16
<211> LENGTH: 31
<212> TYPE: DNA
<213> ORGANISM: Chlamydomonas reinhardtii

<400> SEQUENCE: 16
tgtatttaac tgtgcacgtt taacacacaa c 31

<210> SEQ ID NO 17
<211> LENGTH: 31
<212> TYPE: DNA
<213> ORGANISM: Volvox carteri

<400> SEQUENCE: 17
ttatgcatgg agcgcatgtg tatttaattt t 31

<210> SEQ ID NO 18
<211> LENGTH: 85
<212> TYPE: PRT
<213> ORGANISM: Chlamydomonas reinhardtii

<400> SEQUENCE: 18

```
Ala Ala Gly Ser Arg Ala Pro Val Ser His Ser Thr Val Glu Lys Gln
1               5                   10                  15

Arg Arg Asp Arg Ile Asn Ser Leu Ile Asp Glu Leu Arg Asp Leu Val
            20                  25                  30

Pro Pro Thr Gln Gln Gln Gln Gln Gln Gln Gln Gln Ile Gly Val Val
        35                  40                  45

Thr Ile Gly Val Ser Asp Asn Pro Glu Ala Ser Ser Arg Arg Pro Lys
    50                  55                  60

His Val Val Leu Ala Asp Thr Ile Asn Leu Leu Lys Ala Leu Arg Gln
65                  70                  75                  80

Arg Val Ser Phe Ala
                85
```

<210> SEQ ID NO 19
<211> LENGTH: 76
<212> TYPE: PRT
<213> ORGANISM: Chlamydomonas reinhardtii

<400> SEQUENCE: 19

```
Met Ala Glu Pro Lys Gly Gln Ile Ser His Ser Thr Val Glu Lys Gln
1               5                   10                  15

Arg Arg Asp Arg Ile Asn Ser Leu Ile Asp Glu Leu Arg Glu Leu Val
            20                  25                  30

Pro Pro Gln Gln Arg Gly Gly Ala Asn Gly Ala Ala Ala Ala Ala Ala
        35                  40                  45

Asn Asp Ala Gly Gly Leu Glu Ala Arg Arg Pro Lys His Val Val Leu
    50                  55                  60

Ala Asp Thr Ile Gln Leu Leu Lys His Leu Gln Leu
65                  70                  75
```

<210> SEQ ID NO 20
<211> LENGTH: 75
<212> TYPE: PRT
<213> ORGANISM: Volvox carteri

<400> SEQUENCE: 20

```
Val Val Glu Val Lys Gly Gln Ile Ser His Ser Thr Val Glu Lys Gln
1               5                   10                  15

Arg Arg Asp Arg Ile Asn Ser Leu Ile Asp Glu Leu Arg Glu Leu Val
            20                  25                  30

Pro Pro Gln Ser Arg Ser Asn Asn Asn Gly Ala Thr Gly Glu Gly Leu
        35                  40                  45

Glu Ala Arg Arg Pro Lys His Val Val Leu Ala Asp Thr Ile Gln Leu
    50                  55                  60

Leu Lys His Leu Gln Gln Lys Leu Gln Val Thr
65                  70                  75
```

<210> SEQ ID NO 21
<211> LENGTH: 74
<212> TYPE: PRT
<213> ORGANISM: Auxenochlorella protothecoides

<400> SEQUENCE: 21

Pro Gly Met Pro His Pro Gly Ala Ile His Ser Thr Val Glu Lys Gln
1 5 10 15

Arg Arg Asp Arg Ile Asn Ser Leu Ile Asp Glu Leu Arg Asp Leu Val
20 25 30

Pro Pro Gln Ala Gly Cys Gly Thr Gly Glu Ala Ala Glu Gly Ser Asp
35 40 45

Ser Arg Arg Pro Lys His Val Val Leu Ala Asp Thr Ile Gln Leu Val
50 55 60

Arg Asp Leu Gln Glu Lys Leu Val Thr Ser
65 70

<210> SEQ ID NO 22
<211> LENGTH: 75
<212> TYPE: PRT
<213> ORGANISM: Coccomyxa subellipsoidae

<400> SEQUENCE: 22

Gly Ser Gly Thr Lys Gln His Thr Ser His Ser Thr Val Glu Lys Asn
1 5 10 15

Arg Arg Asp Arg Ile Asn Ser Leu Ile Asp Glu Leu Arg Asp Leu Val
20 25 30

Pro Pro Gln Gln Lys Glu Ser Ala Asn Thr Ser Gln Asp Asn Leu Asp
35 40 45

Pro Thr Lys Arg Pro Lys His Val Val Leu Ser Asp Thr Ile Leu Leu
50 55 60

Val Lys Ser Leu Ala Asp Lys Val His Ala Thr
65 70 75

<210> SEQ ID NO 23
<211> LENGTH: 670
<212> TYPE: DNA
<213> ORGANISM: Adenovirus

<400> SEQUENCE: 23
cggcggggag ctcgctgagg cttgacatga ttggtgcgta tgtttgtatg aagctacagg 60
actgatttgg cgggctatga gggcggggga agctctggaa gggccgcgat ggggcgcgcg 120
gcgtccagaa ggcgccatac ggcccgctgg cggcacccat ccggtataaa agcccgcgac 180
cccgaacggt gacctccact ttcagcgaca aacgagcact tatacatacg cgactattct 240
gccgctatac ataaccactc agctagctta agatcccatc aagcttgcat gccgggcgcg 300
ccagaaggag cgcagccaaa ccaggatgat gtttgatggg gtatttgagc acttgcaacc 360
cttatccgga agccccctgg cccacaaagg ctaggcgcca atgcaagcag ttcgcatgca 420
gcccctggag cggtgccctc ctgataaacc ggccaggggg cctatgttct ttactttttt 480
acaagagaag tcactcaaca tcttaaaatg gccaggtgag tcgacgagca agcccggcgg 540
atcaggcagc gtgcttgcag atttgacttg caacgcccgc attgtgtcga cgaaggcttt 600
tggctcctct gtcgctgtct caagcagcat ctaaccctgc gtcgccgttt ccatttgcag 660
gatggccatg 670

<210> SEQ ID NO 24
<211> LENGTH: 10
<212> TYPE: DNA
<213> ORGANISM: Artificial
<220> FEATURE:

-continued

<223> OTHER INFORMATION: Synthetic algal promoter or element

<400> SEQUENCE: 24
accccatcgc 10

<210> SEQ ID NO 25
<211> LENGTH: 10
<212> TYPE: DNA
<213> ORGANISM: Artificial
<220> FEATURE:
<223> OTHER INFORMATION: Synthetic algal promoter or element

<400> SEQUENCE: 25
cccccatcgc 10

<210> SEQ ID NO 26
<211> LENGTH: 10
<212> TYPE: DNA
<213> ORGANISM: Artificial
<220> FEATURE:
<223> OTHER INFORMATION: Synthetic algal promoter or element

<400> SEQUENCE: 26
cgcccattgc 10

<210> SEQ ID NO 27
<211> LENGTH: 10
<212> TYPE: DNA
<213> ORGANISM: Artificial
<220> FEATURE:
<223> OTHER INFORMATION: Synthetic algal promoter or element

<400> SEQUENCE: 27
gccccaatgc 10

<210> SEQ ID NO 28
<211> LENGTH: 10
<212> TYPE: DNA
<213> ORGANISM: Artificial
<220> FEATURE:
<223> OTHER INFORMATION: Synthetic algal promoter or element

<400> SEQUENCE: 28
gccccagcgc 10

<210> SEQ ID NO 29
<211> LENGTH: 10
<212> TYPE: DNA
<213> ORGANISM: Artificial
<220> FEATURE:
<223> OTHER INFORMATION: Synthetic algal promoter or element

<400> SEQUENCE: 29
gccccattgc 10

<210> SEQ ID NO 30
<211> LENGTH: 10
<212> TYPE: DNA
<213> ORGANISM: Artificial
<220> FEATURE:
<223> OTHER INFORMATION: Synthetic algal promoter or element

<400> SEQUENCE: 30
gcgccatcgc 10

-continued

<210> SEQ ID NO 31
<211> LENGTH: 10
<212> TYPE: DNA
<213> ORGANISM: Artificial
<220> FEATURE:
<223> OTHER INFORMATION: Synthetic algal promoter or element

<400> SEQUENCE: 31
ggcccaacgc 10

<210> SEQ ID NO 32
<211> LENGTH: 10
<212> TYPE: DNA
<213> ORGANISM: Artificial
<220> FEATURE:
<223> OTHER INFORMATION: Synthetic algal promoter or element

<400> SEQUENCE: 32
ggcccactgc 10

<210> SEQ ID NO 33
<211> LENGTH: 10
<212> TYPE: DNA
<213> ORGANISM: Artificial
<220> FEATURE:
<223> OTHER INFORMATION: Synthetic algal promoter or element

<400> SEQUENCE: 33
ggcccagcgc 10

<210> SEQ ID NO 34
<211> LENGTH: 10
<212> TYPE: DNA
<213> ORGANISM: Artificial
<220> FEATURE:
<223> OTHER INFORMATION: Synthetic algal promoter or element

<400> SEQUENCE: 34
ggcccatcgc 10

<210> SEQ ID NO 35
<211> LENGTH: 10
<212> TYPE: DNA
<213> ORGANISM: Artificial
<220> FEATURE:
<223> OTHER INFORMATION: Synthetic algal promoter or element

<400> SEQUENCE: 35
ggcccattcc 10

<210> SEQ ID NO 36
<211> LENGTH: 10
<212> TYPE: DNA
<213> ORGANISM: Artificial
<220> FEATURE:
<223> OTHER INFORMATION: Synthetic algal promoter or element

<400> SEQUENCE: 36
ggcccattgc 10

<210> SEQ ID NO 37
<211> LENGTH: 10
<212> TYPE: DNA
<213> ORGANISM: Artificial
<220> FEATURE:
<223> OTHER INFORMATION: Synthetic algal promoter or element

<400> SEQUENCE: 37
gggccattgc 10

<210> SEQ ID NO 38
<211> LENGTH: 500
<212> TYPE: DNA
<213> ORGANISM: Artificial
<220> FEATURE:
<223> OTHER INFORMATION: Synthetic algal promoter or element

<400> SEQUENCE: 38
caccaggaca tccctctctc agctcctaga agctgtctcg tgccagcttc ggtcgggccg 60
caagtaaagc gagacccaag agcgacgttt gccaccttgc gcgtgctttg agcatgtcgc 120
gaagaaaccc cgaaggcatg gggcccattc gcgaagcaaa tctggtgtgc aaccattaag 180
gctttaaagc gagcgagcga gcaggaggcc catgcagcgc gcgcgaggcg aacatagaat 240
gggcccgctc ttccgctgcg cgttagaagc gaggcagcat catattcata ttcattagca 300
ccaatgctcg caggtataca aattttgtgc agaagcgaaa atgcaagcaa tttgcatggg 360
gcgtacggcc gcatggggct tttttttttg gggctcaagt ctcagagcgc gcgcgcaatg 420
gcgccctctc ctctcttttc ctcgtcgcga ccgaacccag caaggtgcgt caagatcgct 480
gtcgggtaag agccaaggct 500

<210> SEQ ID NO 39
<211> LENGTH: 500
<212> TYPE: DNA
<213> ORGANISM: Artificial
<220> FEATURE:
<223> OTHER INFORMATION: Synthetic algal promoter or element

<400> SEQUENCE: 39
cacatgctga ctacgagcag gcgctgggca gaatggcatg aaggcttctg agcgactcgg 60
cgacgaactc atccctcaag tgttgcacaa aagcgccgag cgctccgcgt tcgagggcga 120
atgacccgcg cgaatgggcc ccacaaatga ccaggcaacc tcaagctaac gcagcggcct 180
tttacgtata gagcgactgc aagcaagtat gcagctcgtt gcgcggtcgc gagtccaagt 240
cgcgctgcgc gcacatcctc gagcgcgcgc cgcggccacc aagtggaatg ggcccatcat 300
gcatgtttgc ttggccccga taaagcccgc aattttggga aaaaggtacg gcgcgcgccc 360
catgcgagat gtacgcccat tgcatggggc aacttgctca aagccgagcg agcccgctgc 420
aggttagtct ttcttttagc gtgtgcccac acctttctag tcgttcttcg ccaccaccaa 480
caagaaagcc ggcggcctcg 500

<210> SEQ ID NO 40
<211> LENGTH: 500
<212> TYPE: DNA
<213> ORGANISM: Artificial
<220> FEATURE:
<223> OTHER INFORMATION: Synthetic algal promoter or element

<400> SEQUENCE: 40
gaagccctcc ataatggccc cgtctccgca tctcccgcac tgttcgcggg caacagcagg 60
gagacgagag gaacccaaga agcgcgccac tgcagcgctt cgcgcagtgg gcccattccg 120
gcaattatga cccccgaccg cgcgggtatg aagctgtttt caagcaactc ggcgcagttc 180
ttggcactcg atttgcgcga gagcgagttt cagaatgggc cctctttttg cttgcttttg 240
cgcgtcgacc gcctcgcgaa atggtggggc ctgcacccat tgtttcattc tatgtatcaa 300
tgccatttat aatcattagg agcaattttg gtacggcgtg cgtcacttgc atggggctgg 360
cccattgcaa tgagatgggc gcatggggcg ctcaattgtc tgcgacttgc gagccacttc 420
tctcttccct ctctcgccgt caaccgaccg actcacttcg tcgcaaccac ctttcgtgag 480
taggtagtgt gtaagaaggt 500

<210> SEQ ID NO 41
<211> LENGTH: 500
<212> TYPE: DNA
<213> ORGANISM: Artificial
<220> FEATURE:
<223> OTHER INFORMATION: Synthetic algal promoter or element

<400> SEQUENCE: 41
ccccctgcct cctcgcgcat gcgtgaggca tgagagcgtg gcataaggcc gtaaagcaaa 60
gcgacaaggg gcttccaggt gtgcacgcat gcaagcacgc gaaacttttt ttctgcgctg 120
ggtttgtcgc tttcctagtt tgtaatgtgt tccaaccctt ttaggcgtgg cagcagaggc 180
gcgcggcgcc atttgggaaa gcaagttagt gcaaaatgca aacatgcgca agggcgcggg 240
gttcgcgacc atcgcgagct ccatagcgct ggtggctatg caccattcca tgcatgcata 300
caattcatta tgggcccatt caaattttgg gggcgttctt atccttccct ggagggccca 360
ttctcgtacg gcattgcatg gggccgcccc atgcggactt gcttatcctg cgagcgcgcg 420
acagctttct cttttacttg tcgcaggttg cgccgaacac ttctctttca aaacaccagt 480
gagcaggccc tcgcccccaa 500

<210> SEQ ID NO 42
<211> LENGTH: 500
<212> TYPE: DNA
<213> ORGANISM: Artificial
<220> FEATURE:
<223> OTHER INFORMATION: Synthetic algal promoter or element

<400> SEQUENCE: 42
cgggtgttgt gctcagagtg gcttccgcat gataaacgca gcgctgaagc tattaaagca 60
gggggaaccc tcgctcaaga gatcgcaagc accagcgcac gcgttgcgcg catgtcgcgc 120
agcaattggc agaaaccgct tgaaattcgc atcaatgcat gtcaaggcgc aatagctatg 180
cgcaaggcct cccggctatg cgtagacaag ggcccattcc tagaatcagg ggaatcaagc 240
gggttcgtgc aagcgtgggc ccattctcag gccagcatag cgaggataaa gctagcataa 300
attgcgcccc atgcatgggc agaatttttg gcgcttccaa cgcgaagcag cagcgcatgg 360
ggcgatgccg tacggcgaga tcgcctctca agtctttgtc gcaagtcgcg agccactgca 420
ccacctttcc tctctctctt tgtccaccgc taggcaaggg tggccgcaaa aaacaagtac 480
agggtaagaa cagggctctt 500

<210> SEQ ID NO 43
<211> LENGTH: 500
<212> TYPE: DNA
<213> ORGANISM: Artificial
<220> FEATURE:
<223> OTHER INFORMATION: Synthetic algal promoter or element

<400> SEQUENCE: 43
aggctagaac agtttctcct ctccatggca atatcccgca ccagggcacg agggcactta 60
aagcacggga gagggtgttg ggtctccgga aagcactaga acctgacagt gaatgggccc 120

-continued

```
tttccccggc atgggcaagc aagcaagaag gcaagcagcg gcagaagcaa agtgcggaat    180

gggcccttgc gcgtatatat ttcgggcaag agcgacggaa agcggtcgct cgcctgcaga    240

ggcgttgaat taaattctgc gcgcgcgaat gcgattaaag catacagcat gcactggccc    300

attgcataca attcaaatta tctgggcccc atgcgcggtc cacgaaaagg ctgcattggg    360

gcgccgtacg gcgtcgcgct catgcgcccc atgcagatgg ccgccggtct tcctttcttt    420

ctctctctct ttctctttca ggtgcccctc ctaggacact tcgccttaaa gtaacaccaa    480

caagaagcgc gccctggccc                                                500
```

```
<210> SEQ ID NO 44
<211> LENGTH: 500
<212> TYPE: DNA
<213> ORGANISM: Artificial
<220> FEATURE:
<223> OTHER INFORMATION: Synthetic algal promoter or element

<400> SEQUENCE: 44

cctgcttcag gccagggcgt gagataaagc atgcatttgg cagcgatgtc aggggctttc     60

tgaaagccgc ttttggcacg gtgtgacatg cgtgcacgcg tttcgggtga gcagcaatgt    120

tcagcaaccc ccgcaatgcg gggcccattc tgggcaaccc ttccaacaaa gttgaagtga    180

gcaatcgatt ttggcagaat gggcccacgc gggtcgcggc atgcgcttgc gccggggaga    240

attcatggcc tcgcgcaagg cagcgcgcga aatattgcgg tggtctcacg catagcaacc    300

agggggcact cgcaaaggct gtatattagt ttataggccc taggccccat gcggtttgta    360

cggcccattg aggccccatg ccccatgcaa attttgcgcc agcgctcacc tccccactct    420

ttctctttct ttcctcccgt ggaacaccag tcaccagtcc tcattcagca aggagcaagc    480

cgccggtgag caggtgagcc                                                500
```

```
<210> SEQ ID NO 45
<211> LENGTH: 500
<212> TYPE: DNA
<213> ORGANISM: Artificial
<220> FEATURE:
<223> OTHER INFORMATION: Synthetic algal promoter or element

<400> SEQUENCE: 45

cctggaaagg aggctagggc gcatgtcgtt ttgcaaaaaa acgcgtggca ggagtgggac     60

aaggaaccgc ttcttcgctt cttctttggc agtgcaaggc gcagcaccaa gtgcagcgag    120

cagtgaaaca atgggttcgc gaatgggccc tcttggaagc aacctcaaac cattctgcca    180

gggctcaact gagcacgcgg cgctatgcgt gagcaaacat gcgctttttg tgctgcaaga    240

attcctcggc aagctgattt tcgtcgctcc cagcgtcacc cagggccttg gcttctatgc    300

atgcatgggg cagagcatgg gtgtttaatt ttggaatggg ccccagcccc atgcgcccaa    360

ttaacgcccc attcgcccgc cgtacggcga gtcttgcgga gcgcaagtct ctttctcctt    420

gcctctcttt ctctctttct cgtcgaccgt cgccgaccac ctaggtcaat tttgaagtca    480

agacctgaag cgcgctcttc                                                500
```

```
<210> SEQ ID NO 46
<211> LENGTH: 500
<212> TYPE: DNA
<213> ORGANISM: Artificial
<220> FEATURE:
<223> OTHER INFORMATION: Synthetic algal promoter or element
```

<400> SEQUENCE: 46
atgggagcag ctcctcctct ctctgtctgc ttctgggcct acacgagtgt cgatgtgcct 60
ttggcacgga gaagcgagag gaaagcgcat gcctcaaaaa tcccgaagtg ccaagcatgg 120
ggcaaccccc gacgcgaaat tattgtcaaa gccagcagtg tcattcatgc tggcagaagg 180
aaagtgctcg cgtttaaagg aggcagacag agcgcgcgcg ggcggtcgca tgcgcgccaa 240
aatctcgcga cctcgcgaaa tgcgagcgcg ggccaccttt agaagtagca aaatgccatt 300
gaatgggccc agaatgggcc cgtgatgtct atgtgcatga gggccccatg caaggcagaa 360
agtcgatcgt accgagatcg ccccatgcga gcgccgtact ccgcggagaa gtcgcgcggg 420
cgcaagctag ttctctttct cacttcccgt agtcgaccgt gcttcacgtc agtccaccac 480
cacgcggcca tctttagccg 500

<210> SEQ ID NO 47
<211> LENGTH: 500
<212> TYPE: DNA
<213> ORGANISM: Artificial
<220> FEATURE:
<223> OTHER INFORMATION: Synthetic algal promoter or element

<400> SEQUENCE: 47
gcttcgtcac gcaggcagct gggcaggcag gaaaagcata agggcacttc atcatcgtgg 60
gagagaaggc ctggaaggag aagggacaca aaagcgcttc gaccttgcgc ccttgaggca 120
ccgtcgaccc tttggagcta ccttttggag cagtgttctg gggcccattc ccaaaagggt 180
gctgcgcaag gcgagcgact tttaggcaga gcaaaagcat gcttgccagt ctgggcgcca 240
agccttccgc gcacggtgct cgaatgggcc ctggcctttc atgccttgct ctgattttca 300
ttagcatcgt ggccccatgc gaaagccgaa agcgcgagct cctgcgcatg gggcgatctt 360
cctggcgcca cggcagagat cgccgtacga gtgcagagtc ttccgcgcgc gagcgcgact 420
ttctctttct ctttcccatc ttaggaaaca cttcgccact gctttcgtta agagccgccg 480
gaaggccctc cgcgccctgg 500

<210> SEQ ID NO 48
<211> LENGTH: 500
<212> TYPE: DNA
<213> ORGANISM: Artificial
<220> FEATURE:
<223> OTHER INFORMATION: Synthetic algal promoter or element

<400> SEQUENCE: 48
ctggtcccag ttgtgcattc tcatgtgagg aaccctgggc caactgaggg gcagagggca 60
gacgagaaac ggtccgcacg gtcgcaagcg cacaaagcac gcgttcgact gcgctctaat 120
ggggctgagc gtgtctgacc ttttagctca gcaaatcagg cagaagcaga aagctaacct 180
acaagtgggc ctcatagaat gggccccacg gcgcgcgcga tgacacgcag tcgcttgcgt 240
cgcggcaagc ggaagctgcg agccacgagc gaatgggccc tttcatgcca tgctagatgc 300
taaatttcca caaagagaca aaattaatgc gagggcccca tgcaggcggt acggcagatc 360
gcttgcccca tgcgatcgcc cccatcgcga gacccttgcg agcgagcgcc tgcaccgttg 420
ccctctttct ctctcttgtc ctgtcgcctt tctaggaaag ggcgccacct ttgcagaaag 480
aacaagaggg cctcgcaggt 500

<210> SEQ ID NO 49

<211> LENGTH: 500
<212> TYPE: DNA
<213> ORGANISM: Artificial
<220> FEATURE:
<223> OTHER INFORMATION: Synthetic algal promoter or element

<400> SEQUENCE: 49
atgcctcctc gcttagcgct agaaagccgt ctgtccttaa aaaagccagc gcagagcgac 60
tgcacttctt ggctcaagag atcgcacgcg cgccgacccg ccaggtctgg gtcgcgagag 120
cgtctctcgc cgggcgctgt cgaccgcttt agcactgtgt catttcaagt catgagctgc 180
tacaagtcgc agccgaggag cagaatgggc cctgggcggc atgcgcattt cccgctcgcc 240
agggttcact cagcaagccc tcagcgctgc aggctcacac attctttgct gattatgcat 300
gcaagcatgc cccatgcatg gtactgcgcc cgtgcgagag aatgggcccc tctcgccgta 360
ccattctcgc cgcaattgca tggggcgact tttgaaggcc gactttgcga gcgcgcgccg 420
agcctctttc tctttgtcgt cgccttgttc gacacttcag tcacctcgcc tccaccaagg 480
gtggccctcg caagaaggag 500

<210> SEQ ID NO 50
<211> LENGTH: 500
<212> TYPE: DNA
<213> ORGANISM: Artificial
<220> FEATURE:
<223> OTHER INFORMATION: Synthetic algal promoter or element

<400> SEQUENCE: 50
ctgcgtgcat tttaggagga agaaagcctc cgcagagccg cactgacttc gcgagccctt 60
gcgtagaaat ctctgaaacc ccatcgcacc aagtgacctt tctcagcgct cgcgttggca 120
cgcgtcgctt tctgccgcac acgcaattgc tcagcaacaa agaggcaagc tattagtatc 180
aaggctatgc gcgagcggag acctcgcgcg cgcgctggcg gctcacggcg cctgggcaac 240
ttggggttcg cttcgggccc attcatagcg ctgagtggcc attcaagggc ccattcaagg 300
tcgcagggga ttagcatacc aaaatgtaat gcagaatgcc ttctctgcgc gcatggggcg 360
caatggccca attctcgccg tactcgctcg cgcatggggc ggagtctcgc caaagcgcgt 420
tctttctctt tgtgccgcta gtcgtcgcag gtgagcgtta gatcaccttg ctcctttttt 480
ccgccccgcg ctgtgagtac 500

<210> SEQ ID NO 51
<211> LENGTH: 500
<212> TYPE: DNA
<213> ORGANISM: Artificial
<220> FEATURE:
<223> OTHER INFORMATION: Synthetic algal promoter or element

<400> SEQUENCE: 51
tgcctccaga agataaagca tctcatgtag gtcaggaaga actccaggaa aagcaacagc 60
aagcaagggg acacgctgct acacagagct tcgaaaatcg aaacttcggc cctgacataa 120
ccgcaagtgt gtgcagcgag ggcccattct gttctaagaa agcccaccaa cctcaagtgc 180
tggtcgacgc agcatccgcg agcgcgcgcg ccaaaaagtt gtgcagtttg ggtgcgcgtc 240
gtgcgacggt cgctcttccc tcagcgcgaa atccattccc catcatttgg gtctctgcac 300
ccatgcatgt ttgtgcgagc gtcgcgcggg ccccatgcgg tacggctttt ctgaatgggc 360
ccccccgctt gcatgggcgc ggtcgaccgc atggggcgag agcgcaacaa aacagcgcgt 420

```
tctctctctc cctctttcca aaccggttgg ccgaacaacc acttatcatc ttcgttgccc    480

cagcaggccc tgtccaagaa                                                500


<210> SEQ ID NO 52
<211> LENGTH: 500
<212> TYPE: DNA
<213> ORGANISM: Artificial
<220> FEATURE:
<223> OTHER INFORMATION: Synthetic algal promoter or element

<400> SEQUENCE: 52

aatggcccgc cctggacatg gcgcagcctg agggccctgt tgcaaaacgg cttaaaaaca     60

cttaaatcgc tggcagggac acttcgtgcg ggtctgccga gcgcaaggcg cgtttcgggc    120

cccggcaccg tcgctgtttc ggacccccgt tcgtgccagc gcgctcaact aatgcgagaa    180

tgggcccaga aaacagagca aaatgcaaga gcagcaaaac tgcgcatgcg ccactgttgt    240

ctcactcgct cgcgcaagct ccacggccct ggggcccatt ccagcgcgta aataagccac    300

cattttgcgg tctggcagca gcaccaaaat ttttaatgca tggggctccg cgaaatggcg    360

ccgtacggca ccgagatctg cccatgcatg catggggcgg agtcaaagcg cgcgccgagc    420

tctttcttct tgtcagcacc gcaggttgct cacgtaggac acttctttgc gcgtcgcccc    480

tgccttcggg cacgggtaag                                                500


<210> SEQ ID NO 53
<211> LENGTH: 500
<212> TYPE: DNA
<213> ORGANISM: Artificial
<220> FEATURE:
<223> OTHER INFORMATION: Synthetic algal promoter or element

<400> SEQUENCE: 53

cacgagtttg ctggacatcc tggctttctc agtggcagcg ccgtaggtcg ggcagaggga     60

gaaacccttc gcttctcagg agaagcatac gttcgttcgg tggggggcga agaaccacag    120

cagaatgggc ccgctttcgc ggcatcaatg catgctcatc accaagcaga ggctcagagc    180

ctcctcaaat caggggaaaa ctgacgcgcg cgtgagcgcg cttccgacgc gatggcgctc    240

gcttgggttg cgtgagcagg ctgcgagagc gctggctgtt acattcattg aatgggccca    300

tgcatggggc aaatagtgcg gcgcttccat gcaagcaagc gagcgcgacg cgcatggggc    360

gcctgtacgg ccgcccccat tccccatgcc gtacagagtc tgggtcttcc ttcctgcaca    420

gcacttcttt cctcgagttg ttcgtcgtcg catcgccact tctggccagc aacacaccgg    480

aagcgcaggc cctggccctc                                                500


<210> SEQ ID NO 54
<211> LENGTH: 500
<212> TYPE: DNA
<213> ORGANISM: Artificial
<220> FEATURE:
<223> OTHER INFORMATION: Synthetic algal promoter or element

<400> SEQUENCE: 54

gttgccctgc ttccgtccat gatggcgcat gcctgaagca gggcaggccg cacatgactt     60

caagcgtcct ggggttcgca atcaagagct ttcgcgtgtc tgcgggtcgc gctcgcacag    120

cggccccgcg cgtgccgagc tcgacactcg ttcgcgttag gcaactcaaa accaagctac    180

aacaagcagt ataccttgcg cagcaaggag catgcttttc tccggtcgcg cccaacgacg    240
```

atttcctcgc tggtgcaagc tcccgagctc ccagcgcgcg cgaatagcaa atagcaaatg 300
gaatgggccc ttgtttataa cgcgcgcgca tggggcgaac gtacggcgaa atttgcatcg 360
gtttgcccca tgcatgcaga atgggcccat ttttgccctc gcgctgcgca agcgcgagct 420
ctttctttct ctttcgggtc tttctccgtt tgttgacacc tcaagtaaaa ggcttttctc 480
acaccagtcc gcggtgagcc 500

<210> SEQ ID NO 55
<211> LENGTH: 500
<212> TYPE: DNA
<213> ORGANISM: Artificial
<220> FEATURE:
<223> OTHER INFORMATION: Synthetic algal promoter or element

<400> SEQUENCE: 55
cacctgctgc tggggcagaa tggccatgtg gccagcgcac tgttgttgtg acactgagct 60
cgagaaggac aaggtgtgca agtgacatgt gcacgcgaag gggaatgggc cccaagggcc 120
cattcgtgca gcgggtgctg ccgcattgaa gcaaccaaca aagctaatgc gctaatgcgc 180
tgacgcgttc cgtggaaggc gagacgcaag cgcgagcgcg gaaagcaggc gattcactcg 240
cgccaagcct cgcgggagcg ctactagccc atacggccca atagcaagca tacagcaagc 300
ctctgcgcat ggggccaatg catggggccg ttctggtacg gctatgcctt tctcccattt 360
gcaatggcaa tggggccccc atgcagatcg cgacgagggt ctcttccgct cagtcagcgt 420
tctctttctc ttttcgagct cccgtcgtcg cttgcacaag aaggccgcac agcagtcttg 480
cgctcgccca attagccctg 500

<210> SEQ ID NO 56
<211> LENGTH: 500
<212> TYPE: DNA
<213> ORGANISM: Artificial
<220> FEATURE:
<223> OTHER INFORMATION: Synthetic algal promoter or element

<400> SEQUENCE: 56
ggatgctgga caagagaaga acatgccagc catgacacct gcctgaactc cagctcgaga 60
gacactattt cgacccaagg tgttgagtgc agatcgcagc tttcgcaaac gcagctctcg 120
ggtttgtgaa atgaccccgt gtctgaagca gtcagcgggg gcatgtcttg gttattggaa 180
gggcgcggtg gaagtgggtc cagcaaaacg ggtctcgcag cgcgagcagc gccaagaacg 240
agtgcaagcg aatgggccct caaaggccat cgccccccagc gctgacccca ttgaacatgc 300
atgtttgcgc atggggcaac atagtgcagc ccgcgagcga aaaagggccc attcttgcat 360
ggggcgccaa tggccgtacg agcgagtcgg ggtctctcaa gtgcttgcga gcgcgcgctc 420
tttctctttc ctctcctttc tttgagcagc ttcactgatc acgtacttct tcgcaacaag 480
cagggtaaga agcggtgcgt 500

<210> SEQ ID NO 57
<211> LENGTH: 500
<212> TYPE: DNA
<213> ORGANISM: Artificial
<220> FEATURE:
<223> OTHER INFORMATION: Synthetic algal promoter or element

<400> SEQUENCE: 57
ggatgactcc gtgcatgcaa atgccgcacg tctgcgaggg ctttcgcgac gagaaggaaa 60
tcaagaaggg agaaacccaa cctccgagaa gcatgttcgc gcgtttgagc agcgagggac 120
tctctcgcgg agccttcccg aagaaagtct tggggcccat tctcgcgttt tcaccaatgg 180
cctcgaggct cagtaggatt ttcgcgcgcg cgcgcgtgag catgcgcgcg cgagtctggg 240
ttgaatgggc cctcctgcga gcttccccag gcagcggggc ccattcagca agcatacaat 300
gcttgtgatt gcttagcccg tgcgccccat gcgcagagag agccccatgc atgggctgta 360
cggcagatct cgcgcccccc gtacggcgcg acgagtctgc tgcgagagcg cgcgcgctcc 420
ttctctctct ttcacgtgta ggcgcaggtc gccttaccac ctaggaaggt gcgtccctca 480
ccctctgtga gcccaagggc 500

<210> SEQ ID NO 58
<211> LENGTH: 500
<212> TYPE: DNA
<213> ORGANISM: Artificial
<220> FEATURE:
<223> OTHER INFORMATION: Synthetic algal promoter or element

<400> SEQUENCE: 58
ctgccccagt ttgcttaaat gcgtgcatga tgcattctcg taggtcgttc atggcagctc 60
gagatagttc cgaaacgacc gcaagcaccc cgccacccga gcacgctctt ttttcgaccg 120
caaagaaccg cgcccgctg ttccaatgca tgtcaagcaa tgtcaactcg ccgctattaa 180
gggcccattc tttctgcgcg cgcgacatgc tttgagagca aaatgcaact gcttttgttt 240
tgcaagctca aaggccttct tcgggtgggt tcagttctat atcaccattc attcattgcg 300
cgcaggcaga taaatagaat gggcccgcgg cgccccatgc atgaggccgt acttggcaga 360
tgcatggggc gccccctgga gctcgctcgc tcggggtgaa gagcgccttc ttgtctttcc 420
tttctctcct ttccttacct tcgtcgagcc tgccaagatc ggtggcgtca gtgcgtcgcc 480
ttaagcaggc cctgtgagta 500

<210> SEQ ID NO 59
<211> LENGTH: 500
<212> TYPE: DNA
<213> ORGANISM: Artificial
<220> FEATURE:
<223> OTHER INFORMATION: Synthetic algal promoter or element

<400> SEQUENCE: 59
atgacttggt ggactgccct gcacgccttc cgcatgtcct ggccccagcg cacttcttgg 60
cagtaaagcg gcaagcgggg acacacttcg cgtgcgcgct gccaagtgcc cgggagtgcc 120
ctcgacccgc gactcctatc aataaagccc gctcgccttc cttccttggt gttggtgctc 180
gcgtcaatcc tgcaagcaga agcccagctc gcaaaatgca gcgcgagcaa gttgcgccac 240
tcattcactt gcgcgcctcg aatgggccca gcgccagggc ccattcaagt ggttaagcta 300
tgtatgcaat gcggcgctcc aaattatttt gtttctggcc gtacagggtc ggtacgaccc 360
aagatctcgc cccatgcggg cccatcgcat ggggcgcccc ttgcaagccg agcaagcgcg 420
agttctcgcc ctttctttct cttcgaccta ggcacaccgt gggcgccgca caccacagca 480
gcagtgtgtc ctcccggcaa 500

<210> SEQ ID NO 60
<211> LENGTH: 500
<212> TYPE: DNA
<213> ORGANISM: Artificial
<220> FEATURE:
<223> OTHER INFORMATION: Synthetic algal promoter or element

<400> SEQUENCE: 60 cccggcagg gcgacgtcca ctgcacagcc agccatgttc gcctgcccat atttggtccg 60
gcgagggttc gctgctacac aggggggagt gcaagcgcta ccttgcgtcg acagcggcat 120
gaagggccca cgcagaatgg gcccgcaatg cattgcaatg ttcaagctca tgattaacgc 180
gctgcaacgc gccagagcga gagagcgcgc gagcgctctg gggtccttgt cgctcgcttt 240
tgttttcgcg ggcaagctcg ctgtgggccc tccagcgcat ttttttttcta tcatagtgac 300 atgacctttg aatgggccct gtgggcgcgg cccagaaaat tttttttct ctttctccgc 360 cccatgcggc gatggcgcca tcgccgtact gcatggggct cttttgagaa gtgcgagcaa 420
cactctttcc tctctttctc tcaaacacca gtcgatccaa ccacaccatt ttcctatctg 480
tgcgctcttc cgcggcggcc 500

<210> SEQ ID NO 61
<211> LENGTH: 500
<212> TYPE: DNA
<213> ORGANISM: Artificial
<220> FEATURE:
<223> OTHER INFORMATION: Synthetic algal promoter or element

<400> SEQUENCE: 61
tgctccagga tctgggcttt gggcatgtgt ctgtccttaa ccaggcactg aagcctgcaa 60
cacttcccct ttggcttccg agaaagcatg cgtgcgttgc gtgtggggcc cattcgggag 120
tgaaattatg tctgctaggc attgtgaagc tatgcagtgt tggtgccaga gcctcgcggc 180
gcggccgcgt aaagcaagag ccattttgcg caaagtcgcg gaatgccggg aatgggccca 240
acgcttcctc tcgcgagttg cgcccgagcg tagcgccttt cagtttcatt ccagctgggt 300
atgcgcccca tgcaattttg cgcatggggc gcttccgcag tttgcgcgaa atcgtacggc 360
gtacggcttg cattccccat gcgctcgcgc tcttctcttg ctgcgcgcgg acttcacctt 420
tctctctttg aacggtctag cccgcaggcc gaacaccaga tcttcacgtc ccgccaagcc 480
gcaacttgca ggtgccgcgg 500

<210> SEQ ID NO 62
<211> LENGTH: 500
<212> TYPE: DNA
<213> ORGANISM: Artificial
<220> FEATURE:
<223> OTHER INFORMATION: Synthetic algal promoter or element

<400> SEQUENCE: 62
ggtagtggcc ctctcctctt gcacctattt gccccgcaca gcagcgcagg agggcagcgc 60
tgccttcact tcccctcctt cgagagatcg caagctggct catcacacgc tcggaaaaga 120
accggcacgc gcgagcaatt gaatcgcagt agctccagcg ctcgcgcccc ggctggtgcg 180
ggcccattct acagcaaggc gaagtatgcg ggccttcagc gcgatggcgc gcgtcgcgaa 240
cgagtcataa gatgggtttt gccagcgcca gcgtagcacc agccattcat gctcgggccc 300
attccacagt gtttgcgagg ccaaaaattt tgcaaggcaa gcaagcaagt cgcgccgtac 360
gatggcccca tgcagcaaat ggcgcatggg gccggagtct gcagagcgag cgcacttctt 420
tcttctctct ctctctttag gtgcccacac ttcgcttcgc aagatcagca acctcgcaag 480
gttgagcttc ggggaagctt 500

<210> SEQ ID NO 63
<211> LENGTH: 27

<212> TYPE: DNA
<213> ORGANISM: Artificial
<220> FEATURE:
<223> OTHER INFORMATION: PCR primer

<400> SEQUENCE: 63
gttgagtgac ttctcttgta aaaaagt 27

<210> SEQ ID NO 64
<211> LENGTH: 30
<212> TYPE: DNA
<213> ORGANISM: Artificial
<220> FEATURE:
<223> OTHER INFORMATION: PCR primer

<400> SEQUENCE: 64
cccttggaca ccatatgcat ggccatcctg 30

<210> SEQ ID NO 65
<211> LENGTH: 30
<212> TYPE: DNA
<213> ORGANISM: Artificial
<220> FEATURE:
<223> OTHER INFORMATION: PCR primer

<400> SEQUENCE: 65
gggtttaatt tctagacggc ggggagctcg 30

<210> SEQ ID NO 66
<211> LENGTH: 20
<212> TYPE: DNA
<213> ORGANISM: Artificial
<220> FEATURE:
<223> OTHER INFORMATION: PCR primer

<400> SEQUENCE: 66
atcgcgcttc aaatacgccc 20

<210> SEQ ID NO 67
<211> LENGTH: 21
<212> TYPE: DNA
<213> ORGANISM: Artificial
<220> FEATURE:
<223> OTHER INFORMATION: PCR primer

<400> SEQUENCE: 67
aagcgcgata tcaagcttct t 21

<210> SEQ ID NO 68
<211> LENGTH: 31
<212> TYPE: DNA
<213> ORGANISM: Artificial
<220> FEATURE:
<223> OTHER INFORMATION: PCR primer

<400> SEQUENCE: 68
ggtcttaatg gtacccgctt caaatacgcc c 31

<210> SEQ ID NO 69
<211> LENGTH: 35
<212> TYPE: DNA
<213> ORGANISM: Artificial
<220> FEATURE:
<223> OTHER INFORMATION: PCR primer

<400> SEQUENCE: 69
gctgagggtt taattctaga acatgctgac tacga 35

<210> SEQ ID NO 70
<211> LENGTH: 18
<212> TYPE: DNA
<213> ORGANISM: Artificial
<220> FEATURE:
<223> OTHER INFORMATION: PCR primer

<400> SEQUENCE: 70
cccttggaca ccatatgc 18

<210> SEQ ID NO 71
<211> LENGTH: 35
<212> TYPE: DNA
<213> ORGANISM: Artificial
<220> FEATURE:
<223> OTHER INFORMATION: PCR primer

<400> SEQUENCE: 71
gctgagggtt taattctaga aagcaagtat gcagc 35

<210> SEQ ID NO 72
<211> LENGTH: 35
<212> TYPE: DNA
<213> ORGANISM: Artificial
<220> FEATURE:
<223> OTHER INFORMATION: PCR primer

<400> SEQUENCE: 72
gctgagggtt taattctaga gcatgtttgc ttggc 35

<210> SEQ ID NO 73
<211> LENGTH: 35
<212> TYPE: DNA
<213> ORGANISM: Artificial
<220> FEATURE:
<223> OTHER INFORMATION: PCR primer

<400> SEQUENCE: 73
gctgagggtt taattctaga aagccgagcg agccc 35

<210> SEQ ID NO 74
<211> LENGTH: 18
<212> TYPE: DNA
<213> ORGANISM: Artificial
<220> FEATURE:
<223> OTHER INFORMATION: PCR primer

<400> SEQUENCE: 74
cccttggaca ccatatgc 18

<210> SEQ ID NO 75
<211> LENGTH: 35
<212> TYPE: DNA
<213> ORGANISM: Artificial
<220> FEATURE:
<223> OTHER INFORMATION: PCR primer

<400> SEQUENCE: 75
gctgagggtt taattctaga acatgctgac tacga 35

<210> SEQ ID NO 76

<211> LENGTH: 18
<212> TYPE: DNA
<213> ORGANISM: Artificial
<220> FEATURE:
<223> OTHER INFORMATION: PCR primer

<400> SEQUENCE: 76
cccttggaca ccatatgc 18

<210> SEQ ID NO 77
<211> LENGTH: 27
<212> TYPE: DNA
<213> ORGANISM: Artificial
<220> FEATURE:
<223> OTHER INFORMATION: PCR primer

<400> SEQUENCE: 77
ggggtttttt ttacatgcat gatgggc 27

<210> SEQ ID NO 78
<211> LENGTH: 26
<212> TYPE: DNA
<213> ORGANISM: Artificial
<220> FEATURE:
<223> OTHER INFORMATION: PCR primer

<400> SEQUENCE: 78
tgtaaaaaaa accccgataa agcccg 26

<210> SEQ ID NO 79
<211> LENGTH: 26
<212> TYPE: DNA
<213> ORGANISM: Artificial
<220> FEATURE:
<223> OTHER INFORMATION: PCR primer

<400> SEQUENCE: 79
cgcaaaaaaa atttcccaaa attgcg 26

<210> SEQ ID NO 80
<211> LENGTH: 29
<212> TYPE: DNA
<213> ORGANISM: Artificial
<220> FEATURE:
<223> OTHER INFORMATION: PCR primer

<400> SEQUENCE: 80
gggaaatttt ttttgcgcgc gccccatgc 29

<210> SEQ ID NO 81
<211> LENGTH: 24
<212> TYPE: DNA
<213> ORGANISM: Artificial
<220> FEATURE:
<223> OTHER INFORMATION: PCR primer

<400> SEQUENCE: 81
acattttttt tggggcgcgc gccg 24

<210> SEQ ID NO 82
<211> LENGTH: 26
<212> TYPE: DNA
<213> ORGANISM: Artificial
<220> FEATURE:
<223> OTHER INFORMATION: PCR primer

<400> SEQUENCE: 82
ccccaaaaaa aatgtacgcc cattgc 26

<210> SEQ ID NO 83
<211> LENGTH: 26
<212> TYPE: DNA
<213> ORGANISM: Artificial
<220> FEATURE:
<223> OTHER INFORMATION: PCR primer

<400> SEQUENCE: 83
tgcttttttt tatgggcgta catctc 26

<210> SEQ ID NO 84
<211> LENGTH: 27
<212> TYPE: DNA
<213> ORGANISM: Artificial
<220> FEATURE:
<223> OTHER INFORMATION: PCR primer

<400> SEQUENCE: 84
ccataaaaaa aagcaacttg ctcaaag 27

<210> SEQ ID NO 85
<211> LENGTH: 26
<212> TYPE: DNA
<213> ORGANISM: Artificial
<220> FEATURE:
<223> OTHER INFORMATION: PCR primer

<400> SEQUENCE: 85
ctattttttt tactaacctg cagcgg 26

<210> SEQ ID NO 86
<211> LENGTH: 27
<212> TYPE: DNA
<213> ORGANISM: Artificial
<220> FEATURE:
<223> OTHER INFORMATION: PCR primer

<400> SEQUENCE: 86
tagtaaaaaa aatagcgtgt gcccaca 27

<210> SEQ ID NO 87
<211> LENGTH: 744
<212> TYPE: DNA
<213> ORGANISM: Chlamydomonas reinhardtii

<400> SEQUENCE: 87
atgggcgagc agctgaggca acagggaacc gtaaagtggt tcaacgccac caaaggcttc 60
ggcttcatca cgcctggtgg tggcggcgag gacctctttg tgcaccagac caacatcaac 120
tcggagggct tccgcagcct gcgggagggt gaagtcgtcg agttcgaggt tgaggctggg 180
ccggatggac gctctaaggc tgtgaacgtg acgggccccg gaggggccgc gcccgagggc 240
gctccgcgga acttccgcgg tggcggccgc ggccgcggcc gcgctcgcgg cgcccgcggc 300
ggctatgctg ctgcgtacgg ctacccgcag atggcgccgg tctaccccgg ctactacttc 360
ttccccgcgg accccacggg ccggggacgg ggtcgcggcg gccgcggcgg cgccatgccc 420
gccatgcagg gcgtgatgcc gggtgtggcg tacccgggca tgcccatggg cggggtgggc 480
atggagccga cgggcgagcc gtcggggctg caggtggtgg tgcacaacct gccgtggagc 540

-continued

```
tgccagtggc agcagctcaa ggaccacttc aaggagtggc gggtggagcg cgcagacgtc    600

gtgtacgacg cctggggccg ctcgcggggc ttcggcaccg tgcgcttcac gaccaaggag    660

gacgccgcga cggcgtgcga caagttgaac aacagccaaa tcgacgggcg cacgataagc    720

gtccggctcg accgtttcgc ttga                                          744
```

<210> SEQ ID NO 88
<211> LENGTH: 540
<212> TYPE: DNA
<213> ORGANISM: Chlamydomonas reinhardtii

<400> SEQUENCE: 88

```
atggctggtg acaaggctgc caccaaggag aagaaggccg cagagcccaa gggcaagcgg     60

aaggagactg agggcaaggc cgagcccccc gccaagaagg ctgccaaggc tcccccccaag    120

gagaagcccg ccaagaaggc gcccgccaag aaggagaaga aggccaagga ccccaacgcc    180

cccaagaagc ccctcacttc cttcatgtac ttctcgaacg ccatccgtga gagcgtgaag    240

tccgagaacc ctggcattgc cttcggcgag gtcggcaagg tgatcggcga gaagtggaag    300

ggcctgtccg ctgacgacaa gaaggagtac gatgagaagg cggctaagga caaggagcgc    360

taccagaagg agatggagtc ttacggcggc tcgtcgggtg cctccaagaa gcccgcggcc    420

aagaaggaga aggctgcgcc caagaagaag gctaaggagg aggaggagga ggacgagcct    480

gaggccgatg acgatggtga tgacgacgac gaggacgatg atggtgatga cgatgagtaa    540
```

<210> SEQ ID NO 89
<211> LENGTH: 1368
<212> TYPE: DNA
<213> ORGANISM: Chlamydomonas reinhardtii

<400> SEQUENCE: 89

```
atgcagcagt cttcgcagct tgggctgcct gaccagctcg ctctgctcag cggattcccg     60

gccgcgctct tcccccagca gtacgggtcg ggagaccgcg acctacagct cggcggcctg    120

cgtaatgtgg gcaaaacgaa gtcttctgac agccggagct caagtgccta cgcgagcagg    180

caccaagcgg ctgagcaacg ccgccgaact cgaatcaatg agaggctgga gctcctgcgc    240

aagctggtgc cgcatgcgga gcgcgccaac acggcgtgct ttctggagga ggtcatcaag    300

tacatcgagg cgctgaaggc gcgcacactg gatctagagt cgcaggtgga ggccctgacg    360

ggcaagccgg tgcccaagtc gctggcgctg cccaccggca tgccgtcggt gctggccgga    420

ggctccacca gcgcggacaa caccaacgcc agcccgcgca tggttggcgc agcgacatcg    480

tcgcagggcg ggcccgcggg ctcgctgcca tcggggcagc cgggcgccgg cggggcgggc    540

gcgggctccc tagccagccc ctccaccacg ccgcccccta ccatgaccgc gcagcaggcc    600

tcccagcagc tctcgctcat gcagtcgggc gggcaggcgg gcggctcgca gggcctgccg    660

tcacagctga cgctgcccag tggcggcgcc ggcgcggggc tgctctcggc ggcgcagcag    720

agcctgctgg gtttccccca gtcgggcggc ctgtccctct caggcgccgg cctgtcactg    780

ggcggcagcg gcctgggcca cggcaccagc ggcatcagcc tgacccagtt cgccggcaac    840

ctgcaggcgg ccgccgcggc cgccgccgcg gcgtcgcacg gcgccggcag ccagtcccac    900

tcgcagtcgc agtcgcagca ctccggcctc agcctgggct cgcaccacgt caccgcgtcg    960

cagctgaacg aactgcaggc catgcaaatg atgcagtcgc tgcagcagca ccacaaccag   1020

cacgcggcgg ccgccgcggt ggtcgcggcc gcgggtggcg gcggcggttc ccgcccggga   1080

tccacgttcc accccaccaa caacaaggcg ttcctgcact tcaacgagga cgcctacgcc   1140
```

```
ttcagcggca agcccgagct gtcgctaccc gcgcgcagcc tgctgggtgc agccgcggcc   1200

tccgccgcca cgcccagcac gtctctccag ctgaccaccg tgcagctgcc cgcggactcg   1260

aacacgctgc tccaggtgga gatggcgcgc aaggccgcgt cgggctctcc cgtgtccagc   1320

gaggagagcg gcgtgccgct gaagaagcgc aaagtgctgg tgctgtaa                 1368
```

<210> SEQ ID NO 90
<211> LENGTH: 1233
<212> TYPE: DNA
<213> ORGANISM: Chlamydomonas reinhardtii

<400> SEQUENCE: 90

```
atgtcgagtt gcgtcgtgtg cgcggccgca gcggtcgttt ggtgccagaa tgacaaggcg     60

ctgctttgca aggactgcga tgtgcgcatc cacaccagca acgcggtcgc tgcgcgccat    120

acccgcttcg tgccctgcca gggctgcaac aaggccggtg ctgcgctcta ctgcaagtgc    180

gacgccgcgc acatgtgcga ggcttgccac agctccaacc ccctagctgc tacgcacgag    240

accgagccgg tggcgccgct gccgtcagtc gagcagggcg ctgcaccgga gcctcaggtc    300

ctgaacatgc cctgcgagtc tgtggcgcag tctgcggcca gccccgcggc ttggtttgtg    360

gacgacgaga agatgggcac gaccagcttc tttgatgcgc ctgcggtgct gtcgccctcg    420

ggcagcgagg ccgtggtgcc cgtcatgtcc gcccctatcg aggacgagtt tgcattcgcg    480

gccgccccgg cgacgttcaa ggaaatcaag gacaagctcg agttcgaggc tctggacctg    540

gacaacaact ggctcgacat gggcttcgat ttcactgata tcctgtccga cggcccctct    600

gatgtgggcc tggtccccac cttcgatgcc gtcgatgagg ccgcggatgc cgtggctgac    660

gctatcgtgc ccaccttcga ggaggagcag ccccagttac agcagcagga gcccctggtg    720

ctggctcccg ccccggagga gtcggctgct agccgcaagc gcgctgccgc cgaggaggcc    780

gcggaggagc cggccgccaa ggtgccggcc ctgactcacc aggcgctgct gcaggcgcag    840

gccgccgcct tccaggccgt gccccaggcg tcagcgctgt tcttccagcc gcagatgctg    900

gccgcgctgc cgcacctgcc gctgctgcag cagcccatga tgccggcagc cgtcgccccg    960

gcgcccgtgc ccaagagcgg cagcgccgcc gccagcgcgg ccctcgccgc cggtgccaac   1020

ctgactcgcg agcagcgcgt ggcgcgctac cgcgagaagc ggaagaaccg ctctttcgcc   1080

aagaccatcc gctacgcttc ccgcaaggcg tatgcggaga tccgcccccg cattaagggc   1140

cgcttcgcca agaaggagga gattgaggcc tggaaggcgg cgcacggcgg cgacgacgcc   1200

attgttcccg aggtcctgga cgctgagtgc taa                                1233
```

<210> SEQ ID NO 91
<211> LENGTH: 822
<212> TYPE: DNA
<213> ORGANISM: Chlamydomonas reinhardtii

<400> SEQUENCE: 91

```
atggccgagc acttggctag catcttcggc acggagaagg accgcgtgaa ctgcccgttc     60

tacttcaaga ttggagcgtg ccgccatggc gatcgctgct cgcgcctgca caaccggccg    120

acgattagcc cgaccattct aatggcgaac atgtaccaga atccgctttt gaacgctccg    180

ctggggccgg acgggctgcc cattcgggtg gatcccaggg ctgctcagga acacttcgag    240

gacttctatg aggacgtgtt tgaggagctg gcggcgcacg gtgaactgga gaacctgaac    300

gtgtgcgata acttcgctga ccatatggtc gggaacgtgt acgccaagtt ccgggacgag    360
```

-continued

```
gacgcggctg cacgcgcgct gacggcgctg cagggccgct actacgacgg gcggcccatc    420

atcgtggaat tcagccccgt gactgacttc cgtgaggcca cgtgccgcca gtacgaggaa    480

aacacgtgca accgcggcgg ctactgcaac ttcatgcacc tgaagcccat cagccgggag    540

ctgcgcaaga agctgtttgg gaggtacaag cgccgggagc gcagccgcag cccacggcgc    600

gaccgcggcg accgcgggga ccgcggcgat cggcgcgagc gggaccgtga ctgggaccgt    660

ggcgaccggg accgcgggcg gggtcgcagc cgcagccgca gccgcgagcg ggggggtggc    720

gaccggcgcc gcgagacgtc ggaggagcgc cgcgcaaaga ttgcagcatg gaacacagag    780

cgtgacggaa gtgctggtgg cggcggcggt ggtgggtggt ga                        822
```

<210> SEQ ID NO 92
<211> LENGTH: 621
<212> TYPE: DNA
<213> ORGANISM: Chlamydomonas reinhardtii

<400> SEQUENCE: 92

```
atgctgcgct acgctgctct ccgcactgtc ccgcgcgcca tcgcgcccgc ccgccgggcc     60

atggtgattc ggtctttctc ggaaagcaac gatgccgcgc ccccggctaa gaaggcaacc    120

aagcccgcca aggcggagaa ggcgccgaag gcggagaagg cgccgaaggt ggagaagccg    180

aaggcgatgc gcgcgccaag cgcttacaac ctgttctata aggcgatctt ccagcaagtg    240

cgcagcgaga accccgacaa gaaggttact gagctcgggt caaaggtccg cgacaagtgg    300

gcttccattt cggcactgga gcgggcgccg tatgaggcgc aggctgccgc gcgcaagaag    360

gaagtggatg ccaagagggc tgaggtgctg gctgccaaga aggccgccgc ccggcccgtg    420

accgcctaca tcgcgttcgc caatgccaag cgtcccgaga tcaaggcgca gaaccctgac    480

aagaccatgg cgcaggtggc gagcctgctg ggtccattt ggaaggggat gtcggaggag    540

cagcagaagc cgtaccgtga ccaggccaag gcggcgatgg acgcgtggaa ggccaagcag    600

caggcgcagc agtccgcgta a                                               621
```

<210> SEQ ID NO 93
<211> LENGTH: 1032
<212> TYPE: DNA
<213> ORGANISM: Chlamydomonas reinhardtii

<400> SEQUENCE: 93

```
atggagacgc tgtggccggc tccatacgcc ctaccgctcc agtctgcggc gatggcgctg     60

tccgaacagc agcttggcca acacattgat tctggcagcg aggaggacca catcgcggtc    120

gtggcgcagg tccagactgg caagaagcga cgcagtgtga gcgcggaaga ggacccagac    180

tatgaggacg ccgcgcaagg cgcgcaaggc ataacgcatg atggtacatc aaacaaggcc    240

ggctaccgag gcgtacggcg ccggccatgg ggctcctacg ccgccgagat tcgggacgca    300

ggctgcggca agcgccggtg gattggcacg ttcaagactg ctgaggaggc tgcacgggcg    360

tacgatgagg ccgccattgc gctgcatggg cctcgcgcca agaccaactt cacctacccc    420

tgccagcagc agagcgccgc cgccgcgcca gccgccgcac acaaggccca caagccgcac    480

gccgccgccg cgccgcagca ccacaagccg gcgcaccaca gccagcaacc tgctcagccg    540

cgcaagcagc cgctgcaccc ccggcagccg taccagcagc accagccccc ccagctgccg    600

acgcatcagg aggaggagca gtaccggcgc aagtcggacg actcagacac ctctatgacc    660

gctgcgctgc cgctgccgct gtcgctgacg gggcagctgg gcctgccgcc gctgacgctg    720

ccggggcttg agggtctgga cctgatggcg ctgcagtcca accccgcgct gctagccgcg    780
```

```
ctgctcgccg ccacgcggca gcacctcccg gggttggccg ggccggatgc gcagcccgcc    840

tgcctgccgg agcagcagct gtcggagcgg gtctgggtcc aggagcagcc ggtgcagggg    900

tgcgaggagg aggaggacgg gttggaggag ccggagccgc cgcaggtgct gcggccggag    960

cagcttcggt cgctgcaggt gctggcggag gtggcgcacc tgttcgggcg ccgcgacttc   1020

tgcatgtcgt ga                                                       1032
```

<210> SEQ ID NO 94
<211> LENGTH: 2034
<212> TYPE: DNA
<213> ORGANISM: Chlamydomonas reinhardtii

<400> SEQUENCE: 94

```
atgaaggtta ttatcgccgg cgcgggcatc ggcggcctgg tgctagccgt tgcacttctg     60

aagcagggct tccaggttca ggtctttgag cgcgacctga cggccatccg cggcgagggc    120

aagtaccgtg gacccatcca ggttcaaagc aatgcgctcg ctgcgctgga ggctatcgat    180

cccgaggtgg ccgcggaggt gctgcgcgag ggctgcatca ctggcgaccg tatcaacggg    240

ctctgcgacg gcctgactgg cgagtggtac gtcaagttcg acacgttcca cccggcggtc    300

agcaagggcc tgccggtgac ccgcgtcatc agccgcctca cgctgcagca gatcctggcc    360

aaagccgtgg agcgctacgg cggccccggc accatccaga acggctgcaa cgtgaccgag    420

ttcacggagc gccgcaacga caccaccggc aacaacgagg tgactgtgca gctggaggac    480

gggcgcacgt ttgcggccga cgtgctggtg ggcgccgacg gcatctggtc caagatccgt    540

aagcagctca ttggcgagac caaggccaac tacagcgggt acacctgcta caccggcatc    600

tcggacttta cgccggcgga cattgacatt gtgggctacc gcgtgttcct gggcaacggc    660

cagtactttg tcagcagcga cgtgggcaac ggcaagatgc agtggtacgg cttccacaag    720

gagccgtctg gcggcaccga ccccgagggc agccgcaagg cgcgcctgct gcagatcttt    780

ggccactgga acgacaacgt ggtggacctg atcaaggcca cgcccgagga ggacgtgctg    840

cgccgcgaca tctttgacag gccgcccatc ttcacctgga gcaagggccg cgtggccctg    900

ctgggcgaca gcgcgcacgc catgcagccc aacctgggcc agggcggctg catggccatt    960

gaggacgcct acgagctggc catcgacctc agccgcgccg tgtccgacaa ggccggaaac   1020

gcggcggcgg tggacgtgga gggcgtgctg cgcagctacc aggacagccg catttgcgc    1080

gtcagcgcca ttcacggcat ggcgggcatg gctgccttca tggccagcac ctacaagtgc   1140

tacctgggcg agggctggag caagtgggtt gaggggctgc gcatcccgca ccccggccgc   1200

gtggtggggc ggctggtgat gctgctcacc atgcccagcg tgctggagtg ggtgctgggc   1260

ggcaacaccg accacgtggc gccgcaccgc accagctact gctcgctggg cgacaagccc   1320

aaggctttcc ccgagagccg cttccccgag ttcatgaaca acgacgcctc catcatccgc   1380

tcctcccacg ccgactggct gctggtggcg gagcgcgacg ccgccacggc cgccgccgcc   1440

aacgtgaacg ccgccaccgg cagcagcgcc gccgcggccg ccgccgccga cgtgaacagc   1500

agctgccagt gcaagggcat ctacatggcg gactcggcgg ccctggtggg ccgctgcggc   1560

gccacctcgc gccccgcgct ggccgtggac gacgtgcacg tcgccgagag tcacgcgcag   1620

gtctggcgcg gcctcgccgg cctccccccc tcctcgtcgt ccgcctccac cgccgccgcc   1680

tctgcgtccg ccgcctcctc tgccgccagc ggcaccgcca gcaccctggg cagctcggag   1740

ggctactggc tccgcgacct gggcagcggc cgcggcacct gggtcaacgg caagcgcctg   1800
```

cccgacggcg ccacggtgca gctgtggccc ggcgacgcgg tggagttcgg ccggcacccc 1860
agccacgagg tgttcaaggt gaagatgcag cacgtgacgc tgcgcagcga cgagctcagc 1920
ggccaggcct acaccacgct catggtgggc aagatccgga acaacgacta cgtcatgccc 1980
gagtcgcggc cggacggcgg cagccagcag ccgggccgcc tggtgacggc ttaa 2034

<210> SEQ ID NO 95
<211> LENGTH: 1731
<212> TYPE: DNA
<213> ORGANISM: Chlamydomonas reinhardtii

<400> SEQUENCE: 95
atggctcgac aacagcagca tcagcagcaa gcctctgacc agcagcagac cggcgctcga 60
gcgaacggcc ggcgagcttg tcggcgcggc agcgacgagc ccgcagagga ggtgaacgcc 120
atggacagcc cctcctcctc accagcaggt gccgggaagg tgagccagcg cggccgcaag 180
gccgcagcgg cctccggcgc cgcggcgacc aagcgcggca ccagcgcatc cggagccggc 240
tcagggccgg acgagggtgg cgcccccggc aacaacggca gcggcagctt cgcgctgccc 300
ctgtctaccg gcggcggcgc acgcagccgg caccggcgca gccccagtga cctcagcgag 360
ccctcggcca gcggcctgcc gggcgcactg ccactgccgc tgcccctagt ggccgacaag 420
ccgctgagcg agttcgtggg ccagacccgc gccaacgcgc tggacccggc gcagctggac 480
cccaagcgcg cgcgccgcat catcgccaac cggcagtcgg cgcaccgcag ccgcatgaag 540
aagctgcagc tcatccacga gctggagcag cgggtgacga ccgcgcgcgc cgccacggac 600
gcggtgcggc agcagaacgt cgcggcggcg gagcggcggc gcgagctgct cacggcggcg 660
gcgacggcgc agcagcagct ggcggagctg cggcgcgagg cggcggctgt ggcggccatg 720
cacagcgccc tggcggcgga gctcgccaag ataggcatcg cggggccgcc gccagcgccc 780
gcggcagcag agccggcggc ggcgcccgcc gacggcatgg aggttgggct gcgtggctcg 840
agcggcggtg cggtggcgcc cgcgacgccg cctaatggct cggaggtggg cgccgagctg 900
cacggccgca tgtcagtcaa cggggccgcc acccgcgccg ccggcggccc gtcggcttcc 960
ggcagctccg gcacatcggc gtccatgggt caggctgggg ctgcgggctc ccagcctggc 1020
ggcgcggcgg tgcctgagag ccccttcctc ctgccgcacc tgccgccgcc gcacatcatg 1080
tccgctcaca ccgccgccgc ggctggcagt ggcggtggcg gcggctcgtt ttcaaaccac 1140
caccatcacc accacagcca cagtcacagt gggagcggca gcgctatgcc gctgctgtcc 1200
gctcccggtg ccgcctccta cacctttggg cagcagcaca acccagccca ccagcagcag 1260
caccagcagc agcccgcgcc gttcctgcaa ggtgccctgc cgcagcacac gcagctggcg 1320
caccccgcgc cctcgcacag ccgcaacccc tccgccagca gcctggccgg cccggcgcct 1380
tcgcaaccca gcgccgccgt ggaggctgcg gctgccttcc agcaggcgcc cacagccgct 1440
gacgtcacgc cggagccggg cgccaggcag gatggcggcg gcggcggtgg cggcgaagtg 1500
gctcacggca gttcgcccat ggccctggac gggtttggcc tggcagggct gatggggctg 1560
ggcatgggca acgacggcct ggcaggaggc ggcggcatcg gaggaggcgg aggcgagggg 1620
gaggcggggg cggtggggga cagtgacacg gacgtgggcg acttcttgtt gatgggcatg 1680
ggagacggcg atggggacga cacggcgccc acggacgggg cgggattgtg a 1731

<210> SEQ ID NO 96
<211> LENGTH: 1194
<212> TYPE: DNA
<213> ORGANISM: Chlamydomonas reinhardtii

<400> SEQUENCE: 96
atggcccccg ccccagcttt cgagccgtcc tgctccatgc tgtccgtctt cagcatgtgc 60
accgcgctac cgctggcgga gcgtgacgtg aacggcgccg gcgcctgctt ctcaggagcc 120
tccgcgctgg cgtgcccctc caaaccggct tcgatacgcc gtggggcgtc gttcctcgat 180
gtggaggatg cctgtgtggg cctgactagc gccgaccgtg cctgcttcct catacctgag 240
gacagcgtgt atgtgtcgcc cgcctgctcc gctcgcgaga acgccggcgc cggcccccgc 300
ctgccgctgc ccagcggcac cttcaccacc gccgtcgcca cctcgacgag cggtgccagc 360
ctcagcggcc tctccgctgc gcccaccggc tttctggcgg gctgcgagga gtttgtccat 420
gcgtccgtgt gctttgagaa ggcagcccag gcgctggagg ccgtcacccg cccgccgccc 480
gcggttccct cgtgtagccc tagcacgagc tccggtgccg cgaacggcgc gcaggccgac 540
gagcccgctg ccggtctctt ccggcgcgtg agctctctgg cgccctcccc cgctgccagc 600
agccatgaga accaccagca ccagcaccag gacggctcct gttgctcttc ggcggaggcg 660
gtggaggcgc cggcggcgcc cgtcgtgtcg gacggtgcgg cggcctgtgc ggagcagctt 720
ccccagcagg tattgctgcc ccaggtgcct ctggagcacc accggcatga atacctggac 780
gcgtcgagcg cagcgctgca gctgcaggct cagctgccca cgatgctcga ggagcagcag 840
cagcaatcgc cggaggaggc ggctcagcct gagcagttgc agctgctgca ggcggtcccg 900
gccccggctc cggctccccg ggccttccac cacaagactg gtggcccctg tgatcactgc 960
ggcgccacgg agtcgccgca gtggcgccgc ggcccgcccg ccaagcccat gctgtgcaac 1020
gcctgcggca cccgataccg ccgcactaac cagctcggcc ctgtgggcgc acacacgccg 1080
gcgggccgtg ctgcagccgc ggcagcagct gcgggcgcgt ccgtgtctgg cggcaagcgc 1140
atcagcaagg gacacggcgg cgccgcggcc aaacgcaacc gtgcgagcta ctga 1194

<210> SEQ ID NO 97
<211> LENGTH: 696
<212> TYPE: DNA
<213> ORGANISM: Chlamydomonas reinhardtii

<400> SEQUENCE: 97
atggctccca cggcatatat gctcttctgc aatcagcata gagaatccgt gcgccagcgg 60
ctagcagcag agggccagga gaagatagcg gtgacggtcg tggccaagga gctgggccaa 120
atatggaaag ctcttaccga ggaggaaaag gccaagtacc gggcgcaagc agaggagcag 180
aagcagcagc aacagcagca acaagcgggc gacgggagcg agacgcaagg cgaggggaac 240
gcggaggggg gccagagggc tggcagcccc gccaaggctg ccgctgctgc ttcgctaccg 300
gcgtcctggg tgcgcaaagt ggtcaacctg gaccctgaaa tccagcgctg ctccgctgag 360
ggcgtgctgg cgctgtcggc ggccgcggag gtgttcctgt ccgccgtgtg cgccaaggcc 420
acggcggcgg cggcggcagg caagcggcgc acggtgcgcc tggatgacat ggagaagtgc 480
attcggggcg acaagcggct catggccgcg ggcttcaccg ccgtcatcaa catggtgtcg 540
gctgcagcgg ccacagaggc ggagggcaag gctgctgcgg tggctgcagc gggcgcgccg 600
ccgggaaaaa agcaaaaggt ggacaaggcc gccgcaccgg cggcaggggc ggataagcac 660
aacagcattg agaaggcgtt tggtatggcg tcatga 696

<210> SEQ ID NO 98
<211> LENGTH: 633
<212> TYPE: DNA

<213> ORGANISM: Chlamydomonas reinhardtii

<400> SEQUENCE: 98
atgcgaggct ccactggcgg cccctgctgc cactgcggca ccgtcgcgac tccctgctgg 60
cgaaaggggc cctgcgacaa gccggtgctc tgcaatgcgt gcggcagccg gtacctggtc 120
aagggctcac tcgctgggta cttccctggc gcgcgccggg cgagtgcggg cacccgtagc 180
gaggcgcctc agattcaggc gaccgtcgtt tccgcggccg gcaagtctgc tgcgcggaaa 240
tccgccgcgc tgtcgtcagt agccgcatct gctggtgcca agcgcaaggt gcaagagctg 300
gacgggaacg aaaccggtgc caagcgcatc ttcaacaact acgaggccct ggaggagctg 360
cgcgcgttct ttgccagcag ccgagggccg caggcgccag cccagacctc ggactctcag 420
gactcgcaag gccaattccg ggacgaggcg cagtacctag acgcgagctc cgacgatggc 480
ctggagcacc ccgactcgga gccggtggcg gctttgcgcc acatgcgtgc ccccctcaac 540
gccaccacgg cggcaaacta ctcggcaccg cacgtgccga ctttccagcg gcggccgcgc 600
aagcagctgc acccggtgcc gtgctcctgc taa 633

<210> SEQ ID NO 99
<211> LENGTH: 837
<212> TYPE: DNA
<213> ORGANISM: Chlamydomonas reinhardtii

<400> SEQUENCE: 99
atggaggcac aaatagagaa gcctgaggca gatgcggagc tgccgcgagc gctaattcgg 60
cgaattgtca agtctaaact cgcactcctc gcgggcgacg atgcaaagga attcagtgtg 120
aataaggacg ctcttacagc acttgcagag tgcaccaaag tcttcataag ctgcttggca 180
tcgacttcca atgacatttg ccaggagaag cggcggtcaa ccgtgaacgc tgacgacgtg 240
ctcacggcgc tgcacgacct ggatttccca gagctcgtgg ggcccctgcg ggagcagctt 300
gaagccttca aggaggcagc aaaggagcgc aacaagaacc ggcagcaggc cggcggcaac 360
aagaagcgca agagcggcgc cgcagccgac gagccgcccc cagtggcgcc gcgcagctct 420
ctgcaggcgg cgccagcgga ggccgcgccg gaggctgagg acggcagcgg cggcgcgggc 480
cccagccatg ccgacgacga cgacgacggc gcactggtgc cggggaccgg catgggcatt 540
ggcggcgccg gcggctttgg cgaggacggg cttggaggca tcgggctggg tgtgggcatg 600
ggcgtgggcg tgggattaga cgcgccgggg ctggcgctgt ctcctggcgg cctggcgatg 660
ggcggcgcgg aggccggcgc ggtggcggcg gcggatgtgg cggcgcaccc gcagcagcag 720
gaagcggcag gtgctgctgc gcaacagcag cagcgagcag tggaggaagt ggcgccggag 780
gcggtggtgg aggaggaggt gcaagtggag gacatgttgg tcgacgcgct gccgtga 837

<210> SEQ ID NO 100
<211> LENGTH: 534
<212> TYPE: DNA
<213> ORGANISM: Chlamydomonas reinhardtii

<400> SEQUENCE: 100
atggacggcg ccttccccaa tcgtcggggg gacggatacg ggggcagcca gggtgatggc 60
gagggccagg gagggaagcc tcgcggcttc aggggcaccg cggagaatgc caagaccaag 120
gtctgcacta ggtggctgca gggcgattgc cgctttggcg cgcgctgcaa ctttgcccat 180
ggcgagcacg agctgcggaa gctgcccgag cgtcagggcg ggcgcggtgg tggtggccgg 240
ggctatggag gcaatgctgg tccctacggt ggccggggcg gctacggcgg tggtggctac 300
ggcggccagc ccggcatgcc cggcggctac ggcggcggcc agggcggcgc gcccggcccc 360
aacgtgtcgg aggacgtgtg ggcggcgcag ggctacccgg tgcagggccc taacggttgg 420
gtgcagtacc gcacccgcga caccggggag ccctacttcc acaaccaccg gacaaacgag 480
acggtgtggg accggcccgc ggactggccg gtcacgatgc agggccagat ctga 534

<210> SEQ ID NO 101
<211> LENGTH: 768
<212> TYPE: DNA
<213> ORGANISM: Chlamydomonas reinhardtii

<400> SEQUENCE: 101
atgctgttca atccacctga gtgggccagc caaccctgta gaatcgcgag ccttgaggtt 60
tattccggca accgacggat tgttgttcat cctgtggaca tcgagcccta ttacacgttc 120
ggacggcaag ctgagtcggt gtcaattgca ctcgagcacc attcgtgtag ccgcgtgcac 180
gctgctctcg tccaccacaa cgacggtcgc atcttcttaa tcgacctcca gtcgacacaa 240
ggcacgactg ttgacggccg ccgcatcgca cccaacaagc cggtagtgct taaagacaac 300
acgcgcattc gcttcggcga gctagagtac gactacgttc ttcgctgcga gtctgcagcc 360
gagaagcgct ccgccgccgg tgaccccgac gccgcccacg cgcagccgca caagcgcgcc 420
gccatggccg acgcccgcgt ccgcgcctcc cacctgctgg tcaaacacaa ggacgtgcgc 480
cgccccagct cctggaagga gcccgtggtg acccgcaccc gggaggaggc gctggccatg 540
atcgagcact tccactccat gctggtcaag ggcgaggtgg agttcgcggc gctggccgca 600
caggagagcc actgcagcag cgccaagcgc ggcggggacc tgggggagtt cggtcgcggc 660
gagatgcaga agccgttcga ggacgccacc tacgccctca aggtgggcga gctgagcggc 720
cccgtgttca gcgactcggg cgtgcacctc atcctgcgca caggctga 768

<210> SEQ ID NO 102
<211> LENGTH: 1437
<212> TYPE: DNA
<213> ORGANISM: Chlamydomonas reinhardtii

<400> SEQUENCE: 102
atgtccggcg acagcagcgc cggcgagcgc cgtaggcgat atccactggc taacataaag 60
ggcggctggt ctgcggtgga ggacacaaca ctgaagaggc ttgtggagga gtttggtgag 120
ggcaactgga gcgtcatcgc ccgtcacctt aacgcatcgc tgggcaagcc ctcggactcg 180
ggccgcatcg gcaagcagtg ccgcgagcgc tacaaccacc accttcggcc agacatcaag 240
aaggatgcct ggactgagga ggaggagtcg ctgctagtgg cggcacacct gcgctacggc 300
aaccgctgga gtgacatcgc caaggtcatt cgcggccgta ccgagaacgc agtgaagaac 360
cactggaacg caaccctgag gcgcaaggac ggcgacaagg ccatccgcag cggtaccgca 420
ccgcaatcgt gcgtgcttaa gaactacatg atccgcctgc acctgctgcc cgggccacca 480
gtcggcccga ccgccgccac gacggcactg cctgacaacg cggcggctgc cgttgcaccg 540
ctccccgcca agcccgtcgc caagcgcgcc cggtcctcgg tggcggctga gtctcccaag 600
gtcgctggtg gcgtccaccc agcggacccg gcgcagcccg gcccatcgcc ctcctcctcc 660
accagcactc acgacggcgt cagctccagc ccgcaccgca gctttgatgc cagcgtggcg 720
tcgccggccg gcggggcagc cgccaaccgc aagcggccgc gcatcatcac ttttgccgcc 780
gcgcccgacc cggcggccgc tatcgcagcc tccaccctgt cgcgtcacgc ttcgccggcg 840
cccctggctg caatgcccat gcaggacggc atgcccatgc ccctcttcgc gccgctgtcg 900
ctcctggccg tgcccaactt aaccggccag gtgacagccg cgcccacggc gcccgtggcg 960
atgcggatgc agttccagat gcagcagcag caacagcaag acatgcaccc gcagatgcag 1020
cagcaggtgg ccatgcagcc gtccgcgccg gccatgcgtc gccccagccc gcgtccgcag 1080
ccggtgcagc agcagcagca gcagcagcag atgcgcggca gcagccagcc gcgcacgtcg 1140
cagccaccgc agcgcggctc ggcgccgctg ggctgggcgt ccgacagcgc cgaggacagc 1200
ctgtacggca gccccgtgtc tgacaggttt gtggacatgc agtttgagga ggactacctg 1260
tgcagccacg gtgccggggg ccagaaggcg gcagcgatcg cagcccggc ctcctataag 1320 gcagctgatg agacgcaagg gcaggagcta cagctgcagt tggcgggcgt gggcagcagc 1380
gaggtgcagg cggcgcagat catgctcgcc ctgcggagcc tggcgggcgg cctgtga 1437

<210> SEQ ID NO 103
<211> LENGTH: 1227
<212> TYPE: DNA
<213> ORGANISM: Chlamydomonas reinhardtii

<400> SEQUENCE: 103
atggcgccga aggcagcccc caaagtagac aaggcgaaag cggctgccaa acagaaggcc 60
gctgaggaca agactttcgg ccttaaaaat aagaacaagt cggccaaggt gcaaaagtat 120
gtgcaaaacg tcaagacgaa cgcgacgcag aaccttggcg cctacaagcc cgtggaggcg 180
aagaagaagg acaaggctcc ggatgagctg ggcaacattt ttctgccgac cattaagcag 240
ccaaaggtgc cggacggcgt ggaccccaag tccatcgtgt gcgagttctt ccgccacaac 300
cagtgcacca agggcaacaa gtgcaagttc agccacgacc tgtcggtgga gcgcaagggc 360
cccaagatct cgctgtacgc cgaccagcgc gacctgggca aggacggcga ggacaaggag 420
ggcatggagg actgggacca ggccacgctg gaggcggcgg tgaagcagaa gcacgccaac 480
gagaacaagc ccacggacat catctgcaaa ttcttcctgg aggccgtgga gaagaagctg 540
tatggatggt tctggaagtg ccccaacggc gaggactgca agtaccggca cgcgctgccg 600
cacaactacg tgctcaagag ccagatgaag gagctgctag aggaggaggc gcgcaacacc 660
aaggacattg cggagtccat tgaggaggag cgcgccaagg tggtggcgcg cacgcccatc 720
acccaggaga cgttcagtgc ctggcaccgg gcgaagcgcg aggccaaggc ggccaagcgg 780
gcgacggacg aggaggagcg gcgcaagaag ggcatcctca acggccgcga gatcttcatg 840
caggagggct tcgtggccaa cgacgacgcc agcgcggcgg acgagtacgg cttcgaggtg 900
gacgaggagg aggaaatcaa ggccatgatc gagcgcgcgg cggcggcggc ggaggcggcc 960
aggcagcagg cggagctggg gccagtgccg gaggaggcgg aggaggcgaa cgagggcgcg 1020
gggccatccg gcagcggcgc cgggccatcc acacacctca acctagaaga cgaggaggcg 1080
caggagctgt tcgatgacga tgatgacgac gacgaggaaa tggaggacga cgaggaaatg 1140
gacgacgacg acgacgacga cgacgagctg gaggggctgg aggaccacgt gaaggggatg 1200
cacgtgggcg gggcagcagg gcaatga 1227

<210> SEQ ID NO 104
<211> LENGTH: 1368
<212> TYPE: DNA
<213> ORGANISM: Chlamydomonas reinhardtii

<400> SEQUENCE: 104
atgagcggcg agccctcgcc cctcgaggag caaccggacc tagataactc tgaggaccta 60
cacaacagct ctgacgctgc gaacgccagc agccggaagg gtcagccatg gagcgaggag 120
gagcacaggg cgttcttggc aggcctgaag tcactcggca aaggtagctg gcgacaaatt 180
agccagcagt tcgtgccgac gcggacccct acgcaggtgg ccagccacgc acaaaagcac 240
tttatgcgtg tagccggtgc taccaagcgg aagagccgct tcacggcgct cgagaccgag 300
gttctgccgc ccgccaagat tgctcatgtt gattcgaggc agcacggttc ggagcagacg 360
gagcagctgg agccgcagcc ccaggcgcag gcgcgacagc cggcgatggc cccgcaggcg 420
cagcaggcag gcgcacccgc ggcctcgcag tttgggccga tggccgcctt tgggcctatg 480
gctgcgttcc cgttcatgaa ccccatgatg ttcggcttcc cggcgccctt cttcccgccc 540
ttcatgtgcc cgccccccgc cttcgcggcc gcggcgatgc agagcatgaa cgcgatgcag 600
aagtctggta tggctcccgg catgatgatg ccgccgctgt tcgcgcccat gatggccgcc 660
atggccgcag cctccacgcc cttcttcatg gcgcagcaaa tgcaggccat ggcggcgcag 720
gcggcggcag cgcagcagca ggcggcgcag gccgcagcgg cacagcagca gcagcagtac 780
gcagcgacgc aggcggccac cagcggcgcc gccaccacgg ccggcaccgc caccgccaca 840
tccgacacag ccaacagcga tgacgcggtg cggcgccgcc acgcctccgt cgccgcgccc 900
agcgttggca acaatgccgg cttgggcggc tcctcgcctg cggtcaaggc cgagcccgtg 960
ttgcacgtgc agatccccgc gcggccgccg tcggcctgcg gcgtcgccgg cagcaccaac 1020
accagcccag gccgtgttgc ggccgcgacg ccggggcctg acgcagtggc ggcgacgggc 1080
ggagagtcgc cggcagcggc acaggccggc gccagcaatg cggcgccgcc gcgggagcag 1140
gcgaagagct gtggcggcgc ccctggcggc gttggtgcca ggtgtagcgg cagcggcgtg 1200
gcggtgcccg cgggcggctg cggcctggag cagcagcagc agccgctgca gcggcgggtg 1260
tcgggtgggc gcggcgagga aggtggtgcg gcgttgccct tccatgcgtc ctcgcactcg 1320
gctttccggc cgccgcaggc gcagcaggag atcaaggccg agagctag 1368

<210> SEQ ID NO 105
<211> LENGTH: 1875
<212> TYPE: DNA
<213> ORGANISM: Chlamydomonas reinhardtii

<400> SEQUENCE: 105
atggtagacg gtggttcgcg tgctgcctct ggccagctgg atgactgggc cgcaggcgtc 60
gcggctgacc tagaccaggg agagggcgac cgcgcagggg cgaggcgacg acctgcgcgc 120
gacgccagcc cggcgccgga tgctcgcaaa gtgacaacgt tcacaaacaa aaagcgcccg 180
gcatcggaca gggacagcag cccggaggag gacgacgagg agcaggctca gaaaggctcc 240
ctcaaagcgg atggaactcg ccccaagctt ccacgccccg acaagaagga ggcatgccct 300
cgctgcaaca gcatggacac caaattctgc tactacaaca attacaacat caagcagccc 360
cgcttttact gcaagacgtg tcagcggtac tggactgccg gcggcacgtt gaggaacatc 420
gctccgggct ccggtcggcg caagagcaag agcaaagccg cgcgtgagaa gaacagcccc 480
tcgctcgccg agcagctcac ggcggttgcg gcgggacagg gcatgttcgg gctcggaggc 540
gggggcgggt acaacggcat cagcccggcg ctggcgctcg ccgcggccac cgatcccaca 600
gggctgctgg ccgcgaatag cgccgcggcg tacggtctgg gtggccacgg aaccatctcc 660
ggcctgaagc tgggcggtgt gggtgggctg ccggcgcagt tcaacagtga gttggcgctg 720
cgggagcacc ttgcagggca gcacagcctg gagacacggc tgctgctgaa cgggcacctc 780
agcgccgagg acctgccgaa cggcatgtcg gcggcggcgc tggcacaggc cagtgcacag 840
ctgcacgctc tgcacgggca gggcagtggc attgcgcagt cgctggcggc cggcaacggg 900
cacacggggt cgccctcgcc ctcacctcct ccggccggga acggcgggca gcagcacccg 960
ctgtcttcct ccccgcagca cggcggcggc tcgcaggcct cgcagcagcc gtctcctcct 1020
cagcagggct cggacgacgc cgagggcggt ggcgaggagc gctatgtggc gcagggccgc 1080
cgcgtgcgcg tgaaggcgga gttggacggc aacgccgtca gcagcagcct cgcaatgggc 1140
ggcggcggtg gctcgggtgc gtacgccaac ggcgctagca ttgcctcctc cattgccaac 1200
gcccagctcg cggccagcct cagcatgccg cccagcatgg gcgcgctggc ggctgtgatg 1260
ggccctggcg gcggccccag cggcctccac ccactgcttg cgcaggacaa tggtggcagc 1320
ctgcttgacg ccggcctgac gcggcagcaa ctgctagtgc tgcaacagca ccaggccatg 1380
cagcaggcgc agcagcagga gagcctccag cagctcagca gcttgcagca gctgcagggc 1440
cttgccgcgc tgcacggcca gcactcggcg gcgggcctgg cggggctgga cccgctgcag 1500
cgcagcgcgc tgctgcactc ggcggccggg ctaggcggcg tgggcgtggg tggctggctg 1560
cagggcggcg gcggagggaa ctcgctcgca gccgctgctg cgctggagtc gcttcaggcg 1620
cagcaccttc tccaggcgca gcaggtgcac ccctcggcgg ccgctgccct catcggtggc 1680
ggtggcagca gcgccgcagc gcagatgttg caggcgcagg ccgccgccgc cgccgcgggt 1740
gggggcggag gctggcaggg cgtggcctca gcagcgaatt ggccgtcggc ctggtcgtcg 1800
tacagcggcc cgtcgtctgg cagctacgcc ggctacgcac tgcaggcggc ggccgcttac 1860
tcgggtgcta ggtga 1875

<210> SEQ ID NO 106
<211> LENGTH: 1725
<212> TYPE: DNA
<213> ORGANISM: Chlamydomonas reinhardtii

<400> SEQUENCE: 106
atggaccaat accagcttgc tcagcttcag cagcggtttc aggaggttaa cctgagcggc 60
ggggttgacc agggcgccat gctcaagtca gcaggtgacc tgctgtcatc cgctgaggcc 120
acaacacagt acagctcatc agagtctagc tctggagccg acaacttgaa ccagctggac 180
agctccagcc tcctggacac aggcatgctc gctacagcgc ggcaaagtga tggcgcgcgc 240
tctaccgggc aaccgtcgca ggagggaaag gcgcagattt gcttcgactt cacaaagggc 300
gtgtgctcac gtggcgacaa gtgcaagtac tcgcacgacc tcgcaaccat cgtgcatttc 360
aacagcaagg agaagggcat ctgctttgac tacctgcgca accagtgcca ccgcggcctc 420
ctgtgccggt tcagccacga cctctcaaac attgcgcaac agtgccaggt gaacaacggt 480
gtagcccgcg gtccggcaca gggcgccaag ccaaacgcca tctgctacga cttcgtcaaa 540
ggcgtctgcc aacgcggcgc ggagtgccgc tacagccacg acctgtccct catcgcgcgc 600
atggcccgcg gcggcagcgc gcagcccaag gctggcgagg tctgctacga ctacctcagg 660
ggccgctgca accgcggcgc cacctgcaag tactcgcaca acatcgcctt cctggcggcg 720
cccggtttcc tgggcaacgc catgtcgtcg gacggtgtgc ccatggctgc gcaggcgccg 780
ggcggccaca tgtcggctgg cggtgcgccg ccgctcggcc ccatgcctgt ccccggcggc 840
ccaggcttca tgggcatggg cggcatgtcc ggcatgggcc cgcgcccccct gcacaccgcg 900 ctgagcgccg accaggccac gctgagccac gtcctggcgg cggcggggcc gggcgccgtc 960
agccagatgc tggcggcaca ggcggcggcg cagcagagca acggcttggc ggccgaggcg 1020
gcggacgggc gccggcgctc caacagcctg aacggcgaca tgggcaacga cacgctcgcc 1080
gtcaacgacc agccgcactg gaacgccaag ggcctggcca tggcacagca cgcggccatc 1140
atgcagcgca tggcgggcat ggcggcggct gctggcatgc agcaggcctt cggcggcggc 1200
atgggccagg gcatgcccgg acgaggcatg ccgccgggcg ctgacgccat gtcccacttg 1260
tacggcaagc cgccgccatc catgggctcc tacggcggcc acgacacaag cgcgggcatg 1320
cggcggccgc cgctgccgcc cggcggcggc agcgtgcccg ccgagtttgc ggccctgctg 1380
gcggccggcg gcatggcgga cagtcatgcg ctgtacgctg agacgatcaa ggcgcagctc 1440
caggcgcagc agggcgcgcg catggtgccc aacctcagcg gtggcggcgc gccgcccatg 1500
atggccgctg cgccgcaacc catccccgga cgcgacagcc agggctacga cgtcgccgcg 1560
gcgcaatacg cgcagcaggg cggctcgcag tctggcggcg gcgcgccatc ctcggacagc 1620
ggcagcctct cgcggagcgc gccgtcggca ggcgccccgg tcaaccccga cctactcccg 1680
atgatcaagg agatttggag caagcccggg cagatagcgg catga 1725

<210> SEQ ID NO 107
<211> LENGTH: 828
<212> TYPE: DNA
<213> ORGANISM: Chlamydomonas reinhardtii

<400> SEQUENCE: 107
atgacaatcc ctgacgagga ggttctcact aagctgcgtg agcttctgaa acacgcagac 60
ctgaatgtca ccaccgaaaa gatgctgcgc aagcagcttg aggagcactt taagcaggac 120
atgacagacc ggaagcccat tattcgagcc gaggttgagc gatatttagc tgagggagca 180
ggggatgagg aagaggagga ggaagaggag gaggacgacg acgacgcgcc ggctcgggga 240
agcggcatgg gctcgtggtt gtcagagccg ctgcaggcct tcctgggggt ggagtcgctg 300
ccccgcacgc aagtagtcaa gcggctgtgg gagtacatca aggccaacaa cctgcaggac 360
cccaaggaca agcgcaaaat cctgctggat gacaagctca agacattgtt cacctcgccg 420
ctcaccatgt tcaccatgaa ttcgcagctg agcaaacacg tcaaggtgta tgacggggac 480
gatgaggagc ccaaggccaa gtcagccaag cggccagcga gcaaagcggg caaggagaag 540
cccaagaagg tcaagaccga gatggatgag gagaagcgga agaagaacgc gttcaccaag 600
cccgtgcggc tgtccccgga gctggcggcg ctgacgggca aggagtccat ggggcggccg 660
gaggtgacgt cgttcttctg ggcgtacgtc aaggagaagg gcctcaagga tcccgcgaac 720
ggccagttca ttatctgcga cgcggcgctc aagaagatca caggcgagga gcgcttcaag 780
gggtttggct tcatgaagta cttcgcgccg cacatgctca aggactga 828

<210> SEQ ID NO 108
<211> LENGTH: 1242
<212> TYPE: DNA
<213> ORGANISM: Chlamydomonas reinhardtii

<400> SEQUENCE: 108
atggcgacca acctgtgcgc cgagtgcggc ataaagctgt cgcggcccga gtatcagaag 60
cacatgcagg aggtgcacgg cgtctccatc cagcacgaca gcgacgacga gcgcgataag 120
gaggccccgg ccgccggcga ggacggcgcc gatgccaagc cgcagcgcca gcgccgccgt 180

```
ggcggcaaca aggagggcgc cgccgagggc gcggagggtg ccgaggaggg cgccgccggc    240

gaggacggcg cccggcctcc gcgcgagcgt cggcgccgcg gtgggcgcaa gcccgccggt    300

gagggtgcag atggcgaggc tcccgctggc gacttcgcct gcggcgactg cgaccgcacc    360

ttcgccagcc agcagggcct gaggcgccac ctgcaggcca agcaccctga gtctgaggcg    420

acggccgctg cggtggccgc cgcggcagcc gaggccccgg cggccggcgc gcgccgtggt    480

ggccgcggcc gtggccgcgg caccaaggcc gaggccggtg agggcgccgc ggatggcgcg    540

gcagctgacg gcgcggaggg tgccaagccc gcggcgggtg gtcgcagccg tggccgtggc    600

ggccgcaccg gccgcggccg cggcgccgcc gctgcccccg tgccggacga ccccaccgcc    660

gccgctgcaa tggctgcggc tgcggccaag gcggcgattg gcggcgcggc cgctgagccc    720

gcggcggagc gtcaggtgac gctgttccgc tgcaagcagt gcgagcaggg cttcaagagc    780

cgcaatcgcg cccgcgagca cgttattgag gcacacgccg ccgacgtgcc cgcggaggcc    840

cctgccgagg cgccgggcgt caagccgccg ccgccggagg gcgtggagct gccgccgggc    900

cgccgcgcgc cggcgccggt ggtgcccgtg cccgctgacg ccctgctgga ggtcgcggag    960

gtgaccacca agcgcgcgcc ccgcgcgtcg cgccggcgga agccgcgcac ggccaacggc   1020

gacgagccgt caggcgatgc ggcggagggc gaggagggcg ccgcggaggg cggccgcgcg   1080

cgcggcggtc gccgcggtgg tcgcggcggc gacgccgcgg ctccggctgc cggtggtgac   1140

gcggccgctg cctccggtga tgcgcccgcg cctgctggcg gcgccaagcg cagtggcgcg   1200

cccacggacg agctggcggc tctgggcatc accgcgagct aa                      1242
```

<210> SEQ ID NO 109
<211> LENGTH: 2259
<212> TYPE: DNA
<213> ORGANISM: Chlamydomonas reinhardtii

<400> SEQUENCE: 109

```
atggcgcttc caggctccac aatgaacctt acaacccgct gctctactac accgcggtcg     60

gctgtggttg cgcgcgcggt ggctgcgccc acgcgaccca ccaccaagtc tgcggtgcca    120

gagctgctgg atagccggcc aggcgagcgc aatctcaact tcatggagta tgctcaggcg    180

actcagatgc tggaccggct caagggccag gcctctgacc tggaattgct gctggaccag    240

ctcaacgcgc tggaggccag cctcgacgag agcgttctgg cgccgcccac ggtggacgac    300

cccaaggagc gggctgcgcg acaagcacgg cgcgctgcca agcgtgcaga gcgtagggcc    360

caggcgacat ccgcaacagt cgcggccgcg gctgggccgg caatgtcagc agtggtctcg    420

cattccacgc cgacgaaggc tgctgctgcg ccggccacgt caacagcgag cagcagctcc    480

agcgatagtg gtttgctaga cctggtgagc tttgttggcg gctttgacac gcggccgatc    540

ccggcaacga cgtctgcacc ccctgctggc gccagcagct ccgacgtgca gcacctggag    600

gacctcttca aactcagcgt cggcgagccc gacatccccc gggcctccgc ttcagcagcg    660

cctgcggtgc tgcggccacg caagctcaca ccaaagaagc cctctgcggc accctccgcg    720

gcggtgacgg cagcaccctc gccggcaccc acgctcccca gcacgcccag caccagcgcg    780

cgcattgcgc ccgcgcccgg ctccctcgcg gatgagctgg agcggttact ggggcccacc    840

acgtcacggg aggcggctga gtctgaggac gaggacagct tcgcggggcc gtctgaggac    900

gacctgctgg cgctggagca ggaggtgtcg cgcaagtcgt cacggctgcc tgtgctagac    960

gaggaagacg aggaggatga gcagcagcag ctggaggaca acgaggagga cgcggtggcg   1020

gggcccggct ctttggaggc gtcggcaatg gcgactcgga cgtccagcca gctgtccatc   1080
```

atgcagacgg ggccgtcgct gcttagcctg gtcccagcat ccgcggcgcc aggccgcagc 1140
gccaaggcgc gcgcctcccg gcgcgcggcg cgcaacggtc acgctagcgg gcggctgggt 1200
ggcgcgacag ctaacgcggc ggggcggggc aaggtgggca gcaaggacgg gaccatgaac 1260
ttcctgggca aggtggagtc attgtcaacg ctggacgtgg agaaggaacg cgaggtgacg 1320
gcagtttgcc gcgacttcct gttcctggag aaggtgaagc ggcagtgcga gaagacgctg 1380
caccggcccg ccacgtctga ggagattgcg gcggccgtgg ccatggatgt cgagagcctg 1440
aagctccgct atgacgccgg tctgaaggcc aaggagctgc tgctcaagtc caactacaag 1500
ctggtcatga cggtgtgcaa gtcgtttgtg ggcaagggcc cgcacatcca ggacctggtg 1560
tcggagggcg tcaagggcct gctcaagggc gtggaaaagt acgacgccac caagggcttc 1620
cgcttcggca cgtacgcgca ctggtggatc cgccaggccg tgtcgcgctc gctggcggag 1680
acgggccgcg cagtcaggct gcccatgcac atgatcgagc agctgacgcg gctcaagaac 1740
ctgtccgcca agctgcagac gcagctggcg cgagagccca cgctgcccga gctggccaag 1800
gcggctggtc tgcctgtgac gcgcgttcag atgctcatgg agacggcgcg ctccgccgcg 1860
tccctggaca cgcccatcgg cggcaacgag ctgggcccga ccgtgaagga ctccgtggag 1920
gacgagcgcg aggcggcgga cgaggagttt ggcagcgaca gtctgcgcaa cgacatggag 1980
gcgatgttgt tggagctgcc ggagcgcgag gcgcgcgtgg tgcggctgcg cttcgggctg 2040
gacgacggca aggagtggac gctggaggag attggagagg cgctgaacgt aacacgcgag 2100
cgcatccgtc agattgaggc caaggcgctg cgcaagctgc gtgtgaagac tattgacgtg 2160
agcggcaagc tgatggagta cggcgagaac ctggagatgc tgatggacgg ctcgcgcgag 2220
atggctgcgc gcaccagcag cggcacccgc aagacgtaa 2259

<210> SEQ ID NO 110
<211> LENGTH: 1575
<212> TYPE: DNA
<213> ORGANISM: Chlamydomonas reinhardtii

<400> SEQUENCE: 110
atggacgtgg atggcctgga cctggcggcc cttctggctg aagggccaga ctcgggagtc 60
ggcccgtcgc ttctggacga tgaactgttt tccgaggatc tgatgcagtt cttggaaacg 120
atagagggcc agccgacttc aacgcagtgc caccagaagc tagccgcaca gcaacagcag 180
cagccggtgc cggcgcctgc cccagctcct gctcccgcgg tgcccattcc tgttgcgacc 240
tcctcgcccg cggtcgcgat gtcgcccact gcgtcgacct cgtccggctg ctcttcgggc 300
gtcgtggctg cacctgcgcc cattcctaca ccagtagcgc cagcagctgc ggccgtggcc 360
ctggctgcgc tgcaacaggc gcaaatgcag caattgcagc cggcctgcgc tgccatgctg 420
ccgcgcctgg tcaccacaac agcagcgcag cagatgtgga ctgctatgct tcaagcagcg 480
tgcacagtta cgccggcact ggctgccgct cacgcacctg ctgcggcctc ggtcgatgac 540
gctaaggcgc gcgcccagcc cgctgggacg agccgacaag gaagccgcga ggactccggc 600
gactcctccg acaccgacca agatgatgat atggtggact ccaagggcaa gtccgtgggc 660
aacaagcgca aggcacccga ggtggactgg cggcaaatcg aggacccggc ggagaggcgc 720
cggcaacggc gactggcgaa gaaccgtgtt accgcggcgc ggtcccgcga gcgcaagaag 780
gccgcctgga gcgagcttga ggagcgcctg aagggcatcg agaccgagaa tgcgcagctc 840
cgcgccatgc tggagacctt cgcgcgcgag aacaccgccc tcaaggcgca gctgctcacc 900
gtggcagcag ccggcggcgt gccaggcctg aaccacggcc aggcgggcaa gaccatggac 960
cctgctagcg tcctcccagt atttatagct atcatgctgg tggtctctgc cctcctgcct 1020
ggtgacaagg cctgcgcgct gctcggctcg ctgctgccgc tggcgctgat cgcctcgatg 1080
atgggcgccg ccggctcggg cgctaacgcc aacggcggcg ccgccttcga ctgcctgttc 1140
cgcctaatgc acagcctcag cacgctgcta tccaagagca gtagaacgct gcagcgcagc 1200
ctaaagcgca tgctactggc tcgacagcgt tatctgggcg ccaaaggcat ggccaagctc 1260
ggcaccgccg gcgcgcggct cttcgaccag ctcctgacga cccccttcgcc aacgtcgccg 1320 agtgccgctg aggaccccgg gatagcgcct gggtctcctt cggactcgga cggccgcaac 1380
aacgccgaca tggatgttga cgtggccacc gtgcttgccg cagagccggc cgagcaggcg 1440
ccgccaaccg ccacctgcgc cgctgccgta ttgggcgcta agcccacggc ggaggcgccg 1500
gtggtggcga tggcgggggc cctgcaggcg ggctgcggag gcgtggtggt ggtgaagcag 1560
gagccggtgt gctaa 1575

<210> SEQ ID NO 111
<211> LENGTH: 1920
<212> TYPE: DNA
<213> ORGANISM: Chlamydomonas reinhardtii

<400> SEQUENCE: 111
atggacacca gcattccatt tccgcgacct atcaacgcgc ggggccctgc tccgggccag 60
actccatctc aattgagctc gctgcccccg agccttcaag cgcggctcgg actgggcgcc 120
acgcacgact cgcctgttct gcttccacta ctccagcagg tcgaggcttc tcctacaacc 180
ggcattcatc agctgtgccc gccgctgttc cagccagctc agccggctcg ggtgcccctg 240
ccgattccag cccgaacgga ggcggcctcg gcagcgccag agcccactcg ggccattaaa 300
cgcgagtacg agccccgcgc tggaaatggc aaacagtcag tggccaactc ggacggctgg 360
cagtggcgga agtacggcga gaagctggtg aagggcagcc cgaacccgcg cagctactac 420
aagtgcagcc atccgggctg cctggccaag aagattgttg agcgctccga ctcggacggc 480
acagtgctgt ccacggagta caagggggat cactgccacc cggcgcccag cgccgtcaag 540
gcctcacgct tcaagccgaa gcccaagacg gagccgccgg tcatggttgc accgccagtg 600
ttcagtgccg tcgacatcac ggtgcccaac ggatttccgc cgggcgcgaa cgggcgggtc 660
ggctttccgc tgtctggcgg tgacatgctc cccatcccgg aggcgctgaa gagcgacttc 720
ccagtgccgc acgctgctgg tgcggcggcc gcacacgagg acgacacgga cacaagtgaa 780
ccggagcccg ctgcggcgct gaaggcggcg ccacaggaca ctcgtgctgc gcaggctgcc 840
gccactgcta tccgcaaagt ccgcgacagc gctgaatcgc cgagcaagcg cctcgacatg 900
ctggcagcgt acgctgagga ggcggagcgc cagctcaaat caagcagcaa cagcccggag 960
caaggcccca gcgccaagcg ccagcggaca gaagctgggg ctatgcggac gcgcgccaat 1020
cccgacgatg acgacgatgg cagcggcgca cctagcacgt cgggcatgca gcgtgtggtg 1080
gacatcacca acatggacga tggctacagg tggcgcaaat acggccagaa gcaggtgaag 1140
ggcagtccct tcccccgcgc gtactacaag tgcacgcaca tgggctgctc ggtccgcaag 1200
cacgtggagc gcagcgcgga ggacgagaca cggttcgtag tcacgtacga gggcacacat 1260
agccaccggc taccaaccgg gagccggcgg cggagcgcca gggatatggc ggaagatgac 1320
gaggattacg agggcgagga cgccgaggag gacagctcgc agcccaccag cccgcagtac 1380
ggcaatgtca acggttcggg gggtccgggc cagcacgcag cctccaaggc cgcggcgcag 1440
ggcgcgcagc tggtgcaccc gtcgggtgcg cagccggcca gcgcggactt cggccagcag 1500
ctgcagcagc tctcgaccag cctgctggcg tccaccgtac tgcagcaggc ggcactgagc 1560
ggcgtgctgc cgctgctgca gtacaactcg ctgtcgtcgg aggcgctcgc cagcctgggc 1620
gtgaactcgg aggcgctcca gggcgtggag cagctcaacc tcgcgtcggt cggcaactta 1680
gccgacttga ccaaccttct tcgccagcac gcgcagatgg acctggcgct ggcagcgcag 1740
gctcaggcca tcgacgcggc gaacgcgaac tgggacccgc tggcgtgcct tatcacgcca 1800
cggcccaacg tctcgccggc gggccagggt cacgccatgg gccaggcgcc gtccgcgggc 1860
actggccggc agactaaagc agctgtgttt cagaagcaag tggcgactac tgaagcgtga 1920

<210> SEQ ID NO 112
<211> LENGTH: 1356
<212> TYPE: DNA
<213> ORGANISM: Chlamydomonas reinhardtii

<400> SEQUENCE: 112
atggactctg atagcgacga tgagcgtgcg gcgggctacg tgccagtgtt ggcagcatca 60
atgccacgag ctgctgcagc ggcggcagtg gccagccccg cggcgaagca accttccaac 120
gttctacaag atggtgtttc gctttacacc aatgagctgt tcaccgacaa caacggggat 180
gtgctgggcg agggtcctgg gctcgcgtct cccagcggag cggcgcccgg cagcgcacga 240
aaaggcctgg ctgcgaaacg gcaggagcgg ttgcagggga acgcatacac gccaaactcg 300
ctcctaaaga acgcctcact gcgtaacccc ggtgcccctg cgtcgccggg tatgcgggac 360
tcgccctcct ccttccggcc atccaccctg tcgcaaacgg ggaccgccac cacagtggaa 420
acgacattgg tcagccccaa ccgcaacagc aacaaccagg gcatcgccgg gggcgtggga 480
atggtgcacg gcttgcgcgc cagctacgac cccaacgagg ggcaggagga gcctgtgccc 540
tccacgcggt acgtggcgcc ggcagcggtg ccggtggcac gcgccgtgcc ccagctggac 600
ctttcagaca tgccggcatt cctgcagcag ccggggccta agaatgggcc ggtgcagtgc 660
gtcatcgtgc gcgaccgcgg gtctgcaaag atgtacccgc ggtactcgct gttcctggag 720
gaggggcggc gctttctgct gtcagcgcgc aagcggaaga agcagaccac cagcaactac 780
atcatatcca tggactacga ggacctcagc cgggagagcg ggtcgttctt tgggaaggtc 840
cgcgccaact tcgtgggtac ggagttcacg gtgtatgacc ggggggttaa ggcgggcaag 900
aaggacgccc agggcgacgg ccagcgcgag gagctggggg cggtgacgta ccagtacaac 960
gtgctgggca cgcgggggcc gcgcaagatg atggcggcca tccccggggt ggacggcagc 1020
gggcggcgca tgttcaaccc cagcggcgac gcggacacca tcctggagcg gctcaaacac 1080
cggaagggac tggaggagct ggtggtgatg ggcaacaagc cgccgcgctg gaatgacgag 1140
ctgaacgcct actgcctgaa cttcaacggg cgcgtgacgg aggcgtccgt gaagaacttc 1200
cagctggtgt cggacgacaa ccacaaccac gtcatcctgc agttcggcaa ggtcggcaag 1260
gacacgttca ccatggacta ccagtggccc atctccgcgt ttcaggcgtt cgccatctgc 1320
atgtcgtcct ttgacaacaa gctggcgtgc gagtaa 1356

<210> SEQ ID NO 113
<211> LENGTH: 2253
<212> TYPE: DNA
<213> ORGANISM: Chlamydomonas reinhardtii

<400> SEQUENCE: 113

```
atgttgcctt ccgagccgcc ctcagcaccg agctccgacc cgaagggagc cggccaggag     60
gctcagcaag ctgaagactc gccgctatac aagacggatg aattccgcat gttttgcttc    120
aaggtgctgc catgctccaa gcgatatgtg cacgactgga cagtatgtcc gttcgcgcac    180
cctggcgaga aggctaagcg ccgggaccct cgcgtgttca cctacactgg cgtcgcgtgc    240
ccggatatga agaagtgcca acgcggagac gcgtgcccat acgcgcacaa cgtgttcgag    300
tactggatgc acccaagcag gtatcgcacg cagctgtgca acgacggcat tgggtgcaag    360
cggaaggtgt gcttcttcgc gcacacgctg gaggagctgc gcgtctccaa cgtcaagctg    420
ctgcccgccg acatcgcggc gggggtggac gtggacctgg acccccttccg ccgcccggag    480
cccgccagtg gcctgcgctc cgccaacaag gcgggtgggg gcggctccaa tgcggccgcg    540
tcgtccggca acgaggccct ggtggaggcg ctgcgtgtgc agcagcagca acaacagcaa    600
gtcaagaagg cggcggcggc gctgcagcgc aacgcatcgc gcgggctggc ggtagagctg    660
cagcagctgc aggcgctaca gcagctacag gcggtgctgg ccagcactcc cggcttggca    720
gctctggcgc cgcagctgca ggcgcagcag atggcggcag ccgcggccgc ctcgcccgac    780
tcattcctga acgccatgat ggccaacctc cgcatggcgg gtgctggtgc aggggccggg    840
tcgggaatgc cgcacggcgg cggctccggc cacggcggcc tgggcagcgg cgccgcgggc    900
aacggcgcgg cactgattga cgcggtggtg cagcaggcgg tgcagcaggt gctgtcaaac    960
agcgcggcgc agcaggccgc cacggcgctg ctgatcatgc aacagcagca gcaacaccag   1020
cagcaggctg ccgctgctgc ggcggctgcc gcggcgatgg cgcagcagca gcagcaacac   1080
cagcagcagc aggccgcggc ggccaaccac caggcggcgc aggcgcaagc gcacgcgctg   1140
cttgggcacc tgctcatgca gcagcagcac caccagcagc agcaacaaca gggcggcccc   1200
agccccgccg ccatgcaggc tgcgctggcc atgctgcagc agcagcaggc cgcggcaggc   1260
cacggcggcc cgcacatgcc gccgcaatac atgcagggcg cccgcccgct gagccccatg   1320
ggttcgggca tggaggcggc catggcggct atgcatgcgc atcagcagca ccaacaccag   1380
cagcaccaac agcacatggg ccagcagccc tcgctgccgg gctcggtgcg ctcctccgcc   1440
actggcatga tgtcggctgt cggcggcccc gtcggcccgc ccggctcgcg caacggcgac   1500
gccgccgccg tccctggcgg cccgggctcc cctcacggct cgccctctgg ctcgccgccg   1560
ggcgacggcc cgctgggcgg tcccggtggc gctgccgcgg cgggcgccgc attctcggca   1620
gctgctactg ccgctgccag ctattacagc caggaggcca gccgcagtag ctttgagagc   1680
taccgcagca gcgaggtcga cctgggcctg gggctgggcc tggggctggg cgcgcaccac   1740
tcgatgcacc accaccacca acagcagcag cacgccatgc agcagcagca gcagcaccag   1800
ttcggcggcg ccggcatgca ctcgagcggc cccagcagcg gcggcacgca gcgcagctcg   1860
ctggagctca tgcagccgcc gccgcagcag cagcagcagc agcagcagca tggctacagc   1920
cacttcgccg gcggcccgca gccgccgcac aaggccttca tgggcgatgc ggcctttgcg   1980
ggcccgccct tcgccggcgg cctgccgtcg catgccgcgg cgcccggccc gcgcagcccc   2040
agcgccacgt cgtcgggcct gcccgccgcc gccgaggagg aggccgcgcg tcagcaggcg   2100
aacgccaacg gcctgtttgc ggcggtgcag gcggcggcgg cggcgggcgc gcaggccggc   2160
ggtgccggcg ccggtgcgca gcttaacctg cccgagtcgc tgctcgccga gcccgtaggc   2220
cccgcggcga tggccgcggc gttccggatt tga                                2253
```

<210> SEQ ID NO 114
<211> LENGTH: 1407
<212> TYPE: DNA
<213> ORGANISM: Chlamydomonas reinhardtii

<400> SEQUENCE: 114
atgaacgagg cgctggactt tgggatcggc gactcgcagt atgtcttcac ggatttagag 60
ctcaacgagc tgctgggcgt gatagagcgc aaagcagccg gcgaggccga gcctgacgct 120
ctcgatttcc tgcgcgccac tgacggcaat ggacttgctc ttcagttcca accgcgttct 180
caaaaggaca acggcagtgg gtgcagcctc gagcagagcg cggttgcagc agcggtcaag 240
ctggaggata gcgcgctgtc atcggcactg gcgtcaccgg tagacacacc cgcactcacc 300
ggcgtcgccg acccagcgtc cctctacggt agcggtgcag agatatcgat catgcccatg 360
cctcacgccg ccgctgcttc cgctccgacg tcacttcacg cctacaccct gccgggcacc 420
gcggggcacg cggcgcttgt tggcagctcg ccggcgctag tgagcaccct tgtcgccgcc 480
gccactgccg cacagcaggc gcaacacaat gcgcaactgg cggcagccgc ggccggctgc 540
ctgcacgtgc acgccccact ccagctggcg cgcttcgcat cggttccggc accgccgggc 600
aaagccatgt ccatgtccat gtccatggct gagcccaagg gccagatcag ccactccacg 660
gtggagaagc agcgccgcga ccgcatcaac tcactgattg acgagctgcg cgagcttgtg 720
ccgccgcagc agcgtggtgg agccaacggt gccgccgccg ccgccgccaa cgacgcggga 780
ggcctggaag ctcggcggcc caagcacgtt gtactggcag acaccatcca actgctcaag 840
cacctgcagc tcaagctatc aatgggcgcg ctggaagtgg gcggcgccac caatggctgc 900
tacgtcaacg ggaatggcgg ctactgcaat ggaggcggcg gcggcggcag cggcggcgcc 960
gtcgggcggc tgggcagtgg cttcaacggg gaggaggaca cggccaactc ggagggcaag 1020
gccagcaagg gatcctccag tcacgaggag atggaggtcg gcggcgctcc tcagatgcca 1080
cacatcccct gccagatgac gcagatgtcg ggcgtgacgg tggagcgcgg ccccgactgc 1140
tactacgtgc aggtcaagtg ccgcgaccgc aaggggctgc tgtccgacat catcaacgcc 1200
ctgagacagc tgccactgga gatccgcacc gccgccgtga ccaccaccaa cggcacggtg 1260
cgtgacgtgt ttgaggtgaa gttggacgac cccgggctca gccccgagga cgtccagaac 1320
ctggtgcacg acgccctgtt ccagagccac ctgttggcgg cgcagagcga gagcctggcc 1380
gcagccggca agcggcctcg cgcctag 1407

<210> SEQ ID NO 115
<211> LENGTH: 1416
<212> TYPE: DNA
<213> ORGANISM: Chlamydomonas reinhardtii

<400> SEQUENCE: 115
atgcgcacct cagataatag aaacacgctg tctctcgaga cagcagcgcc ggtctatggc 60
gcagcggagc tggtggaggg acaggcggtg ctcagccttt tagagagctt ggatgtcgaa 120
tcgatcgacc tgatggtgta tgggtacgag gtcgtgggct gggaggaggc gcacgcgaag 180
gagcccaagc tcccggcggc ggacccatac gcccctagcc agctggtgac acccttggac 240
tcacagcagc agcaacagca gcagcaacag ccgccgccgc catctgcggc ctccaaggct 300
tcgccactgg gcgtgcccag acacggccag cgaaccatct tcaatatctg ccaggtatgc 360
gtggacggcc ggacgtttcg gctggccggc acaccagcac gcaccattgg agacgtgagc 420
taccggaacc tctctggcga ggtcagctac ggcttgcagg tggaggtgcg gcgtccgagc 480
agtttcgcgt cggcagccga acagcagcag caccagttgg cggttctgcg tgctgattgc 540
gagctcgtga ttatacagcg cgcggaggcg gcgcagggcc cgccagcccc cgaggagcat 600
acgtcggctg gggcggcggc ggccaggggc ccagcagcag gcggagctga agcggcggag 660
gcggccgcgc cggtgccgtg cgatgaggtg gtgaccctgg tgccggcctt cttcttctgc 720
tgcagtagcg gcggccgcgt gacggtgcgg ctgcggccgg ggcgggatgg ctacgtggca 780
ggcgaggcgg cggaggtggt ggtcgaggtt gacaaccggt cgaatcagga gtttcgggat 840
gtgcggcttg aagtggagcg ccgcctcaca ttggtcagca acagcgccgg cggaggcggt 900
agcgccggca gcagcggcag cggcagtagc agcgccaccg cggggcttgt gccgggatgc 960
ttcactgaag aggagcggat cttcaagagc aagaccacgg ccgccctact accgggagcc 1020
tgctacctgg gagccaacgc gctgcggctg ccggtgcccc tgccctccaa cacgccgccc 1080
tccacctccg gcgcgcttgt gcgctgctcc tacaccgcca cggtggaggt gctgccggcg 1140
tcggcgacag cgctgcgcgg cgcggcgccg ccgcggctgc gtgtgccgct gaccgtgttc 1200
gcatccgcgc cgagctcgtt cgccacggcg gcggcacggc atgctcacct gcagcaggac 1260
gcaagcgagc aagcgccggc gcacgtgttg gtggtggtgc cgcccgtgga tgtagtgctc 1320
cccgcagctg cgccgcagct gcctcccacc gccgaggtaa atgtcaaaca gcacaacggc 1380
gtggctggcg caaacccgat gtacgcgggc ccgtag 1416

<210> SEQ ID NO 116
<211> LENGTH: 2022
<212> TYPE: DNA
<213> ORGANISM: Chlamydomonas reinhardtii

<400> SEQUENCE: 116
atgaccgaga ccgaccaccg ccgcagccgc cccgactggt cccgcgctca gagcctgcgc 60
ctgatccagc tgcacgtcaa gctgggcaac agctggaccg agatcgccaa gcagctgccc 120
ggccgcaccc agaacgactg caagaacttc ttcttcggcg ccctgcgcgc caagcgcggc 180
taccgcgaca acctggtgta cgcctacgct cgcgctctgc cccccgctag cgcttccgct 240
tgcggcagct gggagcagga caagcgcggc cccgacgctc tgacccgcgc tgctgcttac 300
aaggccgcca tgcagcaggt cgccgctcag gaggtggccg agcagatgga gaagcagcag 360
cggagccagc agcaggaggg cgaggacggc ggctgcggca gcggcgctgc tggcgctacc 420
gctgaggacg gcggcgagcc cggcgctgtg gctgctgcta gccgccgcag cagcagcgtg 480
tccgtgggcg ctgacggcgc tgctcccacc gctcagggcg acggcatgga cacccaggag 540
gacgctgctt ccgctcccgc ttgccccgct tcggctgctg cttcccccgt gggccccggc 600
gacgtgtccg tgcgccgcct gagcagcacc ggcgacaccg tggtcaccga cgctgctggc 660
acccgcaccg tggtggctgc tggcgtggtc gctggcggct ggcgcagcgt ggccgctgcc 720
gctagcatgc ccgctcaccc cgctgctgtg gtgtcgatgc cccccgtggt gcccgcttcg 780
gtggtggcgg ctgcttccgg cgtgctgggc gctgctgccg tgcccgctgc cggcgctccc 840
ggcgaccgcc tgagcctgca gtccctgcag cccccccccc acggcttcgc tgctctgccg 900
cagtccgctg ctcccgccat tggcagcagc tccgctagcc ccttctggca gcaccagcag 960
cagcaccacc tgatgggccc ccgcgtgcag ctgctgagcc acgagagcct ggctctgctg 1020
caccagcagc accagcaggc ccagcagcac agccacgtgg tgctgcacgt ggcgcccccg 1080
ttcctgcagc agcaccacca gaacccccac caccagcacc tgatggtgca gctggagggc 1140
gctggcgctg gcgctcccgc tggcgcgttc cagctgcagc accaccagca cctgcacccc 1200
caccacgtgc agggctccgg ccccgctgac ggcagctcgg gccccgtgct gctgatgggc 1260
ccggctggcc cccacgccgc tgctctgcag ctgctgggca gccacccgca ccaccagcac 1320
cagcaccacc agcagctggt cctgctgccc tccagcgtgc ccggcgctcc gccccagcac 1380
gtcctgctgc cgatggctgt gcgccccccc cacctgctgc agtacggcgg cgcccacggc 1440
gcttccgccg ctgctagcgc tgccgcggct gctccctcgg ctggcatggg cgctttcgtg 1500
ttccaccccc acccccagca gcagcagctg ccccccgctg ctgccgctgc tttcgctgct 1560
gccagcgccg ctccctccca gcccgctgcg gtggctgccg ctgtgcactc cctggctccc 1620
gctgcttcgg ccgctctgag cctgagcggc agctccgtgc tggaggctac caccaccacg 1680
acccgcatca ccacgaccac cgctgctgct gtcgccgctg cggctgctgg cgcggctgtc 1740
gctgccggcg tcaagaccga gcccgcttcc gctgaggctg ctaccggctg ggctcagcag 1800
cagcagcaga aggctcacgc tggcgtcagc cgcagctgca gctccagctc gagcagctcg 1860
gctgcctgcg gcgcttgctc gacctgcacc gctggcgtcg gcgctacccc cgctaccgct 1920
acccagctgc cccagcacca gcaggaccac cagctgctgg gcgacgactg gtgcgctggc 1980
gacgaggagt gggctgagct gggccgcatt ctgctgggct ga 2022

<210> SEQ ID NO 117
<211> LENGTH: 2100
<212> TYPE: DNA
<213> ORGANISM: Chlamydomonas reinhardtii

<400> SEQUENCE: 117
atggaggccc tggacgccca ggacagcctg cagctggacg tggtgtcccc cagcgctcgc 60
cccgctgctg ctggcggcga caagcgcgac cccgagcgct tctactgccc ctaccccggc 120
tgcaaccgca gcttcgctga gctgtggcgc ctgaaggtgc actaccgcgc tccccccgac 180
attcgcggca gcggcaagga gcgcggccac ggcaccgagc tgacccactg ccccaagtgc 240
ggcaagaccc tgaagcccgg caagcaccac gtgggctgca gcggcggcaa gagcgctccc 300
cgccagaccg ctagcaagcg caaccgcacc ggcgctgacg acgccgacga ggctgtgccc 360
ggcagccccc acagcaagca cgtgcgcggc accgacatgg acggcgaccc ccacaagagc 420
tggcaggact tcgctctgac ccacgccggc tacgccatcg gcgctcccgc tatgctggct 480
cccctgaagc aggagcaccc cgagtggccc ccccaccgtgc cccagggcgt gttcgtgggc 540
cacggcgacc gcgtgtcctg gctgcccggc caggtcaacg gcttcgtgcc ccagctgcag 600
ccccagcgct accagcagcc ccagttcccg cccgagctgg cccaggcttt cgccgctgct 660
ggcacccacg ctccccacgt gtacgctcag caggtcccct tcgccagcat tcccggctac 720
cccggccagc ccggcgtggc caccctgcag gtcaccaccg agagcggcca ggtgctgagc 780
atccccgcca acatggctgg catgcccccc ggcatggccg gcctgcccgg caccctggtg 840
taccaccagc agccgccccc ccacgacgct gctgctagct acctggctca ggcccaggcc 900
cacgctcagc acgccgctgc tatgcacgcc gtgaacagcg ctcacgccca gcagcagcag 960
cagcagcagc agcagcagca gcagcagcag cccggcgtgc ccgctgctcc ccccgctgtg 1020
ccgggcgtgc acgacggcat gccgccgggc accgtcgccg ctgccgctgc ggccgctgct 1080
gcggctgccg ccgtgggcgg cagcgctccc agcgctctgc agaccgacgt cggcggccgc 1140
cccggcgctg ctctgccgcc gcaggctgct cccggcacgg gcgctggcca gggcgctggc 1200
gctccggctg gcgctgctga cggcggcgcg gctccggctg ctggcgacgc tgccgcttcg 1260

```
ggcggcgcta agcccgtggc tgacgaggac aacctgggca ccgtgttcga cgacgtcgag   1320

gagttcaccc gcgacttcgg ccgcattccc agcccccccc ccctgccccc cgacttccac   1380

accgctgcta ccggcggcaa cggcatgctg ttcaacttca gccagttcgg ccagaagctg   1440

ccccgcaccc agagccacac ccgcctggac cgcagcctga gcgctgtcgg cctgggccac   1500

ctggacgtgg gcgtcgacgg cgacgtgatg tacgaccaca ccgacgacgg cgacctgatg   1560

cagctgctgt tcggcgtgcc ggacgagctg cccaccatgg ccaccatcca cctgcacaag   1620

tggtccaacg aggaggacga ggacgacgac gccgctgagc ccggcggcgg cggcgcggcc   1680

gcggcgggcg gcggcggcgg cgctgctgct ggcgctggcg gcgagggcgg cggcggcgcg   1740

ggcgcgggcg gcggcggcgc cggcgctggc gctggcgagg ctaacgctgc tgctggccgg   1800

ggcggcgcgg gccccggccc cggcctggag gctggcggcg gcggcggcgg cggcggcgcc   1860

ggcgagggcg gccccggcgc tggccagcag ccccccccacc accagcagag cgtgggcggc   1920

cacgaccagc gccccctgaa cggcaagacg ctgcacggcc acgacgccag cctggctgtg   1980

ctgcccgctc ccggcggcaa gtcgctgatg aacggcggcg ctggccacgc tggcgaggag   2040

caccaccgcg accacctgct ggacgctgag accttccgcc tgctgcagag ctgcgactag   2100
```

```
<210> SEQ ID NO 118
<211> LENGTH: 516
<212> TYPE: DNA
<213> ORGANISM: Chlamydomonas reinhardtii

<400> SEQUENCE: 118

atgcaggacc cccatttaca agaaacgaca gcttcggagc cgctgacaat ggaggaggag     60

tatgaaatgc agcgctcctg ggcgcaagat gaggacaagc tcacattcat agtgctggac    120

aggggtttcc ccgatgtgcc gggcaccggc agccatggcg gcggcatggc gggcgatgta    180

aacctgtttt ttacgctgga cgaggaggag ggcgggcggc aggcggcgga gattgaggtc    240

atggtggcag agcagggctc gcggggcaag ggcatcgcca aggaagcgct ccgtgcgctt    300

atggcatacg ccagcaggga gctgggggtg aagcgcttcg tggccaagat acacgaggtc    360

aatgcgccgt cccgaaagct gtttgagggc ctcggcttcg aggagttcaa gagggtggca    420

tgctttggcg aggtccacta ccagctctcg acggacaagg ctgccgactg gctgccgcaa    480

ctgcaggagg ggctcaatct tggcaagtac gagtag                              516
```

```
<210> SEQ ID NO 119
<211> LENGTH: 837
<212> TYPE: DNA
<213> ORGANISM: Chlamydomonas reinhardtii

<400> SEQUENCE: 119

atgcacacaa taaaatgcaa ccggccctgc tctgtggcgt cgtcacgcgc aaagaacttg     60

ccgacgcatt tcaagctcgg ggcgctgccc attttgcaca gcgctgaaac agcactacat    120

agcgctaggg agcatggatc agctccacac acccggcgat gcggcgtggt ccgctgcgcg    180

tcggaagccc cagcgggccc gcacaccacc gtgccgcatc acacggaggt ggctgtgctg    240

ggtggccgcc tggtcgtgag acccatcacc gccggggaga tccaggccgc aggcgtggtc    300

ctgacccgtg cgttcgcggg ctcatcggag gcggtgtcct tgaaggaagt gctgcaagat    360

ctggagaccc agggcggcgc cggaggcgct gccgcggcaa ctggctgctt cctggttgcc    420

cgcctgtacc cctccacctc ctcctcgggc gccagtggca gcagcaacgt acagctgccg    480
```

ccgggccagg actcgcgact ggtggccact gcttccgtgt cgctgagcgc acaggacatg 540
ctggtgcgcc gcctgccgcc gcccaacccg ccgccggccg ccgccgccta cataagtaac 600
atggcggtgg accccaagtt tcggagacag ggcattgcgc gagccctgct ggcggcgtgc 660
gaggaggtgg cgcgcggcgc ggggctccgg gaggcgtcgc tgcacgtgcg ggaggctgac 720
tcggcggcgc gtgcgctgta cgatagttcc gggtacacag tcgtggtcaa ggactcatgg 780
gtggacacca tgcggcacaa tattcggcca cgactcctga tgaagcggac gctttaa 837

<210> SEQ ID NO 120
<211> LENGTH: 480
<212> TYPE: DNA
<213> ORGANISM: Chlamydomonas reinhardtii

<400> SEQUENCE: 120
atggctaaac gcgagcttgc tgtcagcttt gacattgtta gagaaaagaa ccttgagcaa 60
cttaagctgc taaacagcgt tatcttcccg atgaagtatg cggatgaggt gtaccggcaa 120
tgcatggcgt gcggcgacct gactcagcta gcataccaca acgacgtcct ggtgggggcc 180
atcacggtgc gctgcgagcg ccagcccaat ggcaaggcga aggcctacat cgccacgcta 240
ggcgtgctgg cgccgtatcg caacttcgct atcggcgcca agctgctgca gcgctcgctg 300
gctgcggcgc agcaggaccc caacatcgag gaggcgtttg tgcatgtgca ggtcgacaac 360
gaggacgcca tccgcttcta ccagcggcac ggctttgaga agggcgaggt ggtcaaggac 420
tattacaaga agctgtcgcc gccggacgca gtggtcatga gcaagaagct ggcagcatag 480

<210> SEQ ID NO 121
<211> LENGTH: 1005
<212> TYPE: DNA
<213> ORGANISM: Chlamydomonas reinhardtii

<400> SEQUENCE: 121
atgctccgct gcgaccggtt cttctcgagc acacgcctcg tcgacaatca gactcttcaa 60
atcagctgca aatatatcaa caacaagtta tctagtccac tttacgcatc ttgcaattgc 120
aatcaaggaa gcggccttgc aagtctgcga cgcagctcga gcagctgtta tagctcaaga 180
caggtccctg cggccattgc ggaagttaat gtccgctcgg tgcgcagcct cagccgctgg 240
cgatggcagg acctcgctca ggtggccttc ctgctagcgg catcgttcta tgaggacggc 300
gaatcatggc agctcgagag ccccccggtc ccggcgacaa gtagcaccgc agtaagccag 360
gatgtaacag aactgttgcc tgcatcgact gatgccaggc agtcggcaag cggcgccggc 420
cgtagcagca ggaacagcag cagcagcagg gcaagcagca gtggcagtgg agcaatcaac 480
cggccactgt caggagctgc tctgctgttc ggtgcgtcct cgctcctggc catcttgatc 540
cagcacgcca catatggtgc gcgccacgtc acgctgcttg cggagttgca ggagtccggc 600
gaggtgattg gctgctgcgg gctgacgttc gatgctgctc cagccgacgt cgtggaggcc 660
accggcgcgc cacagggctg cgagtatgcg ctgctcacgg gcttagcagt tgcgccgccg 720
cagcgccgcc gtggtgtcgc atcggcactg ctgcaggcgg cagagcagga ggcgcggcgg 780
ggccctggcc aggcacggcg gggccctggc ccggcacggc gccggctgcc ggcacttctg 840
gcattgctgg tttccaaact caacgccgcg ggaaggaggc tgtacgagcg gaacttgtac 900
gaggaggcag aagactgggt ggacacgcgg tgggagctgg acgcagagaa gggccgtgtt 960
gggaagcccc ggcggctgct cctctttcgc cgattgacac aatag 1005

<210> SEQ ID NO 122
<211> LENGTH: 471
<212> TYPE: DNA
<213> ORGANISM: Chlamydomonas reinhardtii

<400> SEQUENCE: 122
atgcactggc aatatccatg ttccaatctt tactgtttta cattgctgct ctgcatccgc 60
tgcgtttcgc aaggggacgg tgagctttct gggcctgttg tttcgcaagt cgcggcaagc 120
cggcaaagtg caccagcgca tttgcatagg cgatcctact acagaaggaa aatgccacgc 180
gctgccaagg agaagccgga gaagaaagag aagaaggtca aggaccccaa tgcccctaag 240
aagcccatgg gcgcctacat gtggttctgc aaggagatgc gggagcaggt gaaggccgac 300
aacccggagt tcagcgtcac cgacatcggc cggcggttgg gggagctatg gaaggagtgc 360
gaggacgacg acaagaagaa gttccaggac ttggcggaca aggacaagga gcggtacaac 420
aaggagaacg ccgcgtacca gaagaaggag aaggaggcaa agtcggaata a 471

<210> SEQ ID NO 123
<211> LENGTH: 474
<212> TYPE: DNA
<213> ORGANISM: Chlamydomonas reinhardtii

<400> SEQUENCE: 123
atgattgacc tactgctggg agcatcgttg tctccctcgg atatcggaca ggttctgcta 60
gcgtatccac aggccttcca gctctccctg gaccgcgctc gggaggtgct ggacttcctg 120
cgcgacgaca tgcacctcag cgagtcccag gtccgcacgg tgctgacgcg ctatccaagc 180
atcctcaaca tgaacgtcaa gggccagttg cgccccccagg tagcgtacct caactcgctg 240
ggcgtgggcc cagagtcgct gccggagctg gtgctgagcc ggcctctggt gctggggccc 300
ggcatcgaca ccgtcatcac cttcctcaag cggctgggcg tgccgcgctc gcagatgcac 360
cgcatgctgc gctcctgccc tctggactac cgggttcagt tcaagagctt tagcgccgcg 420
gcgccgggtg gcagctcttc ctcctcgtcc tccggcggca tgggccgcaa ctag 474

<210> SEQ ID NO 124
<211> LENGTH: 447
<212> TYPE: DNA
<213> ORGANISM: Chlamydomonas reinhardtii

<400> SEQUENCE: 124
atgacgtcag aggagctatc tgtacgcaaa cttgagcaag gagatttcga taagggcttt 60
cttactgtcc ttgggcatct gacaacggtg ggggatgtga cgcgggagat gtttgaagag 120
caaatacgtc ggcgagatgc agtgggtggc taccacacgg tggtcataga agacaacagc 180
cgcatcgtcg ccacggccag catggtggtg gagctcaagt tcatccacgg ctgcagcaag 240
gtggggcaca tcgaggatgt ggtggtggac cccgcgtacc ggggcaagcg cctggggctc 300
aagctgatcg aggcgctcat cgagtcggcc cgcggagatg gctgttacaa ggtgatcctg 360
gactgcgcgg agggcaatgt gcccttttac gagaaggccg ggctggtgcg caaggaggtg 420
cagatggtgc gctacctgga ccggtga 447

<210> SEQ ID NO 125
<211> LENGTH: 591
<212> TYPE: DNA
<213> ORGANISM: Chlamydomonas reinhardtii

<400> SEQUENCE: 125
atgacaaagc ataaacgccg agagctgccc agtgcggtcc acgatggaga ggagtataaa 60
ccaggggact gcgtgctaat caacccggac gcctctgcgc ccgcctacat tgcacggatc 120
cggaagctca tacagatcgg cgcggagcca gagcaggtgg aactggaggt gacctggttc 180
taccgaccag aggaggccat cggggggcgc aaggccttcc acggcgaggc ggaggtgttc 240
gactctgacc accaggataa agcaccacta gctgccatcc tgggtcgctg caacgtacac 300
aacgtgtcac ggtatgagtc gctagaacgg cgagacgaga acgacttttt ctgccgcttc 360
acatacaagc cccgcaccaa gcagtttgag ccggatcgcg tgccagtgta ctgcgtatgc 420
gagctgccat acaacccaga caggccgatg atcaactgcg acaactgcga cgagtggtac 480
cacccgcagt gcctgggcct tggccagcac gtgctgcagc aggaccactt cgtgtgccct 540
acttgcacca cgccgcagca gcccgccaag aagtcccgtc ctggggcatg a 591

<210> SEQ ID NO 126
<211> LENGTH: 717
<212> TYPE: DNA
<213> ORGANISM: Chlamydomonas reinhardtii

<400> SEQUENCE: 126
atgctgctgt cacgtctcgc tcattccgct ctccctgcct cgctccgcgc ctcggccgcg 60
agctcggcct cgtcgcagct ccatgctgtg ccccgtgtcg cgagcgccgc tccgcgggcg 120
ccgtcgcacg tcgcgcagta cagcaacggc tctgcggcgc ccgtccctcc caacttcgct 180
gctcccaatg accgcgccgc caccagctcc agcgaccgtg tatacaccaa ctattacgtg 240
tacaagaccc gcgcggccat gtgcctgcgg ctgctgccgc ccacgttcgc caaggcgcaa 300
gccggcaagg tcctggaacg tgacggcacc atgctgcttg agtttgccac tgccaacgcg 360
gccgcaccgg gcgctggcag cggccccgca ggcaacgtca accgcaccta caactggggc 420
aacaaggtga cgttcgctct gagcccggtg gagcttggaa acatcctggc gggggatgcg 480
gtggcctcgg acaaggggct ggtgctgtgg cacgacccag ccaagctagg caagaccggc 540
gagcccatta agaagctgag tctgaagcag ctcccagacg gcaacatcag cttcaacctc 600
accgccgggc ccgagaactt cagcgtgccc gtcaccaagg gcgagtttga ggtgataaag 660
tcggtcgcgc agttcgccat cccccggctg ctgggctttg acgccgtttt cgaatag 717

<210> SEQ ID NO 127
<211> LENGTH: 1026
<212> TYPE: DNA
<213> ORGANISM: Chlamydomonas reinhardtii

<400> SEQUENCE: 127
atgggcaagg actactatgc aatccttgga gtgcagaaag gagcagatga aaatgaactt 60
aagaaagcgt atcgaaaatt ggcgatgaag tggcacccgg acaagaaccc agacaacaag 120
gaggaggctg ccgccaagtt caaggagatc tctgaagctt acgaggtgct gacggatcca 180
gacaagcggg aggtgtacga caagttcggg gaggaggggc tcaagggagg catgggcggc 240
gggccgggcg gcggaccggg cggccaggc ggcttccact tccggagacc cgaggacatc 300
ttcgcggagc tgttcggggg ccgcagtccg ttcggcatgg acgacgacga catgtacgcg 360
ggcggcagct tcggcggcgg cggcggcggc ttcccctttg gcgcgttcgg cggcatgggc 420
ggcttcccgg gcggcggcat gggcggcatg ggcgggatgc ctggcatggg gcaacggcgg 480
ccatccgggc cagtcaaggc caaggccatt gagcacaagc tcaacctctc gctcgaggag 540
ctgtacgcgg gcaccaccaa gaagatgaag atcaaccgca aggtcaaggg ccggccgcag 600
gaggagatcc tggagatcgc ggtccgcccg ggctggaaga agggcaccaa gatcaccttc 660
caggagaagg gcgacgagga tcaaggcatc attcccgcgg acattgtctt cgtcattgat 720
gagaagccgc acccacggtt caggcgcgag ggcaacgacc tgtacttcac ggcggtggtg 780
tcgctggcgg acgcgctgtg cggcaccacg ttgcagattc cgcacttgga cggcaccacg 840
atagacctgc caatccggga cgtcatccgg cctggcgaga gcaaggtgtt gcgcggcaag 900
ggcatgcccg tcaccaagga gccgggcgcg tttgggaaca tggtgctcaa gttcgacgtc 960
aagttcccgc gcgagctcag cgacgccact aagcagcagc tgcgagccat cctgccctcg 1020
cactga 1026

<210> SEQ ID NO 128
<211> LENGTH: 396
<212> TYPE: DNA
<213> ORGANISM: Chlamydomonas reinhardtii

<400> SEQUENCE: 128
atggccatgg ccaaggagac cgaggacctg gacctgccag aggcaaccgc ccacgcgggc 60
gtgctcgctg tgctggaggg caaaacgcac gcggcgtatt acctgctgga gcagtcgggg 120
gaggtcgtgg cgcagctgat gatcacactg gaatggagcg attggcgagc ctccgacatc 180
tggtggatcc aatctgtgta cgttaggcca gactgccggc gccggggcca cttccgggca 240
ctgtacgcgc acgtgcggga ggagtgccgg cgggcgggtg cctgcgggct gcggctgtac 300
gcggacactg ggaacgagcg ggcacacgcc gcgtacgagg gcctgggcat gagcagccac 360
tacaaggtgt ttgaagacat gttcacccag tactga 396

<210> SEQ ID NO 129
<211> LENGTH: 630
<212> TYPE: DNA
<213> ORGANISM: Chlamydomonas reinhardtii

<400> SEQUENCE: 129
atgagcgggg acgagggcga cggtcgagat ggcaacagca atgcgcgtga gcaggacagg 60
ttcctgccca tcgccaacat cagcagaatt atgaagaagg cgctcccgaa caacgcgaaa 120
atagccaagg atgcaaagga gacggtccag gagtgcgtct cggagttcat tagcttcatc 180
acgtcggagg ctagtgacaa gtgccagcgg gagaagcgga aaacaattaa cggcgacgac 240
ctgctgtggg ccatgacgac gttgggcttt gaggagtacc tggagccgct caaactctac 300
ttagccaagt tcagagaggc tgaggcggcg acatccaata agccaggggg cggctcaggt 360
gccaacgcgg aggcaaagcg tgaggcggcc gcggcggctg cggctgcggc cgcagctgcg 420
gctgcagttt cgcagcaaca ggcggcgcag cagcagatgg cggcgcagct gcaagctggc 480
atggcgttcc cggggctcat gccggcgcag ttccaggggc taccgcccgg catgattccc 540
gctggcttcc ccggactgcc gctgcctccg ggcgtgccgg gcctgatgat gccaggtggc 600
gttgtgccca agcaggagcc ccccaagtag 630

<210> SEQ ID NO 130
<211> LENGTH: 555
<212> TYPE: DNA
<213> ORGANISM: Chlamydomonas reinhardtii -continued

<400> SEQUENCE: 130
atggccgatg agggaccgtc aacgtctggg gacgtgcgct tcactgttcc cacacgccta 60
aagctgattg tgaccgaggg gccttgcgag ggacagattt ttgacgccgc agaaatggac 120
gcctgtttcc tgacgctcgg gcggacaaag aaaaccaaaa tccacctgaa ggatgactcc 180
atctcggaga agcacgccga gttcgcatgg actgggagcc actggacggt cacagacacg 240
tgcagctcca acggcacccg agtgaatggg gccaagctca aaccaaacga gccgcacgtg 300
ctaaaggcgg gtgagcacgt ggcgctgggt gatgagacca tcatgaccgt ggagctgtcg 360
cagcagtcgc tcgcgaacgt gtcactggaa tggctgatgc gggcgcactt cgagagcagc 420
tgccaggggc tggaggctgg cggcgcggac aaggcgcggg agatggtccg ccgctgccac 480
gaggccctgg actcgctgat ggacccggcg gcggctgtag cgcccgcggc cgcagccacg 540
gcgggaggga agtag 555

<210> SEQ ID NO 131
<211> LENGTH: 1005
<212> TYPE: DNA
<213> ORGANISM: Chlamydomonas reinhardtii

<400> SEQUENCE: 131
atggagcttg gactcgcaga gagtctgggc gacgccgact ccctagcagc ctacctaaat 60
ggcagtttca tcggtggagg ctcgctggag cagacgctgg aggcaccttc atttttaggc 120
gagctcgctg ccattacggg gtctatggag gctccttatg cggcggcagc acctgagctg 180
ccggcagagc tcaagccaga ggagctgcct tcgacaagcg gcgcaggctt cctgccacag 240
tcggaggcgg ggccgatgtc cgaggccggg ctctccgccg atggcgggct tatgtcggag 300
gacgacgcgg agggcggcgc aacgtcctgc aagggcggcg gcaagcgccg tcggcggata 360
cgcaccgaga ggcagcaggt gctgaatcgc ctagcacagc agcgatacag gcagcgcaag 420
aaggagaagg tccaggcgct tcagcacaac gtggacgcct tgcagatgca gctggagcgg 480
gtcagcttcc tggagtcgca gtgcgactca ctgcgcggca cggtggctca gctaggcgcg 540
gaccttgctg ccaaggacgc ggggctggcg gcggcgcagg cgcagctgcg gcaggcggcg 600
gtactgctaa agggcgcgca ggacaaatgc gcttcgcagg agcggcagct ggcggagcag 660
gcgcaggcgc tggaggcgca gcgctcacag ctgcgtgtgt ccaacctggc cagcctggac 720
ccccaggccc tgtccgaccg gctgctggcg ctggtgaagg aggccttcgc cgccgctgcc 780
gcagagcgca gctcggagat tgacggctcc gggatggcgg cgccggcggc ggctgccgcg 840
gcgccttcgg cgccgccacc gctggcgatg tcggaggagg tggtggcggc tctgagccgc 900
agcctcacca gctgctgccg cgagctggtg tttgctagca agggcctggg cggcaagcag 960
gcggcggcgg aggcaccgtc cgtcatcccc gtgcagtgct gctaa 1005

<210> SEQ ID NO 132
<211> LENGTH: 1476
<212> TYPE: DNA
<213> ORGANISM: Chlamydomonas reinhardtii

<400> SEQUENCE: 132
atggccaagc tcattaagaa cgtcggagct tcactaaggg caaggaccca cgacgaggac 60
gacacaatga tgaagcagaa aggagcgaca ggggtgttca gaaacctcgc gttcgcggac 120
gctgacgaca acttggtctc cacctccgca cgcgcgatgg caacttcgga aagtaccaag 180

```
aagaacaact tctttggtgg cagtcaggac aacattgcgt ccatagatgt cacgccgcgg    240

tcacgcgacg cgggcaacgg agcgtcctcc tgggcgcacg ctgacctccc cacctcggcc    300

agcaagcgcg tgggcagcac cggcagcgca tctacacctg tgaagagcgc aacctttgca    360

cgcaccgctt cggcacaaaa gcgcgccaag aacgcgacag ccattcagga aatctctgcg    420

tttgagcacg agcacgctgt gatggacgag atgtcgggct ccgaagacgg cgagcggcca    480

gcgggcctag tgagcggcgg cagcgccatc ggcgccacca ctagcaccac cgtcattgcc    540

gtgcgctccg tcgcgcgcgg ccccagcatc acgcagcagg tcagcaccag cggcagcgtg    600

cgggcgtggg aggaggaggt gaagcggctt atcgccagcg ggcggcacga ggacgcggtg    660

cggtgggtgg ccccctcgga cggcatcatc cgctgcactg tgcgtcgcgt gaagaacttc    720

ctggggcata cgctcgccta ccagctcttc ttggactctg gagacacgtt cgtgctggcg    780

gcgcgtaagc gcaagaagag caaggcctcc aacttcgtgc tgagcaccag ccaggaggac    840

ctcggcaagg actcggacca ctgcatcgcc aagctgcgag ccaacttcgt gggcactgag    900

tacggcctgg tgtcgcgcac cggcggccac atcagcggca gcatggacat tgacggcggc    960

gcgcagtcgg gcggcaagct ggcgccgccg gccgagccct tctcccgcga ggagattgcg   1020

gtgcactaca agcagaccgc gctgacggcc aagggcggac cccgcaccat gctggtcgcc   1080

acgccgctgc cggaagtgag ctgggccccc agcgccgctg acggctcgga ctcgctcgcc   1140

aactgccttg aggcggcgcg ccggcgggag ctgtcgccgc gcatggagcg gcagctgtgc   1200

atgctggcca cgcggccgcc ggagtgggac cccagcctga aggcgtacac gctcgacttc   1260

cacggccgca tccgcgccag cagcgtgaag aacttccagc tggtgcactg ggaccacaac   1320

acggaccgca agggctctga cctggtgctg cagtttggaa agattgacga gaacactgac   1380

gacttcgcgc tggatttcac ctacccgctc agcctgcaga aggcgttcgc catcgcgctc   1440

gcaagcaccg acacaaagct gtgctacgcg ttgtaa                             1476
```

<210> SEQ ID NO 133
<211> LENGTH: 642
<212> TYPE: DNA
<213> ORGANISM: Chlamydomonas reinhardtii

<400> SEQUENCE: 133

```
atggcagaag agacaggccg gtcgcagagc ggcgccgagg cgacgaccag cgatgccatc     60

cgatatgtcc aatacaaagg cgaggaggac ctgcccatcg taatgggcct ggtcgacaag    120

gagctcagcg agccctacag catcttcacg tatcgctact ttctgcagca atggccacac    180

ctatgttaca ttgcatatga cggtgacaag ccgttcggca cggtcgtgtg caaaatggac    240

atgcaccggg accgggcgct gcgcggctat gtcgcaatgc tcgtggttga caaggagtac    300

cgtggcaagc gcgtgggctc tgagctggtg aagatgggga ttcgggagat gattgcgggc    360

ggctgcgagg aggtggtgct ggaggcggag gtcgtaaaca ccggcgccct caagctatac    420

caggggctgg gcttcgtgcg ggaaaagcgc cttcacaggt actacctgaa cggtgtggac    480

gcctaccgcc tcaagctgct gctgccgctg accgaagaga agaaggcggc gctggcggcg    540

gccgcggcgg cggaggcggc ggagctggag ggggtggagc tggaggcggc ggcggtggac    600

gcaggggcag tcgcggcggc ggcggagcct gccattgcgt ga                       642
```

<210> SEQ ID NO 134
<211> LENGTH: 1515
<212> TYPE: DNA
<213> ORGANISM: Chlamydomonas reinhardtii

<400> SEQUENCE: 134

```
atggtcggca acaagctgtc agctgtaagg tctgtgctgc gaaaggctcg acagctcaag      60
gaccctctcg gtgagctcgt cagcactgca aggccctgcc gcgtcgacgg ccagcaacac     120
acgcacttcc ggtcgcacca tgccgccgac cttcccaagc agcagctgga atggtgtctg     180
gacgtgtgcc gggagaacat ggcggccttt tatgagcgcg tgtggtcttg gagcgatgtg     240
aaaaagaggc ggcagttcac ctcgagcgct tctcggttcc tgatagcata tgacgtgaac     300
gctgctcgcg tccctgttgg ctacatcaac ttcaggttcg agtacgagga cggcgaggcg     360
gtgctgtact gctacgagct gcaggtggcg cgggcggcgc agcagcgggg cctgggccga     420
gccatgatgg agctgctgga gcaaattgcg tggggcgccg gaatgagcaa ggtgatgctg     480
acggtgttca ccgaaaacgt cccggcactg gcgttctact ccaaactggg ttaccggctt     540
gatgagacgt cccccgacta tagccccgca agcggcaact gtagtcccct ggagttggcg     600
cacagcgcgg gcggcggtgg cagtagccgg tgcagtccgg agcttggcgc ggcggcggcg     660
gtgacagcta ctggtacggg ctgcagtggc aaccgtagcg caagcggaag cccggagggc     720
ggtggcagcg ctgctgtcag cagcagcatg gctgtcagca gcgggagcgc tgggggtgct     780
gggagcggcg agggcagcgg gagcggctac cacattctca gcaagcggat tccatcggac     840
tggcgggagg aggtgaggct tcagcaggag gcgcagcagc agcgagacgt gcagcgtgct     900
gaggtgcagc agcaagtggc agtgcggaac gtggcgcccg ggcatcaggc tcacgaggag     960
caccaggtgc accagcaagg ccagtcgccg cagccactgc cacagcagct ggcaccgctg    1020
cggcaggcag tggaggccgt ggctgccatg gcagaggcgg ccttgcctgt ggcagcagca    1080
gcggcctcgc cggccgcagt ctgcgccccg gaggccgagg ctgaagagcc tggcagtcgg    1140
aaaaagcagc gcgtatcctg cacgccggat gtcaccggcg caggcaggag cggcagttgc    1200
gggccggagc tggaggaccg cgctgaggga gcagcgcaaa gcgacgtcgc ggccaccgcc    1260
ggacacgacc tgtcacggaa tggcacaccg gtgcccatgg tgatccatga gggcacgggt    1320
gctggttctg gcgccggtgc tgcagcggct gggacctcga gcacagagca ggagaaggca    1380
gagcaggtga agccgggggc tgcagagccc gcggcggtac cgccggcgca ggatggcgag    1440
gccgcggggg ctggcatgaa gatatgtgga gcgtgcagca gcaatggtgc agcggccgct    1500
gagcacatac cgtag                                                     1515
```

<210> SEQ ID NO 135
<211> LENGTH: 501
<212> TYPE: DNA
<213> ORGANISM: Chlamydomonas reinhardtii

<400> SEQUENCE: 135

```
atgctggacc gaattcatga acttgaagct gcctcttacc cagaggacga ggccgctact      60
tacgataagc taaagttcag gatcgaaaac gcgtcgaacg tgttcctggt cgcgctgtcg     120
gcggagggcg acggggagcc caaggtcgtc gggtttgtgt gcggcacgca aacgcgcgcg     180
tctaagctga cacacgagtc catgtcaacg cacgatgccg acggcgcact actgtgcatc     240
cactcggtgg tggtggacgc cgcgctgcgc cggcgcggcc tggccacccg catgctccga     300
gcctacaccg cctatgtggc cgctacctcc ccggacctga ccgggatacg gctgctgacc     360
aagcagaacc tgatcccgct gtacgagggc gcgggcttta cgctgctggg tccctcggat     420
```

gtggagcacg gcgccgatct gtggtacgaa tgcgccatgg agcttgaggc ggaggaggag 480
gcggaggtgg cggaagccta g 501

<210> SEQ ID NO 136
<211> LENGTH: 972
<212> TYPE: DNA
<213> ORGANISM: Chlamydomonas reinhardtii

<400> SEQUENCE: 136
atggcagcca gcttctctat ctctggcgat tttgcctgtg gccagtctac tggtcacgcg 60
acgttctggc ggcttgaaga gaacaaagtc ttcgaggtag cccttgcaag acactacgcg 120
gacgtggaca ggttcgagcg catcgcctct tatctgccaa acaagacgcc taacgacatt 180
cagaagcggc tccgcgacct cgaggacgac ttgcgacgca tcgatgaggg gtgtaacgag 240
ggcgcctcag ctcagagcgc ccccgcggcg acccccgcac gttcagagga ctcggcgccg 300
aacgccaagc ggccaaagac cgatgtgcca gccaacggtg accgtcgcaa gggtgtgccc 360
tggacggagg aggagcaccg gttgttcctg ctcgggctcg ccaagttcgg caagggtgac 420
tggcgttcca tcgcccgcaa cttcgtcatt tctcggacgc caacccaggt ggcgagccat 480
gcgcaaaagt atttcatccg cttaaacagc atgaacaaga aggacaagcg ccgggcgtcg 540
atccacgaca tcaccagccc gacgctgccc gcctcggtgg ccaaccccgc cccgaccacg 600
gggctagcgc ctgcagcggc ctcgggcaag gccacctcgt cattggtgca gggcgcgacc 660
tcctccgcca ccactgccac ctcgcagccc atggccgccg cggcggccgc tgcagcggca 720
gccttccccg cggctgcgca cgtcgccgct gccgctgccg cggccgccgc cgccgccacc 780
agcaccacca gcgttttcgc gcagctggct atgcacgggc ttgccatgca gccggtgatg 840
cagcaagcgg ctgcggctgc ggcagcagcg ggcatgatgc ctcagctcaa cgcggcggcc 900
gcggccgctg cggccgccgg catgccggcg cccgtgcttc ccaacgcggc gcagtacatg 960
gtgcaggtct aa 972

<210> SEQ ID NO 137
<211> LENGTH: 1566
<212> TYPE: DNA
<213> ORGANISM: Chlamydomonas reinhardtii

<400> SEQUENCE: 137
atgcgcagcc aatacttgct taacacacgc cggtgggtgg ttcgccttgc cgatcagtgc 60
agccagcgcg cgagccttac ggtgagcgcg caagccgccg ccgcaaacga gccagtcact 120
gatctaccgg agctagtatc ttgggtcttg caccgaggag gtcgagtgga tggcgcaacg 180
ctcgcgaacc tggctgggcg cgatggcggc agcggctggg ggctgaagtg caccagagac 240
gtgcagcaag ggcatcggct catcacgctg ccgaacgcag cgcacctgac ctacggcgcc 300
aacgacgatc ctcggctcct ggctctgatc gagaaggtgc cctcagagtt gtggggcgct 360
aagctggcgc tccagctgat cgctcagcgg cttcaggggg gcgagtcgca gtttgcctcg 420
tacgtggcgg agctacccaa gggcttcccc ggcatccccg tgttcttccc ccgcaccgcg 480
ctggacatga tcgactaccc accctgctcg cagcaggtga agaagcgctg caagtggctg 540
tacgagttca gcactgaggt gctggccaga ctgccgggta gccccgagga ccccttcggc 600
ggcgtggcgg tggacatcaa cgccctgggc tgggccatgg cggcggtgag ctcacgtgcc 660
ttccgcacgc gcggccccac acagcccgcc gccatgctgc cgctgatcga catggccaac 720

-continued

```
cacacettta gccccaacgc cgaggtgctg ccgcttgagg gcggcggcgg cgcggtgggc    780

ctgtttgcgc ggcgggccat tactgagggc gagccgctgc tgctgagcta cggccagctg    840

tccaacgact tcctgttcat ggactatggc ttcatcgtgg aggacaaccc gtacgactct    900

gtgcagctga ggttcgacgt caacctgctg caggccggcg cgctggtggc caacgtgagt    960

gatgcactgg gcgccccct ggacctggcg ccccgcacct ggcagctgca gctgctggcc    1020

gagctggggc tggtgggccc agccgccaac accgagctca acatcggcgg cggcggcccg    1080

ggcgctgagc tgctggacgg gcggctgctg gcggcggcgc gcatcatggt ggcgcgggcc    1140

gatggcgagg tgtcggggcg cggcgtggag cggctgtgtg ctgtggaccg accgctgggt    1200

cgggacaacg agctggcggc actgcgcact gtgggcggcg tgctggcgtt tgcgctgagc    1260

aattttgcaa ccaccctgga ccaggacaag acactgctgg cggggcagcc cgtggcggtg    1320

ccgcaggcgg gcggggtggg cgagcgcgag ctgccacccc ttgccagtga ggacgaggct    1380

ctggcggtgc ggttccggct ggagaagaag aagatcctca gccgggcgct gcagcgggtg    1440

ggcgcattaa gtcaggcggc cgcgggcaac agcgagctga ggcagacggc aggctctgca    1500

gcagcaaaga agggcagcaa gccggcgccg gccactggca agggcttcgg ctccaagaag    1560

cggtga                                                               1566
```

<210> SEQ ID NO 138
<211> LENGTH: 222
<212> TYPE: DNA
<213> ORGANISM: Chlamydomonas reinhardtii

<400> SEQUENCE: 138

```
atggcagacg caacgggctc aacgcaagac gacggctcca acaccgtgat tgttattgta     60

ggagtggtgc ttgtcatagt tggaggcgcg ctgctttatt cttttattca ataccagcgg    120

atgatggcca acgcgcccgc acggccaaag aagaagctag gggcgaagca gatcaagcgc    180

gaaaagctga agatgggcgt tcggccgccg ggcgacgact ga                        222
```

<210> SEQ ID NO 139
<211> LENGTH: 420
<212> TYPE: DNA
<213> ORGANISM: Chlamydomonas reinhardtii

<400> SEQUENCE: 139

```
atgaacatga actctcaaga ctgggacacc gttgtgcttc gcaagaagca gcctactggc     60

gcagcgctga aggacgaagc cgctgtcaat gcggcacggc ggcaaggtgc agctgtggag    120

acgtcgcaga aatttaacgc tggaaagaac aagcctggtg cggctcagac tgtgagcggc    180

aagcctgcag ccaagctgga gcaggagacg gaggacttcc atcacgagcg cgtgtcttcg    240

aacctcaagc agcagattgt gcaggcgcgc acggcgaaga agatgaccca ggcgcagcta    300

gcgcaggcta tcaacgagaa gccgcaggtg atccaggagt acgagcaggg caaggccatc    360

cccaaccccc aggtgctctc gaagctgtcc cgtgcgctcg gcgtggtgct gaagaagtaa    420
```

<210> SEQ ID NO 140
<211> LENGTH: 672
<212> TYPE: DNA
<213> ORGANISM: Chlamydomonas reinhardtii

<400> SEQUENCE: 140

```
atgggcagca catcaggtgt tcgcacgttc agcaaatccg atgacccggt cgcagcggag     60

gagtgctgca acacggttgg caagggtttc gcctccgagc ccaacaacgt gttcttctgt    120
```

```
gcggaccccg cgctcttcga gggcaggtgg agggccatcg cccacaacag cctactgcgc    180
agccccgaga ccccccctgct gcactcggtg gcctccggcg atacgcagca cgcggccgtt    240
gcatttgctt actcctaccc cgagcagaag acaccggatg acgcgccgga gccgcccggt    300
gtcatcgacc tgtccggcag cggccggccc gaggcggtac ccacacggga tgagatgctc    360
aagtacctcg ggacaagaa gaccgagttc taccagcggc gcgggccgtt cgagtacgtg    420
gccttcctcg ccactcggcc cgagcactgg gggcgaggcc tggggtcgcg gctgctgaag    480
cacctgaccg acagggctga cgccgggggc cggtgggcgt acctggaggc gaccaacgcg    540
gacaacgcgc ggctgtatgc caggcacggc ttccgcgaga tcgagaccaa ggtgtggacg    600
ctcgagtgcc tgcccgggca gcgcatgatg ctgatttaca tggagcgacc accctcggca    660
cagcagcagt ag                                                        672

<210> SEQ ID NO 141
<211> LENGTH: 744
<212> TYPE: DNA
<213> ORGANISM: Chlamydomonas reinhardtii

<400> SEQUENCE: 141

atgacggatt acctaaagga cttcattgac agggctgcag atgtgcccct gcagctgcgt     60
cggcgccttg ccctcatccg tgacctagac gagaaggcac aggcgctgca tcgtgaaata    120
gatgagcact gcaagcgcac gctggcggag aaatcgcagc agcacgcagc taagaaacag    180
aagcaggctg cgggggagga cgctggcggg tcagcagcgg cgccgtacga cgtggagtcg    240
gctctgaagc ggctcatagg tctcggggac gagaaggtca acattgctaa ccagatttac    300
gacttcatgg acaaccacat caaccagcta gacacggact tgcagcagct ggacggggag    360
attgaggcgg accgcaagga gctagggctg gagggtgacg agacggcctg cgaaaagctg    420
ggcatagagg cgccgcaggg gtcacggccg cacacggtcg ggaaaggggc agcggaccag    480
aagaagaagc gcgggcggaa gaaggacgag tcgacggcag ctgcagccgg tgggctgccg    540
cccatcgaga acgagccggc gtactgcatc tgcaacaagc cgtcggcggg gcagatggtg    600
ggctgcgaca accccgagtg caccatcgag tggttccact tcgagtgcgt ggggctgacg    660
gaggagccca agggcaagtg gtactgcccc gtgtgccgcg gggacctgca ggtcaagtcg    720
ggcaagaaga gcgggcggcg gtga                                           744

<210> SEQ ID NO 142
<211> LENGTH: 1005
<212> TYPE: DNA
<213> ORGANISM: Chlamydomonas reinhardtii

<400> SEQUENCE: 142

atggggaaga agaagaagca gaaggaaatc gagcagtgct tttgctatta ttgcgaccgc     60
attttcgatg atgagtcggc gttgattgtg caccagaaaa acaagcactt caaatgccca    120
gaatgcaacc gcaaaatgaa caccgcccag ggcctggcaa cgcacgcgtt ccaggtgcac    180
aaactaacca tcactgctgt gcccgccgcc aaggccggga gagattccat ggctgtggag    240
atcttcggca tggcgggcgt gccggacgac gtgcggcccg ccaagcttca gggtgatggg    300
cctgcgctca agaaggcgcg cgcggacgac gacgatgacg tgacgccgcc gcccgcgccg    360
ccgccgccgc cgggcggcat gccgccgccg atgggcggct accaccctgg catgccgccg    420
cccatgggct acccgcccta cggcgcacca ccgccgtatg ggtatccgcc ctacgggccg    480
```

-continued

```
cccccgccgg ggtacccgcc gcgcccgggc atgccgcctc cctacggcgc gccgcctccc    540

tacggcatgc cgcctcccgg ctacccgcct cgcccccgga tgccgccccc aggcatgcca    600

ccgggtgcgc cgccgccgct gggcggcccg cggccgccct tcccgcccta cggcatgccg    660

ccaccgggca tgccgcctcc gggcatgcct ccccccggaa tgccgccacc aggcatgccg    720

ccgccagggg caccaggcgg gcccctcttc cccatcgggc aagcgccacc gggcgcgccg    780

ccggcacttt tccccattgg ctcttcggcg cagccgccgg ctgcaggggc agatgcaggg    840

gcaggggccg ccgcagcgcc cgccgcggcg ggatcggtgg cgccggcgcc cggcgacggg    900

tcggtggtgg tgtggacgga tgaggagtgt tccattgagg agcggcgggc gcagctgcct    960

cgctacgcga tcgcggccgg ggggccaggg cgcaacgggg catga                   1005
```

<210> SEQ ID NO 143
<211> LENGTH: 1023
<212> TYPE: DNA
<213> ORGANISM: Chlamydomonas reinhardtii

<400> SEQUENCE: 143

```
atgaaggacg acgcggcagc ggcagcggag cgcccggcgg acatgcccac ggacgccgcg     60

gacgctgccg ggccgggccc caactcagct gccgtggccg cggccgctgg ctcagcaggc    120

atgttccgcc gcaaaaaggg tggcgccaac attcgtaagc gcggcggggc ggagggcggc    180

agcgacgacg acgaggcggg gggtggcgtg gtgcgcaagg ccaaggccgc caagtcggac    240

gcgccgctgg cgttcacgac caagaaggac gacaaggaga cgttaatggt ggagtttgcg    300

ggctccaagg cgctgcagga cgggaaagac acgctcgcga cacgcgtgct ggagacggag    360

acggaatatg accgggacgc acgggcgcgg cgcgaggagg tgcttaagca ggccacggcg    420

gcggagggcg cggcggacga cggcacgtac aagggcatga acgcatacgt cgactaccgc    480

aagggcttcc ggcgcgagca cacggtggcg gcagagaagg gcaccggctc gcacggcccc    540

ctgcgcggca acgcctacgt gcgcgtgacg gcccgcttcg actaccagcc ggacgtgtgc    600

aaggactaca aggagaccgg ctactgctcg tacggcgaca cgtgcaagtt catgcacgac    660

cgtggagact acaagagcgg ctgggagctg gataagatgt gggaggagga gcagaagcgc    720

aaggcggagg cccttgccaa gggctggaac ccggacgccg atggcgagga ggaggaggag    780

cagggaggcg gccgggagga tgacgagctg ccgttcgctt gcttcatctg ccgcgagccc    840

tgggaggcct gcaagtcgcc gccggtggtg acgcgctgta aacactactt ttgtgaaaag    900

tgcgcgctca aacacaacgc caagacgacc aagtgtgcgg tgtgcggagt ggccacacag    960

ggcatcttta atgtggcgca ggacatcatc aagcgccaga agcgcatggg cgtggtgggg   1020

tga                                                                 1023
```

<210> SEQ ID NO 144
<211> LENGTH: 1182
<212> TYPE: DNA
<213> ORGANISM: Chlamydomonas reinhardtii

<400> SEQUENCE: 144

```
atggagcgct ttgactccca gatgctgttc agcgtcttta ggaacgacga gggtgaaaac     60

cttttgccgt ttgatgaact ggcggagctg cttcagatgg atctggctcc caatggcgac    120

gccggggcca cgccagcatc gttcgcaccg gacgccgctc tgcccctaga cctcccacac    180

ctgcaccacg cgccacccat catcaccgcg ccgctagtca ccaccgcgcc gcccaccggc    240

cccattccct ctgacgagcg cgccgcagcg ctgacgcacc aaagcactct gcccagcccc    300
```

agcggcggta gcagcgacca cacacgcgcc cagaactggg ccggctcgaa cccatcatca 360
gaggacggcg acggagatgg cgaccgcgac ggacgcgacg gtgacggcga cagcggagac 420
tcagacatgg accacaccac acagacgccg ggcgtcagcg gggccggcga cgcgggcggc 480
cgcgggcggc ggggcagcag caagggcggc aaggcgtcat cgggtgtgaa gaagcggcgg 540
cagcgcaatg ccgagcagat ggagtccaac cgcatcgcgc agcagaagta caggcagcgt 600
aagaagggcg agcagagcgc gctgcagacg gctgtggact tgctcacggc gcaggtggcg 660
gcactcaagg ccgtggaggt ccgcaacggc gagctggagg cggccgcagc ggctctgcag 720
tccacggtgt ctcagcaggc cgccgccgtg gcctcgctgc agcagcacag cgccgggcag 780
gcggcggagc tggaggcaac tcgcgcggcg ctggggcaca gccagcagca ggtggccgcc 840
cagcaccgca tcatcgtgga ccagggcacc aagctgaggc tgcaggagca ggtgattgca 900
agcctgaagg accgactgaa ggaggagatc gacgaggcat tgaagtgcgt ggcgccaaac 960
accgtgtgcg agaagatggt ggcggcggtc aaggccgcgc tgtacggtgc caaggacgtc 1020
agcggactgc aggacgtgct gtcccagctg ccggagcacc tggtgcacga catctgcaag 1080
aacatctggc aggtgtgcaa ggagtcctgg cccgacctgc gcagccgctg cgccaccctg 1140
cacgccgccg gctgccccac cagcggcttc ggcactgcct ga 1182

<210> SEQ ID NO 145
<211> LENGTH: 1212
<212> TYPE: DNA
<213> ORGANISM: Chlamydomonas reinhardtii

<400> SEQUENCE: 145
atgttgcgcc agctttgcag ccgcagcctg cagagcctgg catctctgca gggccgctgc 60
acctcgggct tggcgacgac gcttcgtgct gcgagcagcc tgagcgagct gtcacggcca 120 gcccccttcag tggcgacctc gcaatcacca gcatggtcat atagaaatag caacttgcta 180
gcggcgccac ctctgggctt gggactggcg ccccaggtcc gcgtaacccc ggacgcctcc 240
accatcctca gcctctttgt aagccagcgg cgcaacgcag ccgcagcggc tgccgcggcc 300
gccgtaaaga aggccgcacc ggcaaagaag aagaagaaga gcgcgccgaa aacggcggca 360
agcagcaagc ctaagcccaa gcccaaatcg acagcagcag ccgcaaccaa gggccgcgtg 420
cggaccagac ccgccaaagc cccggcgcgc aagtcgacca ccaccgccgc ggccaaacgc 480
aagaagcccg tccgcaattc catctccgcc gccggccgca aggccgcgaa ggccgcggag 540
gtcaaggccc ggctgcgagt gcgcgcgaca gcgcagcgcg cacgcgcgcg tgccgccaag 600
gccctggcca tgaagcggga gcgcgccaag ctcgcgcgga tcaggcggcg cgagcgcgaa 660
gcgctcagga agcagaagca gcgggaaaag ctggccgcgg caaaggccag ggccaaggag 720
aaggaggcgg cacgcatcaa gaaggcgcca tcggccttcg gcctgtacct gcaagaccac 780
tccaaggcgg tgcgcgacgc cctgcccgcc ggcgccgcca gcggcatgca gcgccaggcg 840
ctcgcgttca aggtgctggc ggagcgcttc aaggtgctgc cggaggcgga gaaggcgccg 900
tacgaggcgc gctcggcggc gctgaaggcg aaggtggcgg aggcgcgcgc ccaggccaag 960
gcggagaaca gcgccaaggc ggccctcacg ccctacatct tgttcttcaa ggagtcctac 1020
agcgccacgc gcgccgcgca cccggacctc aacgcgaagc aggtggctgc caagatgggg 1080
cagttgtgga aggcgatgcc ggcggagcag cagcagcgct accgcgacct ttcagaggcg 1140
gaccggaagg cgaagggcct gcctgagctg aagaagaagg cggcagcgca gactcaggcc 1200
aagcgggcgt ga 1212

<210> SEQ ID NO 146
<211> LENGTH: 1212
<212> TYPE: DNA
<213> ORGANISM: Chlamydomonas reinhardtii

<400> SEQUENCE: 146
atggctagcc tggtctactc ccacgagtgg ctgatctcca actttttgaa agtggaggcc 60
cagtccgtcg actcgccttc ctttaagctg ggccctcatg cctggaagct tcaactctac 120
ccctctcagg ataaaacgca cctgtccgtg tacctgcgct ccgtggagcc gaaagcaccg 180
cgagcagtga acttcaagtt cgtgctgcgc aattggcaag accccaagga tgacttcaaa 240
agcgcagacg caagctacac ctacaccgac gcgtgcgtgg cgggatatgg ctttcccagc 300
ttcattcctc gcgagaagct cagtatcgcc tccggcttcc tgcgtcccac tagtcccacc 360
aacggcggcg cgttgctgct gcgtatagag ctcgagtaca acacacttcc ggcggcctcc 420
agcgcggcgg cggatggcag cagcggcggt gacggcggcg gtggcgttta cccggcaact 480
gtgtgcgacg gcgcggtctc tgccggtagc ggcgacattg ccacggacct gctctcactc 540
tggaagcgcc ccggccccac ctccgatctc attatcatcg ctaccgcgcc cgccggtgcg 600
gcggcggcag tggcggccaa cccaacagca gaggtcttgg gaacgggagc gggcgcggct 660
gctaccatca aacccaccac tgccacggcg gcggctgacg gcggcggcag cagctgcggc 720
cccagcaaca ccggcatgcg gcgcttcgac gtgcaccgcg ccatcgtggc cgcgcgctgc 780
ccctacttcg ccacgctgtt tgacagcggc atgcgcgaca gcagcgcacg cgaactgccg 840
ctgcccgaca ccgaccccgc cgctctggag ccgctgctgc acttcatgta cggtggcggg 900
ctcaccgtca ctacccgcca gcaggcgcgc agctccttgg agctggcaga ccggctgctg 960
ctgcccaagg tggcggcgct gctgcggacg cacctgctgt ccaccgtgac tgtggccagc 1020
gtggtgcaag aagttctgtg ggcggcggac gcggcgcaaa cagagctgtt gacgggcctg 1080
ctagatttcg cggcggaggc agaggctgac ctgccagagc gcgacctgca gcagctggcg 1140
gcgcagcagc cggcgctgat ggcacagctg ttcacggccg ctcgccgcgc cgcgaaacgc 1200
tcgtgcacgt aa 1212

<210> SEQ ID NO 147
<211> LENGTH: 1506
<212> TYPE: DNA
<213> ORGANISM: Chlamydomonas reinhardtii

<400> SEQUENCE: 147
atgaagatgt tggaatttcg cctgaagctg ggcaccggag cagactggga ggcgctcgga 60
cctattccag agccgtttcc gttctccatc gacgcggact gcaccacttt ggcttttaag 120
cactacctca gccacaaaat cctaaatggg gtcttcgagc ctggaaactt tcagcttcgg 180
ctgcagggct gcgacaagga gctggaggac gtcgctgacg ccggccaacc caccacttcc 240
acgcaccaac cccagctgcg gcggcttgcc agccagggcg tgtgcaacgg cagcgtgctg 300
cagcttgacg tgtgtgcgac tgaggaggag ctgcagcggt tcctggacgc agcggaggag 360
tgcggcacgg ctaacgagct tgggcacgtc gaggagcagc aggaggcgca gacgccacca 420
gcggcaggtg tcgatccgcg gcagcggcac gcagcagaag gcagtgcggc ggcggcgggc 480

```
gacgggccaa ccgggcggcc cagccttggc atgatgcaca cgcctgcggg cacggtgggc    540

acctttctgg acgatgaaga cgcggactac ctgcaggagg acctagaggc gctggtgcag    600

ccggcggcgc agcgggctgg ggaggaggag ctcgatcact taaacgtggc ggccgacggc    660

gagcctttttg aggccgagga cgctgaggac tttgaggcgc atggcaggga gttgcgagga    720

gcaggaggcg ttgtgggggc ccctcagcaa cagcatccgg ccttcgcggc tgcggcggag    780

gggcgagagc aggaaggtga cgacgaggac tggggcgaca tgggcctgcg gtcagccggc    840

actcggaccg cgggccagcc cgaacggcgg gctgcggtcg cgacgccggc gcggaagcag    900

caacagcaac agcagcgacc gcgggctaac ctccagtcag cggccaagcg ggcgcgcagg    960

gaggcgccgg aagaggagct tgacttcgtg tcggggtcag cggacgaggg cgctcagccc   1020

gcccagcaac agcagtgcac gcatggcgcg gcgatcgtcg gcggcagcac cagaggcgcc   1080

gccgcgcctg cacgcgcggc ggcaacgggt gctgccactg ctgctggcgc cgccgcacct   1140

aggtcgcagc cgccgcgaca gccggcactt gcacggtcta cgggactgcc ggcggccatg   1200

cagcctgcag tggacacggg cgcatttagc gcctacggcg gtggcggtgg ccagcagcga   1260

gcctcaagtg gcttctggtc gctggaggag actgaacgcc tggtggagtg ggttgactcg   1320

cacggcgcgc ggcagtggac catgttcgta cagctgaaca ccgacttaca cagagacgtg   1380

gagcaagtga agatgaagtg gcgtaacctc aagaacgcca gcaagaagcg ctggaccgtt   1440

gcgcggagag tacctccgcc ggacctgcgg gcacgcatcg acgagattgt gcgtcgggac   1500

acttag                                                               1506
```

<210> SEQ ID NO 148
<211> LENGTH: 900
<212> TYPE: DNA
<213> ORGANISM: Chlamydomonas reinhardtii

<400> SEQUENCE: 148

```
atggctgcaa gcacgctcgg ggatgcgcag caggtcgaat cctttgtgca ccagctcata     60

aatcctgcga cacgcgagaa tgcgttgttg gagctgagca agaagcggga gaatttcccg    120

gagcttgcgc cctacctctg gcactccttc ggggcaatcg cggcgctgct tcaggagatc    180

gtggccattt acccgctgct ctcgccgccg tcgttgacag cacatgcatc aaatcgcgtg    240

tgcaatgctc tggcgctgct gcaatgcgtg gcgtctcaca atgagacgag ggcactgttc    300

ctccaagcgc acatcccgct cttcctgtac cccttcctcc aaaccatgag caaaacgcgg    360

ccgttcgagt acctgcgcct gaccagcctg ggcgtgatcg gcgcgctggt caaggtggac    420

gacacggacg tgatcaactt cctgctgtcc accgagatca tcccgctgtg cctgcgcacc    480

atggagatcg gcacggagct gtccaagacc gtggccacct tcatcgtgca gaagatcctg    540

ctggacgacg tgggcctgaa ctacatctgc gccactgccg agcgcttctt cgcggtgggc    600

gccgtgctgg gcaacatggt ggtggcgcag gcgcagatgg tggaccagcc cagccagcgg    660

ctgctcaagc acatcatccg ctgctacctg cgcctgtccg acaacccgcg cgcgcgcgag    720

gcgctgcggt cctgcctgcc ggagctgctg cgcaacacgc agttcacggc gtgcctgaag    780

aacgacgaca ccacgcgcag gtggctggcg cagctgctca tgaacgtggg cttctccgac    840

tccgccgcgg cactgggtgc gcccgacgtg gtgcagccat cgcccgtcat gggcgcgtga    900
```

<210> SEQ ID NO 149
<211> LENGTH: 999
<212> TYPE: DNA
<213> ORGANISM: Chlamydomonas reinhardtii

<400> SEQUENCE: 149
atggggagca gcagcgaacg attgccagca ggttctggta gctgcctaca ccctggctgc 60
agcggattgt gctgtctggc aaaagcccca gtctccgaca ccatcgtcgt ttctaccgcg 120
gccccctccg cgggttgtga cctgaagctg gtgtgctgcg acggcgcgct gatggccagc 180
cgctgcgtgc tgtgccgcgc ctcgtccgtg ctgcggtcaa cgctggagct ggagctgccg 240
gaagcaggcg agctgcgcct gccggcagac aaggccgagt cgtggcgcat ggccctcagc 300
ttgctgagcc tggaggcgta cccgctatcg ctcgtgacat cggacaacgt cgtggacctg 360
ctgctgctgg ccgacaagta cgacataccc atcgtccggg gcgcctgtgc gcacttcctg 420
cacctgaacg cgcggcagct atctctagtg ccgccgctgt cctctgcctc caacctgctc 480
accgccgcca gcctggtcat caagttcgta cagccgtacc cggggctgca gcagtacggc 540
agtacggtac aggcccgact ggatgatgag ctggcgatgc tgaggatgcc gccggacgtg 600
ctgctggcgg ctgtccaggc tgcgggcggc ccgggcgccc cggaccgcgc cgcctccgct 660
ctggcggcct ggcagcgcga cctggtgcgg ctgacgtccg agctgcacgt cctggtgggc 720
gccgccgact acgcaggcac cgtggcgccg gaggtgcagg cggctgtgac cttggggctg 780
ctggcggcgg tgcggcacag cgcctcccgt gtggcgccca cgtgcggccg ctgcggcggc 840
gtgctgcagg cgggcccagg ggcactgcac gcagactgcg cggcagcgca atacacagac 900
ctgcacacac gcggctgccg gctgtgcaat gcgcccatgc tgcccaccca tgcgcgcttc 960
tgcaactcgt gcgcctaccg caagcacaag aagtcataa 999

<210> SEQ ID NO 150
<211> LENGTH: 1011
<212> TYPE: DNA
<213> ORGANISM: Chlamydomonas reinhardtii

<400> SEQUENCE: 150
atggggtttc cgcagctgat ggtgcaggtg ctgccagcgc aggcggccct ggcagcccac 60
cttcaacagc agcaacagca gtccatagcg gcggcactcg cgccccagct ggcggcggcg 120
gtgcacgcac acgctgcgcc catggcgcct ctagctgcgc cgccggcgca gatacccgcg 180
cgcgtggcct cgcccacgta ccgtcatacc gggagagcgc aagccgcgga agccgccgcc 240
gggtcgcgag caccggttag ccatagcacg gtggaaaagc agcggcgcga ccgcatcaac 300
tcgctgatcg acgagctgcg ggacctcgtg ccgccgacgc agcagcaaca gcagcaacag 360
cagcagattg ggtggtcac cattggtgtg agcgacaacc cggaggcctc gtcgcggcgg 420
cccaagcacg tggttctggc ggacactatc aacctgctga aagcgctgag gcagcgggtg 480
tcgtttgcgg ctgtgacggc ggagctgcag cagctaccgg cgggcggcag cggcggtggc 540
ggtggcggcg gcggcggcgc actaccactg ccactgccgg tgccaggcat gtacggtgct 600
gtggcaggcg cgggcatggt gccgggcatg cccgggagcg gcgtgcagcc agtgaagcag 660
gagccgcagg ggtcatccag ccaagatgat gacgacatgg gacaccccgg gggccccggc 720
gtcacagtca agaaggggcc agactgtttc tacgtccagg tcacatgtcc ggaccgcaag 780 ggctgctgt cggacatcac cgacacgttg cggaacttat cactggaggt ccgcacggcc 840
gccgtcacca ccaatggcgg ctcggtgcgt gacgtgttcg aagtggtgcc ccctgacggc 900
gccgtcgcac tggcgcccga ggcggtccaa agcatggtgc agggcgcgct gtcgcagcgc 960
gtggcggagg ggcagcagga ggtcacggca ggcaagcgcc cgcgtgcatg a 1011

<210> SEQ ID NO 151
<211> LENGTH: 1197
<212> TYPE: DNA
<213> ORGANISM: Chlamydomonas reinhardtii

<400> SEQUENCE: 151

```
atgtttccaa acccattttt cggcatgggc gcgcccttcg ggccgggcat gaataacatg     60
ggtggtatgc cgggacagga gatggctggg atgccggggt tcccgggcat gcctggtggc    120
acgatgggtc cggggatgcc cggcggcaac atgggtggtg gaggcggtat gatgggcggt    180
ggcccgatgg gcggccaggg acacggcgga ggcggaggag gcggaggcgg tggcggcgag    240
ggccaccggg gcggcatggg cggcggcgga gggcggggcc ctggcggcga caagcgcccg    300
ggtatgtgcg tcaggtggtc caacagcggc agctgccagt tcggagacag gtgcaggtac    360
ctgcacgggc aaggcgacag ccggtacccg ccagggccat ccgacggcgg gccgggaggg    420
ttcatgggcg gcggcggtgg cggcggcggc ggcggtccca tccgccgcgg cgggagaggc    480
ggcggcggcg acgatgggcc gggcggccgc ggctcccgcc ctacgggccc caagacgcgc    540
ctgtgtgaga agttcatggc cacgggaacg tgtcggtacg gcgacacctg catatttgca    600
cacgggatgg aggagctgcg gccgggccgt gacgccggag gcccgcctcc cccgcagccg    660
ccgccacaac aggcgcagca gatgcagcag cagcaacagc agcagcacca acagcagcac    720
cagcagcagc aacagcagca acaccggcag cagcaacaag acgggggcaa cgccacgtca    780
ccttcgcgag gcgcctttgg cgggccgagc gggagaccgc aggcgcagca gggtgggccg    840
gcggcgggtg cccgtgggca gccaccacca gcagcagcaa gtgcgccaca ggatgcagcc    900
gctgcgacag gcgcacaagc agccacagct gcagcaaccg cagccgcacc ctccaagccc    960
caggaggtca cctttgtgga caaggtgcgc gcgctgtgcg gcgtgctgca catcggccag   1020
gcggcggcgc tggcggcgga gaagccgctg gcgctcacca ccgcggccat gtcgctgcga   1080
gccggcaccg cctacaagga gaacccttttt gcggacggag tggagagata cgtggcgatc   1140
tcggccggtg gagggggagg gggaggcagc gccggccagg ggcagatgca gcactag      1197
```

<210> SEQ ID NO 152
<211> LENGTH: 1065
<212> TYPE: DNA
<213> ORGANISM: Chlamydomonas reinhardtii

<400> SEQUENCE: 152

```
atgattaaag gcgtgaaccg accagccatt ttctatgact tggtcgggct tgcgcactca     60
ggcgtggtat ctgtgggcag agagagcgat tctactatac gcctcgactg cccggaagtc    120
cctttcctgc tctcgcgcaa gcatgctaaa atttgcgtca atccagacgg cagccttatt    180
ctgaaggaca tcaactccac gaacggcacc tacatcgctc gtgaaggcga atttctcagg    240
cggctgcggt cggatgaggg ctgggagcta cgccgcggcg acctgattgg ctttggcggg    300
ccggagacca ttgttgcgcg tagcgatgtg ccggacgtca ccgtcgccaa cccccttcctg    360
ttccgctaca cgccgctgga cgacgatgca gatagtgcgt ttaactcgtc tgcagagcag    420
cagctgctgg gcaacggagc gcagggtcgc gcacggaaat tcagcgaaat tgaagaccgc    480
tgccagcaag aggacatgga ctgcgaggtg gcgtccacca gctcacccga caaagagagc    540
aagaaggcca agacggcggt gacagcaaag gacatcgtgt ctaacctagc aaaccaccta    600
acgtgtgcca tctgccacga ctggctcgct ggtgcacatg cgctaacatg cgggcatatg    660
ttctgcggca tctgcctcgc ggggtggctg gcacaaaagc aatcctgccc ggagtgccgg    720
```

```
aaaccgagtg caggtgtccc tgtgaggtgc cgcggtgtcg acaactccat ctctgacatc    780

ctccaacaca acctggtgtc gccgaactca aagcgtgaaa ggcgtcggaa gcagctggcg    840

tgggaggagg tcggagacgg tgtgcttgaa agctggacaa atgcgatgca gcagcggcgg    900

caacaggctg tgaacgtagc atcgcaacac ctagcaaacc tgacggggca acctgcacct    960

gcgccggttg ctgctgcacc acgaccagac ggcgccgtgg ttggtcagaa cacgcggcgg   1020

gccaaccaag gcggcgcgcc gccagtcaac cggccagccc ggtga                   1065
```

<210> SEQ ID NO 153
<211> LENGTH: 1179
<212> TYPE: DNA
<213> ORGANISM: Chlamydomonas reinhardtii

<400> SEQUENCE: 153

```
atggagggct ggggagcagc atccaccatc ctcggggtgg cccatttgcc acccggcaac     60

gcttggggcc cggaggagtg cctaaccttt catacccgaa ccgcggtgta ccgccttccg    120

ctcagcgcaa ccgcctccgg aggcggcgcg acgccgcagc tgctggcggg gcaggagagc    180

gagcggggcg cagcgagggt cgatggcagc ggtgccgacg cccggttcca tcacctcagc    240

agtgcaggcc tccaggtcaa cgcagacggt cggctgttgc tccttgactt ggactcaaca    300

gcggatgtaa cgcgcctgcg cctcgttgct cctggtggaa ctgttagcac ggtgacaggc    360

gtggagctgg ctggccggtg ggtagacctg gtaatcctgc caaacggcta cctagctgca    420

cgtgaaattg cacaagtgca gtctgacggg gacctggatg aagacgaaat ggcagagccg    480

tactgggaga gcaagcgcgt tgcggtgatt gcgaccagct tcacaccact ggcgcttgtg    540

gcaacagcag cagcggcggg gccgccgccg cgcagcctgc ccgccgacct gggtgcgctg    600

gtggaggacg cgcagcaacc tggcggcggc ggcgcagtag cagacctggt cattcgcgtg    660

ggcgagcggc gctttcactg ccaccgggcc atcctgtccg cgcgctgcga ctacttcaag    720

caccgcctgg cgggcgacgc gttcgaagac gcgcgcgcgg cggagctgga gctgccggac    780

gcggaccccg acaccttcgc gctgctgctg cgctggttgt acacgggcgg cgcggacatt    840

ttgcctaaac aggcgcgcgg cgtggctgag ctggcggacc ggctgctcct gcctgagctg    900

tgcgcccgcg cgttggacgt gttgttcgcg tcagtggacg ccggaagcat cgtggacagc    960

ctgctgtggg ccgcgggctg ctgcgaggcg cacggtggcg gcggcgcttt cgatcagctg   1020

ttgctgcggc tgaagcgctg gtacgtcgag cgggcggcgg aggtgcgggc cgcggcgcga   1080

gacagcctgc gggcgctgat gacccagcag cctgacctga tgctagagct gatggaggcg   1140

agcgagcagc gggcggtgaa gcgggcccgg accaagtag                          1179
```

<210> SEQ ID NO 154
<211> LENGTH: 1590
<212> TYPE: DNA
<213> ORGANISM: Chlamydomonas reinhardtii

<400> SEQUENCE: 154

```
atggcggagc ttgaggatga tgtcctcgtt caggccggcg agcaggacga tgccaacgac     60

ctcaaccggc agctgttcgg tgccgatagc gacgatgagg gcgcgccgcc cgcggccgac    120

ccgcacgccc aggcgcagca cctggcggag caggaggcgc tgctggagga tgacttggag    180

gacgcagacg tagacgccga ggcggcgcta gaggacgagc tgtcgggcgg cagcagcgac    240

gacggcgggg cggtcaagaa gggcaagaag gataagaagc tgcgcaagaa gcgcgagggt    300
```

```
ggcaaggacg acaagcccaa aaagaagcgc cagcggggcg agggcggcaa gggtgagaag    360
ggcgacaagg cgggaaagaa gggcaaagcc ccgaaggaga ccatcgccac gggcaggtct    420
cggcggacgc cgggcggtgg cgaggcgggc gaggagcagc agccgcgccc acgccgcccc    480
gtgggcgagg gcggagacga cctgcccagt gatgagctgc aggagcagga ggcggaccgt    540
gccttcattg acgatgacgg tgcggagccg gttgccagtg atgatgagaa tgcgccgcgt    600
gtggtggcgg acgaggcgga ggaggcgatt gacgcggacg aggaccaccc cttcaagcgc    660
aagaagcgga agaaggagaa caccggcaac gtggagctgg agatcaagga gatgctgggc    720
aagatggagg cggccatgga gcatgacttc gagacggtgg cgcgcaacgc gggcgtggag    780
ctgaagaagg acagcggcga caacctggtg acggacgcgg aggggcacta cgtggtggcg    840
cgcaaggggc cgccgccggc ctccaagagc cccgccatca gcaagctcag gctgctgccg    900
gagctggagc tgttcctggc gcagcgcaag taccacgaga gcttcctgca gcagggcggg    960
ctgggtgtgc tgaagggctg gctggagccc tactttgacg gcacgctgcc caccatgcgc   1020
gtgcgcacgg cggtgctcaa ggggctgcag accctgccca tcgacacgcg atttgaggac   1080
cacaaggaga tgctgcgcaa aagccaggtg ggcaagaacg tgatgttcct gttcaagtgc   1140
tcggaggaga cggccgacaa ccgccgcatc gccaaggagc tggtgcaccg ctggagcaga   1200
cccatcttct acgaccagga ggcggaggag gccaagaagc agctgcacca gcagcagctg   1260
ctggaggctc ggcgcatgga gctggagcgc cgccaggcag acggcggcga ggaggacaag   1320
agcgcgtcgg cgcaagtgcg caacaaggcc atgcgcatcc acgcgctcat cccgcgggcg   1380
tccaagctgg actacgtgaa caacccgggt gcggccaagg acttcaacga gagcgaggtg   1440
gccaacgccg ccgccgccgc cggccccaag tccaagcagg tggacgcgct caccaagcgc   1500
ctgcgtgagc agcagaagaa gctcaaggac ggcagcgcac gcgccatgaa gcccagtgtg   1560
gagggccgca acattgtgct catgaagtag                                    1590
```

<210> SEQ ID NO 155
<211> LENGTH: 861
<212> TYPE: DNA
<213> ORGANISM: Chlamydomonas reinhardtii

<400> SEQUENCE: 155

```
atgtcggtcg tgtcagcgaa cagcagcact ggccgggagc cggagcccgc cacctccagc     60
acctcctctc ccgccacagc cgcgcccacg ctgccactac gcagtgccgc atccggggac    120
gccacggatt ctgagtccaa cagccccggc cccagcaccc cctccgcccc ggggccgcgg    180
caggtaccca ccgtggatgc agtattcccc acgcggtacg gcacacgctt ccgcgtgcgg    240
ccgtacagca acaacgagta cggctccatc attgacttgc agtcagaggc cttccacacg    300
ctcaacccgg tgcccttcct gaatgacttc acctacaagc gcttccgggc cgaggtggtg    360
gatgcgttga agcagaagac caaatactcg gacccctccg tcttccagct cctcgtggcg    420
ttggagcagg agccggagca ggagccatca ggcagcagca gcagcagcag cagcaacaac    480
ggcgatggca gtagcaacgg caacagcagc agcagcagca gcagtgccaa ggtggtgggg    540
gtggtggagg tgtccctgat ggaggagcgg ggggtgctgg ggtgcctgcc gcccggcacg    600
cgcgagtacg cctacgtcag cagcatgtgt gtggcgccca ccgccaggcg gcgaggcgtg    660
gcgcaggcgc tcatgagcgc ggcggaggag caggcgcggc tgtggggtca gcagcagctg    720
gcgctgcacg tgtaccgcga caacacgccc gcggtgcagc tgtacggcgg ctggggcatg    780
```

gccgtactca acaccgaccc cgactggaag gcctggttcg gagaccgcgt gcggctgctc 840
atgcacaagc ggttggcgta g 861

<210> SEQ ID NO 156
<211> LENGTH: 861
<212> TYPE: DNA
<213> ORGANISM: Chlamydomonas reinhardtii

<400> SEQUENCE: 156
atgcgtaccg caatcctcgc cccatcccac ggccctgcct cctccttcca gcaacgcaca 60
aattcggtgc acacgcggac tgtactcgcg cacggcgctg cggggtcggc gaatcgctcc 120
tctgcaccat cggcatcgac gacccctcg gcctcatccg cgctggatgc aacccaaccc 180
atcatccgga cgctgaagga gtgcgacact ggagccatca cgcgcgcgtc ggtgtgcttt 240
ggccggtcga tgcggaccga ccccaccatg acctacgtca ccgggggccg ctgcccggag 300
cgcgtggggg cgctgttcga gcaggtggca accatgtgca tgcgcggtgc ccgcgacccc 360
gccaccacct ggctgctgga gacgccccgc agcggcggcg acagcgacag tgcggatgtg 420
gtgtgcatcg catgcgagta cccggcggcc taccccagcg actgggagct gctgcgcgcc 480
gggctgctgc gtgtgctgct ggcctgcccg ggctggggcg tgctgcgcgc gctgatgaac 540
atgctggacc agttcaacgc caccaaggcg cagttcaaca aggagcacgg cgatttcctg 600
tacattgcgt gctttggcac tgccccggag cagcagggcc gcgggctggg ctcacagctg 660
atgcggcggg tgctgcagca cgcagacgcc aaagacctgc ccgtctacct ggaggccagt 720
ggcgccgcgt cggcggcgtt ctaccgccgc cacggattcc aggacattaa gcaggtccgg 780
gccagccccg gcgccccaga cctcatcatc atggcccggc cccgcgcctc gcagctgcag 840
cagcacggcc agcagcagta g 861

<210> SEQ ID NO 157
<211> LENGTH: 1182
<212> TYPE: DNA
<213> ORGANISM: Chlamydomonas reinhardtii

<400> SEQUENCE: 157
atgagcgtcg ccaagtatac atacgagtgg ctcatcaagc gttccgctga gctccctgac 60
gctgtcgaga cacccgactt cgtgctgggc ttctatacct ggaggctgcg gctgcatctg 120
cgccagtcga tcaaccttcg aaagcacgtg cccctgtacc tgcaccatgt gccagtacgg 180
ggaggcgtgg acgcgccgcc gcccctgaag tacacttttg tagtgaagaa ctggaaggac 240
ccatccaagg accatgtgac tgagggcaag cccggtacgg tcttcaacct caaaaacgca 300
aaatggggca aagagctgat cttgcgggac cagctgatgt ccattgacac ggggttcctg 360
cgctgtgacg gctccctgct gctgcggctg gagcttcaaa tgccggagaa gaaacaatgg 420
agcgatgacg atgacgactc gaaatatgac tcggatgagg aggaggccta ccctgcggtc 480
ctcaaggagg gctcgggcgg cggcagcagc atcggcagcg atttcctctc gctgctggcc 540
gatcccggcc ccaccactga cctcaccatc accgcgacag cagcggtcgc gggcggtgtt 600
acgggggccg ggaaagaggg gggaagtaag aagcgaaaag ccgacaccgc cagcagcaac 660
ggcggcagca ctggcgcaag cagcagccgc ttccccgtgc accgcgccat cctggccgcg 720
cgctgcccct acttcgccac gcacttcgcc agcgggctcg gcgacagcaa cacgcgcgag 780
ctgcacatgc cggacaccga cccggacgcg ctggcggcac tgctgcgctt cgtgtacggc 840
ggggagcttc gtgtggcttc ccgggagcag gcgtcgcgct gcctagcgct ggcggaccgg 900
ctgctgctgc ccaaggcggc agggctgctg cgagcgcacc tgctggccac cctgtctccg 960
gctaccgtca tggcggacct gacgtgggcg gcgggtctgg cggagggcca ggggcaggcg 1020
gagttgctga cggggcttgt ggactacgcc gcagagcagg aggcggacat tgcagaggag 1080
caggtggagc agctggcggc ggcacagccc gcgctcatgg cgaagctctt tacggcgcgg 1140
gtgcaggctg ccaagcgctg ccgcgtgtgg aaggcatgct ga 1182

<210> SEQ ID NO 158
<211> LENGTH: 1230
<212> TYPE: DNA
<213> ORGANISM: Chlamydomonas reinhardtii

<400> SEQUENCE: 158
atggataact cacctgcagt gctcaatgga gcagcggaca actcggaact gcccatggct 60
caagttaaaa ggataatgca cagtagaggc gtcacgtcaa atgcggaaag cagctttctg 120
gtcgcccgtg ctgcggagat gttcttggat gcgcttgtgg cgcgcgccgg cggcgccatg 180
gcagcggggg gcgaggcgga gctccgatac gatcacgtgg ccgacggcgt ccagacctgg 240
gcgccaggga gccgcctgct gtcagacgcg gtaccgaagc gcgtgcatgc cgggcagctg 300
cgacgggacc cgcgcttcaa cggccgcacg ccgtgggtgc tgccgccgcc agccgggcag 360
cagcagcagc ctcatcagga gcacacggcg gtggcggcgg cggcacaacg aggcccggcg 420
gcggccgcag cggtggcgca gccgatgggt gtgccccagg gcgtgcctct gggtgtgcct 480
caagcgtccg cgccagggat ggcgcatgcg cacgtgccgc atctgcccat acacgcagct 540
gccatgcagc agcagcagca gtcgcacaac catgttggcc cggcgcaggt accgcaagcg 600
gtgttgccac cgccgcagca gcatcagcac caacaccaac aacagcaaca gcagcagcaa 660
cagcaacagc agcaagccgc tttcgcgcag cacctgcagc aacagatgct catgcagcag 720
caagtactac tgcagcagca gcagcagcag gcgcaggcac agcagcaagc gcttgcgcag 780
cagcaggcgc agcagcaaca acaacagcaa caggaggccg ctgcggcggc ggcggcggcg 840
gcggcggtgg cagccgcgac ggcggcgcag cagcaggctg tgagctctgt agcgaccgtg 900
tcgcaagctg ttgcgggtat ggtgccgggc ggcgtgccgg cgccgcagga cccgcaccag 960
caacatcaac aacaagccgc agccctggcc atgcagcatc agcttatgct acagctgcag 1020
caccagcagc aaatgcagat gacgttgatg tttcaacaac agctacagca gcagcagcaa 1080
caacagcagc agcaacagca gcatatgatg atgatagggg caggtcagca tccctacttc 1140
ctcggcggcg cggcggcggc ggcggcgagt gctggcggcg gcttcggcgg gggctctgtg 1200
atgggcatgc cggcacaggg cgggcagtga 1230

<210> SEQ ID NO 159
<211> LENGTH: 1416
<212> TYPE: DNA
<213> ORGANISM: Chlamydomonas reinhardtii

<400> SEQUENCE: 159
atgtcaagat gttcgttggc gctggggctg tttggacttt tgctggcggg catggcgggc 60
atggatggtg tggatgctgc tggcagcaaa ataactgccg cggacctagc aaacctcaac 120
ctatacaagg tgttgggtgt cacagccaag gctacttccg tggagattgc aaaggcctac 180
cgcaagctgg ccatcaagta tcaccctgat aagaatcctc agggtcagga ccagttcatc 240
aaaattgcat acgcctatga gatcctgggt gatgagacca agcgggcgcg ctacgacgcc 300

```
ggcggcttcg ctgcggccac cgagttcgcg gcgcaggcgc ccaactggga cacctggcag    360
ccgcccgagg cgcccagcgc cactgtgttc gaggagtggc aaaaccacaa catctactac    420
gacctggcca tgctagtggc actgctggcg ggcggcgcgg cggcctgggt ggcgtgggtg    480
caggcctctg agcggctcaa gcgggcacgc aaggcagcac gcaaggcagc ggggggcggc    540
aagtcggctc cggcaagcgg cgccggcagc agccgcccac ggcggcagcg ggtgcagtcc    600
agcggcgcgc tgtcaacagg gtcgggcgcg ggcatgggcg gcagcgacag cgacagtgac    660
gaggccggcg ggggcgccag ggccgatcaa ccagacacgg cggcccgggg tccctccggc    720
tcgctgctgc tgcagcccgc caaaccggcc ggtggctcgg ctgcagctgc catgcgggag    780
tggagcgccg aggagctgcg gctgctagac aagggtctga agaagttccc cgtgggcacc    840
gtcaagcgct gggaggcggt gacgggcgtg gtacgcactc gcaccctgga ggaggtgctg    900
gtcatggtca agaactacaa gggcgggtcg catctgcggg ccagagtgca ggaggattgg    960
aaggcggggc ggaaggcggg ggccgcaacg gtagcggtgg cagcctctca ggcggcgccc   1020
gacatacgtt acgatggccc gcccactgtg aatggcggac cagcggacgg agagcacaca   1080
gcagcggtgg cggcagcggt ggcagcaaca gcagcagcaa ccgccggggg tcaggtgcta   1140
gccaccggtg gcgggaccaa ggcggccaag gcgccggcag ggacagagaa ggcgggcgtg   1200
gatgcgccat ggaccgaggc ccaggaggtg gcactggtgg cggcgctgaa gcagtgcccc   1260
aaggagctgg gcgcggagcg ctgggacgcg gtggccaagc tggtgccggg gcgcagcaag   1320
gcgcagtgct tcaagcgctt caaggagctg agggacgcct tccgcagcaa gaagggggcg   1380
gggggtggag cggagggaga tgacggcgac gactga                             1416
```

<210> SEQ ID NO 160
<211> LENGTH: 1458
<212> TYPE: DNA
<213> ORGANISM: Chlamydomonas reinhardtii

<400> SEQUENCE: 160

```
atgcatgaag gacaaaacac atgtggccct gcgaccagag gtcatgccga cggaggtggt     60
ctcggcgtgc acttgcttgt ggcgggagcg attctccacg gccttgcgtg tgacgcgccg    120
gctgcgctcg cagcactttg gcttgaacgc tgtatcgcct ataatcctgt gcttctgaca    180
cacctcgacg gcgtcaacga cctgccagcg ccacggaggt gcggctgggg ccgcgcggcc    240
ctgccctggg cggcggtgag cttggccggc ggcctcccag ccattgacaa gggcagcacc    300
acacgtcacg tgtgtgctgg ctgccaccag cacctcacca cctctgacct cgcacgcctg    360
gaggagcagc aggagcagtc ggcgccgcgc cacctgcacc cgcacccgca accgcagacc    420
ccaggcgcag tgctgcagtg cgatggctgc caccgctgct tccacggccc ctgccaccgg    480
cggtgggccg ctgcggcgga gcaggagcag cgtcggcggg cacgggtaca cgcggcacgt    540
gatggccggg acgggtcggg gaggcggcaa cagccggagg ccgtgagggc atcggcggcg    600
gcggtggagg ctggggaccc gggcgacgac ggggcttggt tccatgatac ggagtgcaaa    660
caggtccggg tggcgctgct gcggctgtgc cggcgggggg acatatggct gcctgagggc    720
acatcaacat cgccgccagc aatagcagct gcaccacccg caccagcagc cgcgagcagc    780
agcagcggca gcagcctcgt tgcagcacca gaccacgcgg ccgcttcagg tcgcccagat    840
gctgcgccag gcgccagccc gcccacgacc ttgacctcga ccgcgacacc acacagcgta    900
cctgagtccc cgcagcagcc gcggcaacgg ctgcgcatgc gggtgtacga ctgcaatgac    960
```

ggcgggccgg cggcggctgt cggtctgcgg cgtgtgcacg gcgtgctgcg tgccgcgggc 1020
tttggctacg gcctgagcga cctccggcag tttgatgtgg cggcgttgct gatggccgag 1080
gactcgggcc aggccctgtc cgccgccgta ctggacgtgt acggctcaca ctttgcggag 1140
ctgtacctgc tggccacatg cgccgccgta cagcggcgcg ggtacggccg ggcgctggtg 1200
cggcaactgg agcaggagct agcggccagc ggcgtgcggc ggcttctggt gtcggtggac 1260
gatgacgacc tggtcaatca ggggctgtgg caccacgcga tggggtttgg gtccgtgcct 1320
gacgcagagc tccggcagct ggcgaggagc tgggggggcgt tcgggccggc ggcgcggcgc 1380
ggcaccgtgt tcctgtaccg gcccctgctt ggcggagctg gcgaggcgca ggggcagggg 1440
cagcacggca agcggtga 1458

<210> SEQ ID NO 161
<211> LENGTH: 1023
<212> TYPE: DNA
<213> ORGANISM: Chlamydomonas reinhardtii

<400> SEQUENCE: 161
atggttgcca gcagcagcgc cgaggagcag ccgcgcgtag tctcgttgag ctcggccaat 60
cggcagcagc tctcgcgcgc ggcagtctgc ttcggtgcgt ctatggtgga ggacccgatc 120
ctcatgtggg caacggacgg caagaacccc gccggctcag taggcttcta cacaaagatg 180
gcggaggtgt tcttcaatgc gatggcggac cgcagctggt gctgggcgtt gcaggcgcca 240
gccaatgcca aagcgctacc cgtggtgggc ggtgaactgg acgcccacac tccgcagagc 300
gtgtgccttg cttgtgaggt gccgcgcgcc taccccctccg actggcagct cctgtgcgcg 360
ggcatggtgg ggctgggcct gcgctccccc agttggcgct gcgtgcggat gttcctgcac 420
ctcacgcccg agttccagaa gcggcacaag gccttccaca cggagcacgg gcccttcgtc 480
tacatcgccg cgttcggtac ccggcccaag ctgtggcgcc gcggccgcgg ctcccagctc 540
atgtcggctg tcctcaagat ggcagaccag aagaacatgc actgctacct ggaggccagc 600
agcgacgaca gccgccgctt ctacgcccga cacggctttg cgctgaagga ggagctctgc 660
gtgctgccgc tcacagcctc cgacgccgcc ggcgcgccgc tgctgtacat tatggtgcgg 720
ccgccccagg gcgccggtgc tggaggtgcg ggcggtggtg gtggcggcgc gggtgcgctg 780
gcggccggtg ttggaggcaa gggcgccgct gcggctggcg ctgcggtggg accggtggcg 840
gcgccggcga aagcggcgga ggtggtggtg acggcggcgg gcggcatcgc ggcgacggtg 900
gcggtgccag aggcggcggc ggcagcggct gcatccacag agccgcagaa gcagacggcg 960
gcggcggcgg ctgaggctgg gcaagctgga gagcgtgcgc gacaggggga tgagcaggtg 1020
tag 1023

<210> SEQ ID NO 162
<211> LENGTH: 618
<212> TYPE: DNA
<213> ORGANISM: Chlamydomonas reinhardtii

<400> SEQUENCE: 162
atgtctgacg atagcgatgt ttcattgcca aggactacct tacaaaaaat gatcaaggac 60
ttacttccac cggacatgcg ctgcgctaat gacacggtgg agatggtcat tgcgtgctgc 120
accgagttca tccagcttct gtccagcgag tctaatgagg tggcgacgcg ggagggccgc 180
tccatcatcc accctgacca cgtcatgcgc gcgctcacgg agctgggctt ccaggagttt 240
gtgggcgagg tgaacgcagc gctgcacacc ttcaaggaag agaccaagac ggcgcactcg 300

```
cggaaggccg acctgaggaa gacgggcgcc gagcaggcgg ggctcacgga ggaggagcag    360

atcgctctac aacagcagat gtttgcagcg gcacgtgcgc agtccatgac cacgagtgag    420

gtcgccgcct ccatgaccgc ctcctacgac cgaatggcaa tggcggcggc ggcggcagcg    480

gcggcggcgg ggggcggcgg aggcgccggc ggcgcggcgg ggcaagcgcc agggatagcg    540

ccaggccttg cggcgccgat gccgccgttg caggggcagg tgccgctgcc ggatgcggcg    600

ccgccagctg agcagtag                                                  618
```

<210> SEQ ID NO 163
<211> LENGTH: 894
<212> TYPE: DNA
<213> ORGANISM: Chlamydomonas reinhardtii

<400> SEQUENCE: 163

```
atgctagcgc gcagcgctca cgtgcagcgc tgtgcatgca gccagcgccg gcgcttgtcg     60

gtgtggggcc ggcgcatacg cgcccgcccc gtagcccccg cctcggcgtc cgcgcccgcg    120

gtctcgtcat ccagcggacc cccacgactg gtggatgtaa acgtccggaa agcgtccacc    180

gccgcggagc tgcgcgcagc tgcctacctg cgcgccatca gcttctacac ctacccagag    240

ggccggagcg agttcgcggc tcggtcacac cggcgcatga aagcggatac ggagtgggag    300

accgtcacca agaaagtgga aggccgcgat gaagcctaca aggacctgga cgtgagctgc    360

ttcgtggcgt gtgtggcgga cgacctggtg gcgctgcccg ggcccggcag tagcgccgcc    420

agcgtcagtg gcagtagcgg cggcgaccca gatcggcagg agctgctggc ggcgctgcgg    480

gcggggctgg acgcgtcggc gcagcttcct gcggatccgg cagcgggtgt cagccgtcag    540

ctggtggtgg ggtcgttgga tctgaacgtg gggcacacgt tgccgtcgga ggagctgatt    600

ggcaggcagc cgaaggaaga cccgcgccac cggagagcct acctaagcaa cgtgtgtgtg    660

gcgccggcgg cgcggcggat gggcctggcg cgggcgctgc tgcgcgttgc ggaggaggag    720

gcgcgcagca aaggtgtgca gtggctgtac gtacatgtgg tggcagacaa ccagcccgcc    780

gtgaagctgt actgtgaggc aatggggttc gaggtggagc aggcggagtc ggagggttac    840

gcacgctcgc tgcagcggcc ccggcgattg attcttgcaa aggaacttgc gtga          894
```

<210> SEQ ID NO 164
<211> LENGTH: 1068
<212> TYPE: DNA
<213> ORGANISM: Chlamydomonas reinhardtii

<400> SEQUENCE: 164

```
atgtacccac accaagataa ggagccccgc acgcacatct ctttgttcct ggaggctgtc     60

gatgtcgcag caggggcaca gccgcccaca ctagcattca agctttacgt gaagcactgg    120

aaggactcca acaaagactc catctgcgaa agcaaggagc cgaaaacctt caacgtgagg    180

tggggcttca gcgctttctt tccccgcgct caactcacga cggactctgg tttcatccgc    240

cgccgcgatg gcgccctgct cctggccgcg gagattgagc tgccggctgg gctggcggcg    300

gcagcaggag cagctgccgg cggcagctgc cgcagcagca gctccagcgc atacccagct    360

agcatcacag acggcgcggc gcgccaggac gttagcggtg acctcctggc cctgctggaa    420

aagccaggct ccacctctga cctgaccatc gtcgcgatcg ctggcagcga cagcggtgcc    480

gatacgggag gctcaggaaa tggtgaggca ccggcggcta cgtggctgaa acggaagtta    540

gtcacggaca agggacggaa gggcggctgc gtgggcagcc cggacacgag gcgcaggttc    600
```

```
gacgtgcacc gcgccatcct ggcggcgcgc tgcccctact tcgccacaca cttcgccagc    660

ggcatgggcg acagcgcggc ccgcgagcta gatatgccgg acacggaccc gggcgcgctg    720

gcggcgctgc ttcgcttcat ctacggcggc gagcttgttg tcgcctcccg cgcgcaggcc    780

cgcgccggcc tggccctggc ggaccggctg ctgctgccca aggcggtggc gctgctgcgc    840

gcgcagctgc tggccagcct gtgccccagc gccatcgccg ccgacctgat gtgggcggct    900

gggtgcggcg accaggcggg gctgctggtg gagctgctgg acttcgcggc ggaggctgca    960

gacgaggtgc cccagtccga cttgcagcag ctggcggcgg cgcacccggg gctcacggcg   1020

cagctgttcg ccgccagcgt gcgcgccgcc aagcgctcga aatcttga                1068
```

<210> SEQ ID NO 165
<211> LENGTH: 1467
<212> TYPE: DNA
<213> ORGANISM: Chlamydomonas reinhardtii

<400> SEQUENCE: 165

```
atggcgcata aagaaaaggg cggctcggag gcgaagaccg tggacgcaga cgcaatcttc     60

aggattttca cagcttgcca gggcgacatc cccacgattg tcatagacac tcgggcgcag    120

aaggagttca aggtgtccca catatgcggc gcgttctgcg tccgactcag cgccaacggg    180

caggtcctgg cggactactc ctcatccagc tacaacatca agtggagcca ggactgctgg    240

tggggccgta acgtgcttgt gtacggcgag ccgggcctca agaaggacca ccctgtgatc    300

gccttcctgt cgcgccaggg caagtgccgc aacctgcgct actacaagga tgggtttgag    360

gccttcgcca aggcgtaccc ctacctgtgc accacctccc tcaagtccat ttgcattaag    420

cgctacccca gccagatcct gccggggcag ttgtacctag gtgactggga gcacgccgcg    480

gacaacgagc ggctggcaga gatgggcata aggaggatcc tgaccatcca caaccacccc    540

gagaacctcc ggccgccggc cggcatcaag cacctgcggc aacagctacc ggacatcgag    600

gacgcggaca tctccgccta cttctctgag gcgtttgact tcattgacga ggggagagag    660

cgcaagcaac ctgtgctggt gcactgcggc gcgggcgtaa gccgtagcgc caccctggtc    720

atgatgtacc tcatgcgccg caacagctgg tcggcggccc gggcgcgcgg ctacgtggtg    780

gagcggcgca gtgtggtgtg catcaacgac ggcttctaca tgaccctatg cgccctggag    840

ccgcagctgg gcatcgcgga gcggagcgac cccaacgcca cattcgggtt ccgtggcgcc    900

gatgcacccg agccgcagca gatcaaggtg gtgctgagtg aagacgcggc ggggcagaag    960

gtgccggtgc gcctgctggc agccaaggag gcggcgcagg cggcggaggc ggacaaggcc   1020

ggcgcggcgg gggccaagcg gccgcgggag ggtggcgagg gcggcgatac cctggcagcc   1080

aagcgcagcc gaccgggcga gccggcgtcc gccgcaggcg gcgcgggtgc gttcacactg   1140

gtgttcgatg tggtgaagcc ggaagggctg gtggggcggc tggaggcggg gcccatgcgg   1200

cccagccagc gcctgctgct gggccgccag ccgggcgtgt gcgatgtggt gctggagcac   1260

gcatccatca gcaggcagca cgcggcgttg agtgtggacc gggccggtgc ggctttcgtg   1320

acagacctgc agagcgccca tggcaccaag gtggcggaca cctggatcaa gcccaacgcg   1380

ccgcggcagc tgaccccggg gacggtggtc agcttcggcg ccagcacgcg agcctacaag   1440

ttggtccgcg tcagcaaggc ggactag                                       1467
```

<210> SEQ ID NO 166
<211> LENGTH: 753
<212> TYPE: DNA
<213> ORGANISM: Chlamydomonas reinhardtii

<400> SEQUENCE: 166
atggccgcgg cggccaccaa cggtgccacc atgcgcgagg cctacccgcc gccgccctcg 60
ctgttcaacc tgtaccgccc ggatgacggc gtgtcgccgc tgccgcccgg gcccccgccc 120
atccccacgc ccgcggacgt gtcggcgctg cgggagcgca aggtggagct caaggtgctg 180
ggcaatcccc tgaagctgca cgaggagctg gtgccgccgc tcaccaccgc ggcgctgtac 240
cggccggcgg gtccggacgg acacatagac ttcaagtctg agctgcggcg gctcagccgc 300
gagctggcct tcatgctgct tgagctgacc aaagcagtgg cggagcagcc cggcagctat 360
gcctcccagc tgacgcacgt gaacctgctg ttcgccaacc tggtgcagct caccaacatg 420
ctaaggccgt accaggcacg tgccaccctg gaagccacct tgggcctgca gctgtccaac 480
atgcgggcgg cgctgggccg gctgcggcag caggtggcgg cggcagatgc ggctctgggc 540
ggcatggcgc gagcgctggt ggaggcggga gagggggaca gcgcggagag cgcggcacga 600
cctgcagagg cggggacagc ggaggcgggg gcggcgggtg ctgaagctgg tgttgcagca 660
ggggaggggg cagggacaga ggcggcggtg gcggcggcgc gaggggcgga tgcgggcagg 720
acagcggctc cggacgccat ggaggagttt tga 753

<210> SEQ ID NO 167
<211> LENGTH: 1128
<212> TYPE: DNA
<213> ORGANISM: Chlamydomonas reinhardtii

<400> SEQUENCE: 167
atggaggaca caaaggaggt ggcgctcata tttgctgagt cctttggccg cggcaacttc 60
cctggtgtcc aggcagaggc actggatgcg ttagaaacca gctatgtggg cgccattgag 120
cgcgagatga ccgataaact gcgggaaact atggaggcca aggtgcaggc ctctcgcgag 180
caccgcgagt accggatgca gcagtacctg cagttactgc gggcgcagct ggcggcgctg 240
agaggcgagc ccgcgcgctt ccccacacag ccctcgccct cggatgagcg caacctgcaa 300
cggctgcggc gggcgcggca gttcctggtg ctcgtggcgg aggaacggcc gacggctgag 360
gctggtgagg ctggtggcca agcctctgcc tcgtcctcag tagcagcgga ggcggcggcg 420
gagccggaac cggaggcagc ggcgccgggg cccgggcccg gctcggcggc ttgtgctaca 480
ggggccgcgg cctcggcagc ggcgtatggg ggggcgcgga ggcggggcca ggcggtggcg 540
gcggcgtcac tgtcgctgct gcagccagag gctctgctgc cgccgccctt cccctccaac 600
aagccctacc gcctgtacgt gtccaacatg agtgtggtgc ccgcgcaccg gcggcgcggc 660
ctggccaaaa ggctgctgct gcagtgcgag cgcgtggccc ggctatgggg ccatgagtcc 720
atctggctcc acgtcaagcg cagcaacgcc gccgccgccg cgttgtacgc ctccatgggc 780
tacacaccgg tggagtcggg cggcatgagg ctgctgccgg ggccgctcag ccaggtgctg 840
atgactaaga ccctgccgcc gctcagaggc agctgccgag tggagctggg acggggcggg 900
gccagcaggt cgcaggcggc agccggcagc agcagcagca gtggcagcag cggcaacggc 960
ggcagtagca gcagcggagc cggcggcgtg tcggcgggcg aggcggtagt gagcggggtg 1020
tcggggaggt cccgagagaa ggatggtgtg tttgtgtggg gtgccgtggt ggagggggca 1080
ggagacgtgg ggcccaccga caagggggcg gagcggccag ggcagtag 1128

<210> SEQ ID NO 168
<211> LENGTH: 1371
<212> TYPE: DNA

<213> ORGANISM: Chlamydomonas reinhardtii

<400> SEQUENCE: 168
atggcagacg aaacgggtat cgtaaagcag gccgtgctcg agttcctgaa gacggccgac 60
atgaatgtaa caacggagcg cacagtcctg aatcacctgg cggccacgct gcagctaagc 120
caggaggtca aggcgtacaa ggcggtcgtg tcggccacga ttgacgacta cctatcggct 180
ctggatgacg ccgaggatga ggaggaagcc gcggagcaag aggaggagga ggacgcaggc 240
gcagccaagg caggcggccg caagcgcgcc ggcggcgcag ccggcggcgc tgccgctaag 300
aagagccgca gcagcagtgg cgccgctggc ggcggcggcg acgacgtgct gctgcacgtg 360
gacctgagcg agcggcgcaa ggcgcgtgta cggcgctacg aggggcggct gcacgttgat 420
gtacgggagt tctacaagaa ggacggcgag gacgcgccca cacagaaggg gctgtccatg 480
gacccggggc agtgggcccg actggcgcgg gagctgccgc ggctggtggc ggcgcagcgg 540
gcgggcgctg caggcggcgg cggcggcgag gtgccgccgg cgcagctggc caagactcgg 600
ctggcctccg tcagcgagtt caagggcact tactacctag ggttgcgcga gtactacgag 660
aaggatggcc agctgctgcc gggcaagaag ggcgtgagcc tgaacccctc ggaagcggag 720
gccctgctcg ccgccgccgc cgccatcacc actgccgccg gcggcgtgcc ggccgacctg 780
ccgccgctcg agccctctgc actgctgccc accgccggct ccggctccgc agcctccggg 840
gccactgcca aagccagcgc gagcgcgggg ccctccaagg cggcggcggc ggcagcagcg 900
gcgccagcgg ccggtaccgt tgccagcggc gagccgactg aggtggtgga gctggggtcg 960
aacaagcggc tgagcatcag tcacttcggc gggcgcacca gcgtagacct gcgcgagttc 1020
tacgacgtaa gctacagagg tgttggtgct gagaaagacg ggcagaagct tccaggcaag 1080
aagggcattg cgctggcccc ggctgactgg gccacgatgt gcgccgccct gcccgccatc 1140
agctccgccc tggccaaacg cgacatgggc tatgtgctgc agctcagcgg caagcggcgt 1200
gtgtccttgt ccgaattcaa gggtgcggtg tatgtgggcg tgcgcgagtt ctacgagaag 1260
gacggtcagc tgctgccggg cgccaagggc ctgtctatga acgcggccca gtgggcggcg 1320
ctggtggcgg gcgcgccggg cttcaacgcc gcactccaga gccaagagta g 1371

<210> SEQ ID NO 169
<211> LENGTH: 1587
<212> TYPE: DNA
<213> ORGANISM: Chlamydomonas reinhardtii

<400> SEQUENCE: 169
atgttttcgc tcagcacgac gaatatatcc gatgtgccgc tgttctggga aactgtcaac 60
ctagtgtacg attcctttac cgagagcttc atcgtggtca ctggcgcatg cattcagcag 120
ctgatccctg ccctccacgg cgaggacgac gagccgctcg tgctcgctgc agtggcggga 180
gctatactac cggtccgtgt gcaggcaaat ggccgtggta acgtggcgca gttcggcaag 240
cccacgcata ttgccaccga cggcaagggc acgctgtacg tgctcgatca ggccaacatc 300
cgcaagctgc agctgccggc ggcggcgcgc taccagcccc atcagcagcg ccagcgcatc 360
aactccatgc aggtggaggt caccacgttg tcgcagcagc ttcccccgga tatgacagcc 420
agcggaatgg tttacgtccc cgcgggggag agccctggcg gcagcgagtg cctgatcctg 480
gcgggcacca agggcatcta ccggctgccc ctgtgcaata atgacgcagc aattgaagca 540
ggcggcaagg ctgggatgca gggcagcggc agtggtgccg tggctggcgg cacgggtgga 600
gcagcggagg ccaccaccgc cactggcagc ctacaccggt tggcaggcaa tagtgacacc 660
gcaggaagct ggggaatccg ttttgatgca tttggtgcgc aggccaagat gctcgccatc 720
tcctccggcc ttgcactcac tggtgatggc cgcgtggtgt tcttggacta ttccgcaacc 780
cagagggaca cggccgtgcg gtgcatacgg atgtccgatg ggcgcgtgtc cacgctttac 840
gaaggcctgg acgggcagtg gcagtggccg tgcctgctcc ccagcggctg cctggccatg 900
acgagtggca aggacctctt catcatcgac ctggcccttc cgccgccacg gccgccgcca 960
ccgccgccca gcaccggccc gccgccgcgt agcctggcct cggacctggg cgcgctgcta 1020
gacggcgcgg cgggcgcggc cagctccgac ctgaccatcc tggtcggcgg acgggccttc 1080
aaggcgcacc gcgtcatcct ggccgcgcgc tgcgagtact tcgccaagcg cctggaggag 1140
ggcgcctacg cggacggcgc caagcaggag ctggagctgc cggaagcgga gcccgcggcg 1200
ttcgaggtgc tgcttcgctg gctgtacacc ggcgccgcgg acgtcccggc tgagctggcg 1260
caggaggtgg cggtcctggc ggaccgcctc gtgctgccgg agctgtgcga tgctgcgcag 1320
gcggtggtgc tcgagtctgt gacccctggg tcggttgcgg cggcgctggt gtgggcggcg 1380
agctgcgtgc ctgggcgtgg cagcagcttc gagcaggtgc tgcgccggct gaagaagtgg 1440
tacgtggcgc actatgacaa ggtgcggagc gaggcgcgcg cgagcgtggt ggcgctgatg 1500
gccagcaacc ccgagctggc gatggagctg caggaggagg tgctgggggc cacggagcgg 1560
cgggtgagca agaagcagcg ggtttag 1587

<210> SEQ ID NO 170
<211> LENGTH: 543
<212> TYPE: DNA
<213> ORGANISM: Chlamydomonas reinhardtii

<400> SEQUENCE: 170
atggtctgca ttcgcccagc aacgattgac gacctaatgc agatgcagcg gtgcaacctg 60
ctgtgtctac ctgagaacta ccagctgaag tactacctgt accacatcct gtcctggccc 120
cagctgctgc aagtggcgga ggactacgac ggcaagattg tgggatacgt gctggccaag 180
atggaggagg aggccagcga gcagcacgga cacatcacct cggtggcggt ggcgcgcacg 240
caccgcaaac ttggcctggc cacaaagctc atgagctcca cgcacaaggc catggaggag 300
gtgttcggcg cgcagtacgt gtcgctgcac gtgcgcgtca ccaacaaggt ggccgtgcac 360
ctgtacacgc agaccctggg ctaccagatc tacgacatcg agggcaagta ctacgccgac 420
ggtgaggacg cctacgagat gcgcaagtac tttggccctg cgccgcccgc cctggccaag 480
aaggccgcgg cgctcacggc gcaggccacc ggactgcccg cgcccacagc cgccagcagc 540
tga 543

<210> SEQ ID NO 171
<211> LENGTH: 891
<212> TYPE: DNA
<213> ORGANISM: Chlamydomonas reinhardtii

<400> SEQUENCE: 171
atgggggacc agtataacta ttatccgggc gggtacactg gtggaatccc gccgaaccac 60
caccaagctg aggcgctcaa gtctttttgg caagcacagc tggtcgaggt gtctgaggtc 120
ccacctgacc caactgtatt caagaaccac cagctgcctc tggcccgcat caaaaagatt 180
atgaagtcgg atgaggacgt gcgcatgatc agcgcggagg cccccgtgct gtttgccaag 240
gcgtgtgaga tgttcatcct ggagctgacg ctgcggtcgt ggatgcacgc ggaggaaaac 300

-continued

```
aagcggcgca cgctgcagcg caacgacgtg gcggcggcta tcaccaaaac agacatcttt    360

gacttcctga tcgacattgt gccccgggag gatggcaagc cggaggaggg cggcgccgcg    420

gcgcccggcg gcgcggcccc cgcgactgcg ccgtcaccgg ccgggcccgg cggctccgga    480

aaccagcagg cagcttccgc tgcctcgacg gctgccccgg cagcggccgc gccgcggccg    540

cccgcgccac cgggcatgcc caccgcgcca ggcatgttct tcccgccgcc cttcccaatg    600

ccgccgggcg cgctggggga ccccagccac gcggccgcgg cggcagcggc ggcggcggtg    660

atgatgcggc cacccatggg tgtggacccc aacctggtcc tgcagtacca gcagcagata    720

ttggcggggc aggcgccagg gtggccgcac ctgccggggt tgccgccgcc gccgacgtcg    780

cagccgggcg ccgcggctgc ggccgctgcg gcggcggcgg cggcggcagc tgccgcagca    840

gcgggagctg cggcagcaga ggggcaggcg gaggctgcaa agcaggagta a             891
```

<210> SEQ ID NO 172
<211> LENGTH: 1008
<212> TYPE: DNA
<213> ORGANISM: Chlamydomonas reinhardtii

<400> SEQUENCE: 172

```
atgacgaagg atgagcaggc attgctagat tgggttattg ctgagggcgg cgaactgcgg     60

gtgacgattt cccgcgatga ggcgggggtg cggggccttt acaccacgca gccagtgaag    120

aagggcgagg taatagtctc catccctcag cacatcgtcc tcagcgtgaa gaatgtggca    180

gctgcggaag cctcccccca gctgctcaag gagattcact cgccctgctc acggctcaga    240

ccgtacctgg acacactgcc tggcctgac ggggtgctca cggcgtacaa ctggcctgag    300

gagtacatca agtacctggc cgaccccgcg atggaggagc agttgaagaa ctccttcaag    360

ttgcacgcgc gcaacacgtg gctcgggcac aacgacgatg aaatggaggt gaccatccca    420

gaggccatcg gccgcaagaa cattacattg aaggagtggg agcacgttgt gtcactgctg    480

agctcgcgga cgttcagcat ccgcaagggc gccttgtcgc tggtgcccgt gctagatctg    540

gtcaaccacg atgtgcggga catcaaccag ctcggcaaca gcagcactgt cgatctggtc    600

gccggcaagg acctggctgc tggcgagcaa gtgaccatca cctacggctc catgcgcaat    660

gacgagctgc tcatgtacta tgggttcgtt gacacggtga cggagccgcc ccgcctgttc    720

tccgttgacc accgcgattt caagctgtac gaggccaacc cgctcagcga cagtccgttg    780

gaaggcccgc cggaggtgct gcggacagag ctggcgcgtc tgcgtggcat cctcaccgcg    840

tttgaggcca gactggacgg gctgggccca attcccgaca cacagccgta cgtggcgtcg    900

ctgctgcggg acgcacacga ccggaggcgg cgcgcgctgc atgcggagat aggccgcctg    960

gagcagcagc tgcaaggggc cagcggcagc ggcggcgagg agctatag               1008
```

<210> SEQ ID NO 173
<211> LENGTH: 1329
<212> TYPE: DNA
<213> ORGANISM: Chlamydomonas reinhardtii

<400> SEQUENCE: 173

```
atgtcgatgc gcaacaacaa gcgccgcgct ctggcaagcg ctggcgccgc cagcaagcaa     60

tctgcggtgg ccgacgccgt cctggacgtg gccaaccgca agggcgtccg ctgctgcgta    120

gagtgcgggg cgacgtccac tccgcagtgg cgtgaaggcc cgatgggccc caagacgctg    180

tgcaacgcct gtggcgtgcg ccgccagcgc ctcatccgca agcagcaggc cgctgtcgct    240

ggcgtcacgc ccaccgcgcc tgtcgccgcc gtgcaggctc gccgccgtct ggccacccgc    300
```

```
cgccgccccg gcgcctctgc ctcgctcatc gccgacgagg atgtctttgc gcccgcgggc    360

gccggctccg tgtcggagca gtcgagcgac gaggcggaga tgacggtgat gggctggcgc    420

acaacggcgg cggaggtgcc ccggccgcag cgcgggcagc actcggctgc caccggcacc    480

gacgttgagg acagctgcaa cgaagaggag acggccgcct acgacctgct cttcttcgcc    540

ggctttgact gcggcgacta tggctactcg gcgccgtccg ggcccagcca cggccacaac    600

acacgccgcc aagccgcgcc gcagcgccgc tcggacgact tctattatta cgaggagcag    660

gaccacgagg gcgagcacgg ggtggccgcc ggagagcatg agcggctgcc catgtcggct    720

ccggcgctgc agcaggtgtc gtccatcaag cgccggcgcg tgctggcggc cccgcccaaa    780

gtgcacatcc gccccggccg gtccgcgatg acgagcttcc cgtcttcctc ggccgagcac    840

gaggcagcgg ctgtaccggc cgtgagcaac atgagcagcc tgccggcggc cgcggggcct    900

gcgcctgcat cgtcctcaga cgccgcaacg gcggagttgc tgccggcggc gccggcggtg    960

ctaccgtcct ctgccatgct ggcgctgcag ctgccgctgc tgccgctcgc gcttccggcg   1020

ctgtcgcttc cgggggcggt tgtggcgggc ggcgcaagcc cggcggacct ggagatgatt   1080

gccgcactgc acgccgagtt ccagcgtgcc tgcatgcaga tgcagcaggc tgtggctgcg   1140

gcggaggcgg tcggcgcggt agcggcagag cggcgcgacg ccgcggacgc ggcgcatgct   1200

gtcgccgctg tggcgtcgca gcgcctggcg gacggcgcta aggtcgtggc ggccctgccg   1260

gaggtgcgtg acgtgctcgc ggagctgcac accggcccag tcgccatggc cgttgcgccg   1320

cccctgtaa                                                           1329
```

<210> SEQ ID NO 174
<211> LENGTH: 1044
<212> TYPE: DNA
<213> ORGANISM: Chlamydomonas reinhardtii

<400> SEQUENCE: 174

```
atggcgctcg tatcacatca tggtgtatat aaccagcgtt gtaaacatgc aaacggcggt     60

cgttccgctc ctgggtggcg cctctcgcaa ccacagcctg ctcagccccg gcgacatcgc    120

catgtcgtgt ccgccgcgcg ttcgccgcag cagcccgctc cgctgccgcc tcgggtgagc    180

tgtggcgagg agggcggagc gccgctgcac atacgcgccg cggagctccg cgactactgg    240

ccggcagcgg acctacacac gcgggtgttc tgtccggagg cggagtcaga ccgaagtaag    300

gcgctgtcca tgcgtgtgga ccgcatcata gcgctgcaga tcaacgaccg catatccaga    360

gagggcggcg gcaactctgt gttgctgctg gcattcaacg gggaggcgcc gggcagtgcg    420

gaggagcgca cggcggcgga ggcggcgttt gcggcggcgg cgcaggcggc acagacgccc    480

gggtctgtca cccacctgtc caccgccttc cccaacccca tgtggtggct ggcgcggccg    540

ctggggccgg gcgtgcgggc cggcatgggc gtggcggccg agtccgtggg cctggtgggg    600

gtggcggcgg tggacagctt ctgtgacctg gtgccgccgc gggagctgga cccgcggcgg    660

gacggcgcgt tcggcttgta ccgccgggac ggctacgcct acgtgagcaa cgtggcggtg    720

ctgccggcgg cgcggcggcg cggcgtggcg cgtcagctca tggcggcggc ggaggcgctg    780

gcggcggagt gggggtgcaa ggcggtgggg ctgcactgca acaccaagaa gacggcgcca    840

tgggcgctgt accgcagcct gggctaccgg gacagcggtg tggtggagcc ctggatcatg    900

ccctacctgc agggccggcc gcccgaccgc tgctcgttcc tggtgaaacg cgtgccgctg    960
```

caacgcagc cgcaaccgca gccggaggca ggggcggggg gggcggggcg cacggagggt 1020
tcggggccag ccgggctccg gtag 1044

<210> SEQ ID NO 175
<211> LENGTH: 1173
<212> TYPE: DNA
<213> ORGANISM: Chlamydomonas reinhardtii

<400> SEQUENCE: 175
atgcccaagg agtacatcgt gcgcctggtg tttgaccggc ggcaccgctc cgtggcgctg 60
ctgaagcgca acggcaccgt catcggcggc atcacctacc gcgccttcca cgagcaggca 120
ttcggcgaga tcgccttctg cgccgtgacc agccacgagc aggtcaaggg ctacggcacg 180
cggctcatga accagaccaa ggagttcgcg cgcaccgtgg accgcctcac gcacttcctc 240
acctacgccg acaacaacgc ggtggggtac tttgagaagc agggcttcac gcgcgagatc 300
acgctggcgc gggagcgctg gcagggctac atcaaggact acgacggcgg cacgctgatg 360
gagtgcgtca tgcacccgcg cgtcagctac accgccctgc ccgacctcat ccgcacgcag 420
cgcctggcgc tggacgaccg cgttcgccag gtctccaact cccacgtggt gcggaccggg 480
ctgaggcact tccaggagga ggacgcgcgg ctggcggcgg ccacggcagc agcagcggcg 540
gcggcggggg cagcaggagg gagaggcgcg ggcggtgtag gggccggggc gccggctggt 600
gacgcggcgg cggcaacagc ggacaccgac ccggcgttgc ggcgacgtat gctggacatc 660
ggcggcatcc caggggtgcg ggaggcgggc tggtcgccgg acatggtgca gcaggggccg 720
cgcttccggc tgctgctgga cgaggcgggg gcgggtccgg cggtggaggc ggggtcggag 780
gcgctgcacc ggttcctggt gctgctgctg gagcacgtca aggggctgga ggacgcctgg 840
ccgttccggg agcgggtggc ggtgcaggac gcgcccgact actacgacat catcaaggac 900
cccatggctc tggacgtgat ggaggagcgc ctggcctcgc gcggctacta cgtcaccctg 960
gacatcttca ccgccgacct gcgccgcgtg ttcgacaact gccgcctcta caacgcgccg 1020
gacaccatct actacaagct ggccaacaag ctggaggcgc aggtcaacgc cttcatgtcc 1080
aaccacgtgc tgtacgagga tgaggcaggg ccggcggcgg cggcagcggc agcggcagct 1140
gggactgggg ctggagcagg cgctgggcgg tag 1173

<210> SEQ ID NO 176
<211> LENGTH: 426
<212> TYPE: DNA
<213> ORGANISM: Chlamydomonas reinhardtii

<400> SEQUENCE: 176
atgcagcagc ccgctcgcag gacctggacg gaccaggaac tggcaatcag cggctttgag 60
cggttcgccc ttgaattgga gttcttgcag tgcctggcca atcctcttta catcaattgg 120
ctcgcaacga aacagtattt tgacaaccca gcgtttttga actaccttaa gtacctgcag 180
tactggaagc agcctgcata cgcagtgcac atcacgtacc cgcactgcct gttcttctta 240
gacctggttc aggatgcgga cttccgcaac gcaataaagg atttctcata cgcggagcat 300
atccgccagg cacaggactc gtttttccgc aacttccact ccaaccgggt ggcggaggcg 360
gagggcaagg ccacggccgc gccggcagca gatggcgacg gtggcgcagg tgatgccatg 420
gattga 426

<210> SEQ ID NO 177

<211> LENGTH: 1311
<212> TYPE: DNA
<213> ORGANISM: Chlamydomonas reinhardtii

<400> SEQUENCE: 177
atggactcgg agcagcagcc ggccagcccg agggctgcgc ctggtgcaag cggaggccga 60
cgcttgcctg gtcggacacc ttctggtcta ttgggacagg cagcgcaggg gccgcagcaa 120
cctcagcccc aacttggcaa gggagcactt cagctcaatc agtccagcag cgcagcgaca 180
accgcgttgc cggtgaaacg tcgggggagt ttccagcagt tgaagaaaat aggtgccgcc 240
ggggggcgag atggcagctc ttcgcacctg gactcggact cggcaccatc aattttcgcc 300
attgtgaaaa agtccacaca ctgggaaaag tatggcacgg tgctcgtgct gctcgttgcc 360
gacgagctca gcagtgacaa ggaggcggtg gtgcagatgc tgagcgcaga gggatacgat 420
gaccagacgt cggacagcat cgaggaggcg gtgaagttgt tttcggaaag ggaggtgtac 480
ccggacattg ttattgttga ttcagacaat gagctggtgg acaccaaaca gctcatcaag 540
gcgctgcagg cgctgaaccc cacggtggcg gtgctggtac tgggcagccg cggcgggccc 600
atgggcgcgg tggcggcgct gcaggcgggc gcggcggact acatggtgaa gccgctggat 660
ctggatgagg tggttgcccg cgtggagcga cacgtgcagc gacagcactg catcaagttg 720
gaaatggaaa aggcgctgga gcacgccaag gagatgatgc agcagctcat gccggcatca 780
ctactcgggg acgtgatgtt gcggaaagac ggcagcgccg cgggcggcgc gccggcgggc 840
ggcaaggcga gtctcaacag cgtggcggag accgactttg aggagcagat gagcgagctg 900
agcgaggaga accaccgctt gggccagaag gtgcaggaga tggagcgcaa gcttgagctc 960
aaggaccagg agaaccgcga cctggaagcc aaactcaacg ccatcgaccg caaagtcagc 1020
gcgctggccg ccagccgcga gatgggcggc ggcaacggcg gcggcaacgg cggcggcggg 1080
gggtcgggct gcacggccgt ggggcctgag cagcgtgccg cggcgcagca ggcggcgcag 1140
gcggcccagg cctcgttgca ggggcagctg aacagcgtgg cacaggccaa cgaggacctc 1200
cgacataaag tggacgagct ggagcggctg atgcagtcgc acacaggcgt caccagcgcc 1260
agcaaccaaa acctgcgcct gagcgtcaac ggtgggcagc agcagggcta g 1311

<210> SEQ ID NO 178
<211> LENGTH: 1254
<212> TYPE: DNA
<213> ORGANISM: Chlamydomonas reinhardtii

<400> SEQUENCE: 178
atggcggccc ggctcctgcg ggatcctgaa gcagacggat gggagcgctc ggatatgccc 60
atcgtgtgcg agacgtgctt gggacccaat cctttcgtgc gcatgcagcg gatcgagttc 120
ggcggcacct gccacatttc tggtcgcccc tacacggtct tccgctggcg ccccggcaac 180
gacgctaggt acaagaagac ggtgatctgc caggaggtgg ccaaggccaa gaacgtgtgc 240
caggtgtgcc tgctggacct cgagtacgga ctgcccgtgc aggtccgtga cgccgccatg 300
ggcgtgaagc cggacgagga gccccagagc gaggtgggca aggagtacaa gctgcagatg 360
gaggcggacg cgggcacact gggcggcggc ggcgtgggcg gggccagcag cagctacgcg 420
gcgggccggc ccaacgagat gctgcagaag ctgcagcgct cgcagcccta ctacaagcgc 480
aaccaagcgc gcgtgtgctc cttcttcgcc aaggggcagt gcacgcgcgg cgccgagtgc 540
ccctaccggc acgagctgcc caccgccgac ccggcgctgg ccaaccagtc ctacaaggac 600
cgctactacg gcacaaacga ccccgtggcc gccaagatgc tcaagcgggt ggacgagctc 660
aacaagctca cgccgccgga ggacacctcc atcaccacgc tgtacgtggg cggggtggac 720
gcctccatca ccgaggacga cgtgcgggac gccttctact cattcggaga gctggccagc 780
gtgcgcaaga tggacgtcaa gagctgcgcc ttcgtgacct acaccacgcg ctccgccgcg 840
gagaaggcgg cggaggagct gggcggcaac ccgctcatca agggcgcgcg cgtcaagctc 900
atgtggggcc gcccgccgcc cgcgcccgca gcccgcaacg ccgccgccgc cgaccccatg 960
cagccctcca ccagcggcgc cggcggctac ggcggcgcgg cgcccggcag cgccgcctcc 1020
tactacccgt ccatggaccc ctcggccatg ggctcgcggg cgccgggcgg gccgcccggc 1080
atgcggccag gcggggaagg cggcggcccc ggaggccccg gaggcatggc gccgccgcgg 1140
cccatgggct acggcgcgcc gcccgggtac ggcgcgccgc cgcctggcta catgccgccg 1200
ccgcgcccca tggtgtctgc cagcatgcag ccgccgcagc agcagcacca gtag 1254

<210> SEQ ID NO 179
<211> LENGTH: 310
<212> TYPE: DNA
<213> ORGANISM: Chlamydomonas reinhardtii

<400> SEQUENCE: 179
tgaaagacgg gcaagacacg attatcctgc aggcaattgc cggcgcgagc ttggggcgcc 60
ccttcagcgt cccatcggcg gtcgcttttt gccccggtgt cgccgttcct ggttctcggc 120
agcccaagat aatttaatct agtagtaata atcatgtgca gcgttgtggc agctgccccc 180
aaaggaaact gtggcgggaa gcgccccagt cgcgcaagct tatcgctcgg tcgcgcgtcg 240
gggccaccct gaagaccctg aattatttgt gcgacaatat agcagccact tcttttcatt 300
tgaatggttt 310

<210> SEQ ID NO 180
<211> LENGTH: 310
<212> TYPE: DNA
<213> ORGANISM: Chlamydomonas reinhardtii

<400> SEQUENCE: 180
aggggagggg aggggcgggg cggggcgggg cggggcgggg cggggcgggg aggggagggg 60
cggggcgggg cggggcgggg cggggagggg aggggcgggg cggggcggac aaataggtca 120
gcaaatggat gaacatgacc gcaaattgat aatcatacct ggcttgcaag ctcgcgccca 180
gcgagatgga gtacggacga tggagatctg gccgcgattg gcgagccggg caagaaaaac 240
agccgagcgc tgcatataac acttgtcaca ccgtcgacct tgttcgttca gtcacttgaa 300
cagcaacacc 310

<210> SEQ ID NO 181
<211> LENGTH: 310
<212> TYPE: DNA
<213> ORGANISM: Chlamydomonas reinhardtii

<400> SEQUENCE: 181
cacaacacct cgccacgggc acaccgccag ccacccgccc caccagcgaa ctagaccgac 60
ccgacaaaca ggcacgcgcg cgcccggagg cgaacaggcg caccagccgc ccgggcgccc 120
gggcaacagc cgcccaggca ctcacaaccc gacacccggg actacccgac cagcgtcatc 180
tgctgcctaa cggtccctga accgccatgc tacgaacggc acccgcaacc taactatctg 240
ctgagccagc aaggccgccg gtggagacga cagcgggcca ggcggcacga ggagaggcgc 300
acagggctgc 310

<210> SEQ ID NO 182
<211> LENGTH: 310
<212> TYPE: DNA
<213> ORGANISM: Chlamydomonas reinhardtii

<400> SEQUENCE: 182
ggcgcacagg gctgcgtgca tggccaaacc ctcagttggg aaattcggac aggaagcagt 60
gaatggggca cagtactata ctaggggaaa cgataacgtg atctcagggg cgtggggggg 120
gggctagaag ggaaggggcg ctgtaactgg attgcgtggt gtgcgcggtg cattcttcgc 180
acacctcggc agcagcccgg ccccgcgttc cctggcctag tgacgccggt tgccaccagc 240
aaccaaatgc catgcatgcg gccagtatgc gcatgcgtcg cccccgcggc cgagctgcac 300
gcacatgccg 310

<210> SEQ ID NO 183
<211> LENGTH: 310
<212> TYPE: DNA
<213> ORGANISM: Chlamydomonas reinhardtii

<400> SEQUENCE: 183
tgcacgcaca tgccgaccga aaggaaatgg gtgttgcgcg tcagagcggg tttgaacaag 60
tgatttcttc gctccgccat gcacagcaag ctagctaagc tggatgtatt aggggcttgg 120
tttgttcatt tgcacctctc caacacgtac gacctccaac cctcctacaa ttgcccatgc 180
gccgggtttt ataggtcgcc ggtgcgtatg atgggctgca gtaacaacat tcttctcgtg 240
gttgtgtgtt aaacgtgcac agttaaatac attacatatc tcgttgacac tacaaaccag 300
cgatagaagg 310

<210> SEQ ID NO 184
<211> LENGTH: 310
<212> TYPE: DNA
<213> ORGANISM: Chlamydomonas reinhardtii

<400> SEQUENCE: 184
cgtgattgcc ggcggcgagg cggggccatg gacggggcta cgggcagggc gacgccacgg 60
ttactcgcac tgcccagccg ttcacctgtg ctgacatgca tggcagtctg gcagacctca 120
cgcaagacca ctggatgagg cgtggccgtg tggggctcgt cgtcgcactc agctgttggc 180
aggcccccgc tagttgccct gtgtccgccc tcttcggtgc tcagcctgac caaggccttg 240
ggggcgccgg caaccacaaa cccaactgag gctgtatact tggacgcaac ccatccgtgg 300
ccaggtttct 310

<210> SEQ ID NO 185
<211> LENGTH: 310
<212> TYPE: DNA
<213> ORGANISM: Chlamydomonas reinhardtii

<400> SEQUENCE: 185
cgtggccagg tttctatcga cgtcctccga cagtgaaggg ttccgcaaaa ccgcctcacc 60
gacatgtgag acatgcgaca tgtgccctca ggtctctcag cccctgtgct cctggagcgc 120
tacgttatgc gcagcatgac catcgcagct actcaagaaa acaaaagacc ataagctgtg 180
agccgttgac tgagttgacc gtcgcgaaac agcgtccttt ctcagcaagc cttgccagcc 240
gaacccgaat ttatttacct tcacggcaat acaccatgta cgttttgaat gcctgcaatc 300
gggtttcggc 310

<210> SEQ ID NO 186
<211> LENGTH: 310
<212> TYPE: DNA
<213> ORGANISM: Chlamydomonas reinhardtii

<400> SEQUENCE: 186
caatcgggtt tcggcctcgc cctgggcctg ctaagaaatt cacaactccc cgcgagaatg 60
ctggccgtgc actcaattaa atatgctcat gcaagtaagc tgattacatg catatttgag 120
gagcggggcg gggccattcc tccaggaaat ggggaactcc taccacaacc tcctacaatg 180
tacggaatgg cccatcgccg cgggcagctt gcacttaagc ttgccggccg gcgcgcacag 240
attcaccttc aggcaagcac tcgcagccgc tccatctgta gcgtcgacct ttcagaacca 300
ctccaaaaca 310

<210> SEQ ID NO 187
<211> LENGTH: 310
<212> TYPE: DNA
<213> ORGANISM: Chlamydomonas reinhardtii

<400> SEQUENCE: 187
tggatgaggc aggggttccc ctcagctgag gcaaccatgc tgccgtggca aggcggcgcg 60
ttaatgtgct ccgttgctca cggtcacagg cgtgcatagg ctgcattacg ctgcgtgtcg 120
cttattactc tggacgccct ctgcttcggg tggggctatg ccagtgccgt gcgcacctcg 180
tgcaagtaga ctatggtacc aaggtagacc cagcttgatt ccacgcgtga tccatgttag 240
tgcgtaggct catagaaaga cacaccggtg agaaagacac atggaggcgc ggcactgcgg 300
acgctgcgga 310

<210> SEQ ID NO 188
<211> LENGTH: 310
<212> TYPE: DNA
<213> ORGANISM: Chlamydomonas reinhardtii

<400> SEQUENCE: 188
tgcggacgct gcggagaaag gcacatggag gcgtgccggt gtgttccggc agtgctgctg 60
acatgcaact gtgttgaccg ttgacatgcc cgtgccgtaa gtgccccagc gacgagttcg 120
tggcccctag cagtggcttg acatggggct ttgggcccac aattaagcca tgtgagcaac 180
gcaccttgac gcgggcttaa atctggcagt ccaaacgaca cgcgtgtgaa acccgccagc 240
ttcttttccc tgttgacgat tcgccaagct cccggcaacc cccgcttgcc cattgcaaat 300
tcccaagtgt 310

<210> SEQ ID NO 189
<211> LENGTH: 310
<212> TYPE: DNA
<213> ORGANISM: Chlamydomonas reinhardtii

<400> SEQUENCE: 189
caaattccca agtgtactcc cgtcctcgcg gctttaaaat atggcagtcc gtccggcttg 60
aacatgcgca agtcgcattt cccaacgaca atcctcttcg tagcgcgcac gttgccaggc 120
agcgaaatat tctatcatgt ttttgctggg ttgaatgcaa ttgaacaccg gtttggtttc 180
ggcaggcagc tccccgaccg tcaaggcttg catgggatag ggttgcccat cgccgatagc 240
gaccggctac ttcagccagc cctcgcagtg aggtagtgct tttgggtcta tatacaaaat 300
ggccgctatg 310

<210> SEQ ID NO 190
<211> LENGTH: 310
<212> TYPE: DNA
<213> ORGANISM: Chlamydomonas reinhardtii

<400> SEQUENCE: 190
cggcacacaa cagggacaca gcacggcgca cagcacatgg cacacactgc agtggcaggc 60
tgacgctgca cattggctgt ctgcagtctt gcttgcggcc cctcctaaat cttgttccgg 120
gctcgcgggt tagctctcgc cagtccccca gcccccagca cgcctgcact gttggccctg 180
gccctggccc tggttttcgt gggacagttg tcgagcaatg tcacttcaac tccttgacgt 240
tcgggcgcat catgtgtgaa cctacggggg ctctcctggc ggttgggggg tatacattac 300
gatactattt 310

<210> SEQ ID NO 191
<211> LENGTH: 310
<212> TYPE: DNA
<213> ORGANISM: Chlamydomonas reinhardtii

<400> SEQUENCE: 191
attacgatac tattttttag gggccgacat ttggggtgag tattgagtag agggacgcct 60
ggactgcggt gcctagatgc gcgaggcggc aactcggcac ggtcagcgcg tttcgccccc 120
cgcacccagg gctgacccgc tcgctcgctt gcgccaaccg accgaagttc aaacgtcagc 180
gtcgcgtcga aaccccaaat catgccgtca gtaagtcggc agcggatgac acggcacatg 240
caatgaggtc agcctttgtt ccaaggactg cacatgtggg gcgaaagggc gccgtcgacg 300
gcgcgactgc 310

<210> SEQ ID NO 192
<211> LENGTH: 310
<212> TYPE: DNA
<213> ORGANISM: Chlamydomonas reinhardtii

<400> SEQUENCE: 192
cgacggcgcg actgcaaatg caaccaccgc cgacagcgcg agcaagcggc cacaattttg 60
ttctacgcgg ttgcagcatg ctcaatacga tgtgcaattt tgcagcgcat gagcgcgcac 120
gttggtgggg tctccgacgt agagtagggc ggttgtgtac ggaacataca acggggctct 180
gcgcgaactc aataaactcc gctgttggtg tgcaattttc aaacatctgt agcggcaagt 240
actggcaata gtccaggcta taacgcaacg attcagggct agacgcacag tcgagtttag 300
acgcgcaaag 310

<210> SEQ ID NO 193
<211> LENGTH: 310
<212> TYPE: DNA
<213> ORGANISM: Chlorella vulgaris

<400> SEQUENCE: 193
tagagaagag cactggcggc cgaaggctcg gcagcgctgg ctgctcgaca ccgcgctgcg 60
caaacgctta cccactagcg caaacagcac caccagcaca agtttgagca gggccgcggg 120
gcacaccatc gcaaccagat ccctggtcac gccagttgcg ctgcgctacc ccacagagac 180
tgcgcgggca gcagcgaagg ctggcgcctg acacactttc aaaagggccc agggcagctg 240
tacagcgctg taccctcggc accagcgggg aagctggcag ggaagctgta acaacaccat 300
cagcagcatc 310

<210> SEQ ID NO 194
<211> LENGTH: 310
<212> TYPE: DNA
<213> ORGANISM: Chlorella vulgaris

<400> SEQUENCE: 194
accatcagca gcatcaattc tggagccacg acaagccctc cacgctgccc aatgtgcatt 60
tgattggatt tgatccccaa aaggcagctg cactctgccc ccctctcctg tcctcctgct 120
gcctgtggcg ccccgctcaa aagccgtgtg catggagcag ctggttggac agcgggtttt 180
gacccacaag cagccagtcg cgaggaaggg atttgggccc ggctgctgag gccaggcctc 240
atggagctgg cagagccctg accaccgtcg ccaccgacca gcgccaaccg ccccacggtc 300
tcgtccgcca 310

<210> SEQ ID NO 195
<211> LENGTH: 310
<212> TYPE: DNA
<213> ORGANISM: Chlorella vulgaris

<400> SEQUENCE: 195
cggtctcgtc cgccaacacc ctgctccagg cgccacacac cctcccctcc ccgcctctcc 60
ctcctctcta gcttccagga agtagcaaag aacggttact gtggtgttac agcgcgcata 120
cgcggctggg ggtggatgcg agtataatcg tgtcgaggtg ggagttgaaa attatcctct 180
ctggggacga gtggcggggc accaaaccaa atgctgaaag cacaagcaga acaaagggag 240
acaagctaaa agctacaaca cctgcgccgc catcaagcgg gcgccggcgg accaagcggg 300
ggtgcggcat 310

<210> SEQ ID NO 196
<211> LENGTH: 310
<212> TYPE: DNA
<213> ORGANISM: Chlorella vulgaris

<400> SEQUENCE: 196
tcttactgtt gtggggctgc gcctgtgcta agctggctgc ccgccgcctg cactgaacac 60
ctggcatgcc tgccctggag ctgcggtgca gatgcatgtg catgtggcgc agctcgacac 120
agcactgcag accttcctca aaagcgtggc agtggatgcc ccagactgga aatatgcaaa 180
ttgcaccggg tggcagagct tgaggtgtgc agccaccaac aaagccacgg gagtggctgc 240
tgtgtgcaag tcggtcaacg ctgggcgggg cccctccgat gcggtgcctt ttgaaagcgt 300
ctacggcaca 310

<210> SEQ ID NO 197
<211> LENGTH: 310
<212> TYPE: DNA

<213> ORGANISM: Chlorella vulgaris

<400> SEQUENCE: 197
agcgtctacg gcacatacaa cagcactgct accatgctgg ccaccacagc agtttactcg 60
ccgcgtgaca atgtcttttg cgtccttcgg gcaactgacc ggccggtggg caggcggcca 120
gctgcggcat gccctgctgc cgtctgggcg gcacaggctg cttccttccc atctgtgtgt 180
tgggttgatg gtgtgctggc tgcccctgtt gcaggctgag tgtctgctcc gatgcaagac 240
ggagtgccaa tcaaaggctg gcatcaagtg cccgtgagcc gccccacctt cctgtggtgg 300
tcagcgcctc 310

<210> SEQ ID NO 198
<211> LENGTH: 310
<212> TYPE: DNA
<213> ORGANISM: Chlorella vulgaris

<400> SEQUENCE: 198
gccggtttac gcaaggcgcg gcaaagcaaa gcacccggcg caggcgtgca cgaaggatcg 60
cagggtgggg caggctgagg catgccggca ggcatgggag gcggtgagtg cgagccagca 120
cagcgcgggt ggaggctcac gctttgctgc cagaggcctt gccgctgcca gcggtgggcc 180
cctcctcccg ccgccgcttg ttcctgcatg cgggtgcggc gcggaaatgc agcatgcttg 240
gcagcatcac ggtgtagcgg tgcccccggg gctggtgtgg ggcaatgcca gccagctgca 300
gtgtcccggc 310

<210> SEQ ID NO 199
<211> LENGTH: 310
<212> TYPE: DNA
<213> ORGANISM: Chlorella vulgaris

<400> SEQUENCE: 199
ctgcagtgtc ccggcggtgt ggcccaaaac ggcaccgccc aggtcgggcg acgctggcgg 60
cagcgacggc ggcggcgcag gggtggggcc tggcccccat ctgcgggcgg catctaggtg 120
gcggagggat gctgcgtagt ttcaaggcgc agggagcgca cctggagggc ggcaaagcgg 180
tgggcggccc catctccacg acagctgttc cgctgcgccc ctccccgctg ccagggctgt 240
tcactgcgtc aaccgctccc gattgcgcgg tcagacgccc agcttttggg tcgccagccg 300
gtacaggtgt 310

<210> SEQ ID NO 200
<211> LENGTH: 310
<212> TYPE: DNA
<213> ORGANISM: Chlorella vulgaris

<400> SEQUENCE: 200
agccggtaca ggtgtacccc aggctgggtt gacgcccaaa gtcgcaatgc gcgtgggatc 60
gggcctctgt gttgcttgtg tgcccaggac agaagcagca gagcaggcac catggccgct 120
gccaccttct ccgcccaggc gaccgtcgca gcccgtgtgg cgaccaccgc caagagctcc 180
accagcatga aggtccgatg gggcgccggg ggcatcgttg ccggccttcg atatgccagg 240
gagccaagcg gggccctggg cgccgtctta tccgctgcct tgcattgatg ccctgcaggt 300
ggctccccgc 310

<210> SEQ ID NO 201
<211> LENGTH: 310

<212> TYPE: DNA
<213> ORGANISM: Chlorella vulgaris

<400> SEQUENCE: 201
ggcgggggac acgcggcggg cagccccgag gcggcaccgg gcgccggccc cggcagcgcc 60
ggcgtcagcc cgccgcagcc gcccgccgcg gccgagcgcg cgcagcccag ccccggcagc 120
ggcggcggcg gcgaggtgcg ccgctcctgg ggcagcctca agtccaagtt tggcagcctg 180
agcgggcggg gaggcagcaa ggaggaggag gcggtggcgg ctggggcggc cgccaacaca 240
ccacgcaaat aggggcacgc gcatctgctg cctggcccct gccggatggt tgatgtgtac 300
agaagagttg 310

<210> SEQ ID NO 202
<211> LENGTH: 310
<212> TYPE: DNA
<213> ORGANISM: Chlorella vulgaris

<400> SEQUENCE: 202
tgtacagaag agttgagagc gtcagtaggg ttgtggtggg gtgccggttg ccccgcccat 60
ctcatcccag ttgtttccct tcaaaaccaa ccccagccaa taggttctta accagtacat 120
cgtagacgca actctgaaca tccgggccac tgattcttgt cgatttatct tgttgattgg 180
ttgagcagca cgtgtgcatc cccgctactc tgtatgtatc cagccatgcc gtctgttccc 240
cttgccagcg gtgcaacact tgttttcttt gtcttgcaac atttcggtgt gatggaagtg 300
aaggaaaaaa 310

<210> SEQ ID NO 203
<211> LENGTH: 310
<212> TYPE: DNA
<213> ORGANISM: Chlorella vulgaris

<400> SEQUENCE: 203
aagtgaagga aaaaagccac agtgaagaaa tgaggtaagc aatgaaggca gggacaaagg 60
gagagcaggg caccgggaaa gagagcagca tgacacggga cgagtagacg gctcacaacc 120
caccggcggg agcagggaag aatggaaggg gaggcgagcc aggcggcagc acccgtctca 180
atgtgacttc tacttggcat cggcggcacc tggcaggcgg aacctgcctc ctcgaagggc 240
gcgggtgcgc cccgccaggc ttacggctgg gcagcggcca tgccagtcgc tgcgttgccc 300
tgacaactcc 310

<210> SEQ ID NO 204
<211> LENGTH: 310
<212> TYPE: DNA
<213> ORGANISM: Volvox carteri

<400> SEQUENCE: 204
aggcccatgg ttcgccttgg agtttgtgcc ttcttggaaa ttacaataga aggcgtgcag 60
aacacattta gtgcattttt atataaggta ttctcatggg cttctctgac agttaaacaa 120
cactacgtag agccgcgcac ccgcccctgc gctgtgtttc ggcccggtca gggcccccgg 180
tgctcgtcct ttttcggggt gagccgtgag ccgccccaca gcgtaacacc ccaacactcc 240
tgtagaaaca tgacattagc caaaagcatc tccctgtcac agcttcgcta atgattgtgg 300
ttgtgaacaa 310

<210> SEQ ID NO 205

<211> LENGTH: 310
<212> TYPE: DNA
<213> ORGANISM: Volvox carteri

<400> SEQUENCE: 205
tgtggttgtg aacaaaatcc ctccttggac agggtcgttt gcaggtaaca taactccctc 60
gagcctcgta actttactcc agcgtacttg tactgtgcgt taacaagaca acctgtctgg 120
aagtaatgct ttgctaggaa tccttctaca acgcttcatg catgtaaaca gcgactacga 180
agaaaactaa aagggagcaa tccatatcag tatcatacgt aaaggggtac tacatttctc 240
acgtagtggc ccattcagtt tcaggggtgt atacttgctt ttgcaagtgg tttgcaaaat 300
catgtaagct 310

<210> SEQ ID NO 206
<211> LENGTH: 310
<212> TYPE: DNA
<213> ORGANISM: Volvox carteri

<400> SEQUENCE: 206
aaaatcatgt aagctatttg atttagccac gcaaatccga aagaatgcca tacaagcagt 60
gtcatcctgt acccgaagct tcagagctct tcacttgccc atcattataa ataagctaag 120
agagtaatgc acaaactttt ataacctaat gcacacaggt acaggaagcg gtcctgacgg 180
aagaggtcac gtcgtacgca tagggccctc gatcacagca aggaacaccc ttttatgggc 240
gcagcagcgc tggtatggac acttgcgctg cccttctctt cttgtgtgtt ctaaacagta 300
gccagtcaaa 310

<210> SEQ ID NO 207
<211> LENGTH: 310
<212> TYPE: DNA
<213> ORGANISM: Volvox carteri

<400> SEQUENCE: 207
aagctccact agctccgaag ttccgacacg gtctcacacg cgctcgttaa ctaacttcaa 60
aacattacac tgcaagtcaa aattgcgcag cgctgcttga tcagctacct taacgcgcgg 120
cacgacaaga cgcgttggtt atgccagcac tgacccgcct caagcaatac ggcaagataa 180
ggatcttccc cgtggcaggg ttggaagttg ctgttggcat gcggagagct gtgaggtcac 240
atctcacatg gaaacgcgtg tagcacaact cttggctgcc tatgccagtc ctgaaggaca 300
ctttcagaac 310

<210> SEQ ID NO 208
<211> LENGTH: 310
<212> TYPE: DNA
<213> ORGANISM: Volvox carteri

<400> SEQUENCE: 208
ggacactttc agaactgttg agatcataag ctactcggct acaacacatc tgtaaagtta 60
actgccagcg acaactctaa aaactgcggc cttttgcggc cacatgccgt gcgattgcca 120
actgcttggg tgtaaaggtt ggaattccgg tagttgatgc acaatttctc actgtttcta 180
agcattattc atgagaatgt ggcttagtaa tctaattaag tcatcttggc tcgatactgt 240
agtctacatc cacatggttc aggctgccga aggcctggcc atacgatgac cggaagtcag 300
tcgcgctaca 310

<210> SEQ ID NO 209
<211> LENGTH: 310
<212> TYPE: DNA
<213> ORGANISM: Volvox carteri

<400> SEQUENCE: 209

```
gtcagtcgcg ctacatacat gagctatgct tctttagttt ggcattctaa gcgaagctga     60

tacaatttca tttcatcatg tttaaatgcc actacgcccc atttctcctt tacacatccc    120

ggggaagacg agttacaatg tattaaatct tcaatcatat atacttgatt cttggcatgc    180

aggatggaaa gcgagttgta gggtgtgttg tcgtgcatcg cacgacatcg catgtagtag    240

tagtaggaac atgtcctcac ccgccaacac ataaggagcc aacgctaacc aagtctggcc    300

aatcagttca                                                           310
```

<210> SEQ ID NO 210
<211> LENGTH: 310
<212> TYPE: DNA
<213> ORGANISM: Volvox carteri

<400> SEQUENCE: 210

```
atagcgactt ggcggggcca ttgctttgcg gtttaggatt taaccgggtt ttctctggat     60

gaagagcgcg gacagctgac gagctttcct gcaaccgtat gttggcgacc ctggaagtgt    120

tagaaagctt agaaagctta gaaagttaga aagctcgata tagtcgaaca atgagcacaa    180

aggaatgtgc tatgtgcttg ggaaattgca agaggccagc acaaatttgc tatgttgtcc    240

tcagcgccca cccaaagcct tcgggcctca gctttgcatg ggccaagttc ctgctcttaa    300

tttcggcaat                                                           310
```

<210> SEQ ID NO 211
<211> LENGTH: 310
<212> TYPE: DNA
<213> ORGANISM: Volvox carteri

<400> SEQUENCE: 211

```
cttaatttcg gcaattccat caattaggca tacaacatcg ttagcaggca taaatctctg     60

ctgtccatga ctatgtagag gaggcgcgca agcataacag ttgagtatct ctactgccga    120

accatttttt tatagatgca ttgtcttcaa gacctagtcc tgttcttctt atgctttacc    180

acaacgagaa gcgcggaggg atatcgctgt acctatgtgt aacgaaaagg gcttgcatgc    240

atgcatgcac catgaagcaa atcctaaaga aaggcgtaaa tgtaaaaaca tgtatggcaa    300

agccaacgat                                                           310
```

<210> SEQ ID NO 212
<211> LENGTH: 310
<212> TYPE: DNA
<213> ORGANISM: Volvox carteri

<400> SEQUENCE: 212

```
ggcaaagcca acgatgttaa acatgtgagc gtggaactga cgtgtgcaaa gtacaactcg     60

aacttgcagc agtaaatctt ccaaatagct aacgtatcca tatagcatag gaaaattaaa    120

tacacatgcg ctccatgcat aaattctcca actggacgag ctaccatgtc tggttgagag    180

acctgccgta ccccaaccct accacgtccg tactcttttg gataaaacaa aggtggcccc    240

aatgtccaag catcattcac attttgagct gcaccgcatt cgtcgttcat tgtaatctcc    300

ttataacaag                                                           310
```

<210> SEQ ID NO 213
<211> LENGTH: 310
<212> TYPE: DNA
<213> ORGANISM: Volvox carteri

<400> SEQUENCE: 213
gtacggttgc gtgctattat atctatgggt tgtgtttgga agtttttagc aagacatgct 60
atcgaggggt cacatttgaa gttgcatcat ggtagcgaat catgatgcac aaccaattga 120
cagctcctcc tcattgcagc ttgacgtaat ccgctaatgt ccccgaccgc agtgagccca 180
tgttgacgag tttggcaaat cataagatgg ggtatgcgta cacacccacg tgtcaagcgg 240
ttagacttga ggacaaacca taagcttcgg agcttcagat gctatcggtg cacttgcgga 300
caactgcagc 310

<210> SEQ ID NO 214
<211> LENGTH: 310
<212> TYPE: DNA
<213> ORGANISM: Volvox carteri

<400> SEQUENCE: 214
gcggacaact gcagctccag agggggaatt caaaggtctt ggagtcgcgg gtttagggtg 60
catttccagt gcggattaag gccaaagatt aaccctctgt cctccatcga tacttgctca 120
aacggctaag ttgttggcaa acttacctcg acttttcaac ctttggttcc cttatggaac 180
aaaactatgt ggtaagctcg taccaaggac ttccgtgccc taatccctgg ccttaatccg 240
cactggaaat gcgcccttaa agatggagtg atgtcccatt gcaaggccgc aattgaaagg 300
agctccttgc 310

<210> SEQ ID NO 215
<211> LENGTH: 310
<212> TYPE: DNA
<213> ORGANISM: Volvox carteri

<400> SEQUENCE: 215
aaaggagctc cttgccagca tcgcctgagt agtctatatg gtctttttaaa ctctgacttc 60 cctgcaagag gcttgctatt gcctgaccca tacgcagcgg acagtgtcct gtttcacaag 120
taatgtgcaa taaaactatg caaagaaact tttcataata tgactaaata ttgtaatagt 180
ctgagtctcc ctatttagta ggaatgcgca ccgcggtact atagcagata aggtgccgta 240
catagactga agcggcaaga acaagagggg tgcagcagca tagatccttg ctttagggtc 300
aattgcaaag 310

<210> SEQ ID NO 216
<211> LENGTH: 310
<212> TYPE: DNA
<213> ORGANISM: Volvox carteri

<400> SEQUENCE: 216
gtacttggca aggtgctata gaagtagaag ataggagacg atgattgaca ctttggtccg 60
actatttggc tcgacattcg cacgacattc ctagctgatg agagggatgt caagatgtca 120
gggcaatcaa tcctgtcaca ttcagtcttg ttgaaataat cgtagtgtct tggtttcatt 180
ataaatcggg gagttgcaga ggagacgttc ccaccagcga gcgatgcctg aagatgtcta 240
tgtgcacaga ctgttgcatt ttcagatgat atgcaataaa gataagaaca caagtcgtgc 300
aggaaaaacg 310

<210> SEQ ID NO 217
<211> LENGTH: 310
<212> TYPE: DNA
<213> ORGANISM: Volvox carteri

<400> SEQUENCE: 217
cgtgcaggaa aaacgcgcaa cgatgcttta acgcatagtg gtttaagatg ggcgcgctga 60
attgatccgg catggagcgc gatgcgaatt atgtttgaat acatgaagca ttcatgtaaa 120
caattaaata cgtttggtca aaaataaagt gcgcaccacc aacgcatcgt ccctgtctcg 180
cagaaaatca tacttccaat ttctcatcta aacggatcaa attgcagcta ctgaaacatc 240
aagcaaatat aacgacatcc tccgtgcaag atcaaaaatg attcacattg cactttcgcc 300
attgatcccg 310

<210> SEQ ID NO 218
<211> LENGTH: 310
<212> TYPE: DNA
<213> ORGANISM: Volvox carteri

<400> SEQUENCE: 218
tcgccattga tcccggaatt cgtttgacag cgcgaaccca taagccaatc accctatcat 60
aaagcataaa tcttccatta aacataccct atcaacctgg ccgcaacttg tggggatgta 120
actgtatgtg ggtttgtgtg tgtgggtgct cggccaaata cagccggcgt acgacatcac 180
actgacctac tacctttctt atctttttta tatatgctgc tatgcacccg gcttactcgt 240
atagcagtgt tacaaagcta gttggtttca gtagtgtgtt gttcctcatt gatcatcata 300
tctggaaagc 310

<210> SEQ ID NO 219
<211> LENGTH: 310
<212> TYPE: DNA
<213> ORGANISM: Zea mays

<400> SEQUENCE: 219
agttgtcacc acaaaccaaa cgggcgttat ttgttcttcc atcttattgc cttttcaagg 60
atgagtcatg tcttggacaa aacttcagca attttctaat aaaagaacat tcctatggtg 120
tatgatgtta atcatcgttt ctcccacctc tcttttccag ggacactgtc gatgcaatat 180
ttgaagagct ggttataaac accaagaagc ttgtggctgc aacgtcaaaa tgaatcgaaa 240
aatagcgttg agtggcacca ctgcattgtc gtctctatta atcagcttga acaggcggta 300
ggacttagtc 310

<210> SEQ ID NO 220
<211> LENGTH: 310
<212> TYPE: DNA
<213> ORGANISM: Zea mays

<400> SEQUENCE: 220
cggtaggact tagtcctaga atgcagcctg ttgatctcat gacattctat taattatgag 60
cgtagttagg taggatactg acacaacaca catggtttct ggtccatatt tattagttac 120
attccagtat attgtggatt gctcatcact tgttaaatta gagaaaattg atgctctgag 180
cttcagatga actttgtttc gtgcttgtgc gtgtgttctt cacccttctg gtatcagtgt 240
gtggccagca cttgttgtct cggcgctctc tctcactcac tctggttggt tcccctaggt 300
ctttgtctat 310

<210> SEQ ID NO 221
<211> LENGTH: 310
<212> TYPE: DNA
<213> ORGANISM: Zea mays

<400> SEQUENCE: 221
taggtctttg tctatcttgt ttgggccatt tggcgctaac taaccaacaa gtgcacaaga 60
ggcccctcaa gctgccacat cagcaccctc atctgccaag tcagcacagc ctgcccaatc 120
gcctccaggc aacagatagc cctgatgggc acccatccaa tggcagctcc gatggccaaa 180
tctctgctag gcccacagca tcctccgatc ctcattttca tccatttaaa ctagctcgcc 240
ttttcctcca caagccccca tcagccatcc cctcccgcgg caagtctctc tgaattgtgg 300
gtctccggcg 310

<210> SEQ ID NO 222
<211> LENGTH: 310
<212> TYPE: DNA
<213> ORGANISM: Zea mays

<400> SEQUENCE: 222
cagtgagaaa aggccttgcc actctacgta tctgatgttg ttaataattt cagaagtcgt 60
cgtatatacc atggggtgtt taattgtcgt atatacgatg ggatgcttaa ttgtcgtata 120
tacgatggta tgatgaaaca actgacttaa acatcacact gaacaatttc agaaaacgat 180
ccatgccgtc gtatatatac gacaacaaaa taccagaagc aaacctccca gacccaaggg 240
gaaataaacg ggcctgcttc tggtcgctag cttgggggcg ctggagctgc agtgcgtagg 300
cccgtccgat 310

<210> SEQ ID NO 223
<211> LENGTH: 310
<212> TYPE: DNA
<213> ORGANISM: Zea mays

<400> SEQUENCE: 223
gtaggcccgt ccgatccgtg gctcgtctcg gcatggccac acaaaccacg aacggtcgtc 60
gtgcaccgca gcgcggcccc cccgttctat cttctccagc tccaaatggc gccatcgcgg 120
cggccgggtt atcttgtcca gacgtgcatc atatcctccg tgtgatccat tcatccccgc 180
gccgtgctag cttgctagtt gcaagcacca gccgaccacc aaacggtagc gcacgcggac 240
aatttaacag catcaggttt aggccctgct gccgtcgtcg agcgcccggg ccaccgcaca 300
cctgaaagca 310

<210> SEQ ID NO 224
<211> LENGTH: 310
<212> TYPE: DNA
<213> ORGANISM: Arabidopsis thaliana

<400> SEQUENCE: 224
ttctggtaat gtgtatggtt tgagtgctga tttttggtgc tatgagttgt tctttatggc 60
tcaacttgga tcaatatgga ggttgagttt gagattttct ctcagtttaa ggaggtagaa 120
tagtgcgtat agtggcacag tgagctcagc tctagggcca aagggcataa attcattata 180
gctctttcga ttctaccgta gtactgtgtg tgaaccggca ctgtgaacca agatgattaa 240
attttcgtat tctctatgta catgatcctg cggctcaatc gcttcagttt cgatccacat 300
gatgtatatg 310

<210> SEQ ID NO 225
<211> LENGTH: 310
<212> TYPE: DNA
<213> ORGANISM: Arabidopsis thaliana

<400> SEQUENCE: 225
cacatgatgt atatgttata gaattgtggg aaactccttg tagaaagagt atgttcacgt 60
ctaggactag tcggatgatt cgtttctctt tttggtgtaa tgagtatgtt cataactgtt 120
gatacaatgt gaaaatctaa ccgttgagct tgggagtttt acgtctatat gaaaattccg 180
gttgtcgtct acattacggt agtaaacagg accacagtga ttccaaatgt cccaaggaat 240
ttactgaaaa ccccaactag gactgtgaaa ggcttgtgga tgacatttaa cagttgagat 300
tttcatgtgt 310

<210> SEQ ID NO 226
<211> LENGTH: 310
<212> TYPE: DNA
<213> ORGANISM: Arabidopsis thaliana

<400> SEQUENCE: 226
gagattttca tgtgtttgag attcttgtaa cacattttgc tgtataggtg aaagcttagc 60
cacacaaaag gagaaacaga ggatatggat aaaataaatt atccaacaaa aaccaatcta 120
aaagccacat cagcatccac aaccaatcag aggacagaat catatttcac attttcaatc 180
cagaccaatc aaaatcctga acgaatccta ctctccacct tataggagca gtttcgtctc 240
ttcctccttc tttcacttag ctcttcctag tgttaaacca gagtaaagct tgaaactttg 300
gactaaaaga 310

<210> SEQ ID NO 227
<211> LENGTH: 310
<212> TYPE: DNA
<213> ORGANISM: Arabidopsis thaliana

<400> SEQUENCE: 227
tataatttgg tttgtatgtc attggtgatg taaactgaaa ttgaagataa tagaatctca 60
taaccacaca aaaaatgaat gaacgcaaat caaagcctct caacacatct ctttgcctcg 120
gtctctctct cgcccaattg cccatcacca gagcttaatc atatcttctt cagttactgc 180
cacgtgtcac tctgaccgtg aacagccttt atctcttcca agtccacttg tgttcttgat 240
tattttgtct tcaccattct ctctactcaa agctcttctt cttcgatcaa aaaacctcga 300
gcttctaaca 310

<210> SEQ ID NO 228
<211> LENGTH: 11
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t

<400> SEQUENCE: 228
tgngcanntn n 11

<210> SEQ ID NO 229
<211> LENGTH: 10
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 229 narycctcgn 10

<210> SEQ ID NO 230
<211> LENGTH: 10
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 230 bnbctcttcn 10

<210> SEQ ID NO 231
<211> LENGTH: 13
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t

<400> SEQUENCE: 231
nrwmcgttac rww 13

<210> SEQ ID NO 232
<211> LENGTH: 11
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t
<220> FEATURE:

<221> NAME/KEY: misc_feature
<222> LOCATION: (11)..(11)
<223> OTHER INFORMATION: n is a, c, g, or t

<400> SEQUENCE: 232
nvythagcgb n 11

<210> SEQ ID NO 233
<211> LENGTH: 13
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 233
nwwyyrgatc trn 13

<210> SEQ ID NO 234
<211> LENGTH: 11
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 234
ngvtgacgts n 11

<210> SEQ ID NO 235
<211> LENGTH: 10
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 235 nygmcagsyn 10

<210> SEQ ID NO 236
<211> LENGTH: 10
<212> TYPE: DNA
<213> ORGANISM: Artificial
<220> FEATURE:
<223> OTHER INFORMATION: Synthetic algal promoter or element
<220> FEATURE:
<221> NAME/KEY: misc_feature
<222> LOCATION: (1)..(1)
<223> OTHER INFORMATION: n is a, c, g, or t -continued

```
<220> FEATURE:
<221> NAME/KEY: misc_feature
<222> LOCATION: (10)..(10)
<223> OTHER INFORMATION: n is a, c, g, or t

<400> SEQUENCE: 236

nghatmtwcn                                                              10
```

SYNTHETIC ALGAL PROMOTERS

STATEMENT OF GOVERNMENTAL SUPPORT

This invention was made with government support under DE-EE-0003373 from the United States Department of Energy. The government has certain rights in the invention.

CROSS-REFERENCE TO RELATED APPLICATIONS

This application is a U.S. 371 National Phase of International Application No. PCT/US2017/018196, filed on Feb. 16, 2017, which claims the benefit under 35 U.S.C. § 119(e) of U.S. Provisional Application No. 62/295,997, filed on Feb. 16, 2016, which are hereby incorporated herein by reference in their entireties.

INCORPORATION BY REFERENCE OF SEQUENCE LISTING PROVIDED AS A TEXT FILE

A Sequence Listing is provided herewith as a text file, "UCSDP044US_corrected2.txt" created on Dec. 14, 2020 and having a size of 205,667 bytes. The contents of the text file are incorporated by reference herein in their entirety.

BACKGROUND

Algae are among the most ancient and diverse organisms on the planet. Microalgae have evolved to adapt to a wide range of environments and consequently have proven to be a rich source of genetic and chemical diversity (Blunt et al., 2012; Gimpel et al., 2013; Parker et al., 2008). This diversity has been exploited as a unique source of bioactive compounds, including antioxidants, omega 3 fatty acids, and potentially novel therapeutic drugs (Cardozo et al., 2007). In addition, microalgae have also proven to be cost-effective and safe hosts for expressing a wide array of recombinant proteins, including human and animal therapeutics, vaccines, and industrial enzymes (Georgianna et al., 2013; Griesbeck and Kirchmayr, 2012; Rosales-Mendoza et al., 2012; Specht et al., 2010).

*Chlamydomonas reinhardtii* is a long established model system for studying molecular and genetic systems of algae. The most successful advances in recombinant protein expression within *C. reinhardtii* have been within the chloroplast where exogenous protein levels have reached almost 10% of total soluble protein (Manuell et al., 2007). This progress has been aided by the fact that gene integration occurs exclusively by homologous recombination within the plastid (Fischer et al., 1996). The chloroplast also has strong, well-characterized promoters and regulatory untranslated regions (UTRs) to enable high levels of transgene expression (Rosales-Mendoza et al., 2012; Specht et al., 2010). The most successful regulatory elements are those from endogenous highly expressed photosynthetic proteins (Gimpel and Mayfield, 2013; Rosales-Mendoza et al., 2012; Specht et al., 2010). However, recent work in the Mayfield laboratory has shown that high-throughput analysis of synthetic 5' UTRs can identify novel regulatory elements and lead to increased transgene expression within the plastid (Specht and Mayfield, 2012).

While advancements have been made in heterologous nuclear gene expression in *C. reinhardtii* over the last several years (Rasala et al., 2013; Rasala et al., 2012; Schroda et al., 2000), these tools still lags significantly behind both plastid gene expression in algae, as well heterologous gene expression in many other eukaryotic organisms. Controlled nuclear gene expression is an essential tool for synthetic biology in any industrial microorganisms. Recent advances also allow protein products to be targeted to any cellular location in *C. reinhardtii* (Rasala et al., 2013). Targeted expression is essential for metabolic engineering, since enzymes need to be localized to their functional site. Proper localization is also important for the production of high-value protein products. Specific organelles may be better suited for proper post-translational modification and folding of complex proteins. In particular, chloroplasts lack the enzymes involved in protein glycosylation, an essential modification for many therapeutic proteins (Lingg et al., 2012). Finally, nuclear expression allows for the secretion of recombinant proteins, which can lead to simpler and cheaper downstream processing (Corchero et al., 2013).

One of the main reasons for poor heterologous gene expression from the nuclear genome of algae is the lack of strong promoters (Rosales-Mendoza et al., 2012; Specht et al., 2010). Studies have identified several endogenous promoters that promote exogenous gene expression, including those from the well-characterized and highly expressed genes such as those for the Rubisco small subunit (RBCS2), heat shock protein 70A (HSP70A), and photosystem I protein psaD (Cerutti et al., 1997; Schroda et al., 2000; Fischer and Rochaix, 2001). In an attempt to increase expression above the modest levels achieved with these native promoters, chimeric promoters have been developed that contain the heat shock 70A promoter region fused upstream of the RBCS2 promoter (arl), which has led to increased transcription (Schroda et al., 2002; Schroda et al., 2000; Wu et al., 2008). However, protein accumulation from exogenous genes expressed using this best chimeric promoter is still poor, with recombinant protein levels peaking around 0.25% of total soluble protein, which is well below the level of economic viability for almost any recombinant protein product. Finally, viral promoters that are favored in higher plant expression systems have been shown to be minimally successful in algal systems (Diaz-Santos et al., 2013). Therefore, novel regulatory elements must be identified or generated and combined into robust promoters capable of driving high rates of transcription in order to achieve the robust exogenous protein expression required to make algae a true industrial organisms.

Several recent reviews have highlighted the generation of synthetic promoters and promoter libraries as important biobricks for protein expression and, in particular, systems engineering (Blazeck and Alper, 2013; Hammer et al., 2006; Mukherji and van Oudenaarden, 2009; Ruth and Glieder, 2010). Engineered promoters have demonstrated the ability to drive exogenous gene expression above levels achieved by the best native promoter systems. In addition, development of libraries of designer promoters is essential for systems engineering. The synthetic nature of these promoters reduces or eliminates the chance of homology dependent gene silencing and can potentially allow them to be utilized in multiple species or cell lines. In this study, publicly available mRNA expression data was utilized to identify cis-motifs found in promoters of highly expressed *C. reinhardtii* genes. These motifs were then used to generate a novel set of completely synthetic algal promoters (saps) that allowed for high constitutive gene expression within the *C. reinhardtii* nucleus. A combination of analyzes of these native promoters and novel saps revealed previously uncharacterized *C. reinhardtii* promoter structures including a newly identified core DNA motif important for promoter function in highly transcribed genes.

SUMMARY

Provided are synthetic promoters useful for high level transcription or expression of polynucleotides in an algal cell. Accordingly, in one aspect, provided is a synthetic promoter capable of promoting and/or initiating transcription of a polynucleotide in an algal cell. In varying embodiments, the synthetic promoter comprising from 3 to 30, e.g., from 3 to 27, e.g., from 3 to 25, e.g., from 3 to 20, e.g., from 3 to 15, e.g., from 3 to 10, e.g., from 3 to 5, promoter (cis)-elements selected from the group consisting of the sequences in Tables 1 and 2, and FIGS. 16A and 16B. In varying embodiments, the promoter (cis)-elements are positioned or located within the promoter relative to the transcriptional start site (TSS) as indicated in Table 1. In varying embodiments, the synthetic promoter comprises one or more transcriptional factor binding site motifs selected from the group consisting of the sequences in FIGS. 17A, 17B, and 17C. In varying embodiments, the promoter comprises a nucleic acid sequence of any one of the sequences in Table 4 (e.g., any one of SEQ ID NOs:38-62). In varying embodiments, the promoter is responsive to light exposure and comprises one or more promoter (cis)-elements selected from the group consisting of the sequences in FIG. 16A. In varying embodiments, the promoter is responsive to dark exposure and comprises one or more promoter (cis)-elements selected from the group consisting of the sequences in FIG. 16B. In varying embodiments, the promoter is at least about 200 bp in length and up to about 500 bp, 600 bp, 700 bp, 750 bp, 800 bp, 900 bp or 1000 bp in length. In varying embodiments, the synthetic promoter promotes transcription levels that are at least about 2-fold greater, e.g., 3-fold, 4-fold, 5-fold, 6-fold, 7-fold, 8-fold, 9-fold, 10-fold, or more, greater than a control promoter (e.g., a random polynucleotide sequence or a native promoter). In varying embodiments, the promoter (cis)-elements are positioned or arranged within a promoter scaffold or backbone. In varying embodiments, the nucleic acid base of highest probability or second highest probability at a particular position of the promoter scaffold or backbone (e.g., based on known native promoter sequences) relative to the transcriptional start site (TSS) is assigned to that position, e.g., as indicated in Table 3. In varying embodiments, the algal cell is a green algal cell. In varying embodiments, the green algal cell is a *Chlamydomonas* cell. In varying embodiments, the green algal cell is a *Chlamydomonas reinhardtii* cell.

In another aspect, provided is an expression cassette comprising a synthetic promoter as described above and herein.

In another aspect, provided is a vector comprising the expression cassette comprising a synthetic promoter as described above and herein. In varying embodiments, the vector is a plasmid vector.

In another aspect, provided is a cell comprising a synthetic promoter, or an expression cassette or vector comprising the synthetic promoter, as described above and herein. In varying embodiments, the cell is a green algal cell. In varying embodiments, the cell is a *Chlamydomonas* cell. In varying embodiments, the cell is a *Chlamydomonas reinhardtii* cell. In varying embodiments, the cell overexpresses, e.g., by at least about 10%, 20%, 30%, 40%, 50%, 60%, 70%, 80%, 90%, 100%, 150%, 200%, or more, greater than a control, one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO:150 (TF64). In varying embodiments, the cell underexpresses, e.g., by at least about 10%, 20%, 30%, 40%, 50%, 60%, 70%, 80%, 90%, 100%, 150%, 200%, or more, less than a control, one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs: 87-178, e.g., SEQ ID NO: 150 (TF64).

In a further aspect, provided is a method of transcribing or expressing a polynucleotide, e.g., in vitro or in an algal cell. In varying embodiments, the methods comprise contacting a polymerase to a polynucleotide comprising the synthetic promoter operably linked to a coding polynucleotide under conditions that allow the polymerase to transcribe the coding polynucleotide under the control of the synthetic promoter. In varying embodiments, the methods comprise introducing into the algal cell the polynucleotide operably linked to, e.g., and under the promoter control of, a synthetic promoter as described and herein. In a further aspect, provided is a method of increasing the transcription of a polynucleotide in an algal cell. In varying embodiments, the methods comprise introducing into the algal cell the polynucleotide operably linked to, e.g., and under the promoter control of, a synthetic promoter as described and herein. In varying embodiments, transcription of the polynucleotide is increased in response to light exposure and the synthetic promoter comprises one or more promoter (cis)-elements selected from the group consisting of the sequences in FIG. 16A. In varying embodiments, transcription of the polynucleotide is increased in response to dark exposure and the synthetic promoter comprises one or more promoter (cis)-elements selected from the group consisting of the sequences in FIG. 16B. In some embodiments, the transcription levels of the polynucleotide are increased at least about 2-fold greater, e.g., 3-fold, 4-fold, 5-fold, 6-fold, 7-fold, 8-fold, 9-fold, 10-fold, or more, greater than a control promoter (e.g., a random polynucleotide sequence or a native promoter). In varying embodiments, the (coding) polynucleotide operably linked to the synthetic promoter is codon-biased or codon-optimized for expression in an algal cell. In varying embodiments, the algal cell is a green algal cell. In varying embodiments, the algal cell is a *Chlamydomonas* cell. In varying embodiments, the algal cell is a *Chlamydomonas reinhardtii* cell. In some embodiments, the cell comprises one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO: 150 (TF64). In varying embodiments, the cell overexpresses, e.g., by at least about 10%, 20%, 30%, 40%, 50%, 60%, 70%, 80%, 90%, 100%, 150%, 200%, or more, greater than a control, one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO:150 (TF64). In varying embodiments, the cell underexpresses, e.g., by at least about 10%, 20%, 30%, 40%, 50%, 60%, 70%, 80%, 90%, 100%, 150%, 200%, or more, less than a control, one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO: 150 (TF64).

In a further aspect, provided is a method of designing, constructing and/or assembling a synthetic promoter, e.g., as described herein. In varying embodiments, the methods comprise assembling or arranging at least about 3 (cis)-elements, e.g., from 3 to 30, e.g., from 3 to 27, e.g., from 3 to 25, e.g., from 3 to 20, e.g., from 3 to 15, e.g., from 3 to 10, e.g., from 3 to 5, promoter (cis)-elements selected from the sequences in Tables 1 and 2, and FIGS. 16A and 16B within a promoter scaffold or backbone. In varying embodiments, the synthetic promoter comprises one or more transcriptional factor binding site motifs selected from the group consisting of the sequences in FIGS. 17A, 17B, and 17C. In varying embodiments, the promoter (cis)-elements are positioned or located within the promoter relative to the transcriptional start site (TSS) as indicated in Table 1. In varying embodiments, the promoter is at least about 200 bp in length and up to about 500 bp, 600 bp, 700 bp, 750 bp, 800 bp, 900 bp or 1000 bp in length. In varying embodiments, the synthetic promoter promotes transcription levels that are at least 2-fold greater, e.g., 3-fold, 4-fold, 5-fold, 6-fold, 7-fold, 8-fold, 9-fold, 10-fold, or more, greater than a control promoter (e.g., a random polynucleotide sequence or a native promoter). In varying embodiments, the nucleic acid base of highest probability or second highest probability at a particular position of the promoter scaffold or backbone relative to the transcriptional start site (TSS) is assigned to that position, e.g., as indicated in Table 3. In varying embodiments, the method is computer implemented.

In a further aspect, provided is a synthetic nuclear transcription system, the system comprising a synthetic promoter as described above and herein, operably linked to a polynucleotide of interest, and one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO: 150 (TF64). The systems can be used for in vitro or in vivo transcription. In some embodiments of the system, transcription of the polynucleotide is increased in response to light exposure and the synthetic promoter comprises one or more promoter (cis)-elements selected from the group consisting of the sequences in FIG. 16A. In some embodiments of the system, transcription of the polynucleotide is increased in response to dark exposure and the synthetic promoter comprises one or more promoter (cis)-elements selected from the group consisting of the sequences in FIG. 16B. Further provided is a cell or population of cells comprising the system as described above and herein. In some embodiments, the cell is a green algal cell. In some embodiments, the cell is a *Chlamydomonas* cell. In some embodiments, the cell is a *Chlamydomonas reinhardtii* cell. In varying embodiments, the cell overexpresses, e.g., by at least about 10%, 20%, 30%, 40%, 50%, 60%, 70%, 80%, 90%, 100%, 150%, 200%, or more, greater than a control, one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO:150 (TF64). In varying embodiments, the cell underexpresses, e.g., by at least about 10%, 20%, 30%, 40%, 50%, 60%, 70%, 80%, 90%, 100%, 150%, 200%, or more, less than a control, one or more transcription factors encoded by a polynucleotide comprising at least about 60% sequence identity, e.g., 70%, 75%, 80%, 85%, 90%, 91%, 92%, 93%, 94%, 95%, 96%, 97%, 98%, 99%, 100% sequence identity, to SEQ ID NOs:87-178, e.g., SEQ ID NO:150 (TF64).

In another aspect, provided is a kit comprising a synthetic promoter, or an expression cassette or vector or cell comprising the synthetic promoter, as described above and herein. In another aspect, provided is a kit comprising the synthetic nuclear transcription system, including green algal cells comprising the synthetic promoters and optionally overexpressed or underexpressed transcription factors, as described herein.

Definitions

Unless otherwise provided, all technical and scientific terms used herein have the same meaning as commonly understood by one of ordinary skill in the art of genetics, bioinformatics, and gene design. General dictionaries containing many of the terms used in this disclosure are: Singleton et al. (1994) Dictionary of Microbiology and Molecular Biology, 2nd Ed., John Wiley and Sons, New York; and Hale and Marham (1991) The Harper Collins Dictionary of Biology, Harper Perennial, New York. Any methods and materials similar or equivalent to those described herein may be used in the practice or testing of embodiments of the invention, though certain methods and materials are exemplified by those disclosed herein.

Codon optimization: As used herein, the term "codon optimization" refers to processes employed to modify an existing coding sequence, or to design a coding sequence in the first instance, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. Codon optimization also includes, for example, the process sometimes referred to as "codon harmonization," wherein codons of a codon sequence that are recognized as low-usage codons in the source organism are altered to codons that are recognized as low-usage in the new expression host. This process may help expressed polypeptides to fold normally by introducing natural and appropriate pauses during translation/extension. Birkholtz et al. (2008) Malaria J. 7:197-217. Codon optimization can also include codon abundance in relation to tRNA availability under certain conditions.

It will be understood that, due to the redundancy of the genetic code, multiple DNA sequences may be designed to encode a single amino acid sequence. Thus, optimized DNA sequences may be designed, for example, to remove superfluous restriction sites and undesirable RNA secondary structures, while optimizing the nucleotide sequence of the coding region so that the codon composition resembles the overall codon composition of the host in which the DNA is to be expressed.

Modify: As used herein, the terms "modify" or "alter," or any forms thereof, mean to modify, alter, replace, delete, substitute, remove, vary, or transform.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; and polyadenylation recognition sequences. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell.

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, and protein coating).

Expression: As used herein, the term "expression" may refer to the transcription and stable accumulation of mRNA encoded by a polynucleotide, or to the translation of such an mRNA into a polypeptide. The term "over-expression," as used herein, refers to expression that is higher than endogenous expression of the same or a closely related gene. A heterologous gene is over-expressed if its expression is higher than that of a closely-related endogenous gene (e.g., a homolog).

The terms "identical" or percent "identity," and variants thereof in the context of two or more polynucleotide sequences, refer to two or more sequences or subsequences that are the same. Sequences are "substantially identical" if they have a specified percentage of nucleic acid residues or nucleotides that are the same (i.e., at least 60% identity, optionally at least 65%, 70%, 75%, 80%, 85%, 90%, 95%, 96%, 97%, 98%, or 99% identity over a specified region (or the whole reference sequence when not specified)), when compared and aligned for maximum correspondence over a comparison window, or designated region as measured using one of the following sequence comparison algorithms (e.g., as described below and herein) or by manual alignment and visual inspection. The present invention provides polynucleotides improved for expression in algal host cells that are substantially identical to the polynucleotides AAACCCAAC, AAACCCATC, AACAGCCAG, AACTGAGG, ACCCCATCGC (Seq ID NO: 24), ACGGCCAT, AGCAAGTC, AGCAAGTC, AGCAATTT, ATGCATTA, CAACACACC, CACGAACC, CACGCCCTG, CGCTCGGC, and/or CGGGCCCA. Optionally, the identity exists over a region that is at least about 50 amino acids in length, or more preferably over a region that is 100, 200, 300, 400, 500, 600, 800, 1000, or more, nucleic acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul *Proc. Natl. Acad. Sci. USA,* 87: 2264-2268(1990), or by manual alignment and visual inspection (see, e.g., Ausubel et al., Current Protocols in Molecular Biology (1995 supplement)). Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (on the internet at ncbi.nlm.nih.gov/).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates TC rich identified by POWRs in the top 50 native promoters.

FIG. 5, panels A-D, illustrate promoter and motif deletions of sap11. Panel A) The expression vector was rearranged to have the hygromycin resistance cassette downstream of the mCherry cassette. sap11 was cloned upstream of the mCherry cassette with the rbcs2 5' and 3' UTRs (U) and the first rbcs2 intron (I). Portions of the sap11 promoter were removed through SLiCE cloning to leave −250, −150, and −50 bp of sap11 sequence upstream of the sap11 TSS. Panel B) Flow cytometry analysis for mCherry fluorescence of 5,000 transformants of the original and shortened sap11 constructs. Populations that are statistically different are indicated (a-c, Tukey's test, $p<0.05$). Panel C) Putative cis-motifs (underlined) in the −150 to 0 bp region of sap11 (SEQ ID NO:1) were targeted for mutational analysis. Eight residues (bold) were replaced with either polyA (A) or polyT (T) residues to generate six sap11Δm mutants including one in which both motif 3 and 4 were replaced (sap11Δm3-4). Panel D) Flow cytometry analysis for mCherry fluorescence of 5,000 transformants of the sap11 construct compared with sap11 motif deletion constructs.

FIG. 13, panels A-D, illustrates Basic Helix-Loop-Helix transcription factor alignment, strain construction and growth. Panel A) Protein sequence alignment of TF64-related proteins. The *C. reinhardtii* TF64 sequence from the PlnTFD was used as a query in a BLAST search for related proteins. Selected top hits are shown. *C. reinhardtii* strain 503 (in bold, used as a reference strain in this study due to the lack of a published sequence for strain cc1010) was among the top hits. Proteins from other related algal species are also shown. Alignment is focused on the basic Helix-Loop-Helix region. Functionally important conserved residues are indicated by color. *C. rein* PTFD (SEQ ID NO: 18), *C. rein* cc503 (SEQ ID NO:19), *V. carteri* (SEQ ID NO: 20), A. protothecoides (SEQ ID NO:21), *C. subelliposoidea* (SEQ ID NO: 22). Panel B) Schematic of the pTM207 vectors used to constitutively express the gene encoding TF64 and GFP. The ble gene confers zeocin resistance and 2A is a linker peptide that is cleaved post-translationally. The pTM207 vector also encodes an N-terminal 3×FLAG-tag fused to each TF, not shown. Panel C) Immunoblot of whole cell lysates of wild type (WT) *C. reinhardtii* and engineered strains producing TF64 (64-4, 64-7, 64-8, 64-9, 64-11) or GFP, separated by SDS-PAGE and probed with anti-FLAG antibody. Higher molecular weight product is prior to 2A cleavage. Panel D) Growth curves of wild type (cc1010) *C. reinhardtii* and strains producing TF64 (TF64-7) or GFP, cultured for four days in TAP medium under constant light. Growth was measured at OD750. Data is plotted from three biological replicates with the SEM for each strain. The "Exponential Growth" graph indicates the slope of the line during log phase growth for each strain by color.

FIGS. 16A and 16B, illustrate position frequency matrices rendered with Weblogo (Crooks et al., Genome Res. 2004 June; 14(6):1188-90). Letter height indicates relative frequency of nucleotides in the 8-letter motif. Below the position weight matrices is a nucleotide consensus sequence given for the motif. A probability cut off of 0.1 (out of 1) in the position probability matrix for the motif was used for the inclusion in the consensus sequence. N=A,T,G, or C. [X/Z] notation indicates that either nucleotide X or Z could be represented at a single position (e.g., A[G/C]T indicates that the first nucleotide in the motif is A and the second is either G or C while the third is T resulting in the variants AGT or ACT of the motif). FIG. 16A shows unique light-upregulated motif as position weight matrix rendered with Weblogo and IUPAC nucleotide consensus of light-upregulated motifs. FIG. 16B shows unique dark-upregulated motif as position weight matrix rendered with Weblogo and IUPAC nucleotide consensus of dark-upregulated motifs.

FIGS. 17A, 17B, and 17C illustrate predicted binding sites for *Chlamydomonas reinhardtii* transcription factor families as deduced by the Plant Transcription Factor Database. Letter height indicates relative frequency of nucleotides in the proposed binding sequence. To the right of the position weight matrices is a nucleotide consensus sequence given for the motif. A probability cut off of 0.1 (out of 1) in the position probability matrix for the motif was used for the inclusion in the consensus sequence.

FIG. 18 illustrates AR1 promoter sequence (SEQ ID NO:23) with putative bHLH-family TF binding sites identified by underlined and bolded text.

FIG. 19 illustrates orange fluorescent protein (OFP) fluorescence when driven by AR1 in a TF64 expressing strain.

DETAILED DESCRIPTION

1. Introduction

Figure 1:
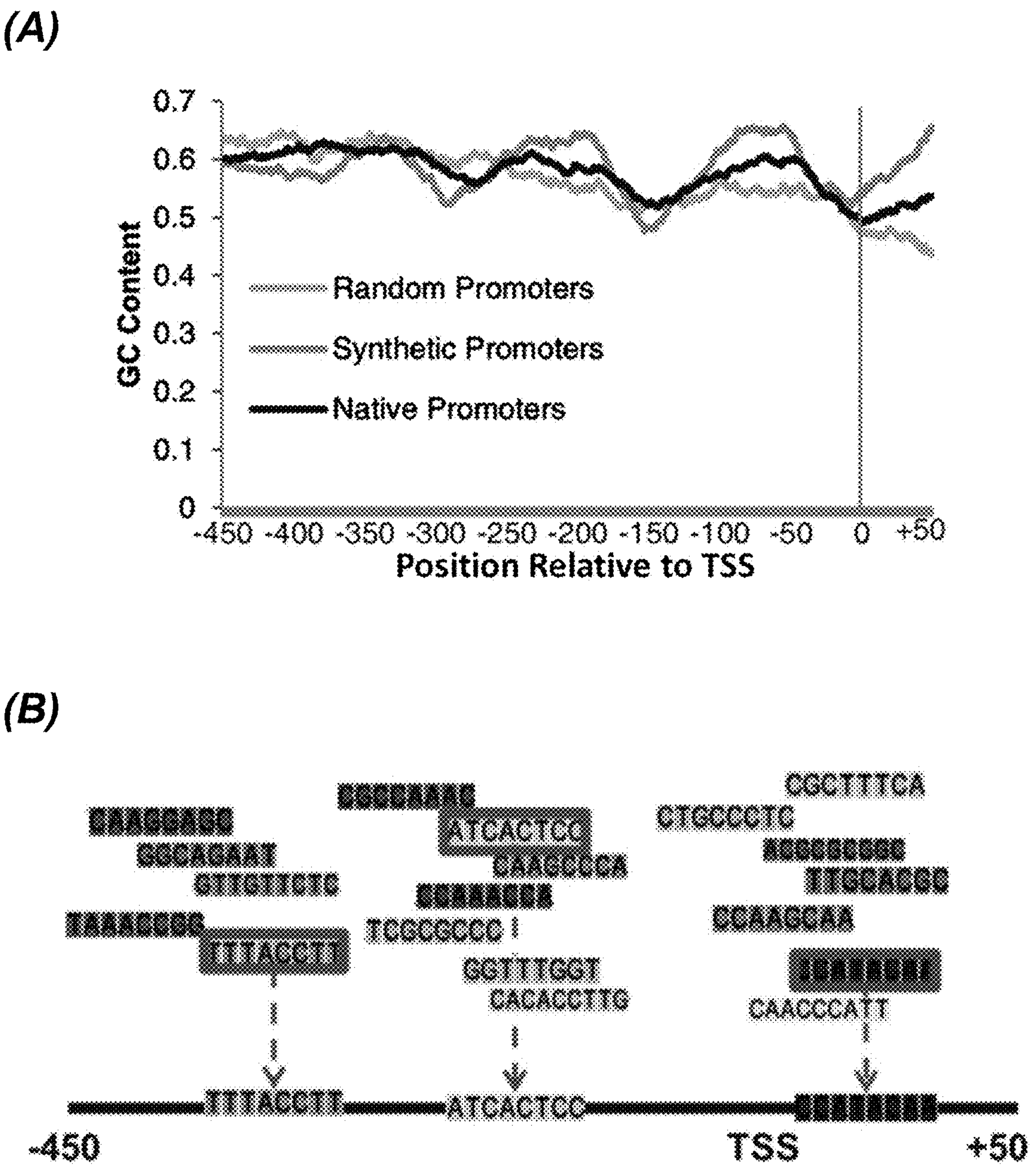
FIG. 1, panels A-E, illustrates design of synthetic algal promoters and expression vector construction. Panel A) Relative GC content of the top 50 native promoters was analyzed (moving window 20 bp). Synthetic and random promoters were generated to mimic the AT-skew. Panel B) Motifs discovered in the top 50 native promoters were placed in a synthetic backbone in positions similar to their position in the native promoters. The overall promoter was designed to mimic −450 to +50 bp relative to TSS. Panel C) Synthetic algal promoters (saps) were placed upstream of mCherry expression cassette, which included the RBCS2 5' and 3' UTR (U) and first intron (I) in order to drive expression. A separate hygromycin expression cassette was place upstream of the mCherry cassette to allow for screening of transformants independent of synthetic promoter function. Synthetic promoters were compared to the hsp70/rbcs2 hybrid promoter (arl). Panel D) Randomly generated sequences are used to drive mCherry. The relative mCherry fluorescence of 5,000 transformants is compared to 5,000 transformants of the arl construct by flow cytometry. Populations that are statistically different are indicated (a-b, Tukey's test, $p<0.05$) Box and whisker plot indicates max (top of line), min (bottom of line), first quartile (bottom of box), second quartile (median; middle line), third quartile (top of box). Panel E) sap transformants were compared to arl transformants by flow cytometry. Populations transformed with seven of the sap promoters have more mCherry fluorescence than arl transformed cells (*, Tukey's test, $p<0.05$).

Algae have enormous potential as bio-factories for the efficient production of a wide array of high-value products, and eventually as a source of renewable biofuels. However, tools for engineering the nuclear genomes of algae remain scarce and limited in functionality. We generated synthetic algal promoters (saps) as a tool for increasing nuclear gene expression and as a model for understanding promoter elements and structure in green algae. Promoters were generated to mimic native cis-motif elements, structure, and overall nucleotide composition of top expressing genes from *Chlamydomonas reinhardtii*. Twenty five saps were used to drive expression of a fluorescent report in transgenic algae. A majority of the promoters were functional in vivo and seven were identified to drive expression of the fluorescent reporter better than the current best endogenous promoter in *C. reinhardtii*, the chimeric hsp70/rbs2 promoter. Further analysis of the best synthetic promoter, sap11, revealed a new DNA motif essential for promoter function that is widespread and highly conserved in *C. reinhardtii*. These data demonstrate the utility of synthetic promoters to drive gene expression in green algae, and lays the groundwork for the development of a suite of saps capable of driving the robust and complex gene expression that will be required for algae to reach their potential as an industrial platform for photosynthetic bio-manufacturing.

2. Synthetic Promoters

Provided are synthetic promoters useful for high level transcription or expression of polynucleotides in an algal cell. Accordingly, in one aspect, provided is a synthetic promoter capable of promoting and/or initiating transcription of a polynucleotide in an algal cell. In varying embodiments, the synthetic promoter comprising from 3 to 30, e.g., from 3 to 27, e.g., from 3 to 25, e.g., from 3 to 20, e.g., from 3 to 15, e.g., from 3 to 10, e.g., from 3 to 5, promoter (cis)-elements selected from the group consisting of promoter (cis)-elements shown in Table 1 and (FIGS. 16A and 16B). In varying embodiments, the promoter (cis)-elements are positioned or located within the promoter relative to the transcriptional start site (TSS) as indicated in Table 1.

TABLE 1

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 20 | sap_19 | -377 | -369 | + | AAACCCAAC | |
| 20 | sap_25 | -199 | -191 | - | AAACCCATC | |
| 11 | sap_15 | -178 | -170 | - | AACAGCCAG | |
| 100 | sap_9 | -408 | -401 | + | AACTGAGG | |
| 1 | sap_12 | -372 | -363 | + | ACCCCATCGC | 24 |
| 62 | sap_18 | -80 | -73 | - | ACGGCCAT | |
| 104 | sap_1 | -54 | -47 | - | AGCAAGTC | |
| 104 | sap_25 | -106 | -99 | + | AGCAAGTC | |
| 104 | sap_22 | -129 | -122 | + | AGCAATTT | |
| 104 | sap_8 | -104 | -97 | + | AGCAATTT | |
| 51 | sap_7 | -359 | -352 | - | AGCGCTTT | |
| 5 | sap_14 | -116 | -109 | - | ATGCATTA | |
| 5 | sap_4 | -419 | -412 | + | ATGCATTT | |
| 20 | sap_15 | 20 | 28 | + | CAACACACC | |
| 20 | sap_22 | -9 | -1 | + | CAACCGACC | |
| 46 | sap_17 | -380 | -372 | - | CACACCTTG | |
| 46 | sap_21 | -368 | -360 | + | CACACTTCG | |
| 46 | sap_25 | -4 | 4 | + | CACACTTCG | |
| 69 | sap_2 | -208 | -201 | - | CACGAACC | |
| 69 | sap_15 | -203 | -196 | - | CACGCAAC | |
| 69 | sap_24 | -354 | -347 | - | CACGCAAC | |
| 37 | sap_1 | -432 | -425 | - | CACGCATG | |
| 37 | sap_1 | -366 | -359 | + | CACGCATG | |
| 37 | sap_24 | -363 | -356 | - | CACGCATG | |
| 37 | sap_4 | -363 | -356 | - | CACGCATG | |
| 14 | sap_4 | -437 | -429 | - | CACGCCCTG | |
| 37 | sap_1 | -161 | -154 | + | CATGCATG | |
| 37 | sap_1 | -161 | -154 | - | CATGCATG | |
| 37 | sap_10 | -137 | -130 | + | CATGCATG | |
| 37 | sap_10 | -137 | -130 | - | CATGCATG | |
| 37 | sap_11 | -152 | -145 | + | CATGCATG | |
| 37 | sap_11 | -152 | -145 | - | CATGCATG | |
| 37 | sap_13 | -148 | -141 | + | CATGCATG | |
| 37 | sap_13 | -148 | -141 | - | CATGCATG | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 37 | sap_14 | -67 | -60 | + | CATGCATG | |
| 37 | sap_14 | -63 | -56 | + | CATGCATG | |
| 37 | sap_14 | -67 | -60 | - | CATGCATG | |
| 37 | sap_14 | -63 | -56 | - | CATGCATG | |
| 37 | sap_15 | -151 | -144 | + | CATGCATG | |
| 37 | sap_15 | -151 | -144 | - | CATGCATG | |
| 37 | sap_16 | -81 | -74 | + | CATGCATG | |
| 37 | sap_16 | -81 | -74 | - | CATGCATG | |
| 37 | sap_18 | -154 | -147 | + | CATGCATG | |
| 37 | sap_18 | -154 | -147 | - | CATGCATG | |
| 37 | sap_19 | -104 | -97 | + | CATGCATG | |
| 37 | sap_19 | -104 | -97 | - | CATGCATG | |
| 37 | sap_2 | -140 | -133 | + | CATGCATG | |
| 37 | sap_2 | -140 | -133 | - | CATGCATG | |
| 37 | sap_20 | -114 | -107 | + | CATGCATG | |
| 37 | sap_20 | -114 | -107 | - | CATGCATG | |
| 37 | sap_5 | -150 | -143 | + | CATGCATG | |
| 37 | sap_5 | -150 | -143 | - | CATGCATG | |
| 37 | sap_1 | -432 | -425 | + | CATGCGTG | |
| 37 | sap_1 | -366 | -359 | - | CATGCGTG | |
| 37 | sap_24 | -363 | -356 | + | CATGCGTG | |
| 37 | sap_4 | -363 | -356 | + | CATGCGTG | |
| 64 | sap_1 | -261 | -254 | + | CCATTTGG | |
| 1 | sap_9 | -71 | -62 | + | CCCCCATCGC | 25 |
| 117 | sap_7 | 36 | 43 | + | CCCTCCGC | |
| 116 | sap_21 | -42 | -35 | + | CCGAGCAA | |
| 116 | sap_20 | -353 | -346 | + | CCGAGCAC | |
| 116 | sap_11 | -46 | -39 | + | CCGAGCGA | |
| 116 | sap_20 | -63 | -56 | - | CCGAGCGA | |
| 116 | sap_11 | -231 | -224 | - | CCGCGCAA | |
| 54 | sap_11 | -41 | -34 | + | CGAGCCCG | |
| 54 | sap_17 | -395 | -388 | - | CGAGCTCA | |
| 54 | sap_11 | -220 | -213 | + | CGAGTCCA | |
| 60 | sap_12 | -42 | -35 | + | CGCCAAAG | |
| 1 | sap_11 | -76 | -67 | + | CGCCCATTGC | 26 |
| 69 | sap_1 | -352 | -345 | + | CGCGAAAC | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 69 | sap_11 | -232 | -225 | - | CGCGCAAC | |
| 69 | sap_2 | -347 | -340 | - | CGCGCAAC | |
| 117 | sap_11 | -184 | -177 | + | CGCGCCGC | |
| 117 | sap_24 | -274 | -267 | - | CGCGCCGC | |
| 14 | sap_16 | 35 | 43 | - | CGCGGACTG | |
| 117 | sap_9 | -326 | -319 | - | CGCTCAGC | |
| 117 | sap_11 | -349 | -342 | + | CGCTCCGC | |
| 117 | sap_5 | -54 | -47 | - | CGCTCCGC | |
| 2 | sap_19 | -35 | -28 | + | CGCTCCTT | |
| 117 | sap_11 | -355 | -348 | - | CGCTCGGC | |
| 117 | sap_11 | -47 | -40 | - | CGCTCGGC | |
| 117 | sap_14 | -354 | -347 | - | CGCTCGGC | |
| 24 | sap_14 | 37 | 44 | + | CGGGCACG | |
| 54 | sap_12 | -196 | -189 | + | CGGGCCCA | |
| 54 | sap_15 | -324 | -317 | - | CGGGCCCA | |
| 54 | sap_20 | -130 | -123 | - | CGGGCCCA | |
| 54 | sap_21 | -73 | -66 | + | CGGGCCCA | |
| 54 | sap_23 | -312 | -305 | - | CGGGCCCA | |
| 54 | sap_25 | -271 | -264 | + | CGGGCCCA | |
| 54 | sap_25 | -156 | -149 | + | CGGGCCCA | |
| 54 | sap_6 | -135 | -128 | - | CGGGCCCA | |
| 54 | sap_8 | -210 | -203 | - | CGGGCCCA | |
| 3 | sap_1 | -85 | -77 | + | CGTACGGCA | |
| 3 | sap_14 | -88 | -80 | + | CGTACGGCA | |
| 3 | sap_2 | -84 | -76 | - | CGTACGGCA | |
| 3 | sap_23 | -65 | -57 | + | CGTACTGCA | |
| 14 | sap_16 | -338 | -330 | + | CTCGCACAG | |
| 2 | sap_13 | -24 | -17 | + | CTCTCCCT | |
| 2 | sap_18 | -19 | -12 | + | CTCTCCTT | |
| 2 | sap_20 | -26 | -19 | + | CTCTCCTT | |
| 2 | sap_19 | -25 | -18 | + | CTCTCTTT | |
| 2 | sap_2 | -16 | -9 | + | CTCTCTTT | |
| 2 | sap_23 | -20 | -13 | + | CTCTCTTT | |
| 2 | sap_24 | -28 | -21 | + | CTCTCTTT | |
| 2 | sap_25 | -19 | -12 | + | CTCTCTTT | |
| 2 | sap_3 | -25 | -18 | + | CTCTCTTT | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 2 | sap_5 | -27 | -20 | + | CTCTCTTT | |
| 2 | sap_5 | -19 | -12 | + | CTCTCTTT | |
| 2 | sap_8 | -19 | -12 | + | CTCTCTTT | |
| 116 | sap_12 | -303 | -296 | - | CTGAGCAA | |
| 2 | sap_20 | -35 | -28 | + | CTTTCCTT | |
| 2 | sap_20 | -21 | -14 | + | CTTTCCTT | |
| 2 | sap_6 | -273 | -266 | - | CTTTCCTT | |
| 2 | sap_11 | -21 | -14 | + | CTTTCTTT | |
| 2 | sap_16 | -29 | -22 | + | CTTTCTTT | |
| 2 | sap_18 | -14 | -7 | + | CTTTCTTT | |
| 2 | sap_21 | -19 | -12 | + | CTTTCTTT | |
| 2 | sap_3 | -37 | -30 | + | CTTTCTTT | |
| 2 | sap_4 | -25 | -18 | + | CTTTCTTT | |
| 20 | sap_20 | -186 | -178 | - | GAACCCACC | |
| 46 | sap_16 | 5 | 13 | + | GACACCTCA | |
| 24 | sap_1 | -274 | -267 | + | GAGGCGCG | |
| 24 | sap_21 | -198 | -191 | - | GAGGCGCG | |
| 86 | sap_10 | -122 | -115 | - | GCACGGGC | |
| 86 | sap_19 | -134 | -127 | - | GCACGGGC | |
| 86 | sap_14 | 40 | 47 | + | GCACGGGT | |
| 86 | sap_6 | 5 | 12 | - | GCACGGTC | |
| 86 | sap_9 | -374 | -367 | + | GCACGGTC | |
| 50 | sap_23 | -259 | -252 | + | GCCAGAGC | |
| 50 | sap_24 | -285 | -278 | + | GCCAGAGC | |
| 50 | sap_21 | -414 | -407 | - | GCCAGGAC | |
| 50 | sap_15 | 39 | 46 | - | GCCAGGGC | |
| 50 | sap_21 | -177 | -170 | + | GCCAGGGC | |
| 50 | sap_3 | 41 | 48 | - | GCCAGGGC | |
| 50 | sap_4 | -439 | -432 | + | GCCAGGGC | |
| 50 | sap_5 | -273 | -266 | + | GCCAGGGC | |
| 50 | sap_7 | -182 | -175 | - | GCCAGGGC | |
| 1 | sap_3 | -97 | -88 | - | GCCCCAATGC | 27 |
| 1 | sap_21 | -408 | -399 | + | GCCCCAGCGC | 28 |
| 1 | sap_17 | -83 | -74 | - | GCCCCATTGC | 29 |
| 50 | sap_24 | -188 | -181 | + | GCCCGAGC | |
| 50 | sap_25 | -159 | -152 | - | GCCCGAGC | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 113 | sap_12 | -66 | -59 | - | GCGAGCGA | |
| 113 | sap_14 | -204 | -197 | - | GCGAGCGA | |
| 113 | sap_18 | -117 | -110 | + | GCGAGCGA | |
| 113 | sap_20 | -67 | -60 | - | GCGAGCGA | |
| 113 | sap_23 | -220 | -213 | - | GCGAGCGA | |
| 113 | sap_3 | -224 | -217 | - | GCGAGCGA | |
| 113 | sap_7 | -259 | -252 | + | GCGAGCGA | |
| 113 | sap_8 | -261 | -254 | + | GCGAGCGA | |
| 113 | sap_8 | -257 | -250 | + | GCGAGCGA | |
| 113 | sap_9 | -52 | -45 | + | GCGAGCGA | |
| 113 | sap_1 | -40 | -33 | + | GCGAGCGC | |
| 113 | sap_10 | -43 | -36 | + | GCGAGCGC | |
| 113 | sap_12 | -344 | -337 | - | GCGAGCGC | |
| 113 | sap_13 | -252 | -245 | + | GCGAGCGC | |
| 113 | sap_15 | -215 | -208 | - | GCGAGCGC | |
| 113 | sap_15 | -111 | -104 | + | GCGAGCGC | |
| 113 | sap_16 | -341 | -334 | - | GCGAGCGC | |
| 113 | sap_17 | -238 | -231 | + | GCGAGCGC | |
| 113 | sap_17 | 30 | 37 | - | GCGAGCGC | |
| 113 | sap_18 | -43 | -36 | + | GCGAGCGC | |
| 113 | sap_23 | -241 | -234 | + | GCGAGCGC | |
| 113 | sap_24 | -69 | -62 | - | GCGAGCGC | |
| 113 | sap_25 | -292 | -285 | - | GCGAGCGC | |
| 113 | sap_25 | -44 | -37 | + | GCGAGCGC | |
| 113 | sap_6 | -188 | -181 | + | GCGAGCGC | |
| 113 | sap_6 | -63 | -56 | + | GCGAGCGC | |
| 113 | sap_7 | -41 | -34 | + | GCGAGCGC | |
| 113 | sap_9 | -48 | -41 | + | GCGAGCGC | |
| 1 | sap_15 | -221 | -212 | - | GCGCCATCGC | 30 |
| 1 | sap_23 | -75 | -66 | + | GCGCCATCGC | 30 |
| 1 | sap_23 | -81 | -72 | - | GCGCCATCGC | 30 |
| 1 | sap_25 | -229 | -220 | - | GCGCCATCGC | 30 |
| 1 | sap_8 | -35 | -26 | - | GCGCCATTGC | 30 |
| 113 | sap_1 | -36 | -29 | + | GCGCGCGA | |
| 113 | sap_12 | -246 | -239 | - | GCGCGCGA | |
| 113 | sap_16 | -174 | -167 | + | GCGCGCGA | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 113 | sap_19 | -248 | -241 | - | GCGCGCGA | |
| 113 | sap_19 | -224 | -217 | + | GCGCGCGA | |
| 113 | sap_20 | -252 | -245 | + | GCGCGCGA | |
| 113 | sap_23 | -245 | -238 | + | GCGCGCGA | |
| 113 | sap_3 | -189 | -182 | + | GCGCGCGA | |
| 113 | sap_4 | -187 | -180 | + | GCGCGCGA | |
| 113 | sap_7 | -45 | -38 | + | GCGCGCGA | |
| 113 | sap_8 | -231 | -224 | + | GCGCGCGA | |
| 113 | sap_9 | -237 | -230 | + | GCGCGCGA | |
| 113 | sap_10 | -39 | -32 | + | GCGCGCGC | |
| 113 | sap_10 | -39 | -32 | - | GCGCGCGC | |
| 113 | sap_11 | -187 | -180 | + | GCGCGCGC | |
| 113 | sap_11 | -187 | -180 | - | GCGCGCGC | |
| 113 | sap_11 | -99 | -92 | + | GCGCGCGC | |
| 113 | sap_11 | -99 | -92 | - | GCGCGCGC | |
| 113 | sap_12 | -244 | -237 | + | GCGCGCGC | |
| 113 | sap_12 | -242 | -235 | + | GCGCGCGC | |
| 113 | sap_12 | -244 | -237 | - | GCGCGCGC | |
| 113 | sap_12 | -242 | -235 | - | GCGCGCGC | |
| 113 | sap_13 | -248 | -241 | + | GCGCGCGC | |
| 113 | sap_13 | -246 | -239 | + | GCGCGCGC | |
| 113 | sap_13 | -248 | -241 | - | GCGCGCGC | |
| 113 | sap_13 | -246 | -239 | - | GCGCGCGC | |
| 113 | sap_14 | -42 | -35 | + | GCGCGCGC | |
| 113 | sap_14 | -42 | -35 | - | GCGCGCGC | |
| 113 | sap_16 | -176 | -169 | + | GCGCGCGC | |
| 113 | sap_16 | -176 | -169 | - | GCGCGCGC | |
| 113 | sap_16 | -128 | -121 | + | GCGCGCGC | |
| 113 | sap_16 | -128 | -121 | - | GCGCGCGC | |
| 113 | sap_18 | -39 | -32 | + | GCGCGCGC | |
| 113 | sap_18 | -39 | -32 | - | GCGCGCGC | |
| 113 | sap_19 | -246 | -239 | + | GCGCGCGC | |
| 113 | sap_19 | -244 | -237 | + | GCGCGCGC | |
| 113 | sap_19 | -242 | -235 | + | GCGCGCGC | |
| 113 | sap_19 | -246 | -239 | - | GCGCGCGC | |
| 113 | sap_19 | -244 | -237 | - | GCGCGCGC | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 113 | sap_19 | -242 | -235 | − | GCGCGCGC | |
| 113 | sap_19 | -226 | -219 | + | GCGCGCGC | |
| 113 | sap_19 | -226 | -219 | − | GCGCGCGC | |
| 113 | sap_19 | -42 | -35 | + | GCGCGCGC | |
| 113 | sap_19 | -40 | -33 | + | GCGCGCGC | |
| 113 | sap_19 | -42 | -35 | − | GCGCGCGC | |
| 113 | sap_19 | -40 | -33 | − | GCGCGCGC | |
| 113 | sap_20 | -254 | -247 | + | GCGCGCGC | |
| 113 | sap_20 | -254 | -247 | − | GCGCGCGC | |
| 113 | sap_3 | -191 | -184 | + | GCGCGCGC | |
| 113 | sap_3 | -191 | -184 | − | GCGCGCGC | |
| 113 | sap_6 | -238 | -231 | + | GCGCGCGC | |
| 113 | sap_6 | -238 | -231 | − | GCGCGCGC | |
| 113 | sap_8 | -233 | -226 | + | GCGCGCGC | |
| 113 | sap_8 | -233 | -226 | − | GCGCGCGC | |
| 113 | sap_8 | -43 | -36 | + | GCGCGCGC | |
| 113 | sap_8 | -41 | -34 | + | GCGCGCGC | |
| 113 | sap_8 | -43 | -36 | − | GCGCGCGC | |
| 113 | sap_8 | -41 | -34 | − | GCGCGCGC | |
| 113 | sap_9 | -239 | -232 | + | GCGCGCGC | |
| 113 | sap_9 | -239 | -232 | − | GCGCGCGC | |
| 59 | sap_10 | -364 | -357 | − | GCGCGCGT | |
| 59 | sap_15 | -244 | -237 | + | GCGCGCGT | |
| 59 | sap_15 | -246 | -239 | − | GCGCGCGT | |
| 59 | sap_16 | -130 | -123 | − | GCGCGCGT | |
| 59 | sap_19 | -240 | -233 | + | GCGCGCGT | |
| 59 | sap_25 | -223 | -216 | + | GCGCGCGT | |
| 113 | sap_11 | -191 | -184 | − | GCGCTCGA | |
| 113 | sap_1 | -40 | -33 | − | GCGCTCGC | |
| 113 | sap_10 | -43 | -36 | − | GCGCTCGC | |
| 113 | sap_12 | -344 | -337 | + | GCGCTCGC | |
| 113 | sap_13 | -252 | -245 | − | GCGCTCGC | |
| 113 | sap_15 | -215 | -208 | + | GCGCTCGC | |
| 113 | sap_15 | -111 | -104 | − | GCGCTCGC | |
| 113 | sap_16 | -341 | -334 | + | GCGCTCGC | |
| 113 | sap_17 | -238 | -231 | − | GCGCTCGC | |
| 113 | sap_17 | 30 | 37 | + | GCGCTCGC | |
| 113 | sap_18 | -43 | -36 | − | GCGCTCGC | |
| 113 | sap_23 | -241 | -234 | − | GCGCTCGC | |
| 113 | sap_24 | -69 | -62 | + | GCGCTCGC | |
| 113 | sap_25 | -292 | -285 | + | GCGCTCGC | |
| 113 | sap_25 | -44 | -37 | − | GCGCTCGC | |
| 113 | sap_6 | -188 | -181 | − | GCGCTCGC | |
| 113 | sap_6 | -63 | -56 | − | GCGCTCGC | |
| 113 | sap_7 | -41 | -34 | − | GCGCTCGC | |
| 113 | sap_9 | -48 | -41 | − | GCGCTCGC | |
| 59 | sap_12 | -342 | -335 | + | GCTCGCGT | |
| 59 | sap_21 | -273 | -266 | + | GCTCGCGT | |
| 59 | sap_6 | -264 | -257 | + | GCTCGCGT | |
| 60 | sap_17 | -420 | -413 | + | GGCCAGCG | |
| 1 | sap_24 | -215 | -206 | + | GGCCCAACGC | 31 |
| 1 | sap_22 | -346 | -337 | − | GGCCCACTGC | 32 |
| 1 | sap_21 | -185 | -176 | + | GGCCCAGCGC | 33 |
| 1 | sap_21 | -71 | -62 | + | GGCCCATCGC | 34 |
| 1 | sap_11 | -165 | -156 | − | GGCCCATTCC | 35 |
| 1 | sap_14 | -177 | -168 | + | GGCCCATTCC | 35 |
| 1 | sap_16 | -150 | -141 | − | GGCCCATTCC | 35 |
| 1 | sap_17 | -348 | -339 | − | GGCCCATTCC | 35 |
| 1 | sap_2 | -239 | -230 | + | GGCCCATTCC | 35 |
| 1 | sap_22 | -340 | -331 | + | GGCCCATTCC | 35 |
| 1 | sap_24 | -221 | -212 | − | GGCCCATTCC | 35 |
| 1 | sap_25 | -154 | -145 | + | GGCCCATTCC | 35 |
| 1 | sap_3 | -274 | -265 | − | GGCCCATTCC | 35 |
| 1 | sap_5 | -117 | -108 | − | GGCCCATTCC | 35 |
| 1 | sap_7 | -288 | -279 | + | GGCCCATTCC | 35 |
| 1 | sap_22 | -91 | -82 | + | GGCCCATTGC | 36 |
| 1 | sap_3 | -154 | -145 | + | GGCCCATTGC | 36 |
| 60 | sap_13 | -346 | -339 | − | GGCCGAAG | |
| 60 | sap_25 | -60 | -53 | + | GGCCGGAG | |
| 47 | sap_12 | -46 | -39 | − | GGCGAGAC | |
| 47 | sap_17 | -252 | -245 | + | GGCGAGAC | |
| 47 | sap_16 | -225 | -218 | − | GGCGCGAC | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 47 | sap_19 | -65 | -58 | + | GGCGCGAC | |
| 47 | sap_25 | -101 | -94 | - | GGCGCGAC | |
| 117 | sap_14 | -106 | -99 | + | GGCTCCGC | |
| 117 | sap_19 | -323 | -316 | - | GGCTCCGC | |
| 47 | sap_20 | -7 | 0 | - | GGCTCGAC | |
| 1 | sap_12 | -90 | -81 | - | GGGCCATTGC | 37 |
| 24 | sap_13 | -123 | -116 | - | GGGGCCCG | |
| 24 | sap_14 | -334 | -327 | - | GGGGCCCG | |
| 24 | sap_11 | -96 | -89 | - | GGGGCGCG | |
| 24 | sap_19 | -79 | -72 | - | GGGGCGCG | |
| 24 | sap_20 | -321 | -314 | - | GGGGCGCG | |
| 24 | sap_25 | -287 | -280 | - | GGGGCGCG | |
| 3 | sap_9 | -102 | -94 | + | GGTACGGCA | |
| 57 | sap_23 | -434 | -427 | + | GTCCACTG | |
| 14 | sap_23 | -443 | -435 | - | GTCGCCCTG | |
| 47 | sap_8 | -6 | 1 | + | GTCGCGAC | |
| 47 | sap_8 | -6 | 1 | - | GTCGCGAC | |
| 47 | sap_17 | -63 | -56 | - | GTCGCGAT | |
| 105 | sap_19 | -130 | -123 | + | GTGCGCCC | |
| 105 | sap_11 | -9 | -2 | + | GTGTGCCC | |
| 57 | sap_18 | -161 | -154 | - | GTTCAATG | |
| 57 | sap_23 | -383 | -376 | + | GTTCGCTG | |
| 11 | sap_17 | -159 | -151 | + | TACAGCAAG | |
| 11 | sap_25 | -260 | -252 | + | TACAGCAAG | |
| 11 | sap_21 | -115 | -107 | - | TACGGCCAG | |
| 26 | sap_5 | -285 | -278 | + | TCAAACCA | |
| 113 | sap_11 | -191 | -184 | + | TCGAGCGC | |
| 113 | sap_1 | -36 | -29 | - | TCGCGCGC | |
| 113 | sap_12 | -246 | -239 | + | TCGCGCGC | |
| 113 | sap_16 | -174 | -167 | - | TCGCGCGC | |
| 113 | sap_19 | -248 | -241 | + | TCGCGCGC | |
| 113 | sap_19 | -224 | -217 | - | TCGCGCGC | |
| 113 | sap_20 | -252 | -245 | - | TCGCGCGC | |
| 113 | sap_23 | -245 | -238 | - | TCGCGCGC | |
| 113 | sap_3 | -189 | -182 | - | TCGCGCGC | |
| 113 | sap_4 | -187 | -180 | - | TCGCGCGC | |

TABLE 1-continued

Location of motif (cis)-elements in the synthetic algal promoters (saps) relative to the transcription start site (TSS).

| Motif number | Promoter | Start | Stop | Strand | matched sequence (promoter element) | SEQ ID NO: |
|---|---|---|---|---|---|---|
| 113 | sap_7 | -45 | -38 | - | TCGCGCGC | |
| 113 | sap_8 | -231 | -224 | - | TCGCGCGC | |
| 113 | sap_9 | -237 | -230 | - | TCGCGCGC | |
| 59 | sap_19 | -353 | -346 | + | TCGCGCGT | |
| 59 | sap_25 | -323 | -316 | - | TCGCGCGT | |
| 113 | sap_12 | -66 | -59 | + | TCGCTCGC | |
| 113 | sap_14 | -204 | -197 | + | TCGCTCGC | |
| 113 | sap_18 | -117 | -110 | - | TCGCTCGC | |
| 113 | sap_20 | -67 | -60 | + | TCGCTCGC | |
| 113 | sap_23 | -220 | -213 | + | TCGCTCGC | |
| 113 | sap_3 | -224 | -217 | + | TCGCTCGC | |
| 113 | sap_7 | -259 | -252 | - | TCGCTCGC | |
| 113 | sap_8 | -261 | -254 | - | TCGCTCGC | |
| 113 | sap_8 | -257 | -250 | - | TCGCTCGC | |
| 113 | sap_9 | -52 | -45 | - | TCGCTCGC | |
| 59 | sap_10 | -338 | -331 | - | TCTCGCGA | |
| 59 | sap_24 | -201 | -194 | + | TCTCGCGA | |
| 59 | sap_6 | -207 | -200 | + | TCTCGCGA | |
| 59 | sap_9 | -65 | -58 | - | TCTCGCGA | |
| 59 | sap_19 | -289 | -282 | + | TCTCGCGT | |
| 54 | sap_19 | 38 | 45 | + | TGAGCCCA | |
| 63 | sap_1 | -372 | -365 | - | TGCACACC | |
| 63 | sap_17 | -377 | -370 | - | TGCACACC | |
| 63 | sap_8 | -286 | -279 | - | TGCACACC | |
| 3 | sap_21 | -435 | -427 | - | TGCAGGGCA | |
| 109 | sap_21 | -200 | -193 | + | TGCGCGCC | |
| 109 | sap_6 | -219 | -212 | + | TGCGCGCC | |
| 51 | sap_5 | -230 | -223 | + | TGCGCTTT | |
| 51 | sap_6 | -368 | -361 | - | TGCGCTTT | |
| 109 | sap_4 | -344 | -337 | - | TGCTCACC | |
| 109 | sap_4 | 35 | 42 | - | TGCTCACC | |
| 109 | sap_23 | -38 | -31 | - | TGCTCGCA | |
| 109 | sap_8 | -145 | -138 | + | TGCTCGCA | |
| 38 | sap_5 | -447 | -440 | + | TGGAAAGG | |
| 38 | sap_19 | 2 | 9 | - | TGGTAAGG | |
| 3 | sap_15 | -63 | -55 | - | TGTACGGCA | |

TABLE 1-continued

| Location of motif (cis)-elements in the synthetic algal promoters (saps) relative to the transcription start site (TSS). | | | | | | |
|---|---|---|---|---|---|---|
| Motif number | Promoter | Start | Stop | Strand | matched sequence (promoter element) | SEQ ID NO: |
| 3 | sap_19 | -93 | -85 | + | TGTACGGCA | |
| 109 | sap_23 | -414 | -407 | + | TGTTCGCC | |
| 109 | sap_8 | -223 | -216 | - | TGTTCGCC | |
| 108 | sap_18 | -348 | -341 | + | TTCGCAAA | |
| 108 | sap_5 | -314 | -307 | + | TTCGCGAA | |
| 108 | sap_5 | -314 | -307 | - | TTCGCGAA | |
| 108 | sap_8 | -302 | -295 | + | TTCGCGAA | |
| 108 | sap_8 | -302 | -295 | - | TTCGCGAA | |
| 51 | sap_18 | -205 | -198 | - | TTCGCTTG | |

* The start and stop values are relative to the artificial TSS that is part of the synthetic promoter sequence. So a motif at -50 would actually be at -100 to the 3∝ end of the whole sap sequence.

Various additional cis elements are shown in Table 2.

TABLE 2

| Illustrative additional cis elements. |
|---|
| Sequence |
| TCTTTACTT |
| TACAGCCAG |
| CTCGCACTG |
| CAACCCAGC |
| CAGGCGCG |
| TCAAACCA |
| ACATACAA |
| CACGCGTG |

TABLE 2-continued

| Illustrative additional cis elements. |
|---|
| Sequence |
| TGGAAACG |
| TACACCTCG |
| GCCAGAAC |
| TTCGCTTT |
| CGAGCCCA |
| GTTCACTG |
| GGCCAAAG |
| ACGGCCGA |
| TACACACC |
| CCGTTCGG |
| CACGAAAC |
| GCACGTGC |
| TGATATCA |
| AACTCAGG |
| GTGGGACC |
| TTCGCCAA |

In certain embodiments, the synthetic promoter comprises one or more Myb family, SBP family, bHLH family, C2H2 family, bZIP family, C3H family, Dof family or G2 family transcriptional factor binding site motifs. In certain embodiments, the synthetic promoter comprises one or more transcriptional factor binding site motifs selected from the group consisting of the sequences in FIGS. 17A-17C.

The (cis)-elements are positioned or arranged within a promoter scaffold or backbone. In varying embodiments, the nucleic acid base of highest probability or second highest probability at a particular position of the promoter scaffold or backbone (e.g., based on known native promoter sequences) relative to the transcriptional start site (TSS) is assigned to that position, e.g., as indicated in Table 3.

TABLE 3

| Average nucleotide composition of native *C. reinhardtii* promoters. | | | | | | | | |
|---|---|---|---|---|---|---|---|---|
| position relative to TSS: | −449 | −448 | −447 | −446 | −445 | −444 | −443 | −442 |
| A | 0.191 | 0.191 | 0.191 | 0.191 | 0.191 | 0.191 | 0.191 | 0.191 |
| C | 0.298 | 0.299 | 0.299 | 0.299 | 0.299 | 0.299 | 0.299 | 0.299 |
| G | 0.317 | 0.316 | 0.316 | 0.316 | 0.315 | 0.315 | 0.315 | 0.315 |
| T | 0.192 | 0.192 | 0.192 | 0.193 | 0.193 | 0.193 | 0.193 | 0.194 |
| position relative to TSS: | −441 | −440 | −439 | −438 | −437 | −436 | −435 | −434 |
| A | 0.191 | 0.191 | 0.191 | 0.191 | 0.191 | 0.192 | 0.192 | 0.192 |
| C | 0.299 | 0.299 | 0.299 | 0.299 | 0.300 | 0.299 | 0.299 | 0.299 |
| G | 0.314 | 0.314 | 0.314 | 0.313 | 0.313 | 0.313 | 0.313 | 0.312 |
| T | 0.194 | 0.194 | 0.194 | 0.194 | 0.194 | 0.194 | 0.195 | 0.195 |
| position relative to TSS: | −433 | −432 | −431 | −430 | −429 | −428 | −427 | −426 |
| A | 0.193 | 0.193 | 0.193 | 0.193 | 0.193 | 0.193 | 0.193 | 0.193 |
| C | 0.299 | 0.299 | 0.299 | 0.299 | 0.299 | 0.299 | 0.299 | 0.299 |

TABLE 3-continued

| Average nucleotide composition of native *C. reinhardtii* promoters. | | | | | | | | |
|---|---|---|---|---|---|---|---|---|
| G | 0.312 | 0.311 | 0.311 | 0.310 | 0.310 | 0.310 | 0.310 | 0.309 |
| T | 0.194 | 0.195 | 0.195 | 0.196 | 0.196 | 0.196 | 0.196 | 0.197 |
| position relative to TSS: | −425 | −424 | −423 | −422 | −421 | −420 | −419 | −418 |
| A | 0.194 | 0.194 | 0.194 | 0.194 | 0.194 | 0.194 | 0.195 | 0.195 |
| C | 0.299 | 0.299 | 0.298 | 0.298 | 0.298 | 0.298 | 0.298 | 0.298 |
| G | 0.309 | 0.309 | 0.309 | 0.309 | 0.309 | 0.308 | 0.308 | 0.308 |
| T | 0.197 | 0.197 | 0.197 | 0.197 | 0.197 | 0.197 | 0.197 | 0.198 |
| position relative to TSS: | −417 | −416 | −415 | −414 | −413 | −412 | −411 | −410 |
| A | 0.195 | 0.194 | 0.195 | 0.195 | 0.195 | 0.195 | 0.195 | 0.195 |
| C | 0.297 | 0.297 | 0.297 | 0.297 | 0.297 | 0.297 | 0.297 | 0.296 |
| G | 0.308 | 0.308 | 0.308 | 0.308 | 0.308 | 0.308 | 0.308 | 0.308 |
| T | 0.198 | 0.198 | 0.198 | 0.198 | 0.198 | 0.198 | 0.199 | 0.199 |
| position relative to TSS: | −409 | −408 | −407 | −406 | −405 | −404 | −403 | −402 |
| A | 0.195 | 0.195 | 0.195 | 0.195 | 0.195 | 0.196 | 0.196 | 0.196 |
| C | 0.296 | 0.296 | 0.296 | 0.295 | 0.294 | 0.294 | 0.294 | 0.294 |
| G | 0.307 | 0.308 | 0.308 | 0.308 | 0.308 | 0.308 | 0.308 | 0.308 |
| T | 0.199 | 0.200 | 0.200 | 0.200 | 0.200 | 0.201 | 0.200 | 0.200 |
| position relative to TSS: | −401 | −400 | −399 | −398 | −397 | −396 | −395 | −394 |
| A | 0.196 | 0.196 | 0.196 | 0.196 | 0.196 | 0.196 | 0.196 | 0.196 |
| C | 0.294 | 0.294 | 0.293 | 0.293 | 0.293 | 0.293 | 0.293 | 0.292 |
| G | 0.308 | 0.308 | 0.308 | 0.308 | 0.308 | 0.308 | 0.308 | 0.308 |
| T | 0.200 | 0.200 | 0.201 | 0.201 | 0.201 | 0.201 | 0.201 | 0.201 |
| position relative to TSS: | −393 | −392 | −391 | −390 | −389 | −388 | −387 | −386 |
| A | 0.196 | 0.196 | 0.196 | 0.196 | 0.196 | 0.196 | 0.196 | 0.196 |
| C | 0.292 | 0.291 | 0.292 | 0.291 | 0.291 | 0.291 | 0.290 | 0.290 |
| G | 0.309 | 0.309 | 0.309 | 0.309 | 0.310 | 0.309 | 0.310 | 0.310 |
| T | 0.201 | 0.202 | 0.202 | 0.202 | 0.201 | 0.202 | 0.202 | 0.202 |
| position relative to TSS: | −385 | −384 | −383 | −382 | −381 | −380 | −379 | −378 |
| A | 0.195 | 0.195 | 0.195 | 0.195 | 0.195 | 0.195 | 0.195 | 0.195 |
| C | 0.290 | 0.289 | 0.290 | 0.290 | 0.290 | 0.289 | 0.289 | 0.289 |
| G | 0.311 | 0.311 | 0.311 | 0.312 | 0.312 | 0.312 | 0.313 | 0.313 |
| T | 0.202 | 0.202 | 0.202 | 0.202 | 0.202 | 0.202 | 0.201 | 0.201 |
| position relative to TSS: | −377 | −376 | −375 | −374 | −373 | −372 | −371 | −370 |
| A | 0.194 | 0.194 | 0.195 | 0.195 | 0.195 | 0.195 | 0.194 | 0.194 |
| C | 0.289 | 0.289 | 0.289 | 0.289 | 0.290 | 0.290 | 0.290 | 0.289 |
| G | 0.313 | 0.313 | 0.313 | 0.313 | 0.313 | 0.313 | 0.314 | 0.314 |
| T | 0.201 | 0.201 | 0.201 | 0.201 | 0.201 | 0.201 | 0.201 | 0.200 |
| position relative to TSS: | −369 | −368 | −367 | −366 | −365 | −364 | −363 | −362 |
| A | 0.195 | 0.195 | 0.195 | 0.195 | 0.195 | 0.194 | 0.194 | 0.194 |
| C | 0.289 | 0.289 | 0.289 | 0.289 | 0.290 | 0.290 | 0.290 | 0.290 |
| G | 0.314 | 0.315 | 0.315 | 0.315 | 0.315 | 0.315 | 0.315 | 0.315 |
| T | 0.200 | 0.200 | 0.200 | 0.200 | 0.199 | 0.199 | 0.199 | 0.199 |
| position relative to TSS: | −361 | −360 | −359 | −358 | −357 | −356 | −355 | −354 |
| A | 0.194 | 0.194 | 0.194 | 0.193 | 0.193 | 0.193 | 0.193 | 0.193 |
| C | 0.290 | 0.290 | 0.290 | 0.290 | 0.290 | 0.290 | 0.290 | 0.291 |
| G | 0.316 | 0.316 | 0.316 | 0.316 | 0.316 | 0.316 | 0.316 | 0.316 |
| T | 0.199 | 0.199 | 0.199 | 0.198 | 0.198 | 0.198 | 0.198 | 0.198 |
| position relative to TSS: | −353 | −352 | −351 | −350 | −349 | −348 | −347 | −346 |
| A | 0.193 | 0.193 | 0.193 | 0.193 | 0.193 | 0.193 | 0.193 | 0.193 |
| C | 0.291 | 0.291 | 0.292 | 0.292 | 0.292 | 0.292 | 0.292 | 0.293 |
| G | 0.316 | 0.316 | 0.316 | 0.316 | 0.316 | 0.316 | 0.316 | 0.316 |
| T | 0.198 | 0.198 | 0.198 | 0.198 | 0.198 | 0.197 | 0.197 | 0.196 |
| position relative to TSS: | −345 | −344 | −343 | −342 | −341 | −340 | −339 | −338 |
| A | 0.193 | 0.193 | 0.193 | 0.193 | 0.193 | 0.193 | 0.193 | 0.193 |
| C | 0.293 | 0.293 | 0.293 | 0.293 | 0.293 | 0.293 | 0.293 | 0.293 |

TABLE 3-continued

Average nucleotide composition of native *C. reinhardtii* promoters.

| | | | | | | | | |
|---|---|---|---|---|---|---|---|---|
| G | 0.316 | 0.316 | 0.316 | 0.316 | 0.316 | 0.316 | 0.316 | 0.316 |
| T | 0.196 | 0.196 | 0.196 | 0.196 | 0.196 | 0.196 | 0.196 | 0.196 |
| position relative to TSS: | −337 | −336 | −335 | −334 | −333 | −332 | −331 | −330 |
| A | 0.193 | 0.193 | 0.193 | 0.193 | 0.194 | 0.194 | 0.193 | 0.194 |
| C | 0.293 | 0.293 | 0.293 | 0.293 | 0.292 | 0.293 | 0.293 | 0.293 |
| G | 0.316 | 0.316 | 0.316 | 0.316 | 0.316 | 0.315 | 0.315 | 0.315 |
| T | 0.196 | 0.196 | 0.196 | 0.196 | 0.196 | 0.196 | 0.197 | 0.197 |
| position relative to TSS: | −329 | −328 | −327 | −326 | −325 | −324 | −323 | −322 |
| A | 0.193 | 0.193 | 0.193 | 0.193 | 0.193 | 0.193 | 0.194 | 0.194 |
| C | 0.293 | 0.293 | 0.293 | 0.293 | 0.293 | 0.293 | 0.293 | 0.293 |
| G | 0.315 | 0.314 | 0.314 | 0.314 | 0.314 | 0.314 | 0.314 | 0.313 |
| T | 0.197 | 0.197 | 0.197 | 0.198 | 0.198 | 0.198 | 0.198 | 0.198 |
| position relative to TSS: | −321 | −320 | −319 | −318 | −317 | −316 | −315 | −314 |
| A | 0.194 | 0.195 | 0.195 | 0.195 | 0.195 | 0.195 | 0.195 | 0.196 |
| C | 0.293 | 0.293 | 0.293 | 0.293 | 0.293 | 0.293 | 0.293 | 0.293 |
| G | 0.313 | 0.312 | 0.311 | 0.312 | 0.311 | 0.311 | 0.311 | 0.311 |
| T | 0.198 | 0.198 | 0.198 | 0.198 | 0.198 | 0.199 | 0.199 | 0.199 |
| position relative to TSS: | −313 | −312 | −311 | −310 | −309 | −308 | −307 | −306 |
| A | 0.196 | 0.196 | 0.196 | 0.196 | 0.196 | 0.196 | 0.196 | 0.197 |
| C | 0.292 | 0.292 | 0.292 | 0.292 | 0.292 | 0.292 | 0.292 | 0.291 |
| G | 0.311 | 0.310 | 0.310 | 0.310 | 0.309 | 0.309 | 0.308 | 0.308 |
| T | 0.199 | 0.200 | 0.200 | 0.201 | 0.201 | 0.201 | 0.201 | 0.202 |
| position relative to TSS: | −305 | −304 | −303 | −302 | −301 | −300 | −299 | −298 |
| A | 0.197 | 0.198 | 0.198 | 0.198 | 0.199 | 0.199 | 0.200 | 0.200 |
| C | 0.290 | 0.290 | 0.289 | 0.289 | 0.288 | 0.288 | 0.288 | 0.288 |
| G | 0.307 | 0.307 | 0.307 | 0.307 | 0.306 | 0.305 | 0.305 | 0.304 |
| T | 0.203 | 0.203 | 0.203 | 0.204 | 0.205 | 0.205 | 0.205 | 0.206 |
| position relative to TSS: | −297 | −296 | −295 | −294 | −293 | −292 | −291 | −290 |
| A | 0.201 | 0.201 | 0.202 | 0.202 | 0.202 | 0.202 | 0.202 | 0.203 |
| C | 0.287 | 0.287 | 0.287 | 0.286 | 0.286 | 0.285 | 0.284 | 0.284 |
| G | 0.304 | 0.303 | 0.303 | 0.302 | 0.302 | 0.302 | 0.303 | 0.302 |
| T | 0.206 | 0.206 | 0.207 | 0.207 | 0.207 | 0.208 | 0.208 | 0.209 |
| position relative to TSS: | −289 | −288 | −287 | −286 | −285 | −284 | −283 | −282 |
| A | 0.203 | 0.204 | 0.204 | 0.205 | 0.206 | 0.206 | 0.206 | 0.207 |
| C | 0.284 | 0.283 | 0.282 | 0.281 | 0.281 | 0.280 | 0.280 | 0.279 |
| G | 0.302 | 0.302 | 0.302 | 0.301 | 0.301 | 0.301 | 0.300 | 0.300 |
| T | 0.209 | 0.209 | 0.209 | 0.210 | 0.210 | 0.211 | 0.211 | 0.212 |
| position relative to TSS: | −281 | −280 | −279 | −278 | −277 | −276 | −275 | −274 |
| A | 0.207 | 0.207 | 0.208 | 0.209 | 0.209 | 0.210 | 0.210 | 0.210 |
| C | 0.278 | 0.278 | 0.277 | 0.276 | 0.276 | 0.275 | 0.275 | 0.274 |
| G | 0.300 | 0.300 | 0.300 | 0.300 | 0.299 | 0.299 | 0.300 | 0.299 |
| T | 0.212 | 0.213 | 0.213 | 0.213 | 0.213 | 0.214 | 0.214 | 0.215 |
| position relative to TSS: | −273 | −272 | −271 | −270 | −269 | −268 | −267 | −266 |
| A | 0.210 | 0.210 | 0.211 | 0.211 | 0.212 | 0.212 | 0.213 | 0.213 |
| C | 0.273 | 0.273 | 0.273 | 0.272 | 0.272 | 0.271 | 0.270 | 0.270 |
| G | 0.299 | 0.299 | 0.299 | 0.299 | 0.299 | 0.298 | 0.298 | 0.299 |
| T | 0.215 | 0.215 | 0.215 | 0.215 | 0.215 | 0.216 | 0.216 | 0.216 |
| position relative to TSS: | −265 | −264 | −263 | −262 | −261 | −260 | −259 | −258 |
| A | 0.213 | 0.213 | 0.213 | 0.213 | 0.213 | 0.213 | 0.213 | 0.213 |
| C | 0.270 | 0.270 | 0.269 | 0.270 | 0.269 | 0.269 | 0.269 | 0.269 |
| G | 0.299 | 0.299 | 0.299 | 0.298 | 0.299 | 0.298 | 0.298 | 0.298 |
| T | 0.216 | 0.216 | 0.217 | 0.217 | 0.217 | 0.217 | 0.217 | 0.217 |
| position relative to TSS: | −257 | −256 | −255 | −254 | −253 | −252 | −251 | −250 |
| A | 0.214 | 0.214 | 0.214 | 0.214 | 0.214 | 0.214 | 0.214 | 0.214 |
| C | 0.268 | 0.268 | 0.268 | 0.268 | 0.268 | 0.268 | 0.268 | 0.267 |

TABLE 3-continued

Average nucleotide composition of native *C. reinhardtii* promoters.

| | | | | | | | | |
|---|---|---|---|---|---|---|---|---|
| G | 0.299 | 0.299 | 0.299 | 0.300 | 0.300 | 0.300 | 0.300 | 0.301 |
| T | 0.217 | 0.216 | 0.216 | 0.216 | 0.216 | 0.216 | 0.216 | 0.215 |
| position relative to TSS: | −249 | −248 | −247 | −246 | −245 | −244 | −243 | −242 |
| A | 0.214 | 0.213 | 0.213 | 0.213 | 0.213 | 0.213 | 0.213 | 0.213 |
| C | 0.268 | 0.267 | 0.267 | 0.268 | 0.268 | 0.268 | 0.268 | 0.268 |
| G | 0.301 | 0.302 | 0.302 | 0.302 | 0.303 | 0.303 | 0.303 | 0.304 |
| T | 0.215 | 0.215 | 0.215 | 0.215 | 0.214 | 0.214 | 0.214 | 0.213 |
| position relative to TSS: | −249 | −248 | −247 | −246 | −245 | −244 | −243 | −242 |
| A | 0.214 | 0.213 | 0.213 | 0.213 | 0.213 | 0.213 | 0.213 | 0.213 |
| C | 0.268 | 0.267 | 0.267 | 0.268 | 0.268 | 0.268 | 0.268 | 0.268 |
| G | 0.301 | 0.302 | 0.302 | 0.302 | 0.303 | 0.303 | 0.303 | 0.304 |
| T | 0.215 | 0.215 | 0.215 | 0.215 | 0.214 | 0.214 | 0.214 | 0.213 |
| position relative to TSS: | −241 | −240 | −239 | −238 | −237 | −236 | −235 | −234 |
| A | 0.212 | 0.212 | 0.212 | 0.212 | 0.211 | 0.211 | 0.211 | 0.211 |
| C | 0.268 | 0.268 | 0.268 | 0.268 | 0.269 | 0.269 | 0.269 | 0.270 |
| G | 0.305 | 0.305 | 0.305 | 0.306 | 0.306 | 0.306 | 0.306 | 0.306 |
| T | 0.213 | 0.212 | 0.212 | 0.212 | 0.211 | 0.211 | 0.211 | 0.210 |
| position relative to TSS: | −233 | −232 | −231 | −230 | −229 | −228 | −227 | −226 |
| A | 0.211 | 0.212 | 0.212 | 0.212 | 0.212 | 0.212 | 0.212 | 0.212 |
| C | 0.270 | 0.269 | 0.270 | 0.270 | 0.270 | 0.270 | 0.270 | 0.270 |
| G | 0.307 | 0.307 | 0.307 | 0.307 | 0.308 | 0.308 | 0.308 | 0.308 |
| T | 0.210 | 0.210 | 0.210 | 0.209 | 0.209 | 0.208 | 0.208 | 0.207 |
| position relative to TSS: | −225 | −224 | −223 | −222 | −221 | −220 | −219 | −218 |
| A | 0.212 | 0.212 | 0.212 | 0.212 | 0.212 | 0.212 | 0.212 | 0.212 |
| C | 0.270 | 0.270 | 0.270 | 0.270 | 0.270 | 0.271 | 0.271 | 0.270 |
| G | 0.308 | 0.309 | 0.309 | 0.309 | 0.310 | 0.310 | 0.310 | 0.310 |
| T | 0.207 | 0.207 | 0.207 | 0.206 | 0.206 | 0.205 | 0.205 | 0.205 |
| position relative to TSS: | −217 | −216 | −215 | −214 | −213 | −212 | −211 | −210 |
| A | 0.212 | 0.212 | 0.212 | 0.212 | 0.212 | 0.212 | 0.213 | 0.213 |
| C | 0.270 | 0.270 | 0.270 | 0.270 | 0.270 | 0.271 | 0.270 | 0.271 |
| G | 0.310 | 0.310 | 0.310 | 0.310 | 0.310 | 0.309 | 0.309 | 0.308 |
| T | 0.205 | 0.205 | 0.206 | 0.206 | 0.206 | 0.206 | 0.206 | 0.206 |
| position relative to TSS: | −209 | −208 | −207 | −206 | −205 | −204 | −203 | −202 |
| A | 0.213 | 0.213 | 0.214 | 0.215 | 0.215 | 0.215 | 0.216 | 0.216 |
| C | 0.271 | 0.271 | 0.271 | 0.271 | 0.271 | 0.271 | 0.270 | 0.271 |
| G | 0.308 | 0.308 | 0.307 | 0.307 | 0.306 | 0.306 | 0.306 | 0.305 |
| T | 0.206 | 0.206 | 0.206 | 0.206 | 0.206 | 0.207 | 0.207 | 0.207 |
| position relative to TSS: | −201 | −200 | −199 | −198 | −197 | −196 | −195 | −194 |
| A | 0.216 | 0.216 | 0.216 | 0.217 | 0.217 | 0.217 | 0.218 | 0.218 |
| C | 0.270 | 0.270 | 0.270 | 0.270 | 0.270 | 0.269 | 0.269 | 0.268 |
| G | 0.305 | 0.304 | 0.303 | 0.303 | 0.303 | 0.302 | 0.302 | 0.301 |
| T | 0.208 | 0.208 | 0.209 | 0.209 | 0.209 | 0.210 | 0.210 | 0.211 |
| position relative to TSS: | −193 | −192 | −191 | −190 | −189 | −188 | −187 | −186 |
| A | 0.218 | 0.218 | 0.218 | 0.218 | 0.218 | 0.218 | 0.219 | 0.219 |
| C | 0.268 | 0.268 | 0.268 | 0.268 | 0.268 | 0.267 | 0.267 | 0.266 |
| G | 0.301 | 0.300 | 0.300 | 0.299 | 0.299 | 0.299 | 0.298 | 0.297 |
| T | 0.212 | 0.212 | 0.213 | 0.213 | 0.214 | 0.215 | 0.216 | 0.216 |
| position relative to TSS: | −185 | −184 | −183 | −182 | −181 | −180 | −179 | −178 |
| A | 0.219 | 0.219 | 0.219 | 0.220 | 0.220 | 0.221 | 0.221 | 0.221 |
| C | 0.266 | 0.265 | 0.265 | 0.264 | 0.264 | 0.263 | 0.262 | 0.261 |
| G | 0.297 | 0.296 | 0.296 | 0.295 | 0.294 | 0.294 | 0.293 | 0.293 |
| T | 0.217 | 0.218 | 0.219 | 0.220 | 0.221 | 0.222 | 0.223 | 0.223 |
| position relative to TSS: | −177 | −176 | −175 | −174 | −173 | −172 | −171 | −170 |
| A | 0.221 | 0.222 | 0.222 | 0.223 | 0.224 | 0.224 | 0.225 | 0.225 |
| C | 0.260 | 0.260 | 0.259 | 0.258 | 0.257 | 0.257 | 0.255 | 0.254 |

TABLE 3-continued

| Average nucleotide composition of native *C. reinhardtii* promoters. | | | | | | | | |
|---|---|---|---|---|---|---|---|---|
| G | 0.293 | 0.293 | 0.292 | 0.292 | 0.291 | 0.291 | 0.291 | 0.290 |
| T | 0.224 | 0.225 | 0.225 | 0.225 | 0.226 | 0.227 | 0.228 | 0.229 |
| position relative to TSS: | −177 | −176 | −175 | −174 | −173 | −172 | −171 | −170 |
| A | 0.221 | 0.222 | 0.222 | 0.223 | 0.224 | 0.224 | 0.225 | 0.225 |
| C | 0.260 | 0.260 | 0.259 | 0.258 | 0.257 | 0.257 | 0.255 | 0.254 |
| G | 0.293 | 0.293 | 0.292 | 0.292 | 0.291 | 0.291 | 0.291 | 0.290 |
| T | 0.224 | 0.225 | 0.225 | 0.225 | 0.226 | 0.227 | 0.228 | 0.229 |
| position relative to TSS: | −169 | −168 | −167 | −166 | −165 | −164 | −163 | −162 |
| A | 0.226 | 0.226 | 0.227 | 0.228 | 0.228 | 0.228 | 0.228 | 0.229 |
| C | 0.253 | 0.252 | 0.251 | 0.250 | 0.249 | 0.248 | 0.247 | 0.246 |
| G | 0.290 | 0.290 | 0.290 | 0.289 | 0.289 | 0.289 | 0.289 | 0.288 |
| T | 0.230 | 0.230 | 0.231 | 0.232 | 0.233 | 0.234 | 0.234 | 0.235 |
| position relative to TSS: | −161 | −160 | −159 | −158 | −157 | −156 | −155 | −154 |
| A | 0.230 | 0.231 | 0.232 | 0.232 | 0.232 | 0.233 | 0.233 | 0.233 |
| C | 0.245 | 0.244 | 0.243 | 0.241 | 0.241 | 0.240 | 0.238 | 0.238 |
| G | 0.288 | 0.288 | 0.287 | 0.288 | 0.288 | 0.287 | 0.288 | 0.288 |
| T | 0.235 | 0.236 | 0.237 | 0.238 | 0.238 | 0.239 | 0.239 | 0.239 |
| position relative to TSS: | −153 | −152 | −151 | −150 | −149 | −148 | −147 | −146 |
| A | 0.234 | 0.235 | 0.235 | 0.236 | 0.237 | 0.237 | 0.238 | 0.238 |
| C | 0.237 | 0.236 | 0.235 | 0.234 | 0.233 | 0.232 | 0.231 | 0.231 |
| G | 0.288 | 0.288 | 0.288 | 0.288 | 0.288 | 0.288 | 0.288 | 0.288 |
| T | 0.240 | 0.240 | 0.241 | 0.241 | 0.241 | 0.241 | 0.241 | 0.242 |
| position relative to TSS: | −145 | −144 | −143 | −142 | −141 | −140 | −139 | −138 |
| A | 0.239 | 0.239 | 0.240 | 0.240 | 0.241 | 0.241 | 0.241 | 0.241 |
| C | 0.230 | 0.229 | 0.229 | 0.228 | 0.227 | 0.227 | 0.227 | 0.227 |
| G | 0.289 | 0.289 | 0.289 | 0.290 | 0.290 | 0.291 | 0.291 | 0.292 |
| T | 0.241 | 0.242 | 0.241 | 0.241 | 0.240 | 0.240 | 0.240 | 0.239 |
| position relative to TSS: | −137 | −136 | −135 | −134 | −133 | −132 | −131 | −130 |
| A | 0.242 | 0.242 | 0.242 | 0.241 | 0.241 | 0.240 | 0.240 | 0.240 |
| C | 0.226 | 0.226 | 0.226 | 0.226 | 0.226 | 0.227 | 0.227 | 0.227 |
| G | 0.292 | 0.293 | 0.293 | 0.294 | 0.295 | 0.295 | 0.296 | 0.297 |
| T | 0.239 | 0.238 | 0.238 | 0.238 | 0.237 | 0.237 | 0.236 | 0.235 |
| position relative to TSS: | −129 | −128 | −127 | −126 | −125 | −124 | −123 | −122 |
| A | 0.240 | 0.240 | 0.239 | 0.239 | 0.238 | 0.238 | 0.237 | 0.237 |
| C | 0.227 | 0.228 | 0.228 | 0.229 | 0.229 | 0.229 | 0.230 | 0.230 |
| G | 0.299 | 0.300 | 0.300 | 0.301 | 0.303 | 0.304 | 0.305 | 0.306 |
| T | 0.233 | 0.232 | 0.231 | 0.230 | 0.229 | 0.228 | 0.228 | 0.227 |
| position relative to TSS: | −121 | −120 | −119 | −118 | −117 | −116 | −115 | −114 |
| A | 0.236 | 0.235 | 0.234 | 0.233 | 0.233 | 0.233 | 0.232 | 0.231 |
| C | 0.231 | 0.231 | 0.232 | 0.233 | 0.234 | 0.235 | 0.235 | 0.236 |
| G | 0.308 | 0.309 | 0.310 | 0.312 | 0.313 | 0.314 | 0.315 | 0.316 |
| T | 0.225 | 0.224 | 0.222 | 0.220 | 0.219 | 0.218 | 0.217 | 0.215 |
| position relative to TSS: | −113 | −112 | −111 | −110 | −109 | −108 | −107 | −106 |
| A | 0.231 | 0.230 | 0.229 | 0.228 | 0.227 | 0.226 | 0.225 | 0.224 |
| C | 0.238 | 0.238 | 0.239 | 0.240 | 0.241 | 0.242 | 0.243 | 0.244 |
| G | 0.316 | 0.318 | 0.319 | 0.320 | 0.321 | 0.322 | 0.323 | 0.325 |
| T | 0.214 | 0.213 | 0.212 | 0.210 | 0.209 | 0.208 | 0.207 | 0.206 |
| position relative to TSS: | −105 | −104 | −103 | −102 | −101 | −100 | −99 | −98 |
| A | 0.223 | 0.222 | 0.221 | 0.220 | 0.219 | 0.218 | 0.217 | 0.216 |
| C | 0.245 | 0.246 | 0.247 | 0.248 | 0.249 | 0.251 | 0.251 | 0.253 |
| G | 0.326 | 0.327 | 0.328 | 0.328 | 0.329 | 0.330 | 0.331 | 0.331 |
| T | 0.204 | 0.204 | 0.202 | 0.202 | 0.201 | 0.200 | 0.199 | 0.198 |
| position relative to TSS: | −97 | −96 | −95 | −94 | −93 | −92 | −91 | −90 |
| A | 0.216 | 0.215 | 0.215 | 0.214 | 0.214 | 0.213 | 0.212 | 0.211 |
| C | 0.254 | 0.255 | 0.256 | 0.257 | 0.257 | 0.258 | 0.260 | 0.261 |

TABLE 3-continued

| Average nucleotide composition of native *C. reinhardtii* promoters. | | | | | | | | |
|---|---|---|---|---|---|---|---|---|
| G | 0.331 | 0.332 | 0.332 | 0.332 | 0.332 | 0.332 | 0.333 | 0.333 |
| T | 0.198 | 0.197 | 0.196 | 0.195 | 0.195 | 0.195 | 0.194 | 0.193 |
| position relative to TSS: | −89 | −88 | −87 | −86 | −85 | −84 | −83 | −82 |
| A | 0.211 | 0.210 | 0.209 | 0.209 | 0.209 | 0.208 | 0.207 | 0.207 |
| C | 0.262 | 0.263 | 0.264 | 0.265 | 0.266 | 0.267 | 0.268 | 0.269 |
| G | 0.332 | 0.332 | 0.332 | 0.332 | 0.331 | 0.331 | 0.330 | 0.330 |
| T | 0.193 | 0.193 | 0.193 | 0.193 | 0.193 | 0.193 | 0.192 | 0.192 |
| position relative to TSS: | −81 | −80 | −79 | −78 | −77 | −76 | −75 | −74 |
| A | 0.207 | 0.206 | 0.206 | 0.205 | 0.205 | 0.204 | 0.204 | 0.203 |
| C | 0.271 | 0.271 | 0.273 | 0.274 | 0.275 | 0.275 | 0.276 | 0.277 |
| G | 0.329 | 0.328 | 0.327 | 0.327 | 0.326 | 0.325 | 0.325 | 0.324 |
| T | 0.192 | 0.192 | 0.192 | 0.192 | 0.193 | 0.193 | 0.193 | 0.194 |
| position relative to TSS: | −73 | −72 | −71 | −70 | −69 | −68 | −67 | −66 |
| A | 0.203 | 0.203 | 0.203 | 0.202 | 0.202 | 0.202 | 0.202 | 0.201 |
| C | 0.278 | 0.279 | 0.280 | 0.282 | 0.283 | 0.284 | 0.285 | 0.286 |
| G | 0.323 | 0.322 | 0.321 | 0.320 | 0.319 | 0.318 | 0.317 | 0.316 |
| T | 0.194 | 0.194 | 0.194 | 0.194 | 0.194 | 0.194 | 0.195 | 0.195 |
| position relative to TSS: | −65 | −64 | −63 | −62 | −61 | −60 | −59 | −58 |
| A | 0.201 | 0.202 | 0.202 | 0.203 | 0.203 | 0.204 | 0.204 | 0.205 |
| C | 0.287 | 0.288 | 0.290 | 0.290 | 0.291 | 0.291 | 0.292 | 0.293 |
| G | 0.314 | 0.311 | 0.309 | 0.306 | 0.304 | 0.301 | 0.299 | 0.296 |
| T | 0.195 | 0.196 | 0.197 | 0.199 | 0.200 | 0.202 | 0.203 | 0.204 |
| position relative to TSS: | −57 | −56 | −55 | −54 | −53 | −52 | −51 | −50 |
| A | 0.205 | 0.206 | 0.206 | 0.206 | 0.206 | 0.207 | 0.208 | 0.209 |
| C | 0.293 | 0.293 | 0.294 | 0.295 | 0.295 | 0.296 | 0.297 | 0.297 |
| G | 0.294 | 0.292 | 0.289 | 0.287 | 0.285 | 0.283 | 0.280 | 0.278 |
| T | 0.206 | 0.207 | 0.209 | 0.210 | 0.211 | 0.212 | 0.213 | 0.214 |
| position relative to TSS: | −49 | −48 | −47 | −46 | −45 | −44 | −43 | −42 |
| A | 0.209 | 0.210 | 0.210 | 0.211 | 0.211 | 0.212 | 0.213 | 0.215 |
| C | 0.297 | 0.298 | 0.298 | 0.299 | 0.299 | 0.299 | 0.299 | 0.299 |
| G | 0.275 | 0.273 | 0.271 | 0.268 | 0.266 | 0.263 | 0.260 | 0.258 |
| T | 0.217 | 0.218 | 0.219 | 0.221 | 0.223 | 0.224 | 0.225 | 0.227 |
| position relative to TSS: | −41 | −40 | −39 | −38 | −37 | −36 | −35 | −34 |
| A | 0.215 | 0.216 | 0.217 | 0.218 | 0.219 | 0.220 | 0.221 | 0.222 |
| C | 0.299 | 0.299 | 0.299 | 0.299 | 0.298 | 0.298 | 0.298 | 0.298 |
| G | 0.255 | 0.253 | 0.250 | 0.247 | 0.244 | 0.241 | 0.239 | 0.237 |
| T | 0.229 | 0.231 | 0.233 | 0.234 | 0.236 | 0.239 | 0.240 | 0.242 |
| position relative to TSS: | −33 | −32 | −31 | −30 | −29 | −28 | −27 | −26 |
| A | 0.223 | 0.225 | 0.226 | 0.227 | 0.228 | 0.230 | 0.232 | 0.233 |
| C | 0.297 | 0.296 | 0.296 | 0.295 | 0.294 | 0.293 | 0.291 | 0.289 |
| G | 0.234 | 0.231 | 0.229 | 0.226 | 0.223 | 0.221 | 0.220 | 0.218 |
| T | 0.244 | 0.246 | 0.248 | 0.250 | 0.253 | 0.254 | 0.255 | 0.257 |
| position relative to TSS: | −25 | −24 | −23 | −22 | −21 | −20 | −19 | −18 |
| A | 0.235 | 0.237 | 0.239 | 0.240 | 0.242 | 0.245 | 0.245 | 0.246 |
| C | 0.289 | 0.287 | 0.285 | 0.284 | 0.282 | 0.280 | 0.281 | 0.279 |
| G | 0.217 | 0.214 | 0.213 | 0.213 | 0.212 | 0.209 | 0.211 | 0.209 |
| T | 0.258 | 0.260 | 0.262 | 0.262 | 0.263 | 0.264 | 0.261 | 0.264 |
| position relative to TSS: | −17 | −16 | −15 | −14 | −13 | −12 | −11 | −10 |
| A | 0.247 | 0.250 | 0.252 | 0.253 | 0.254 | 0.255 | 0.256 | 0.257 |
| C | 0.278 | 0.276 | 0.275 | 0.274 | 0.273 | 0.273 | 0.271 | 0.271 |
| G | 0.208 | 0.207 | 0.205 | 0.205 | 0.204 | 0.203 | 0.204 | 0.204 |
| T | 0.266 | 0.266 | 0.267 | 0.267 | 0.267 | 0.268 | 0.268 | 0.268 |
| position relative to TSS: | −9 | −8 | −7 | −6 | −5 | −4 | −3 | −2 |
| A | 0.257 | 0.259 | 0.259 | 0.260 | 0.261 | 0.262 | 0.262 | 0.263 |
| C | 0.270 | 0.269 | 0.268 | 0.268 | 0.267 | 0.266 | 0.265 | 0.265 |

TABLE 3-continued

Average nucleotide composition of native *C. reinhardtii* promoters.

| | | | | | | | | |
|---|---|---|---|---|---|---|---|---|
| G | 0.203 | 0.203 | 0.203 | 0.202 | 0.202 | 0.202 | 0.202 | 0.202 |
| T | 0.268 | 0.268 | 0.268 | 0.269 | 0.269 | 0.269 | 0.269 | 0.269 |
| position relative to TSS: | −1 | 0 | 1 | 2 | 3 | 4 | 5 | 6 |
| A | 0.264 | 0.264 | 0.265 | 0.266 | 0.266 | 0.267 | 0.267 | 0.267 |
| C | 0.264 | 0.264 | 0.262 | 0.261 | 0.261 | 0.261 | 0.260 | 0.260 |
| G | 0.202 | 0.202 | 0.203 | 0.204 | 0.204 | 0.205 | 0.206 | 0.206 |
| T | 0.269 | 0.269 | 0.269 | 0.268 | 0.268 | 0.267 | 0.266 | 0.266 |
| position relative to TSS: | 7 | 8 | 9 | 10 | 11 | 12 | 13 | 14 |
| A | 0.268 | 0.268 | 0.268 | 0.269 | 0.269 | 0.269 | 0.268 | 0.267 |
| C | 0.259 | 0.260 | 0.260 | 0.259 | 0.259 | 0.259 | 0.259 | 0.260 |
| G | 0.207 | 0.207 | 0.208 | 0.209 | 0.210 | 0.211 | 0.212 | 0.212 |
| T | 0.265 | 0.264 | 0.263 | 0.262 | 0.262 | 0.260 | 0.260 | 0.260 |
| position relative to TSS: | 15 | 16 | 17 | 18 | 19 | 20 | 21 | 22 |
| A | 0.268 | 0.267 | 0.266 | 0.265 | 0.264 | 0.263 | 0.260 | 0.261 |
| C | 0.261 | 0.261 | 0.262 | 0.263 | 0.263 | 0.264 | 0.266 | 0.264 |
| G | 0.212 | 0.212 | 0.214 | 0.215 | 0.216 | 0.218 | 0.221 | 0.219 |
| T | 0.259 | 0.259 | 0.258 | 0.256 | 0.256 | 0.255 | 0.253 | 0.256 |
| position relative to TSS: | 23 | 24 | 25 | 26 | 27 | 28 | 29 | 30 |
| A | 0.261 | 0.260 | 0.258 | 0.256 | 0.255 | 0.255 | 0.255 | 0.254 |
| C | 0.265 | 0.267 | 0.268 | 0.269 | 0.270 | 0.270 | 0.270 | 0.271 |
| G | 0.221 | 0.223 | 0.224 | 0.227 | 0.228 | 0.228 | 0.229 | 0.230 |
| T | 0.253 | 0.250 | 0.250 | 0.248 | 0.248 | 0.247 | 0.246 | 0.246 |
| position relative to TSS: | 31 | 32 | 33 | 34 | 35 | 36 | 37 | 38 |
| A | 0.253 | 0.253 | 0.252 | 0.251 | 0.250 | 0.250 | 0.249 | 0.248 |
| C | 0.271 | 0.271 | 0.272 | 0.272 | 0.272 | 0.273 | 0.274 | 0.275 |
| G | 0.231 | 0.232 | 0.233 | 0.234 | 0.235 | 0.236 | 0.237 | 0.238 |
| T | 0.246 | 0.244 | 0.244 | 0.243 | 0.242 | 0.241 | 0.240 | 0.240 |
| position relative to TSS: | 39 | 40 | 41 | 42 | 43 | 44 | 45 | 46 |
| A | 0.247 | 0.246 | 0.245 | 0.244 | 0.243 | 0.242 | 0.241 | 0.241 |
| C | 0.275 | 0.275 | 0.276 | 0.277 | 0.278 | 0.279 | 0.279 | 0.280 |
| G | 0.239 | 0.241 | 0.242 | 0.242 | 0.243 | 0.243 | 0.244 | 0.244 |
| T | 0.239 | 0.238 | 0.237 | 0.237 | 0.236 | 0.236 | 0.235 | 0.234 |
| position relative to TSS: | 47 | 48 | 49 | 50 | | | | |
| A | 0.240 | 0.240 | 0.239 | 0.238 | | | | |
| C | 0.281 | 0.281 | 0.282 | 0.283 | | | | |
| G | 0.245 | 0.246 | 0.247 | 0.247 | | | | |
| T | 0.234 | 0.233 | 0.233 | 0.232 | | | | |

*mimics from promoter positions −449 to 50 bp upstream of the TSS and is calculated as described herein.

In varying embodiments, the synthetic promoter scaffold or backbone is derived from a promoter capable of expression of a polynucleotide in an algal cell, e.g., in the nucleus or a plastid organelle (e.g., a chloroplast). In varying embodiments, the synthetic promoter scaffold or backbone is derived from a promoter capable of driving expression in an algal cell selected from the group consisting of psbA, atpA, psbD, TufA and atpB. See, e.g., U.S. Patent Publication No. 2012/0309939.

In varying embodiments, the promoter comprises a nucleic acid sequence of a synthetic promoter shown in Table 4 (e.g., any one of SEQ ID NOs:38-62).

TABLE 4

Illustrative synthetic algal promoters. Underlined sequences show location of elements.

| Promoter | Sequence | SEQ ID NO |
|---|---|---|
| sap8 | CACCAGGACATCCCTCTCTCAGCTCCTAGAAGCTGTCTCGT<br>GCCAGCTTCGGTCGGGCCGCAAGTAAAGCGAGACCCAAGA<br>GCGACGTTTGCCACCTTGCGCGTGCTTTGAGCATGTCGCGA<br>AGAAACCCCGAAGGCATGGGGCCCATTCGCGAAGCAAATC<br>TGGTGTGCAACCATTAAGGCTTTAAAGCGAGCGAGCGAGC | 38 |

TABLE 4-continued

Illustrative synthetic algal promoters. Underlined sequences show location of elements.

| Promoter | Sequence | SEQ ID NO |
|---|---|---|
| | AGGAGGCCCATGCAGCGCGCGCGAGGCGAACATAGAATG<br>GGCCCGCTCTTCCGCTGCGCGTTAGAAGCGAGGCAGCATC<br>ATATTCATATTCATTAGCACCAATGCTCGCAGGTATACAAA<br>TTTTGTGCAGAAGCGAAAATGCAAGCAATTTGCATGGGGC<br>GTACGGCCGCATGGGGCTTTTTTTTTTGGGGCTCAAGTCTC<br>AGAGCGCGCGCGCAATGGCGCCCTCTCCTCTCTTTTCCTCG<br>TCGCGACCGAACCCAGCAAGGTGCGTCAAGATCGCTGTCG<br>GGTAAGAGCCAAGGCT | |
| sap11 | CACATGCTGACTACGAGCAGGCGCTGGGCAGAATGGCATG<br>AAGGCTTCTGAGCGACTCGGCGACGAACTCATCCCTCAAG<br>TGTTGCACAAAAGCGCCGAGCGCTCCGCGTTCGAGGGCGA<br>ATGACCCGCGCGAATGGGCCCCACAAATGACCAGGCAACC<br>TCAAGCTAACGCAGCGGCCTTTTACGTATAGAGCGACTGC<br>AAGCAAGTATGCAGCTCGTTGCGCGGTCGCGAGTCCAAGT<br>CGCGCTGCGCGCACATCCTCGAGCGCGCGCCGCGGCCACC<br>AAGTGGAATGGGCCCATCATGCATGTTTGCTTGGCCCCGAT<br>AAAGCCCGCAATTTTGGGAAAAAGGTACGGCGCGCGCCCC<br>ATGCGAGATGTACGCCCATTGCATGGGGCAACTTGCTCAA<br>AGCCGAGCGAGCCCGCTGCAGGTTAGTCTTTCTTTTAGCGT<br>GTGCCCACACCTTTCTAGTCGTTCTTCGCCACCACCAACAA<br>GAAAGCCGGCGGCCTCG | 39 |
| sap22 | GAAGCCCTCCATAATGGCCCCGTCTCCGCATCTCCCGCACT<br>GTTCGCGGGCAACAGCAGGGAGACGAGAGGAACCCAAGA<br>AGCGCGCCACTGCAGCGCTTCGCGCAGTGGGCCCATTCCG<br>GCAATTATGACCCCCGACCGCGCGGGTATGAAGCTGTTTTC<br>AAGCAACTCGGCGCAGTTCTTGGCACTCGATTTGCGCGAG<br>AGCGAGTTTCAGAATGGGCCCTCTTTTTGCTTGCTTTTGCG<br>CGTCGACCGCCTCGCGAAATGGTGGGGCCTGCACCCATTGT<br>TTCATTCTATGTATCAATGCCATTTATAATCATTAGGAGCA<br>ATTTTGGTACGGCGTGCGTCACTTGCATGGGGCTGGCCCAT<br>TGCAATGAGATGGGCGCATGGGGCGCTCAATTGTCTGCGA<br>CTTGCGAGCCACTTCTCTCTTCCCTCTCTCGCCGTCAACCGA<br>CCGACTCACTTCGTCGCAACCACCTTTCGTGAGTAGGTAGT<br>GTGTAAGAAGGT | 40 |
| sap1 | CCCCCTGCCTCCTCGCGCATGCGTGAGGCATGAGAGCGTG<br>GCATAAGGCCGTAAAGCAAAGCGACAAGGGGCTTCCAGGT<br>GTGCACGCATGCAAGCACGCGAAACTTTTTTTCTGCGCTGG<br>GTTTGTCGCTTTCCTAGTTTGTAATGTGTTCCAACCCTTTTA<br>GGCGTGGCAGCAGAGGCGCGCGGCGCCATTTGGGAAAGCA<br>AGTTAGTGCAAAATGCAAACATGCGCAAGGGCGCGGGGTT<br>CGCGACCATCGCGAGCTCCATAGCGCTGGTGGCTATGCAC<br>CATTCCATGCATGCATACAATTCATTATGGGCCCATTCAAA<br>TTTTGGGGGCGTTCTTATCCTTCCCTGGAGGGCCCATTCTC<br>GTACGGCATTGCATGGGGCCGCCCCATGCGGACTTGCTTAT<br>CCTGCGAGCGCGCGACAGCTTTCTCTTTTACTTGTCGCAGG<br>TTGCGCCGAACACTTCTCTTTCAAAACACCAGTGAGCAGGC<br>CCTCGCCCCCAA | 41 |
| sap2 | CGGGTGTTGTGCTCAGAGTGGCTTCCGCATGATAAACGCA<br>GCGCTGAAGCTATTAAAGCAGGGGGAACCCTCGCTCAAGA<br>GATCGCAAGCACCAGCGCACGCGTTGCGCGCATGTCGCGC<br>AGCAATTGGCAGAAACCGCTTGAAATTCGCATCAATGCAT<br>GTCAAGGCGCAATAGCTATGCGCAAGGCCTCCCGGCTATG<br>CGTAGACAAGGGCCCATTCCTAGAATCAGGGGAATCAAGC<br>GGGTTCGTGCAAGCGTGGGCCCATTCTCAGGCCAGCATAG<br>CGAGGATAAAGCTAGCATAAATTGCGCCCCATGCATGGGC<br>AGAATTTTTGGCGCTTCCAACGCGAAGCAGCAGCGCATGG<br>GGCGATGCCGTACGGCGAGATCGCCTCTCAAGTCTTTGTCG<br>CAAGTCGCGAGCCACTGCACCACCTTTCCTCTCTCTCTTTGT<br>CCACCGCTAGGCAAGGGTGGCCGCAAAAAACAAGTACAGG<br>GTAAGAACAGGGCTCTT | 42 |
| sap3 | AGGCTAGAACAGTTTCTCCTCTCCATGGCAATATCCCGCAC<br>CAGGGCACGAGGGCACTTAAAGCACGGGAGAGGGTGTTGG<br>GGTCTCCGAAAGCACTAGAACCTGACAGTGAATGGGCCCT<br>TTCCCCGGCATGGGCAAGCAAGCAAGAAGGCAAGCAGCGG<br>CAGAAGCAAAGTGCGGAATGGGCCCTTGCGCGTATATATT<br>TCGGGCAAGAGCGACGGAAAGCGGTCGCTCGCCTGCAGAG<br>GCGTTGAATTAAATTCTGCGCGCGCGAATGCGATTAAAGC<br>ATACAGCATGCACTGGCCCATTGCATACAATTCAAATTATC | 43 |

TABLE 4-continued

Illustrative synthetic algal promoters. Underlined sequences show location of elements.

| Promoter | Sequence | SEQ ID NO |
|---|---|---|
| | TGGGCCCCATGCGCGGTCCACGAAAAGGCTGCATTGGGGC<br>GCCGTACGGCGTCGCGCTCATGCGCCCCATGCAGATGGCC<br>GCCGGTCTTCCTTTCTTTCTCTCTCTCTTTCTCTTTCAGGTGC<br>CCCTCCTAGGACACTTCGCCTTAAAGTAACACCAACAAGA<br>AGCGCGCCCTGGCCC | |
| sap4 | CCTGCTTCAGGCCAGGGCGTGAGATAAAGCATGCATTTGG<br>CAGCGATGTCAGGGGCTTTCTGAAAGCCGCTTTTGGCACGG<br>TGTGACATGCGTGCACGCGTTTCGGGTGAGCAGCAATGTTC<br>AGCAACCCCCGCAATGCGGGGCCCATTCTGGGCAACCCTT<br>CCAACAAAGTTGAAGTGAGCAATCGATTTTGGCAGAATGG<br>GCCCACGCGGGTCGCGGCATGCGCTTGCGCCGGGGAGAAT<br>TCATGGCCTCGCGCAAGGCAGCGCGCGAAATATTGCGGTG<br>GTCTCACGCATAGCAACCAGGGGGCACTCGCAAAGGCTGT<br>ATATTAGTTTATAGGCCCTAGGCCCCATGCGGTTTGTACGG<br>CCCATTGAGGCCCCATGCCCCATGCAAATTTTGCGCCAGCG<br>CTCACCTCCCCACTCTTTCTCTTTCTTTCCTCCCGTGGAACA<br>CCAGTCACCAGTCCTCATTCAGCAAGGAGCAAGCCGCCGG<br>TGAGCAGGTGAGCC | 44 |
| sap5 | CCTGGAAAGGAGGCTAGGGCGCATGTCGTTTTGCAAAAAA<br>ACGCGTGGCAGGAGTGGGACAAGGAACCGCTTCTTCGCTT<br>CTTCTTTGGCAGTGCAAGGCGCAGCACCAAGTGCAGCGAG<br>CAGTGAAACAATGGGTTCGCGAATGGGCCCTCTTGGAAGC<br>AACCTCAAACCATTCTGCCAGGGCTCAACTGAGCACGCGG<br>CGCTATGCGTGAGCAAACATGCGCTTTTTGTGCTGCAAGAA<br>TTCCTCGGCAAGCTGATTTTCGTCGCTCCCAGCGTCACCCA<br>GGGCCTTGGCTTCTATGCATGCATGGGGCAGAGCATGGGT<br>GTTTAATTTTGGAATGGGCCCCAGCCCCATGCGCCCAATTA<br>ACGCCCCATTCGCCCGCCGTACGGCGAGTCTTGCGGAGCG<br>CAAGTCTCTTTCTCCTTGCCTCTCTTTCTCTCTTTCTCGTCGA<br>CCGTCGCCGACCACCTAGGTCAATTTTGAAGTCAAGACCTG<br>AAGCGCGCTCTTC | 45 |
| sap6 | ATGGGAGCAGCTCCTCCTCTCTCTGTCTGCTTCTGGGCCTA<br>CACGAGTGTCGATGTGCCTTTGGCACGGAGAAGCGAGAGG<br>AAAGCGCATGCCTCAAAAATCCCGAAGTGCCAAGCATGGG<br>GCAACCCCCGACGCGAAATTATTGTCAAAGCCAGCAGTGT<br>CATTCATGCTGGCAGAAGGAAAGTGCTCGCGTTTAAAGGA<br>GGCAGACAGAGCGCGCGCGGGCGGTCGCATGCGCGCCAAA<br>ATCTCGCGACCTCGCGAAATGCGAGCGCGGGCCACCTTTA<br>GAAGTAGCAAAATGCCATTGAATGGGCCCAGAATGGGCCC<br>GTGATGTCTATGTGCATGAGGGCCCCATGCAAGGCAGAAA<br>GTCGATCGTACCGAGATCGCCCCATGCGAGCGCCGTACTCC<br>GCGGAGAAGTCGCGCGGGCGCAAGCTAGTTCTCTTTCTCAC<br>TTCCCGTAGTCGACCGTGCTTCACGTCAGTCCACCACCACG<br>CGGCCATCTTTAGCCG | 46 |
| sap7 | GCTTCGTCACGCAGGCAGCTGGGCAGGCAGGAAAAGCATA<br>AGGGCACTTCATCATCGTGGGAGAGAAGGCCTGGAAGGAG<br>AAGGGACACAAAAGCGCTTCGACCTTGCGCCCTTGAGGCA<br>CCGTCGACCCTTTGGAGCTACCTTTTGGAGCAGTGTTCTGG<br>GGCCCATTCCCAAAAGGGTGCTGCGCAAGGCGAGCGACTT<br>TTAGGCAGAGCAAAAGCATGCTTGCCAGTCTGGGCGCCAA<br>GCCTTCCGCGCACGGTGCTCGAATGGGCCCTGGCCTTTCAT<br>GCCTTGCTCTGATTTTCATTAGCATCGTGGCCCCATGCGAA<br>AGCCGAAAGCGCGAGCTCCTGCGCATGGGGCGATCTTCCT<br>GGCGCCACGGCAGAGATCGCCGTACGAGTGCAGAGTCTTC<br>CGCGCGCGAGCGCGACTTTCTCTTTCTCTTTCCCATCTTAGG<br>AAACACTTCGCCACTGCTTTCGTTAAGAGCCGCCGGAAGG<br>CCCTCCGCGCCCTGG | 47 |
| sap9 | CTGGTCCCAGTTGTGCATTCTCATGTGAGGAACCCTGGGCC<br>AACTGAGGGGCAGAGGGCAGACGAGAAACGGTCCGCACG<br>GTCGCAAGCGCACAAAGCACGCGTTCGACTGCGCTCTAAT<br>GGGGCTGAGCGTGTCTGACCTTTTAGCTCAGCAAATCAGGC<br>AGAAGCAGAAAGCTAACCTACAAGTGGGCCTCATAGAATG<br>GGCCCCACGGCGCGCGCGATGACACGCAGTCGCTTGCGTC<br>GCGGCAAGCGGAAGCTGCGAGCCACGAGCGAATGGGCCCT<br>TTCATGCCATGCTAGATGCTAAATTTCCACAAAGAGACAA<br>AATTAATGCGAGGGCCCCATGCAGGCGGTACGGCAGATCG<br>CTTGCCCCATGCGATCGCCCCCATCGCGAGACCCTTGCGAG<br>CGAGCGCCTGCACCGTTGCCCTCTTTCTCTCTCTTGTCCTGT | 48 |

TABLE 4-continued

Illustrative synthetic algal promoters. Underlined sequences show location of elements.

| Promoter | Sequence | SEQ ID NO |
|---|---|---|
| | CGCCTTTCTAGGAAAGGGCGCCACCTTTGCAGAAAGAACA<br>AGAGGGCCTCGCAGGT | |
| sap10 | ATGCCTCCTCGCTTAGCGCTAGAAAGCCGTCTGTCCTTAAA<br>AAAGCCAGCGCAGAGCGACTGCACTTCTTGGCTCAAGAGA<br>TCGCACGCGCGCCGACCCGCCAGGTCTGGGTCGCGAGAGC<br>GTCTCTCGCCGGGCGCTGTCGACCGCTTTAGCACTGTGTCA<br>TTTCAAGTCATGAGCTGCTACAAGTCGCAGCCGAGGAGCA<br>GAATGGGCCCTGGGCGGCATGCGCATTTCCCGCTCGCCAG<br>GGTTCACTCAGCAAGCCCTCAGCGCTGCAGGCTCACACATT<br>CTTTGCTGATTATGCATGCAAGCATGCCCCATGCATGGTAC<br>TGCGCCCGTGCGAGAGAATGGGCCCCTCTCGCCGTACCATT<br>CTCGCCGCAATTGCATGGGGCGACTTTTGAAGGCCGACTTT<br>GCGAGCGCGCGCCGAGCCTCTTTCTCTTTGTCGTCGCCTTG<br>TTCGACACTTCAGTCACCTCGCCTCCACCAAGGGTGGCCCT<br>CGCAAGAAGGAG | 49 |
| sap12 | CTGCGTGCATTTTAGGAGGAAGAAAGCCTCCGCAGAGCCG<br>CACTGACTTCGCGAGCCCTTGCGTAGAAATCTCTGAAACCC<br>CATCGCACCAAGTGACCTTTCTCAGCGCTCGCGTTGGCACG<br>CGTCGCTTTCTGCCGCACACGCAATTGCTCAGCAACAAAGA<br>GGCAAGCTATTAGTATCAAGGCTATGCGCGAGCGGAGACC<br>TCGCGCGCGCGCTGGCGGCTCACGGCGCCTGGGCAACTTG<br>GGGTTCGCTTCGGGCCCATTCATAGCGCTGAGTGGCCATTC<br>AAGGGCCCATTCAAGGTCGCAGGGGATTAGCATACCAAAA<br>TGTAATGCAGAATGCCTTCTCTGCGCGCATGGGGCGCAATG<br>GCCCAATTCTCGCCGTACTCGCTCGCGCATGGGGCGGAGTC<br>TCGCCAAAGCGCGTTCTTTCTCTTTGTGCCGCTAGTCGTCG<br>CAGGTGAGCGTTAGATCACCTTGCTCCTTTTTTCCGCCCCG<br>CGCTGTGAGTAC | 50 |
| sap13 | TGCCTCCAGAAGATAAAGCATCTCATGTAGGTCAGGAAGA<br>ACTCCAGGAAAAGCAACAGCAAGCAAGGGGACACGCTGCT<br>ACACAGAGCTTCGAAAATCGAAACTTCGGCCCTGACATAA<br>CCGCAAGTGTGTGCAGCGAGGGCCCATTCTGTTCTAAGAA<br>AGCCCACCAACCTCAAGTGCTGGTCGACGCAGCATCCGCG<br>AGCGCGCGCGCCAAAAAGTTGTGCAGTTTGGGTGCGCGTC<br>GTGCGACGGTCGCTCTTCCCTCAGCGCGAAATCCATTCCCC<br>ATCATTTGGGTCTCTGCACCCATGCATGTTTGTGCGAGCGT<br>CGCGCGGGCCCCATGCGGTACGGCTTTTCTGAATGGGCCCC<br>CCCGCTTGCATGGGCGCGGTCGACCGCATGGGGCGAGAGC<br>GCAACAAAACAGCGCGTTCTCTCTCTCCCTCTTTCCAAACC<br>GGTTGGCCGAACAACCACTTATCATCTTCGTTGCCCCAGCA<br>GGCCCTGTCCAAGAA | 51 |
| sap14 | AATGGCCCGCCCTGGACATGGCGCAGCCTGAGGGCCCTGT<br>TGCAAAACGGCTTAAAAACACTTAAATCGCTGGCAGGGAC<br>ACTTCGTGCGGGTCTGCCGAGCGCAAGGCGCGTTTCGGGC<br>CCCGGCACCGTCGCTGTTTCGGACCCCCGTTCGTGCCAGCG<br>CGCTCAACTAATGCGAGAATGGGCCCAGAAAACAGAGCAA<br>AATGCAAGAGCAGCAAAACTGCGCATGCGCCACTGTTGTC<br>TCACTCGCTCGCGCAAGCTCCACGGCCCTGGGGCCCATTCC<br>AGCGCGTAAATAAGCCACCATTTTGCGGTCTGGCAGCAGC<br>ACCAAAATTTTTAATGCATGGGGCTCCGCGAAATGGCGCC<br>GTACGGCACCGAGATCTGCCCATGCATGCATGGGGCGGAG<br>TCAAAGCGCGCGCCGAGCTCTTTCTTCTTGTCAGCACCGCA<br>GGTTGCTCACGTAGGACACTTCTTTGCGCGTCGCCCCTGCC<br>TTCGGGCACGGGTAAG | 52 |
| sap15 | CACGAGTTTGCTGGACATCCTGGCTTTCTCAGTGGCAGCGC<br>CGTAGGTCGGGCAGAGGGAGAAACCCTTCGCTTCTCAGGA<br>GAAGCATACGTTCGTTCGGTGGGGGGCGAAGAACCACAGC<br>AGAATGGGCCCGCTTTCGCGGCATCAATGCATGCTCATCAC<br>CAAGCAGAGGCTCAGAGCCTCCTCAAATCAGGGGAAAACT<br>GACGCGCGCGTGAGCGCGCTTCCGACGCGATGGCGCTCGC<br>TTGGGTTGCGTGAGCAGGCTGCGAGAGCGCTGGCTGTTAC<br>ATTCATTGAATGGGCCCATGCATGGGGCAAATAGTGCGGC<br>GCTTCCATGCAAGCAAGCGAGCGCGACGCGCATGGGGCGC<br>CTGTACGGCCGCCCCCATTCCCCATGCCGTACAGAGTCTGG<br>GTCTTCCTTCCTGCACAGCACTTCTTTCCTCGAGTTGTTCGT<br>CGTCGCATCGCCACTTCTGGCCAGCAACACACCGGAAGCG<br>CAGGCCCTGGCCCTC | 53 |

TABLE 4-continued

Illustrative synthetic algal promoters. Underlined sequences show location of elements.

| Promoter | Sequence | SEQ ID NO |
|---|---|---|
| sap16 | GTTGCCCTGCTTCCGTCCATGATGGCGCATGCCTGAAGCAG<br>GGCAGGCCGCACATGACTTCAAGCGTCCTGGGGTTCGCAA<br>TCAAGAGCTTTCGCGTGTCTGCGGGTCGCGCTCGCACAGCG<br>GCCCCGCGCGTGCCGAGCTCGACACTCGTTCGCGTTAGGCA<br>ACTCAAAACCAAGCTACAACAAGCAGTATACCTTGCGCAG<br>CAAGGAGCATGCTTTTCTCCGGTCGCGCCCAACGACGATTT<br>CCTCGCTGGTGCAAGCTCCCGAGCTCCCAGCGCGCGCGAA<br>TAGCAAATAGCAAATGGAATGGGCCCTTGTTTATAACGCG<br>CGCGCATGGGGCGAACGTACGGCGAAATTTGCATCGGTTT<br>GCCCCATGCATGCAGAATGGGCCCATTTTTGCCCTCGCGCT<br>GCGCAAGCGCGAGCTCTTTCTTTCTCTTTCGGGTCTTTCTCC<br>GTTTGTTGACACCTCAAGTAAAAGGCTTTTCTCACACCAGT<br>CCGCGGTGAGCC | 54 |
| sap17 | CACCTGCTGCTGGGGCAGAATGGCCATGTGGCCAGCGCAC<br>TGTTGTTGTGACACTGAGCTCGAGAAGGACAAGGTGTGCA<br>AGTGACATGTGCACGCGAAGGGGAATGGGCCCCAAGGGCC<br>CATTCGTGCAGCGGGTGCTGCCGCATTGAAGCAACCAACA<br>AAGCTAATGCGCTAATGCGCTGACGCGTTCCGTGGAAGGC<br>GAGACGCAAGCGCGAGCGCGGAAAGCAGGCGATTCACTCG<br>CGCCAAGCCTCGCGGGAGCGCTACTAGCCCATACGGCCCA<br>ATAGCAAGCATACAGCAAGCCTCTGCGCATGGGGCCAATG<br>CATGGGGCCGTTCTGGTACGGCTATGCCTTTCTCCCATTTG<br>CAATGGCAATGGGGCCCCCATGCAGATCGCGACGAGGGTC<br>TCTTCCGCTCAGTCAGCGTTCTCTTTCTCTTTTCGAGCTCCC<br>GTCGTCGCTTGCACAAGAAGGCCGCACAGCAGTCTTGCGC<br>TCGCCCAATTAGCCCTG | 55 |
| sap18 | GGATGCTGGACAAGAGAAGAACATGCCAGCCATGACACCT<br>GCCTGAACTCCAGCTCGAGAGACACTATTTCGACCCAAGG<br>TGTTGAGTGCAGATCGCAGCTTTCGCAAACGCAGCTCTCGG<br>GTTTGTGAAATGACCCCGTGTCTGAAGCAGTCAGCGGGGG<br>CATGTCTTGGTTATTGGAAGGGCGCGGTGGAAGTGGGTCC<br>AGCAAAACGGGTCTCGCAGCGCGAGCAGCGCCAAGAACG<br>AGTGCAAGCGAATGGGCCCTCAAAGGCCATCGCCCCCAGC<br>GCTGACCCCATTGAACATGCATGTTTGCGCATGGGGCAAC<br>ATAGTGCAGCCCGCGAGCGAAAAAGGGCCCATTCTTGCAT<br>GGGGCGCCAATGGCCGTACGAGCGAGTCGGGGTCTCTCAA<br>GTGCTTGCGAGCGCGCGCTCTTTCTCTTTCCTCTCCTTTCTT<br>TGAGCAGCTTCACTGATCACGTACTTCTTCGCAACAAGCAG<br>GGTAAGAAGCGGTGCGT | 56 |
| sap19 | GGATGACTCCGTGCATGCAAATGCCGCACGTCTGCGAGGG<br>CTTTCGCGACGAGAAGGAAATCAAGAAGGGAGAAACCCA<br>ACCTCCGAGAAGCATGTTCGCGCGTTTGAGCAGCGAGGGA<br>CTCTCTCGCGGAGCCTTCCCGAAGAAAGTCTTGGGGCCCAT<br>TCTCGCGTTTTCACCAATGGCCTCGAGGCTCAGTAGGATTT<br>TCGCGCGCGCGCGTGAGCATGCGCGCGCGAGTCTGGGT<br>TGAATGGGCCCTCCTGCGAGCTTCCCCAGGCAGCGGGGCC<br>CATTCAGCAAGCATACAATGCTTGTGATTGCTTAGCCCGTG<br>CGCCCCATGCGCAGAGAGAGCCCCATGCATGGGCTGTACG<br>GCAGATCTCGCGCCCCCCGTACGGCGCGACGAGTCTGCTG<br>CGAGAGCGCGCGCGCTCCTTCTCTCTCTTTCACGTGTAGGC<br>GCAGGTCGCCTTACCACCTAGGAAGGTGCGTCCCTCACCCT<br>CTGTGAGCCCAAGGGC | 57 |
| sap20 | CTGCCCCAGTTTGCTTAAATGCGTGCATGATGCATTCTCGT<br>AGGTCGTTCATGGCAGCTCGAGATAGTTCCGAAACGACCG<br>CAAGCACCCCGCCACCCGAGCACGCTCTTTTTTCGACCGCA<br>AAGAACCGCGCCCCGCTGTTCCAATGCATGTCAAGCAATG<br>TCAACTCGCCGCTATTAAGGGCCCATTCTTTCTGCGCGCGC<br>GACATGCTTTGAGAGCAAAATGCAACTGCTTTTGTTTTGCA<br>AGCTCAAAGGCCTTCTTCGGGTGGGTTCAGTTCTATATCAC<br>CATTCATTCATTGCGCGCAGGCAGATAAATAGAATGGGCC<br>CGCGGCGCCCCATGCATGAGGCCGTACTTGGCAGATGCAT<br>GGGGCGCCCCCTGGAGCTCGCTCGCTCGGGGTGAAGAGCG<br>CCTTCTTGTCTTTCCTTTCTCTCCTTTCCTTACCTTCGTCGAG<br>CCTGCCAAGATCGGTGGCGTCAGTGCGTCGCCTTAAGCAG<br>GCCCTGTGAGTA | 58 |
| sap21 | ATGACTTGGTGGACTGCCCTGCACGCCTTCCGCATGTCCTG<br>GCCCCAGCGCACTTCTTGGCAGTAAAGCGGCAAGCGGGGA<br>CACACTTCGCGTGCGCGCTGCCAAGTGCCCGGGAGTGCCCT | 59 |

TABLE 4-continued

Illustrative synthetic algal promoters. Underlined sequences show location of elements.

| Promoter | Sequence | SEQ ID NO |
|---|---|---|
| | CGACCCGCGACTCCTATCAATAAAGCCCGCTCGCCTTCCTT<br>CCTTGGTGTTGGTGCTCGCGTCAATCCTGCAAGCAGAAGCC<br>CAGCTCGCAAAATGCAGCGCGAGCAAGTTGCGCCACTCAT<br>TCACTTGCGCGCCTCGAATGGGCCCAGCGCCAGGGCCCATT<br>CAAGTGGTTAAGCTATGTATGCAATGCGGCGCTCCAAATTA<br>TTTTGTTTCTGGCCGTACAGGGTCGGTACGACCCAAGATCT<br>CGCCCCATGCGGGCCCATCGCATGGGGCGCCCCTTGCAAG<br>CCGAGCAAGCGCGAGTTCTCGCCCTTTCTTTCTCTTCGACC<br>TAGGCACACCGTGGGCGCCGCACACCACAGCAGCAGTGTG<br>TCCTCCCGGCAA | |
| sap23 | CCCCGGCAGGGCGACGTCCACTGCACAGCCAGCCATGTTC<br>GCCTGCCCATATTTGGTCCGGCGAGGGTTCGCTGCTACACA<br>GGGGGGAGTGCAAGCGCTACCTTGCGTCGACAGCGGCATG<br>AAGGGCCCACGCAGAATGGGCCCGCAATGCATTGCAATGT<br>TCAAGCTCATGATTAACGCGCTGCAACGCGCCAGAGCGAG<br>AGAGCGCGCGAGCGCTCTGGGGTCCTTGTCGCTCGCTTTTG<br>TTTTCGCGGGCAAGCTCGCTGTGGGCCCTCCAGCGCATTTT<br>TTTTCTATCATAGTGACATGACCTTTGAATGGGCCCTGTGG<br>GCGCGGCCCAGAAAATTTTTTTTTCTCTTTCTCCGCCCCATG<br>CGGCGATGGCGCCATCGCCGTACTGCATGGGGCTCTTTTGA<br>GAAGTGCGAGCAACACTCTTTCCTCTCTTTCTCTCAAACAC<br>CAGTCGATCCAACCACACCATTTTCCTATCTGTGCGCTCTT<br>CCGCGGCGGCC | 60 |
| sap24 | TGCTCCAGGATCTGGGCTTTGGGCATGTGTCTGTCCTTAAC<br>CAGGCACTGAAGCCTGCAACACTTCCCCTTTGGCTTCCGAG<br>AAAGCATGCGTGCGTTGCGTGTGGGGCCCATTCGGGAGTG<br>AAATTATGTCTGCTAGGCATTGTGAAGCTATGCAGTGTTGG<br>TGCCAGAGCCTCGCGGCGCGGCCGCGTAAAGCAAGAGCCA<br>TTTTGCGCAAAGTCGCGGAATGCCGGGAATGGGCCCAACG<br>CTTCCTCTCGCGAGTTGCGCCCGAGCGTAGCGCCTTTCAGT<br>TTCATTCCAGCTGGGTATGCGCCCCATGCAATTTTGCGCAT<br>GGGGCGCTTCCGCAGTTTGCGCGAAATCGTACGGCGTACG<br>GCTTGCATTCCCCATGCGCTCGCGCTCTTCTCTTGCTGCGCG<br>CGGACTTCACCTTTCTCTCTTTGAACGGTCTAGCCCGCAGG<br>CCGAACACCAGATCTTCACGTCCCGCCAAGCCGCAACTTGC<br>AGGTGCCGCGG | 61 |
| sap25 | GGTAGTGGCCCTCTCCTCTTGCACCTATTTGCCCCGCACAG<br>CAGCGCAGGAGGGCAGCGCTGCCTTCACTTCCCCTCCTTCG<br>AGAGATCGCAAGCTGGCTCATCACACGCTCGGAAAAGAAC<br>CGGCACGCGCGAGCAATTGAATCGCAGTAGCTCCAGCGCT<br>CGCGCCCCGGCTGGTGCGGGCCCATTCTACAGCAAGGCGA<br>AGTATGCGGGCCTTCAGCGCGATGGCGCGCGTCGCGAACG<br>AGTCATAAGATGGGTTTTGCCAGCGCCAGCGTAGCACCAG<br>CCATTCATGCTCGGGCCCATTCCACAGTGTTTGCGAGGCCA<br>AAAATTTTGCAAGGCAAGCAAGCAAGTCGCGCCGTACGAT<br>GGCCCCATGCAGCAAATGGCGCATGGGGCCGGAGTCTGCA<br>GAGCGAGCGCACTTCTTTCTTCTCTCTCTCTTTAGGTGCC<br>CACACTTCGCTTCGCAAGATCAGCAACCTCGCAAGGTTGA<br>GCTTCGGGGAAGCTT | 62 |

In varying embodiments, the promoter is at least about 200 bp in length and up to about 500 bp, 600 bp, 700 bp, 750 bp, 800 bp, 900 bp or 1000 bp in length. In varying embodiments, the synthetic promoter promotes transcription levels that are at least about 2-fold greater, e.g., 3-fold, 4-fold, 5-fold, 6-fold, 7-fold, 8-fold, 9-fold, 10-fold, or more, greater than a control promoter (e.g., a random polynucleotide sequence or a native promoter). In varying embodiments, the control promoter is the arl promoter. In varying embodiments, the control promoter is selected from psbA, atpA, psbD, TufA and atpB.

The synthetic promoters find use, e.g., for the expression of a polynucleotide of interest in an algal cell, e.g., a green algal cell, including a *Chlamydomonas, Dunaliella, Haematococcus, Chlorella*, or *Scenedesmaceae* cell.

3. Expression Cassettes, Vectors, Algal Cells, Kits a. Expression Cassettes

Further provided are expression cassettes comprising the synthetic promoters as described above and herein, operably linked to a polynucleotide of interest to be transcribed. In some embodiments, the polynucleotide encodes a protein of interest, e.g., for expression in an algal cell. In varying embodiments, coding polynucleotide sequences can be improved for expression in photosynthetic organisms (e.g., algae) by changing codons that are not common in the algae host cell (e.g., used less than ~20% of the time). A codon usage database of use is found at kazusa.or.jp/codon/. For improved expression of coding polynucleotide sequences in *C. reinhardtii* host cells, codons rare or not common to the nucleus or chloroplast of *C. reinhardtii* in the native nucleic acid sequences are reduced or eliminated. A representative codon table summarizing codon usage in the *C. reinhardtii* chloroplast is found on the internet at kazusa.or.jp/codon/cgi-bin/showcodon.cgi?species=3055.chloroplast.

As appropriate, the expression cassettes can further comprise terminating sequences, enhancers and other regulatory and/or linking sequences. In varying embodiments, the expression cassette comprises a transcriptional and translational initiation region, which may be inducible or constitutive, where the coding region is operably linked under the transcriptional control of the transcriptional initiation region, and a transcriptional and translational termination region. Certain control regions (including subsequences within the synthetic promoter) may be native to the gene, or may be derived from an exogenous source.

b. Vectors

Further provided are vectors comprising the synthetic promoters and/or expression cassettes as described above and herein. The vector can be any appropriate form known in the art for introduction of a recombinant expression cassette comprising the synthetic promoters in an algal cell. In varying embodiments, the vectors can integrate into the genome of an algal cell (nuclear or plastid, e.g., chloroplast), or can support episomal expression (e.g., in either the algal cell nucleus or plastid, e.g., chloroplast). In varying embodiments, the vector is a DNA plasmid. In varying embodiments, the vector is a virus. In varying embodiments, the vector is a polynucleotide suitable for homologous recombination, e.g., into the genome of an algal cell.

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, pET21a-d(+) vectors (Novagen), and pSVLSV40 (Pharmacia). However, any other plasmid or other vector may be used so long as it is compatible with the host cell. For example, illustrative vectors including without limitation, psbA-kanamycin vector can be used for the expression of one or more proteins, e.g., in the plastids of a photosynthetic organism. The synthetic promotors described herein can replace the promoters in the commercially available plasmid.

Knowledge of the chloroplast genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, J. Mol. Biol. 312:425-438, 2001; Staub and Maliga, Plant Cell 4:39-45, 1992; and Kavanagh et al., Genetics 152:1111-1122, 1999, each of which is incorporated herein by reference). The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link; J. Maul, J. W. Lilly, and D. B. Stern, unpublished results; revised Jan. 28, 2002; to be published as GenBank Ace. No. AF396929; and Maul, J. E., et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast. In this respect, the website containing the *C. reinhardtii* chloroplast genome sequence also provides maps showing coding and non-coding regions of the chloroplast genome, thus facilitating selection of a sequence useful for constructing a vector (also described in Maul, I. E., et al. (2002) The Plant Cell, Vol. 14 (2659-2679)). For example, the chloroplast vector, p322, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chloro140.html").

Expression vectors generally have convenient restriction sites located near the promoter sequence to provide for the insertion of nucleic acid sequences encoding exogenous proteins. A selectable marker operative in the expression host may be present in the vector.

The expression cassettes comprising the synthetic promoters disclosed herein may be inserted into a vector by a variety of methods. In the most common method the sequences are inserted into an appropriate restriction endonuclease site(s) using procedures commonly known to those skilled in the art and detailed in, for example, Green and Sambrook, Molecular Cloning, A Laboratory Manual, 4th Ed., Cold Spring Harbor Press, (2012) and Ausubel et al., Current Protocols in Molecular Biology, John Wiley & Sons (through 2016). Polymerase and recombinase methods such as restriction free cloning (Bond, et al., Nucleic Acids Res. (2012) July; 40(Web Server issue):W209-13; PMID: 22570410) and Seamless Ligation Cloning Extract (SLiCE) (Zhang, et al, Nucleic Acids Res. (2012) April; 40(8):e55; PMID: 22241772) may also be employed.

c. Algal Cells

Further provided is a cell or population of cells comprising the synthetic promoters and/or expression cassettes and/or vectors as described above and herein. The algal cells may comprise the synthetic promoter integrated into their genome (plastid or nuclear), or within an episomal vector. In varying embodiments, the cell or population of cells are algal cells. In some embodiments, the cell or population of cells are green algal cells. In varying embodiments, the green algae is selected from the group consisting of *Chlamydomonas, Dunaliella, Haematococcus, Chlorella*, and *Scenedesmaceae*. In some embodiments, the *Chlamydomonas* is a *Chlamydomonas reinhardtii*. In varying embodiments, the green algae can be a *Chlorophycean*, a *Chlamydomonas, C. reinhardtii, C. reinhardtii* 137c, or a psbA deficient *C. reinhardtii* strain.

Transformation of host cells to contain the synthetic promoters and/or expression cassettes and/or vectors as described above and herein includes transformation with circular vectors, linearized vectors, linearized portions of a vector, or any combination of the above. Thus, a host cell comprising a vector may contain the entire vector in the cell (in either circular or linear form), or may contain a linearized portion of a vector of the present disclosure.

d. Kits

Further provided is a kit comprising the synthetic promoters and/or expression cassettes and/or vectors and/or cells or population of cells and/or synthetic nuclear transcription systems as described above and herein. In varying embodiments, the expression cassettes and/or vectors can comprise multiple cloning sites to allow for the convenient insertion of a coding polynucleotide that is operably linked to the synthetic promoter. In varying embodiments, the kits comprising a synthetic nuclear transcription system additionally comprise one or more transcription factors, or cell comprising one or more transcription factors, e.g., as encoded by one or more of SEQ ID NOs:87-178, e.g., SEQ ID NO:150 (TF64). In varying embodiments, the kits can comprise an algal cell or population of algal cells as described herein. As appropriate, the algal cells can be fresh or frozen. The algal cells may comprise the synthetic promoter integrated into their genome (nuclear or plastid, e.g., chloroplast), or within an episomal vector.

4. Methods of Designing Synthetic Promoters

Further provided is a method of designing, constructing and/or assembling a synthetic promoter, e.g., as described herein. In varying embodiments, the methods comprise assembling or arranging at least about 3 (cis)-elements, e.g., from 3 to 30, e.g., from 3 to 27, e.g., from 3 to 25, e.g., from 3 to 20, e.g., from 3 to 15, e.g., from 3 to 10, e.g., from 3 to 5, promoter (cis)-elements selected from the group consisting of the sequences in Tables 1 and 2 within a promoter scaffold or backbone. As appropriate, the placement of the (cis)-elements or the constructing of the promoter scaffold or backbone can be designed, constructed or assembled first. In varying embodiments, the promoter (cis)-elements are positioned or located within the promoter relative to the transcriptional start site (TSS) as indicated in Table 1. In varying embodiments, the promoter is at least about 200 bp in length and up to about 500 bp, 600 bp, 700 bp, 750 bp, 800 bp, 900 bp or 1000 bp in length. In varying embodiments, the synthetic promoter promotes transcription levels that are at least 2-fold greater, e.g., 3-fold, 4-fold, 5 fold, 6-fold, 7-fold, 8-fold, 9-fold, 10 fold, or more, greater than a control promoter (e.g., a random polynucleotide sequence or a native promoter). In varying embodiments, the nucleic acid base of highest probability or second highest probability at a particular position of the promoter scaffold or backbone relative to the transcriptional start site (TSS) is assigned to that position, e.g., as indicated in Table 3. In varying embodiments, the method is computer implemented.

5. Methods of Making Synthetic Promoters

The synthetic promoters can be made using any method known in the art, including recombinant and chemically synthesized techniques. Chemically synthesized promoters can by comprised entirely of native or naturally occurring DNA bases, or can contain one or more modified bases or derivatives. Modified bases are well known in the art, and include, e.g., 2-Aminopurine, 2,6-Diaminopurine (2-Amino-dA), 5-Bromo-deoxyuridine, deoxyUridine, inverted dT, Inverted Dideoxy-T, Dideoxycytidine (ddC), 5-Methyl deoxycytidine, 2'-deoxyInosine (dI), DeoxyInosine, 5-hydroxybutynl-2'-deoxyuridine, 8-aza-7-deazaguanosine, locked nucleic acids (LNAs), 5-Nitroindole, 2'-O-Methyl RNA, Hydroxmethyl dC, Unlocked Nucleic Acids (UNAs) (UNA-A, UNA-U, UNA-C, UNA-G), Iso-dG, Iso-dC, and 2' Fluoro bases (Fluro A, Fluro C, Fluoro G, Fluoro U).

6. Methods of Promoting Transcription

Further provided is a method of transcribing or expressing a polynucleotide, e.g., in vitro or in an algal cell. In varying embodiments, the methods comprise contacting a polymerase to a polynucleotide comprising the synthetic promoter operably linked to a coding polynucleotide under conditions that allow the polymerase to transcribe the coding polynucleotide under the control of the synthetic promoter. In varying embodiments, the methods comprise introducing into the algal cell the polynucleotide operably linked to, e.g., and under the promoter control of, a synthetic promoter as described and herein. In a further aspect, provided is a method of increasing the transcription of a polynucleotide in an algal cell. In varying embodiments, the methods comprise introducing into the algal cell the polynucleotide operably linked to, e.g., and under the promoter control of, a synthetic promoter as described and herein. In some embodiments, the transcription levels of the polynucleotide are increased at least about 2-fold greater, e.g., 3-fold, 4-fold, 5 fold, 6-fold, 7-fold, 8-fold, 9-fold, 10-fold, or more, greater than a control promoter (e.g., a random polynucleotide sequence or a native promoter). In varying embodiments, the (coding) polynucleotide operably linked to the synthetic promoter is codon-biased or codon-optimized for expression in an algal cell. A representative codon table summarizing codon usage in the *C. reinhardtii* chloroplast is found on the internet at "kazusa.or.jp/codon/cgi-bin/showcodon.cgi?species=3055.chloroplast." In various embodiments, preferred or more common codons for amino acid residues in *C. reinhardtii* are shown in Table 5.

TABLE 5

Codons for amino acid residues in *C. reinhardtii*.

| Amino Acid Residue | Preferred codons for improved expression in algae |
|---|---|
| Ala | GCT, GCA |
| Arg | CGT |
| Asn | AAT |
| Asp | GAT |
| Cys | TGT |
| Gln | CAA |
| Glu | GAA |
| Gly | GGT |
| Ile | ATT |
| His | CAT |
| Leu | TTA |
| Lys | AAA |
| Met | ATG |
| Phe | TTT |
| Pro | CCA |
| Ser | TCA |
| Thr | ACA, ACT |
| Trp | TGG |
| Tyr | TAT |
| Val | GTT, GTA |
| STOP | TAA |

In varying embodiments, the algal cell is a green algal cell, as described herein. In varying embodiments, the algal cell is a *Chlamydomonas* cell. In varying embodiments, the algal cell is a *Chlamydomonas reinhardtii* cell.

To generate a genetically modified host cell, a polynucleotide, or a polynucleotide cloned into a vector, is introduced stably or transiently into a host cell, using established techniques, including, but not limited to, electroporation, biolistic, calcium phosphate precipitation, DEAE-dextran mediated transfection, and liposome-mediated transfection. For transformation, a polynucleotide of the present disclosure will generally further include a selectable marker, e.g., any of several well-known selectable markers such as restoration of photosynthesis, or kanamycin resistance or spectinomycin resistance.

A polynucleotide or recombinant nucleic acid molecule described herein, can be introduced into a cell (e.g., alga cell) using any method known in the art. A polynucleotide can be introduced into a cell by a variety of methods, which are well known in the art and selected, in part, based on the particular host cell. For example, the polynucleotide can be introduced into a cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus, Ann. Rev. Plant. Physiol. Plant Mol. Biol. 42:205-225, 1991).

As discussed above, microprojectile mediated transformation can be used to introduce a polynucleotide into a cell (for example, as described in Klein et al., Nature 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed, into a cell using a device such as the BIOLISTIC PD-1000 particle gun (BioRad; Hercules Calif). Methods for the transformation using biolistic methods are well known in the art (for example, as described in Christou, Trends in Plant Science 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (for example, as described in Duan et al., Nature Biotech. 14:494-498, 1996; and Shimamoto, Curr. Opin. Biotech. 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

The basic techniques used for transformation and expression in photosynthetic microorganisms are similar to those commonly used for *E. coli, Saccharomyces cerevisiae* and other species. Transformation methods customized for photosynthetic microorganisms, e.g., the chloroplast of a strain of algae, are known in the art. These methods have been described in a number of texts for standard molecular biological manipulation (see Packer & Glaser, 1988, "Cyanobacteria", Meth. Enzymol., Vol. 167; Weissbach & Weissbach, 1988, "Methods for plant molecular biology," Academic Press, New York, Green and Sambrook, Molecular Cloning, A Laboratory Manual, 4th Ed., Cold Spring Harbor Press, (2012); and Clark M S, 1997, Plant Molecular Biology, Springer, N.Y.). These methods include, for example, biolistic devices (See, for example, Sanford, Trends In Biotech. (1988).delta.: 299-302, U.S. Pat. No. 4,945,050; electroporation (Fromm et al., Proc. Nat'l. Acad. Sci. (USA) (1985) 82: 5824-5828); use of a laser beam, electroporation, microinjection or any other method capable of introducing DNA into a host cell.

Plastid transformation is a routine and well known method for introducing a polynucleotide into a plant cell chloroplast (see U.S. Pat. Nos. 5,451,513, 5,545,817, and 5,545,818; WO 95/16783; McBride et al., Proc. Natl. Acad. Sci., USA 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation (Svab et al., *Proc. Natl. Acad. Sci. USA,* 87:8526-8530, 1990), and can result in stable homoplasmic transformants, at a frequency of approximately one per 100 bombardments of target leaves.

In some embodiments, an alga is transformed with one or more polynucleotides which encode one or more polypeptides, as described herein. In one embodiment, a transformation may introduce a nucleic acid into a plastid of the host alga (e.g., chloroplast). In another embodiment, a transformation may introduce a second nucleic acid into the chloroplast genome of the host alga. In still another embodiment, a transformation may introduce two protein coding regions into the plastid genome on a single gene, or may introduced two genes on a single transformation vector.

Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Product screening may be performed by any method known in the art, for example mass spectrometry, SDS PAGE protein gels, or HPLC or FPLC chromatography.

The expression of the protein can be accomplished by inserting a polynucleotide sequence (gene) encoding the protein or enzyme into the chloroplast genome of a microalgae. The modified strain of microalgae can be made homoplasmic to ensure that the polynucleotide will be stably maintained in the chloroplast genome of all descendants. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given locus of interest.

EXAMPLES

The following examples are offered to illustrate, but not to limit the claimed invention.

Example 1

Synthetic Promoters Capable of Driving Robust Nuclear Gene Expression in the Green Alga *Chlamydomonas reinhardtii*

Materials and Methods.

POWRS Motif Identification. The top 50 highest-expressed endogenous genes were identified based on their RNA accumulation under ambient conditions according to previously published RNA-seq data (Fang et al., 2012). Since promoter structure is not strictly defined in *Chlamydomonas reinhardtii* the sequence between −1000 and +50 for the top 50 genes were analyzed using the POWRS motif identification program (Davis et al., 2012) (Phytozome 10.2, *Chlamydomonas reinhardtii* v4.3 and/or v5.5). All default settings on POWRS were used, except that the minimum number of sequences that a valid motif must match was lowered to ten.

Figure 2:
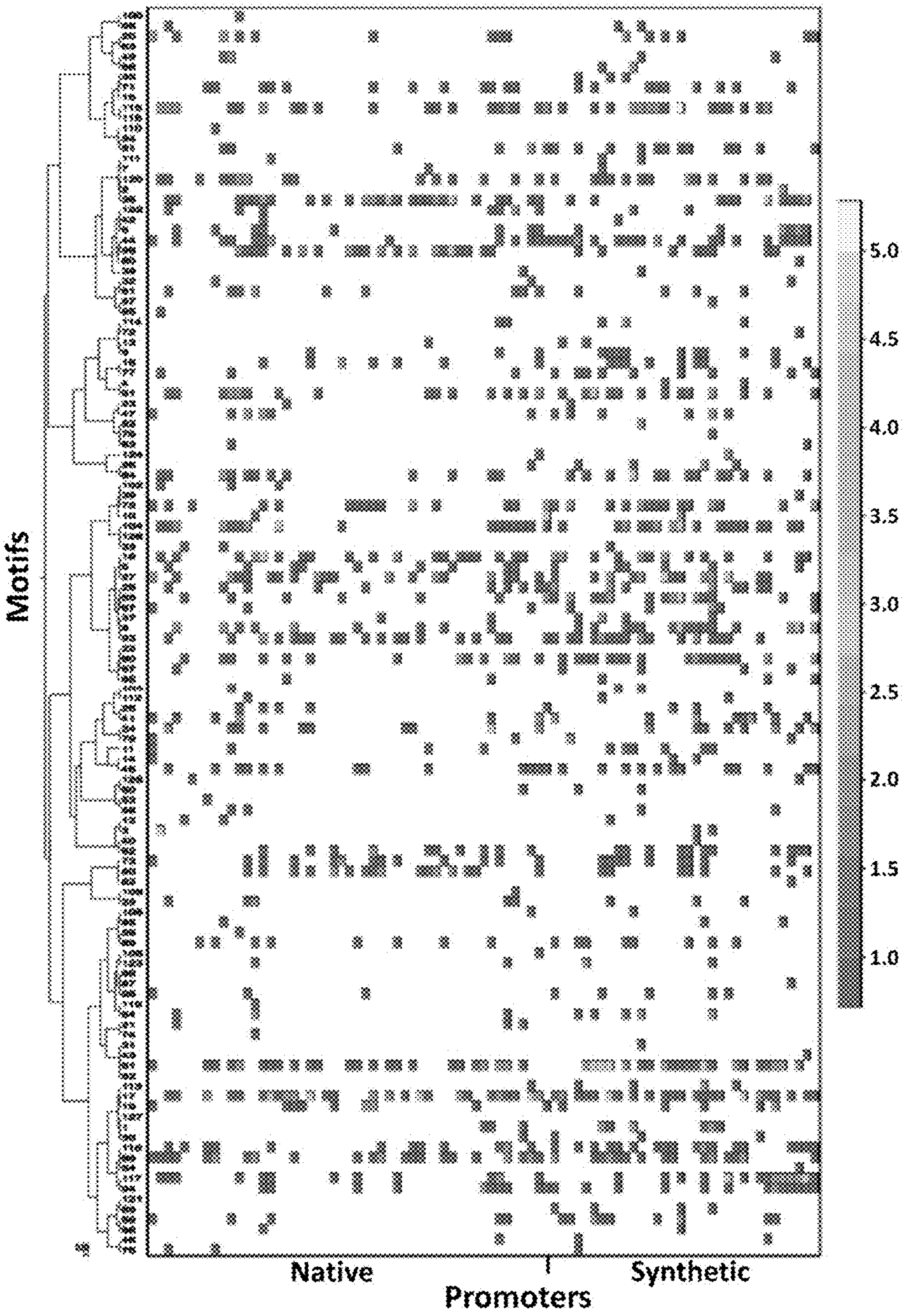
FIG. 2 illustrates frequency of POWRs motifs in the top 50 native promoters and the 25 sap promoters.

Generation of synthetic promoters. Promoters were generated using random insertion of POWRs motifs, constraining positions relative to the positions of the motif clusters in the native sequences. Promoter backbones were generated to ensure similar GC content as the native promoters, including a periodic AT-rich regions (FIG. 1, panel A). Finally, all promoters contained at least one copy of a TC rich motif around the TSS (FIG. 2). Random promoters were generated by choosing 500 random nucleotides based on the Markov model that described the native promoter GC content without periodic AT-rich regions (Table 6).

TABLE 6

Markov model for random promoter generation.

| | −500 to −200 | −199 to −100 | −99 to 0 |
|---|---|---|---|
| A | 0.2 | 0.2 | 0.28 |
| C | 0.3 | 0.25 | 0.24 |
| G | 0.3 | 0.35 | 0.2 |
| T | 0.2 | 0.2 | 0.28 |

Plasmid construction. The synthetic algal promoters were synthesized as gBlocks (IDT, Coralville, Iowa) integrating in DNA ends that allowed cloning via SLiCE technology (Zhang et al., 2012) (Table 7). All restriction enzymes were purchased from New England Biolabs (Ipswich, Mass.). The pBR4 expression vector with the hygromycin B resistance gene under the control of the B-tubulin promoter and a separate cassette with the mCherry gene driven by the arl promoter was used as the backbone (Berthold et al., 2002; Rasala et al., 2012). pBR4 was digested with NdeI and XbaI to remove the arl promoter up to end of the RBCS2 5'UTR and generate ends for SLiCE cloning. Synthetic promoters were cloned with the RBCS2 5'UTR, which was amplified with appropriate primers to allow 15 bp overhangs with the synthetic promoters as well the digested backbone (Table 7), resulting in the constructs in FIG. 1, panel B. To rearrange sap11 with the hygromycin cassette downstream of the mCherry cassette, each half of pBR4 was amplified with appropriate primers for USER cloning into the HCR1, a modified pBlueScript II (Agilent, Santa Clara, Calif.), as previously described (Specht et al., 2015) (Table 7). The rearranged construct was then digested with NdeI and XbaI to remove arl and replace it with sap11 which was PCR amplified and SliCE cloned into the rearranged pBR4. Promoter and motif deletions were performed by SLiCE cloning. polyA and polyT mutations were introduced using overlapping primers and PCR pieces generated were cloned into a pBR4-rearranged backbone which had been digested with EcoRI and NdeI (Table 7). All constructs were confirmed by restriction digest and sequencing.

TABLE 7

Primers used for expression vector constructions.

| Primer Use | Primer Name | Sequence | SEQ ID NO |
|---|---|---|---|
| 5'UTR amplification | 5'UTR_F | GTTGAGTGACTTCTCTTGTAAAAAAGT | 63 |
| | 5'UTR_R | CCCTTGGACACCATATGCATGGCCATCCTG | 64 |
| Expression Vector Rearrange | mCherry_F | GGGTTTAAUTCTAGACGGCGGGGAGCTCG | 65 |
| | mCherry_R | ATCGCGCTUCAAATACGCCC | 66 |
| | hyg_F | AAGCGCGAUATCAAGCTTCTT | 67 |
| | hyg_R | GGTCTTAAUGGTACCCGCTTCAAATACGCCC | 68 |
| sap11 introduction into rearranged vector | sap11_F | GCTGAGGGTTTAATTCTAGAACATGCT | 69 |
| | sap11_R | CCCTTGGACACCATATGC | 70 |
| Promoter deletion sap11 | sap11Δ-230_F | GCTGAGGGTTTAATTCTAGAAAGCAAGTATGCAGC | 71 |
| | sap11Δ-130_F | GCTGAGGGTTTAATTCTAGAGCATGTTTGCTTGGC | 72 |
| | sap11Δ-30_F | GCTGAGGGTTTAATTCTAGAAAGCCGAGCGAGCCC | 73 |
| | sap11_R | CCCTTGGACACCATATGC | 74 |

TABLE 7-continued

| Primers used for expression vector constructions. | | | |
|---|---|---|---|
| Primer Use | Primer Name | Sequence | SEQ ID NO |
| Motif Deletion | sap11_F | GCTGAGGGTTTAATTCTAGAACATGCTGACTACGA | 75 |
| | sap11_R | CCCTTGGACACCATATGC | 76 |
| | m1_F | GGGGTTTTTTTTACATGCATGATGGGC | 77 |
| | m1_R | TGTAAAAAAAACCCCGATAAAGCCCG | 78 |
| | m2_F | CGCAAAAAAAAATTTCCCAAAATTGCG | 79 |
| | m2_R | GGGAAATTTTTTTTGCGCGCGCCCCATGC | 80 |
| | m3_F | ACATTTTTTTTGGGGCGCGCGCCG | 81 |
| | m3_R | CCCCAAAAAAAAATGTACGCCCATTGC | 82 |
| | m4_F | TGCTTTTTTTTATGGGCGTACATCTC | 83 |
| | m4_R | CCATAAAAAAAAGCAACTTGCTCAAAG | 84 |
| | m5_F | CTATTTTTTTTACTAACCTGCAGCGG | 85 |
| | m5_R | TAGTAAAAAAAATAGCGTGTGCCCACA | 86 |

*C. reinhardtii* growth and transformation. Wild-type (cc1690) *C. reinhardtii* were grown and transformed using the methods described previously using 1 μg of plasmid DNA (Rasala et al., 2012). Plasmid constructs were digested with KpnI to linearize them prior to electroporation. Transformants were first screened on TAP (Tris-acetate-phosphate)/agar plates containing 15 μg/ml hygromycin, resulting in approximately 5,000 to 12,000 transformants per selection. The entire transformant pool was then collected and transferred to liquid TAP medium for two days, followed by screening on the flow cytometer.

Flow cytometry measurement of mCherry fluorescence. mCherry fluorescence was visualized by a BD LSRII flow cytometer and analyzed using FlowJo v10.0.8. The population was gated using the following strategy: the FSC and SSC parameters were obtained using a 488 nm blue laser and were used to eliminate smaller non-algal samples and clumps of algae that can be misread as a single cell. Next, the 488 nm laser using a 685LP and a 710/50 filter set was used in combination with a 405 nm violet laser and 450/50 filter to remove dead cells and remaining debris from the population. The mCherry fluorescence was then measured with a 561 nm yellow/green laser with a 600LP and 610/20 filter set. To better visualize the population, the mCherry fluorescence channel was plotted against the window created by the 405 nm laser with a 505LP and 535/30 filter set. Using the untransformed parent strain as a reference, the events containing only background fluorescence were removed from the analysis. What remained was considered single-cell, living, *C. reinhardii* that is expressing mCherry. A representative window was selected from the remaining population and the mCherry fluorescence channel was broken down into individual events, resulting in 80 to 10,000 data points.

Genomic promoter motif analysis. For whole genome promoter analysis, genome sequence and annotation for Creinhardtii_281_v5.5 was obtained from phytozome.jgi-.doe.gov (Merchant et al., 2007). Annotated 5' UTR start sites were compared to PASA assembled EST start sites. Only 4,412 of the 22,892 total annotated 5' UTR start sites were within 10 bp of a PASA EST start site and considered EST validated sites. Sequence from −1000 bp upstream to +500 bp downstream of the validated 5' UTR start sites were analyzed for new motifs using DREME (Bailey, 2011). Then the promoter sequences were analyzed by CentriMo to identify POWRS or DREME motifs that are enriched in specific regions relative to the TSS (Bailey and Machanick, 2012).

96-well vs flow cytometry mCherry fluorescence measurement. Two independent pools of *C. reinhardtii* were grown and transformed as described in experimental procedures. Differences in transformation efficiencies resulted in twice as many transformants in pool 2 as in pool 1. Each pool was transformed twice each with arl or sap11 resulting in four independent pools of transformants. After selection on solid media, 24 transformants were picked from each plate and transferred to a 96-well plate with 200 μl TAP, grown to saturation, then diluted 1:20 in TAP. Transformed cells were grown until late log phase in TAP media without antibiotics. Cells (100 μl) were transferred to a black 96-well plate (Corning Costar, Tewksbury, Mass.). mCherry fluorescence (575 nm/608 nm) was read using a Tecan plate reader (Tecan Infinite M200 PRO, Männedorf, Switzerland). Fluorescence signals were normalized to chlorophyll fluorescence (440 nm/680 nm). After first 24 transformants were selected, the remaining transformants were collected from each plate and transferred to 50 ml TAP. mCherry fluorescence was measured as in experimental procedures. While, measurement of 24 transformants per construct resulted in variable results between experiments, measurement of 6000+ transformants resulted in consistent, reproducible results. This result was also independent of transformation efficiency.

Results

Native motif identification and saps generation. In order to generate saps capable of driving high heterologous gene expression, native *C. reinhardtii* genes were analyzed that showed the highest RNA accumulation in wild type (wt) cells grown under ambient conditions. The top 50 genes were identified based on previously published RNA-seq data (Fang et al., 2012). This data set was chosen because the growth conditions best match typical ambient small scale laboratory growth conditions for green algae. Promoter regions (−1000 to +50 nt from the transcription start site) from these genes were analyzed using the POWRs software (Davis et al., 2012). POWRs identifies motifs based not only on enriched sequences but also on the position of these elements within the promoter region. POWRs clusters sequences together based on similarity to create motif clusters that can be characterized by position weight matrixes.

POWRs identified 127 motif clusters containing 979 unique motifs within the top 50 native gene promoters (FIG. 2). Upon inspection of the motifs, nine TC rich motifs were identified, some of which were localized around the transcription start site (TSS; FIG. 3). In *Arabidopsis thaliana*, a TC-like motif near the TSS may function similarly to the TATA box (Bernard et al., 2010). Therefore, these TC rich motifs were added to every synthetic promoter and enriched around the TSS.

Analysis of the top 50 native promoters also revealed that there is a decrease in the GC content within 500 bp around the transcription start site (FIG. 1, panel A). This trend is in direct contrast with the promoters of higher plant species, which skew towards higher GC content near the TSS (Calistri et al., 2011; Fujimori et al., 2005). *C. reinhardtii* promoter GC content structure most resembles *Saccharomyces cerevisiae* and some prokaryotic species that increase AT-content towards the TSS. This trend in *C. reinhardtii* does not appear to be due simply to the higher overall GC content of its nuclear genome, since species like the red alga *Cyanidioschyzon merolae* also have high GC content but have an increase in GC towards the TSS (Calistri et al., 2011). In addition to a general AT-increase at the TSS, there also appeared to be smaller dips in GC content at approximately −280 and −140 bp upstream of the TSS. These AT-rich regions have a similar periodicity as that of nucleosome wrapped DNA, which is around 147 bp (Lodha and Schroda, 2005). These AT-rich regions were incorporated in the synthetic promoters.

Synthetic promoters were generated to include nucleotide backbones that had a similar GC profile as the native promoters, including the aforementioned AT-bias towards the TSS and AT rich regions at −280 and −140 bp (FIG. 1, panel A). Promoters were designed to be 500 bp in length for ease of synthesis and analysis. Since many motifs are localized across and downstream of the TSS, promoters were designed to mimic −450 bp upstream and 50 bp downstream of the TSS in order to not cutoff important motifs. This is a similar strategy to previous native hybrid promoter designs (Schroda et al., 2000). Motifs were overlaid onto nucleotide backbones constrained to a similar region to where they were found in the native sequences (Davis et al., 2012; FIG. 2, FIG. 1, panel B).

Synthetic promoters drive transcription in vivo. Twenty five saps were studied for their ability to drive the expression of the mCherry fluorescent reporter protein. The saps were synthesized and cloned in front of an mCherry reporter gene, which also contained the 5' and 3' RBCS2 UTRs as well as the first RBCS2 intron (FIG. 1, panel C). These elements have all been previously shown to improve mRNA accumulation and protein synthesis of heterologous genes in *C. reinhardtii* (Rasala et al., 2013; Lumbrears et al., 1998). The vector construct also included a hygromycin resistance cassette, which was driven by the beta tubulin (TUBB2) promoter to select for transformed algae independent of synthetic promoter function (Berthold et al., 2002). This allowed large scale mCherry analysis of all promoters including weak or non-functioning promoters.

Transformation of the *C. reinhardtii* nucleus occurs almost exclusively through non-homologous end-joining (Gumpel et al., 1994; Sodeinde and Kindle, 1993). This results in random insertion, multiple insertions, and highly variable exogenous gene expression. Typical promoter analysis involves measuring the expression of 10-50 individual transformants. However, measuring individual transformants is time and resource consuming, and the variability in expression is still high unless many individual are measured. Alternatively, if many transformants are pooled and protein or RNA levels are measured of the total population, noise from positional insertion effects can be reduced, but this does not allow measurement of the range of expression over the population pool. Therefore, for this study flow cytometry was used to measure promoter strength. Flow cytometry allows measurement of both a large number of transformants while also recording the data for individual transgenic cells. This provides a highly confident average as well as the range of expression for our reporter gene for each promoter tested.

To determine if our synthetic promoters were functional based on our design principles, and not just coincidental, random promoters were also generated whose sequence had a similar GC content to both native and our synthetic promoters, but with no periodical AT rich regions upstream or placement of motifs (FIG. 1, panel A, Table 1). These promoters would also serve as a negative control for random positional effects since exogenous gene expression can occur simply due to insertion next to a native promoter (Haring and Beck, 1997).

Figure 4:
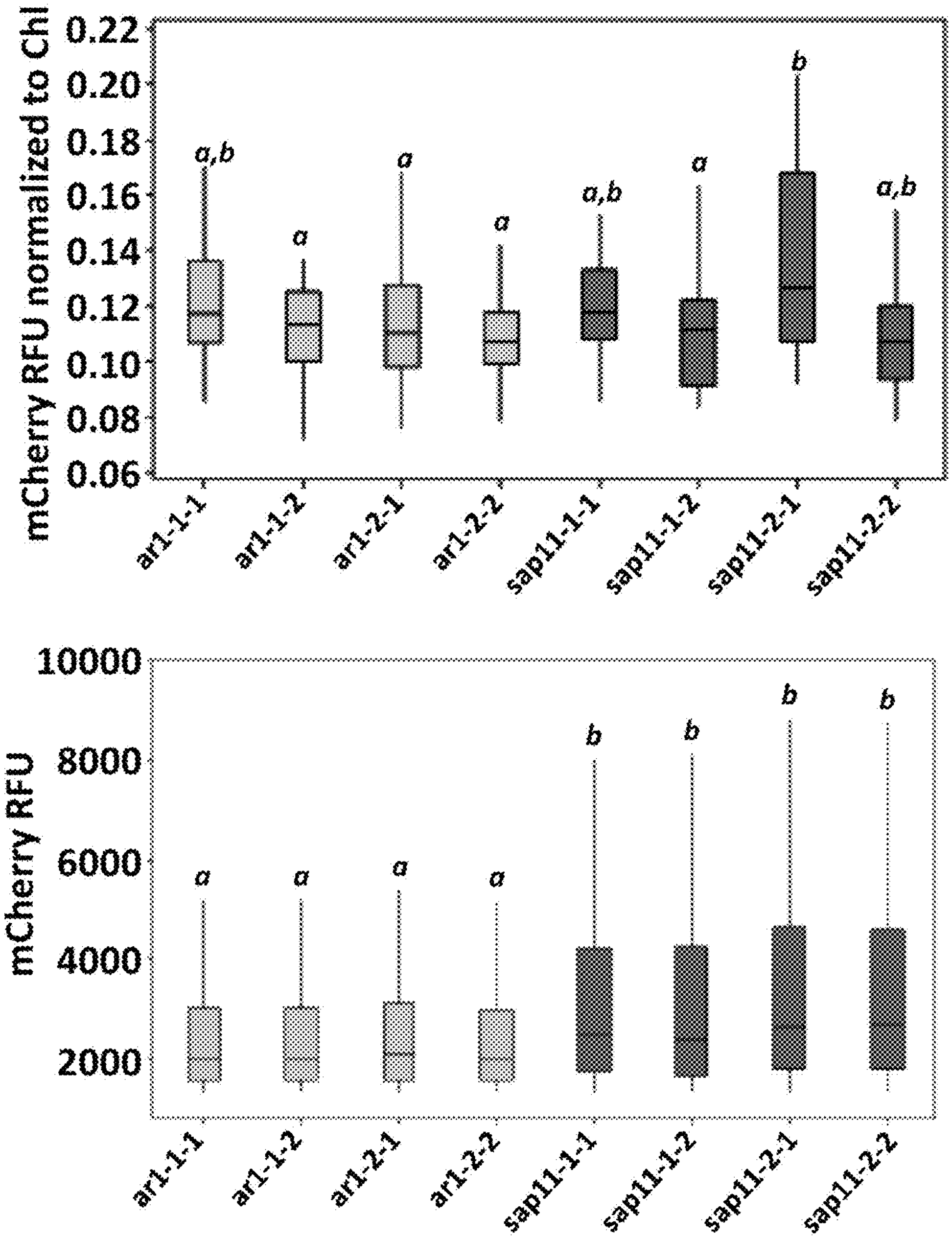
FIG. 4, panels A and B, illustrates a comparison of robustness of plate vs flow cytometry data for *C. reinhardtii* promoter strength analysis. Panel A) Constructs were transformed into two independent *C. reinhardtii* cultures (Replicate 1 and 2) and plated on two separate plates (ex: 1-1, 1-2). Twenty-four individuals were picked from each plate and screened using a Tecan plate reader. The remainder of the transformants from each plate were pooled and screened by flow cytometry. Populations that are statistically different are indicated (a-b, Tukey's test, $p<0.05$). Panel B) *C. reinhardtii* was transformed with arl and sap11 rearranged so that the hyg construct was downstream of mCherry in two independent transformation events. mCherry expression was measured for the pooled transformants. Rearrangement did not alter promoter function for either promoter.

Analysis of mCherry expression driven by the 25 saps revealed a wide range of functionality compared to arl. As expected, there was low level of mCherry fluorescence above the WT background in our random promoter transformants (FIG. 1*d*). It is important to note that while five random promoters were generated, only two provided had enough mCherry positive transformants to perform proper statistical analysis and are shown in FIG. 1, panel D. Multiple transformations and screenings were performed to increase the number of positive events for statistical analysis, but none could be successfully reproduced. Eight saps were found to be no better than these randomly generated promoters (FIG. 1, panel E). However, 10 saps were not only better than our random controls, but were as good as arl. Encouragingly, seven saps were actually better than arl (Tukey HSD, $p<0.05$) with both average and max mCherry fluorescent levels almost twice as high as arl. These results were consistent over multiple transformations and screenings (FIG. 4, panel A).

sap11 contains a positive cis-effector motif. In order to determine which motifs contribute to the promoter strength of the high-expressing saps, we chose sap11 for further analysis, as it consistently produced the greatest amount of mCherry. First, a deletion series was performed in which nucleotides were deleted from the 5' end so that −250, −150, or −50 bp upstream of the TSS remained (FIG. 5, panel A). For this study, the expression vector was rearranged so that the hygromycin resistance cassette was downstream of the mCherry cassette. This rearrangement avoided any confounding data due to the relative shift of the position of the 3'UTR from the hygromycin cassette after promoter deletion. Rearrangement did not affect the promoter function of either arl or sap11 (FIG. 4, panel B). The relative mCherry fluorescence from sap11 in this rearranged vector was unchanged from the original design (FIG. 1, panel E, and FIG. 5, panel B). Analysis of mCherry fluorescence in sap11Δ mutants revealed only a slight reduction in expression in sap11Δ-250 and sap11Δ-150 mutants (FIG. 5, panel B). However, a significant drop in expression was observed in sap11Δ-50 where there was no expression above those found for the random promoters. These results are consistent with the fact that core motifs are often found within 200 bp upstream of the TSS (Berendzen et al., 2006; Maston et al., 2006; Yamamoto et al., 2007).

To further narrow down specific motifs essential for sap11 function, motif deletion analysis was performed. Four regions contained POWRs identified motifs between −150 and −50 bp from the TSS (FIG. 5, panel C). Eight A residues were used to replace the entire motif or the majority of the bases of the motif for those longer than 8 nucleotides. For motif 2, polyT residues were used to replace the motif since the region was highly A rich. Motif 5 comprised of a TC-rich motif that resided around the TSS. This motif was also deleted since it is homologous to the TC motifs found in *Arabidopsis*, and was therefore thought to be a functional element (Bernard et al., 2010). However, deletion of motif 5 (sap11Δm5) did not result in significant reduction in mCherry production (FIG. 5, panel D). Therefore, either this particular iteration of the motif was not utilized in sap11 or the TC motifs are not essential in *C. reinhardtii*. The deletion of both motif 3 and 4 (sap11Δm3 and sap11Δm4) resulted in significant decreases in promoter function, while deletion of motif 1 and 2 (sap11Δm1 and sap11Δm2) had little effect. Interestingly, regions 3 and 4 have nearly identical reverse complement motifs (CCCATGCGA and TGCATGGG, respectively), suggesting they could be targeted by the same transcription factor. In order to determine if regions 3 and 4 were redundant, a double mutant was generated in which both regions were replaced with polyA nucleotides (sap11Δm3-4). This promoter functioned similarly to the individual motif 3 and 4 KOs, suggesting that motif 4 may be redundant with motif 3 or that KO of motifs 3 and 4 already eliminate any expression above background (FIG. 5, panel D). It is important to note while this motif was essential for promoter function in sap11, this motif alone is not sufficient for expression as several of the non-functioning saps also contained this motif in a similar location (see, e.g., FIG. 2).

Figure 6:
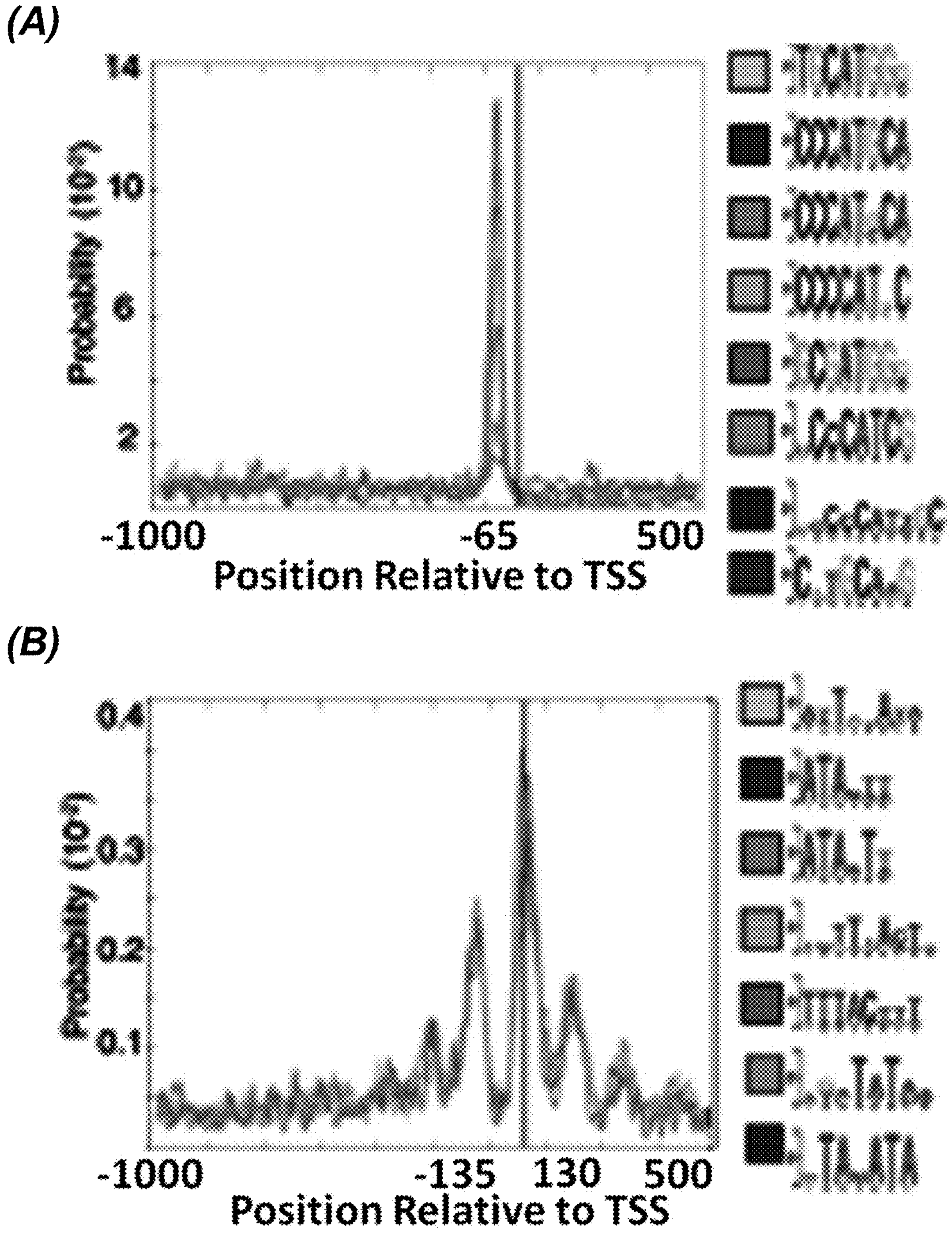
FIG. 6, panels A-C, illustrates locally enriched POWRs and DREME motifs in top 4,412 promoters from *C. reinhardtii* nuclear genome. EST validated promoters were analyzed with CentriMo for locally enriched motifs. Relative enrichment of motifs relative to the TSS for the top three categories of motifs is shown (panels A-C).
Figure 7:
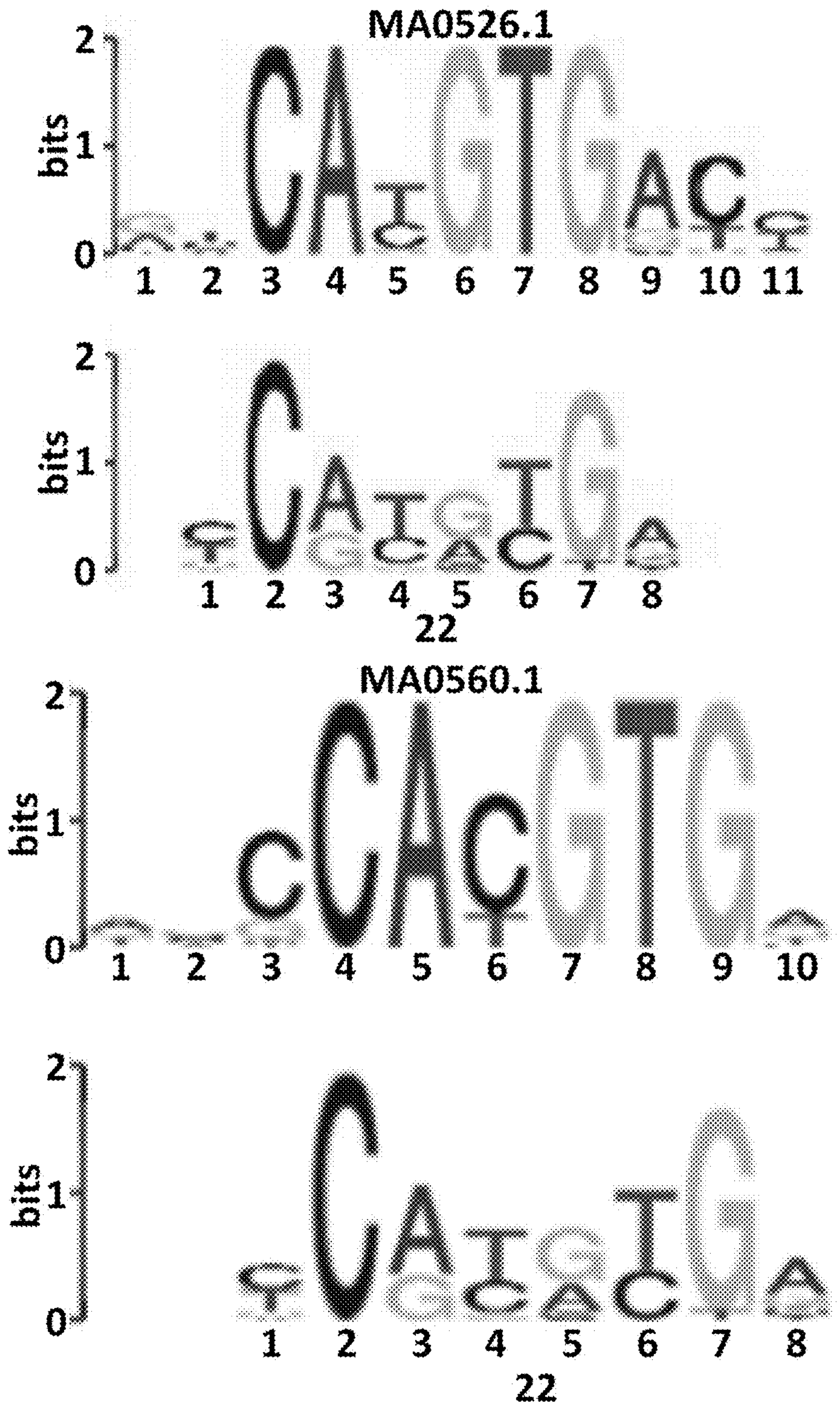
FIG. 7 illustrates alignment of CCCAT motif with homologous motifs in *H. sapiens* and *Arabidopsis thaliana.*

Because the CCCAT motifs had such a significant impact on sap11 function, we set out to determine if it may be a core motif within *C. reinhardtii*. One method to identify core motifs is to identify motifs that are relatively enriched at specific locations relative to the TSS in a large number of promoters. Therefore, we analyzed the promoter regions of 4,412 genes in *C. reinhardtii*. Promoters were chosen if their 5' UTR start sites (*Chlamydomonas reinhardtii* v5.5) were within 10 bp of the start site of PASA(Program to Assemble Spliced Alignments; Phytozome 10.2) assembled EST. Promoter sequences from −1000 to +500 of the 5' UTR site were analyzed to identify motifs that are enriched in similar regions (Bailey and Machanick, 2012). Surprisingly, the top eight motifs identified were all CCCAT-like motifs that were highly enriched only at −100 to −40 bp upstream of the TSS with a peak at −65 bp (FIG. 6, panel A). Moreover, 10.6% (467 promoters) of all the promoters analyzed had exactly CCCATGCA sequence at this location, while 35.4% (1564 promoters) had some variation of this motif at this location. This suggests that the CCCAT motif is a core motif within the *C. reinhardtii* promoter.

Motif sequence similarity search using TOMTOM analysis of this motif sequence revealed some homology to the cis-motif recognized by the *Arabidopsis* phytochrome interacting factor (PIFs; FIG. 4; Gupta et al., 2007). PIFs are involved in light-regulated gene expression (Castillon et al., 2007). Similarly, functional analysis of CCCAT motif-containing genes revealed enrichment in pathways that are diurnally regulated (e.g., Ribosomes, antenna proteins). However, the CCCAT motif was found in over 1,500 genes, the vast majority of which were not diurnally regulated (<5% overlap with differentially regulated genes identified in Zones et al., 2015). The role the CCCAT motif within the context of these native promoters remains to be determined. Interestingly, only one helix-loop-helix transcription factor (Cre14.g620850) could be identified in *C. reinhardtii* with homology to the PIF proteins in *Arabidopsis*, based on amino acid similarity. It will be interesting to determine if this putative transcription factor can bind to the CCCAT motif in *C. reinhardtii*. If it does, it most likely has a unique function compared to *Arabidopsis* based on its target genes in *C. reinhardtii*.

Figure 8:
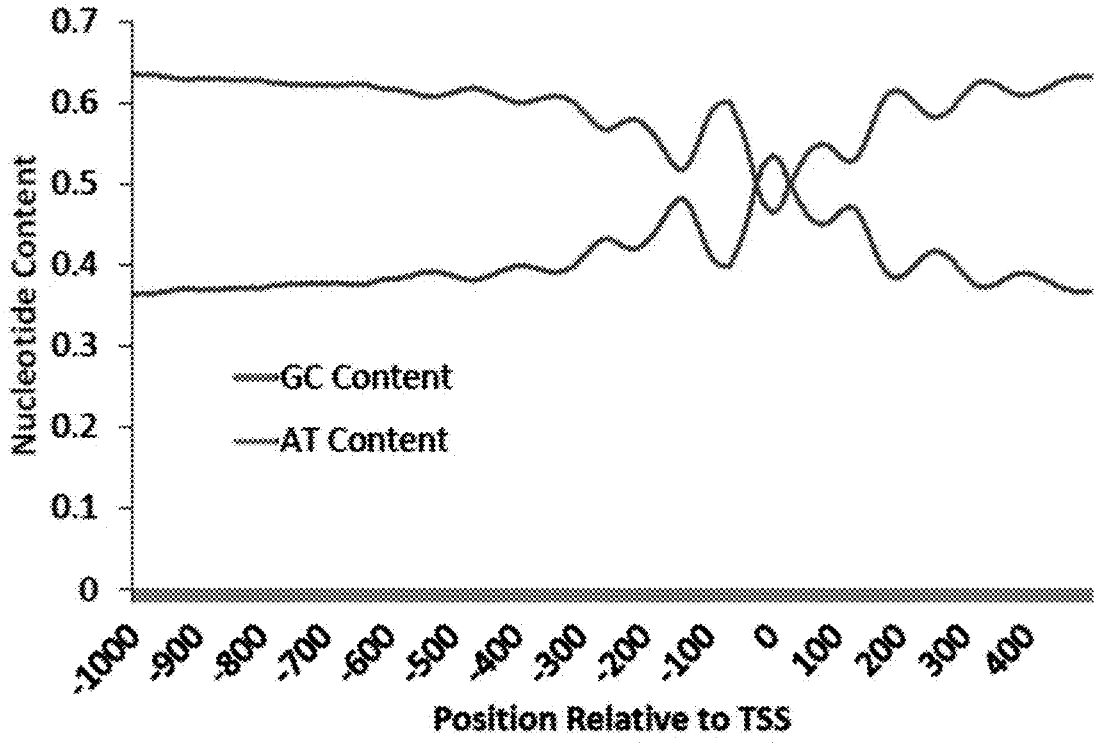
FIG. 8 illustrates GC and AT content of top 4,412 EST validated *C. reinhardtii* promoters.

*C. reinhardtii* promoters contain AT and TC rich motifs near TSS. CentriMo analysis of the *C. reinhardtii* promoters revealed other motifs that were enriched at specific regions relative to the TSS. Of note, AT-rich motifs appeared to peak at the TSS and then at periodic but decreasing intervals both upstream and downstream of the TSS (FIG. 6, panel B). These intervals appeared ~130 bp apart from each other. These regions correspond to the AT-rich regions found in the top 50 genes (FIG. 1, panel A), and when the relative GC content is analyzed in the larger genomic promoter set a similar pattern of AT-rich regions is seen (FIG. 8). Initially this periodicity suggests a relationship to nucleosome positioning. However, nucleosomes in *C. reinhardtii* protect 147 bp of DNA and typically have a period of ~170 bp (Fu et al., 2015; Lodha and Schroda, 2005). Interestingly, this period more closely follows the period of 6 mA methylated sites around the TSS which have a period of ~134 bp (Fu et al., 2015). However, the AT-rich sites are not located at the same position as either the nucleosomes or the 6 mA sites. Finally, CentriMo analysis found TC rich motifs that were enriched around the TSS of *C. reinhardtii* promoters. However, their enrichment was far less significant than the CCCAT or TA rich motifs (FIG. 6, panel C). This is consistent with the motif deletion analysis that demonstrated that this motif is not essential in the sap11 promoter.

Discussion

In this study, synthetic promoters were successfully generated that were capable of driving exogenous gene expression within the *C. reinhardtii* nucleus. The saps generated in this study were based on native DNA motifs identified using the POWRs algorithm. Using a stochastic method of motif placement that was based on motif location relative to the TSS in native promoters, we were able to generate saps that were as successful as, or better than, the best native promoters in *C. reinhardtii* (Schroda et al., 2002; Schroda et al., 2000). The current best promoter for *C. reinhardtii* is a non-native promoter arl that is a hybrid between two endogenous promoter regions. Our novel saps rely on a completely synthetic promoter backbone with a cis-regulatory motif structure informed from annotation based and experimentally derived genomic information. It should be noted that the HSP70A promoter acts as a transcriptional state enhancer, which increases the probability of transcription of the neighboring promoter (Schroda et al., 2008). It would be interesting to see if fusing the HSP70A promoter upstream our synthetic promoter further improves their function similarly to HSP70A's effect on RBCS2. Alternatively, our promoters could also be fused with other native 5' and 3' UTRs, such as psaD, which in one study showed similar improvements over arl for luciferase expression (Kumar et al., 2013).

Bioinformatic analysis used to identify motifs within native promoters led to the identification of novel elements as well as information about promoter structure within the nuclear genome of *C. reinhardtii*. First, *C. reinhardtii* promoters have an AT-bias near the TSS, which is unique from other plant species studied thus far (FIG. 1, panel A; Calistri et al., 2011; Fujimori et al., 2005). This bias more than likely affects the structure of the DNA in this location and may be important for nucleosome organization or other DNA-protein interactions (Gabrielian et al., 1999; Kanhere and Bansal, 2005). In addition to an overall AT-bias, there were also pockets of AT-rich regions upstream of the TSS, which correlated with AT-rich motifs found in the EST validated promoters (FIG. 1, panel A and 6, panel B). The pattern of the AT-rich regions corresponds to a similar periodic pattern of 6 mA methylation sites around the TSS, but is shifted by ~30 bp (Fu et al., 2015). It has been suggested that the periodicity of the 6 mA sites may help establish nucleosome organization around the TSS. Therefore, the AT-bias with specific AT-rich periodic regions may work together with the 6 mA methylation site to establish nucleosome packing and encourage transcription factor and RNA polymerase binding around the TSS.

In addition to AT-rich regions, TC-rich regions were also enriched in *C. reinhardtii* promoters. This enrichment was more significant in the top 50 expressed genes compared to the genome-in whole (FIG. 6, panel C). This enrichment in top expressed genes is consistent with similar motifs found in *Arabidopsis* (Bernard et al., 2010). However, when this motif was removed from sap11, there was little loss in promoter function. It is important to note that TC motif analysis in *Arabidopsis* was only performed in silico. Therefore, the relative importance or function of these motifs has yet to be established in vivo. It is also possible that this motif is a consequence of the relative AT enrichment around the TSS and only its relative AT content is important. Since the motif was replaced with a polyA sequence, the AT content was not significantly changed. Further work is still required to rule out the relevance of the TC-rich motifs in *C. reinhardtii.*

Promoter motif deletion analysis did reveal the presence of an essential motif within the sap11 promoter. Motif regions 3 and 4 contained nearly identical CCCAT motifs. Knock out of these motifs led to severe reduction of sap11 function. Bioinformatic analysis further revealed that this motif is highly enriched at −65 bp upstream of the TSS of 1564 genes with 446 having the exact CCCATGCA sequence (FIG. 6, panel A). However, many versions of the CCCAT motif contain the conserved CATG 6 mA sequence (Fu et al., 2015). Therefore, the CCCAT motif may function as a target for DNA methylation in its role in transcriptional regulation. While one putative *C. reinhardtii* transcription factor has been predicted to bind to the CCCAT motif based on in silico homology analysis, further in vitro and in vivo work is required to identify the true transcription factor partner.

The combination of bioinformatic analysis of gene structure and expression and in vivo testing of synthetic primers based on these analyses has proven a fruitful area of research for discovery of unknown cis elements and for use in designing strong synthetic promoters (Blazeck and Alper, 2013; Koschmann et al., 2012; Venter, 2007). The knowledge gained in this study gives us a synthetic template to generate large promoter libraries. These libraries will be used to generate more significant data about the importance of individual motifs and overall promoter structure in *C. reinhardtii*, which will ideally enable us to generate successive rounds of engineered promoters to achieve exogenous gene expression above currently achieved levels. Large promoter libraries will also allow for the integration of multiple genes into the same host by allowing separate transgenes to be driven by unique promoters to reduce genomic rearrangements brought about by sequence specific targeting that may arise from a genome laced with identical sequences. This latter feature is particularly important in metabolic engineering, which often requires the introduction of multiple enzymes into the host organism. Finally, as we have demonstrated in this study, synthetic promoters provide a platform on which to identify motifs in vivo involved in transcriptional regulation in *C. reinhardtii*. In the future, this can be expanded to motifs predicted to be involved in inducible regulation such as heat shock, nickel or nitrate addition or iron-deficiency. Together these tools will represent a large step forward in the synthetic engineering of algae for the production of biofuels and bio-products.

References for Example 1

Bailey, T. L. (2011) DREME: motif discovery in transcription factor ChIP-seq data. Bioinformatics 27, 1653-1659.

Bailey, T. L. and Machanick, P. (2012) Inferring direct DNA binding from ChIP-seq. Nucleic Acids Res 40, e128.

Berendzen, K. W., Stuber, K., Harter, K. and Wanke, D. (2006) Cis-motifs upstream of the transcription and translation initiation sites are effectively revealed by their positional disequilibrium in eukaryote genomes using frequency distribution curves. BMC bioinformatics 7, 522.

Bernard, V., Brunaud, V. and Lecharny, A. (2010) TC-motifs at the TATA-box expected position in plant genes: a novel class of motifs involved in the transcription regulation. Bmc Genomics 11, 1-15.

Berthold, P., Schmitt, R. and Mages, W. (2002) An engineered *Streptomyces hygroscopicus* aph 7" gene mediates dominant resistance against hygromycin B in *Chlamydomonas reinhardtii*. Protist 153, 401-412.

Blazeck, J. and Alper, H. (2013) Promoter engineering: recent advances in controlling transcription at the most fundamental level. Biotechnology Journal 8, 46-58.

Blunt, J. W., Copp, B. R., Keyzers, R. A., Munro, M. H. G. and Prinsep, M. R. (2012) Marine natural products. Natural Product Reports 29, 144-222.

Calistri, E., Livi, R. and Buiatti, M. (2011) Evolutionary trends of GC/AT distribution patterns in promoters. Molecular Phylogenetics and Evolution 60, 228-235.

Cardozo, K. H. M., Guaratini, T., Barros, M. P., Falcão, V. R., Tonon, A. P., Lopes, N. P., Campos, S., Torres, M. A., Souza, A. O., Colepicolo, P. and Pinto, E. (2007) Metabolites from algae with economical impact. Comparative biochemistry and physiology. Toxicology & pharmacology 146, 60-78.

Castillon, A., Shen, H. and Huq, E. (2007) Phytochrome Interacting Factors: central players in phytochrome-mediated light signaling networks. Trends Plant Sci 12, 514-521.

Cerutti, H., Johnson, A., Gillham, N. and Boynton, J. (1997) A eubacterial gene conferring spectinomycin resistance on *Chlamydomonas reinhardtii*: integration into the nuclear genome and gene expression. Genetics 145, 97-110.

Corchero, J., Gasser, B., Resina, D., Smith, W., Parrilli, E., Vázquez, F., Abasolo, I., Giuliani, M., Jäntti, J., Ferrer, P., Saloheimo, M., Mattanovich, D., Schwartz, S., Tutino, M. and Villaverde, A. (2013) Unconventional microbial systems for the cost-efficient production of high-quality protein therapeutics. Biotechnology Advances 31, 140-153.

Davis, I., Benninger, C., Benfey, P. and Elich, T. (2012) POWRS: position-sensitive motif discovery. Plos One 7, e40373.

Diaz-Santos, E., de la Vega, M., Vila, M., Vigara, J. and Leon, R. (2013) Efficiency of different heterologous promoters in the unicellular microalga *Chlamydomonas reinhardtii*. Biotechnology Progress 29, 319-328.

Dufresne, A., Ostrowski, M., Scanlan, D. J., Garczarek, L., Mazard, S., Palenik, B. P., Paulsen, I. T., de Marsac, N. T., Wincker, P., Dossat, C., Ferriera, S., Johnson, J., Post, A. F., Hess, W. R. and Partensky, F. (2008) Unraveling the genomic mosaic of a ubiquitous genus of marine cyanobacteria. Genome biology 9, R90.91-15.

Fang, W., Si, Y., Douglass, S., Casero, D., Merchant, S., Pellegrini, M., Ladunga, I., Liu, P. and Spalding, M. (2012) Transcriptome-wide changes in *Chlamydomonas reinhardtii* gene expression regulated by carbon dioxide and the CO2-concentrating mechanism regulator CIA5/CCM1. Plant Cell 24, 1876-1893.

Fischer, N. and Rochaix, J. (2001) The flanking regions of PsaD drive efficient gene expression in the nucleus of the green alga *Chlamydomonas reinhardtii*. Molecular Genetics and Genomics 265, 888-894.

Fischer, N., Stampacchia, O., Redding, K. and Rochaix, J. D. (1996) Selectable marker recycling in the chloroplast. Molecular and General Genetics 251, 373-380.

Fu, Y., Luo, G. Z., Chen, K., Deng, X., Yu, M., Han, D., Hao, Z., Liu, J., Lu, X., Dore, L. C., Weng, X., Ji, Q., Mets, L. and He, C. (2015) N6-methyldeoxyadenosine marks active transcription start sites in *Chlamydomonas*. Cell 161, 879-892.

Fujimori, S., Washio, T. and Tomita, M. (2005) GC-compositional strand bias around transcription start sites in plants and fungi. Bmc Genomics 6.

Gabrielian, A. E., Landsman, D. and Bolshoy, A. (1999) Curved DNA in promoter sequences. In Silico Biol 1, 183-196.

Georgianna, D. R., Michael, J. H., Marina, M., Shuiqin, W., Kyle, B., Alex, J. L., James, H., Michael, M. and Stephen, P. M. (2013) Production of recombinant enzymes in the marine alga *Dunaliella tertiolecta*. Algal Research 2, 2-9.

Gimpel, J., Specht, E., Georgianna, D. and Mayfield, S. (2013) Advances in microalgae engineering and synthetic biology applications for biofuel production. Current opinion in chemical biology 17, 489-495.

Gimpel, J. A. and Mayfield, S. P. (2013) Analysis of heterologous regulatory and coding regions in algal chloroplasts. Applied microbiology and biotechnology 97, 4499-4510.

Griesbeck, C. and Kirchmayr, A. (2012) Algae: An alternative to the higher plant system in gene farming. In: Molecular Farming in Plants: Recent Advances and Future Prospects (Wang, A. and Ma, S. eds), pp. 125-143. Dordrecht, Netherlands: Springer Science & Business Media.

Gumpel, N.J., Rochaix, J. D. and Purton, S. (1994) Studies on homologous recombination in the green alga *Chlamydomonas reinhardtii*. Curr Genet 26, 438-442.

Gupta, S., Stamatoyannopoulos, J. A., Bailey, T. L. and Noble, W. S. (2007) Quantifying similarity between motifs. Genome Biology 8, R24.

Hammer, K., Mijakovic, I. and Jensen, P. (2006) Synthetic promoter libraries-tuning of gene expression. Trends in Biotechnology 24, 53-55.

Haring, M. A. and Beck, C. F. (1997) A promoter trap for *Chlamydomonas reinhardtii*: Development of a gene cloning method using 5' RACE-based probes. Plant J 11, 1341-1348.

Kanhere, A. and Bansal, M. (2005) Structural properties of promoters: similarities and differences between prokaryotes and eukaryotes. Nucleic Acids Res 33, 3165-3175.

Koschmann, J., Machens, F., Becker, M., Niemeyer, J., Schulze, J., Billow, L., Stahl, D. and Hehl, R. (2012) Integration of bioinformatics and synthetic promoters leads to the discovery of novel elicitor-responsive cis-regulatory sequences in *Arabidopsis*. Plant Physiology 160, 178-191.

Kumar, A., Falcao, V. R. and Sayre, R. T. (2013) Evaluating nuclear transgene expression systems in *Chlamydomonas reinhardtii*. Algal Res 2, 321-332.

Lingg, N., Zhang, P., Song, Z. and Bardor, M. (2012) The sweet tooth of biopharmaceuticals: importance of recombinant protein glycosylation analysis. Biotechnology Journal 7, 1462-1472.

Lodha, M. and Schroda, M. (2005) Analysis of chromatin structure in the control regions of the *Chlamydomonas* HSP70A and RBCS2 genes. Plant Mol Biol 59, 501-513.

Lodha M, Schulz-Raffelt M, Schroda M. (2008) A new assay for promoter analysis in *Chlamydomonas* reveals roles for heat shock elements and the TATA box in HSP70A promoter-mediated activation of transgene expression. Eukaryotic Cell 7, 72-176.

Lumbreras, V., Stevens, D., and Purton, S. (1998) Efficient foreign gene expression in *Chlamydomonas reinhardtii* mediated by an endogenous intron. The Plant Journal 14, 441-447.

Manuell, A. L., Beligni, M. V., Elder, J. H., Siefker, D. T., Tran, M., Weber, A., McDonald, T. L. and Mayfield, S. P. (2007) Robust expression of a bioactive mammalian protein in *Chlamydomonas* chloroplast. Plant Biotechnology Journal 5, 402-412.

Maston, G. A., Evans, S. K. and Green, M. R. (2006) Transcriptional regulatory elements in the human genome. Annual review of genomics and human genetics 7, 29-59.

Merchant, S. S., Prochnik, S. E., Vallon, O., Harris, E. H., Karpowicz, S. J., Witman, G. B., Terry, A., Salamov, A., Fritz-Laylin, L. K., Maréchal-Drouard, L. and others (2007) The *Chlamydomonas* genome reveals the evolution of key animal and plant functions. Science 318, 245-250.

Mukherji, S. and van Oudenaarden, A. (2009) Synthetic biology: understanding biological design from synthetic circuits. Nature Reviews Genetics 10, 859-871.

Parker, M. S., Mock, T. and Armbrust, E. V. (2008) Genomic insights into marine microalgae. Annual Review of Genetics 42, 619-645.

Rasala, B., Barrera, D., Ng, J., Plucinak, T., Rosenberg, J., Weeks, D., Oyler, G., Peterson, T., Haerizadeh, F. and Mayfield, S. (2013) Expanding the spectral palette of fluorescent proteins for the green microalga *Chlamydomonas reinhardtii*. The Plant Journal 74, 545-556.

Rasala, B. A., Lee, P. A., Shen, Z. X., Briggs, S. P., Mendez, M. and Mayfield, S. P. (2012) Robust expression and secretion of xylanase1 in *Chlamydomonas reinhardtii* by fusion to a selection gene and processing with the FMDV 2A peptide. PloS one 7, e43349.

Rosales-Mendoza, S., Paz-Maldonado, L. M. T. and Soria-Guerra, R. E. (2012) *Chlamydomonas reinhardtii* as a viable platform for the production of recombinant proteins: current status and perspectives. Plant Cell Rep 31, 479-494.

Ruth, C. and Glieder, A. (2010) Perspectives on synthetic promoters for biocatalysis and biotransformation. Chembiochem 11, 761-765.

Schroda, M., Beck, C. and Vallon, 0. (2002) Sequence elements within an HSP70 promoter counteract transcriptional transgene silencing in *Chlamydomonas*. The Plant Journal 31, 445-455.

Schroda, M., Blöcker, D. and Beck, C. (2000) The HSP70A promoter as a tool for the improved expression of transgenes in *Chlamydomonas*. The Plant Journal 21, 121-131.

Sharma, N. K., Tiwari, S. P., Tripathi, K. and Rai, A. K. (2011) Sustainability and cyanobacteria (blue-green algae): facts and challenges. Journal of Applied Phycology 23, 1059-1081.

Sodeinde, O. A. and Kindle, K. L. (1993) Homologous recombination in the nuclear genome of *Chlamydomonas reinhardtii*. Proceedings of the National Academy of Sciences 90, 9199-9203.

Specht, E. and Mayfield, S. P. (2012) Synthetic oligonucleotide libraries reveal novel regulatory elements in *Chlamydomonas* chloroplast mRNAs. ACS Synthetic Biology 2, 34-46.

Specht, E., Miyake-Stoner, S. and Mayfield, S. (2010) Micro-algae come of age as a platform for recombinant protein production. Biotechnology letters 32, 1373-1383.

Specht, E. A., Nour-Eldin, H. H., Hoang, K. T. D. and Mayfield, S. P. (2015) An improved ARS2-derived nuclear reporter enhances the efficiency and ease of genetic engineering in *Chlamydomonas*. Biotechnology Journal 10, 473-479.

Venter, M. (2007) Synthetic promoters: genetic control through cis engineering. Trends Plant Sci 12, 118-124.

Wu, J., Hu, Z., Wang, C., Li, S. and Lei, A. (2008) Efficient expression of green fluorescent protein (GFP) mediated by a chimeric promoter in *Chlamydomonas reinhardtii*. Chinese Journal of Oceanology and Limnology 26, 242-247.

Yamamoto, Y. Y., Ichida, H., Matsui, M., Obokata, J., Sakurai, T., Satou, M., Seki, M., Shinozaki, K. and Abe, T. (2007) Identification of plant promoter constituents by analysis of local distribution of short sequences. Bmc Genomics 8, 67.

Zhang, Y., Werling, U. and Edelmann, W. (2012) SLiCE: a novel bacterial cell extract-based DNA cloning method. Nucleic Acids Res 40, e55.

Zones, J. M., Blaby, I. K., Merchant, S. S. and Umen, J. G. (2015) High-Resolution Profiling of a Synchronized Diurnal Transcriptome from *Chlamydomonas reinhardtii* Reveals Continuous Cell and Metabolic Differentiation. The Plant Cell 10, 2743-2769

Example 2

A Synthetic Nuclear Transcription System in Green Algae: Characterization of *Chlamydomonas reinhardtii* Nuclear Transcription Factors and Identification of Targeted Promoters This example is published as Anderson, et al, Algal Research (2017) 22:47-55. which is hereby incorporated herein by reference in its entirety for all purposes.

Methods

Algal Strains, Culture Conditions, and Genetic Transformation. *Chlamydomonas reinhardtii* cc1010 (*Chlamydomonas* Resource Center, St. Paul, N. Mex.) was used as the wild type strain for this study. Algal strains were cultured in TAP (Tris-Acetate-Phosphate) medium [25] at 23° C. under constant illumination (5,000 lux) and with constant shaking (100 rmp). *C. reinhardtii* was transformed by electroporation as previously described [19] with the exception of the 40 mM sucrose supplement. Transformants were selected on TAP medium agar plates supplemented with 10 μg/ml zeocin. Gene-positive colonies were screened by PCR.

Generation of Transcription Factor Library. Initial gene models for 346 identified *C. reinhardtii* TFs were obtained from the PlnTFDB (http://pintfdb.bio.uni-potsdam.de/v3.0/) [24,26]. These were then cross-referenced by BLAST against the Phytozome database (http://phytozome.jgi.doe-.gov) to obtain the most up-to-date and accurate gene models. Primers were designed to anneal to the 5' and 3' ends of each gene (Integrated DNA Technologies). RNA was isolated from cc1010 cultures grown to 6×108 cells per ml using PureLink Plant RNA Reagent (Ambion by Life Technologies) and cDNA libraries generated with Verso cDNA Synthesis Kit (Thermo Fisher Scientific). Gene coding sequences were amplified with Phusion Polymerase using the GC buffer (Thermo Fisher Scientific) supplemented with 0.5 to 1M Betaine (Sigma) with a touchdown PCR protocol [27]. Successfully amplified CDSs were then cloned into the pENTR/D-TOPO vector in *E. coli* via TOPO cloning (Life Technologies). Resulting clones were sequence verified by Sanger sequencing. Silent mutations were deemed acceptable. In the case of non-silent mutations, these were allowed only after multiple independent clones were confirmed with the same difference(s) from the published gene model. Clones were transferred to pDEST22 (*S. cerevisiae* Y1H vector) or pTM207 (ble2A-derived [19] *C. reinhardtii* nuclear expression vector) via Gateway LR-Clonase (Life Technologies).

Yeast Culture Conditions and Yeast One-Hybrid Assay. Culture conditions and mating of *Saccharomyces cerevisiae* YM4271 and Y1H assay were performed following the MATCHMAKER One-Hybrid System protocol (CLONTECH Laboratories, Inc.). Reporter plasmids were chromosomally integrated in the *S. cerevisiae* YM4271 genome. Briefly, Y1H library strains were inoculated into 96 well plates and cultured overnight (0/N). The OD600 was measured from 100 μl of 0/N culture. Using white 96 well plates (Greiner), 50 μl of 0/N culture was combined with 50 μl of Luciferase Assay Reagent (Promega) using an injector on a Tecan plate reader (Tecan Infinite M200 PRO). Luminescence was measured five seconds post-injection. Luminescence was first normalized to the OD600 and then for each TF normalized to the empty vector control. A one sided Grubbs' test for outliers (0.05 level) was used to determine fold increases in luminescence that were outside the distribution. Assays were repeated with replicates for outlier samples. Values were determined significant by Student's t-test and/or greater than two standard deviations from the mean of the empty vector luminescence control.

Immunoblotting. Cells were cultured until mid to late log phase, washed in PBS-T (Phosphate-Buffered Saline-Tween) buffer, and lysed by sonication. Total soluble protein pellets were resuspended in SDS-PAGE loading buffer. Boiled samples were separated on a 12% SDS-PAGE gel, transferred to nitrocellulose, and probed with anti-GAL4-AD antibody (Sigma) for *S. cerevisiae* or anti-FLAG monoclonal antibody conjugated to alkaline phosphatase (Sigma) for *C. reinhardtii.*

RNA Purification. RNA was extracted from *C. reinhardtii* strains of interest after 3-4 days of growth in TAP medium under constant light using PureLink Plant RNA Reagent (Ambion by Life Technologies) according to the manufacture's protocol. RNA was treated with 4 U of TURBO DNase (Thermo Fisher Scientific) for 30 min at 37° C.

RNA-Sequencing and Analysis. RNA from three biological replicates for each strain analyzed was sent to the Institute for Genomic Medicine at the University of California, San Diego for Next-Generation Sequencing on an Illumina HiSeq2500. Single-end 50 bp reads were generated. Reads were aligned to the latest reference index (Chlre4_Augustus5_transcripts.fasta) downloaded from the Joint Genome Institute (JGI) at www.phytozome.net using TopHat open software on Galaxy (usegalaxy.org) [28-30]. Differential expression analysis was performed using Cufflinks also on Galaxy. For gene identification, *C. reinhardtii* strain 503 was used as a reference strain due to the lack of a published sequence for strain cc1010. The average log 2 (fold change) of all FPKM (Fragments Per Kilobase of transcript per Million mapped reads) values ≥1.0 for the experimental strain (transcription factor constitutive-expression) compared to the control strain (GFP constitutive-expression strain) was plotted.

Reverse Transcriptase Quantitative Polymerase Chain Reaction. 1 μg of purified RNA was reverse transcribed using the Verso cDNA synthesis kit (Thermo Fisher Scientific). cDNA was diluted 1:2 for qPCR analysis using Power SYBR Green PCR Master Mix (Applied Biosystems). qPCR was performed on a My iQ thermocycler (Bio Rad). Two biological replicates were performed each with technical triplicates. The ΔΔCt method was used for relative quantification of gene expression [31]. RACK1 was used as an internal standard. The mean log 2 (fold change) and SEM from biological replicates was plotted.

Promoter Motif Identification. Promoter sequences were obtained from NCBI. DNA sequences were analyzed using the software programs MEME [32,33], AME [34], and Jalview [35].

Results.

Construction of a putative transcription factor library. One of our main goals with this project was to narrow down the list of potential cognate TF-promoter pairs, i.e., which TFs bind and regulate which nuclear promoters, in *C. reinhardtii*. An understanding of the global network of regulatory interactions within the nuclear genome is critical for the engineering of synthetic transcription systems, a long-range goal for our laboratory. Therefore, we set out to construct a library of recombinant *C. reinhardtii* nuclear transcription factors (TFs). Just after the *C. reinhardtii* genome sequence was completed [11], putative TFs, as well as transcription regulators (TRs), were identified by presence of homology to known TF/TR domains and available at the Plant Transcription Factor Database (PlnTFDB) [24,26]. In order to have the most up-to-date gene model for the TFs and TRs, we took fragments from the identified genes and used a BLAST search against the latest gene models from Phytozome. The TF/TR library (referred to simply as the TF library from here on) was generated using TOPO cloning such that the gene encoding each TF was PCR amplified from *C. reinhardtii* cc1010 cDNA and ligated into the pENTR/D-TOPO vector, followed by transformation into *Escherichia coli* (see Materials and Methods). We were able to successfully construct plasmid vectors encoding 92 different putative TFs predicted in the *C. reinhardtii* genome (Table 8) (from a total of over 300 TFs identified by bioinformatics). Our library contains TFs belonging to multiple TF families including but not limited to: High Mobility Group (HMG) box, basic Helix-Loop-Helix (bHLH), Cys2His2 zinc finger (C2H2), Cys3His zinc finger (C3H), Forkhead-associated (FHA), basic Leucine Zipper (bZIP), MYB (myeloblastosis), Gcn5-related N-acetyltransferase (GNAT), Tubby bipartite (TUB), Tumor necrosis factor receptor-associated (TRAF), SET (histone methyltransferases), and CCAAT-enhancer-binding proteins (CCAAT). A complete list of each TF and relevant information can be found in Table 8.

TABLE 8

Transcription factor library.

| TF# | Augustus u10.2 gene ID # | v4.0 gene ID # | PTFDB TF family | CDS length bp | TF Library Clone Notes |
|---|---|---|---|---|---|
| 1 | Cre06.g268600 | 126810 | CSD | 744 | |
| 2 | Cre06.g261450.t1.1 | 142283 | HMG (high mobility group) box | 540 | |
| 3 | Cre14.g620850.t1.1 | 183777 | bHLH | 1368 | silent T681C |
| 4 | Cre13.g596300.t1.1 | 159133 | C2H2 / C2C2-CO-like | 1233 | silent T1074C |
| 5 | Cre06.g250950.t1.1 | 142476 | C3H | 822 | |
| 6 | Cre16.g672300.t1.1 | 184386 | HMG (high mobility group) box | 621 | |
| 7 | Cre14.g620500.t1.1 | 347049 | AP2-EREBP | 1032 | |
| 8 | Cre02.g082550.t1.1 | 53522 | FHA | 2034 | |
| 9 | Cre20.g758600.t1.1 | 290169 | bZIP | 1731 | |
| 10 | Cre05.g242600.t1.1 | 187360 | C2C2-GATA | 1194 | |

TABLE 8-continued

Transcription factor library.

| | | | | | |
|---|---|---|---|---|---|
| 11 | Cre03.g193900 | 147364 | CCAAT | 696 | |
| 12 | Cre08.g378800.t1.1 | 345074 | C2C2-GATA | 633 | |
| 13 | Cre07.g341800.t1.1 | 378904 | CCAAT | 837 | |
| 14 | Cre32.g781700.t1.1 | 22211 | C3H | 534 | |
| 15 | Cre16.g671900.t1.1 | 34069 | FHA | 768 | |
| 16 | Cre03.g197100 | 117291 | MYB | 1437 | |
| 17 | Cre01.g014050.t1.1 | 146239 | C3H | 1227 | |
| 18 | Cre03.g198800.t1.1 | 417388 | MYB-related | 1368 | |
| 19 | Cre12.g521150.t1.1 | 205894 | C2C2-Dof | 1875 | |
| 20 | Cre06.g293750 | 194555 | C3H | 1725 | silent G1380A, appears to have 15 bp repeat at 322 & 685 |
| 21 | Cre02.g118250.t1.1 | 194816 | SWI/SNF-BAF60b | 828 | 6 silent A147T, G444A, G465A, G555A, T567C, C738T; plus C222G causes D→E mutation. Apr. 20, 2012 - Confirmed real differences between CC1010 (WT) and CC503 (reference sequence) |
| 22 | Cre03.g152150.t1.1 | 149734 | C2H2 | 1242 | 15 bp repeat at 222 & 1050 |
| 23 | Cre03.g194950.t1.1 | 190458 | Sigma70 | 2259 | |
| 24 | Cre05.g238250.t1.1 | 410640 | bZIP | 1575 | |
| 25 | Cre04.g228400.t1.2 | 205718 | WRKY | 1920 | |
| 26 | Cre12.g520650.t1.1 | 17453 | TUB | 1356 | |
| 27 | Cre07.g326150.t1.2 | 205729 | C3H | 2253 | |
| 28 | Cre04.g216200 | 177225 | bHLH | 1407 | silent G1056A |
| 29 | Cre14.g624800.t1.1 | 147817 | | 1416 | real length is 1485, different splice site from predicted |
| 30 | Cre02.g136800.t1.1 | 205561 | MYB-related | 2022 | |
| 31 | Cre02.g096300.t1.2 | 186972 | C2H2 | 2100 | |

TABLE 8-continued

| Transcription factor library. | | | | |
|---|---|---|---|---|
| 32 | Cre03.g184150.t1.1 | 115555 | GNAT | 516 | |
| 33 | Cre16.g657150.t1.2 | 287999 | GNAT | 837 | |
| 34 | Cre02.g101850.t1.1 | 377090 | GNAT | 480 | |
| 35 | Cre01.g048800.t1.2 | 283458 | GNAT | 1005 | |
| 36 | Cre11.g480950.t1.1 | 192899 | HMG | 471 | |
| 37 | Cre12.g542500.t1.1 | 79755 | mTERF | 474 | |
| 38 | Cre12.g560200.t1.1 | 165420 | GNAT | 447 | |
| 39 | Cre01.g063450.t1.1 | 193681 | PHD | 591 | |
| 40 | Cre02.g091550.t1.1 | 186648 | PBF-2-like | 717 | |
| 41 | Cre10.g420100.t1.1 | 96716 | SBP | 1026 | 7 silent T159C, A180G, G159A, C660T, C861T, T873G, C966T |
| 42 | Cre11.g475100.t1.1 | 160596 | GNAT | 396 | |
| 43 | Cre02.g079200.t1.1 | 111791 | CCAAT | 630 | |
| 44 | Cre09.g402350.t1.1 | 191829 | FHA | 555 | |
| 45 | Cre13.g590350.t1.1 | 147286 | PZIP | 1005 | |
| 46 | Cre16.g667450.t1.1 | 26047 | TUB | 1476 | silent C939T |
| 47 | Cre14.g623800.t1.2 | 117568 | GNAT | 642 | |
| 48 | Cre10.g431450.t1.1 | 420467 | GNAT | 1515 | |
| 49 | Cre17.g729750.t1.1 | 289541 | GNAT | 501 | |
| 50 | Cre10.g430750.t1.2 | 338485 | MYB-related | 972 | 702-773 in frame deletion (present in 6 clones, 24 AA long mostly Alanine repeat) |
| 51 | Cre27.g774300.t1.2 | 154505 | SET | 1566 | |
| 52 | Cre29.g778700.t1.1 | 407701 | SlFa-like | 222 | |
| 53 | Cre02.g108450.t1.1 | 76570 | MBF1 | 420 | |
| 54 | Cre07.g351850.t1.1 | 337711 | GNAT | 672 | |
| 55 | Cre16.g668200.t1.1 | 288229 | PHD | 744 | |

TABLE 8-continued

| Transcription factor library. | | | | | |
|---|---|---|---|---|---|
| 56 | Cre06.g305200.t1.2 | 156694 | C2H2 | 1005 | |
| 57 | Cre06.g254650.t1.1 | 134186 | C3H | 1023 | |
| 58 | Cre07.g321550.t1.1 | 187531 | bZIP | 1182 | |
| 59 | Cre17.g702650.t1.1 | 145251 | HMG | 1212 | |
| 60 | Cre01.g022950.t1.1 | 146398 | TRAF | 1212 | |
| 61 | Cre16.g672400.t1.1 | 149109 | MYB-related | 1506 | |
| 62 | Cre12.g540400.t1.1 | 137355 | Rcd1 | 900 | |
| 63 | Cre06.g286700.t1.1 | 402799 | TRAF | 999 | |
| 64 | Cre02.g109700.t1.2 | 415443 | bHLH | 1011 | |
| 65 | Cre01.g035150.t1.2 | 406697 | C3H | 1197 | |
| 66 | Cre12.g516050.t1.1 | 423729 | FHA | 1065 | |
| 67 | Cre04.g218400.t1.2 | 423158 | TRAF | 1179 | |
| 68 | Cre10.g441000.t1.1 | 379612 | IWS1 | 1590 | |
| 69 | Cre06.g269100.t1.2 | 142152 | GNAT | 861 | |
| 70 | Cre13.g586450.t1.1 | 143712 | GNAT | 861 | |
| 71 | Cre11.g479800.t1.2 | 379890 | TRAF | 1182 | |
| 72 | Cre04.g226400.t1.1 | 189471 | CCAAT | 1230 | |
| 73 | Cre16.g695600.t1.1 | 178083 | MYB-related | 1416 | |
| 74 | Cre09.g392300.t1.2 | 148265 | GNAT | 1458 | |
| 75 | Cre13.g593900.t1.1 | 205788 | GNAT | 1023 | v4.3 had extra intron (263-271) corrected v5.3 |
| 76 | Cre17.g739450.t1.2 | 135809 | CCAAT | 618 | |
| 77 | Cre02.g084550.t1.1 | 290467 | GNAT | 894 | |
| 78 | Cre13.g597500.t1.1 | 151334 | TRAF | 1068 | |
| 79 | Cre07.g316600.t1.1 | 142718 | FHA | 1467 | |
| 80 | Cre23.g766800.t1.1 | 391557 | MED7 | 753 | |
| 81 | Cre13.g581150.t1.1 | 413200 | GNAT | 1128 | |

TABLE 8-continued

Transcription factor library.

| | | | | | |
|---|---|---|---|---|---|
| 82 | Cre26.g772400. t1.2 | 398164 | Coactivator p15 | 1371 | deletion 1027-1053 from v4.3 |
| 83 | Cre04.g215450. t1.1 | 151740 | TRAF | 1587 | |
| 84 | Cre08.g364450. t1.1 | 95444 | GNAT | 543 | |
| 85 | Cre12.g556400. t1.2 | 117655 | CCAAT | 891 | |
| 86 | Cre06.g283200. t1.1 | 295365 | SET | 1008 | |
| 87 | Cre07.g319701. t1.1 | 127044 | C2C2-GATA | 1329 | |
| 88 | Cre16.g662650. t1.2 | 288117 | GNAT | 1044 | |
| 89 | Cre06.g256200. t1.1 | 142398 | GNAT | 1173 | silent G510A |
| 90 | Cre12.g520850. t1.1 | 424885 | SOH1 | 426 | |
| 91 | Cre10.g446450. t1.1 | 281993 | Orphan | 1311 | |
| 92 | Cre02.g075650. t1.1 | 417182 | C3H | 1254 | |

| TF# | SEQ ID NO | Reference Sequence |
|---|---|---|
| 1 | 87 | ATGGGCGAGCAGCTGAGGCAACAGGGAACCGTAAAG TGGTTCAACGCCACCAAAGGCTTCGGCTTCATCACGC CTGGTGGTGGCGGCGAGGACCTCTTTGTGCACCAGAC CAACATCAACTCGGAGGGCTTCCGCAGCCTGCGGGAG GGTGAAGTCGTCGAGTTCGAGGTTGAGGCTGGGCCGG ATGGACGCTCTAAGGCTGTGAACGTGACGGGCCCCGG AGGGGCCGCGCCCGAGGGCGCTCCGCGGAACTTCCGC GGTGGCGGCCGCGGCCGCGGCCGCGCTCGCGGCGCCC GCGGCGGCTATGCTGCTGCGTACGGCTACCCGCAGAT GGCGCCGGTCTACCCCGGCTACTACTTCTTCCCCGCGG ACCCCACGGGCCGGGGACGGGGTCGCGGCGGCCGCG GCGGCGCCATGCCCGCCATGCAGGGCGTGATGCCGGG TGTGGCGTACCCGGGCATGCCCATGGGCGGGGTGGGC ATGGAGCCGACGGGCGAGCCGTCGGGGCTGCAGGTG GTGGTGCACAACCTGCCGTGGAGCTGCCAGTGGCAGC AGCTCAAGGACCACTTCAAGGAGTGGCGGGTGGAGCG CGCAGACGTCGTGTACGACGCCTGGGGCCGCTCGCGG GGCTTCGGCACCGTGCGCTTCACGACCAAGGAGGACG CCGCGACGGCGTGCGACAAGTTGAACAACAGCCAAAT CGACGGGCGCACGATAAGCGTCCGGCTCGACCGTTTC GCTTGA |
| 2 | 88 | ATGGCTGGTGACAAGGCTGCCACCAAGGAGAAGAAG GCCGCAGAGCCCAAGGGCAAGCGGAAGGAGACTGAG GGCAAGGCCGAGCCCCCCGCCAAGAAGGCTGCCAAG GCTCCCCCCAAGGAGAAGCCCGCCAAGAAGGCGCCC GCCAAGAAGGAGAAGAAGGCCAAGGACCCCAACGCC CCCAAGAAGCCCCTCACTTCCTTCATGTACTTCTCGAA CGCCATCCGTGAGAGCGTGAAGTCCGAGAACCCTGGC ATTGCCTTCGGCGAGGTCGGCAAGGTGATCGGCGAGA AGTGGAAGGGCCTGTCCGCTGACGACAAGAAGGAGT ACGATGAGAAGGCGGCTAAGGACAAGGAGCGCTACC AGAAGGAGATGGAGTCTTACGGCGGCTCGTCGGGTGC CTCCAAGAAGCCCGCGGCCAAGAAGGAGAAGGCTGC GCCCAAGAAGAAGGCTAAGGAGGAGGAGGAGGAGGA CGAGCCTGAGGCCGATGACGATGGTGATGACGACGAC GAGGACGATGATGGTGATGACGATGAGTAA |
| 3 | 89 | ATGCAGCAGTCTTCGCAGCTTGGGCTGCCTGACCAGC TCGCTCTGCTCAGCGGATTCCCGGCCGCGCTCTTCCCC CAGCAGTACGGGTCGGGAGACCGCGACCTACAGCTCG |

TABLE 8-continued

Transcription factor library.

| | | |
|---|---|---|
| | | GCGGCCTGCGTAATGTGGGCAAAACGAAGTCTTCTGA<br>CAGCCGGAGCTCAAGTGCCTACGCGAGCAGGCACCAA<br>GCGGCTGAGCAACGCCGCCGAACTCGAATCAATGAGA<br>GGCTGGAGCTCCTGCGCAAGCTGGTGCCGCATGCGGA<br>GCGCGCCAACACGGCGTGCTTTCTGGAGGAGGTCATC<br>AAGTACATCGAGGCGCTGAAGGCGCGCACACTGGATC<br>TAGAGTCGCAGGTGGAGGCCCTGACGGGCAAGCCGGT<br>GCCCAAGTCGCTGGCGCTGCCCACCGGCATGCCGTCG<br>GTGCTGGCCGGAGGCTCCACCAGCGCGGACAACACCA<br>ACGCCAGCCCGCGCATGGTTGGCGCAGCGACATCGTC<br>GCAGGGCGGGCCCGCGGGCTCGCTGCCATCGGGGCAG<br>CCGGGCGCCGGCGGGGCGGGCGCGGGCTCCCTAGCCA<br>GCCCCTCCACCACGCCGCCCCCTACCATGACCGCGCA<br>GCAGGCCTCCCAGCAGCTCTCGCTCATGCAGTCGGGC<br>GGGCAGGCGGGCGGCTCGCAGGGCCTGCCGTCACAGC<br>TGACGCTGCCCAGTGGCGGCGCCGGCGCGGGGCTGCT<br>CTCGGCGGCGCAGCAGAGCCTGCTGGGTTTCCCCCAG<br>TCGGGCGGCCTGTCCCTCTCAGGCGCCGGCCTGTCACT<br>GGGCGGCAGCGGCCTGGGCCACGGCACCAGCGGCAT<br>CAGCCTGACCCAGTTCGCCGGCAACCTGCAGGCGGCC<br>GCCGCGGCCGCCGCCGCGGCGTCGCACGGCGCCGGCA<br>GCCAGTCCCACTCGCAGTCGCAGTCGCAGCACTCCGG<br>CCTCAGCCTGGGCTCGCACCACGTCACCGCGTCGCAG<br>CTGAACGAACTGCAGGCCATGCAAATGATGCAGTCGC<br>TGCAGCAGCACCACAACCAGCACGCGGCGGCCGCCGC<br>GGTGGTCGCGGCCGCGGGTGGCGGCGGCGGTTCCCGC<br>CCGGGATCCACGTTCCACCCCACCAACAACAAGGCGT<br>TCCTGCACTTCAACGAGGACGCCTACGCCTTCAGCGG<br>CAAGCCCGAGCTGTCGCTACCCGCGCGCAGCCTGCTG<br>GGTGCAGCCGCGGCCTCCGCCGCCACGCCCAGCACGT<br>CTCTCCAGCTGACCACCGTGCAGCTGCCCGCGGACTC<br>GAACACGCTGCTCCAGGTGGAGATGGCGCGCAAGGCC<br>GCGTCGGGCTCTCCCGTGTCCAGCGAGGAGAGCGGCG<br>TGCCGCTGAAGAAGCGCAAAGTGCTGGTGCTGTAA |
| 4 | 90 | ATGTCGAGTTGCGTCGTGTGCGCGGCCGCAGCGGTCG<br>TTTGGTGCCAGAATGACAAGGCGCTGCTTTGCAAGGA<br>CTGCGATGTGCGCATCCACACCAGCAACGCGGTCGCT<br>GCGCGCCATACCCGCTTCGTGCCCTGCCAGGGCTGCA<br>ACAAGGCCGGTGCTGCGCTCTACTGCAAGTGCGACGC<br>CGCGCACATGTGCGAGGCTTGCCACAGCTCCAACCCC<br>CTAGCTGCTACGCACGAGACCGAGCCGGTGGCGCCGC<br>TGCCGTCAGTCGAGCAGGGCGCTGCACCGGAGCCTCA<br>GGTCCTGAACATGCCCTGCGAGTCTGTGGCGCAGTCT<br>GCGGCCAGCCCCGCGGCTTGGTTTGTGGACGACGAGA<br>AGATGGGCACGACCAGCTTCTTTGATGCGCCTGCGGT<br>GCTGTCGCCCTCGGGCAGCGAGGCCGTGGTGCCCGTC<br>ATGTCCGCCCCTATCGAGGACGAGTTTGCATTCGCGG<br>CCGCCCCGGCGACGTTCAAGGAAATCAAGGACAAGCT<br>CGAGTTCGAGGCTCTGGACCTGGACAACAACTGGCTC<br>GACATGGGCTTCGATTTCACTGATATCCTGTCCGACGG<br>CCCCTCTGATGTGGGCCTGGTCCCCACCTTCGATGCCG<br>TCGATGAGGCCGCGGATGCCGTGGCTGACGCTATCGT<br>GCCCACCTTCGAGGAGGAGCAGCCCCAGTTACAGCAG<br>CAGGAGCCCCTGGTGCTGGCTCCCGCCCCGGAGGAGT<br>CGGCTGCTAGCCGCAAGCGCGCTGCCGCCGAGGAGGC<br>CGCGGAGGAGCCGGCCGCCAAGGTGCCGGCCCTGACT<br>CACCAGGCGCTGCTGCAGGCGCAGGCCGCCGCCTTCC<br>AGGCCGTGCCCCAGGCGTCAGCGCTGTTCTTCCAGCC<br>GCAGATGCTGGCCGCGCTGCCGCACCTGCCGCTGCTG<br>CAGCAGCCCATGATGCCGGCAGCCGTCGCCCCGGCGC<br>CCGTGCCCAAGAGCGGCAGCGCCGCCGCCAGCGCGGC<br>CCTCGCCGCCGGTGCCAACCTGACTCGCGAGCAGCGC<br>GTGGCGCGCTACCGCGAGAAGCGGAAGAACCGCTCTT<br>TCGCCAAGACCATCCGCTACGCTTCCCGCAAGGCGTA<br>TGCGGAGATCCGCCCCCGCATTAAGGGCCGCTTCGCC<br>AAGAAGGAGGAGATTGAGGCCTGGAAGGCGGCGCAC<br>GGCGGCGACGACGCCATTGTTCCCGAGGTCCTGGACG<br>CTGAGTGCTAA |
| 5 | 91 | ATGGCCGAGCACTTGGCTAGCATCTTCGGCACGGAGA<br>AGGACCGCGTGAACTGCCCGTTCTACTTCAAGATTGG<br>AGCGTGCCGCCATGGCGATCGCTGCTCGCGCCTGCAC<br>AACCGGCCGACGATTAGCCCGACCATTCTAATGGCGA<br>ACATGTACCAGAATCCGCTTTTGAACGCTCCGCTGGG<br>GCCGGACGGGCTGCCCATTCGGGTGGATCCCAGGGCT<br>GCTCAGGAACACTTCGAGGACTTCTATGAGGACGTGT<br>TTGAGGAGCTGGCGGCGCACGGTGAACTGGAGAACCT |

TABLE 8-continued

Transcription factor library.

| | | |
|---|---|---|
| | | GAACGTGTGCGATAACTTCGCTGACCATATGGTCGGG<br>AACGTGTACGCCAAGTTCCGGGACGAGGACGCGGCTG<br>CACGCGCGCTGACGGCGCTGCAGGGCCGCTACTACGA<br>CGGGCGGCCCATCATCGTGGAATTCAGCCCCGTGACT<br>GACTTCCGTGAGGCCACGTGCCGCCAGTACGAGGAAA<br>ACACGTGCAACCGCGGCGGCTACTGCAACTTCATGCA<br>CCTGAAGCCCATCAGCCGGGAGCTGCGCAAGAAGCTG<br>TTTGGGAGGTACAAGCGCCGGGAGCGCAGCCGCAGCC<br>CACGGCGCGACCGCGGCGACCGCGGGGACCGCGGCG<br>ATCGGCGCGAGCGGGACCGTGACTGGGACCGTGGCGA<br>CCGGGACCGCGGGCGGGGTCGCAGCCGCAGCCGCAG<br>CCGCGAGCGGGGGGGTGGCGACCGGCGCCGCGAGAC<br>GTCGGAGGAGCGCCGCGCAAAGATTGCAGCATGGAA<br>CACAGAGCGTGACGGAAGTGCTGGTGGCGGCGGCGGT<br>GGTGGGTGGTGA |
| 6 | 92 | ATGCTGCGCTACGCTGCTCTCCGCACTGTCCCGCGCGC<br>CATCGCGCCCGCCCGCCGGGCCATGGTGATTCGGTCTT<br>TCTCGGAAAGCAACGATGCCGCGCCCCCGGCTAAGAA<br>GGCAACCAAGCCCGCCAAGGCGGAGAAGGCGCCGAA<br>GGCGGAGAAGGCGCCGAAGGTGGAGAAGCCGAAGGC<br>GATGCGCGCGCCAAGCGCTTACAACCTGTTCTATAAG<br>GCGATCTTCCAGCAAGTGCGCAGCGAGAACCCCGACA<br>AGAAGGTTACTGAGCTCGGGTCAAAGGTCCGCGACAA<br>GTGGGCTTCCATTTCGGCACTGGAGCGGGCGCCGTAT<br>GAGGCGCAGGCTGCCGCGCGCAAGAAGGAAGTGGAT<br>GCCAAGAGGGCTGAGGTGCTGGCTGCCAAGAAGGCC<br>GCCGCCCGGCCCGTGACCGCCTACATCGCGTTCGCCA<br>ATGCCAAGCGTCCCGAGATCAAGGCGCAGAACCCTGA<br>CAAGACCATGGCGCAGGTGGCGAGCCTGCTGGGGTCC<br>ATTTGGAAGGGGATGTCGGAGGAGCAGCAGAAGCCG<br>TACCGTGACCAGGCCAAGGCGGCGATGGACGCGTGGA<br>AGGCCAAGCAGCAGGCGCAGCAGTCCGCGTAA |
| 7 | 93 | ATGGAGACGCTGTGGCCGGCTCCATACGCCCTACCGC<br>TCCAGTCTGCGGCGATGGCGCTGTCCGAACAGCAGCT<br>TGGCCAACACATTGATTCTGGCAGCGAGGAGGACCAC<br>ATCGCGGTCGTGGCGCAGGTCCAGACTGGCAAGAAGC<br>GACGCAGTGTGAGCGCGGAAGAGGACCCAGACTATG<br>AGGACGCCGCGCAAGGCGCGCAAGGCATAACGCATG<br>ATGGTACATCAAACAAGGCCGGCTACCGAGGCGTACG<br>GCGCCGGCCATGGGGCTCCTACGCCGCCGAGATTCGG<br>GACGCAGGCTGCGGCAAGCGCCGGTGGATTGGCACGT<br>TCAAGACTGCTGAGGAGGCTGCACGGGCGTACGATGA<br>GGCCGCCATTGCGCTGCATGGGCCTCGCGCCAAGACC<br>AACTTCACCTACCCCTGCCAGCAGCAGAGCGCCGCCG<br>CCGCGCCAGCCGCCGCACACAAGGCCCACAAGCCGCA<br>CGCCGCCGCCGCGCCGCAGCACCACAAGCCGGCGCAC<br>CACAGCCAGCAACCTGCTCAGCCGCGCAAGCAGCCGC<br>TGCACCCCCGGCAGCCGTACCAGCAGCACCAGCCCCC<br>CCAGCTGCCGACGCATCAGGAGGAGGAGCAGTACCG<br>GCGCAAGTCGGACGACTCAGACACCTCTATGACCGCT<br>GCGCTGCCGCTGCCGCTGTCGCTGACGGGGCAGCTGG<br>GCCTGCCGCCGCTGACGCTGCCGGGGCTTGAGGGTCT<br>GGACCTGATGGCGCTGCAGTCCAACCCCGCGCTGCTA<br>GCCGCGCTGCTCGCCGCCACGCGGCAGCACCTCCCGG<br>GGTTGGCCGGGCCGGATGCGCAGCCCGCCTGCCTGCC<br>GGAGCAGCAGCTGTCGGAGCGGGTCTGGGTCCAGGAG<br>CAGCCGGTGCAGGGGTGCGAGGAGGAGGAGGACGGG<br>TTGGAGGAGCCGGAGCCGCCGCAGGTGCTGCGGCCGG<br>AGCAGCTTCGGTCGCTGCAGGTGCTGGCGGAGGTGGC<br>GCACCTGTTCGGGCGCCGCGACTTCTGCATGTCGTGA |
| 8 | 94 | ATGAAGGTTATTATCGCCGGCGCGGGCATCGGCGGCC<br>TGGTGCTAGCCGTTGCACTTCTGAAGCAGGGCTTCCA<br>GGTTCAGGTCTTTGAGCGCGACCTGACGGCCATCCGC<br>GGCGAGGGCAAGTACCGTGGACCCATCCAGGTTCAAA<br>GCAATGCGCTCGCTGCGCTGGAGGCTATCGATCCCGA<br>GGTGGCCGCGGAGGTGCTGCGCGAGGGCTGCATCACT<br>GGCGACCGTATCAACGGGCTCTGCGACGGCCTGACTG<br>GCGAGTGGTACGTCAAGTTCGACACGTTCCACCCGGC<br>GGTCAGCAAGGGCCTGCCGGTGACCCGCGTCATCAGC<br>CGCCTCACGCTGCAGCAGATCCTGGCCAAAGCCGTGG<br>AGCGCTACGGCGGCCCCGGCACCATCCAGAACGGCTG<br>CAACGTGACCGAGTTCACGGAGCGCCGCAACGACACC<br>ACCGGCAACAACGAGGTGACTGTGCAGCTGGAGGAC<br>GGGCGCACGTTTGCGGCCGACGTGCTGGTGGGCGCCG<br>ACGGCATCTGGTCCAAGATCCGTAAGCAGCTCATTGG |

TABLE 8-continued

| Transcription factor library. | | |
|---|---|---|
| | | CGAGACCAAGGCCAACTACAGCGGGTACACCTGCTAC |
| | | ACCGGCATCTCGGACTTTACGCCGGCGGACATTGACA |
| | | TTGTGGGCTACCGCGTGTTCCTGGGCAACGGCCAGTA |
| | | CTTTGTCAGCAGCGACGTGGGCAACGGCAAGATGCAG |
| | | TGGTACGGCTTCCACAAGGAGCCGTCTGGCGGCACCG |
| | | ACCCCGAGGGCAGCCGCAAGGCGCGCCTGCTGCAGAT |
| | | CTTTGGCCACTGGAACGACAACGTGGTGGACCTGATC |
| | | AAGGCCACGCCCGAGGAGGACGTGCTGCGCCGCGAC |
| | | ATCTTTGACAGGCCGCCCATCTTCACCTGGAGCAAGG |
| | | GCCGCGTGGCCCTGCTGGGCGACAGCGCGCACGCCAT |
| | | GCAGCCCAACCTGGGCCAGGGCGGCTGCATGGCCATT |
| | | GAGGACGCCTACGAGCTGGCCATCGACCTCAGCCGCG |
| | | CCGTGTCCGACAAGGCCGGAAACGCGGCGGCGGTGG |
| | | ACGTGGAGGGCGTGCTGCGCAGCTACCAGGACAGCCG |
| | | CATTTTGCGCGTCAGCGCCATTCACGGCATGGCGGGC |
| | | ATGGCTGCCTTCATGGCCAGCACCTACAAGTGCTACCT |
| | | GGGCGAGGGCTGGAGCAAGTGGGTTGAGGGGCTGCG |
| | | CATCCCGCACCCCGGCCGCGTGGTGGGGCGGCTGGTG |
| | | ATGCTGCTCACCATGCCCAGCGTGCTGGAGTGGGTGC |
| | | TGGGCGGCAACACCGACCACGTGGCGCCGCACCGCAC |
| | | CAGCTACTGCTCGCTGGGCGACAAGCCCAAGGCTTTC |
| | | CCCGAGAGCCGCTTCCCCGAGTTCATGAACAACGACG |
| | | CCTCCATCATCCGCTCCTCCCACGCCGACTGGCTGCTG |
| | | GTGGCGGAGCGCGACGCCGCCACGGCCGCCGCCGCCA |
| | | ACGTGAACGCCGCCACCGGCAGCAGCGCCGCCGCGGC |
| | | CGCCGCCGCCGACGTGAACAGCAGCTGCCAGTGCAAG |
| | | GGCATCTACATGGCGGACTCGGCGGCCCTGGTGGGCC |
| | | GCTGCGGCGCCACCTCGCGCCCCGCGCTGGCCGTGGA |
| | | CGACGTGCACGTCGCCGAGAGTCACGCGCAGGTCTGG |
| | | CGCGGCCTCGCCGGCCTCCCCCCCTCCTCGTCGTCCGC |
| | | CTCCACCGCCGCCGCCTCTGCGTCCGCCGCCTCCTCTG |
| | | CCGCCAGCGGCACCGCCAGCACCCTGGGCAGCTCGGA |
| | | GGGCTACTGGCTCCGCGACCTGGGCAGCGGCCGCGGC |
| | | ACCTGGGTCAACGGCAAGCGCCTGCCCGACGGCGCCA |
| | | CGGTGCAGCTGTGGCCCGGCGACGCGGTGGAGTTCGG |
| | | CCGGCACCCCAGCCACGAGGTGTTCAAGGTGAAGATG |
| | | CAGCACGTGACGCTGCGCAGCGACGAGCTCAGCGGCC |
| | | AGGCCTACACCACGCTCATGGTGGGCAAGATCCGGAA |
| | | CAACGACTACGTCATGCCCGAGTCGCGGCCGGACGGC |
| | | GGCAGCCAGCAGCCGGGCCGCCTGGTGACGGCTTAA |
| 9 | 95 | ATGGCTCGACAACAGCAGCATCAGCAGCAAGCCTCTG |
| | | ACCAGCAGCAGACCGGCGCTCGAGCGAACGGCCGGC |
| | | GAGCTTGTCGGCGCGGCAGCGACGAGCCCGCAGAGG |
| | | AGGTGAACGCCATGGACAGCCCCTCCTCCTCACCAGC |
| | | AGGTGCCGGGAAGGTGAGCCAGCGCGGCCGCAAGGC |
| | | CGCAGCGGCCTCCGGCGCCGCGGCGACCAAGCGCGGC |
| | | ACCAGCGCATCCGGAGCCGGCTCAGGGCCGGACGAG |
| | | GGTGGCGCCCCCGGCAACAACGGCAGCGGCAGCTTCG |
| | | CGCTGCCCCTGTCTACCGGCGGCGGCGCACGCAGCCG |
| | | GCACCGGCGCAGCCCCAGTGACCTCAGCGAGCCCTCG |
| | | GCCAGCGGCCTGCCGGGCGCACTGCCACTGCCGCTGC |
| | | CCCTAGTGGCCGACAAGCCGCTGAGCGAGTTCGTGGG |
| | | CCAGACCCGCGCCAACGCGCTGGACCCGGCGCAGCTG |
| | | GACCCCAAGCGCGCGCGCCGCATCATCGCCAACCGGC |
| | | AGTCGGCGCACCGCAGCCGCATGAAGAAGCTGCAGCT |
| | | CATCCACGAGCTGGAGCAGCGGGTGACGACCGCGCGC |
| | | GCCGCCACGGACGCGGTGCGGCAGCAGAACGTCGCG |
| | | GCGGCGGAGCGGCGGCGCGAGCTGCTCACGGCGGCG |
| | | GCGACGGCGCAGCAGCAGCTGGCGGAGCTGCGGCGC |
| | | GAGGCGGCGGCTGTGGCGGCCATGCACAGCGCCCTGG |
| | | CGGCGGAGCTCGCCAAGATAGGCATCGCGGGGCCGCC |
| | | GCCAGCGCCCGCGGCAGCAGAGCCGGCGGCGGCGCC |
| | | CGCCGACGGCATGGAGGTTGGGCTGCGTGGCTCGAGC |
| | | GGCGGTGCGGTGGCGCCCGCGACGCCGCCTAATGGCT |
| | | CGGAGGTGGGCGCCGAGCTGCACGGCCGCATGTCAGT |
| | | CAACGGGGCCGCCACCCGCGCCGCCGGCGGCCCGTCG |
| | | GCTTCCGGCAGCTCCGGCACATCGGCGTCCATGGGTC |
| | | AGGCTGGGGCTGCGGGCTCCCAGCCTGGCGGCGCGGC |
| | | GGTGCCTGAGAGCCCCTTCCTCCTGCCGCACCTGCCGC |
| | | CGCCGCACATCATGTCCGCTCACACCGCCGCCGCGGC |
| | | TGGCAGTGGCGGTGGCGGCGGCTCGTTTTCAAACCAC |
| | | CACCATCACCACCACAGCCACAGTCACAGTGGGAGCG |
| | | GCAGCGCTATGCCGCTGCTGTCCGCTCCCGGTGCCGC |
| | | CTCCTACACCTTTGGGCAGCAGCACAACCCAGCCCAC |
| | | CAGCAGCAGCACCAGCAGCAGCCCGCGCCGTTCCTGC |
| | | AAGGTGCCCTGCCGCAGCACACGCAGCTGGCGCACCC |
| | | CGCGCCCTCGCACAGCCGCAACCCCTCCGCCAGCAGC |

TABLE 8-continued

| Transcription factor library. | | |
|---|---|---|
| | | CTGGCCGGCCCGGCGCCTTCGCAACCCAGCGCCGCCG<br>TGGAGGCTGCGGCTGCCTTCCAGCAGGCGCCCACAGC<br>CGCTGACGTCACGCCGGAGCCGGGCGCCAGGCAGGAT<br>GGCGGCGGCGGCGGTGGCGGCGAAGTGGCTCACGGC<br>AGTTCGCCCATGGCCCTGGACGGGTTTGGCCTGGCAG<br>GGCTGATGGGGCTGGGCATGGGCAACGACGGCCTGGC<br>AGGAGGCGGCGGCATCGGAGGAGGCGGAGGCGAGGG<br>GGAGGCGGGGGCGGTGGGGGACAGTGACACGGACGT<br>GGGCGACTTCTTGTTGATGGGCATGGGAGACGGCGAT<br>GGGGACGACACGGCGCCCACGGACGGGGCGGGATTG<br>TGA |
| 10 | 96 | ATGGCCCCCGCCCCAGCTTTCGAGCCGTCCTGCTCCAT<br>GCTGTCCGTCTTCAGCATGTGCACCGCGCTACCGCTGG<br>CGGAGCGTGACGTGAACGGCGCCGGCGCCTGCTTCTC<br>AGGAGCCTCCGCGCTGGCGTGCCCCTCCAAACCGGCT<br>TCGATACGCCGTGGGGCGTCGTTCCTCGATGTGGAGG<br>ATGCCTGTGTGGGCCTGACTAGCGCCGACCGTGCCTG<br>CTTCCTCATACCTGAGGACAGCGTGTATGTGTCGCCCG<br>CCTGCTCCGCTCGCGAGAACGCCGGCGCCGGCCCCCG<br>CCTGCCGCTGCCCAGCGGCACCTTCACCACCGCCGTC<br>GCCACCTCGACGAGCGGTGCCAGCCTCAGCGGCCTCT<br>CCGCTGCGCCCACCGGCTTTCTGGCGGGCTGCGAGGA<br>GTTTGTCCATGCGTCCGTGTGCTTTGAGAAGGCAGCCC<br>AGGCGCTGGAGGCCGTCACCCGCCCGCCGCCCGCGGT<br>TCCCTCGTGTAGCCCTAGCACGAGCTCCGGTGCCGCG<br>AACGGCGCGCAGGCCGACGAGCCCGCTGCCGGTCTCT<br>TCCGGCGCGTGAGCTCTCTGGCGCCCTCCCCCGCTGCC<br>AGCAGCCATGAGAACCACCAGCACCAGCACCAGGAC<br>GGCTCCTGTTGCTCTTCGGCGGAGGCGGTGGAGGCGC<br>CGGCGGCGCCCGTCGTGTCGGACGGTGCGGCGGCCTG<br>TGCGGAGCAGCTTCCCCAGCAGGTATTGCTGCCCCAG<br>GTGCCTCTGGAGCACCACCGGCATGAATACCTGGACG<br>CGTCGAGCGCAGCGCTGCAGCTGCAGGCTCAGCTGCC<br>CACGATGCTCGAGGAGCAGCAGCAGCAATCGCCGGA<br>GGAGGCGGCTCAGCCTGAGCAGTTGCAGCTGCTGCAG<br>GCGGTCCCGGCCCCGGCTCCGGCTCCCCGGGCCTTCC<br>ACCACAAGACTGGTGGCCCCTGTGATCACTGCGGCGC<br>CACGGAGTCGCCGCAGTGGCGCCCGCGGCCCGCCCGCC<br>AAGCCCATGCTGTGCAACGCCTGCGGCACCCGATACC<br>GCCGCACTAACCAGCTCGGCCCTGTGGGCGCACACAC<br>GCCGGCGGGCCGTGCTGCAGCCGCGGCAGCAGCTGCG<br>GGCGCGTCCGTGTCTGGCGGCAAGCGCATCAGCAAGG<br>GACACGGCGGCGCCGCGGCCAAACGCAACCGTGCGA<br>GCTACTGA |
| 11 | 97 | ATGGCTCCCACGGCATATATGCTCTTCTGCAATCAGCA<br>TAGAGAATCCGTGCGCCAGCGGCTAGCAGCAGAGGGC<br>CAGGAGAAGATAGCGGTGACGGTCGTGGCCAAGGAG<br>CTGGGCCAAATATGGAAAGCTCTTACCGAGGAGGAAA<br>AGGCCAAGTACCGGGCGCAAGCAGAGGAGCAGAAGC<br>AGCAGCAACAGCAGCAACAAGCGGGCGACGGGAGCG<br>AGACGCAAGGCGAGGGGAACGCGGAGGGGGGCCAGA<br>GGGCTGGCAGCCCCGCCAAGGCTGCCGCTGCTGCTTC<br>GCTACCGGCGTCCTGGGTGCGCAAAGTGGTCAACCTG<br>GACCCTGAAATCCAGCGCTGCTCCGCTGAGGGCGTGC<br>TGGCGCTGTCGGCGGCCGCGGAGGTGTTCCTGTCCGC<br>CGTGTGCGCCAAGGCCACGGCGGCGGCGGCGGCAGG<br>CAAGCGGCGCACGGTGCGCCTGGATGACATGGAGAA<br>GTGCATTCGGGGCGACAAGCGGCTCATGGCCGCGGGC<br>TTCACCGCCGTCATCAACATGGTGTCGGCTGCAGCGG<br>CCACAGAGGCGGAGGGCAAGGCTGCTGCGGTGGCTGC<br>AGCGGGCGCGCCGCCGGGAAAAAAGCAAAAGGTGGA<br>CAAGGCCGCCGCACCGGCGGCAGGGGCGGATAAGCA<br>CAACAGCATTGAGAAGGCGTTTGGTATGGCGTCATGA |
| 12 | 98 | ATGCGAGGCTCCACTGGCGGCCCCTGCTGCCACTGCG<br>GCACCGTCGCGACTCCCTGCTGGCGAAAGGGGCCCTG<br>CGACAAGCCGGTGCTCTGCAATGCGTGCGGCAGCCGG<br>TACCTGGTCAAGGGCTCACTCGCTGGGTACTTCCCTGG<br>CGCGCGCCGGGCGAGTGCGGGCACCCGTAGCGAGGC<br>GCCTCAGATTCAGGCGACCGTCGTTTCCGCGGCCGGC<br>AAGTCTGCTGCGCGGAAATCCGCCGCGCTGTCGTCAG<br>TAGCCGCATCTGCTGGTGCCAAGCGCAAGGTGCAAGA<br>GCTGGACGGGAACGAAACCGGTGCCAAGCGCATCTTC<br>AACAACTACGAGGCCCTGGAGGAGCTGCGCGCGTTCT<br>TTGCCAGCAGCCGAGGGCCGCAGGCGCCAGCCCAGAC<br>CTCGGACTCTCAGGACTCGCAAGGCCAATTCCGGGAC |

TABLE 8-continued

| Transcription factor library. | | |
|---|---|---|
| | | GAGGCGCAGTACCTAGACGCGAGCTCCGACGATGGCC<br>TGGAGCACCCCGACTCGGAGCCGGTGGCGGCTTTGCG<br>CCACATGCGTGCCCCCCTCAACGCCACCACGGCGGCA<br>AACTACTCGGCACCGCACGTGCCGACTTTCCAGCGGC<br>GGCCGCGCAAGCAGCTGCACCCGGTGCCGTGCTCCTG<br>CTAA |
| 13 | 99 | ATGGAGGCACAAATAGAGAAGCCTGAGGCAGATGCG<br>GAGCTGCCGCGAGCGCTAATTCGGCGAATTGTCAAGT<br>CTAAACTCGCACTCCTCGCGGGCGACGATGCAAAGGA<br>ATTCAGTGTGAATAAGGACGCTCTTACAGCACTTGCA<br>GAGTGCACCAAAGTCTTCATAAGCTGCTTGGCATCGA<br>CTTCCAATGACATTTGCCAGGAGAAGCGGCGGTCAAC<br>CGTGAACGCTGACGACGTGCTCACGGCGCTGCACGAC<br>CTGGATTTCCCAGAGCTCGTGGGGCCCCTGCGGGAGC<br>AGCTTGAAGCCTTCAAGGAGGCAGCAAAGGAGCGCA<br>ACAAGAACCGGCAGCAGGCCGGCGGCAACAAGAAGC<br>GCAAGAGCGGCGCCGCAGCCGACGAGCCGCCCCCAG<br>TGGCGCCGCGCAGCTCTCTGCAGGCGGCGCCAGCGGA<br>GGCCGCGCCGGAGGCTGAGGACGGCAGCGGCGGCGC<br>GGGCCCCAGCCATGCCGACGACGACGACGACGGCGC<br>ACTGGTGCCGGGGACCGGCATGGGCATTGGCGGCGCC<br>GGCGGCTTTGGCGAGGACGGGCTTGGAGGCATCGGGC<br>TGGGTGTGGGCATGGGCGTGGGCGTGGGATTAGACGC<br>GCCGGGGCTGGCGCTGTCTCCTGGCGGCCTGGCGATG<br>GGCGGCGCGGAGGCCGGCGCGGTGGCGGCGGCGGAT<br>GTGGCGGCGCACCCGCAGCAGCAGGAAGCGGCAGGT<br>GCTGCTGCGCAACAGCAGCAGCGAGCAGTGGAGGAA<br>GTGGCGCCGGAGGCGGTGGTGGAGGAGGAGGTGCAA<br>GTGGAGGACATGTTGGTCGACGCGCTGCCGTGA |
| 14 | 100 | ATGGACGGCGCCTTCCCCAATCGTCGGGGGGACGGAT<br>ACGGGGGCAGCCAGGGTGATGGCGAGGGCCAGGGAG<br>GGAAGCCTCGCGGCTTCAGGGGCACCGCGGAGAATGC<br>CAAGACCAAGGTCTGCACTAGGTGGCTGCAGGGCGAT<br>TGCCGCTTTGGCGCGCGCTGCAACTTTGCCCATGGCGA<br>GCACGAGCTGCGGAAGCTGCCCGAGCGTCAGGGCGG<br>GCGCGGTGGTGGTGGCCGGGGCTATGGAGGCAATGCT<br>GGTCCCTACGGTGGCCGGGGCGGCTACGGCGGTGGTG<br>GCTACGGCGGCCAGCCCGGCATGCCCGGCGGCTACGG<br>CGGCGGCCAGGGCGGCGCGCCCGGCCCCAACGTGTCG<br>GAGGACGTGTGGGCGGCGCAGGGCTACCCGGTGCAG<br>GGCCCTAACGGTTGGGTGCAGTACCGCACCCGCGACA<br>CCGGGGAGCCCTACTTCCACAACCACCGGACAAACGA<br>GACGGTGTGGGACCGGCCCGCGGACTGGCCGGTCACG<br>ATGCAGGGCCAGATCTGA |
| 15 | 101 | ATGCTGTTCAATCCACCTGAGTGGGCCAGCCAACCCT<br>GTAGAATCGCGAGCCTTGAGGTTTATTCCGGCAACCG<br>ACGGATTGTTGTTCATCCTGTGGACATCGAGCCCTATT<br>ACACGTTCGGACGGCAAGCTGAGTCGGTGTCAATTGC<br>ACTCGAGCACCATTCGTGTAGCCGCGTGCACGCTGCT<br>CTCGTCCACCACAACGACGGTCGCATCTTCTTAATCGA<br>CCTCCAGTCGACACAAGGCACGACTGTTGACGGCCGC<br>CGCATCGCACCCAACAAGCCGGTAGTGCTTAAAGACA<br>ACACGCGCATTCGCTTCGGCGAGCTAGAGTACGACTA<br>CGTTCTTCGCTGCGAGTCTGCAGCCGAGAAGCGCTCC<br>GCCGCCGGTGACCCCGACGCCGCCCACGCGCAGCCGC<br>ACAAGCGCGCCGCCATGGCCGACGCCCGCGTCCGCGC<br>CTCCCACCTGCTGGTCAAACACAAGGACGTGCGCCGC<br>CCCAGCTCCTGGAAGGAGCCCGTGGTGACCCGCACCC<br>GGGAGGAGGCGCTGGCCATGATCGAGCACTTCCACTC<br>CATGCTGGTCAAGGGCGAGGTGGAGTTCGCGGCGCTG<br>GCCGCACAGGAGAGCCACTGCAGCAGCGCCAAGCGC<br>GGCGGGGACCTGGGGGAGTTCGGTCGCGGCGAGATGC<br>AGAAGCCGTTCGAGGACGCCACCTACGCCCTCAAGGT<br>GGGCGAGCTGAGCGGCCCCGTGTTCAGCGACTCGGGC<br>GTGCACCTCATCCTGCGCACAGGCTGA |
| 16 | 102 | ATGTCCGGCGACAGCAGCGCCGGCGAGCGCCGTAGGC<br>GATATCCACTGGCTAACATAAAGGGCGGCTGGTCTGC<br>GGTGGAGGACACAACACTGAAGAGGCTTGTGGAGGA<br>GTTTGGTGAGGGCAACTGGAGCGTCATCGCCCGTCAC<br>CTTAACGCATCGCTGGGCAAGCCCTCGGACTCGGGCC<br>GCATCGGCAAGCAGTGCCGCGAGCGCTACAACCACCA<br>CCTTCGGCCAGACATCAAGAAGGATGCCTGGACTGAG<br>GAGGAGGAGTCGCTGCTAGTGGCGGCACACCTGCGCT<br>ACGGCAACCGCTGGAGTGACATCGCCAAGGTCATTCG |

TABLE 8-continued

| Transcription factor library. | | |
|---|---|---|
| | | CGGCCGTACCGAGAACGCAGTGAAGAACCACTGGAA<br>CGCAACCCTGAGGCGCAAGGACGGCGACAAGGCCAT<br>CCGCAGCGGTACCGCACCGCAATCGTGCGTGCTTAAG<br>AACTACATGATCCGCCTGCACCTGCTGCCCGGGCCAC<br>CAGTCGGCCCGACCGCCGCCACGACGGCACTGCCTGA<br>CAACGCGGCGGCTGCCGTTGCACCGCTCCCCGCCAAG<br>CCCGTCGCCAAGCGCGCCCGGTCCTCGGTGGCGGCTG<br>AGTCTCCCAAGGTCGCTGGTGGCGTCCACCCAGCGGA<br>CCCGGCGCAGCCCGGCCCATCGCCCTCCTCCTCCACC<br>AGCACTCACGACGGCGTCAGCTCCAGCCCGCACCGCA<br>GCTTTGATGCCAGCGTGGCGTCGCCGGCCGGCGGGGC<br>AGCCGCCAACCGCAAGCGGCCGCGCATCATCACTTTT<br>GCCGCCGCGCCCGACCCGGCGGCCGCTATCGCAGCCT<br>CCACCCTGTCGCGTCACGCTTCGCCGGCGCCCCTGGCT<br>GCAATGCCCATGCAGGACGGCATGCCCATGCCCCTCT<br>TCGCGCCGCTGTCGCTCCTGGCCGTGCCCAACTTAACC<br>GGCCAGGTGACAGCCGCGCCCACGGCGCCCGTGGCGA<br>TGCGGATGCAGTTCCAGATGCAGCAGCAGCAACAGCA<br>AGACATGCACCCGCAGATGCAGCAGCAGGTGGCCATG<br>CAGCCGTCCGCGCCGGCCATGCGTCGCCCCAGCCCGC<br>GTCCGCAGCCGGTGCAGCAGCAGCAGCAGCAGCAGC<br>AGATGCGCGGCAGCAGCCAGCCGCGCACGTCGCAGCC<br>ACCGCAGCGCGGCTCGGCGCCGCTGGGCTGGGCGTCC<br>GACAGCGCCGAGGACAGCCTGTACGGCAGCCCCGTGT<br>CTGACAGGTTTGTGGACATGCAGTTTGAGGAGGACTA<br>CCTGTGCAGCCACGGTGCCGGGGGCCAGAAGGCGGCA<br>GCGATCGCAGCCCCGGCCTCCTATAAGGCAGCTGATG<br>AGACGCAAGGGCAGGAGCTACAGCTGCAGTTGGCGG<br>GCGTGGGCAGCAGCGAGGTGCAGGCGGCGCAGATCA<br>TGCTCGCCCTGCGGAGCCTGGCGGGCGGCCTGTGA |
| 17 | 103 | ATGGCGCCGAAGGCAGCCCCCAAAGTAGACAAGGCG<br>AAAGCGGCTGCCAAACAGAAGGCCGCTGAGGACAAG<br>ACTTTCGGCCTTAAAAATAAGAACAAGTCGGCCAAGG<br>TGCAAAAGTATGTGCAAAACGTCAAGACGAACGCGAC<br>GCAGAACCTTGGCGCCTACAAGCCCGTGGAGGCGAAG<br>AAGAAGGACAAGGCTCCGGATGAGCTGGGCAACATTT<br>TTCTGCCGACCATTAAGCAGCCAAAGGTGCCGGACGG<br>CGTGGACCCCAAGTCCATCGTGTGCGAGTTCTTCCGCC<br>ACAACCAGTGCACCAAGGGCAACAAGTGCAAGTTCAG<br>CCACGACCTGTCGGTGGAGCGCAAGGGCCCCAAGATC<br>TCGCTGTACGCCGACCAGCGCGACCTGGGCAAGGACG<br>GCGAGGACAAGGAGGGCATGGAGGACTGGGACCAGG<br>CCACGCTGGAGGCGGCGGTGAAGCAGAAGCACGCCA<br>ACGAGAACAAGCCCACGGACATCATCTGCAAATTCTT<br>CCTGGAGGCCGTGGAGAAGAAGCTGTATGGATGGTTC<br>TGGAAGTGCCCCAACGGCGAGGACTGCAAGTACCGGC<br>ACGCGCTGCCGCACAACTACGTGCTCAAGAGCCAGAT<br>GAAGGAGCTGCTAGAGGAGGAGGCGCGCAACACCAA<br>GGACATTGCGGAGTCCATTGAGGAGGAGCGCGCCAAG<br>GTGGTGGCGCGCACGCCCATCACCCAGGAGACGTTCA<br>GTGCCTGGCACCGGGCGAAGCGCGAGGCCAAGGCGG<br>CCAAGCGGGCGACGGACGAGGAGGAGCGGCGCAAGA<br>AGGGCATCCTCAACGGCCGCGAGATCTTCATGCAGGA<br>GGGCTTCGTGGCCAACGACGACGCCAGCGCGGCGGAC<br>GAGTACGGCTTCGAGGTGGACGAGGAGGAGGAAATC<br>AAGGCCATGATCGAGCGCGCGGCGGCGGCGGCGGAG<br>GCGGCCAGGCAGCAGGCGGAGCTGGGGCCAGTGCCG<br>GAGGAGGCGGAGGAGGCGAACGAGGGCGCGGGGCCA<br>TCCGGCAGCGGCGCCGGGCCATCCACACACCTCAACC<br>TAGAAGACGAGGAGGCGCAGGAGCTGTTCGATGACG<br>ATGATGACGACGACGAGGAAATGGAGGACGACGAGG<br>AAATGGACGACGACGACGACGACGACGACGAGCTGG<br>AGGGGCTGGAGGACCACGTGAAGGGGATGCACGTGG<br>GCGGGGCAGCAGGGCAATGA |
| 18 | 104 | ATGAGCGGCGAGCCCTCGCCCCTCGAGGAGCAACCGG<br>ACCTAGATAACTCTGAGGACCTACACAACAGCTCTGA<br>CGCTGCGAACGCCAGCAGCCGGAAGGGTCAGCCATGG<br>AGCGAGGAGGAGCACAGGGCGTTCTTGGCAGGCCTGA<br>AGTCACTCGGCAAAGGTAGCTGGCGACAAATTAGCCA<br>GCAGTTCGTGCCGACGCGGACCCCTACGCAGGTGGCC<br>AGCCACGCACAAAAGCACTTTATGCGTGTAGCCGGTG<br>CTACCAAGCGGAAGAGCCGCTTCACGGCGCTCGAGAC<br>CGAGGTTCTGCCGCCCGCCAAGATTGCTCATGTTGATT<br>CGAGGCAGCACGGTTCGGAGCAGACGGAGCAGCTGG<br>AGCCGCAGCCCCAGGCGCAGGCGCGACAGCCGGCGA<br>TGGCCCCGCAGGCGCAGCAGGCAGGCGCACCCGCGG |

TABLE 8-continued

| Transcription factor library. | | |
|---|---|---|
| | | CCTCGCAGTTTGGGCCGATGGCCGCCTTTGGGCCTATG<br>GCTGCGTTCCCGTTCATGAACCCCATGATGTTCGGCTT<br>CCCGGCGCCCTTCTTCCCGCCCTTCATGTGCCCGCCCC<br>CCGCCTTCGCGGCCGCGGCGATGCAGAGCATGAACGC<br>GATGCAGAAGTCTGGTATGGCTCCCGGCATGATGATG<br>CCGCCGCTGTTCGCGCCCATGATGGCCGCCATGGCCG<br>CAGCCTCCACGCCCTTCTTCATGGCGCAGCAAATGCA<br>GGCCATGGCGGCGCAGGCGGCGGCAGCGCAGCAGCA<br>GGCGGCGCAGGCCGCAGCGGCACAGCAGCAGCAGCA<br>GTACGCAGCGACGCAGGCGGCCACCAGCGGCGCCGC<br>CACCACGGCCGGCACCGCCACCGCCACATCCGACACA<br>GCCAACAGCGATGACGCGGTGCGGCGCCGCCACGCCT<br>CCGTCGCCGCGCCCAGCGTTGGCAACAATGCCGGCTT<br>GGGCGGCTCCTCGCCTGCGGTCAAGGCCGAGCCCGTG<br>TTGCACGTGCAGATCCCCGCGCGGCCGCCGTCGGCCT<br>GCGGCGTCGCCGGCAGCACCAACACCAGCCCAGGCCG<br>TGTTGCGGCCGCGACGCCGGGGCCTGACGCAGTGGCG<br>GCGACGGGCGGAGAGTCGCCGGCAGCGGCACAGGCC<br>GGCGCCAGCAATGCGGCGCCGCCGCGGGAGCAGGCG<br>AAGAGCTGTGGCGGCGCCCCTGGCGGCGTTGGTGCCA<br>GGTGTAGCGGCAGCGGCGTGGCGGTGCCCGCGGGCGG<br>CTGCGGCCTGGAGCAGCAGCAGCAGCCGCTGCAGCGG<br>CGGGTGTCGGGTGGGCGCGGCGAGGAAGGTGGTGCG<br>GCGTTGCCCTTCCATGCGTCCTCGCACTCGGCTTTCCG<br>GCCGCCGCAGGCGCAGCAGGAGATCAAGGCCGAGAG<br>CTAG |
| 19 | 105 | ATGGTAGACGGTGGTTCGCGTGCTGCCTCTGGCCAGC<br>TGGATGACTGGGCCGCAGGCGTCGCGGCTGACCTAGA<br>CCAGGGAGAGGGCGACCGCGCAGGGGCGAGGCGACG<br>ACCTGCGCGCGACGCCAGCCCGGCGCCGGATGCTCGC<br>AAAGTGACAACGTTCACAAACAAAAAGCGCCCGGCAT<br>CGGACAGGGACAGCAGCCCGGAGGAGGACGACGAGG<br>AGCAGGCTCAGAAAGGCTCCCTCAAAGCGGATGGAAC<br>TCGCCCCAAGCTTCCACGCCCCGACAAGAAGGAGGCA<br>TGCCCTCGCTGCAACAGCATGGACACCAAATTCTGCT<br>ACTACAACAATTACAACATCAAGCAGCCCCGCTTTTA<br>CTGCAAGACGTGTCAGCGGTACTGGACTGCCGGCGGC<br>ACGTTGAGGAACATCGCTCCGGGCTCCGGTCGGCGCA<br>AGAGCAAGAGCAAAGCCGCGCGTGAGAAGAACAGCC<br>CCTCGCTCGCCGAGCAGCTCACGGCGGTTGCGGCGGG<br>ACAGGGCATGTTCGGGCTCGGAGGCGGGGGCGGGTAC<br>AACGGCATCAGCCCGGCGCTGGCGCTCGCCGCGGCCA<br>CCGATCCCACAGGGCTGCTGGCCGCGAATAGCGCCGC<br>GGCGTACGGTCTGGGTGGCCACGGAACCATCTCCGGC<br>CTGAAGCTGGGCGGTGTGGGTGGGCTGCCGGCGCAGT<br>TCAACAGTGAGTTGGCGCTGCGGGAGCACCTTGCAGG<br>GCAGCACAGCCTGGAGACACGGCTGCTGCTGAACGGG<br>CACCTCAGCGCCGAGGACCTGCCGAACGGCATGTCGG<br>CGGCGGCGCTGGCACAGGCCAGTGCACAGCTGCACGC<br>TCTGCACGGGCAGGGCAGTGGCATTGCGCAGTCGCTG<br>GCGGCCGGCAACGGGCACACGGGGTCGCCCTCGCCCT<br>CACCTCCTCCGGCCGGGAACGGCGGGCAGCAGCACCC<br>GCTGTCTTCCTCCCCGCAGCACGGCGGCGGCTCGCAG<br>GCCTCGCAGCAGCCGTCTCCTCCTCAGCAGGGCTCGG<br>ACGACGCCGAGGGCGGTGGCGAGGAGCGCTATGTGG<br>CGCAGGGCCGCCGCGTGCGCGTGAAGGCGGAGTTGGA<br>CGGCAACGCCGTCAGCAGCAGCCTCGCAATGGGCGGC<br>GGCGGTGGCTCGGGTGCGTACGCCAACGGCGCTAGCA<br>TTGCCTCCTCCATTGCCAACGCCCAGCTCGCGGCCAGC<br>CTCAGCATGCCGCCCAGCATGGGCGCGCTGGCGGCTG<br>TGATGGGCCCTGGCGGCGGCCCCAGCGGCCTCCACCC<br>ACTGCTTGCGCAGGACAATGGTGGCAGCCTGCTTGAC<br>GCCGGCCTGACGCGGCAGCAACTGCTAGTGCTGCAAC<br>AGCACCAGGCCATGCAGCAGGCGCAGCAGCAGGAGA<br>GCCTCCAGCAGCTCAGCAGCTTGCAGCAGCTGCAGGG<br>CCTTGCCGCGCTGCACGGCCAGCACTCGGCGGCGGGC<br>CTGGCGGGGCTGGACCCGCTGCAGCGCAGCGCGCTGC<br>TGCACTCGGCGGCCGGGCTAGGCGGCGTGGGCGTGGG<br>TGGCTGGCTGCAGGGCGGCGGCGGAGGGAACTCGCTC<br>GCAGCCGCTGCTGCGCTGGAGTCGCTTCAGGCGCAGC<br>ACCTTCTCCAGGCGCAGCAGGTGCACCCCTCGGCGGC<br>CGCTGCCCTCATCGGTGGCGGTGGCAGCAGCGCCGCA<br>GCGCAGATGTTGCAGGCGCAGGCCGCCGCCGCCGCCG<br>CGGGTGGGGGCGGAGGCTGGCAGGGCGTGGCCTCAG<br>CAGCGAATTGGCCGTCGGCCTGGTCGTCGTACAGCGG<br>CCCGTCGTCTGGCAGCTACGCCGGCTACGCACTGCAG<br>GCGGCGGCCGCTTACTCGGGTGCTAGGTGA |

TABLE 8-continued

| Transcription factor library. | | |
|---|---|---|
| 20 | 106 | ATGGACCAATACCAGCTTGCTCAGCTTCAGCAGCGGT<br>TTCAGGAGGTTAACCTGAGCGGCGGGGTTGACCAGGG<br>CGCCATGCTCAAGTCAGCAGGTGACCTGCTGTCATCC<br>GCTGAGGCCACAACACAGTACAGCTCATCAGAGTCTA<br>GCTCTGGAGCCGACAACTTGAACCAGCTGGACAGCTC<br>CAGCCTCCTGGACACAGGCATGCTCGCTACAGCGCGG<br>CAAAGTGATGGCGCGCGCTCTACCGGGCAACCGTCGC<br>AGGAGGGAAAGGCGCAGATTTGCTTCGACTTCACAAA<br>GGGCGTGTGCTCACGTGGCGACAAGTGCAAGTACTCG<br>CACGACCTCGCAACCATCGTGCATTTCAACAGCAAGG<br>AGAAGGGCATCTGCTTTGACTACCTGCGCAACCAGTG<br>CCACCGCGGCCTCCTGTGCCGGTTCAGCCACGACCTCT<br>CAAACATTGCGCAACAGTGCCAGGTGAACAACGGTGT<br>AGCCCGCGGTCCGGCACAGGGCGCCAAGCCAAACGC<br>CATCTGCTACGACTTCGTCAAAGGCGTCTGCCAACGC<br>GGCGCGGAGTGCCGCTACAGCCACGACCTGTCCCTCA<br>TCGCGCGCATGGCCCGCGGCGGCAGCGCGCAGCCCAA<br>GGCTGGCGAGGTCTGCTACGACTACCTCAGGGGCCGC<br>TGCAACCGCGGCGCCACCTGCAAGTACTCGCACAACA<br>TCGCCTTCCTGGCGGCGCCCGGTTTCCTGGGCAACGCC<br>ATGTCGTCGGACGGTGTGCCCATGGCTGCGCAGGCGC<br>CGGGCGGCCACATGTCGGCTGGCGGTGCGCCGCCGCT<br>CGGCCCCATGCCTGTCCCCGGCGGCCCAGGCTTCATG<br>GGCATGGGCGGCATGTCCGGCATGGGCCCGCGCCCCC<br>TGCACACCGCGCTGAGCGCCGACCAGGCCACGCTGAG<br>CCACGTCCTGGCGGCGGCGGGGCCGGGCGCCGTCAGC<br>CAGATGCTGGCGGCACAGGCGGCGGCGCAGCAGAGC<br>AACGGCTTGGCGGCCGAGGCGGCGGACGGGCGCCGG<br>CGCTCCAACAGCCTGAACGGCGACATGGGCAACGACA<br>CGCTCGCCGTCAACGACCAGCCGCACTGGAACGCCAA<br>GGGCCTGGCCATGGCACAGCACGCGGCCATCATGCAG<br>CGCATGGCGGGCATGGCGGCGGCTGCTGGCATGCAGC<br>AGGCCTTCGGCGGCGGCATGGGCCAGGGCATGCCCGG<br>ACGAGGCATGCCGCCGGGCGCTGACGCCATGTCCCAC<br>TTGTACGGCAAGCCGCCGCCATCCATGGGCTCCTACG<br>GCGGCCACGACACAAGCGCGGGCATGCGGCGGCCGC<br>CGCTGCCGCCCGGCGGCGGCAGCGTGCCCGCCGAGTT<br>TGCGGCCCTGCTGGCGGCCGGCGGCATGGCGGACAGT<br>CATGCGCTGTACGCTGAGACGATCAAGGCGCAGCTCC<br>AGGCGCAGCAGGGCGCGCGCATGGTGCCCAACCTCAG<br>CGGTGGCGGCGCGCCGCCCATGATGGCCGCTGCGCCG<br>CAACCCATCCCCGGACGCGACAGCCAGGGCTACGACG<br>TCGCCGCGGCGCAATACGCGCAGCAGGGCGGCTCGCA<br>GTCTGGCGGCGGCGCGCCATCCTCGGACAGCGGCAGC<br>CTCTCGCGGAGCGCGCCGTCGGCAGGCGCCCCGGTCA<br>ACCCCGACCTACTCCCGATGATCAAGGAGATTTGGAG<br>CAAGCCCGGGCAGATAGCGGCATGA |
| 21 | 107 | ATGACAATCCCTGACGAGGAGGTTCTCACTAAGCTGC<br>GTGAGCTTCTGAAACACGCAGACCTGAATGTCACCAC<br>CGAAAAGATGCTGCGCAAGCAGCTTGAGGAGCACTTT<br>AAGCAGGACATGACAGACCGGAAGCCCATTATTCGAG<br>CCGAGGTTGAGCGATATTTAGCTGAGGGAGCAGGGGA<br>TGAGGAAGAGGAGGAGGAAGAGGAGGAGGACGACG<br>ACGACGCGCCGGCTCGGGGAAGCGGCATGGGCTCGTG<br>GTTGTCAGAGCCGCTGCAGGCCTTCCTGGGGGTGGAG<br>TCGCTGCCCCGCACGCAAGTAGTCAAGCGGCTGTGGG<br>AGTACATCAAGGCCAACAACCTGCAGGACCCCAAGGA<br>CAAGCGCAAAATCCTGCTGGATGACAAGCTCAAGACA<br>TTGTTCACCTCGCCGCTCACCATGTTCACCATGAATTC<br>GCAGCTGAGCAAACACGTCAAGGTGTATGACGGGGAC<br>GATGAGGAGCCCAAGGCCAAGTCAGCCAAGCGGCCA<br>GCGAGCAAAGCGGGCAAGGAGAAGCCCAAGAAGGTC<br>AAGACCGAGATGGATGAGGAGAAGCGGAAGAAGAAC<br>GCGTTCACCAAGCCCGTGCGGCTGTCCCCGGAGCTGG<br>CGGCGCTGACGGGCAAGGAGTCCATGGGGCGGCCGG<br>AGGTGACGTCGTTCTTCTGGGCGTACGTCAAGGAGAA<br>GGGCCTCAAGGATCCCGCGAACGGCCAGTTCATTATC<br>TGCGACGCGGCGCTCAAGAAGATCACAGGCGAGGAG<br>CGCTTCAAGGGGTTTGGCTTCATGAAGTACTTCGCGCC<br>GCACATGCTCAAGGACTGA |
| 22 | 108 | ATGGCGACCAACCTGTGCGCCGAGTGCGGCATAAAGC<br>TGTCGCGGCCCGAGTATCAGAAGCACATGCAGGAGGT<br>GCACGGCGTCTCCATCCAGCACGACAGCGACGACGAG<br>CGCGATAAGGAGGCCCCGGCCGCCGGCGAGGACGGC<br>GCCGATGCCAAGCCGCAGCGCCAGCGCCGCCGTGGCG |

TABLE 8-continued

| Transcription factor library. | | |
|---|---|---|
| | | GCAACAAGGAGGGCGCCGCCGAGGGCGCGGAGGGTG<br>CCGAGGAGGGCGCCGCCGGCGAGGACGGCGCCCGGC<br>CTCCGCGCGAGCGTCGGCGCCGCGGTGGGCGCAAGCC<br>CGCCGGTGAGGGTGCAGATGGCGAGGCTCCCGCTGGC<br>GACTTCGCCTGCGGCGACTGCGACCGCACCTTCGCCA<br>GCCAGCAGGGCCTGAGGCGCCACCTGCAGGCCAAGC<br>ACCCTGAGTCTGAGGCGACGGCCGCTGCGGTGGCCGC<br>CGCGGCAGCCGAGGCCCCGGCGGCCGGCGCGCGCCGT<br>GGTGGCCGCGGCCGTGGCCGCGGCACCAAGGCCGAG<br>GCCGGTGAGGGCGCCGCGGATGGCGCGGCAGCTGAC<br>GGCGCGGAGGGTGCCAAGCCCGCGGCGGGTGGTCGC<br>AGCCGTGGCCGTGGCGGCCGCACCGGCCGCGGCCGCG<br>GCGCCGCCGCTGCCCCCGTGCCGGACGACCCCACCGC<br>CGCCGCTGCAATGGCTGCGGCTGCGGCCAAGGCGGCG<br>ATTGGCGGCGCGGCCGCTGAGCCCGCGGCGGAGCGTC<br>AGGTGACGCTGTTCCGCTGCAAGCAGTGCGAGCAGGG<br>CTTCAAGAGCCGCAATCGCGCCCGCGAGCACGTTATT<br>GAGGCACACGCCGCCGACGTGCCCGCGGAGGCCCCTG<br>CCGAGGCGCCGGGCGTCAAGCCGCCGCCGCCGGAGG<br>GCGTGGAGCTGCCGCCGGGCCGCCGCGCGCCGGCGCC<br>GGTGGTGCCCGTGCCCGCTGACGCCCTGCTGGAGGTC<br>GCGGAGGTGACCACCAAGCGCGCGCCCCGCGCGTCGC<br>GCCGGCGGAAGCCGCGCACGGCCAACGGCGACGAGC<br>CGTCAGGCGATGCGGCGGAGGGCGAGGAGGGCGCCG<br>CGGAGGGCGGCCGCGCGCGCGGCGGTCGCCGCGGTG<br>GTCGCGGCGGCGACGCCGCGGCTCCGGCTGCCGGTGG<br>TGACGCGGCCGCTGCCTCCGGTGATGCGCCCGCGCCT<br>GCTGGCGGCGCCAAGCGCAGTGGCGCGCCCACGGAC<br>GAGCTGGCGGCTCTGGGCATCACCGCGAGCTAA |
| 23 | 109 | ATGGCGCTTCCAGGCTCCACAATGAACCTTACAACCC<br>GCTGCTCTACTACACCGCGGTCGGCTGTGGTTGCGCGC<br>GCGGTGGCTGCGCCCACGCGACCCACCACCAAGTCTG<br>CGGTGCCAGAGCTGCTGGATAGCCGGCCAGGCGAGCG<br>CAATCTCAACTTCATGGAGTATGCTCAGGCGACTCAG<br>ATGCTGGACCGGCTCAAGGGCCAGGCCTCTGACCTGG<br>AATTGCTGCTGGACCAGCTCAACGCGCTGGAGGCCAG<br>CCTCGACGAGAGCGTTCTGGCGCCGCCCACGGTGGAC<br>GACCCCAAGGAGCGGGCTGCGCGACAAGCACGGCGC<br>GCTGCCAAGCGTGCAGAGCGTAGGGCCCAGGCGACAT<br>CCGCAACAGTCGCGGCCGCGGCTGGGCCGGCAATGTC<br>AGCAGTGGTCTCGCATTCCACGCCGACGAAGGCTGCT<br>GCTGCGCCGGCCACGTCAACAGCGAGCAGCAGCTCCA<br>GCGATAGTGGTTTGCTAGACCTGGTGAGCTTTGTTGGC<br>GGCTTTGACACGCGGCCGATCCCGGCAACGACGTCTG<br>CACCCCCTGCTGGCGCCAGCAGCTCCGACGTGCAGCA<br>CCTGGAGGACCTCTTCAAACTCAGCGTCGGCGAGCCC<br>GACATCCCCCGGGCCTCCGCTTCAGCAGCGCCTGCGG<br>TGCTGCGGCCACGCAAGCTCACACCAAAGAAGCCCTC<br>TGCGGCACCCTCCGCGGCGGTGACGGCAGCACCCTCG<br>CCGGCACCCACGCTCCCCAGCACGCCCAGCACCAGCG<br>CGCGCATTGCGCCCGCGCCCGGCTCCCTCGCGGATGA<br>GCTGGAGCGGTTACTGGGGCCCACCACGTCACGGGAG<br>GCGGCTGAGTCTGAGGACGAGGACAGCTTCGCGGGGC<br>CGTCTGAGGACGACCTGCTGGCGCTGGAGCAGGAGGT<br>GTCGCGCAAGTCGTCACGGCTGCCTGTGCTAGACGAG<br>GAAGACGAGGAGGATGAGCAGCAGCAGCTGGAGGAC<br>AACGAGGAGGACGCGGTGGCGGGGCCCGGCTCTTTGG<br>AGGCGTCGGCAATGGCGACTCGGACGTCCAGCCAGCT<br>GTCCATCATGCAGACGGGGCCGTCGCTGCTTAGCCTG<br>GTCCCAGCATCCGCGGCGCCAGGCCGCAGCGCCAAGG<br>CGCGCGCCTCCCGGCGCGCGGCGCGCAACGGTCACGC<br>TAGCGGGCGGCTGGGTGGCGCGACAGCTAACGCGGCG<br>GGGCGGGGCAAGGTGGGCAGCAAGGACGGGACCATG<br>AACTTCCTGGGCAAGGTGGAGTCATTGTCAACGCTGG<br>ACGTGGAGAAGGAACGCGAGGTGACGGCAGTTTGCC<br>GCGACTTCCTGTTCCTGGAGAAGGTGAAGCGGCAGTG<br>CGAGAAGACGCTGCACCGGCCCGCCACGTCTGAGGAG<br>ATTGCGGCGGCCGTGGCCATGGATGTCGAGAGCCTGA<br>AGCTCCGCTATGACGCCGGTCTGAAGGCCAAGGAGCT<br>GCTGCTCAAGTCCAACTACAAGCTGGTCATGACGGTG<br>TGCAAGTCGTTTGTGGGCAAGGGCCCGCACATCCAGG<br>ACCTGGTGTCGGAGGGCGTCAAGGGCCTGCTCAAGGG<br>CGTGGAAAAGTACGACGCCACCAAGGGCTTCCGCTTC<br>GGCACGTACGCGCACTGGTGGATCCGCCAGGCCGTGT<br>CGCGCTCGCTGGCGGAGACGGGCCGCGCAGTCAGGCT<br>GCCCATGCACATGATCGAGCAGCTGACGCGGCTCAAG<br>AACCTGTCCGCCAAGCTGCAGACGCAGCTGGCGCGAG |

TABLE 8-continued

| Transcription factor library. | | |
|---|---|---|
| | | AGCCCACGCTGCCCGAGCTGGCCAAGGCGGCTGGTCT GCCTGTGACGCGCGTTCAGATGCTCATGGAGACGGCG CGCTCCGCCGCGTCCCTGGACACGCCCATCGGCGGCA ACGAGCTGGGCCCGACCGTGAAGGACTCCGTGGAGGA CGAGCGCGAGGCGGCGGACGAGGAGTTTGGCAGCGA CAGTCTGCGCAACGACATGGAGGCGATGTTGTTGGAG CTGCCGGAGCGCGAGGCGCGCGTGGTGCGGCTGCGCT TCGGGCTGGACGACGGCAAGGAGTGGACGCTGGAGG AGATTGGAGAGGCGCTGAACGTAACACGCGAGCGCAT CCGTCAGATTGAGGCCAAGGCGCTGCGCAAGCTGCGT GTGAAGACTATTGACGTGAGCGGCAAGCTGATGGAGT ACGGCGAGAACCTGGAGATGCTGATGGACGGCTCGCG CGAGATGGCTGCGCGCACCAGCAGCGGCACCCGCAA GACGTAA |
| 24 | 110 | ATGGACGTGGATGGCCTGGACCTGGCGGCCCTTCTGG CTGAAGGGCCAGACTCGGGAGTCGGCCCGTCGCTTCT GGACGATGAACTGTTTTCCGAGGATCTGATGCAGTTCT TGGAAACGATAGAGGGCCAGCCGACTTCAACGCAGTG CCACCAGAAGCTAGCCGCACAGCAACAGCAGCAGCC GGTGCCGGCGCCTGCCCCAGCTCCTGCTCCCGCGGTG CCCATTCCTGTTGCGACCTCCTCGCCCGCGGTCGCGAT GTCGCCCACTGCGTCGACCTCGTCCGGCTGCTCTTCGG GCGTCGTGGCTGCACCTGCGCCCATTCCTACACCAGTA GCGCCAGCAGCTGCGGCCGTGGCCCTGGCTGCGCTGC AACAGGCGCAAATGCAGCAATTGCAGCCGGCCTGCGC TGCCATGCTGCCGCGCCTGGTCACCACAACAGCAGCG CAGCAGATGTGGACTGCTATGCTTCAAGCAGCGTGCA CAGTTACGCCGGCACTGGCTGCCGCTCACGCACCTGC TGCGGCCTCGGTCGATGACGCTAAGGCGCGCGCCCAG CCCGCTGGGACGAGCCGACAAGGAAGCCGCGAGGAC TCCGGCGACTCCTCCGACACCGACCAAGATGATGATA TGGTGGACTCCAAGGGCAAGTCCGTGGGCAACAAGCG CAAGGCACCCGAGGTGGACTGGCGGCAAATCGAGGA CCCGGCGGAGAGGCGCCGGCAACGGCGACTGGCGAA GAACCGTGTTACCGCGGCGCGGTCCCGCGAGCGCAAG AAGGCCGCCTGGAGCGAGCTTGAGGAGCGCCTGAAG GGCATCGAGACCGAGAATGCGCAGCTCCGCGCCATGC TGGAGACCTTCGCGCGCGAGAACACCGCCCTCAAGGC GCAGCTGCTCACCGTGGCAGCAGCCGGCGGCGTGCCA GGCCTGAACCACGGCCAGGCGGGCAAGACCATGGAC CCTGCTAGCGTCCTCCCAGTATTTATAGCTATCATGCT GGTGGTCTCTGCCCTCCTGCCTGGTGACAAGGCCTGCG CGCTGCTCGGCTCGCTGCTGCCGCTGGCGCTGATCGCC TCGATGATGGGCGCCGCCGGCTCGGGCGCTAACGCCA ACGGCGGCGCCGCCTTCGACTGCCTGTTCCGCCTAATG CACAGCCTCAGCACGCTGCTATCCAAGAGCAGTAGAA CGCTGCAGCGCAGCCTAAAGCGCATGCTACTGGCTCG ACAGCGTTATCTGGGCGCCAAAGGCATGGCCAAGCTC GGCACCGCCGGCGCGCGGCTCTTCGACCAGCTCCTGA CGACCCCTTCGCCAACGTCGCCGAGTGCCGCTGAGGA CCCCGGGATAGCGCCTGGGTCTCCTTCGGACTCGGAC GGCCGCAACAACGCCGACATGGATGTTGACGTGGCCA CCGTGCTTGCCGCAGAGCCGGCCGAGCAGGCGCCGCC AACCGCCACCTGCGCCGCTGCCGTATTGGGCGCTAAG CCCACGGCGGAGGCGCCGGTGGTGGCGATGGCGGGG GCCCTGCAGGCGGGCTGCGGAGGCGTGGTGGTGGTGA AGCAGGAGCCGGTGTGCTAA |
| 25 | 111 | ATGGACACCAGCATTCCATTTCCGCGACCTATCAACG CGCGGGGCCCTGCTCCGGGCCAGACTCCATCTCAATT GAGCTCGCTGCCCCCGAGCCTTCAAGCGCGGCTCGGA CTGGGCGCCACGCACGACTCGCCTGTTCTGCTTCCACT ACTCCAGCAGGTCGAGGCTTCTCCTACAACCGGCATT CATCAGCTGTGCCCGCCGCTGTTCCAGCCAGCTCAGC CGGCTCGGGTGCCCCTGCCGATTCCAGCCCGAACGGA GGCGGCCTCGGCAGCGCCAGAGCCCACTCGGGCCATT AAACGCGAGTACGAGCCCCGCGCTGGAAATGGCAAA CAGTCAGTGGCCAACTCGGACGGCTGGCAGTGGCGGA AGTACGGCGAGAAGCTGGTGAAGGGCAGCCCGAACC CGCGCAGCTACTACAAGTGCAGCCATCCGGGCTGCCT GGCCAAGAAGATTGTTGAGCGCTCCGACTCGGACGGC ACAGTGCTGTCCACGGAGTACAAGGGGGATCACTGCC ACCCGGCGCCCAGCGCCGTCAAGGCCTCACGCTTCAA GCCGAAGCCCAAGACGGAGCCGCCGGTCATGGTTGCA CCGCCAGTGTTCAGTGCCGTCGACATCACGGTGCCCA ACGGATTTCCGCCGGGCGCGAACGGGCGGGTCGGCTT TCCGCTGTCTGGCGGTGACATGCTCCCCATCCCGGAG |

TABLE 8-continued

Transcription factor library.

| | | |
|---|---|---|
| | | GCGCTGAAGAGCGACTTCCCAGTGCCGCACGCTGCTG<br>GTGCGGCGGCCGCACACGAGGACGACACGGACACAA<br>GTGAACCGGAGCCCGCTGCGGCGCTGAAGGCGGCGCC<br>ACAGGACACTCGTGCTGCGCAGGCTGCCGCCACTGCT<br>ATCCGCAAAGTCCGCGACAGCGCTGAATCGCCGAGCA<br>AGCGCCTCGACATGCTGGCAGCGTACGCTGAGGAGGC<br>GGAGCGCCAGCTCAAATCAAGCAGCAACAGCCCGGA<br>GCAAGGCCCCAGCGCCAAGCGCCAGCGGACAGAAGC<br>TGGGGCTATGCGGACGCGCGCCAATCCCGACGATGAC<br>GACGATGGCAGCGGCGCACCTAGCACGTCGGGCATGC<br>AGCGTGTGGTGGACATCACCAACATGGACGATGGCTA<br>CAGGTGGCGCAAATACGGCCAGAAGCAGGTGAAGGG<br>CAGTCCCTTCCCCCGCGCGTACTACAAGTGCACGCAC<br>ATGGGCTGCTCGGTCCGCAAGCACGTGGAGCGCAGCG<br>CGGAGGACGAGACACGGTTCGTAGTCACGTACGAGGG<br>CACACATAGCCACCGGCTACCAACCGGGAGCCGGCGG<br>CGGAGCGCCAGGGATATGGCGGAAGATGACGAGGAT<br>TACGAGGGCGAGGACGCCGAGGAGGACAGCTCGCAG<br>CCCACCAGCCCGCAGTACGGCAATGTCAACGGTTCGG<br>GGGGTCCGGGCCAGCACGCAGCCTCCAAGGCCGCGGC<br>GCAGGGCGCGCAGCTGGTGCACCCGTCGGGTGCGCAG<br>CCGGCCAGCGCGGACTTCGGCCAGCAGCTGCAGCAGC<br>TCTCGACCAGCCTGCTGGCGTCCACCGTACTGCAGCA<br>GGCGGCACTGAGCGGCGTGCTGCCGCTGCTGCAGTAC<br>AACTCGCTGTCGTCGGAGGCGCTCGCCAGCCTGGGCG<br>TGAACTCGGAGGCGCTCCAGGGCGTGGAGCAGCTCAA<br>CCTCGCGTCGGTCGGCAACTTAGCCGACTTGACCAAC<br>CTTCTTCGCCAGCACGCGCAGATGGACCTGGCGCTGG<br>CAGCGCAGGCTCAGGCCATCGACGCGGCGAACGCGA<br>ACTGGGACCCGCTGGCGTGCCTTATCACGCCACGGCC<br>CAACGTCTCGCCGGCGGGCCAGGGTCACGCCATGGGC<br>CAGGCGCCGTCCGCGGGCACTGGCCGGCAGACTAAAG<br>CAGCTGTGTTTCAGAAGCAAGTGGCGACTACTGAAGC<br>GTGA |
| 26 | 112 | ATGGACTCTGATAGCGACGATGAGCGTGCGGCGGGCT<br>ACGTGCCAGTGTTGGCAGCATCAATGCCACGAGCTGC<br>TGCAGCGGCGGCAGTGGCCAGCCCCGCGGCGAAGCA<br>ACCTTCCAACGTTCTACAAGATGGTGTTTCGCTTTACA<br>CCAATGAGCTGTTCACCGACAACAACGGGGATGTGCT<br>GGGCGAGGGTCCTGGGCTCGCGTCTCCCAGCGGAGCG<br>GCGCCCGGCAGCGCACGAAAAGGCCTGGCTGCGAAA<br>CGGCAGGAGCGGTTGCAGGGGAACGCATACACGCCA<br>AACTCGCTCCTAAAGAACGCCTCACTGCGTAACCCCG<br>GTGCCCCTGCGTCGCCGGGTATGCGGGACTCGCCCTC<br>CTCCTTCCGGCCATCCACCCTGTCGCAAACGGGGACC<br>GCCACCACAGTGGAAACGACATTGGTCAGCCCCAACC<br>GCAACAGCAACAACCAGGGCATCGCCGGGGGCGTGG<br>GAATGGTGCACGGCTTGCGCGCCAGCTACGACCCCAA<br>CGAGGGGCAGGAGGAGCCTGTGCCCTCCACGCGGTAC<br>GTGGCGCCGGCAGCGGTGCCGGTGGCACGCGCCGTGC<br>CCCAGCTGGACCTTTCAGACATGCCGGCATTCCTGCA<br>GCAGCCGGGGCCTAAGAATGGGCCGGTGCAGTGCGTC<br>ATCGTGCGCGACCGCGGGTCTGCAAAGATGTACCCGC<br>GGTACTCGCTGTTCCTGGAGGAGGGGCGGCGCTTTCT<br>GCTGTCAGCGCGCAAGCGGAAGAAGCAGACCACCAG<br>CAACTACATCATATCCATGGACTACGAGGACCTCAGC<br>CGGGAGAGCGGGTCGTTCTTTGGGAAGGTCCGCGCCA<br>ACTTCGTGGGTACGGAGTTCACGGTGTATGACCGGGG<br>GGTTAAGGCGGGCAAGAAGGACGCCCAGGGCGACGG<br>CCAGCGCGAGGAGCTGGGGGCGGTGACGTACCAGTAC<br>AACGTGCTGGGCACGCGGGGGCCGCGCAAGATGATG<br>GCGGCCATCCCCGGGGTGGACGGCAGCGGGCGGCGC<br>ATGTTCAACCCCAGCGGCGACGCGGACACCATCCTGG<br>AGCGGCTCAAACACCGGAAGGGACTGGAGGAGCTGG<br>TGGTGATGGGCAACAAGCCGCCGCGCTGGAATGACGA<br>GCTGAACGCCTACTGCCTGAACTTCAACGGGCGCGTG<br>ACGGAGGCGTCCGTGAAGAACTTCCAGCTGGTGTCGG<br>ACGACAACCACAACCACGTCATCCTGCAGTTCGGCAA<br>GGTCGGCAAGGACACGTTCACCATGGACTACCAGTGG<br>CCCATCTCCGCGTTTCAGGCGTTCGCCATCTGCATGTC<br>GTCCTTTGACAACAAGCTGGCGTGCGAGTAA |
| 27 | 113 | ATGTTGCCTTCCGAGCCGCCCTCAGCACCGAGCTCCG<br>ACCCGAAGGGAGCCGGCCAGGAGGCTCAGCAAGCTG<br>AAGACTCGCCGCTATACAAGACGGATGAATTCCGCAT<br>GTTTTGCTTCAAGGTGCTGCCATGCTCCAAGCGATATG<br>TGCACGACTGGACAGTATGTCCGTTCGCGCACCCTGG |

TABLE 8-continued

Transcription factor library.

| | | |
|---|---|---|
| | | CGAGAAGGCTAAGCGCCGGGACCCTCGCGTGTTCACC<br>TACACTGGCGTCGCGTGCCCGGATATGAAGAAGTGCC<br>AACGCGGAGACGCGTGCCCATACGCGCACAACGTGTT<br>CGAGTACTGGATGCACCCAAGCAGGTATCGCACGCAG<br>CTGTGCAACGACGGCATTGGGTGCAAGCGGAAGGTGT<br>GCTTCTTCGCGCACACGCTGGAGGAGCTGCGCGTCTC<br>CAACGTCAAGCTGCTGCCCGCCGACATCGCGGCGGGG<br>GTGGACGTGGACCTGGACCCCTTCCGCCGCCCGGAGC<br>CCGCCAGTGGCCTGCGCTCCGCCAACAAGGCGGGTGG<br>GGGCGGCTCCAATGCGGCCGCGTCGTCCGGCAACGAG<br>GCCCTGGTGGAGGCGCTGCGTGTGCAGCAGCAGCAAC<br>AACAGCAAGTCAAGAAGGCGGCGGCGGCGCTGCAGC<br>GCAACGCATCGCGCGGGCTGGCGGTAGAGCTGCAGCA<br>GCTGCAGGCGCTACAGCAGCTACAGGCGGTGCTGGCC<br>AGCACTCCCGGCTTGGCAGCTCTGGCGCCGCAGCTGC<br>AGGCGCAGCAGATGGCGGCAGCCGCGGCCGCCTCGCC<br>CGACTCATTCCTGAACGCCATGATGGCCAACCTCCGC<br>ATGGCGGGTGCTGGTGCAGGGGCCGGGTCGGGAATGC<br>CGCACGGCGGCGGCTCCGGCCACGGCGGCCTGGGCAG<br>CGGCGCCGCGGGCAACGGCGCGGCACTGATTGACGCG<br>GTGGTGCAGCAGGCGGTGCAGCAGGTGCTGTCAAACA<br>GCGCGGCGCAGCAGGCCGCCACGGCGCTGCTGATCAT<br>GCAACAGCAGCAGCAACACCAGCAGCAGGCTGCCGC<br>TGCTGCGGCGGCTGCCGCGGCGATGGCGCAGCAGCAG<br>CAGCAACACCAGCAGCAGCAGGCCGCGGCGGCCAAC<br>CACCAGGCGGCGCAGGCGCAAGCGCACGCGCTGCTTG<br>GGCACCTGCTCATGCAGCAGCAGCACCACCAGCAGCA<br>GCAACAACAGGGCGGCCCCAGCCCCGCCGCCATGCAG<br>GCTGCGCTGGCCATGCTGCAGCAGCAGCAGGCCGCGG<br>CAGGCCACGGCGGCCCGCACATGCCGCCGCAATACAT<br>GCAGGGCGCCCGCCCGCTGAGCCCCATGGGTTCGGGC<br>ATGGAGGCGGCCATGGCGGCTATGCATGCGCATCAGC<br>AGCACCAACACCAGCAGCACCAACAGCACATGGGCC<br>AGCAGCCCTCGCTGCCGGGCTCGGTGCGCTCCTCCGC<br>CACTGGCATGATGTCGGCTGTCGGCGGCCCCGTCGGC<br>CCGCCCGGCTCGCGCAACGGCGACGCCGCCGCCGTCC<br>CTGGCGGCCCGGGCTCCCCTCACGGCTCGCCCTCTGG<br>CTCGCCGCCGGGCGACGGCCCGCTGGGCGGTCCCGGT<br>GGCGCTGCCGCGGCGGGCGCCGCATTCTCGGCAGCTG<br>CTACTGCCGCTGCCAGCTATTACAGCCAGGAGGCCAG<br>CCGCAGTAGCTTTGAGAGCTACCGCAGCAGCGAGGTC<br>GACCTGGGCCTGGGGCTGGGCCTGGGGCTGGGCGCGC<br>ACCACTCGATGCACCACCACCACCAACAGCAGCAGCA<br>CGCCATGCAGCAGCAGCAGCAGCACCAGTTCGGCGGC<br>GCCGGCATGCACTCGAGCGGCCCCAGCAGCGGCGGCA<br>CGCAGCGCAGCTCGCTGGAGCTCATGCAGCCGCCGCC<br>GCAGCAGCAGCAGCAGCAGCAGCAGCATGGCTACAG<br>CCACTTCGCCGGCGGCCCGCAGCCGCCGCACAAGGCC<br>TTCATGGGCGATGCGGCCTTTGCGGGCCCGCCCTTCGC<br>CGGCGGCCTGCCGTCGCATGCCGCGGCGCCCGGCCCG<br>CGCAGCCCCAGCGCCACGTCGTCGGGCCTGCCCGCCG<br>CCGCCGAGGAGGAGGCCGCGCGTCAGCAGGCGAACG<br>CCAACGGCCTGTTTGCGGCGGTGCAGGCGGCGGCGGC<br>GGCGGGCGCGCAGGCCGGCGGTGCCGGCGCCGGTGC<br>GCAGCTTAACCTGCCCGAGTCGCTGCTCGCCGAGCCC<br>GTAGGCCCCGCGGCGATGGCCGCGGCGTTCCGGATTT<br>GA |
| 28 | 114 | ATGAACGAGGCGCTGGACTTTGGGATCGGCGACTCGC<br>AGTATGTCTTCACGGATTTAGAGCTCAACGAGCTGCT<br>GGGCGTGATAGAGCGCAAAGCAGCCGGCGAGGCCGA<br>GCCTGACGCTCTCGATTTCCTGCGCGCCACTGACGGCA<br>ATGGACTTGCTCTTCAGTTCCAACCGCGTTCTCAAAAG<br>GACAACGGCAGTGGGTGCAGCCTCGAGCAGAGCGCG<br>GTTGCAGCAGCGGTCAAGCTGGAGGATAGCGCGCTGT<br>CATCGGCACTGGCGTCACCGGTAGACACACCCGCACT<br>CACCGGCGTCGCCGACCCAGCGTCCCTCTACGGTAGC<br>GGTGCAGAGATATCGATCATGCCCATGCCTCACGCCG<br>CCGCTGCTTCCGCTCCGACGTCACTTCACGCCTACACC<br>CTGCCGGGCACCGCGGGGCACGCGGCGCTTGTTGGCA<br>GCTCGCCGGCGCTAGTGAGCACCCTTGTCGCCGCCGC<br>CACTGCCGCACAGCAGGCGCAACACAATGCGCAACTG<br>GCGGCAGCCGCGGCCGGCTGCCTGCACGTGCACGCCC<br>CACTCCAGCTGGCGCGCTTCGCATCGGTTCCGGCACC<br>GCCGGGCAAAGCCATGTCCATGTCCATGTCCATGGCT<br>GAGCCCAAGGGCCAGATCAGCCACTCCACGGTGGAGA<br>AGCAGCGCCGCGACCGCATCAACTCACTGATTGACGA<br>GCTGCGCGAGCTTGTGCCGCCGCAGCAGCGTGGTGGA |

TABLE 8-continued

Transcription factor library.

| | | |
|---|---|---|
| | | GCCAACGGTGCCGCCGCCGCCGCCGCCAACGACGCGG<br>GAGGCCTGGAAGCTCGGCGGCCCAAGCACGTTGTACT<br>GGCAGACACCATCCAACTGCTCAAGCACCTGCAGCTC<br>AAGCTATCAATGGGCGCGCTGGAAGTGGGCGGCGCCA<br>CCAATGGCTGCTACGTCAACGGGAATGGCGGCTACTG<br>CAATGGAGGCGGCGGCGGCGGCAGCGGCGGCGCCGT<br>CGGGCGGCTGGGCAGTGGCTTCAACGGGGAGGAGGA<br>CACGGCCAACTCGGAGGGCAAGGCCAGCAAGGGATC<br>CTCCAGTCACGAGGAGATGGAGGTCGGCGGCGCTCCT<br>CAGATGCCACACATCCCCTGCCAGATGACGCAGATGT<br>CGGGCGTGACGGTGGAGCGCGGCCCCGACTGCTACTA<br>CGTGCAGGTCAAGTGCCGCGACCGCAAGGGGCTGCTG<br>TCCGACATCATCAACGCCCTGAGACAGCTGCCACTGG<br>AGATCCGCACCGCCGCCGTGACCACCACCAACGGCAC<br>GGTGCGTGACGTGTTTGAGGTGAAGTTGGACGACCCC<br>GGGCTCAGCCCCGAGGACGTCCAGAACCTGGTGCACG<br>ACGCCCTGTTCCAGAGCCACCTGTTGGCGGCGCAGAG<br>CGAGAGCCTGGCCGCAGCCGGCAAGCGGCCTCGCGCC<br>TAG |
| 29 | 115 | ATGCGCACCTCAGATAATAGAAACACGCTGTCTCTCG<br>AGACAGCAGCGCCGGTCTATGGCGCAGCGGAGCTGGT<br>GGAGGGACAGGCGGTGCTCAGCCTTTTAGAGAGCTTG<br>GATGTCGAATCGATCGACCTGATGGTGTATGGGTACG<br>AGGTCGTGGGCTGGGAGGAGGCGCACGCGAAGGAGC<br>CCAAGCTCCCGGCGGCGGACCCATACGCCCCTAGCCA<br>GCTGGTGACACCCTTGGACTCACAGCAGCAGCAACAG<br>CAGCAGCAACAGCCGCCGCCGCCATCTGCGGCCTCCA<br>AGGCTTCGCCACTGGGCGTGCCCAGACACGGCCAGCG<br>AACCATCTTCAATATCTGCCAGGTATGCGTGGACGGC<br>CGGACGTTTCGGCTGGCCGGCACACCAGCACGCACCA<br>TTGGAGACGTGAGCTACCGGAACCTCTCTGGCGAGGT<br>CAGCTACGGCTTGCAGGTGGAGGTGCGGCGTCCGAGC<br>AGTTTCGCGTCGGCAGCCGAACAGCAGCAGCACCAGT<br>TGGCGGTTCTGCGTGCTGATTGCGAGCTCGTGATTATA<br>CAGCGCGCGGAGGCGGCGCAGGGCCCGCCAGCCCCC<br>GAGGAGCATACGTCGGCTGGGGCGGCGGCGGCCAGG<br>GGCCCAGCAGCAGGCGGAGCTGAAGCGGCGGAGGCG<br>GCCGCGCCGGTGCCGTGCGATGAGGTGGTGACCCTGG<br>TGCCGGCCTTCTTCTTCTGCTGCAGTAGCGGCGGCCGC<br>GTGACGGTGCGGCTGCGGCCGGGGCGGGATGGCTACG<br>TGGCAGGCGAGGCGGCGGAGGTGGTGGTCGAGGTTG<br>ACAACCGGTCGAATCAGGAGTTTCGGGATGTGCGGCT<br>TGAAGTGGAGCGCCGCCTCACATTGGTCAGCAACAGC<br>GCCGGCGGAGGCGGTAGCGCCGGCAGCAGCGGCAGC<br>GGCAGTAGCAGCGCCACCGCGGGGCTTGTGCCGGGAT<br>GCTTCACTGAAGAGGAGCGGATCTTCAAGAGCAAGAC<br>CACGGCCGCCCTACTACCGGGAGCCTGCTACCTGGGA<br>GCCAACGCGCTGCGGCTGCCGGTGCCCCTGCCCTCCA<br>ACACGCCGCCCTCCACCTCCGGCGCGCTTGTGCGCTG<br>CTCCTACACCGCCACGGTGGAGGTGCTGCCGGCGTCG<br>GCGACAGCGCTGCGCGGCGCGGCGCCGCCGCGGCTGC<br>GTGTGCCGCTGACCGTGTTCGCATCCGCGCCGAGCTC<br>GTTCGCCACGGCGGCGGCACGGCATGCTCACCTGCAG<br>CAGGACGCAAGCGAGCAAGCGCCGGCGCACGTGTTG<br>GTGGTGGTGCCGCCCGTGGATGTAGTGCTCCCCGCAG<br>CTGCGCCGCAGCTGCCTCCCACCGCCGAGGTAAATGT<br>CAAACAGCACAACGGCGTGGCTGGCGCAAACCCGATG<br>TACGCGGGCCCGTAG |
| 30 | 116 | ATGACCGAGACCGACCACCGCCGCAGCCGCCCCGACT<br>GGTCCCGCGCTCAGAGCCTGCGCCTGATCCAGCTGCA<br>CGTCAAGCTGGGCAACAGCTGGACCGAGATCGCCAAG<br>CAGCTGCCCGGCCGCACCCAGAACGACTGCAAGAACT<br>TCTTCTTCGGCGCCCTGCGCGCCAAGCGCGGCTACCG<br>CGACAACCTGGTGTACGCCTACGCTCGCGCTCTGCCC<br>CCCGCTAGCGCTTCCGCTTGCGGCAGCTGGGAGCAGG<br>ACAAGCGCGGCCCCGACGCTCTGACCCGCGCTGCTGC<br>TTACAAGGCCGCCATGCAGCAGGTCGCCGCTCAGGAG<br>GTGGCCGAGCAGATGGAGAAGCAGCAGCGGAGCCAG<br>CAGCAGGAGGGCGAGGACGGCGGCTGCGGCAGCGGC<br>GCTGCTGGCGCTACCGCTGAGGACGGCGGCGAGCCCG<br>GCGCTGTGGCTGCTGCTAGCCGCCGCAGCAGCAGCGT<br>GTCCGTGGGCGCTGACGGCGCTGCTCCCACCGCTCAG<br>GGCGACGGCATGGACACCCAGGAGGACGCTGCTTCCG<br>CTCCCGCTTGCCCCGCTTCGGCTGCTGCTTCCCCCGTG<br>GGCCCCGGCGACGTGTCCGTGCGCCGCCTGAGCAGCA<br>CCGGCGACACCGTGGTCACCGACGCTGCTGGCACCCG |

TABLE 8-continued

| Transcription factor library. | | |
|---|---|---|
| | | CACCGTGGTGGCTGCTGGCGTGGTCGCTGGCGGCTGG<br>CGCAGCGTGGCCGCTGCCGCTAGCATGCCCGCTCACC<br>CCGCTGCTGTGGTGTCGATGCCCCCCGTGGTGCCCGCT<br>TCGGTGGTGGCGGCTGCTTCCGGCGTGCTGGGCGCTG<br>CTGCCGTGCCCGCTGCCGGCGCTCCCGGCGACCGCCT<br>GAGCCTGCAGTCCCTGCAGCCCCCCCCCCACGGCTTC<br>GCTGCTCTGCCGCAGTCCGCTGCTCCCGCCATTGGCAG<br>CAGCTCCGCTAGCCCCTTCTGGCAGCACCAGCAGCAG<br>CACCACCTGATGGGCCCCCGCGTGCAGCTGCTGAGCC<br>ACGAGAGCCTGGCTCTGCTGCACCAGCAGCACCAGCA<br>GGCCCAGCAGCACAGCCACGTGGTGCTGCACGTGGCG<br>CCCCCGTTCCTGCAGCAGCACCACCAGAACCCCCACC<br>ACCAGCACCTGATGGTGCAGCTGGAGGGCGCTGGCGC<br>TGGCGCTCCCGCTGGCGCGTTCCAGCTGCAGCACCAC<br>CAGCACCTGCACCCCCACCACGTGCAGGGCTCCGGCC<br>CCGCTGACGGCAGCTCGGGCCCCGTGCTGCTGATGGG<br>CCCGGCTGGCCCCCACGCCGCTGCTCTGCAGCTGCTG<br>GGCAGCCACCCGCACCACCAGCACCAGCACCACCAGC<br>AGCTGGTCCTGCTGCCCTCCAGCGTGCCCGGCGCTCC<br>GCCCCAGCACGTCCTGCTGCCGATGGCTGTGCGCCCC<br>CCCCACCTGCTGCAGTACGGCGGCGCCCACGGCGCTT<br>CCGCCGCTGCTAGCGCTGCCGCGGCTGCTCCCTCGGCT<br>GGCATGGGCGCTTTCGTGTTCCACCCCCACCCCCAGC<br>AGCAGCAGCTGCCCCCCGCTGCTGCCGCTGCTTTCGCT<br>GCTGCCAGCGCCGCTCCCTCCCAGCCCGCTGCGGTGG<br>CTGCCGCTGTGCACTCCCTGGCTCCCGCTGCTTCGGCC<br>GCTCTGAGCCTGAGCGGCAGCTCCGTGCTGGAGGCTA<br>CCACCACCACGACCCGCATCACCACGACCACCGCTGC<br>TGCTGTCGCCGCTGCGGCTGCTGGCGCGGCTGTCGCTG<br>CCGGCGTCAAGACCGAGCCCGCTTCCGCTGAGGCTGC<br>TACCGGCTGGGCTCAGCAGCAGCAGCAGAAGGCTCAC<br>GCTGGCGTCAGCCGCAGCTGCAGCTCCAGCTCGAGCA<br>GCTCGGCTGCCTGCGGCGCTTGCTCGACCTGCACCGCT<br>GGCGTCGGCGCTACCCCCGCTACCGCTACCCAGCTGC<br>CCCAGCACCAGCAGGACCACCAGCTGCTGGGCGACGA<br>CTGGTGCGCTGGCGACGAGGAGTGGGCTGAGCTGGGC<br>CGCATTCTGCTGGGCTGA |
| 31 | 117 | ATGGAGGCCCTGGACGCCCAGGACAGCCTGCAGCTGG<br>ACGTGGTGTCCCCCAGCGCTCGCCCCGCTGCTGCTGG<br>CGGCGACAAGCGCGACCCCGAGCGCTTCTACTGCCCC<br>TACCCCGGCTGCAACCGCAGCTTCGCTGAGCTGTGGC<br>GCCTGAAGGTGCACTACCGCGCTCCCCCCGACATTCG<br>CGGCAGCGGCAAGGAGCGCGGCCACGGCACCGAGCT<br>GACCCACTGCCCCAAGTGCGGCAAGACCCTGAAGCCC<br>GGCAAGCACCACGTGGGCTGCAGCGGCGGCAAGAGC<br>GCTCCCCGCCAGACCGCTAGCAAGCGCAACCGCACCG<br>GCGCTGACGACGCCGACGAGGCTGTGCCCGGCAGCCC<br>CCACAGCAAGCACGTGCGCGGCACCGACATGGACGG<br>CGACCCCCACAAGAGCTGGCAGGACTTCGCTCTGACC<br>CACGCCGGCTACGCCATCGGCGCTCCCGCTATGCTGG<br>CTCCCCTGAAGCAGGAGCACCCCGAGTGGCCCCCCAC<br>CGTGCCCCAGGGCGTGTTCGTGGGCCACGGCGACCGC<br>GTGTCCTGGCTGCCCGGCCAGGTCAACGGCTTCGTGC<br>CCCAGCTGCAGCCCCAGCGCTACCAGCAGCCCCAGTT<br>CCCGCCCGAGCTGGCCCAGGCTTTCGCCGCTGCTGGC<br>ACCCACGCTCCCCACGTGTACGCTCAGCAGGTCCCCTT<br>CGCCAGCATTCCCGGCTACCCCGGCCAGCCCGGCGTG<br>GCCACCCTGCAGGTCACCACCGAGAGCGGCCAGGTGC<br>TGAGCATCCCCGCCAACATGGCTGGCATGCCCCCCGG<br>CATGGCCGGCCTGCCCGGCACCCTGGTGTACCACCAG<br>CAGCCGCCCCCCCACGACGCTGCTGCTAGCTACCTGG<br>CTCAGGCCCAGGCCCACGCTCAGCACGCCGCTGCTAT<br>GCACGCCGTGAACAGCGCTCACGCCCAGCAGCAGCAG<br>CAGCAGCAGCAGCAGCAGCAGCAGCAGCAGCCCGGC<br>GTGCCCGCTGCTCCCCCCGCTGTGCCGGGCGTGCACG<br>ACGGCATGCCGCCGGGCACCGTCGCCGCTGCCGCTGC<br>GGCCGCTGCTGCGGCTGCCGCCGTGGGCGGCAGCGCT<br>CCCAGCGCTCTGCAGACCGACGTCGGCGGCCGCCCCG<br>GCGCTGCTCTGCCGCCGCAGGCTGCTCCCGGCACGGG<br>CGCTGGCCAGGGCGCTGGCGCTCCGGCTGGCGCTGCT<br>GACGGCGGCGCGGCTCCGGCTGCTGGCGACGCTGCCG<br>CTTCGGGCGGCGCTAAGCCCGTGGCTGACGAGGACAA<br>CCTGGGCACCGTGTTCGACGACGTCGAGGAGTTCACC<br>CGCGACTTCGGCCGCATTCCCAGCCCCCCCCCCCTGCC<br>CCCCGACTTCCACACCGCTGCTACCGGCGGCAACGGC<br>ATGCTGTTCAACTTCAGCCAGTTCGGCCAGAAGCTGC<br>CCCGCACCCAGAGCCACACCCGCCTGGACCGCAGCCT |

TABLE 8-continued

Transcription factor library.

| | | |
|---|---|---|
| | | GAGCGCTGTCGGCCTGGGCCACCTGGACGTGGGCGTC |
| | | GACGGCGACGTGATGTACGACCACACCGACGACGGCG |
| | | ACCTGATGCAGCTGCTGTTCGGCGTGCCGGACGAGCT |
| | | GCCCACCATGGCCACCATCCACCTGCACAAGTGGTCC |
| | | AACGAGGAGGACGAGGACGACGACGCCGCTGAGCCC |
| | | GGCGGCGGCGGCGCGGCCGCGGCGGGCGGCGGCGGC |
| | | GGCGCTGCTGCTGGCGCTGGCGGCGAGGGCGGCGGCG |
| | | GCGCGGGCGCGGGCGGCGGCGGCGCCGGCGCTGGCG |
| | | CTGGCGAGGCTAACGCTGCTGCTGGCCGGGGCGGCGC |
| | | GGGCCCCGGCCCCGGCCTGGAGGCTGGCGGCGGCGGC |
| | | GGCGGCGGCGGCGCCGGCGAGGGCGGCCCCGGCGCT |
| | | GGCCAGCAGCCCCCCCACCACCAGCAGAGCGTGGGCG |
| | | GCCACGACCAGCGCCCCCTGAACGGCAAGACGCTGCA |
| | | CGGCCACGACGCCAGCCTGGCTGTGCTGCCCGCTCCC |
| | | GGCGGCAAGTCGCTGATGAACGGCGGCGCTGGCCACG |
| | | CTGGCGAGGAGCACCACCGCGACCACCTGCTGGACGC |
| | | TGAGACCTTCCGCCTGCTGCAGAGCTGCGACTAG |
| 32 | 118 | ATGCAGGACCCCCATTTACAAGAAACGACAGCTTCGG |
| | | AGCCGCTGACAATGGAGGAGGAGTATGAAATGCAGC |
| | | GCTCCTGGGCGCAAGATGAGGACAAGCTCACATTCAT |
| | | AGTGCTGGACAGGGGTTTCCCCGATGTGCCGGGCACC |
| | | GGCAGCCATGGCGGCGGCATGGCGGGCGATGTAAACC |
| | | TGTTTTTTACGCTGGACGAGGAGGAGGGCGGGCGGCA |
| | | GGCGGCGGAGATTGAGGTCATGGTGGCAGAGCAGGG |
| | | CTCGCGGGGCAAGGGCATCGCCAAGGAAGCGCTCCGT |
| | | GCGCTTATGGCATACGCCAGCAGGGAGCTGGGGGTGA |
| | | AGCGCTTCGTGGCCAAGATACACGAGGTCAATGCGCC |
| | | GTCCCGAAAGCTGTTTGAGGGCCTCGGCTTCGAGGAG |
| | | TTCAAGAGGGTGGCATGCTTTGGCGAGGTCCACTACC |
| | | AGCTCTCGACGGACAAGGCTGCCGACTGGCTGCCGCA |
| | | ACTGCAGGAGGGGCTCAATCTTGGCAAGTACGAGTAG |
| 33 | 119 | ATGCACACAATAAAATGCAACCGGCCCTGCTCTGTGG |
| | | CGTCGTCACGCGCAAAGAACTTGCCGACGCATTTCAA |
| | | GCTCGGGGCGCTGCCCATTTTGCACAGCGCTGAAACA |
| | | GCACTACATAGCGCTAGGGAGCATGGATCAGCTCCAC |
| | | ACACCCGGCGATGCGGCGTGGTCCGCTGCGCGTCGGA |
| | | AGCCCCAGCGGGCCCGCACACCACCGTGCCGCATCAC |
| | | ACGGAGGTGGCTGTGCTGGGTGGCCGCCTGGTCGTGA |
| | | GACCCATCACCGCCGGGGAGATCCAGGCCGCAGGCGT |
| | | GGTCCTGACCCGTGCGTTCGCGGGCTCATCGGAGGCG |
| | | GTGTCCTTGAAGGAAGTGCTGCAAGATCTGGAGACCC |
| | | AGGGCGGCGCCGGAGGCGCTGCCGCGGCAACTGGCTG |
| | | CTTCCTGGTTGCCCGCCTGTACCCCTCCACCTCCTCCT |
| | | CGGGCGCCAGTGGCAGCAGCAACGTACAGCTGCCGCC |
| | | GGGCCAGGACTCGCGACTGGTGGCCACTGCTTCCGTG |
| | | TCGCTGAGCGCACAGGACATGCTGGTGCGCCGCCTGC |
| | | CGCCGCCCAACCCGCCGCCGGCCGCCGCCGCCTACAT |
| | | AAGTAACATGGCGGTGGACCCCAAGTTTCGGAGACAG |
| | | GGCATTGCGCGAGCCCTGCTGGCGGCGTGCGAGGAGG |
| | | TGGCGCGCGGCGCGGGGCTCCGGGAGGCGTCGCTGCA |
| | | CGTGCGGGAGGCTGACTCGGCGGCGCGTGCGCTGTAC |
| | | GATAGTTCCGGGTACACAGTCGTGGTCAAGGACTCAT |
| | | GGGTGGACACCATGCGGCACAATATTCGGCCACGACT |
| | | CCTGATGAAGCGGACGCTTTAA |
| 34 | 120 | ATGGCTAAACGCGAGCTTGCTGTCAGCTTTGACATTGT |
| | | TAGAGAAAAGAACCTTGAGCAACTTAAGCTGCTAAAC |
| | | AGCGTTATCTTCCCGATGAAGTATGCGGATGAGGTGT |
| | | ACCGGCAATGCATGGCGTGCGGCGACCTGACTCAGCT |
| | | AGCATACCACAACGACGTCCTGGTGGGGGCCATCACG |
| | | GTGCGCTGCGAGCGCCAGCCCAATGGCAAGGCGAAG |
| | | GCCTACATCGCCACGCTAGGCGTGCTGGCGCCGTATC |
| | | GCAACTTCGCTATCGGCGCCAAGCTGCTGCAGCGCTC |
| | | GCTGGCTGCGGCGCAGCAGGACCCCAACATCGAGGAG |
| | | GCGTTTGTGCATGTGCAGGTCGACAACGAGGACGCCA |
| | | TCCGCTTCTACCAGCGGCACGGCTTTGAGAAGGGCGA |
| | | GGTGGTCAAGGACTATTACAAGAAGCTGTCGCCGCCG |
| | | GACGCAGTGGTCATGAGCAAGAAGCTGGCAGCATAG |
| 35 | 121 | ATGCTCCGCTGCGACCGGTTCTTCTCGAGCACACGCCT |
| | | CGTCGACAATCAGACTCTTCAAATCAGCTGCAAATAT |
| | | ATCAACAACAAGTTATCTAGTCCACTTTACGCATCTTG |
| | | CAATTGCAATCAAGGAAGCGGCCTTGCAAGTCTGCGA |
| | | CGCAGCTCGAGCAGCTGTTATAGCTCAAGACAGGTCC |
| | | CTGCGGCCATTGCGGAAGTTAATGTCCGCTCGGTGCG |
| | | CAGCCTCAGCCGCTGGCGATGGCAGGACCTCGCTCAG |

TABLE 8-continued

Transcription factor library.

| | | |
|---|---|---|
| | | GTGGCCTTCCTGCTAGCGGCATCGTTCTATGAGGACG<br>GCGAATCATGGCAGCTCGAGAGCCCCCCGGTCCCGGC<br>GACAAGTAGCACCGCAGTAAGCCAGGATGTAACAGA<br>ACTGTTGCCTGCATCGACTGATGCCAGGCAGTCGGCA<br>AGCGGCGCCGGCCGTAGCAGCAGGAACAGCAGCAGC<br>AGCAGGGCAAGCAGCAGTGGCAGTGGAGCAATCAAC<br>CGGCCACTGTCAGGAGCTGCTCTGCTGTTCGGTGCGTC<br>CTCGCTCCTGGCCATCTTGATCCAGCACGCCACATATG<br>GTGCGCGCCACGTCACGCTGCTTGCGGAGTTGCAGGA<br>GTCCGGCGAGGTGATTGGCTGCTGCGGGCTGACGTTC<br>GATGCTGCTCCAGCCGACGTCGTGGAGGCCACCGGCG<br>CGCCACAGGGCTGCGAGTATGCGCTGCTCACGGGCTT<br>AGCAGTTGCGCCGCCGCAGCGCCGCCGTGGTGTCGCA<br>TCGGCACTGCTGCAGGCGGCAGAGCAGGAGGCGCGG<br>CGGGGCCCTGGCCAGGCACGGCGGGGCCCTGGCCCGG<br>CACGGCGCCGGCTGCCGGCACTTCTGGCATTGCTGGTT<br>TCCAAACTCAACGCCGCGGGAAGGAGGCTGTACGAGC<br>GGAACTTGTACGAGGAGGCAGAAGACTGGGTGGACA<br>CGCGGTGGGAGCTGGACGCAGAGAAGGGCCGTGTTG<br>GGAAGCCCCGGCGGCTGCTCCTCTTTCGCCGATTGAC<br>ACAATAG |
| 36 | 122 | ATGCACTGGCAATATCCATGTTCCAATCTTTACTGTTT<br>TACATTGCTGCTCTGCATCCGCTGCGTTTCGCAAGGGG<br>ACGGTGAGCTTTCTGGGCCTGTTGTTTCGCAAGTCGCG<br>GCAAGCCGGCAAAGTGCACCAGCGCATTTGCATAGGC<br>GATCCTACTACAGAAGGAAAATGCCACGCGCTGCCAA<br>GGAGAAGCCGGAGAAGAAAGAGAAGAAGGTCAAGGA<br>CCCCAATGCCCCTAAGAAGCCCATGGGCGCCTACATG<br>TGGTTCTGCAAGGAGATGCGGGAGCAGGTGAAGGCCG<br>ACAACCCGGAGTTCAGCGTCACCGACATCGGCCGGCG<br>GTTGGGGGAGCTATGGAAGGAGTGCGAGGACGACGA<br>CAAGAAGAAGTTCCAGGACTTGGCGGACAAGGACAA<br>GGAGCGGTACAACAAGGAGAACGCCGCGTACCAGAA<br>GAAGGAGAAGGAGGCAAAGTCGGAATAA |
| 37 | 123 | ATGATTGACCTACTGCTGGGAGCATCGTTGTCTCCCTC<br>GGATATCGGACAGGTTCTGCTAGCGTATCCACAGGCC<br>TTCCAGCTCTCCCTGGACCGCGCTCGGGAGGTGCTGG<br>ACTTCCTGCGCGACGACATGCACCTCAGCGAGTCCCA<br>GGTCCGCACGGTGCTGACGCGCTATCCAAGCATCCTC<br>AACATGAACGTCAAGGGCCAGTTGCGCCCCCAGGTAG<br>CGTACCTCAACTCGCTGGGCGTGGGCCCAGAGTCGCT<br>GCCGGAGCTGGTGCTGAGCCGGCCTCTGGTGCTGGGG<br>CCCGGCATCGACACCGTCATCACCTTCCTCAAGCGGC<br>TGGGCGTGCCGCGCTCGCAGATGCACCGCATGCTGCG<br>CTCCTGCCCTCTGGACTACCGGGTTCAGTTCAAGAGCT<br>TTAGCGCCGCGGCGCCGGGTGGCAGCTCTTCCTCCTCG<br>TCCTCCGGCGGCATGGGCCGCAACTAG |
| 38 | 124 | ATGACGTCAGAGGAGCTATCTGTACGCAAACTTGAGC<br>AAGGAGATTTCGATAAGGGCTTTCTTACTGTCCTTGGG<br>CATCTGACAACGGTGGGGGATGTGACGCGGGAGATGT<br>TTGAAGAGCAAATACGTCGGCGAGATGCAGTGGGTGG<br>CTACCACACGGTGGTCATAGAAGACAACAGCCGCATC<br>GTCGCCACGGCCAGCATGGTGGTGGAGCTCAAGTTCA<br>TCCACGGCTGCAGCAAGGTGGGGCACATCGAGGATGT<br>GGTGGTGGACCCCGCGTACCGGGGCAAGCGCCTGGGG<br>CTCAAGCTGATCGAGGCGCTCATCGAGTCGGCCCGCG<br>GAGATGGCTGTTACAAGGTGATCCTGGACTGCGCGGA<br>GGGCAATGTGCCCTTTTACGAGAAGGCCGGGCTGGTG<br>CGCAAGGAGGTGCAGATGGTGCGCTACCTGGACCGGT<br>GA |
| 39 | 125 | ATGACAAAGCATAAACGCCGAGAGCTGCCCAGTGCGG<br>TCCACGATGGAGAGGAGTATAAACCAGGGGACTGCGT<br>GCTAATCAACCCGGACGCCTCTGCGCCCGCCTACATT<br>GCACGGATCCGGAAGCTCATACAGATCGGCGCGGAGC<br>CAGAGCAGGTGGAACTGGAGGTGACCTGGTTCTACCG<br>ACCAGAGGAGGCCATCGGGGGGCGCAAGGCCTTCCAC<br>GGCGAGGCGGAGGTGTTCGACTCTGACCACCAGGATA<br>AAGCACCACTAGCTGCCATCCTGGGTCGCTGCAACGT<br>ACACAACGTGTCACGGTATGAGTCGCTAGAACGGCGA<br>GACGAGAACGACTTTTTCTGCCGCTTCACATACAAGC<br>CCCGCACCAAGCAGTTTGAGCCGGATCGCGTGCCAGT<br>GTACTGCGTATGCGAGCTGCCATACAACCCAGACAGG<br>CCGATGATCAACTGCGACAACTGCGACGAGTGGTACC<br>ACCCGCAGTGCCTGGGCCTTGGCCAGCACGTGCTGCA |

TABLE 8-continued

| Transcription factor library. | | |
|---|---|---|
| | | GCAGGACCACTTCGTGTGCCCTACTTGCACCACGCCG CAGCAGCCCGCCAAGAAGTCCCGTCCTGGGGCATGA |
| 40 | 126 | ATGCTGCTGTCACGTCTCGCTCATTCCGCTCTCCCTGC CTCGCTCCGCGCCTCGGCCGCGAGCTCGGCCTCGTCG CAGCTCCATGCTGTGCCCCGTGTCGCGAGCGCCGCTC CGCGGGCGCCGTCGCACGTCGCGCAGTACAGCAACGG CTCTGCGGCGCCCGTCCCTCCCAACTTCGCTGCTCCCA ATGACCGCGCCGCCACCAGCTCCAGCGACCGTGTATA CACCAACTATTACGTGTACAAGACCCGCGCGGCCATG TGCCTGCGGCTGCTGCCGCCCACGTTCGCCAAGGCGC AAGCCGGCAAGGTCCTGGAACGTGACGGCACCATGCT GCTTGAGTTTGCCACTGCCAACGCGGCCGCACCGGGC GCTGGCAGCGGCCCCGCAGGCAACGTCAACCGCACCT ACAACTGGGGCAACAAGGTGACGTTCGCTCTGAGCCC GGTGGAGCTTGGAAACATCCTGGCGGGGGATGCGGTG GCCTCGGACAAGGGGCTGGTGCTGTGGCACGACCCAG CCAAGCTAGGCAAGACCGGCGAGCCCATTAAGAAGCT GAGTCTGAAGCAGCTCCCAGACGGCAACATCAGCTTC AACCTCACCGCCGGGCCCGAGAACTTCAGCGTGCCCG TCACCAAGGGCGAGTTTGAGGTGATAAAGTCGGTCGC GCAGTTCGCCATCCCCCGGCTGCTGGGCTTTGACGCCG TTTTCGAATAG |
| 41 | 127 | ATGGGCAAGGACTACTATGCAATCCTTGGAGTGCAGA AAGGAGCAGATGAAAATGAACTTAAGAAAGCGTATC GAAAATTGGCGATGAAGTGGCACCCGGACAAGAACC CAGACAACAAGGAGGAGGCTGCCGCCAAGTTCAAGG AGATCTCTGAAGCTTACGAGGTGCTGACGGATCCAGA CAAGCGGGAGGTGTACGACAAGTTCGGGGAGGAGGG GCTCAAGGGAGGCATGGGCGGCGGGCCGGGCGGCGG ACCGGGCGGGCCAGGCGGCTTCCACTTCCGGAGACCC GAGGACATCTTCGCGGAGCTGTTCGGGGGCCGCAGTC CGTTCGGCATGGACGACGACGACATGTACGCGGGCGG CAGCTTCGGCGGCGGCGGCGGCGGCTTCCCCTTTGGC GCGTTCGGCGGCATGGGCGGCTTCCCGGGCGGCGGCA TGGGCGGCATGGGCGGGATGCCTGGCATGGGGCAACG GCGGCCATCCGGGCCAGTCAAGGCCAAGGCCATTGAG CACAAGCTCAACCTCTCGCTCGAGGAGCTGTACGCGG GCACCACCAAGAAGATGAAGATCAACCGCAAGGTCA AGGGCCGGCCGCAGGAGGAGATCCTGGAGATCGCGG TCCGCCCGGGCTGGAAGAAGGGCACCAAGATCACCTT CCAGGAGAAGGGCGACGAGGATCAAGGCATCATTCCC GCGGACATTGTCTTCGTCATTGATGAGAAGCCGCACC CACGGTTCAGGCGCGAGGGCAACGACCTGTACTTCAC GGCGGTGGTGTCGCTGGCGGACGCGCTGTGCGGCACC ACGTTGCAGATTCCGCACTTGGACGGCACCACGATAG ACCTGCCAATCCGGGACGTCATCCGGCCTGGCGAGAG CAAGGTGTTGCGCGGCAAGGGCATGCCCGTCACCAAG GAGCCGGGCGCGTTTGGGAACATGGTGCTCAAGTTCG ACGTCAAGTTCCCGCGCGAGCTCAGCGACGCCACTAA GCAGCAGCTGCGAGCCATCCTGCCCTCGCACTGA |
| 42 | 128 | ATGGCCATGGCCAAGGAGACCGAGGACCTGGACCTGC CAGAGGCAACCGCCCACGCGGGCGTGCTCGCTGTGCT GGAGGGCAAAACGCACGCGGCGTATTACCTGCTGGAG CAGTCGGGGGAGGTCGTGGCGCAGCTGATGATCACAC TGGAATGGAGCGATTGGCGAGCCTCCGACATCTGGTG GATCCAATCTGTGTACGTTAGGCCAGACTGCCGGCGC CGGGGCCACTTCCGGGCACTGTACGCGCACGTGCGGG AGGAGTGCCGGCGGGCGGGTGCCTGCGGGCTGCGGCT GTACGCGGACACTGGGAACGAGCGGGCACACGCCGC GTACGAGGGCCTGGGCATGAGCAGCCACTACAAGGTG TTTGAAGACATGTTCACCCAGTACTGA |
| 43 | 129 | ATGAGCGGGGACGAGGGCGACGGTCGAGATGGCAAC AGCAATGCGCGTGAGCAGGACAGGTTCCTGCCCATCG CCAACATCAGCAGAATTATGAAGAAGGCGCTCCCGAA CAACGCGAAAATAGCCAAGGATGCAAAGGAGACGGT CCAGGAGTGCGTCTCGGAGTTCATTAGCTTCATCACGT CGGAGGCTAGTGACAAGTGCCAGCGGGAGAAGCGGA AAACAATTAACGGCGACGACCTGCTGTGGGCCATGAC GACGTTGGGCTTTGAGGAGTACCTGGAGCCGCTCAAA CTCTACTTAGCCAAGTTCAGAGAGGCTGAGGCGGCGA CATCCAATAAGCCAGGGGGCGGCTCAGGTGCCAACGC GGAGGCAAAGCGTGAGGCGGCCGCGGCGGCTGCGGC TGCGGCCGCAGCTGCGGCTGCAGTTTCGCAGCAACAG GCGGCGCAGCAGCAGATGGCGGCGCAGCTGCAAGCT |

TABLE 8-continued

| Transcription factor library. | | |
|---|---|---|
| | | GGCATGGCGTTCCCGGGGCTCATGCCGGCGCAGTTCC<br>AGGGGCTACCGCCCGGCATGATTCCCGCTGGCTTCCC<br>CGGACTGCCGCTGCCTCCGGGCGTGCCGGGCCTGATG<br>ATGCCAGGTGGCGTTGTGCCCAAGCAGGAGCCCCCCA<br>AGTAG |
| 44 | 130 | ATGGCCGATGAGGGACCGTCAACGTCTGGGGACGTGC<br>GCTTCACTGTTCCCACACGCCTAAAGCTGATTGTGACC<br>GAGGGGCCTTGCGAGGGACAGATTTTTGACGCCGCAG<br>AAATGGACGCCTGTTTCCTGACGCTCGGGCGGACAAA<br>GAAAACCAAAATCCACCTGAAGGATGACTCCATCTCG<br>GAGAAGCACGCCGAGTTCGCATGGACTGGGAGCCACT<br>GGACGGTCACAGACACGTGCAGCTCCAACGGCACCCG<br>AGTGAATGGGGCCAAGCTCAAACCAAACGAGCCGCA<br>CGTGCTAAAGGCGGGTGAGCACGTGGCGCTGGGTGAT<br>GAGACCATCATGACCGTGGAGCTGTCGCAGCAGTCGC<br>TCGCGAACGTGTCACTGGAATGGCTGATGCGGGCGCA<br>CTTCGAGAGCAGCTGCCAGGGGCTGGAGGCTGGCGGC<br>GCGGACAAGGCGCGGGAGATGGTCCGCCGCTGCCACG<br>AGGCCCTGGACTCGCTGATGGACCCGGCGGCGGCTGT<br>AGCGCCCGCGGCCGCAGCCACGGCGGGAGGGAAGTA<br>G |
| 45 | 131 | ATGGAGCTTGGACTCGCAGAGAGTCTGGGCGACGCCG<br>ACTCCCTAGCAGCCTACCTAAATGGCAGTTTCATCGGT<br>GGAGGCTCGCTGGAGCAGACGCTGGAGGCACCTTCAT<br>TTTTAGGCGAGCTCGCTGCCATTACGGGGTCTATGGA<br>GGCTCCTTATGCGGCGGCAGCACCTGAGCTGCCGGCA<br>GAGCTCAAGCCAGAGGAGCTGCCTTCGACAAGCGGCG<br>CAGGCTTCCTGCCACAGTCGGAGGCGGGGCCGATGTC<br>CGAGGCCGGGCTCTCCGCCGATGGCGGGCTTATGTCG<br>GAGGACGACGCGGAGGGCGGCGCAACGTCCTGCAAG<br>GGCGGCGGCAAGCGCCGTCGGCGGATACGCACCGAG<br>AGGCAGCAGGTGCTGAATCGCCTAGCACAGCAGCGAT<br>ACAGGCAGCGCAAGAAGGAGAAGGTCCAGGCGCTTC<br>AGCACAACGTGGACGCCTTGCAGATGCAGCTGGAGCG<br>GGTCAGCTTCCTGGAGTCGCAGTGCGACTCACTGCGC<br>GGCACGGTGGCTCAGCTAGGCGCGGACCTTGCTGCCA<br>AGGACGCGGGGCTGGCGGCGGCGCAGGCGCAGCTGC<br>GGCAGGCGGCGGTACTGCTAAAGGGCGCGCAGGACA<br>AATGCGCTTCGCAGGAGCGGCAGCTGGCGGAGCAGGC<br>GCAGGCGCTGGAGGCGCAGCGCTCACAGCTGCGTGTG<br>TCCAACCTGGCCAGCCTGGACCCCCAGGCCCTGTCCG<br>ACCGGCTGCTGGCGCTGGTGAAGGAGGCCTTCGCCGC<br>CGCTGCCGCAGAGCGCAGCTCGGAGATTGACGGCTCC<br>GGGATGGCGGCGCCGGCGGCGGCTGCCGCGGCGCCTT<br>CGGCGCCGCCACCGCTGGCGATGTCGGAGGAGGTGGT<br>GGCGGCTCTGAGCCGCAGCCTCACCAGCTGCTGCCGC<br>GAGCTGGTGTTTGCTAGCAAGGGCCTGGGCGGCAAGC<br>AGGCGGCGGCGGAGGCACCGTCCGTCATCCCCGTGCA<br>GTGCTGCTAA |
| 46 | 132 | ATGGCCAAGCTCATTAAGAACGTCGGAGCTTCACTAA<br>GGGCAAGGACCCACGACGAGGACGACACAATGATGA<br>AGCAGAAAGGAGCGACAGGGGTGTTCAGAAACCTCG<br>CGTTCGCGGACGCTGACGACAACTTGGTCTCCACCTCC<br>GCACGCGCGATGGCAACTTCGGAAAGTACCAAGAAG<br>AACAACTTCTTTGGTGGCAGTCAGGACAACATTGCGT<br>CCATAGATGTCACGCCGCGGTCACGCGACGCGGGCAA<br>CGGAGCGTCCTCCTGGGCGCACGCTGACCTCCCCACC<br>TCGGCCAGCAAGCGCGTGGGCAGCACCGGCAGCGCAT<br>CTACACCTGTGAAGAGCGCAACCTTTGCACGCACCGC<br>TTCGGCACAAAAGCGCGCCAAGAACGCGACAGCCATT<br>CAGGAAATCTCTGCGTTTGAGCACGAGCACGCTGTGA<br>TGGACGAGATGTCGGGCTCCGAAGACGGCGAGCGGCC<br>AGCGGGCCTAGTGAGCGGCGGCAGCGCCATCGGCGCC<br>ACCACTAGCACCACCGTCATTGCCGTGCGCTCCGTCG<br>CGCGCGGCCCCAGCATCACGCAGCAGGTCAGCACCAG<br>CGGCAGCGTGCGGGCGTGGGAGGAGGAGGTGAAGCG<br>GCTTATCGCCAGCGGGCGGCACGAGGACGCGGTGCGG<br>TGGGTGGCCCCCTCGGACGGCATCATCCGCTGCACTG<br>TGCGTCGCGTGAAGAACTTCCTGGGGCATACGCTCGC<br>CTACCAGCTCTTCTTGGACTCTGGAGACACGTTCGTGC<br>TGGCGGCGCGTAAGCGCAAGAAGAGCAAGGCCTCCA<br>ACTTCGTGCTGAGCACCAGCCAGGAGGACCTCGGCAA<br>GGACTCGGACCACTGCATCGCCAAGCTGCGAGCCAAC<br>TTCGTGGGCACTGAGTACGGCCTGGTGTCGCGCACCG<br>GCGGCCACATCAGCGGCAGCATGGACATTGACGGCGG |

TABLE 8-continued

| Transcription factor library. | | |
|---|---|---|
| | | CGCGCAGTCGGGCGGCAAGCTGGCGCCGCCGGCCGA<br>GCCCTTCTCCCGCGAGGAGATTGCGGTGCACTACAAG<br>CAGACCGCGCTGACGGCCAAGGGCGGACCCCGCACC<br>ATGCTGGTCGCCACGCCGCTGCCGGAAGTGAGCTGGG<br>CCCCCAGCGCCGCTGACGGCTCGGACTCGCTCGCCAA<br>CTGCCTTGAGGCGGCGCGCCGGCGGGAGCTGTCGCCG<br>CGCATGGAGCGGCAGCTGTGCATGCTGGCCACGCGGC<br>CGCCGGAGTGGGACCCCAGCCTGAAGGCGTACACGCT<br>CGACTTCCACGGCCGCATCCGCGCCAGCAGCGTGAAG<br>AACTTCCAGCTGGTGCACTGGGACCACAACACGGACC<br>GCAAGGGCTCTGACCTGGTGCTGCAGTTTGGAAAGAT<br>TGACGAGAACACTGACGACTTCGCGCTGGATTTCACC<br>TACCCGCTCAGCCTGCAGAAGGCGTTCGCCATCGCGC<br>TCGCAAGCACCGACACAAAGCTGTGCTACGCGTTGTA<br>A |
| 47 | 133 | ATGGCAGAAGAGACAGGCCGGTCGCAGAGCGGCGCC<br>GAGGCGACGACCAGCGATGCCATCCGATATGTCCAAT<br>ACAAAGGCGAGGAGGACCTGCCCATCGTAATGGGCCT<br>GGTCGACAAGGAGCTCAGCGAGCCCTACAGCATCTTC<br>ACGTATCGCTACTTTCTGCAGCAATGGCCACACCTATG<br>TTACATTGCATATGACGGTGACAAGCCGTTCGGCACG<br>GTCGTGTGCAAAATGGACATGCACCGGGACCGGGCGC<br>TGCGCGGCTATGTCGCAATGCTCGTGGTTGACAAGGA<br>GTACCGTGGCAAGCGCGTGGGCTCTGAGCTGGTGAAG<br>ATGGGGATTCGGGAGATGATTGCGGGCGGCTGCGAGG<br>AGGTGGTGCTGGAGGCGGAGGTCGTAAACACCGGCGC<br>CCTCAAGCTATACCAGGGGCTGGGCTTCGTGCGGGAA<br>AAGCGCCTTCACAGGTACTACCTGAACGGTGTGGACG<br>CCTACCGCCTCAAGCTGCTGCTGCCGCTGACCGAAGA<br>GAAGAAGGCGGCGCTGGCGGCGGCCGCGGCGGCGGA<br>GGCGGCGGAGCTGGAGGGGGTGGAGCTGGAGGCGGC<br>GGCGGTGGACGCAGGGGCAGTCGCGGCGGCGGCGGA<br>GCCTGCCATTGCGTGA |
| 48 | 134 | ATGGTCGGCAACAAGCTGTCAGCTGTAAGGTCTGTGC<br>TGCGAAAGGCTCGACAGCTCAAGGACCCTCTCGGTGA<br>GCTCGTCAGCACTGCAAGGCCCTGCCGCGTCGACGGC<br>CAGCAACACACGCACTTCCGGTCGCACCATGCCGCCG<br>ACCTTCCCAAGCAGCAGCTGGAATGGTGTCTGGACGT<br>GTGCCGGGAGAACATGGCGGCCTTTTATGAGCGCGTG<br>TGGTCTTGGAGCGATGTGAAAAAGAGGCGGCAGTTCA<br>CCTCGAGCGCTTCTCGGTTCCTGATAGCATATGACGTG<br>AACGCTGCTCGCGTCCCTGTTGGCTACATCAACTTCAG<br>GTTCGAGTACGAGGACGGCGAGGCGGTGCTGTACTGC<br>TACGAGCTGCAGGTGGCGCGGGCGGCGCAGCAGCGG<br>GGCCTGGGCCGAGCCATGATGGAGCTGCTGGAGCAAA<br>TTGCGTGGGGCGCCGGAATGAGCAAGGTGATGCTGAC<br>GGTGTTCACCGAAAACGTCCCGGCACTGGCGTTCTAC<br>TCCAAACTGGGTTACCGGCTTGATGAGACGTCCCCCG<br>ACTATAGCCCCGCAAGCGGCAACTGTAGTCCCCTGGA<br>GTTGGCGCACAGCGCGGGCGGCGGTGGCAGTAGCCGG<br>TGCAGTCCGGAGCTTGGCGCGGCGGCGGCGGTGACAG<br>CTACTGGTACGGGCTGCAGTGGCAACCGTAGCGCAAG<br>CGGAAGCCCGGAGGGCGGTGGCAGCGCTGCTGTCAGC<br>AGCAGCATGGCTGTCAGCAGCGGGAGCGCTGGGGGTG<br>CTGGGAGCGGCGAGGGCAGCGGGAGCGGCTACCACA<br>TTCTCAGCAAGCGGATTCCATCGGACTGGCGGGAGGA<br>GGTGAGGCTTCAGCAGGAGGCGCAGCAGCAGCGAGA<br>CGTGCAGCGTGCTGAGGTGCAGCAGCAAGTGGCAGTG<br>CGGAACGTGGCGCCCGGGCATCAGGCTCACGAGGAGC<br>ACCAGGTGCACCAGCAAGGCCAGTCGCCGCAGCCACT<br>GCCACAGCAGCTGGCACCGCTGCGGCAGGCAGTGGAG<br>GCCGTGGCTGCCATGGCAGAGGCGGCCTTGCCTGTGG<br>CAGCAGCAGCGGCCTCGCCGGCCGCAGTCTGCGCCCC<br>GGAGGCCGAGGCTGAAGAGCCTGGCAGTCGGAAAAA<br>GCAGCGCGTATCCTGCACGCCGGATGTCACCGGCGCA<br>GGCAGGAGCGGCAGTTGCGGGCCGGAGCTGGAGGAC<br>CGCGCTGAGGGAGCAGCGCAAAGCGACGTCGCGGCC<br>ACCGCCGGACACGACCTGTCACGGAATGGCACACCGG<br>TGCCCATGGTGATCCATGAGGGCACGGGTGCTGGTTC<br>TGGCGCCGGTGCTGCAGCGGCTGGGACCTCGAGCACA<br>GAGCAGGAGAAGGCAGAGCAGGTGAAGCCGGGGGCT<br>GCAGAGCCCGCGGCGGTACCGCCGGCGCAGGATGGC<br>GAGGCCGCGGGGGCTGGCATGAAGATATGTGGAGCGT<br>GCAGCAGCAATGGTGCAGCGGCCGCTGAGCACATACC<br>GTAG |

TABLE 8-continued

| Transcription factor library. | | |
|---|---|---|
| 49 | 135 | ATGCTGGACCGAATTCATGAACTTGAAGCTGCCTCTTA CCCAGAGGACGAGGCCGCTACTTACGATAAGCTAAAG TTCAGGATCGAAAACGCGTCGAACGTGTTCCTGGTCG CGCTGTCGGCGGAGGGCGACGGGGAGCCCAAGGTCGT CGGGTTTGTGTGCGGCACGCAAACGCGCGCGTCTAAG CTGACACACGAGTCCATGTCAACGCACGATGCCGACG GCGCACTACTGTGCATCCACTCGGTGGTGGTGGACGC CGCGCTGCGCCGGCGCGGCCTGGCCACCCGCATGCTC CGAGCCTACACCGCCTATGTGGCCGCTACCTCCCCGG ACCTGACCGGGATACGGCTGCTGACCAAGCAGAACCT GATCCCGCTGTACGAGGGCGCGGGCTTTACGCTGCTG GGTCCCTCGGATGTGGAGCACGGCGCCGATCTGTGGT ACGAATGCGCCATGGAGCTTGAGGCGGAGGAGGAGG CGGAGGTGGCGGAAGCCTAG |
| 50 | 136 | ATGGCAGCCAGCTTCTCTATCTCTGGCGATTTTGCCTG TGGCCAGTCTACTGGTCACGCGACGTTCTGGCGGCTTG AAGAGAACAAAGTCTTCGAGGTAGCCCTTGCAAGACA CTACGCGGACGTGGACAGGTTCGAGCGCATCGCCTCT TATCTGCCAAACAAGACGCCTAACGACATTCAGAAGC GGCTCCGCGACCTCGAGGACGACTTGCGACGCATCGA TGAGGGGTGTAACGAGGGCGCCTCAGCTCAGAGCGCC CCCGCGGCGACCCCCGCACGTTCAGAGGACTCGGCGC CGAACGCCAAGCGGCCAAAGACCGATGTGCCAGCCA ACGGTGACCGTCGCAAGGGTGTGCCCTGGACGGAGGA GGAGCACCGGTTGTTCCTGCTCGGGCTCGCCAAGTTC GGCAAGGGTGACTGGCGTTCCATCGCCCGCAACTTCG TCATTTCTCGGACGCCAACCCAGGTGGCGAGCCATGC GCAAAAGTATTTCATCCGCTTAAACAGCATGAACAAG AAGGACAAGCGCCGGGCGTCGATCCACGACATCACCA GCCCGACGCTGCCCGCCTCGGTGGCCAACCCCGCCCC GACCACGGGGCTAGCGCCTGCAGCGGCCTCGGGCAAG GCCACCTCGTCATTGGTGCAGGGCGCGACCTCCTCCG CCACCACTGCCACCTCGCAGCCCATGGCCGCCGCGGC GGCCGCTGCAGCGGCAGCCTTCCCCGCGGCTGCGCAC GTCGCCCGCTGCCGCTGCCGCGGCCGCCGCCGCCGCCA CCAGCACCACCAGCGTTTTCGCGCAGCTGGCTATGCA CGGGCTTGCCATGCAGCCGGTGATGCAGCAAGCGGCT GCGGCTGCGGCAGCAGCGGGCATGATGCCTCAGCTCA ACGCGGCGGCCGCGGCCGCTGCGGCCGCCGGCATGCC GGCGCCCGTGCTTCCCAACGCGGCGCAGTACATGGTG CAGGTCTAA |
| 51 | 137 | ATGCGCAGCCAATACTTGCTTAACACACGCCGGTGGG TGGTTCGCCTTGCCGATCAGTGCAGCCAGCGCGCGAG CCTTACGGTGAGCGCGCAAGCCGCCGCCGCAAACGAG CCAGTCACTGATCTACCGGAGCTAGTATCTTGGGTCTT GCACCGAGGAGGTCGAGTGGATGGCGCAACGCTCGCG AACCTGGCTGGGCGCGATGGCGGCAGCGGCTGGGGGC TGAAGTGCACCAGAGACGTGCAGCAAGGGCATCGGCT CATCACGCTGCCGAACGCAGCGCACCTGACCTACGGC GCCAACGACGATCCTCGGCTCCTGGCTCTGATCGAGA AGGTGCCCTCAGAGTTGTGGGGCGCTAAGCTGGCGCT CCAGCTGATCGCTCAGCGGCTTCAGGGGGGCGAGTCG CAGTTTGCCTCGTACGTGGCGGAGCTACCCAAGGGCT TCCCCGGCATCCCCGTGTTCTTCCCCCGCACCGCGCTG GACATGATCGACTACCCACCCTGCTCGCAGCAGGTGA AGAAGCGCTGCAAGTGGCTGTACGAGTTCAGCACTGA GGTGCTGGCCAGACTGCCGGGTAGCCCCGAGGACCCC TTCGGCGGCGTGGCGGTGGACATCAACGCCCTGGGCT GGGCCATGGCGGCGGTGAGCTCACGTGCCTTCCGCAC GCGCGGCCCCACACAGCCCGCCGCCATGCTGCCGCTG ATCGACATGGCCAACCACACCTTTAGCCCCAACGCCG AGGTGCTGCCGCTTGAGGGCGGCGGCGGCGCGGTGGG CCTGTTTGCGCGGCGGGCCATTACTGAGGGCGAGCCG CTGCTGCTGAGCTACGGCCAGCTGTCCAACGACTTCCT GTTCATGGACTATGGCTTCATCGTGGAGGACAACCCG TACGACTCTGTGCAGCTGAGGTTCGACGTCAACCTGCT GCAGGCCGGCGCGCTGGTGGCCAACGTGAGTGATGCA CTGGGCGCCCCCCTGGACCTGGCGCCCCGCACCTGGC AGCTGCAGCTGCTGGCCGAGCTGGGGCTGGTGGGCCC AGCCGCCAACACCGAGCTCAACATCGGCGGCGGCGGC CCGGGCGCTGAGCTGCTGGACGGGCGGCTGCTGGCGG CGGCGCGCATCATGGTGGCGCGGGCCGATGGCGAGGT GTCGGGGCGCGGCGTGGAGCGGCTGTGTGCTGTGGAC CGACCGCTGGGTCGGGACAACGAGCTGGCGGCACTGC GCACTGTGGGCGGCGTGCTGGCGTTTGCGCTGAGCAA TTTTGCAACCACCCTGGACCAGGACAAGACACTGCTG |

TABLE 8-continued

| Transcription factor library. | | |
|---|---|---|
| | | GCGGGGCAGCCCGTGGCGGTGCCGCAGGCGGGCGGG<br>GTGGGCGAGCGCGAGCTGCCACCCCTTGCCAGTGAGG<br>ACGAGGCTCTGGCGGTGCGGTTCCGGCTGGAGAAGAA<br>GAAGATCCTCAGCCGGGCGCTGCAGCGGGTGGGCGCA<br>TTAAGTCAGGCGGCCGCGGGCAACAGCGAGCTGAGGC<br>AGACGGCAGGCTCTGCAGCAGCAAAGAAGGGCAGCA<br>AGCCGGCGCCGGCCACTGGCAAGGGCTTCGGCTCCAA<br>GAAGCGGTGA |
| 52 | 138 | ATGGCAGACGCAACGGGCTCAACGCAAGACGACGGC<br>TCCAACACCGTGATTGTTATTGTAGGAGTGGTGCTTGT<br>CATAGTTGGAGGCGCGCTGCTTTATTCTTTTATTCAAT<br>ACCAGCGGATGATGGCCAACGCGCCCGCACGGCCAA<br>AGAAGAAGCTAGGGGCGAAGCAGATCAAGCGCGAAA<br>AGCTGAAGATGGGCGTTCGGCCGCCGGGCGACGACTG<br>A |
| 53 | 139 | ATGAACATGAACTCTCAAGACTGGGACACCGTTGTGC<br>TTCGCAAGAAGCAGCCTACTGGCGCAGCGCTGAAGGA<br>CGAAGCCGCTGTCAATGCGGCACGGCGGCAAGGTGCA<br>GCTGTGGAGACGTCGCAGAAATTTAACGCTGGAAAGA<br>ACAAGCCTGGTGCGGCTCAGACTGTGAGCGGCAAGCC<br>TGCAGCCAAGCTGGAGCAGGAGACGGAGGACTTCCAT<br>CACGAGCGCGTGTCTTCGAACCTCAAGCAGCAGATTG<br>TGCAGGCGCGCACGGCGAAGAAGATGACCCAGGCGC<br>AGCTAGCGCAGGCTATCAACGAGAAGCCGCAGGTGAT<br>CCAGGAGTACGAGCAGGGCAAGGCCATCCCCAACCCC<br>CAGGTGCTCTCGAAGCTGTCCCGTGCGCTCGGCGTGG<br>TGCTGAAGAAGTAA |
| 54 | 140 | ATGGGCAGCACATCAGGTGTTCGCACGTTCAGCAAAT<br>CCGATGACCCGGTCGCAGCGGAGGAGTGCTGCAACAC<br>GGTTGGCAAGGGTTTCGCCTCCGAGCCCAACAACGTG<br>TTCTTCTGTGCGGACCCCGCGCTCTTCGAGGGCAGGTG<br>GAGGGCCATCGCCCACAACAGCCTACTGCGCAGCCCC<br>GAGACCCCCCTGCTGCACTCGGTGGCCTCCGGCGATA<br>CGCAGCACGCGGCCGTTGCATTTGCTTACTCCTACCCC<br>GAGCAGAAGACACCGGATGACGCGCCGGAGCCGCCC<br>GGTGTCATCGACCTGTCCGGCAGCGGCCGGCCCGAGG<br>CGGTACCCACACGGGATGAGATGCTCAAGTACCTCGG<br>GGACAAGAAGACCGAGTTCTACCAGCGGCGCGGGCC<br>GTTCGAGTACGTGGCCTTCCTCGCCACTCGGCCCGAGC<br>ACTGGGGGCGAGGCCTGGGGTCGCGGCTGCTGAAGCA<br>CCTGACCGACAGGGCTGACGCCGGGGGCCGGTGGGCG<br>TACCTGGAGGCGACCAACGCGGACAACGCGCGGCTGT<br>ATGCCAGGCACGGCTTCCGCGAGATCGAGACCAAGGT<br>GTGGACGCTCGAGTGCCTGCCCGGGCAGCGCATGATG<br>CTGATTTACATGGAGCGACCACCCTCGGCACAGCAGC<br>AGTAG |
| 55 | 141 | ATGACGGATTACCTAAAGGACTTCATTGACAGGGCTG<br>CAGATGTGCCCCTGCAGCTGCGTCGGCGCCTTGCCCTC<br>ATCCGTGACCTAGACGAGAAGGCACAGGCGCTGCATC<br>GTGAAATAGATGAGCACTGCAAGCGCACGCTGGCGGA<br>GAAATCGCAGCAGCACGCAGCTAAGAAACAGAAGCA<br>GGCTGCGGGGGAGGACGCTGGCGGGTCAGCAGCGGC<br>GCCGTACGACGTGGAGTCGGCTCTGAAGCGGCTCATA<br>GGTCTCGGGGACGAGAAGGTCAACATTGCTAACCAGA<br>TTTACGACTTCATGGACAACCACATCAACCAGCTAGA<br>CACGGACTTGCAGCAGCTGGACGGGGAGATTGAGGCG<br>GACCGCAAGGAGCTAGGGCTGGAGGGTGACGAGACG<br>GCCTGCGAAAAGCTGGGCATAGAGGCGCCGCAGGGG<br>TCACGGCCGCACACGGTCGGGAAAGGGGCAGCGGAC<br>CAGAAGAAGAAGCGCGGGCGGAAGAAGGACGAGTCG<br>ACGGCAGCTGCAGCCGGTGGGCTGCCGCCCATCGAGA<br>ACGAGCCGGCGTACTGCATCTGCAACAAGCCGTCGGC<br>GGGGCAGATGGTGGGCTGCGACAACCCCGAGTGCACC<br>ATCGAGTGGTTCCACTTCGAGTGCGTGGGGCTGACGG<br>AGGAGCCCAAGGGCAAGTGGTACTGCCCCGTGTGCCG<br>CGGGGACCTGCAGGTCAAGTCGGGCAAGAAGAGCGG<br>GCGGCGGTGA |
| 56 | 142 | ATGGGGAAGAAGAAGAAGCAGAAGGAAATCGAGCAG<br>TGCTTTTGCTATTATTGCGACCGCATTTTCGATGATGA<br>GTCGGCGTTGATTGTGCACCAGAAAAACAAGCACTTC<br>AAATGCCCAGAATGCAACCGCAAAATGAACACCGCCC<br>AGGGCCTGGCAACGCACGCGTTCCAGGTGCACAAACT<br>AACCATCACTGCTGTGCCCGCCGCCAAGGCCGGGAGA |

TABLE 8-continued

| Transcription factor library. | | |
|---|---|---|
| | | GATTCCATGGCTGTGGAGATCTTCGGCATGGCGGGCG |
| | | TGCCGGACGACGTGCGGCCCGCCAAGCTTCAGGGTGA |
| | | TGGGCCTGCGCTCAAGAAGGCGCGCGCGGACGACGAC |
| | | GATGACGTGACGCCGCCGCCCGCGCCGCCGCCGCCGC |
| | | CGGGCGGCATGCCGCCGCCGATGGGCGGCTACCACCC |
| | | TGGCATGCCGCCGCCCATGGGCTACCCGCCCTACGGC |
| | | GCACCACCGCCGTATGGGTATCCGCCCTACGGGCCGC |
| | | CCCCGCCGGGGTACCCGCCGCGCCCGGGCATGCCGCC |
| | | TCCCTACGGCGCGCCGCCTCCCTACGGCATGCCGCCTC |
| | | CCGGCTACCCGCCTCGCCCCGGGATGCCGCCCCCAGG |
| | | CATGCCACCGGGTGCGCCGCCGCCGCTGGGCGGCCCG |
| | | CGGCCGCCCTTCCCGCCCTACGGCATGCCGCCACCGG |
| | | GCATGCCGCCTCCGGGCATGCCTCCCCCCGGAATGCC |
| | | GCCACCAGGCATGCCGCCGCCAGGGGCACCAGGCGG |
| | | GCCCCTCTTCCCCATCGGGCAAGCGCCACCGGGCGCG |
| | | CCGCCGGCACTTTTCCCCATTGGCTCTTCGGCGCAGCC |
| | | GCCGGCTGCAGGGGCAGATGCAGGGGCAGGGGCCGC |
| | | CGCAGCGCCCGCCGCGGCGGGATCGGTGGCGCCGGCG |
| | | CCCGGCGACGGGTCGGTGGTGGTGTGGACGGATGAGG |
| | | AGTGTTCCATTGAGGAGCGGCGGGCGCAGCTGCCTCG |
| | | CTACGCGATCGCGGCCGGGGGGCCAGGGCGCAACGG |
| | | GGCATGA |
| 57 | 143 | ATGAAGGACGACGCGGCAGCGGCAGCGGAGCGCCCG |
| | | GCGGACATGCCCACGGACGCCGCGGACGCTGCCGGGC |
| | | CGGGCCCCAACTCAGCTGCCGTGGCCGCGGCCGCTGG |
| | | CTCAGCAGGCATGTTCCGCCGCAAAAAGGGTGGCGCC |
| | | AACATTCGTAAGCGCGGCGGGGCGGAGGGCGGCAGC |
| | | GACGACGACGAGGCGGGGGGTGGCGTGGTGCGCAAG |
| | | GCCAAGGCCGCCAAGTCGGACGCGCCGCTGGCGTTCA |
| | | CGACCAAGAAGGACGACAAGGAGACGTTAATGGTGG |
| | | AGTTTGCGGGCTCCAAGGCGCTGCAGGACGGGAAAGA |
| | | CACGCTCGCGACACGCGTGCTGGAGACGGAGACGGA |
| | | ATATGACCGGGACGCACGGGCGCGGCGCGAGGAGGT |
| | | GCTTAAGCAGGCCACGGCGGCGGAGGGCGCGGCGGA |
| | | CGACGGCACGTACAAGGGCATGAACGCATACGTCGAC |
| | | TACCGCAAGGGCTTCCGGCGCGAGCACACGGTGGCGG |
| | | CAGAGAAGGGCACCGGCTCGCACGGCCCCCTGCGCGG |
| | | CAACGCCTACGTGCGCGTGACGGCCCGCTTCGACTAC |
| | | CAGCCGGACGTGTGCAAGGACTACAAGGAGACCGGCT |
| | | ACTGCTCGTACGGCGACACGTGCAAGTTCATGCACGA |
| | | CCGTGGAGACTACAAGAGCGGCTGGGAGCTGGATAA |
| | | GATGTGGGAGGAGGAGCAGAAGCGCAAGGCGGAGGC |
| | | CCTTGCCAAGGGCTGGAACCCGGACGCCGATGGCGAG |
| | | GAGGAGGAGGAGCAGGGAGGCGGCCGGGAGGATGAC |
| | | GAGCTGCCGTTCGCTTGCTTCATCTGCCGCGAGCCCTG |
| | | GGAGGCCTGCAAGTCGCCGCCGGTGGTGACGCGCTGT |
| | | AAACACTACTTTTGTGAAAAGTGCGCGCTCAAACACA |
| | | ACGCCAAGACGACCAAGTGTGCGGTGTGCGGAGTGGC |
| | | CACACAGGGCATCTTTAATGTGGCGCAGGACATCATC |
| | | AAGCGCCAGAAGCGCATGGGCGTGGTGGGGTGA |
| 58 | 144 | ATGGAGCGCTTTGACTCCCAGATGCTGTTCAGCGTCTT |
| | | TAGGAACGACGAGGGTGAAAACCTTTTGCCGTTTGAT |
| | | GAACTGGCGGAGCTGCTTCAGATGGATCTGGCTCCCA |
| | | ATGGCGACGCCGGGGCCACGCCAGCATCGTTCGCACC |
| | | GGACGCCGCTCTGCCCCTAGACCTCCCACACCTGCAC |
| | | CACGCGCCACCCATCATCACCGCGCCGCTAGTCACCA |
| | | CCGCGCCGCCCACCGGCCCCATTCCCTCTGACGAGCG |
| | | CGCCGCAGCGCTGACGCACCAAAGCACTCTGCCCAGC |
| | | CCCAGCGGCGGTAGCAGCGACCACACACGCGCCCAG |
| | | AACTGGGCCGGCTCGAACCCATCATCAGAGGACGGCG |
| | | ACGGAGATGGCGACCGCGACGGACGCGACGGTGACG |
| | | GCGACAGCGGAGACTCAGACATGGACCACACCACAC |
| | | AGACGCCGGGCGTCAGCGGGGCCGGCGACGCGGGCG |
| | | GCCGCGGGCGGCGGGGCAGCAGCAAGGGCGGCAAGG |
| | | CGTCATCGGGTGTGAAGAAGCGGCGGCAGCGCAATGC |
| | | CGAGCAGATGGAGTCCAACCGCATCGCGCAGCAGAA |
| | | GTACAGGCAGCGTAAGAAGGGCGAGCAGAGCGCGCT |
| | | GCAGACGGCTGTGGACTTGCTCACGGCGCAGGTGGCG |
| | | GCACTCAAGGCCGTGGAGGTCCGCAACGGCGAGCTGG |
| | | AGGCGGCCGCAGCGGCTCTGCAGTCCACGGTGTCTCA |
| | | GCAGGCCGCCGCCGTGGCCTCGCTGCAGCAGCACAGC |
| | | GCCGGGCAGGCGGCGGAGCTGGAGGCAACTCGCGCG |
| | | GCGCTGGGGCACAGCCAGCAGCAGGTGGCCGCCCAG |
| | | CACCGCATCATCGTGGACCAGGGCACCAAGCTGAGGC |
| | | TGCAGGAGCAGGTGATTGCAAGCCTGAAGGACCGACT |
| | | GAAGGAGGAGATCGACGAGGCATTGAAGTGCGTGGC |

TABLE 8-continued

| Transcription factor library. | | |
|---|---|---|
| | | GCCAAACACCGTGTGCGAGAAGATGGTGGCGGCGGTC<br>AAGGCCGCGCTGTACGGTGCCAAGGACGTCAGCGGAC<br>TGCAGGACGTGCTGTCCCAGCTGCCGGAGCACCTGGT<br>GCACGACATCTGCAAGAACATCTGGCAGGTGTGCAAG<br>GAGTCCTGGCCCGACCTGCGCAGCCGCTGCGCCACCC<br>TGCACGCCGCCGGCTGCCCCACCAGCGGCTTCGGCAC<br>TGCCTGA |
| 59 | 145 | ATGTTGCGCCAGCTTTGCAGCCGCAGCCTGCAGAGCC<br>TGGCATCTCTGCAGGGCCGCTGCACCTCGGGCTTGGC<br>GACGACGCTTCGTGCTGCGAGCAGCCTGAGCGAGCTG<br>TCACGGCCAGCCCCTTCAGTGGCGACCTCGCAATCAC<br>CAGCATGGTCATATAGAAATAGCAACTTGCTAGCGGC<br>GCCACCTCTGGGCTTGGGACTGGCGCCCCAGGTCCGC<br>GTAACCCCGGACGCCTCCACCATCCTCAGCCTCTTTGT<br>AAGCCAGCGGCGCAACGCAGCCGCAGCGGCTGCCGC<br>GGCCGCCGTAAAGAAGGCCGCACCGGCAAAGAAGAA<br>GAAGAAGAGCGCGCCGAAAACGGCGGCAAGCAGCAA<br>GCCTAAGCCCAAGCCCAAATCGACAGCAGCAGCCGCA<br>ACCAAGGGCCGCGTGCGGACCAGACCCGCCAAAGCC<br>CCGGCGCGCAAGTCGACCACCACCGCCGCGGCCAAAC<br>GCAAGAAGCCCGTCCGCAATTCCATCTCCGCCGCCGG<br>CCGCAAGGCCGCGAAGGCCGCGGAGGTCAAGGCCCG<br>GCTGCGAGTGCGCGCGACAGCGCAGCGCGCACGCGC<br>GCGTGCCGCCAAGGCCCTGGCCATGAAGCGGGAGCGC<br>GCCAAGCTCGCGCGGATCAGGCGGCGCGAGCGCGAA<br>GCGCTCAGGAAGCAGAAGCAGCGGGAAAAGCTGGCC<br>GCGGCAAAGGCCAGGGCCAAGGAGAAGGAGGCGGCA<br>CGCATCAAGAAGGCGCCATCGGCCTTCGGCCTGTACC<br>TGCAAGACCACTCCAAGGCGGTGCGCGACGCCCTGCC<br>CGCCGGCGCCGCCAGCGGCATGCAGCGCCAGGCGCTC<br>GCGTTCAAGGTGCTGGCGGAGCGCTTCAAGGTGCTGC<br>CGGAGGCGGAGAAGGCGCCGTACGAGGCGCGCTCGG<br>CGGCGCTGAAGGCGAAGGTGGCGGAGGCGCGCGCCC<br>AGGCCAAGGCGGAGAACAGCGCCAAGGCGGCCCTCA<br>CGCCCTACATCTTGTTCTTCAAGGAGTCCTACAGCGCC<br>ACGCGCGCCGCGCACCCGGACCTCAACGCGAAGCAG<br>GTGGCTGCCAAGATGGGGCAGTTGTGGAAGGCGATGC<br>CGGCGGAGCAGCAGCAGCGCTACCGCGACCTTTCAGA<br>GGCGGACCGGAAGGCGAAGGGCCTGCCTGAGCTGAA<br>GAAGAAGGCGGCAGCGCAGACTCAGGCCAAGCGGGC<br>GTGA |
| 60 | 146 | ATGGCTAGCCTGGTCTACTCCCACGAGTGGCTGATCTC<br>CAACTTTTTGAAAGTGGAGGCCCAGTCCGTCGACTCG<br>CCTTCCTTTAAGCTGGGCCCTCATGCCTGGAAGCTTCA<br>ACTCTACCCCTCTCAGGATAAAACGCACCTGTCCGTGT<br>ACCTGCGCTCCGTGGAGCCGAAAGCACCGCGAGCAGT<br>GAACTTCAAGTTCGTGCTGCGCAATTGGCAAGACCCC<br>AAGGATGACTTCAAAAGCGCAGACGCAAGCTACACCT<br>ACACCGACGCGTGCGTGGCGGGATATGGCTTTCCCAG<br>CTTCATTCCTCGCGAGAAGCTCAGTATCGCCTCCGGCT<br>TCCTGCGTCCCACTAGTCCCACCAACGGCGGCGCGTT<br>GCTGCTGCGTATAGAGCTCGAGTACAACACACTTCCG<br>GCGGCCTCCAGCGCGGCGGCGGATGGCAGCAGCGGC<br>GGTGACGGCGGCGGTGGCGTTTACCCGGCAACTGTGT<br>GCGACGGCGCGGTCTCTGCCGGTAGCGGCGACATTGC<br>CACGGACCTGCTCTCACTCTGGAAGCGCCCCGGCCCC<br>ACCTCCGATCTCATTATCATCGCTACCGCGCCCGCCGG<br>TGCGGCGGCGGCAGTGGCGGCCAACCCAACAGCAGA<br>GGTCTTGGGAACGGGAGCGGGCGCGGCTGCTACCATC<br>AAACCCACCACTGCCACGGCGGCGGCTGACGGCGGCG<br>GCAGCAGCTGCGGCCCCAGCAACACCGGCATGCGGCG<br>CTTCGACGTGCACCGCGCCATCGTGGCCGCGCGCTGC<br>CCCTACTTCGCCACGCTGTTTGACAGCGGCATGCGCG<br>ACAGCAGCGCACGCGAACTGCCGCTGCCCGACACCGA<br>CCCCGCCGCTCTGGAGCCGCTGCTGCACTTCATGTACG<br>GTGGCGGGCTCACCGTCACTACCCGCCAGCAGGCGCG<br>CAGCTCCTTGGAGCTGGCAGACCGGCTGCTGCTGCCC<br>AAGGTGGCGGCGCTGCTGCGGACGCACCTGCTGTCCA<br>CCGTGACTGTGGCCAGCGTGGTGCAAGAAGTTCTGTG<br>GGCGGCGGACGCGGCGCAAACAGAGCTGTTGACGGG<br>CCTGCTAGATTTCGCGGCGGAGGCAGAGGCTGACCTG<br>CCAGAGCGCGACCTGCAGCAGCTGGCGGCGCAGCAG<br>CCGGCGCTGATGGCACAGCTGTTCACGGCCGCTCGCC<br>GCGCCGCGAAACGCTCGTGCACGTAA |

TABLE 8-continued

| Transcription factor library. | | |
|---|---|---|
| 61 | 147 | ATGAAGATGTTGGAATTTCGCCTGAAGCTGGGCACCG<br>GAGCAGACTGGGAGGCGCTCGGACCTATTCCAGAGCC<br>GTTTCCGTTCTCCATCGACGCGGACTGCACCACTTTGG<br>CTTTTAAGCACTACCTCAGCCACAAAATCCTAAATGG<br>GGTCTTCGAGCCTGGAAACTTTCAGCTTCGGCTGCAG<br>GGCTGCGACAAGGAGCTGGAGGACGTCGCTGACGCCG<br>GCCAACCCACCACTTCCACGCACCAACCCCAGCTGCG<br>GCGGCTTGCCAGCCAGGGCGTGTGCAACGGCAGCGTG<br>CTGCAGCTTGACGTGTGTGCGACTGAGGAGGAGCTGC<br>AGCGGTTCCTGGACGCAGCGGAGGAGTGCGGCACGGC<br>TAACGAGCTTGGGCACGTCGAGGAGCAGCAGGAGGC<br>GCAGACGCCACCAGCGGCAGGTGTCGATCCGCGGCAG<br>CGGCACGCAGCAGAAGGCAGTGCGGCGGCGGCGGGC<br>GACGGGCCAACCGGGCGGCCCAGCCTTGGCATGATGC<br>ACACGCCTGCGGGCACGGTGGGCACCTTTCTGGACGA<br>TGAAGACGCGGACTACCTGCAGGAGGACCTAGAGGC<br>GCTGGTGCAGCCGGCGGCGCAGCGGGCTGGGGAGGA<br>GGAGCTCGATCACTTAAACGTGGCGGCCGACGGCGAG<br>CCTTTTGAGGCCGAGGACGCTGAGGACTTTGAGGCGC<br>ATGGCAGGGAGTTGCGAGGAGCAGGAGGCGTTGTGG<br>GGGCCCCTCAGCAACAGCATCCGGCCTTCGCGGCTGC<br>GGCGGAGGGGCGAGAGCAGGAAGGTGACGACGAGGA<br>CTGGGGCGACATGGGCCTGCGGTCAGCCGGCACTCGG<br>ACCGCGGGCCAGCCCGAACGGCGGGCTGCGGTCGCG<br>ACGCCGGCGCGGAAGCAGCAACAGCAACAGCAGCGA<br>CCGCGGGCTAACCTCCAGTCAGCGGCCAAGCGGGCGC<br>GCAGGGAGGCGCCGGAAGAGGAGCTTGACTTCGTGTC<br>GGGGTCAGCGGACGAGGGCGCTCAGCCCGCCCAGCA<br>ACAGCAGTGCACGCATGGCGCGGCGATCGTCGGCGGC<br>AGCACCAGAGGCGCCGCCGCGCCTGCACGCGCGGCG<br>GCAACGGGTGCTGCCACTGCTGCTGGCGCCGCCGCAC<br>CTAGGTCGCAGCCGCCGCGACAGCCGGCACTTGCACG<br>GTCTACGGGACTGCCGGCGGCCATGCAGCCTGCAGTG<br>GACACGGGCGCATTTAGCGCCTACGGCGGTGGCGGTG<br>GCCAGCAGCGAGCCTCAAGTGGCTTCTGGTCGCTGGA<br>GGAGACTGAACGCCTGGTGGAGTGGGTTGACTCGCAC<br>GGCGCGCGGCAGTGGACCATGTTCGTACAGCTGAACA<br>CCGACTTACACAGAGACGTGGAGCAAGTGAAGATGA<br>AGTGGCGTAACCTCAAGAACGCCAGCAAGAAGCGCTG<br>GACCGTTGCGCGGAGAGTACCTCCGCCGGACCTGCGG<br>GCACGCATCGACGAGATTGTGCGTCGGGACACTTAG |
| 62 | 148 | ATGGCTGCAAGCACGCTCGGGGATGCGCAGCAGGTCG<br>AATCCTTTGTGCACCAGCTCATAAATCCTGCGACACGC<br>GAGAATGCGTTGTTGGAGCTGAGCAAGAAGCGGGAG<br>AATTTCCCGGAGCTTGCGCCCTACCTCTGGCACTCCTT<br>CGGGGCAATCGCGGCGCTGCTTCAGGAGATCGTGGCC<br>ATTTACCCGCTGCTCTCGCCGCCGTCGTTGACAGCACA<br>TGCATCAAATCGCGTGTGCAATGCTCTGGCGCTGCTGC<br>AATGCGTGGCGTCTCACAATGAGACGAGGGCACTGTT<br>CCTCCAAGCGCACATCCCGCTCTTCCTGTACCCCTTCC<br>TCCAAACCATGAGCAAAACGCGGCCGTTCGAGTACCT<br>GCGCCTGACCAGCCTGGGCGTGATCGGCGCGCTGGTC<br>AAGGTGGACGACACGGACGTGATCAACTTCCTGCTGT<br>CCACCGAGATCATCCCGCTGTGCCTGCGCACCATGGA<br>GATCGGCACGGAGCTGTCCAAGACCGTGGCCACCTTC<br>ATCGTGCAGAAGATCCTGCTGGACGACGTGGGCCTGA<br>ACTACATCTGCGCCACTGCCGAGCGCTTCTTCGCGGTG<br>GGCGCCGTGCTGGGCAACATGGTGGTGGCGCAGGCGC<br>AGATGGTGGACCAGCCCAGCCAGCGGCTGCTCAAGCA<br>CATCATCCGCTGCTACCTGCGCCTGTCCGACAACCCGC<br>GCGCGCGCGAGGCGCTGCGGTCCTGCCTGCCGGAGCT<br>GCTGCGCAACACGCAGTTCACGGCGTGCCTGAAGAAC<br>GACGACACCACGCGCAGGTGGCTGGCGCAGCTGCTCA<br>TGAACGTGGGCTTCTCCGACTCCGCCGCGGCACTGGG<br>TGCGCCCGACGTGGTGCAGCCATCGCCCGTCATGGGC<br>GCGTGA |
| 63 | 149 | ATGGGGAGCAGCAGCGAACGATTGCCAGCAGGTTCTG<br>GTAGCTGCCTACACCCTGGCTGCAGCGGATTGTGCTGT<br>CTGGCAAAAGCCCCAGTCTCCGACACCATCGTCGTTTC<br>TACCGCGGCCCCCTCCGCGGGTTGTGACCTGAAGCTG<br>GTGTGCTGCGACGGCGCGCTGATGGCCAGCCGCTGCG<br>TGCTGTGCCGCGCCTCGTCCGTGCTGCGGTCAACGCTG<br>GAGCTGGAGCTGCCGGAAGCAGGCGAGCTGCGCCTGC<br>CGGCAGACAAGGCCGAGTCGTGGCGCATGGCCCTCAG<br>CTTGCTGAGCCTGGAGGCGTACCCGCTATCGCTCGTG |

TABLE 8-continued

| Transcription factor library. | | |
|---|---|---|
| | | ACATCGGACAACGTCGTGGACCTGCTGCTGCTGGCCG<br>ACAAGTACGACATACCCATCGTCCGGGGCGCCTGTGC<br>GCACTTCCTGCACCTGAACGCGCGGCAGCTATCTCTA<br>GTGCCGCCGCTGTCCTCTGCCTCCAACCTGCTCACCGC<br>CGCCAGCCTGGTCATCAAGTTCGTACAGCCGTACCCG<br>GGGCTGCAGCAGTACGGCAGTACGGTACAGGCCCGAC<br>TGGATGATGAGCTGGCGATGCTGAGGATGCCGCCGGA<br>CGTGCTGCTGGCGGCTGTCCAGGCTGCGGGCGGCCCG<br>GGCGCCCCGGACCGCGCCGCCTCCGCTCTGGCGGCCT<br>GGCAGCGCGACCTGGTGCGGCTGACGTCCGAGCTGCA<br>CGTCCTGGTGGGCGCCGCCGACTACGCAGGCACCGTG<br>GCGCCGGAGGTGCAGGCGGCTGTGACCTTGGGGCTGC<br>TGGCGGCGGTGCGGCACAGCGCCTCCCGTGTGGCGCC<br>CACGTGCGGCCGCTGCGGCGGCGTGCTGCAGGCGGGC<br>CCAGGGGCACTGCACGCAGACTGCGCGGCAGCGCAAT<br>ACACAGACCTGCACACACGCGGCTGCCGGCTGTGCAA<br>TGCGCCCATGCTGCCCACCCATGCGCGCTTCTGCAACT<br>CGTGCGCCTACCGCAAGCACAAGAAGTCATAA |
| 64 | 150 | ATGGGGTTTCCGCAGCTGATGGTGCAGGTGCTGCCAG<br>CGCAGGCGGCCCTGGCAGCCCACCTTCAACAGCAGCA<br>ACAGCAGTCCATAGCGGCGGCACTCGCGCCCCAGCTG<br>GCGGCGGCGGTGCACGCACACGCTGCGCCCATGGCGC<br>CTCTAGCTGCGCCGCCGGCGCAGATACCCGCGCGCGT<br>GGCCTCGCCCACGTACCGTCATACCGGGAGAGCGCAA<br>GCCGCGGAAGCCGCCGCCGGGTCGCGAGCACCGGTTA<br>GCCATAGCACGGTGGAAAAGCAGCGGCGCGACCGCA<br>TCAACTCGCTGATCGACGAGCTGCGGGACCTCGTGCC<br>GCCGACGCAGCAGCAACAGCAGCAACAGCAGCAGAT<br>TGGGGTGGTCACCATTGGTGTGAGCGACAACCCGGAG<br>GCCTCGTCGCGGCGGCCCAAGCACGTGGTTCTGGCGG<br>ACACTATCAACCTGCTGAAAGCGCTGAGGCAGCGGGT<br>GTCGTTTGCGGCTGTGACGGCGGAGCTGCAGCAGCTA<br>CCGGCGGGCGGCAGCGGCGGTGGCGGTGGCGGCGGC<br>GGCGGCGCACTACCACTGCCACTGCCGGTGCCAGGCA<br>TGTACGGTGCTGTGGCAGGCGCGGGCATGGTGCCGGG<br>CATGCCCGGGAGCGGCGTGCAGCCAGTGAAGCAGGA<br>GCCGCAGGGGTCATCCAGCCAAGATGATGACGACATG<br>GGACACCCCGGGGGCCCCGGCGTCACAGTCAAGAAG<br>GGGCCAGACTGTTTCTACGTCCAGGTCACATGTCCGG<br>ACCGCAAGGGGCTGCTGTCGGACATCACCGACACGTT<br>GCGGAACTTATCACTGGAGGTCCGCACGGCCGCCGTC<br>ACCACCAATGGCGGCTCGGTGCGTGACGTGTTCGAAG<br>TGGTGCCCCCTGACGGCGCCGTCGCACTGGCGCCCGA<br>GGCGGTCCAAAGCATGGTGCAGGGCGCGCTGTCGCAG<br>CGCGTGGCGGAGGGGCAGCAGGAGGTCACGGCAGGC<br>AAGCGCCCGCGTGCATGA |
| 65 | 151 | ATGTTTCCAAACCCATTTTTCGGCATGGGCGCGCCCTT<br>CGGGCCGGGCATGAATAACATGGGTGGTATGCCGGGA<br>CAGGAGATGGCTGGGATGCCGGGGTTCCCGGGCATGC<br>CTGGTGGCACGATGGGTCCGGGGATGCCCGGCGGCAA<br>CATGGGTGGTGGAGGCGGTATGATGGGCGGTGGCCCG<br>ATGGGCGGCCAGGGACACGGCGGAGGCGGAGGAGGC<br>GGAGGCGGTGGCGGCGAGGGCCACCGGGGCGGCATG<br>GGCGGCGGCGGAGGGCGGGGCCCTGGCGGCGACAAG<br>CGCCCGGGTATGTGCGTCAGGTGGTCCAACAGCGGCA<br>GCTGCCAGTTCGGAGACAGGTGCAGGTACCTGCACGG<br>GCAAGGCGACAGCCGGTACCCGCCAGGGCCATCCGAC<br>GGCGGGCCGGGAGGGTTCATGGGCGGCGGCGGTGGC<br>GGCGGCGGCGGCGGTCCCATCCGCCGCGGCGGGAGA<br>GGCGGCGGCGGCGACGATGGGCCGGGCGGCCGCGGC<br>TCCCGCCCTACGGGCCCCAAGACGCGCCTGTGTGAGA<br>AGTTCATGGCCACGGGAACGTGTCGGTACGGCGACAC<br>CTGCATATTTGCACACGGGATGGAGGAGCTGCGGCCG<br>GGCCGTGACGCCGGAGGCCCGCCTCCCCCGCAGCCGC<br>CGCCACAACAGGCGCAGCAGATGCAGCAGCAGCAAC<br>AGCAGCAGCACCAACAGCAGCACCAGCAGCAGCAAC<br>AGCAGCAACACCGGCAGCAGCAACAAGACGGGGGCA<br>ACGCCACGTCACCTTCGCGAGGCGCCTTTGGCGGGCC<br>GAGCGGGAGACCGCAGGCGCAGCAGGGTGGGCCGGC<br>GGCGGGTGCCCGTGGGCAGCCACCACCAGCAGCAGC<br>AAGTGCGCCACAGGATGCAGCCGCTGCGACAGGCGCA<br>CAAGCAGCCACAGCTGCAGCAACCGCAGCCGCACCCT<br>CCAAGCCCCAGGAGGTCACCTTTGTGGACAAGGTGCG<br>CGCGCTGTGCGGCGTGCTGCACATCGGCCAGGCGGCG<br>GCGCTGGCGGCGGAGAAGCCGCTGGCGCTCACCACCG<br>CGGCCATGTCGCTGCGAGCCGGCACCGCCTACAAGGA |

TABLE 8-continued

| Transcription factor library. | | |
|---|---|---|
| | | GAACCCTTTTGCGGACGGAGTGGAGAGATACGTGGCG ATCTCGGCCGGTGGAGGGGGAGGGGGAGGCAGCGCC GGCCAGGGGCAGATGCAGCACTAG |
| 66 | 152 | ATGATTAAAGGCGTGAACCGACCAGCCATTTTCTATG ACTTGGTCGGGCTTGCGCACTCAGGCGTGGTATCTGTG GGCAGAGAGAGCGATTCTACTATACGCCTCGACTGCC CGGAAGTCCCTTTCCTGCTCTCGCGCAAGCATGCTAAA ATTTGCGTCAATCCAGACGGCAGCCTTATTCTGAAGG ACATCAACTCCACGAACGGCACCTACATCGCTCGTGA AGGCGAATTTCTCAGGCGGCTGCGGTCGGATGAGGGC TGGGAGCTACGCCGCGGCGACCTGATTGGCTTTGGCG GGCCGGAGACCATTGTTGCGCGTAGCGATGTGCCGGA CGTCACCGTCGCCAACCCCTTCCTGTTCCGCTACACGC CGCTGGACGACGATGCAGATAGTGCGTTTAACTCGTC TGCAGAGCAGCAGCTGCTGGGCAACGGAGCGCAGGG TCGCGCACGGAAATTCAGCGAAATTGAAGACCGCTGC CAGCAAGAGGACATGGACTGCGAGGTGGCGTCCACCA GCTCACCCGACAAAGAGAGCAAGAAGGCCAAGACGG CGGTGACAGCAAAGGACATCGTGTCTAACCTAGCAAA CCACCTAACGTGTGCCATCTGCCACGACTGGCTCGCTG GTGCACATGCGCTAACATGCGGGCATATGTTCTGCGG CATCTGCCTCGCGGGGTGGCTGGCACAAAAGCAATCC TGCCCGGAGTGCCGGAAACCGAGTGCAGGTGTCCCTG TGAGGTGCCGCGGTGTCGACAACTCCATCTCTGACAT CCTCCAACACAACCTGGTGTCGCCGAACTCAAAGCGT GAAAGGCGTCGGAAGCAGCTGGCGTGGGAGGAGGTC GGAGACGGTGTGCTTGAAAGCTGGACAAATGCGATGC AGCAGCGGCGGCAACAGGCTGTGAACGTAGCATCGCA ACACCTAGCAAACCTGACGGGGCAACCTGCACCTGCG CCGGTTGCTGCTGCACCACGACCAGACGGCGCCGTGG TTGGTCAGAACACGCGGCGGGCCAACCAAGGCGGCGC GCCGCCAGTCAACCGGCCAGCCCGGTGA |
| 67 | 153 | ATGGAGGGCTGGGGAGCAGCATCCACCATCCTCGGGG TGGCCCATTTGCCACCCGGCAACGCTTGGGGCCCGGA GGAGTGCCTAACCTTTCATACCCGAACCGCGGTGTAC CGCCTTCCGCTCAGCGCAACCGCCTCCGGAGGCGGCG CGACGCCGCAGCTGCTGGCGGGGCAGGAGAGCGAGC GGGGCGCAGCGAGGGTCGATGGCAGCGGTGCCGACG CCCGGTTCCATCACCTCAGCAGTGCAGGCCTCCAGGT CAACGCAGACGGTCGGCTGTTGCTCCTTGACTTGGACT CAACAGCGGATGTAACGCGCCTGCGCCTCGTTGCTCC TGGTGGAACTGTTAGCACGGTGACAGGCGTGGAGCTG GCTGGCCGGTGGGTAGACCTGGTAATCCTGCCAAACG GCTACCTAGCTGCACGTGAAATTGCACAAGTGCAGTC TGACGGGGACCTGGATGAAGACGAAATGGCAGAGCC GTACTGGGAGAGCAAGCGCGTTGCGGTGATTGCGACC AGCTTCACACCACTGGCGCTTGTGGCAACAGCAGCAG CGGCGGGGCCGCCGCCGCGCAGCCTGCCCGCCGACCT GGGTGCGCTGGTGGAGGACGCGCAGCAACCTGGCGGC GGCGGCGCAGTAGCAGACCTGGTCATTCGCGTGGGCG AGCGGCGCTTTCACTGCCACCGGGCCATCCTGTCCGC GCGCTGCGACTACTTCAAGCACCGCCTGGCGGGCGAC GCGTTCGAAGACGCGCGCGCGGCGGAGCTGGAGCTGC CGGACGCGGACCCCGACACCTTCGCGCTGCTGCTGCG CTGGTTGTACACGGGCGGCGCGGACATTTTGCCTAAA CAGGCGCGCGGCGTGGCTGAGCTGGCGGACCGGCTGC TCCTGCCTGAGCTGTGCGCCCGCGCGTTGGACGTGTTG TTCGCGTCAGTGGACGCCGGAAGCATCGTGGACAGCC TGCTGTGGGCCGCGGGCTGCTGCGAGGCGCACGGTGG CGGCGGCGCTTTCGATCAGCTGTTGCTGCGGCTGAAG CGCTGGTACGTCGAGCGGGCGGCGGAGGTGCGGGCCG CGGCGCGAGACAGCCTGCGGGCGCTGATGACCCAGCA GCCTGACCTGATGCTAGAGCTGATGGAGGCGAGCGAG CAGCGGGCGGTGAAGCGGGCCCGGACCAAGTAG |
| 68 | 154 | ATGGCGGAGCTTGAGGATGATGTCCTCGTTCAGGCCG GCGAGCAGGACGATGCCAACGACCTCAACCGGCAGCT GTTCGGTGCCGATAGCGACGATGAGGGCGCGCCGCCC GCGGCCGACCCGCACGCCCAGGCGCAGCACCTGGCGG AGCAGGAGGCGCTGCTGGAGGATGACTTGGAGGACG CAGACGTAGACGCCGAGGCGGCGCTAGAGGACGAGC TGTCGGGCGGCAGCAGCGACGACGGCGGGGCGGTCA AGAAGGGCAAGAAGGATAAGAAGCTGCGCAAGAAGC GCGAGGGTGGCAAGGACGACAAGCCCAAAAAGAAGC GCCAGCGGGGCGAGGGCGGCAAGGGTGAGAAGGGCG ACAAGGCGGGAAAGAAGGGCAAAGCCCCGAAGGAGA |

TABLE 8-continued

| Transcription factor library. | | |
|---|---|---|
| | | CCATCGCCACGGGCAGGTCTCGGCGGACGCCGGGCGG TGGCGAGGCGGGCGAGGAGCAGCAGCCGCGCCCACG CCGCCCCGTGGGCGAGGGCGGAGACGACCTGCCCAGT GATGAGCTGCAGGAGCAGGAGGCGGACCGTGCCTTCA TTGACGATGACGGTGCGGAGCCGGTTGCCAGTGATGA TGAGAATGCGCCGCGTGTGGTGGCGGACGAGGCGGA GGAGGCGATTGACGCGGACGAGGACCACCCCTTCAAG CGCAAGAAGCGGAAGAAGGAGAACACCGGCAACGTG GAGCTGGAGATCAAGGAGATGCTGGGCAAGATGGAG GCGGCCATGGAGCATGACTTCGAGACGGTGGCGCGCA ACGCGGGCGTGGAGCTGAAGAAGGACAGCGGCGACA ACCTGGTGACGGACGCGGAGGGGCACTACGTGGTGGC GCGCAAGGGGCCGCCGCCGGCCTCCAAGAGCCCCGCC ATCAGCAAGCTCAGGCTGCTGCCGGAGCTGGAGCTGT TCCTGGCGCAGCGCAAGTACCACGAGAGCTTCCTGCA GCAGGGCGGGCTGGGTGTGCTGAAGGGCTGGCTGGAG CCCTACTTTGACGGCACGCTGCCCACCATGCGCGTGC GCACGGCGGTGCTCAAGGGGCTGCAGACCCTGCCCAT CGACACGCGATTTGAGGACCACAAGGAGATGCTGCGC AAAAGCCAGGTGGGCAAGAACGTGATGTTCCTGTTCA AGTGCTCGGAGGAGACGGCCGACAACCGCCGCATCGC CAAGGAGCTGGTGCACCGCTGGAGCAGACCCATCTTC TACGACCAGGAGGCGGAGGAGGCCAAGAAGCAGCTG CACCAGCAGCAGCTGCTGGAGGCTCGGCGCATGGAGC TGGAGCGCCGCCAGGCAGACGGCGGCGAGGAGGACA AGAGCGCGTCGGCGCAAGTGCGCAACAAGGCCATGC GCATCCACGCGCTCATCCCGCGGGCGTCCAAGCTGGA CTACGTGAACAACCCGGGTGCGGCCAAGGACTTCAAC GAGAGCGAGGTGGCCAACGCCGCCGCCGCCGCCGGC CCCAAGTCCAAGCAGGTGGACGCGCTCACCAAGCGCC TGCGTGAGCAGCAGAAGAAGCTCAAGGACGGCAGCG CACGCGCCATGAAGCCCAGTGTGGAGGGCCGCAACAT TGTGCTCATGAAGTAG |
| 69 | 155 | ATGTCGGTCGTGTCAGCGAACAGCAGCACTGGCCGGG AGCCGGAGCCCGCCACCTCCAGCACCTCCTCTCCCGC CACAGCCGCGCCCACGCTGCCACTACGCAGTGCCGCA TCCGGGGACGCCACGGATTCTGAGTCCAACAGCCCCG GCCCCAGCACCCCCTCCGCCCCGGGGCCGCGGCAGGT ACCCACCGTGGATGCAGTATTCCCCACGCGGTACGGC ACACGCTTCCGCGTGCGGCCGTACAGCAACAACGAGT ACGGCTCCATCATTGACTTGCAGTCAGAGGCCTTCCAC ACGCTCAACCCGGTGCCCTTCCTGAATGACTTCACCTA CAAGCGCTTCCGGGCCGAGGTGGTGGATGCGTTGAAG CAGAAGACCAAATACTCGGACCCCTCCGTCTTCCAGC TCCTCGTGGCGTTGGAGCAGGAGCCGGAGCAGGAGCC ATCAGGCAGCAGCAGCAGCAGCAGCAGCAACAACGG CGATGGCAGTAGCAACGGCAACAGCAGCAGCAGCAG CAGCAGTGCCAAGGTGGTGGGGGTGGTGGAGGTGTCC CTGATGGAGGAGCGGGGGGTGCTGGGGTGCCTGCCGC CCGGCACGCGCGAGTACGCCTACGTCAGCAGCATGTG TGTGGCGCCCACCGCCAGGCGGCGAGGCGTGGCGCAG GCGCTCATGAGCGCGGCGGAGGAGCAGGCGCGGCTGT GGGGTCAGCAGCAGCTGGCGCTGCACGTGTACCGCGA CAACACGCCCGCGGTGCAGCTGTACGGCGGCTGGGGC ATGGCCGTACTCAACACCGACCCCGACTGGAAGGCCT GGTTCGGAGACCGCGTGCGGCTGCTCATGCACAAGCG GTTGGCGTAG |
| 70 | 156 | ATGCGTACCGCAATCCTCGCCCCATCCCACGGCCCTG CCTCCTCCTTCCAGCAACGCACAAATTCGGTGCACAC GCGGACTGTACTCGCGCACGGCGCTGCGGGGTCGGCG AATCGCTCCTCTGCACCATCGGCATCGACGACCCCCTC GGCCTCATCCGCGCTGGATGCAACCCAACCCATCATC CGGACGCTGAAGGAGTGCGACACTGGAGCCATCACGC GCGCGTCGGTGTGCTTTGGCCGGTCGATGCGGACCGA CCCCACCATGACCTACGTCACCGGGGGCCGCTGCCCG GAGCGCGTGGGGGCGCTGTTCGAGCAGGTGGCAACCA TGTGCATGCGCGGTGCCCGCGACCCCGCCACCACCTG GCTGCTGGAGACGCCCCGCAGCGGCGGCGACAGCGA CAGTGCGGATGTGGTGTGCATCGCATGCGAGTACCCG GCGGCCTACCCCAGCGACTGGGAGCTGCTGCGCGCCG GGCTGCTGCGTGTGCTGCTGGCCTGCCCGGGCTGGGG CGTGCTGCGCGCGCTGATGAACATGCTGGACCAGTTC AACGCCACCAAGGCGCAGTTCAACAAGGAGCACGGC GATTTCCTGTACATTGCGTGCTTTGGCACTGCCCCGGA GCAGCAGGGCCGCGGGCTGGGCTCACAGCTGATGCGG CGGGTGCTGCAGCACGCAGACGCCAAAGACCTGCCCG |

TABLE 8-continued

| Transcription factor library. | | |
|---|---|---|
| | | TCTACCTGGAGGCCAGTGGCGCCGCGTCGGCGGCGTT CTACCGCCGCCACGGATTCCAGGACATTAAGCAGGTC CGGGCCAGCCCCGGCGCCCCAGACCTCATCATCATGG CCCGGCCCCGCGCCTCGCAGCTGCAGCAGCACGGCCA GCAGCAGTAG |
| 71 | 157 | ATGAGCGTCGCCAAGTATACATACGAGTGGCTCATCA AGCGTTCCGCTGAGCTCCCTGACGCTGTCGAGACACC CGACTTCGTGCTGGGCTTCTATACCTGGAGGCTGCGGC TGCATCTGCGCCAGTCGATCAACCTTCGAAAGCACGT GCCCCTGTACCTGCACCATGTGCCAGTACGGGGAGGC GTGGACGCGCCGCCGCCCCTGAAGTACACTTTTGTAG TGAAGAACTGGAAGGACCCATCCAAGGACCATGTGAC TGAGGGCAAGCCCGGTACGGTCTTCAACCTCAAAAAC GCAAAATGGGGCAAAGAGCTGATCTTGCGGGACCAGC TGATGTCCATTGACACGGGGTTCCTGCGCTGTGACGG CTCCCTGCTGCTGCGGCTGGAGCTTCAAATGCCGGAG AAGAAACAATGGAGCGATGACGATGACGACTCGAAA TATGACTCGGATGAGGAGGAGGCCTACCCTGCGGTCC TCAAGGAGGGCTCGGGCGGCGGCAGCAGCATCGGCA GCGATTTCCTCTCGCTGCTGGCCGATCCCGGCCCCACC ACTGACCTCACCATCACCGCGACAGCAGCGGTCGCGG GCGGTGTTACGGGGGCCGGGAAAGAGGGGGGAAGTA AGAAGCGAAAAGCCGACACCGCCAGCAGCAACGGCG GCAGCACTGGCGCAAGCAGCAGCCGCTTCCCCGTGCA CCGCGCCATCCTGGCCGCGCGCTGCCCCTACTTCGCCA CGCACTTCGCCAGCGGGCTCGGCGACAGCAACACGCG CGAGCTGCACATGCCGGACACCGACCCGGACGCGCTG GCGGCACTGCTGCGCTTCGTGTACGGCGGGGAGCTTC GTGTGGCTTCCCGGGAGCAGGCGTCGCGCTGCCTAGC GCTGGCGGACCGGCTGCTGCTGCCCAAGGCGGCAGGG CTGCTGCGAGCGCACCTGCTGGCCACCCTGTCTCCGG CTACCGTCATGGCGGACCTGACGTGGGCGGCGGGTCT GGCGGAGGGCCAGGGGCAGGCGGAGTTGCTGACGGG GCTTGTGGACTACGCCGCAGAGCAGGAGGCGGACATT GCAGAGGAGCAGGTGGAGCAGCTGGCGGCGGCACAG CCCGCGCTCATGGCGAAGCTCTTTACGGCGCGGGTGC AGGCTGCCAAGCGCTGCCGCGTGTGGAAGGCATGCTG A |
| 72 | 158 | ATGGATAACTCACCTGCAGTGCTCAATGGAGCAGCGG ACAACTCGGAACTGCCCATGGCTCAAGTTAAAAGGAT AATGCACAGTAGAGGCGTCACGTCAAATGCGGAAAGC AGCTTTCTGGTCGCCCGTGCTGCGGAGATGTTCTTGGA TGCGCTTGTGGCGCGCGCCGGCGGCGCCATGGCAGCG GGGGGCGAGGCGGAGCTCCGATACGATCACGTGGCCG ACGGCGTCCAGACCTGGGCGCCAGGGAGCCGCCTGCT GTCAGACGCGGTACCGAAGCGCGTGCATGCCGGGCAG CTGCGACGGGACCCGCGCTTCAACGGCCGCACGCCGT GGGTGCTGCCGCCGCCAGCCGGGCAGCAGCAGCAGCC TCATCAGGAGCACACGGCGGTGGCGGCGGCGGCACA ACGAGGCCCGGCGGCGGCCGCAGCGGTGGCGCAGCC GATGGGTGTGCCCCAGGGCGTGCCTCTGGGTGTGCCT CAAGCGTCCGCGCCAGGGATGGCGCATGCGCACGTGC CGCATCTGCCCATACACGCAGCTGCCATGCAGCAGCA GCAGCAGTCGCACAACCATGTTGGCCCGGCGCAGGTA CCGCAAGCGGTGTTGCCACCGCCGCAGCAGCATCAGC ACCAACACCAACAACAGCAACAGCAGCAGCAACAGC AACAGCAGCAAGCCGCTTTCGCGCAGCACCTGCAGCA ACAGATGCTCATGCAGCAGCAAGTACTACTGCAGCAG CAGCAGCAGCAGGCGCAGGCACAGCAGCAAGCGCTT GCGCAGCAGCAGGCGCAGCAGCAACAACAACAGCAA CAGGAGGCCGCTGCGGCGGCGGCGGCGGCGGCGGCG GTGGCAGCCGCGACGGCGGCGCAGCAGCAGGCTGTG AGCTCTGTAGCGACCGTGTCGCAAGCTGTTGCGGGTA TGGTGCCGGGCGGCGTGCCGGCGCCGCAGGACCCGCA CCAGCAACATCAACAACAAGCCGCAGCCCTGGCCATG CAGCATCAGCTTATGCTACAGCTGCAGCACCAGCAGC AAATGCAGATGACGTTGATGTTTCAACAACAGCTACA GCAGCAGCAGCAACAACAGCAGCAGCAACAGCAGCA TATGATGATGATAGGGGCAGGTCAGCATCCCTACTTC CTCGGCGGCGCGGCGGCGGCGGCGGCGAGTGCTGGCG GCGGCTTCGGCGGGGGCTCTGTGATGGGCATGCCGGC ACAGGGCGGGCAGTGA |
| 73 | 159 | ATGTCAAGATGTTCGTTGGCGCTGGGGCTGTTTGGACT TTTGCTGGCGGGCATGGCGGGCATGGATGGTGTGGAT GCTGCTGGCAGCAAAATAACTGCCGCGGACCTAGCAA |

TABLE 8-continued

Transcription factor library.

| | | |
|---|---|---|
| | | ACCTCAACCTATACAAGGTGTTGGGTGTCACAGCCAA<br>GGCTACTTCCGTGGAGATTGCAAAGGCCTACCGCAAG<br>CTGGCCATCAAGTATCACCCTGATAAGAATCCTCAGG<br>GTCAGGACCAGTTCATCAAAATTGCATACGCCTATGA<br>GATCCTGGGTGATGAGACCAAGCGGGCGCGCTACGAC<br>GCCGGCGGCTTCGCTGCGGCCACCGAGTTCGCGGCGC<br>AGGCGCCCAACTGGGACACCTGGCAGCCGCCCGAGGC<br>GCCCAGCGCCACTGTGTTCGAGGAGTGGCAAAACCAC<br>AACATCTACTACGACCTGGCCATGCTAGTGGCACTGC<br>TGGCGGGCGGCGCGGCGGCCTGGGTGGCGTGGGTGCA<br>GGCCTCTGAGCGGCTCAAGCGGGCACGCAAGGCAGCA<br>CGCAAGGCAGCGGGGGGCGGCAAGTCGGCTCCGGCA<br>AGCGGCGCCGGCAGCAGCCGCCCACGGCGGCAGCGG<br>GTGCAGTCCAGCGGCGCGCTGTCAACAGGGTCGGGCG<br>CGGGCATGGGCGGCAGCGACAGCGACAGTGACGAGG<br>CCGGCGGGGGCGCCAGGGCCGATCAACCAGACACGG<br>CGGCCCCGGGTCCCTCCGGCTCGCTGCTGCTGCAGCC<br>CGCCAAACCGGCCGGTGGCTCGGCTGCAGCTGCCATG<br>CGGGAGTGGAGCGCCGAGGAGCTGCGGCTGCTAGAC<br>AAGGGTCTGAAGAAGTTCCCCGTGGGCACCGTCAAGC<br>GCTGGGAGGCGGTGACGGGCGTGGTACGCACTCGCAC<br>CCTGGAGGAGGTGCTGGTCATGGTCAAGAACTACAAG<br>GGCGGGTCGCATCTGCGGGCCAGAGTGCAGGAGGATT<br>GGAAGGCGGGGCGGAAGGCGGGGGCCGCAACGGTAG<br>CGGTGGCAGCCTCTCAGGCGGCGCCCGACATACGTTA<br>CGATGGCCCGCCCACTGTGAATGGCGGACCAGCGGAC<br>GGAGAGCACACAGCAGCGGTGGCGGCAGCGGTGGCA<br>GCAACAGCAGCAGCAACCGCCGGGGGTCAGGTGCTA<br>GCCACCGGTGGCGGGACCAAGGCGGCCAAGGCGCCG<br>GCAGGGACAGAGAAGGCGGGCGTGGATGCGCCATGG<br>ACCGAGGCCCAGGAGGTGGCACTGGTGGCGGCGCTGA<br>AGCAGTGCCCCAAGGAGCTGGGCGCGGAGCGCTGGG<br>ACGCGGTGGCCAAGCTGGTGCCGGGGCGCAGCAAGG<br>CGCAGTGCTTCAAGCGCTTCAAGGAGCTGAGGGACGC<br>CTTCCGCAGCAAGAAGGGGGCGGGGGGTGGAGCGGA<br>GGGAGATGACGGCGACGACTGA |
| 74 | 160 | ATGCATGAAGGACAAAACACATGTGGCCCTGCGACCA<br>GAGGTCATGCCGACGGAGGTGGTCTCGGCGTGCACTT<br>GCTTGTGGCGGGAGCGATTCTCCACGGCCTTGCGTGT<br>GACGCGCCGGCTGCGCTCGCAGCACTTTGGCTTGAAC<br>GCTGTATCGCCTATAATCCTGTGCTTCTGACACACCTC<br>GACGGCGTCAACGACCTGCCAGCGCCACGGAGGTGCG<br>GCTGGGGCCGCGCGGCCCTGCCCTGGGCGGCGGTGAG<br>CTTGGCCGGCGGCCTCCCAGCCATTGACAAGGGCAGC<br>ACCACACGTCACGTGTGTGCTGGCTGCCACCAGCACC<br>TCACCACCTCTGACCTCGCACGCCTGGAGGAGCAGCA<br>GGAGCAGTCGGCGCCGCGCCACCTGCACCCGCACCCG<br>CAACCGCAGACCCCAGGCGCAGTGCTGCAGTGCGATG<br>GCTGCCACCGCTGCTTCCACGGCCCCTGCCACCGGCG<br>GTGGGCCGCTGCGGCGGAGCAGGAGCAGCGTCGGCG<br>GGCACGGGTACACGCGGCACGTGATGGCCGGGACGG<br>GTCGGGGAGGCGGCAACAGCCGGAGGCCGTGAGGGC<br>ATCGGCGGCGGCGGTGGAGGCTGGGGACCCGGGCGA<br>CGACGGGGCTTGGTTCCATGATACGGAGTGCAAACAG<br>GTCCGGGTGGCGCTGCTGCGGCTGTGCCGGCGGGGGG<br>ACATATGGCTGCCTGAGGGCACATCAACATCGCCGCC<br>AGCAATAGCAGCTGCACCACCCGCACCAGCAGCCGCG<br>AGCAGCAGCAGCGGCAGCAGCCTCGTTGCAGCACCAG<br>ACCACGCGGCCGCTTCAGGTCGCCCAGATGCTGCGCC<br>AGGCGCCAGCCCGCCCACGACCTTGACCTCGACCGCG<br>ACACCACACAGCGTACCTGAGTCCCCGCAGCAGCCGC<br>GGCAACGGCTGCGCATGCGGGTGTACGACTGCAATGA<br>CGGCGGGCCGGCGGCGGCTGTCGGTCTGCGGCGTGTG<br>CACGGCGTGCTGCGTGCCGCGGGCTTTGGCTACGGCC<br>TGAGCGACCTCCGGCAGTTTGATGTGGCGGCGTTGCT<br>GATGGCCGAGGACTCGGGCCAGGCCCTGTCCGCCGCC<br>GTACTGGACGTGTACGGCTCACACTTTGCGGAGCTGT<br>ACCTGCTGGCCACATGCGCCGCCGTACAGCGGCGCGG<br>GTACGGCCGGGCGCTGGTGCGGCAACTGGAGCAGGA<br>GCTAGCGGCCAGCGGCGTGCGGCGGCTTCTGGTGTCG<br>GTGGACGATGACGACCTGGTCAATCAGGGGCTGTGGC<br>ACCACGCGATGGGGTTTGGGTCCGTGCCTGACGCAGA<br>GCTCCGGCAGCTGGCGAGGAGCTGGGGGGCGTTCGGG<br>CCGGCGGCGCGGCGCGGCACCGTGTTCCTGTACCGGC<br>CCCTGCTTGGCGGAGCTGGCGAGGCGCAGGGGCAGGG<br>GCAGCACGGCAAGCGGTGA |

TABLE 8-continued

Transcription factor library.

| | | |
|---|---|---|
| 75 | 161 | ATGGTTGCCAGCAGCAGCGCCGAGGAGCAGCCGCGCG<br>TAGTCTCGTTGAGCTCGGCCAATCGGCAGCAGCTCTC<br>GCGCGCGGCAGTCTGCTTCGGTGCGTCTATGGTGGAG<br>GACCCGATCCTCATGTGGGCAACGGACGGCAAGAACC<br>CCGCCGGCTCAGTAGGCTTCTACACAAAGATGGCGGA<br>GGTGTTCTTCAATGCGATGGCGGACCGCAGCTGGTGC<br>TGGGCGTTGCAGGCGCCAGCCAATGCCAAAGCGCTAC<br>CCGTGGTGGGCGGTGAACTGGACGCCCACACTCCGCA<br>GAGCGTGTGCCTTGCTTGTGAGGTGCCGCGCGCCTAC<br>CCCTCCGACTGGCAGCTCCTGTGCGCGGGCATGGTGG<br>GGCTGGGCCTGCGCTCCCCCAGTTGGCGCTGCGTGCG<br>GATGTTCCTGCACCTCACGCCCGAGTTCCAGAAGCGG<br>CACAAGGCCTTCCACACGGAGCACGGGCCCTTCGTCT<br>ACATCGCCGCGTTCGGTACCCGGCCCAAGCTGTGGCG<br>CCGCGGCCGCGGCTCCCAGCTCATGTCGGCTGTCCTC<br>AAGATGGCAGACCAGAAGAACATGCACTGCTACCTGG<br>AGGCCAGCAGCGACGACAGCCGCCGCTTCTACGCCCG<br>ACACGGCTTTGCGCTGAAGGAGGAGCTCTGCGTGCTG<br>CCGCTCACAGCCTCCGACGCCGCCGGCGCGCCGCTGC<br>TGTACATTATGGTGCGGCCGCCCCCAGGGCGCCGGTGC<br>TGGAGGTGCGGGCGGTGGTGGTGGCGGCGCGGGTGCG<br>CTGGCGGCCGGTGTTGGAGGCAAGGGCGCCGCTGCGG<br>CTGGCGCTGCGGTGGGACCGGTGGCGGCGCCGGCGAA<br>AGCGGCGGAGGTGGTGGTGACGGCGGCGGGCGGCAT<br>CGCGGCGACGGTGGCGGTGCCAGAGGCGGCGGCGGC<br>AGCGGCTGCATCCACAGAGCCGCAGAAGCAGACGGC<br>GGCGGCGGCGGCTGAGGCTGGGCAAGCTGGAGAGCG<br>TGCGCGACAGGGGGATGAGCAGGTGTAG |
| 76 | 162 | ATGTCTGACGATAGCGATGTTTCATTGCCAAGGACTA<br>CCTTACAAAAAATGATCAAGGACTTACTTCCACCGGA<br>CATGCGCTGCGCTAATGACACGGTGGAGATGGTCATT<br>GCGTGCTGCACCGAGTTCATCCAGCTTCTGTCCAGCGA<br>GTCTAATGAGGTGGCGACGCGGGAGGGCCGCTCCATC<br>ATCCACCCTGACCACGTCATGCGCGCGCTCACGGAGC<br>TGGGCTTCCAGGAGTTTGTGGGCGAGGTGAACGCAGC<br>GCTGCACACCTTCAAGGAAGAGACCAAGACGGCGCAC<br>TCGCGGAAGGCCGACCTGAGGAAGACGGGCGCCGAG<br>CAGGCGGGGCTCACGGAGGAGGAGCAGATCGCTCTAC<br>AACAGCAGATGTTTGCAGCGGCACGTGCGCAGTCCAT<br>GACCACGAGTGAGGTCGCCGCCTCCATGACCGCCTCC<br>TACGACCGAATGGCAATGGCGGCGGCGGCGGCAGCG<br>GCGGCGGCGGGGGGCGGCGGAGGCGCCGGCGGCGCG<br>GCGGGGCAAGCGCCAGGGATAGCGCCAGGCCTTGCG<br>GCGCCGATGCCGCCGTTGCAGGGGCAGGTGCCGCTGC<br>CGGATGCGGCGCCGCCAGCTGAGCAGTAG |
| 77 | 163 | ATGCTAGCGCGCAGCGCTCACGTGCAGCGCTGTGCAT<br>GCAGCCAGCGCCGGCGCTTGTCGGTGTGGGGCCGGCG<br>CATACGCGCCCGCCCCGTAGCCCCCGCCTCGGCGTCC<br>GCGCCCGCGGTCTCGTCATCCAGCGGACCCCCACGAC<br>TGGTGGATGTAAACGTCCGGAAAGCGTCCACCGCCGC<br>GGAGCTGCGCGCAGCTGCCTACCTGCGCGCCATCAGC<br>TTCTACACCTACCCAGAGGGCCGGAGCGAGTTCGCGG<br>CTCGGTCACACCGGCGCATGAAAGCGGATACGGAGTG<br>GGAGACCGTCACCAAGAAAGTGGAAGGCCGCGATGA<br>AGCCTACAAGGACCTGGACGTGAGCTGCTTCGTGGCG<br>TGTGTGGCGGACGACCTGGTGGCGCTGCCCGGGCCCG<br>GCAGTAGCGCCGCCAGCGTCAGTGGCAGTAGCGGCGG<br>CGACCCAGATCGGCAGGAGCTGCTGGCGGCGCTGCGG<br>GCGGGGCTGGACGCGTCGGCGCAGCTTCCTGCGGATC<br>CGGCAGCGGGTGTCAGCCGTCAGCTGGTGGTGGGGTC<br>GTTGGATCTGAACGTGGGGCACACGTTGCCGTCGGAG<br>GAGCTGATTGGCAGGCAGCCGAAGGAAGACCCGCGC<br>CACCGGAGAGCCTACCTAAGCAACGTGTGTGTGGCGC<br>CGGCGGCGCGGCGGATGGGCCTGGCGCGGGCGCTGCT<br>GCGCGTTGCGGAGGAGGAGGCGCGCAGCAAAGGTGT<br>GCAGTGGCTGTACGTACATGTGGTGGCAGACAACCAG<br>CCCGCCGTGAAGCTGTACTGTGAGGCAATGGGGTTCG<br>AGGTGGAGCAGGCGGAGTCGGAGGGTTACGCACGCTC<br>GCTGCAGCGGCCCCGGCGATTGATTCTTGCAAAGGAA<br>CTTGCGTGA |
| 78 | 164 | ATGTACCCACACCAAGATAAGGAGCCCCGCACGCACA<br>TCTCTTTGTTCCTGGAGGCTGTCGATGTCGCAGCAGGG<br>GCACAGCCGCCCACACTAGCATTCAAGCTTTACGTGA<br>AGCACTGGAAGGACTCCAACAAAGACTCCATCTGCGA<br>AAGCAAGGAGCCGAAAACCTTCAACGTGAGGTGGGG |

TABLE 8-continued

Transcription factor library.

| | | |
|---|---|---|
| | | CTTCAGCGCTTTCTTTCCCCGCGCTCAACTCACGACGG<br>ACTCTGGTTTCATCCGCCGCCGCGATGGCGCCCTGCTC<br>CTGGCCGCGGAGATTGAGCTGCCGGCTGGGCTGGCGG<br>CGGCAGCAGGAGCAGCTGCCGGCGGCAGCTGCCGCA<br>GCAGCAGCTCCAGCGCATACCCAGCTAGCATCACAGA<br>CGGCGCGGCGCGCCAGGACGTTAGCGGTGACCTCCTG<br>GCCCTGCTGGAAAAGCCAGGCTCCACCTCTGACCTGA<br>CCATCGTCGCGATCGCTGGCAGCGACAGCGGTGCCGA<br>TACGGGAGGCTCAGGAAATGGTGAGGCACCGGCGGCT<br>ACGTGGCTGAAACGGAAGTTAGTCACGGACAAGGGA<br>CGGAAGGGCGGCTGCGTGGGCAGCCCGGACACGAGG<br>CGCAGGTTCGACGTGCACCGCGCCATCCTGGCGGCGC<br>GCTGCCCCTACTTCGCCACACACTTCGCCAGCGGCAT<br>GGGCGACAGCGCGGCCCGCGAGCTAGATATGCCGGAC<br>ACGGACCCGGGCGCGCTGGCGGCGCTGCTTCGCTTCA<br>TCTACGGCGGCGAGCTTGTTGTCGCCTCCCGCGCGCA<br>GGCCCGCGCCGGCCTGGCCCTGGCGGACCGGCTGCTG<br>CTGCCCAAGGCGGTGGCGCTGCTGCGCGCGCAGCTGC<br>TGGCCAGCCTGTGCCCCAGCGCCATCGCCGCCGACCT<br>GATGTGGGCGGCTGGGTGCGGCGACCAGGCGGGGCTG<br>CTGGTGGAGCTGCTGGACTTCGCGGCGGAGGCTGCAG<br>ACGAGGTGCCCCAGTCCGACTTGCAGCAGCTGGCGGC<br>GGCGCACCCGGGGCTCACGGCGCAGCTGTTCGCCGCC<br>AGCGTGCGCGCCGCCAAGCGCTCGAAATCTTGA |
| 79 | 165 | ATGGCGCATAAAGAAAAGGGCGGCTCGGAGGCGAAG<br>ACCGTGGACGCAGACGCAATCTTCAGGATTTTCACAG<br>CTTGCCAGGGCGACATCCCCACGATTGTCATAGACAC<br>TCGGGCGCAGAAGGAGTTCAAGGTGTCCCACATATGC<br>GGCGCGTTCTGCGTCCGACTCAGCGCCAACGGGCAGG<br>TCCTGGCGGACTACTCCTCATCCAGCTACAACATCAA<br>GTGGAGCCAGGACTGCTGGTGGGGCCGTAACGTGCTT<br>GTGTACGGCGAGCCGGGCCTCAAGAAGGACCACCCTG<br>TGATCGCCTTCCTGTCGCGCCAGGGCAAGTGCCGCAA<br>CCTGCGCTACTACAAGGATGGGTTTGAGGCCTTCGCC<br>AAGGCGTACCCCTACCTGTGCACCACCTCCCTCAAGT<br>CCATTTGCATTAAGCGCTACCCCAGCCAGATCCTGCCG<br>GGGCAGTTGTACCTAGGTGACTGGGAGCACGCCGCGG<br>ACAACGAGCGGCTGGCAGAGATGGGCATAAGGAGGA<br>TCCTGACCATCCACAACCACCCCGAGAACCTCCGGCC<br>GCCGGCCGGCATCAAGCACCTGCGGCAACAGCTACCG<br>GACATCGAGGACGCGGACATCTCCGCCTACTTCTCTG<br>AGGCGTTTGACTTCATTGACGAGGGGAGAGAGCGCAA<br>GCAACCTGTGCTGGTGCACTGCGGCGCGGGCGTAAGC<br>CGTAGCGCCACCCTGGTCATGATGTACCTCATGCGCC<br>GCAACAGCTGGTCGGCGGCCCGGGCGCGCGGCTACGT<br>GGTGGAGCGGCGCAGTGTGGTGTGCATCAACGACGGC<br>TTCTACATGACCCTATGCGCCCTGGAGCCGCAGCTGG<br>GCATCGCGGAGCGGAGCGACCCCAACGCCACATTCGG<br>GTTCCGTGGCGCCGATGCACCCGAGCCGCAGCAGATC<br>AAGGTGGTGCTGAGTGAAGACGCGGCGGGGCAGAAG<br>GTGCCGGTGCGCCTGCTGGCAGCCAAGGAGGCGGCGC<br>AGGCGGCGGAGGCGGACAAGGCCGGCGCGGCGGGGG<br>CCAAGCGGCCGCGGGAGGGTGGCGAGGGCGGCGATA<br>CCCTGGCAGCCAAGCGCAGCCGACCGGGCGAGCCGG<br>CGTCCGCCGCAGGCGGCGCGGGTGCGTTCACACTGGT<br>GTTCGATGTGGTGAAGCCGGAAGGGCTGGTGGGGCGG<br>CTGGAGGCGGGGCCCATGCGGCCCAGCCAGCGCCTGC<br>TGCTGGGCCGCCAGCCGGGCGTGTGCGATGTGGTGCT<br>GGAGCACGCATCCATCAGCAGGCAGCACGCGGCGTTG<br>AGTGTGGACCGGGCCGGTGCGGCTTTCGTGACAGACC<br>TGCAGAGCGCCCATGGCACCAAGGTGGCGGACACCTG<br>GATCAAGCCCAACGCGCCGCGGCAGCTGACCCCGGGG<br>ACGGTGGTCAGCTTCGGCGCCAGCACGCGAGCCTACA<br>AGTTGGTCCGCGTCAGCAAGGCGGACTAG |
| 80 | 166 | ATGGCCGCGGCGGCCACCAACGGTGCCACCATGCGCG<br>AGGCCTACCCGCCGCCGCCCTCGCTGTTCAACCTGTAC<br>CGCCCGGATGACGGCGTGTCGCCGCTGCCGCCCGGGC<br>CCCCGCCCATCCCCACGCCCGCGGACGTGTCGGCGCT<br>GCGGGAGCGCAAGGTGGAGCTCAAGGTGCTGGGCAA<br>TCCCCTGAAGCTGCACGAGGAGCTGGTGCCGCCGCTC<br>ACCACCGCGGCGCTGTACCGGCCGGCGGGTCCGGACG<br>GACACATAGACTTCAAGTCTGAGCTGCGGCGGCTCAG<br>CCGCGAGCTGGCCTTCATGCTGCTTGAGCTGACCAAA<br>GCAGTGGCGGAGCAGCCCGGCAGCTATGCCTCCCAGC<br>TGACGCACGTGAACCTGCTGTTCGCCAACCTGGTGCA<br>GCTCACCAACATGCTAAGGCCGTACCAGGCACGTGCC |

TABLE 8-continued

Transcription factor library.

| | | |
|---|---|---|
| | | ACCCTGGAAGCCACCTTGGGCCTGCAGCTGTCCAACA<br>TGCGGGCGGCGCTGGGCCGGCTGCGGCAGCAGGTGGC<br>GGCGGCAGATGCGGCTCTGGGCGGCATGGCGCGAGCG<br>CTGGTGGAGGCGGGAGAGGGGGACAGCGCGGAGAGC<br>GCGGCACGACCTGCAGAGGCGGGGACAGCGGAGGCG<br>GGGGCGGCGGGTGCTGAAGCTGGTGTTGCAGCAGGGG<br>AGGGGGCAGGGACAGAGGCGGCGGTGGCGGCGGCGC<br>GAGGGGCGGATGCGGGCAGGACAGCGGCTCCGGACG<br>CCATGGAGGAGTTTTGA |
| 81 | 167 | ATGGAGGACACAAAGGAGGTGGCGCTCATATTTGCTG<br>AGTCCTTTGGCCGCGGCAACTTCCCTGGTGTCCAGGCA<br>GAGGCACTGGATGCGTTAGAAACCAGCTATGTGGGCG<br>CCATTGAGCGCGAGATGACCGATAAACTGCGGGAAAC<br>TATGGAGGCCAAGGTGCAGGCCTCTCGCGAGCACCGC<br>GAGTACCGGATGCAGCAGTACCTGCAGTTACTGCGGG<br>CGCAGCTGGCGGCGCTGAGAGGCGAGCCCGCGCGCTT<br>CCCCACACAGCCCTCGCCCTCGGATGAGCGCAACCTG<br>CAACGGCTGCGGCGGGCGCGGCAGTTCCTGGTGCTCG<br>TGGCGGAGGAACGGCCGACGGCTGAGGCTGGTGAGG<br>CTGGTGGCCAAGCCTCTGCCTCGTCCTCAGTAGCAGC<br>GGAGGCGGCGGCGGAGCCGGAACCGGAGGCAGCGGC<br>GCCGGGGCCCGGGCCCGGCTCGGCGGCTTGTGCTACA<br>GGGGCCGCGGCCTCGGCAGCGGCGTATGGGGGGCG<br>CGGAGGCGGGGCCAGGCGGTGGCGGCGGCGTCACTGT<br>CGCTGCTGCAGCCAGAGGCTCTGCTGCCGCCGCCCTT<br>CCCCTCCAACAAGCCCTACCGCCTGTACGTGTCCAAC<br>ATGAGTGTGGTGCCCGCGCACCGGCGGCGCGGCCTGG<br>CCAAAAGGCTGCTGCTGCAGTGCGAGCGCGTGGCCCG<br>GCTATGGGGCCATGAGTCCATCTGGCTCCACGTCAAG<br>CGCAGCAACGCCGCCGCCGCCGCGTTGTACGCCTCCA<br>TGGGCTACACACCGGTGGAGTCGGGCGGCATGAGGCT<br>GCTGCCGGGGCCGCTCAGCCAGGTGCTGATGACTAAG<br>ACCCTGCCGCCGCTCAGAGGCAGCTGCCGAGTGGAGC<br>TGGGACGGGGCGGGGCCAGCAGGTCGCAGGCGGCAG<br>CCGGCAGCAGCAGCAGCAGTGGCAGCAGCGGCAACG<br>GCGGCAGTAGCAGCAGCGGAGCCGGCGGCGTGTCGG<br>CGGGCGAGGCGGTAGTGAGCGGGGTGTCGGGGAGGT<br>CCCGAGAGAAGGATGGTGTGTTTGTGTGGGGTGCCGT<br>GGTGGAGGGGGCAGGAGACGTGGGGCCCACCGACAA<br>GGGGGCGGAGCGGCCAGGGCAGTAG |
| 82 | 168 | ATGGCAGACGAAACGGGTATCGTAAAGCAGGCCGTGC<br>TCGAGTTCCTGAAGACGGCCGACATGAATGTAACAAC<br>GGAGCGCACAGTCCTGAATCACCTGGCGGCCACGCTG<br>CAGCTAAGCCAGGAGGTCAAGGCGTACAAGGCGGTC<br>GTGTCGGCCACGATTGACGACTACCTATCGGCTCTGG<br>ATGACGCCGAGGATGAGGAGGAAGCCGCGGAGCAAG<br>AGGAGGAGGAGGACGCAGGCGCAGCCAAGGCAGGCG<br>GCCGCAAGCGCGCCGGCGGCGCAGCCGGCGGCGCTG<br>CCGCTAAGAAGAGCCGCAGCAGCAGTGGCGCCGCTGG<br>CGGCGGCGGCGACGACGTGCTGCTGCACGTGGACCTG<br>AGCGAGCGGCGCAAGGCGCGTGTACGGCGCTACGAG<br>GGGCGGCTGCACGTTGATGTACGGGAGTTCTACAAGA<br>AGGACGGCGAGGACGCGCCCACACAGAAGGGGCTGT<br>CCATGGACCCGGGGCAGTGGGCCCGACTGGCGCGGGA<br>GCTGCCGCGGCTGGTGGCGGCGCAGCGGGCGGGCGCT<br>GCAGGCGGCGGCGGCGGCGAGGTGCCGCCGGCGCAG<br>CTGGCCAAGACTCGGCTGGCCTCCGTCAGCGAGTTCA<br>AGGGCACTTACTACCTAGGGTTGCGCGAGTACTACGA<br>GAAGGATGGCCAGCTGCTGCCGGGCAAGAAGGGCGT<br>GAGCCTGAACCCCTCGGAAGCGGAGGCCCTGCTCGCC<br>GCCGCCGCCGCCATCACCACTGCCGCCGGCGGCGTGC<br>CGGCCGACCTGCCGCCGCTCGAGCCCTCTGCACTGCT<br>GCCCACCGCCGGCTCCGGCTCCGCAGCCTCCGGGGCC<br>ACTGCCAAAGCCAGCGCGAGCGCGGGGCCCTCCAAG<br>GCGGCGGCGGCGGCAGCAGCGGCGCCAGCGGCCGGT<br>ACCGTTGCCAGCGGCGAGCCGACTGAGGTGGTGGAGC<br>TGGGGTCGAACAAGCGGCTGAGCATCAGTCACTTCGG<br>CGGGCGCACCAGCGTAGACCTGCGCGAGTTCTACGAC<br>GTAAGCTACAGAGGTGTTGGTGCTGAGAAAGACGGGC<br>AGAAGCTTCCAGGCAAGAAGGGCATTGCGCTGGCCCC<br>GGCTGACTGGGCCACGATGTGCGCCGCCCTGCCCGCC<br>ATCAGCTCCGCCCTGGCCAAACGCGACATGGGCTATG<br>TGCTGCAGCTCAGCGGCAAGCGGCGTGTGTCCTTGTC<br>CGAATTCAAGGGTGCGGTGTATGTGGGCGTGCGCGAG<br>TTCTACGAGAAGGACGGTCAGCTGCTGCCGGGCGCCA<br>AGGGCCTGTCTATGAACGCGGCCCAGTGGGCGGCGCT |

TABLE 8-continued

| Transcription factor library. | | |
|---|---|---|
| | | GGTGGCGGGCGCGCCGGGCTTCAACGCCGCACTCCAG AGCCAAGAGTAG |
| 83 | 169 | ATGTTTTCGCTCAGCACGACGAATATATCCGATGTGCC GCTGTTCTGGGAAACTGTCAACCTAGTGTACGATTCCT TTACCGAGAGCTTCATCGTGGTCACTGGCGCATGCATT CAGCAGCTGATCCCTGCCCTCCACGGCGAGGACGACG AGCCGCTCGTGCTCGCTGCAGTGGCGGGAGCTATACT ACCGGTCCGTGTGCAGGCAAATGGCCGTGGTAACGTG GCGCAGTTCGGCAAGCCCACGCATATTGCCACCGACG GCAAGGGCACGCTGTACGTGCTCGATCAGGCCAACAT CCGCAAGCTGCAGCTGCCGGCGGCGGCGCGCTACCAG CCCCATCAGCAGCGCCAGCGCATCAACTCCATGCAGG TGGAGGTCACCACGTTGTCGCAGCAGCTTCCCCCGGA TATGACAGCCAGCGGAATGGTTTACGTCCCCGCGGGG GAGAGCCCTGGCGGCAGCGAGTGCCTGATCCTGGCGG GCACCAAGGGCATCTACCGGCTGCCCCTGTGCAATAA TGACGCAGCAATTGAAGCAGGCGGCAAGGCTGGGAT GCAGGGCAGCGGCAGTGGTGCCGTGGCTGGCGGCACG GGTGGAGCAGCGGAGGCCACCACCGCCACTGGCAGC CTACACCGGTTGGCAGGCAATAGTGACACCGCAGGAA GCTGGGGAATCCGTTTTGATGCATTTGGTGCGCAGGC CAAGATGCTCGCCATCTCCTCCGGCCTTGCACTCACTG GTGATGGCCGCGTGGTGTTCTTGGACTATTCCGCAACC CAGAGGGACACGGCCGTGCGGTGCATACGGATGTCCG ATGGGCGCGTGTCCACGCTTTACGAAGGCCTGGACGG GCAGTGGCAGTGGCCGTGCCTGCTCCCCAGCGGCTGC CTGGCCATGACGAGTGGCAAGGACCTCTTCATCATCG ACCTGGCCCTTCCGCCGCCACGGCCGCCGCCACCGCC GCCCAGCACCGGCCCGCCGCCGCGTAGCCTGGCCTCG GACCTGGGCGCGCTGCTAGACGGCGCGGCGGGCGCGG CCAGCTCCGACCTGACCATCCTGGTCGGCGGACGGGC CTTCAAGGCGCACCGCGTCATCCTGGCCGCGCGCTGC GAGTACTTCGCCAAGCGCCTGGAGGAGGGCGCCTACG CGGACGGCGCCAAGCAGGAGCTGGAGCTGCCGGAAG CGGAGCCCGCGGCGTTCGAGGTGCTGCTTCGCTGGCT GTACACCGGCGCCGCGGACGTCCCGGCTGAGCTGGCG CAGGAGGTGGCGGTCCTGGCGGACCGCCTCGTGCTGC CGGAGCTGTGCGATGCTGCGCAGGCGGTGGTGCTCGA GTCTGTGACCCCTGGGTCGGTTGCGGCGGCGCTGGTG TGGGCGGCGAGCTGCGTGCCTGGGCGTGGCAGCAGCT TCGAGCAGGTGCTGCGCCGGCTGAAGAAGTGGTACGT GGCGCACTATGACAAGGTGCGGAGCGAGGCGCGCGC GAGCGTGGTGGCGCTGATGGCCAGCAACCCCGAGCTG GCGATGGAGCTGCAGGAGGAGGTGCTGGGGGCCACG GAGCGGCGGGTGAGCAAGAAGCAGCGGGTTTAG |
| 84 | 170 | ATGGTCTGCATTCGCCCAGCAACGATTGACGACCTAA TGCAGATGCAGCGGTGCAACCTGCTGTGTCTACCTGA GAACTACCAGCTGAAGTACTACCTGTACCACATCCTG TCCTGGCCCCAGCTGCTGCAAGTGGCGGAGGACTACG ACGGCAAGATTGTGGGATACGTGCTGGCCAAGATGGA GGAGGAGGCCAGCGAGCAGCACGGACACATCACCTC GGTGGCGGTGGCGCGCACGCACCGCAAACTTGGCCTG GCCACAAAGCTCATGAGCTCCACGCACAAGGCCATGG AGGAGGTGTTCGGCGCGCAGTACGTGTCGCTGCACGT GCGCGTCACCAACAAGGTGGCCGTGCACCTGTACACG CAGACCCTGGGCTACCAGATCTACGACATCGAGGGCA AGTACTACGCCGACGGTGAGGACGCCTACGAGATGCG CAAGTACTTTGGCCCTGCGCCGCCCGCCCTGGCCAAG AAGGCCGCGGCGCTCACGGCGCAGGCCACCGGACTGC CCGCGCCCACAGCCGCCAGCAGCTGA |
| 85 | 171 | ATGGGGGACCAGTATAACTATTATCCGGGCGGGTACA CTGGTGGAATCCCGCCGAACCACCACCAAGCTGAGGC GCTCAAGTCTTTTTGGCAAGCACAGCTGGTCGAGGTG TCTGAGGTCCCACCTGACCCAACTGTATTCAAGAACC ACCAGCTGCCTCTGGCCCGCATCAAAAAGATTATGAA GTCGGATGAGGACGTGCGCATGATCAGCGCGGAGGCC CCCGTGCTGTTTGCCAAGGCGTGTGAGATGTTCATCCT GGAGCTGACGCTGCGGTCGTGGATGCACGCGGAGGAA AACAAGCGGCGCACGCTGCAGCGCAACGACGTGGCG GCGGCTATCACCAAAACAGACATCTTTGACTTCCTGAT CGACATTGTGCCCCGGGAGGATGGCAAGCCGGAGGA GGGCGGCGCCGCGGCGCCCGGCGGCGCGGCCCCCGC GACTGCGCCGTCACCGGCCGGGCCCGGCGGCTCCGGA AACCAGCAGGCAGCTTCCGCTGCCTCGACGGCTGCCC CGGCAGCGGCCGCGCCGCGGCCGCCCGCGCCACCGGG |

TABLE 8-continued

| Transcription factor library. | | |
|---|---|---|
| | | CATGCCCACCGCGCCAGGCATGTTCTTCCCGCCGCCCT TCCCAATGCCGCCGGGCGCGCTGGGGACCCCAGCCA CGCGGCCGCGGCGGCAGCGGCGGCGGCGGTGATGAT GCGGCCACCCATGGGTGTGGACCCCAACCTGGTCCTG CAGTACCAGCAGCAGATATTGGCGGGGCAGGCGCCAG GGTGGCCGCACCTGCCGGGGTTGCCGCCGCCGCCGAC GTCGCAGCCGGGCGCCGCGGCTGCGGCCGCTGCGGCG GCGGCGGCGGCGGCAGCTGCCGCAGCAGCGGGAGCT GCGGCAGCAGAGGGGCAGGCGGAGGCTGCAAAGCAG GAGTAA |
| 86 | 172 | ATGACGAAGGATGAGCAGGCATTGCTAGATTGGGTTA TTGCTGAGGGCGGCGAACTGCGGGTGACGATTTCCCG CGATGAGGCGGGGGTGCGGGGCCTTTACACCACGCAG CCAGTGAAGAAGGGCGAGGTAATAGTCTCCATCCCTC AGCACATCGTCCTCAGCGTGAAGAATGTGGCAGCTGC GGAAGCCTCCCCCCAGCTGCTCAAGGAGATTCACTCG CCCTGCTCACGGCTCAGACCGTACCTGGACACACTGC CTGGGCCTGACGGGGTGCTCACGGCGTACAACTGGCC TGAGGAGTACATCAAGTACCTGGCCGACCCCGCGATG GAGGAGCAGTTGAAGAACTCCTTCAAGTTGCACGCGC GCAACACGTGGCTCGGGCACAACGACGATGAAATGG AGGTGACCATCCCAGAGGCCATCGGCCGCAAGAACAT TACATTGAAGGAGTGGGAGCACGTTGTGTCACTGCTG AGCTCGCGGACGTTCAGCATCCGCAAGGGCGCCTTGT CGCTGGTGCCCGTGCTAGATCTGGTCAACCACGATGT GCGGGACATCAACCAGCTCGGCAACAGCAGCACTGTC GATCTGGTCGCCGGCAAGGACCTGGCTGCTGGCGAGC AAGTGACCATCACCTACGGCTCCATGCGCAATGACGA GCTGCTCATGTACTATGGGTTCGTTGACACGGTGACG GAGCCGCCCCGCCTGTTCTCCGTTGACCACCGCGATTT CAAGCTGTACGAGGCCAACCCGCTCAGCGACAGTCCG TTGGAAGGCCCGCCGGAGGTGCTGCGGACAGAGCTGG CGCGTCTGCGTGGCATCCTCACCGCGTTTGAGGCCAG ACTGGACGGGCTGGGCCCAATTCCCGACACACAGCCG TACGTGGCGTCGCTGCTGCGGGACGCACACGACCGGA GGCGGCGCGCGCTGCATGCGGAGATAGGCCGCCTGGA GCAGCAGCTGCAAGGGGCCAGCGGCAGCGGCGGCGA GGAGCTATAG |
| 87 | 173 | ATGTCGATGCGCAACAACAAGCGCCGCGCTCTGGCAA GCGCTGGCGCCGCCAGCAAGCAATCTGCGGTGGCCGA CGCCGTCCTGGACGTGGCCAACCGCAAGGGCGTCCGC TGCTGCGTAGAGTGCGGGGCGACGTCCACTCCGCAGT GGCGTGAAGGCCCGATGGGCCCCAAGACGCTGTGCAA CGCCTGTGGCGTGCGCCGCCAGCGCCTCATCCGCAAG CAGCAGGCCGCTGTCGCTGGCGTCACGCCCACCGCGC CTGTCGCCGCCGTGCAGGCTCGCCGCCGTCTGGCCAC CCGCCGCCGCCCCGGCGCCTCTGCCTCGCTCATCGCCG ACGAGGATGTCTTTGCGCCCGCGGGCGCCGGCTCCGT GTCGGAGCAGTCGAGCGACGAGGCGGAGATGACGGT GATGGGCTGGCGCACAACGGCGGCGGAGGTGCCCCG GCCGCAGCGCGGGCAGCACTCGGCTGCCACCGGCACC GACGTTGAGGACAGCTGCAACGAAGAGGAGACGGCC GCCTACGACCTGCTCTTCTTCGCCGGCTTTGACTGCGG CGACTATGGCTACTCGGCGCCGTCCGGGCCCAGCCAC GGCCACAACACACGCCGCCAAGCCGCGCCGCAGCGCC GCTCGGACGACTTCTATTATTACGAGGAGCAGGACCA CGAGGGCGAGCACGGGGTGGCCGCCGGAGAGCATGA GCGGCTGCCCATGTCGGCTCCGGCGCTGCAGCAGGTG TCGTCCATCAAGCGCCGGCGCGTGCTGGCGGCCCCGC CCAAAGTGCACATCCGCCCCGGCCGGTCCGCGATGAC GAGCTTCCCGTCTTCCTCGGCCGAGCACGAGGCAGCG GCTGTACCGGCCGTGAGCAACATGAGCAGCCTGCCGG CGGCCGCGGGGCCTGCGCCTGCATCGTCCTCAGACGC CGCAACGGCGGAGTTGCTGCCGGCGGCGCCGGCGGTG CTACCGTCCTCTGCCATGCTGGCGCTGCAGCTGCCGCT GCTGCCGCTCGCGCTTCCGGCGCTGTCGCTTCCGGGGG CGGTTGTGGCGGGCGGCGCAAGCCCGGCGGACCTGGA GATGATTGCCGCACTGCACGCCGAGTTCCAGCGTGCC TGCATGCAGATGCAGCAGGCTGTGGCTGCGGCGGAGG CGGTCGGCGCGGTAGCGGCAGAGCGGCGCGACGCCG CGGACGCGGCGCATGCTGTCGCCGCTGTGGCGTCGCA GCGCCTGGCGGACGGCGCTAAGGTCGTGGCGGCCCTG CCGGAGGTGCGTGACGTGCTCGCGGAGCTGCACACCG GCCCAGTCGCCATGGCCGTTGCGCCGCCCCTGTAA |

TABLE 8-continued

Transcription factor library.

| | | |
|---|---|---|
| 88 | 174 | ATGGCGCTCGTATCACATCATGGTGTATATAACCAGC GTTGTAAACATGCAAACGGCGGTCGTTCCGCTCCTGG GTGGCGCCTCTCGCAACCACAGCCTGCTCAGCCCCGG CGACATCGCCATGTCGTGTCCGCCGCGCGTTCGCCGC AGCAGCCCGCTCCGCTGCCGCCTCGGGTGAGCTGTGG CGAGGAGGGCGGAGCGCCGCTGCACATACGCGCCGC GGAGCTCCGCGACTACTGGCCGGCAGCGGACCTACAC ACGCGGGTGTTCTGTCCGGAGGCGGAGTCAGACCGAA GTAAGGCGCTGTCCATGCGTGTGGACCGCATCATAGC GCTGCAGATCAACGACCGCATATCCAGAGAGGGCGGC GGCAACTCTGTGTTGCTGCTGGCATTCAACGGGGAGG CGCCGGGCAGTGCGGAGGAGCGCACGGCGGCGGAGG CGGCGTTTGCGGCGGCGGCGCAGGCGGCACAGACGCC CGGGTCTGTCACCCACCTGTCCACCGCCTTCCCCAACC CCATGTGGTGGCTGGCGCGGCCGCTGGGGCCGGGCGT GCGGGCCGGCATGGGCGTGGCGGCCGAGTCCGTGGGC CTGGTGGGGGTGGCGGCGGTGGACAGCTTCTGTGACC TGGTGCCGCCGCGGGAGCTGGACCCGCGGCGGGACGG CGCGTTCGGCTTGTACCGCCGGGACGGCTACGCCTAC GTGAGCAACGTGGCGGTGCTGCCGGCGGCGCGGCGGC GCGGCGTGGCGCGTCAGCTCATGGCGGCGGCGGAGGC GCTGGCGGCGGAGTGGGGGTGCAAGGCGGTGGGGCT GCACTGCAACACCAAGAAGACGGCGCCATGGGCGCTG TACCGCAGCCTGGGCTACCGGGACAGCGGTGTGGTGG AGCCCTGGATCATGCCCTACCTGCAGGGCCGGCCGCC CGACCGCTGCTCGTTCCTGGTGAAACGCGTGCCGCTG CAACCGCAGCCGCAACCGCAGCCGGAGGCAGGGGCG GGGGGGGCGGGGCGCACGGAGGGTTCGGGGCCAGCC GGGCTCCGGTAG |
| 89 | 175 | ATGCCCAAGGAGTACATCGTGCGCCTGGTGTTTGACC GGCGGCACCGCTCCGTGGCGCTGCTGAAGCGCAACGG CACCGTCATCGGCGGCATCACCTACCGCGCCTTCCAC GAGCAGGCATTCGGCGAGATCGCCTTCTGCGCCGTGA CCAGCCACGAGCAGGTCAAGGGCTACGGCACGCGGCT CATGAACCAGACCAAGGAGTTCGCGCGCACCGTGGAC CGCCTCACGCACTTCCTCACCTACGCCGACAACAACG CGGTGGGGTACTTTGAGAAGCAGGGCTTCACGCGCGA GATCACGCTGGCGCGGGAGCGCTGGCAGGGCTACATC AAGGACTACGACGGCGGCACGCTGATGGAGTGCGTCA TGCACCCGCGCGTCAGCTACACCGCCCTGCCCGACCT CATCCGCACGCAGCGCCTGGCGCTGGACGACCGCGTT CGCCAGGTCTCCAACTCCCACGTGGTGCGGACCGGGC TGAGGCACTTCCAGGAGGAGGACGCGCGGCTGGCGGC GGCCACGGCAGCAGCAGCGGCGGCGGCGGGGGCAGC AGGAGGGAGAGGCGCGGGCGGTGTAGGGGCCGGGGC GCCGGCTGGTGACGCGGCGGCGGCAACAGCGGACAC CGACCCGGCGTTGCGGCGACGTATGCTGGACATCGGC GGCATCCCAGGGGTGCGGGAGGCGGGCTGGTCGCCGG ACATGGTGCAGCAGGGGCCGCGCTTCCGGCTGCTGCT GGACGAGGCGGGGGCGGGTCCGGCGGTGGAGGCGGG GTCGGAGGCGCTGCACCGGTTCCTGGTGCTGCTGCTG GAGCACGTCAAGGGGCTGGAGGACGCCTGGCCGTTCC GGGAGCGGGTGGCGGTGCAGGACGCGCCCGACTACTA CGACATCATCAAGGACCCCATGGCTCTGGACGTGATG GAGGAGCGCCTGGCCTCGCGCGGCTACTACGTCACCC TGGACATCTTCACCGCCGACCTGCGCCGCGTGTTCGAC AACTGCCGCCTCTACAACGCGCCGGACACCATCTACT ACAAGCTGGCCAACAAGCTGGAGGCGCAGGTCAACG CCTTCATGTCCAACCACGTGCTGTACGAGGATGAGGC AGGGCCGGCGGCGGCGGCAGCGGCAGCGGCAGCTGG GACTGGGGCTGGAGCAGGCGCTGGGCGGTAG |
| 90 | 176 | ATGCAGCAGCCCGCTCGCAGGACCTGGACGGACCAGG AACTGGCAATCAGCGGCTTTGAGCGGTTCGCCCTTGA ATTGGAGTTCTTGCAGTGCCTGGCCAATCCTCTTTACA TCAATTGGCTCGCAACGAAACAGTATTTTGACAACCC AGCGTTTTTGAACTACCTTAAGTACCTGCAGTACTGGA AGCAGCCTGCATACGCAGTGCACATCACGTACCCGCA CTGCCTGTTCTTCTTAGACCTGGTTCAGGATGCGGACT TCCGCAACGCAATAAAGGATTTCTCATACGCGGAGCA TATCCGCCAGGCACAGGACTCGTTTTTCCGCAACTTCC ACTCCAACCGGGTGGCGGAGGCGGAGGGCAAGGCCA CGGCCGCGCCGGCAGCAGATGGCGACGGTGGCGCAG GTGATGCCATGGATTGA |

TABLE 8-continued

| Transcription factor library. | | |
|---|---|---|
| 91 | 177 | ATGGACTCGGAGCAGCAGCCGGCCAGCCCGAGGGCTG CGCCTGGTGCAAGCGGAGGCCGACGCTTGCCTGGTCG GACACCTTCTGGTCTATTGGGACAGGCAGCGCAGGGG CCGCAGCAACCTCAGCCCCAACTTGGCAAGGGAGCAC TTCAGCTCAATCAGTCCAGCAGCGCAGCGACAACCGC GTTGCCGGTGAAACGTCGGGGGAGTTTCCAGCAGTTG AAGAAAATAGGTGCCGCCGGGGGGCGAGATGGCAGC TCTTCGCACCTGGACTCGGACTCGGCACCATCAATTTT CGCCATTGTGAAAAAGTCCACACACTGGGAAAAGTAT GGCACGGTGCTCGTGCTGCTCGTTGCCGACGAGCTCA GCAGTGACAAGGAGGCGGTGGTGCAGATGCTGAGCG CAGAGGGATACGATGACCAGACGTCGGACAGCATCG AGGAGGCGGTGAAGTTGTTTTCGGAAAGGGAGGTGTA CCCGGACATTGTTATTGTTGATTCAGACAATGAGCTGG TGGACACCAAACAGCTCATCAAGGCGCTGCAGGCGCT GAACCCCACGGTGGCGGTGCTGGTACTGGGCAGCCGC GGCGGGCCCATGGGCGCGGTGGCGGCGCTGCAGGCG GGCGCGGCGGACTACATGGTGAAGCCGCTGGATCTGG ATGAGGTGGTTGCCCGCGTGGAGCGACACGTGCAGCG ACAGCACTGCATCAAGTTGGAAATGGAAAAGGCGCTG GAGCACGCCAAGGAGATGATGCAGCAGCTCATGCCGG CATCACTACTCGGGGACGTGATGTTGCGGAAAGACGG CAGCGCCGCGGGCGGCGCGCCGGCGGGCGGCAAGGC GAGTCTCAACAGCGTGGCGGAGACCGACTTTGAGGAG CAGATGAGCGAGCTGAGCGAGGAGAACCACCGCTTG GGCCAGAAGGTGCAGGAGATGGAGCGCAAGCTTGAG CTCAAGGACCAGGAGAACCGCGACCTGGAAGCCAAA CTCAACGCCATCGACCGCAAAGTCAGCGCGCTGGCCG CCAGCCGCGAGATGGGCGGCGGCAACGGCGGCGGCA ACGGCGGCGGCGGGGGGTCGGGCTGCACGGCCGTGG GGCCTGAGCAGCGTGCCGCGGCGCAGCAGGCGGCGC AGGCGGCCCAGGCCTCGTTGCAGGGGCAGCTGAACAG CGTGGCACAGGCCAACGAGGACCTCCGACATAAAGTG GACGAGCTGGAGCGGCTGATGCAGTCGCACACAGGCG TCACCAGCGCCAGCAACCAAAACCTGCGCCTGAGCGT CAACGGTGGGCAGCAGCAGGGCTAG |
| 92 | 178 | ATGGCGGCCCGGCTCCTGCGGGATCCTGAAGCAGACG GATGGGAGCGCTCGGATATGCCCATCGTGTGCGAGAC GTGCTTGGGACCCAATCCTTTCGTGCGCATGCAGCGG ATCGAGTTCGGCGGCACCTGCCACATTTCTGGTCGCCC CTACACGGTCTTCCGCTGGCGCCCCGGCAACGACGCT AGGTACAAGAAGACGGTGATCTGCCAGGAGGTGGCC AAGGCCAAGAACGTGTGCCAGGTGTGCCTGCTGGACC TCGAGTACGGACTGCCCGTGCAGGTCCGTGACGCCGC CATGGGCGTGAAGCCGGACGAGGAGCCCCAGAGCGA GGTGGGCAAGGAGTACAAGCTGCAGATGGAGGCGGA CGCGGGCACACTGGGCGGCGGCGGCGTGGGCGGGGC CAGCAGCAGCTACGCGGCGGGCCGGCCCAACGAGAT GCTGCAGAAGCTGCAGCGCTCGCAGCCCTACTACAAG CGCAACCAAGCGCGCGTGTGCTCCTTCTTCGCCAAGG GGCAGTGCACGCGCGGCGCCGAGTGCCCCTACCGGCA CGAGCTGCCCACCGCCGACCCGGCGCTGGCCAACCAG TCCTACAAGGACCGCTACTACGGCACAAACGACCCCG TGGCCGCCAAGATGCTCAAGCGGGTGGACGAGCTCAA CAAGCTCACGCCGCCGGAGGACACCTCCATCACCACG CTGTACGTGGGCGGGGTGGACGCCTCCATCACCGAGG ACGACGTGCGGGACGCCTTCTACTCATTCGGAGAGCT GGCCAGCGTGCGCAAGATGGACGTCAAGAGCTGCGCC TTCGTGACCTACACCACGCGCTCCGCCGCGGAGAAGG CGGCGGAGGAGCTGGGCGGCAACCCGCTCATCAAGG GCGCGCGCGTCAAGCTCATGTGGGGCCGCCCGCCGCC CGCGCCCGCAGCCCGCAACGCCGCCGCCGCCGACCCC ATGCAGCCCTCCACCAGCGGCGCCGGCGGCTACGGCG GCGCGGCGCCCGGCAGCGCCGCCTCCTACTACCCGTC CATGGACCCCTCGGCCATGGGCTCGCGGGCGCCGGGC GGGCCGCCCGGCATGCGGCCAGGCGGGGAAGGCGGC GGCCCCGGAGGCCCCGGAGGCATGGCGCCGCCGCGG CCCATGGGCTACGGCGCGCCGCCCGGGTACGGCGCGC CGCCGCCTGGCTACATGCCGCCGCCGCGCCCCATGGT GTCTGCCAGCATGCAGCCGCCGCAGCAGCAGCACCAG TAG |

Figure 9:
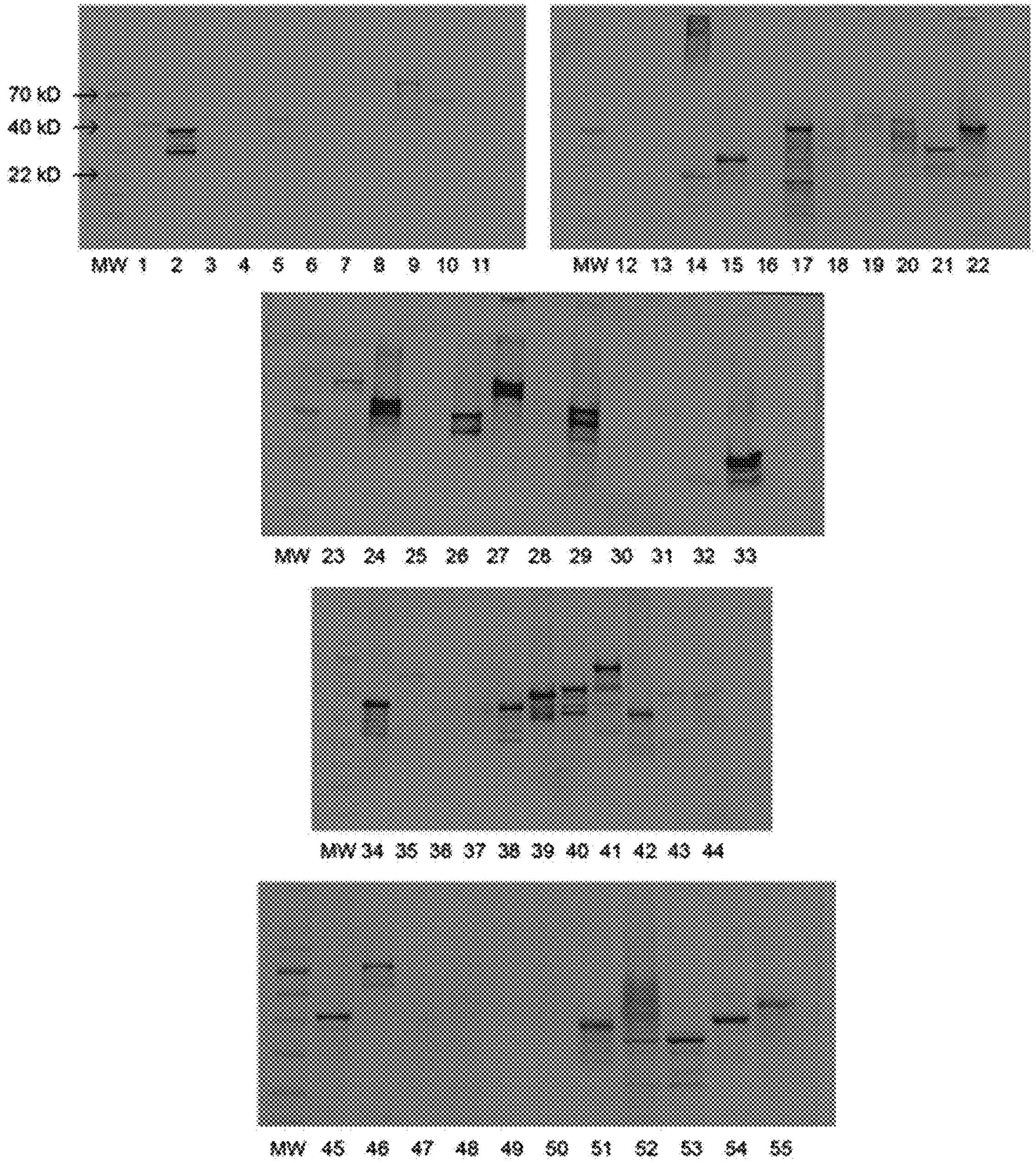
FIG. 9 illustrates production of transcription factor (TF) library proteins in yeast. Immunoblot of whole cell lysates of *S. cerevisiae* strains producing TF library proteins separated by SDS-PAGE and probed with anti-GAL4-AD antibody. Numbers below each blot indicate TF library number.

Putative transcription factors initiate transcription from *C. reinhardtii* promoters in yeast. As an initial screen for potential DNA-binding activity, we performed a high-throughput yeast one-hybrid (Y1H) assay to test our TFs' ability to activate transcription from known *C. reinhardtii* promoters [36,37]. We transferred our entire pENTR-TF library to the Y1H vector pDEST22 via Gateway LF-transferase which allowed the TFs to be fused to the yeast GAL4 transcription activation domain [38]. Separately, "bait" promoters of interest were cloned (in 300 base pair (bp) fragments, labeled A, B, and C (5' to 3'), for a total of 900 bps per promoter (Table 9) 5' to a yeast minimal promoter element followed by the reporter gene *Gaussia* luciferase [39]. Each TF-vector was transformed into separate haploid *Saccharomyces cerevisiae* YM4271 cells and crossed against the opposite mating type of strains harboring DNA bait promoters of interest. *S. cerevisiae* strains producing each TF were also cultured so whole cells could be processed for western blot analysis of TF protein production (FIG. 9).

TABLE 9

Promoter sequences used in yeast one-hybrid assay.

| Fragment | Gene | Species | SEQ ID NO | Sequence |
|---|---|---|---|---|
| A | LHCBM5 | CRE | 179 | TGAAAGACGGGCAAGACACGATTATCCTGC AGGCAATTGCCGGCGCGAGCTTGGGGCGCC CCTTCAGCGTCCCATCGGCGGTCGCTTTTTG CCCCGGTGTCGCCGTTCCTGGTTCTCGGCAG CCCAAGATAATTTAATCTAGTAGTAATAATC ATGTGCAGCGTTGTGGCAGCTGCCCCCAAAG GAAACTGTGGCGGGAAGCGCCCCAGTCGCG CAAGCTTATCGCTCGGTCGCGCGTCGGGGCC ACCCTGAAGACCCTGAATTATTTGTGCGACA ATATAGCAGCCACTTCTTTTCATTTGAATGG TTT |
| C | LHCBM5 | CRE | 180 | AGGGGAGGGGAGGGGCGGGGCGGGGCGGG GCGGGGCGGGGCGGGGCGGGGAGGGGAGG GGCGGGGCGGGGCGGGGCGGGGCGGGGAG GGGAGGGGCGGGGCGGGGCGGACAAATAG GTCAGCAAATGGATGAACATGACCGCAAAT TGATAATCATACCTGGCTTGCAAGCTCGCGC CCAGCGAGATGGAGTACGGACGATGGAGAT CTGGCCGCGATTGGCGAGCCGGGCAAGAAA AACAGCCGAGCGCTGCATATAACACTTGTCA CACCGTCGACCTTGTTCGTTCAGTCACTTGA ACAGCAACACC |
| A | LCIC | CRE | 181 | CACAACACCTCGCCACGGGCACACCGCCAG CCACCCGCCCCACCAGCGAACTAGACCGAC CCGACAAACAGGCACGCGCGCGCCCGGAGG CGAACAGGCGCACCAGCCGCCCGGGCGCCC GGGCAACAGCCGCCCAGGCACTCACAACCC GACACCCGGGACTACCCGACCAGCGTCATCT GCTGCCTAACGGTCCCTGAACCGCCATGCTA CGAACGGCACCCGCAACCTAACTATCTGCTG AGCCAGCAAGGCCGCCGGTGGAGACGACAG CGGGCCAGGCGGCACGAGGAGAGGCGCACA GGGCTGC |
| B | LCIC | CRE | 182 | GGCGCACAGGGCTGCGTGCATGGCCAAACC CTCAGTTGGGAAATTCGGACAGGAAGCAGT GAATGGGGCACAGTACTATACTAGGGGAAA CGATAACGTGATCTCAGGGGCGTGGGGGGG GGGCTAGAAGGGAAGGGGCGCTGTAACTGG ATTGCGTGGTGTGCGCGGTGCATTCTTCGCA CACCTCGGCAGCAGCCCGGCCCCGCGTTCCC TGGCCTAGTGACGCCGGTTGCCACCAGCAAC CAAATGCCATGCATGCGGCCAGTATGCGCAT GCGTCGCCCCCGCGGCCGAGCTGCACGCAC ATGCCG |
| C | LCIC | CRE | 183 | TGCACGCACATGCCGACCGAAAGGAAATGG GTGTTGCGCGTCAGAGCGGGTTTGAACAAGT GATTTCTTCGCTCCGCCATGCACAGCAAGCT AGCTAAGCTGGATGTATTAGGGGCTTGGTTT GTTCATTTGCACCTCTCCAACACGTACGACC TCCAACCCTCCTACAATTGCCCATGCGCCGG GTTTTATAGGTCGCCGGTGCGTATGATGGGC TGCAGTAACAACATTCTTCTCGTGGTTGTGT GTTAAACGTGCACAGTTAAATACATTACATA TCTCGTTGACACTACAAACCAGCGATAGAA GG |

TABLE 9-continued

| Promoter sequences used in yeast one-hybrid assay. | | | | |
|---|---|---|---|---|
| Frag ment | Gene | Species | SEQ ID NO | Sequence |
| A | LCI5 | CRE | 184 | CGTGATTGCCGGCGGCGAGGCGGGGCCATG GACGGGGCTACGGGCAGGGCGACGCCACGG TTACTCGCACTGCCCAGCCGTTCACCTGTGC TGACATGCATGGCAGTCTGGCAGACCTCACG CAAGACCACTGGATGAGGCGTGGCCGTGTG GGGCTCGTCGTCGCACTCAGCTGTTGGCAGG CCCCCGCTAGTTGCCCTGTGTCCGCCCTCTTC GGTGCTCAGCCTGACCAAGGCCTTGGGGGC GCCGGCAACCACAAACCCAACTGAGGCTGT ATACTTGGACGCAACCCATCCGTGGCCAGGT TTCT |
| B | LCI5 | CRE | 185 | CGTGGCCAGGTTTCTATCGACGTCCTCCGAC AGTGAAGGGTTCCGCAAAACCGCCTCACCG ACATGTGAGACATGCGACATGTGCCCTCAG GTCTCTCAGCCCCTGTGCTCCTGGAGCGCTA CGTTATGCGCAGCATGACCATCGCAGCTACT CAAGAAAACAAAAGACCATAAGCTGTGAGC CGTTGACTGAGTTGACCGTCGCGAAACAGC GTCCTTTCTCAGCAAGCCTTGCCAGCCGAAC CCGAATTTATTTACCTTCACGGCAATACACC ATGTACGTTTTGAATGCCTGCAATCGGGTTT CGGC |
| C | LCI5 | CRE | 186 | CAATCGGGTTTCGGCCTCGCCCTGGGCCTGC TAAGAAATTCACAACTCCCCGCGAGAATGCT GGCCGTGCACTCAATTAAATATGCTCATGCA AGTAAGCTGATTACATGCATATTTGAGGAGC GGGGCGGGGCCATTCCTCCAGGAAATGGGG AACTCCTACCACAACCTCCTACAATGTACGG AATGGCCCATCGCCGCGGGCAGCTTGCACTT AAGCTTGCCGGCCGGCGCGCACAGATTCAC CTTCAGGCAAGCACTCGCAGCCGCTCCATCT GTAGCGTCGACCTTTCAGAACCACTCCAAAA CA |
| A | SEBP1 | CRE | 187 | TGGATGAGGCAGGGGTTCCCCTCAGCTGAG GCAACCATGCTGCCGTGGCAAGGCGGCGCG TTAATGTGCTCCGTTGCTCACGGTCACAGGC GTGCATAGGCTGCATTACGCTGCGTGTCGCT TATTACTCTGGACGCCCTCTGCTTCGGGTGG GGCTATGCCAGTGCCGTGCGCACCTCGTGCA AGTAGACTATGGTACCAAGGTAGACCCAGC TTGATTCCACGCGTGATCCATGTTAGTGCGT AGGCTCATAGAAAGACACACCGGTGAGAAA GACACATGGAGGCGCGGCACTGCGGACGCT GCGGA |
| B | SEBP1 | CRE | 188 | TGCGGACGCTGCGGAGAAAGGCACATGGAG GCGTGCCGGTGTGTTCCGGCAGTGCTGCTGA CATGCAACTGTGTTGACCGTTGACATGCCCG TGCCGTAAGTGCCCCAGCGACGAGTTCGTGG CCCCTAGCAGTGGCTTGACATGGGGCTTTGG GCCCACAATTAAGCCATGTGAGCAACGCAC CTTGACGCGGGCTTAAATCTGGCAGTCCAAA CGACACGCGTGTGAAACCCGCCAGCTTCTTT TCCCTGTTGACGATTCGCCAAGCTCCCGGCA ACCCCCGCTTGCCCATTGCAAATTCCCAAGT GT |
| C | SEBP1 | CRE | 189 | CAAATTCCCAAGTGTACTCCCGTCCTCGCGG CTTTAAAATATGGCAGTCCGTCCGGCTTGAA CATGCGCAAGTCGCATTTCCCAACGACAATC CTCTTCGTAGCGCGCACGTTGCCAGGCAGCG AAATATTCTATCATGTTTTTGCTGGGTTGAA TGCAATTGAACACCGGTTTGGTTTCGGCAGG CAGCTCCCCGACCGTCAAGGCTTGCATGGGA TAGGGTTGCCCATCGCCGATAGCGACCGGCT ACTTCAGCCAGCCCTCGCAGTGAGGTAGTGC TTTTGGGTCTATATACAAAATGGCCGCTATG |
| A | NAR1.2 | CRE | 190 | CGGCACACAACAGGGACACAGCACGGCGCA CAGCACATGGCACACACTGCAGTGGCAGGC |

TABLE 9-continued

| Promoter sequences used in yeast one-hybrid assay. | | | | |
|---|---|---|---|---|
| Frag ment | Gene | Species | SEQ ID NO | Sequence |
| | | | | TGACGCTGCACATTGGCTGTCTGCAGTCTTG CTTGCGGCCCCTCCTAAATCTTGTTCCGGGC TCGCGGGTTAGCTCTCGCCAGTCCCCCAGCC CCCAGCACGCCTGCACTGTTGGCCCTGGCCC TGGCCCTGGTTTTCGTGGGACAGTTGTCGAG CAATGTCACTTCAACTCCTTGACGTTCGGGC GCATCATGTGTGAACCTACGGGGGCTCTCCT GGCGGTTGGGGGGTATACATTACGATACTAT TT |
| B | NAR1.2 | CRE | 191 | ATTACGATACTATTTTTTAGGGGCCGACATT TGGGGTGAGTATTGAGTAGAGGGACGCCTG GACTGCGGTGCCTAGATGCGCGAGGCGGCA ACTCGGCACGGTCAGCGCGTTTCGCCCCCCG CACCCAGGGCTGACCCGCTCGCTCGCTTGCG CCAACCGACCGAAGTTCAAACGTCAGCGTC GCGTCGAAACCCCAAATCATGCCGTCAGTA AGTCGGCAGCGGATGACACGGCACATGCAA TGAGGTCAGCCTTTGTTCCAAGGACTGCACA TGTGGGGCGAAAGGGCGCCGTCGACGGCGC GACTGC |
| C | NAR1.2 | CRE | 192 | CGACGGCGCGACTGCAAATGCAACCACCGC CGACAGCGCGAGCAAGCGGCCACAATTTTG TTCTACGCGGTTGCAGCATGCTCAATACGAT GTGCAATTTTGCAGCGCATGAGCGCGCACGT TGGTGGGGTCTCCGACGTAGAGTAGGGCGG TTGTGTACGGAACATACAACGGGGCTCTGCG CGAACTCAATAAACTCCGCTGTTGGTGTGCA ATTTTCAAACATCTGTAGCGGCAAGTACTGG CAATAGTCCAGGCTATAACGCAACGATTCA GGGCTAGACGCACAGTCGAGTTTAGACGCG CAAAG |
| A | LHCBM5 | CVU | 193 | TAGAGAAGAGCACTGGCGGCCGAAGGCTCG GCAGCGCTGGCTGCTCGACACCGCGCTGCGC AAACGCTTACCCACTAGCGCAAACAGCACC ACCAGCACAAGTTTGAGCAGGGCCGCGGGG CACACCATCGCAACCAGATCCCTGGTCACGC CAGTTGCGCTGCGCTACCCCACAGAGACTGC GCGGGCAGCAGCGAAGGCTGGCGCCTGACA CACTTTCAAAAGGGCCCAGGGCAGCTGTAC AGCGCTGTACCCTCGGCACCAGCGGGGAAG CTGGCAGGGAAGCTGTAACAACACCATCAG CAGCATC |
| B | LHCBM5 | CVU | 194 | ACCATCAGCAGCATCAATTCTGGAGCCACG ACAAGCCCTCCACGCTGCCCAATGTGCATTT GATTGGATTTGATCCCCAAAAGGCAGCTGCA CTCTGCCCCCCTCTCCTGTCCTCCTGCTGCCT GTGGCGCCCCGCTCAAAAGCCGTGTGCATG GAGCAGCTGGTTGGACAGCGGGTTTTGACCC ACAAGCAGCCAGTCGCGAGGAAGGGATTTG GGCCCGGCTGCTGAGGCCAGGCCTCATGGA GCTGGCAGAGCCCTGACCACCGTCGCCACC GACCAGCGCCAACCGCCCCACGGTCTCGTCC GCCA |
| C | LHCBM5 | CVU | 195 | CGGTCTCGTCCGCCAACACCCTGCTCCAGGC GCCACACACCCTCCCCTCCCCGCCTCTCCCT CCTCTCTAGCTTCCAGGAAGTAGCAAAGAAC GGTTACTGTGGTGTTACAGCGCGCATACGCG GCTGGGGGTGGATGCGAGTATAATCGTGTC GAGGTGGGAGTTGAAAATTATCCTCTCTGGG GACGAGTGGCGGGGCACCAAACCAAATGCT GAAAGCACAAGCAGAACAAAGGGAGACAA GCTAAAAGCTACAACACCTGCGCCGCCATC AAGCGGGCGCCGGCGGACCAAGCGGGGGTG CGGCAT |
| A | LCIC | CVU | 196 | TCTTACTGTTGTGGGGCTGCGCCTGTGCTAA GCTGGCTGCCCGCCGCCTGCACTGAACACCT GGCATGCCTGCCCTGGAGCTGCGGTGCAGAT GCATGTGCATGTGGCGCAGCTCGACACAGC |

TABLE 9-continued

Promoter sequences used in yeast one-hybrid assay.

| Fragment | Gene | Species | SEQ ID NO | Sequence |
|---|---|---|---|---|
| | | | | ACTGCAGACCTTCCTCAAAAGCGTGGCAGTG GATGCCCCAGACTGGAAATATGCAAATTGC ACCGGGTGGCAGAGCTTGAGGTGTGCAGCC ACCAACAAAGCCACGGGAGTGGCTGCTGTG TGCAAGTCGGTCAACGCTGGGCGGGGCCCC TCCGATGCGGTGCCTTTTGAAAGCGTCTACG GCACA |
| B | LCIC | CVU | 197 | AGCGTCTACGGCACATACAACAGCACTGCT ACCATGCTGGCCACCACAGCAGTTTACTCGC CGCGTGACAATGTCTTTTGCGTCCTTCGGGC AACTGACCGGCCGGTGGGCAGGCGGCCAGC TGCGGCATGCCCTGCTGCCGTCTGGGCGGCA CAGGCTGCTTCCTTCCCATCTGTGTGTTGGG TTGATGGTGTGCTGGCTGCCCCTGTTGCAGG CTGAGTGTCTGCTCCGATGCAAGACGGAGTG CCAATCAAAGGCTGGCATCAAGTGCCCGTG AGCCGCCCCACCTTCCTGTGGTGGTCAGCGC CTC |
| A | SEBP1 | CVU | 198 | GCCGGTTTACGCAAGGCGCGGCAAAGCAAA GCACCCGGCGCAGGCGTGCACGAAGGATCG CAGGGTGGGGCAGGCTGAGGCATGCCGGCA GGCATGGGAGGCGGTGAGTGCGAGCCAGCA CAGCGCGGGTGGAGGCTCACGCTTTGCTGCC AGAGGCCTTGCCGCTGCCAGCGGTGGGCCC CTCCTCCCGCCGCCGCTTGTTCCTGCATGCG GGTGCGGCGCGGAAATGCAGCATGCTTGGC AGCATCACGGTGTAGCGGTGCCCCCGGGGC TGGTGTGGGGCAATGCCAGCCAGCTGCAGT GTCCCGGC |
| B | SEBP1 | CVU | 199 | CTGCAGTGTCCCGGCGGTGTGGCCCAAAAC GGCACCGCCCAGGTCGGGCGACGCTGGCGG CAGCGACGGCGGCGGCGCAGGGGTGGGGCC TGGCCCCCATCTGCGGGCGGCATCTAGGTGG CGGAGGGATGCTGCGTAGTTTCAAGGCGCA GGGAGCGCACCTGGAGGGCGGCAAAGCGGT GGGCGGCCCCATCTCCACGACAGCTGTTCCG CTGCGCCCCTCCCCGCTGCCAGGGCTGTTCA CTGCGTCAACCGCTCCCGATTGCGCGGTCAG ACGCCCAGCTTTTGGGTCGCCAGCCGGTACA GGTGT |
| C | SEBP1 | CVU | 200 | AGCCGGTACAGGTGTACCCCAGGCTGGGTT GACGCCCAAAGTCGCAATGCGCGTGGGATC GGGCCTCTGTGTTGCTTGTGTGCCCAGGACA GAAGCAGCAGAGCAGGCACCATGGCCGCTG CCACCTTCTCCGCCCAGGCGACCGTCGCAGC CCGTGTGGCGACCACCGCCAAGAGCTCCAC CAGCATGAAGGTCCGATGGGGCGCCGGGGG CATCGTTGCCGGCCTTCGATATGCCAGGGAG CCAAGCGGGGCCCTGGGCGCCGTCTTATCCG CTGCCTTGCATTGATGCCCTGCAGGTGGCTC CCCGC |
| A | NAR1.2 | CVU | 201 | GGCGGGGGACACGCGGCGGGCAGCCCCGAG GCGGCACCGGGCGCCGGCCCCGGCAGCGCC GGCGTCAGCCCGCCGCAGCCGCCCGCCGCG GCCGAGCGCGCGCAGCCCAGCCCCGGCAGC GGCGGCGGCGGCGAGGTGCGCCGCTCCTGG GGCAGCCTCAAGTCCAAGTTTGGCAGCCTGA GCGGGCGGGGAGGCAGCAAGGAGGAGGAG GCGGTGGCGGCTGGGGCGGCCGCCAACACA CCACGCAAATAGGGGCACGCGCATCTGCTG CCTGGCCCCTGCCGGATGGTTGATGTGTACA GAAGAGTTG |
| B | NAR1.2 | CVU | 202 | TGTACAGAAGAGTTGAGAGCGTCAGTAGGG TTGTGGTGGGGTGCCGGTTGCCCCGCCCATC TCATCCCAGTTGTTTCCCTTCAAAACCAACC CCAGCCAATAGGTTCTTAACCAGTACATCGT AGACGCAACTCTGAACATCCGGGCCACTGA TTCTTGTCGATTTATCTTGTTGATTGGTTGAG |

TABLE 9-continued

Promoter sequences used in yeast one-hybrid assay.

| Frag ment | Gene | Species | SEQ ID NO | Sequence |
|---|---|---|---|---|
| | | | | CAGCACGTGTGCATCCCCGCTACTCTGTATG TATCCAGCCATGCCGTCTGTTCCCCTTGCCA GCGGTGCAACACTTGTTTTCTTTGTCTTGCA ACATTTCGGTGTGATGGAAGTGAAGGAAAA AA |
| C | NAR1.2 | CVU | 203 | AAGTGAAGGAAAAAAGCCACAGTGAAGAA ATGAGGTAAGCAATGAAGGCAGGGACAAAG GGAGAGCAGGGCACCGGGAAAGAGAGCAG CATGACACGGGACGAGTAGACGGCTCACAA CCCACCGGCGGGAGCAGGGAAGAATGGAAG GGGAGGCGAGCCAGGCGGCAGCACCCGTCT CAATGTGACTTCTACTTGGCATCGGCGGCAC CTGGCAGGCGGAACCTGCCTCCTCGAAGGG CGCGGGTGCGCCCCGCCAGGCTTACGGCTG GGCAGCGGCCATGCCAGTCGCTGCGTTGCCC TGACAACTCC |
| A | LHCB5 | VCA | 204 | AGGCCCATGGTTCGCCTTGGAGTTTGTGCCT TCTTGGAAATTACAATAGAAGGCGTGCAGA ACACATTTAGTGCATTTTTATATAAGGTATT CTCATGGGCTTCTCTGACAGTTAAACAACAC TACGTAGAGCCGCGCACCCGCCCCTGCGCTG TGTTTCGGCCCGGTCAGGGCCCCCGGTGCTC GTCCTTTTTCGGGGTGAGCCGTGAGCCGCCC CACAGCGTAACACCCCAACACTCCTGTAGA AACATGACATTAGCCAAAAGCATCTCCCTGT CACAGCTTCGCTAATGATTGTGGTTGTGAAC AA |
| B | LHCB5 | VCA | 205 | TGTGGTTGTGAACAAAATCCCTCCTTGGACA GGGTCGTTTGCAGGTAACATAACTCCCTCGA GCCTCGTAACTTTACTCCAGCGTACTTGTAC TGTGCGTTAACAAGACAACCTGTCTGGAAGT AATGCTTTGCTAGGAATCCTTCTACAACGCT TCATGCATGTAAACAGCGACTACGAAGAAA ACTAAAAGGGAGCAATCCATATCAGTATCA TACGTAAAGGGGTACTACATTTCTCACGTAG TGGCCCATTCAGTTTCAGGGGTGTATACTTG CTTTTGCAAGTGGTTTGCAAAATCATGTAAG CT |
| C | LHCB5 | VCA | 206 | AAAATCATGTAAGCTATTTGATTTAGCCACG CAAATCCGAAAGAATGCCATACAAGCAGTG TCATCCTGTACCCGAAGCTTCAGAGCTCTTC ACTTGCCCATCATTATAAATAAGCTAAGAGA GTAATGCACAAACTTTTATAACCTAATGCAC ACAGGTACAGGAAGCGGTCCTGACGGAAGA GGTCACGTCGTACGCATAGGGCCCTCGATCA CAGCAAGGAACACCCTTTTATGGGCGCAGC AGCGCTGGTATGGACACTTGCGCTGCCCTTC TCTTCTTGTGTGTTCTAAACAGTAGCCAGTC AAA |
| A | LCIC | VCA | 207 | AAGCTCCACTAGCTCCGAAGTTCCGACACGG TCTCACACGCGCTCGTTAACTAACTTCAAAA CATTACACTGCAAGTCAAAATTGCGCAGCGC TGCTTGATCAGCTACCTTAACGCGCGGCACG ACAAGACGCGTTGGTTATGCCAGCACTGACC CGCCTCAAGCAATACGGCAAGATAAGGATC TTCCCCGTGGCAGGGTTGGAAGTTGCTGTTG GCATGCGGAGAGCTGTGAGGTCACATCTCA CATGGAAACGCGTGTAGCACAACTCTTGGCT GCCTATGCCAGTCCTGAAGGACACTTTCAGA AC |
| B | LCIC | VCA | 208 | GGACACTTTCAGAACTGTTGAGATCATAAGC TACTCGGCTACAACACATCTGTAAAGTTAAC TGCCAGCGACAACTCTAAAAACTGCGGCCTT TTGCGGCCACATGCCGTGCGATTGCCAACTG CTTGGGTGTAAAGGTTGGAATTCCGGTAGTT GATGCACAATTTCTCACTGTTTCTAAGCATT ATTCATGAGAATGTGGCTTAGTAATCTAATT AAGTCATCTTGGCTCGATACTGTAGTCTACA |

TABLE 9-continued

Promoter sequences used in yeast one-hybrid assay.

| Fragment | Gene | Species | SEQ ID NO | Sequence |
|---|---|---|---|---|
| | | | | TCCACATGGTTCAGGCTGCCGAAGGCCTGGCCATACGATGACCGGAAGTCAGTCGCGCTACA |
| C | LCIC | VCA | 209 | GTCAGTCGCGCTACATACATGAGCTATGCTTCTTTAGTTTGGCATTCTAAGCGAAGCTGATACAATTTCATTTCATCATGTTTAAATGCCACTACGCCCCATTTCTCCTTTACACATCCCGGGGAAGACGAGTTACAATGTATTAAATCTTCAATCATATATACTTGATTCTTGGCATGCAGGATGGAAAGCGAGTTGTAGGGTGTGTTGTCGTGCATCGCACGACATCGCATGTAGTAGTAGTAGGAACATGTCCTCACCCGCCAACACATAAGGAGCCAACGCTAACCAAGTCTGGCCAATCAGTTCA |
| A | LCI5 | VCA | 210 | ATAGCGACTTGGCGGGGCCATTGCTTTGCGGTTTAGGATTTAACCGGGTTTTCTCTGGATGAAGAGCGCGGACAGCTGACGAGCTTTCCTGCAACCGTATGTTGGCGACCCTGGAAGTGTTAGAAAGCTTAGAAAGCTTAGAAAGTTAGAAAGCTCGATATAGTCGAACAATGAGCACAAAGGAATGTGCTATGTGCTTGGGAAATTGCAAGAGGCCAGCACAAATTTGCTATGTTGTCCTCAGCGCCCACCCAAAGCCTTCGGGCCTCAGCTTTGCATGGGCCAAGTTCCTGCTCTTAATTTCGGCAAT |
| B | LCI5 | VCA | 211 | CTTAATTTCGGCAATTCCATCAATTAGGCATACAACATCGTTAGCAGGCATAAATCTCTGCTGTCCATGACTATGTAGAGGAGGCGCGCAAGCATAACAGTTGAGTATCTCTACTGCCGAACCATTTTTTTATAGATGCATTGTCTTCAAGACCTAGTCCTGTTCTTCTTATGCTTTACCACAACGAGAAGCGCGGAGGGATATCGCTGTACCTATGTGTAACGAAAAGGGCTTGCATGCATGCATGCACCATGAAGCAAATCCTAAAGAAAGGCGTAAATGTAAAAACATGTATGGCAAAGCCAACGAT |
| C | LCI5 | VCA | 212 | GGCAAAGCCAACGATGTTAAACATGTGAGCGTGGAACTGACGTGTGCAAAGTACAACTCGAACTTGCAGCAGTAAATCTTCCAAATAGCTAACGTATCCATATAGCATAGGAAAATTAAATACACATGCGCTCCATGCATAAATTCTCCAACTGGACGAGCTACCATGTCTGGTTGAGAGACCTGCCGTACCCCAACCCTACCACGTCCGTACTCTTTTGGATAAAACAAAGGTGGCCCCAATGTCCAAGCATCATTCACATTTTGAGCTGCACCGCATTCGTCGTTCATTGTAATCTCCTTATAACAAG |
| A | SEBP1 | VCA | 213 | GTACGGTTGCGTGCTATTATATCTATGGGTTGTGTTTGGAAGTTTTTAGCAAGACATGCTATCGAGGGGTCACATTTGAAGTTGCATCATGGTAGCGAATCATGATGCACAACCAATTGACAGCTCCTCCTCATTGCAGCTTGACGTAATCCGCTAATGTCCCCGACCGCAGTGAGCCCATGTTGACGAGTTTGGCAAATCATAAGATGGGGTATGCGTACACACCCACGTGTCAAGCGGTTAGACTTGAGGACAAACCATAAGCTTCGGAGCTTCAGATGCTATCGGTGCACTTGCGGACAACTGCAGC |
| B | SEBP1 | VCA | 214 | GCGGACAACTGCAGCTCCAGAGGGGGAATTCAAAGGTCTTGGAGTCGCGGGTTTAGGGTGCATTTCCAGTGCGGATTAAGGCCAAAGATTAACCCTCTGTCCTCCATCGATACTTGCTCAAACGGCTAAGTTGTTGGCAAACTTACCTCGACTTTTCAACCTTTGGTTCCCTTATGGAACAAAACTATGTGGTAAGCTCGTACCAAGGACTTCCGTGCCCTAATCCCTGGCCTTAATCCGCACTGGA |

TABLE 9-continued

Promoter sequences used in yeast one-hybrid assay.

| Frag ment | Gene | Species | SEQ ID NO | Sequence |
|---|---|---|---|---|
| | | | | AATGCGCCCTTAAAGATGGAGTGATGTCCCATTGCAAGGCCGCAATTGAAAGGAGCTCCTTGC |
| C | SEBP1 | VCA | 215 | AAAGGAGCTCCTTGCCAGCATCGCCTGAGTAGTCTATATGGTCTTTTAAACTCTGACTTCCCTGCAAGAGGCTTGCTATTGCCTGACCCATACGCAGCGGACAGTGTCCTGTTTCACAAGTAATGTGCAATAAAACTATGCAAAGAAACTTTTCATAATATGACTAAATATTGTAATAGTCTGAGTCTCCCTATTTAGTAGGAATGCGCACCGCGGTACTATAGCAGATAAGGTGCCGTACATAGACTGAAGCGGCAAGAACAAGAGGGGTGCAGCAGCATAGATCCTTGCTTTAGGGTCAATTGCAAAG |
| A | NAR1.2 | VCA | 216 | GTACTTGGCAAGGTGCTATAGAAGTAGAAGATAGGAGACGATGATTGACACTTTGGTCCGACTATTTGGCTCGACATTCGCACGACATTCCTAGCTGATGAGAGGGATGTCAAGATGTCAGGGCAATCAATCCTGTCACATTCAGTCTTGTTGAAATAATCGTAGTGTCTTGGTTTCATTATAAATCGGGGAGTTGCAGAGGAGACGTTCCCACCAGCGAGCGATGCCTGAAGATGTCTATGTGCACAGACTGTTGCATTTTCAGATGATATGCAATAAAGATAAGAACACAAGTCGTGCAGGAAAAACG |
| B | NAR1.2 | VCA | 217 | CGTGCAGGAAAAACGCGCAACGATGCTTTAACGCATAGTGGTTTAAGATGGGCGCGCTGAATTGATCCGGCATGGAGCGCGATGCGAATTATGTTTGAATACATGAAGCATTCATGTAAACAATTAAATACGTTTGGTCAAAAATAAAGTGCGCACCACCAACGCATCGTCCCTGTCTCGCAGAAAATCATACTTCCAATTTCTCATCTAAACGGATCAAATTGCAGCTACTGAAACATCAAGCAAATATAACGACATCCTCCGTGCAAGATCAAAAATGATTCACATTGCACTTTCGCCATTGATCCCG |
| C | NAR1.2 | VCA | 218 | TCGCCATTGATCCCGGAATTCGTTTGACAGCGCGAACCCATAAGCCAATCACCCTATCATAAAGCATAAATCTTCCATTAAACATACCCTATCAACCTGGCCGCAACTTGTGGGGATGTAACTGTATGTGGGTTTGTGTGTGTGGGTGCTCGGCCAAATACAGCCGGCGTACGACATCACACTGACCTACTACCTTTCTTATCTTTTTTATATATGCTGCTATGCACCCGGCTTACTCGTATAGCAGTGTTACAAAGCTAGTTGGTTTCAGTAGTGTGTTGTTCCTCATTGATCATCATATCTGGAAAGCAGTTGTCACCACAAACCAAACGGGCGTTATTTGTTCTTCCATCTTATTGCCTTTTCAAGGATG |
| A | LHCB5 | ZMA | 219 | AGTCATGTCTTGGACAAAACTTCAGCAATTTTCTAATAAAAGAACATTCCTATGGTGTATGATGTTAATCATCGTTTCTCCCACCTCTCTTTTCCAGGGACACTGTCGATGCAATATTTGAAGAGCTGGTTATAAACACCAAGAAGCTTGTGGCTGCAACGTCAAAATGAATCGAAAAATAGCGTTGAGTGGCACCACTGCATTGTCGTCTCTATTAATCAGCTTGAACAGGCGGTAGGACTTAGTC |
| B | LHCB5 | ZMA | 220 | CGGTAGGACTTAGTCCTAGAATGCAGCCTGTTGATCTCATGACATTCTATTAATTATGAGCGTAGTTAGGTAGGATACTGACACAACACACATGGTTTCTGGTCCATATTTATTAGTTACATTCCAGTATATTGTGGATTGCTCATCACTTGTTAAATTAGAGAAAATTGATGCTCTGAGCTTCAGATGAACTTTGTTTCGTGCTTGTGCGTGTGTTCTTCACCCTTCTGGTATCAGTGTGTGGCCAGCACTTGTTGTCTCGGCGCTCTCTCTCACTCACTCTGGTTGGTTCCCCTAGGTCTTTGTCTAT |

TABLE 9-continued

Promoter sequences used in yeast one-hybrid assay.

| Frag ment | Gene | Species | SEQ ID NO | Sequence |
|---|---|---|---|---|
| C | LHCB5 | ZMA | 221 | TAGGTCTTTGTCTATCTTGTTTGGGCCATTTG GCGCTAACTAACCAACAAGTGCACAAGAGG CCCCTCAAGCTGCCACATCAGCACCCTCATC TGCCAAGTCAGCACAGCCTGCCCAATCGCCT CCAGGCAACAGATAGCCCTGATGGGCACCC ATCCAATGGCAGCTCCGATGGCCAAATCTCT GCTAGGCCCACAGCATCCTCCGATCCTCATT TTCATCCATTTAAACTAGCTCGCCTTTTCCTC CACAAGCCCCCATCAGCCATCCCCTCCCGCG GCAAGTCTCTCTGAATTGTGGGTCTCCGGCG |
| B | SEBP1 | ZMA | 222 | CAGTGAGAAAAGGCCTTGCCACTCTACGTAT CTGATGTTGTTAATAATTTCAGAAGTCGTCG TATATACCATGGGGTGTTTAATTGTCGTATA TACGATGGGATGCTTAATTGTCGTATATACG ATGGTATGATGAAACAACTGACTTAAACATC ACACTGAACAATTTCAGAAAACGATCCATG CCGTCGTATATATACGACAACAAAATACCA GAAGCAAACCTCCCAGACCCAAGGGGAAAT AAACGGGCCTGCTTCTGGTCGCTAGCTTGGG GGCGCTGGAGCTGCAGTGCGTAGGCCCGTC CGAT |
| C | SEBP1 | ZMA | 223 | GTAGGCCCGTCCGATCCGTGGCTCGTCTCGG CATGGCCACACAAACCACGAACGGTCGTCG TGCACCGCAGCGCGGCCCCCCCGTTCTATCT TCTCCAGCTCCAAATGGCGCCATCGCGGCGG CCGGGTTATCTTGTCCAGACGTGCATCATAT CCTCCGTGTGATCCATTCATCCCCGCGCCGT GCTAGCTTGCTAGTTGCAAGCACCAGCCGAC CACCAAACGGTAGCGCACGCGGACAATTTA ACAGCATCAGGTTTAGGCCCTGCTGCCGTCG TCGAGCGCCCGGGCCACCGCACACCTGAAA GCA |
| A | LHCB5 | ATH | 224 | TTCTGGTAATGTGTATGGTTTGAGTGCTGAT TTTTGGTGCTATGAGTTGTTCTTTATGGCTCA ACTTGGATCAATATGGAGGTTGAGTTTGAGA TTTTCTCTCAGTTTAAGGAGGTAGAATAGTG CGTATAGTGGCACAGTGAGCTCAGCTCTAGG GCCAAAGGGCATAAATTCATTATAGCTCTTT CGATTCTACCGTAGTACTGTGTGTGAACCGG CACTGTGAACCAAGATGATTAAATTTTCGTA TTCTCTATGTACATGATCCTGCGGCTCAATC GCTTCAGTTTCGATCCACATGATGTATATG |
| B | LHCB5 | ATH | 225 | CACATGATGTATATGTTATAGAATTGTGGGA AACTCCTTGTAGAAAGAGTATGTTCACGTCT AGGACTAGTCGGATGATTCGTTTCTCTTTTT GGTGTAATGAGTATGTTCATAACTGTTGATA CAATGTGAAAATCTAACCGTTGAGCTTGGGA GTTTTACGTCTATATGAAAATTCCGGTTGTC GTCTACATTACGGTAGTAAACAGGACCACA GTGATTCCAAATGTCCCAAGGAATTTACTGA AAACCCCAACTAGGACTGTGAAAGGCTTGT GGATGACATTTAACAGTTGAGATTTTCATGT GT |
| C | LHCB5 | ATH | 226 | GAGATTTTCATGTGTTTGAGATTCTTGTAAC ACATTTTGCTGTATAGGTGAAAGCTTAGCCA CACAAAAGGAGAAACAGAGGATATGGATAA AATAAATTATCCAACAAAAACCAATCTAAA AGCCACATCAGCATCCACAACCAATCAGAG GACAGAATCATATTTCACATTTTCAATCCAG ACCAATCAAAATCCTGAACGAATCCTACTCT CCACCTTATAGGAGCAGTTTCGTCTCTTCCT CCTTCTTTCACTTAGCTCTTCCTAGTGTTAAA CCAGAGTAAAGCTTGAAACTTTGGACTAAA AGA |
| C | SEBP1 | ATH | 227 | TATAATTTGGTTTGTATGTCATTGGTGATGT AAACTGAAATTGAAGATAATAGAATCTCAT AACCACACAAAAAATGAATGAACGCAAATC AAAGCCTCTCAACACATCTCTTTGCCTCGGT |

TABLE 9-continued

| Promoter sequences used in yeast one-hybrid assay. | | | | |
|---|---|---|---|---|
| Frag ment | Gene | Species | SEQ ID NO | Sequence |
| | | | | CTCTCTCTCGCCCAATTGCCCATCACCAGAG<br>CTTAATCATATCTTCTTCAGTTACTGCCACGT<br>GTCACTCTGACCGTGAACAGCCTTTATCTCT<br>TCCAAGTCCACTTGTGTTCTTGATTATTTTGT<br>CTTCACCATTCTCTCTACTCAAAGCTCTTCTT<br>CTTCGATCAAAAAACCTCGAGCTTCTAACA |

Figure 10:
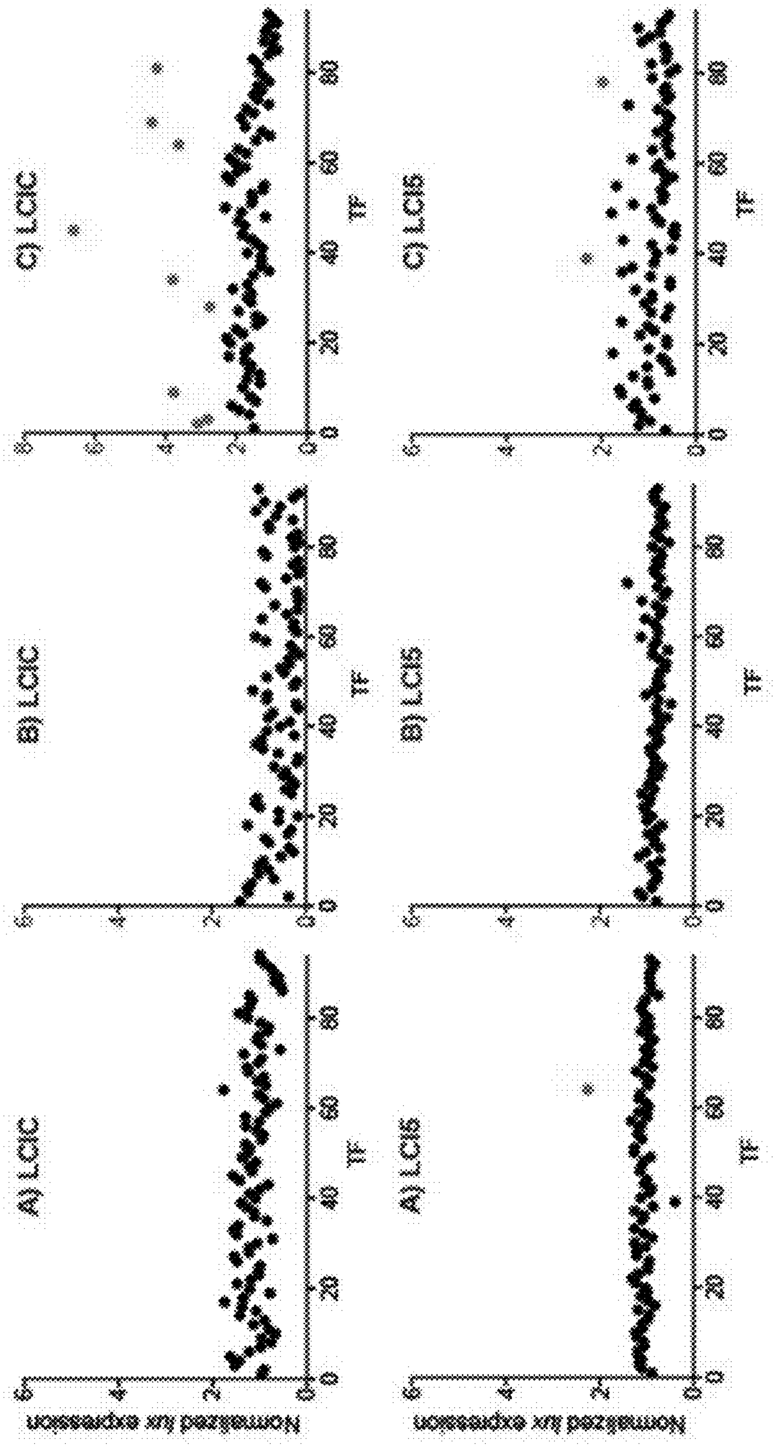
FIG. 10 illustrates *C. reinhardtii* TF library tested for transcription activation from select promoters via yeast one-hybrid assay. Y1H assay performed with all 92 TF library proteins against five *C. reinhardtii* promoters (LCIC, LCI5, SEBP1, Nar1.2, and LHCBM5), each in 300 bp fragments (labeled A, B, and C). Functional read out was expression of the lux gene. Red data points indicate statistical significance of increased lux expression compared to an empty vector control (see Materials and Methods). x axes: TF, transcription factor library number.

We assayed all 92 TFs against five *C. reinhardtii* nuclear promoters: LCIC, LCI5, SEBP1, Nar1.2, and LHCBM5 (FIG. 10). LCIC, LCI5, and Nar1.2 are low CO2-induced genes that play roles in the CO2-concentrating mechanism (CCM) [40-42]. SEBP1 encodes sedoheptulose-1,7-bisphosphatase which functions during the Calvin cycle [43]. LHCBM5 encodes a component of light harvesting complex II and is involved in photosynthesis [44]. These genes were chosen because they were identified from a published RNA-sequencing dataset as highly regulated genes (i.e., they were expressed under laboratory conditions) in *C. reinhardtii* [45].

TFs 2, 3, 9, 28, 34, 45, 64, 69, and 81 each activated transcription from LCIC promoter fragment C (FIG. 10). TF64 activated transcription from LCI5 promoter fragment A; TFs 39 and 78 activated transcription from LCI5 promoter fragment C. TFs 3, 6, 27, 30, and 64 activated transcription from SEBP1 promoter fragment A; TF64 activated transcription from SEBP1 promoter fragment B; TFs 27, 30, 56, and 64 activated transcription from SEBP1 promoter fragment C. TFs 10, 30, and 64 activated transcription from Nar1.2 promoter fragment C. Finally, TF34 activated transcription from LHCBM5 promoter fragment C (FIG. 10). Note that LHCBM5 promoter fragment B was unable to be cloned (due to repeat sequences) and therefore was not assayed here. (See Materials and Methods for statistical information on Y1H assay.)

To summarize these Y1H assays, our data provide information on 1,288 TF-promoter potential binding interactions, 26 of which were positive hits. TF64 was the most active in this assay, activating transcription with four of the five promoters tested. TFs 3, 30, and 34 each activated transcription from two promoters. Note that some TFs bound multiple fragments of the same promoter. Many TFs however did not show activity with any of the five *C. reinhardtii* promoters we assayed. These data are summarized in Table 10.

TABLE 10

| Yeast one-hybrid data summary | | |
|---|---|---|
| Species | Promoter | Transcription Factor |
| *Chlamydomonas reinhardtii* | SEBP1 | 3, 6, 27, 30, 56, 64 |
| *Chlamydomonas reinhardtii* | LCI5 | 39, 64, 78 |
| *Chlamydomonas reinhardtii* | LCIC | 2, 3, 9, 28, 34, 45, 64, 69, 81 |
| *Chlamydomonas reinhardtii* | NAR1.2 | 10, 30, 64 |
| *Chlamydomonas reinhardtii* | LHCBM5 | 34 |
| *Volvox carteri* | SEBP1 | 64 |
| *Volvox carteri* | LCI5 | 2, 64 |
| *Volvox carteri* | LCIC | 2, 21, 45, 57, 64, 69 |
| *Volvox carteri* | NAR1.2 | 2, 3, 4, 5, 13 |
| *Volvox carteri* | LHCBM5 | 58, 64 |
| *Chlorella vulgaris* | SEBP1 | 64 |

TABLE 10-continued

| Yeast one-hybrid data summary | | |
|---|---|---|
| Species | Promoter | Transcription Factor |
| *Chlorella vulgaris* | LCIC | 10 |
| *Chlorella vulgaris* | NAR1.2 | 7 |
| *Chlorella vulgaris* | LHCBM5 | 2, 7, 18, 27, 51 |
| *Zea mays* | SEBP1 | 30, 64 |
| *Zea mays* | LHCBM5 | 2, 6, 14, 28, 37, 64, 76 |
| *Arabidopsis thaliana* | SEBP1 | 56 |
| *Arabidopsis thaliana* | LHCBM5 | 85 |

Figure 11:
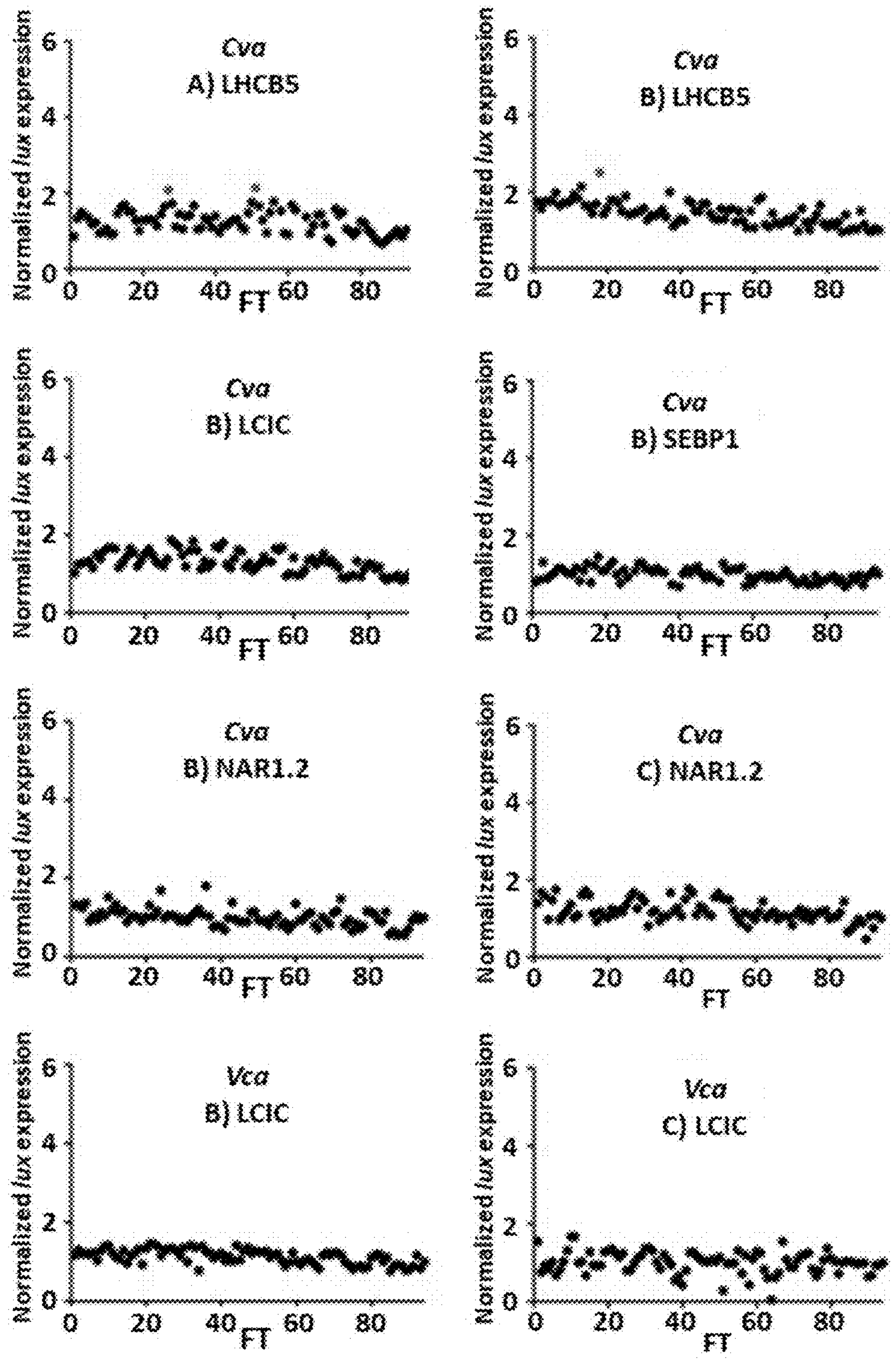
FIG. 11 illustrates yeast one-hybrid assay using orthologous promoters (2.1), TF64-associated promoters (2.2). Y1H assay performed with all 92 TF library proteins against promoters (LCIC, LCI5, SEBP1, Nar1.2, and LHCBM5), each in 300 bp fragments (labeled A, B, and C) from *V. carteri* (Vca), *C. vulgaris* (Cvu), *A. thaliana* (Ath), and *Z. mays* (Zma). Functional read out was expression of the lux gene. Red data points indicate statistical significance of increased lux expression compared to an empty vector control (see Materials and Methods of Example 2).

Putative transcription factors initiate transcription from orthologous promoters from multiple species. We also assayed our TF library with bait promoters from the closely related algal species Volvox carteri and *Chlorella vulgaris*, as well as from the distantly related plant species *Arabidopsis thaliana* and *Zea mays*. Again, we tested promoters LCIC, LCI5, SEBP1, Nar1.2, and LHCBM5 (Table 10, FIG. 11). Like the *C. reinhardtii* promoter data, TF64 was the most active in activating transcription in combination with promoter fragments from other species, specifically *V. carteri* LCIC, LCI5, SEBP1, and LHCB5; *C. vulgaris* SEBP1; and *Z. mays* SEBP1 and LHCBM5 (Table 10, FIG. 11). In full we analyzed 49 promoter fragments against 92 TFs for a total of 4,508 potential binding interactions. We found 65 positive hits and, most importantly, 28 TFs with potential DNA binding activity.

Analysis of potential TF64-binding promoters identified from the Y1H assay. Utilizing the collection of our Y1H data, we hypothesized we could identify commonalities among promoters which may function as specific motifs or binding sites important for gene regulation. We chose to analyze the promoter fragments that activated transcription in combination with TF64 because it provided us with the largest sample size, 13 promoter fragments in total. We used the software program MEME (Multiple Em (Expectation maximization) for Motif Elicitation) [32,33] to search for enriched DNA motifs. Unfortunately, no statistically significant motifs were identified. The top motif found was an 11 nucleotide sequence, TGNGCANNTNN (SEQ ID NO:228) (FIG. 12A). Interestingly, this motif does contains remnants of the canonical binding site, CANNTG (nucleotides 5-10) (FIG. 12B), typical for the basic Helix-Loop-Helix family of transcription factors that TF64 belongs to [46,47].

Constitutive expression of the TF library in *C. reinhardtii*. We next attempted to study our TF library expressed in *C. reinhardtii* cc1010. The gene encoding each TF was cloned from the pENTR vector into a ble-2A expression vector [19], pTM207 (see FIG. 13, panel B). This expression vector results in co-transcription of a gene of interest along with the ble gene (conferring zeocin resistance) followed by post-translation cleavage of the two peptides at the 2A linker peptide site. Each pTM207 plasmid encoding a unique TF under control of the constitutive promoter PAR1 was electroporated into the *C. reinhardtii* nuclear genome. However, we were unable to obtain colonies of *C. reinhardtii* constitutively expressing the genes encoding most TFs. While we attempted transformation of all 92 TFs, gene-positive colonies were only recovered for 59 TFs, and only 21 TFs (1, 2, 4, 5, 14, 22, 31, 34, 38, 40, 41, 47, 52, 53, 55, 62, 63, 64, 75, 76, 84) had over 20% gene-positive colonies of those tested (data not shown). Western blot analyses of whole cell lysates were performed to verify production of the TFs, however protein was detected only in strains transformed with TFs 1, 2, 5, 13, 22, 31, 40, and 64.

In deciding which TF to carry forward with our study, we considered our Y1H data concurrently with our limited ability to produce the recombinant TFs in *C. reinhardtii*. TFs 2 and 64 both showed potential DNA binding activity and were capable of being constitutively produced in *C. reinhardtii*. Ultimately, we chose TF64 to continue our study of TF-promoter binding partners in *C. reinhardtii.*

Figure 12:
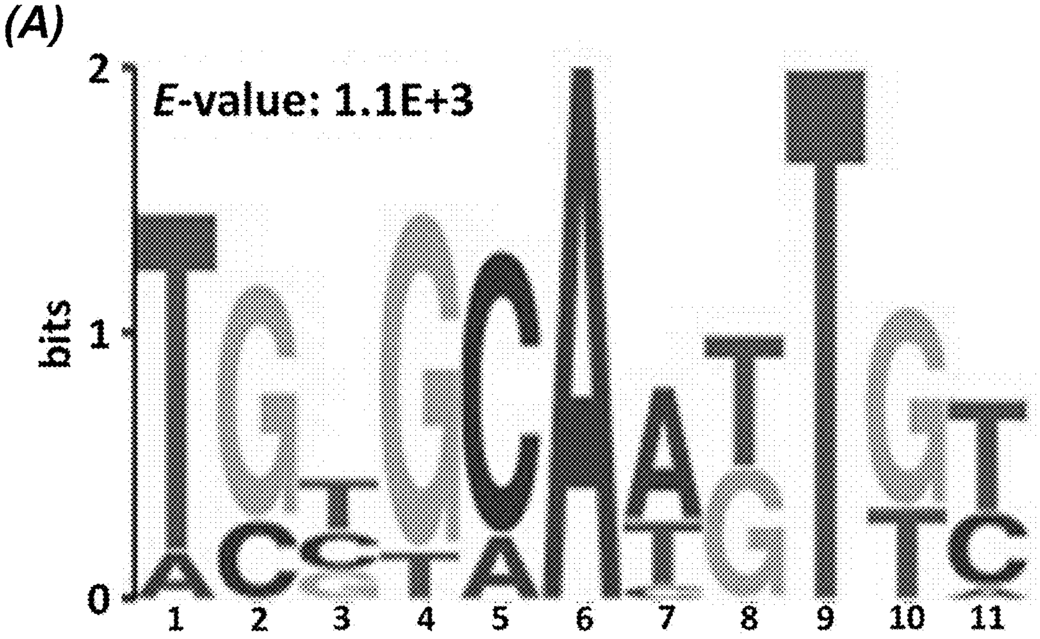
FIG. 12, panels A and B, illustrate alignment of TF64-associated promoter sequences. MEME analysis of the promoter fragments associated with TF64 via Y1H assay. Panel A) Top motif identified among promoters analyzed. Panel B) Promoter sequences showing top motif location. CANNTG sequences are underlined. Sequences: Cre_NAR1.2_C (Seq ID NO:2), Cre_NAR1.2_C (Seq ID NO:3), Cre_LCIC_C (Seq ID NO:4), Vca_LCIC_A (Seq ID NO:5), Vca_SEBP1_A (Seq ID NO:6), Zma_SEBP1_B (Seq ID NO:7), Cre_SEBP1_C (Seq ID NO:8), Vca_LCIC_A (Seq ID NO:9), Cre_SEBP1_C (Seq ID NO:10), Vca_LHCB5_C (Seq ID NO:11), Vca_LHCB5_C (Seq ID NO:12), Cre_LCIC_C (Seq ID NO:13), Cre_LCIC_C (Seq ID NO:14), Cre_SEBP1_B (Seq ID NO:15), Cre_LCIC_C (Seq ID NO:16), Cre_LCI5_C (Seq ID NO:17).

Production of TF64 in *C. reinhardtii*. Basic Helix-Loop-Helix (bHLH) transcription factor family members, like TF64, are highly conserved in their functional and DNA-binding domains, even across distantly related species and genera [46-49]. They recognize a canonical binding site, CANNTG (called the E-box), in promoters of genes they regulate [47,49]. A BLAST search of the PlnTFDB TF64 sequence showed conservation in DNA binding, E-box specificity site, and dimerization interface domains among top hits of TF-like proteins from other microalgae species (FIG. 13, panel A). The remainder of the TF64 protein sequence is highly variable with the exception of a conserved ACT domain in the C-terminus of unknown function typically found in bacterial species [50] (FIG. 12).

We generated multiple strains of cc1010 that constitutively produced TF64 (cc1010::TF64-4, -7, -8, -9, and -11) shown by western blot (FIG. 13 panels B, C). The pTM207 vector encodes an N-terminal 3×FLAG-tag fused to each TF (not shown in FIG. 13, panel B), and the TF64 proteins were detected using antibodies against FLAG-tag. TF64 is predicted to be a 33 kDa protein (FIG. 13, panel C). The 3×FLAG-tag adds 2.7 kDa to the protein product. The higher molecular weight band is the Ble2A-TF64 fusion product prior to 2A cleavage. Through multiple western blot analyses, strain cc1010::TF64-7 appeared produced the least amount of transcription factor protein, and strain cc1010::TF64-9 appeared to produce the most amount of protein (representative data shown in FIG. 13, panel C).

As a control, we also used the pTM207 vector to generate a strain that constitutively produced GFP under control of PAR1 (FIG. 13, panel B). Whole cell lysate of strain cc1010::GFP is shown on the western blot in FIG. 13, panel C.

Growth curves were performed on strains cc1010::TF64-7, cc1010::GFP, and wild type cc1010 cultured in TAP medium under constant light for four days (FIG. 13, panels C, D). While cc1010::TF64-7 did exhibit an extended lag phase in growth, it was capable of reaching an OD750 similar to that of cc1010::GFP and the wild type cc1010 strain (FIG. 13 panels C, D).

Figure 14:
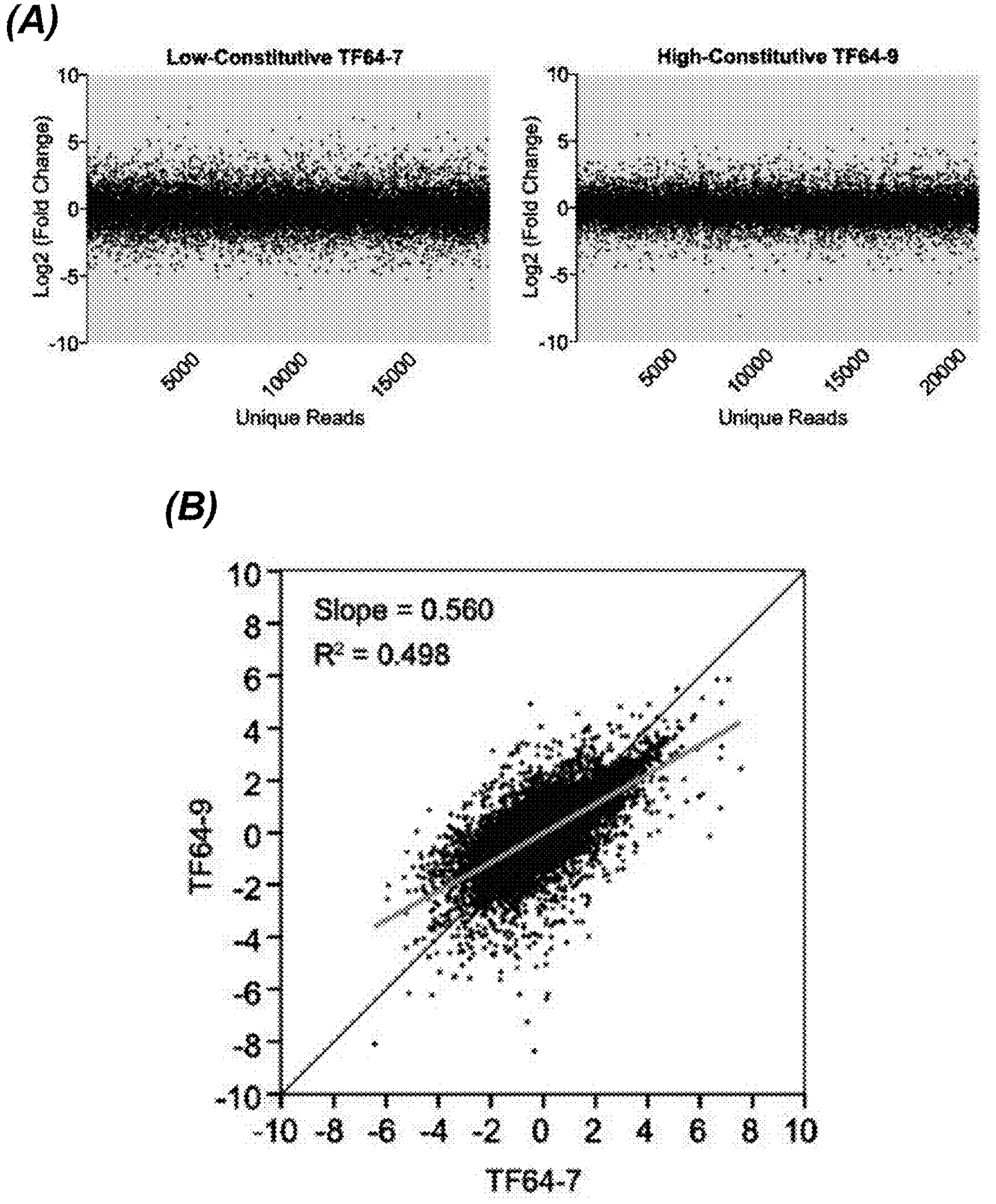
FIG. 14, panels A-C, illustrate RNA-sequencing data from two strains constitutively producing either low or high amounts of TF64. Panel A) Differential transcription analysis of strains cc1010::TF64-7 and cc1010::TF64-9 compared to cc1010::GFP by RNA-sequencing. The log 2 (fold change) was plotted for each unique read with a FPKM value ≥1.0 (see Materials and Methods). Panel B) Comparison of RNA-Seq data from each TF64-producing strain (TF64-7 and TF64-9). Each data point represents a unique read. The log 2 (fold change) was plotted. Purple line represents the best-fit line for all data, R2=0.498, slope=0.560. Panel C) Heat map of expression profiles from the top 20 activated and inhibited genes and Y1H-assayed genes in strains cc1010::TF64-7 and cc1010::TF64-9 compared to cc1010::GFP. Units for heat map key values are log 2 (fold change). Genes of interest are labeled below the heat map. RNA-sequencing data was compiled from three biological replicates.

TF64 regulates many endogenous nuclear genes. To identify the genes/promoters TF64 regulates in *C. reinhardtii*, we performed an RNA-sequencing experiment on two independent strains, cc1010::TF64-7 (referred to as the low-constitutive strain) and cc1010::TF64-9 (referred to as the high-constitutive strain), along with our control strain cc1010::GFP (FIG. 14). RNA from three biological replicates for each strain was sequenced at the UCSD Institute for Genomic Medicine. Transcript abundance and differential expression analysis for each TF64-producing strain was compared to the GFP-producing strain (FIG. 14A). The data indicate that approximately 2.4% and 1.0% of the genome was affected at least 10-fold (log 2 ≥16B, R2=0.498). Furthermore, a greater range of regulation was observed in the low-constitutive strain (TF64-7) compared to the high-constitutive strain (TF64-9) (FIG. 14, panels A, B, C).

The most highly regulated genes, both activated and inhibited, from the low-constitutive and high-constitutive TF64-producing strains were identified by bioinformatics using the BLASTx search function from NCBI (Table 11a, 11b, 11c). Inhibited genes were mostly uncharacterized and showed little similarity in function. Activated genes, particularly from the low-constitutive TF64-7 dataset, fell into relatively distinct functional categories including: photosynthesis, cell structure, cell cycle, and metabolism. Table 12 lists the top 20 activated genes (that have also been previously characterized) identified from the TF64-7 RNA-Seq data. These data suggest TF64, like many bHLH transcription factor family members [51,52], regulates many genes involved in a wide variety of developmental and cellular processes in *C. reinhardtii.*

TABLE 11a

Identification of TF64-regulated genes.

Top 40 Up-Regulated Genes in *C. reinhardtii* TF64-7

| No. | Gene ID | Log2 Fold Change | Gene Symbol | Accession No. | Protein Length |
|---|---|---|---|---|---|
| 1 | jgi\|Chlre4\|513883\| au5.g4042_t1:0-146 | 7.58 | LHCBM7 | XP_001694115 | 249 |
| 2 | jgi\|Chlre4\|523567\| au5.g13085_t1:285-1460 | 7.09 | LHCBM8 | XP_001695467 | 254 |
| 3 | jgi\|Chlre4\|512488\| au5.g2746_t1:76-967 | 6.82 | — | XP_001697347 | 385 |
| 4 | jgi\|Chlre4\|523561\| au5.g13079_t1:149-1280 | 6.81 | LHCBM4 | XP_001695344 | 254 |
| 5 | jgi\|Chlre4\|520677\| au5.g10379_t1:97-2184 | 6.80 | — | XP_001697417 | 258 |
| 6 | jgi\|Chlre4\|518507\| au5.g8360_t1:204-4111 | 6.80 | FAP211 | XP_001701654 | 698 |
| 7 | jgi\|Chlre4\|521087\| au5.g10761_t1:39-2944 | 6.66 | METE | XP_001702934 | 815 |

TABLE 11a-continued

Identification of TF64-regulated genes.

| | | | | | |
|---|---|---|---|---|---|
| 8 | jgi\|Chlre4\|513788\| au5.g3953_t1:2032-4745 | 6.37 | — | XP_001693945 | 370 |
| 9 | jgi\|Chlre4\|512994\| au5.g3208_t1:314-2817 | 6.13 | — | — | — |
| 10 | jgi\|Chlre4\|521595\| au5.g11226_t1:266-2760 | 6.09 | SAH1 | XP_001693339 | 483 |
| 11 | jgi\|Chlre4\|522358\| au5.g11951_t1:421-1892 | 5.96 | — | XP_001697707 | 306 |
| 12 | jgi\|Chlre4\|517273\| au5.g7220_t1:576-2741 | 5.89 | — | XP_001691691 | 381 |
| 13 | jgi\|Chlre4\|515402\| au5.g5474_t1:537-2854 | 5.79 | PHC13 | XP_001690309 | 506 |
| 14 | jgi\|Chlre4\|520083\| au5.g9823_t1:3664-4112 | 5.77 | GCP3 | XP_001699475 | 930 |
| 15 | jgi\|Chlre4\|524734\| au5.g14197_t1:2040-2317 | 5.71 | — | XP_001700124 | 124 |
| 16 | jgi\|Chlre4\|519722\| au5.g9487_t1:300-2262 | 5.51 | — | XP_001694801 | 130 |
| 17 | jgi\|Chlre4\|520120\| au5.g9859_t1:2-129 | 5.39 | LHCBM1 | XP_001700243 | 266 |
| 18 | jgi\|Chlre4\|524285\| au5.g13771_t1:3002-3795 | 5.34 | MCM4 | XP_001700810 | 544 |
| 19 | jgi\|Chlre4\|513665\| au5.g3835_t1:58-185 | 5.33 | — | XP_001692967 | 581 |
| 20 | jgi\|Chlre4\|518165\| au5.g8046_t1:194-1066 | 5.30 | — | XP_001701406 | 86 |
| 21 | jgi\|Chlre4\|526354\| au5.g15724_t1:5515-5842 | 5.20 | — | XP_001696801 | 304 |
| 22 | jgi\|Chlre4\|524988\| au5.g14435_t1:1814-1954 | 5.17 | — | XP_001692594 | 241 |
| 23 | jgi\|Chlre4\|512084\| au5.g2359_t1:10431-10587 | 5.15 | DCL2 | XP_001698921 | 5684 |
| 24 | jgi\|Chlre4\|512529\| au5.g2782_t1:35-1932 | 5.11 | GAP1 | XP_001703199 | 371 |
| 25 | jgi\|Chlre4\|518966\| au5.g8779_t1:1773-1883 | 5.09 | SYP72 | XP_001700031 | 270 |
| 26 | jgi\|Chlre4\|519390\| au5.g9173_t1:283-2258 | 5.07 | FTSZ1 | XP_001702420 | 479 |
| 27 | jgi\|Chlre4\|515943\| au5.g5981_t1:176-2507 | 4.99 | FTSZ2 | XP_001700508 | 434 |
| 28 | jgi\|Chlre4\|512163\| au5.g2437_t1:1012-1109 | 4.91 | — | XP_001699495 | 346 |
| 29 | jgi\|Chlre4\|513021\| au5.g3230_t1:36-1751 | 4.90 | — | XP_001691021 | 93 |
| 30 | jgi\|Chlre4\|520083\| au5.g9823_t1:4197-4255 | 4.79 | GCP3 | XP_001699475 | 930 |
| 31 | jgi\|Chlre4\|519414\| au5.g9197_t1:7768-7861 | 4.77 | — | XP_001702440 | 1844 |
| 32 | jgi\|Chlre4\|518566\| au5.g8414_t1:7331-7954 | 4.76 | — | XP_001701683 | 863 |
| 33 | jgi\|Chlre4\|523024\| au5.g12580_t1:45-2087 | 4.75 | EFG8 | XP_001696344 | 395 |
| 34 | jgi\|Chlre4\|521599\| au5.g11230_t1:910-4556 | 4.74 | — | XP_001693192 | 1300 |
| 35 | jgi\|Chlre4\|513496\| au5.g3676_t1:1531-1934 | 4.73 | GLN3 | XP_001692927 | 375 |
| 36 | jgi\|Chlre4\|512150\| au5.g2424_t1:2797-2877 | 4.70 | — | XP_001699532 | 660 |
| 37 | jgi\|Chlre4\|513333\| au5.g3525_t1:167-1848 | 4.69 | MIND1 | XP_001697031 | 351 |
| 38 | jgi\|Chlre4\|520302\| au5.g10033_t1:278-1558 | 4.66 | TEF13 | XP_001703033 | 150 |
| 39 | jgi\|Chlre4\|514112\| au5.g4259_t1:7-1195 | 4.62 | — | XP_001703138 | 150 |
| 40 | jgi\|Chlre4\|525978\| au5.g15362_t1:230-2771 | 4.62 | — | XP_001694482 | 133 |

| No. | Function | Closest Hit for Hypotheticals | Category |
|---|---|---|---|
| 1 | Chlorophylla-b binding protein of LHCII | — | Photosynthesis |
| 2 | Chlorophylla-b binding protein of LHCII | — | Photosynthesis |
| 3 | Hypothetical protein | Extracellular matrix glycoprotein pherophorin-V32 (Volvox) | Cell structure |

TABLE 11a-continued

Identification of TF64-regulated genes.

| | | | |
|---|---|---|---|
| 4 | Chlorophylla-b binding protein of LHCII | — | Photosynthesis |
| 5 | Predicted protein | Hydroxyproline-rich glycoprotein (*Chlamydomonas reinhardtii*) | Cell structure |
| 6 | Flagellar associated protein | — | Motility |
| 7 | Cobalamin-independent methionine synthasae | — | Metabolism |
| 8 | Predicted protein | Flagellar associated protein (*Chlamydomanas reinhardtii*) | Motility |
| 9 | — | Cell wall protein pherophorin-C4 (*Chlamydomonas reinhardtii*) | Cell structure |
| 10 | S-Adenosyl homocysteine hydrolase | — | Metabolism |
| 11 | Hypothetical protein | None | — |
| 12 | Hypothetical protein | Flagellar associated protein (*Chlamydomanas reinhardtii*) | Motility |
| 13 | Cell wall protein pherophorin-C13 | — | Cell structure |
| 14 | Gamma tubulin interacting protein | — | Cell structure |
| 15 | Predicted protein | None | — |
| 16 | Predicted protein | None | — |
| 17 | Chlorophylla-b binding protein of LHCII | — | Photosynthesis |
| 18 | Minichromosome maintenance protein 4 | — | Cell cycle |
| 19 | Predicted protein, zinc finger DNA binding domain | GATA transcription factor 26 (Auxenochlorella) | Regulation |
| 20 | Predicted protein | None | — |
| 21 | Cohesin subunit SCC1b (Rad21/Rec8 homolog) | — | Cell cycle |
| 22 | Predicted protein | Hypotheticals | — |
| 23 | Dicer-like protein | — | Regulation |
| 24 | Glyceraldehyde 3-phosphate dehydrogenase | — | Metabolism |
| 25 | Qc-SNARE protein, SYP7-family | — | Localization |
| 26 | Plastid division protein | — | Cell cycle |
| 27 | Plastid division protein | — | Cell cycle |
| 28 | Predicted protein | Hypotheticals | — |
| 29 | Hypothetical protein | Hypotheticals | — |
| 30 | Gamma tubulin interacting protein | — | Cell structure/Localization |
| 31 | Predicted protein | Forkhead-associated protein (Geitlerinema) | Regulation/Localization |
| 32 | Predicted protein | Hypotheticals | — |
| 33 | Mitochondrial translation factor Tu | — | Translation |
| 34 | Predicted protein | Flagellar associated protein (*Chlamydomanas reinhardtii*) | Motility |
| 35 | Glutamine synthetase | — | Metabolism |
| 36 | Predicted protein (Peptidase M7) | Hypotheticals | Metabolism |
| 37 | Chloroplast septum site-determining protein | — | Cell cycle |
| 38 | Predicted protein | Aminoacyl-tRNA synthase CAAD domain, Curvature thylakoid | Localization |
| 39 | Glutathione S-transferase | — | Metabolism |
| 40 | RAN binding protein, RANBP1 | — | Cell cycle |

TABLE 11b

Identification of TF64-regulated genes.

Top 20 Down-Regulated Genes in *C. reinhardtii* TF64-7

<table>
<tr><th>No.</th><th>Gene ID</th><th>Log2 Fold Change</th><th>Gene Symbol</th><th>Acession No.</th><th>Protein Length</th></tr>
<tr><td>1</td><td>jgi|Chlre4|516390| au5.g6397_t1:9021-11277</td><td>−6.45</td><td>—</td><td>XP_001701467</td><td>415</td></tr>
<tr><td>2</td><td>jgi|Chlre4|518525| au5.g8375_t1:24-151</td><td>−5.94</td><td>—</td><td>XP_001701867</td><td>274</td></tr>
<tr><td>3</td><td>jgi|Chlre4|525738| au5.g15143_t1:11-124</td><td>−5.91</td><td>—</td><td>XP_001694214</td><td>433</td></tr>
<tr><td>4</td><td>jgi|Chlre4|525694| au5.g15099_t1:14-125</td><td>−5.31</td><td>—</td><td>XP_001694228</td><td>264</td></tr>
<tr><td>5</td><td>jgi|Chlre4|522989| au5.g12549_t1:37-201</td><td>−5.24</td><td>MSRA2</td><td>XP_001696359</td><td>335</td></tr>
<tr><td>6</td><td>jgi|Chlre4|511147| au5.g1489_t1:2524-2687</td><td>−5.22</td><td>—</td><td>XP_001690001</td><td>198</td></tr>
<tr><td>7</td><td>jgi|Chlre4|515954| au5.g5992_t1:1663-3048</td><td>−5.19</td><td>—</td><td>XP_001700503</td><td>335</td></tr>
<tr><td>8</td><td>jgi|Chlre4|523962| au5.g13460_t1:2301-9088</td><td>−5.14</td><td>—</td><td>XP_001691410</td><td>1549</td></tr>
<tr><td>9</td><td>jgi|Chlre4|515035| au5.g5129_t1:1-2180</td><td>−5.13</td><td>—</td><td>XP_001699067</td><td>202</td></tr>
<tr><td>10</td><td>jgi|Chlre4|518356| au5.g8226_t1:0-167</td><td>−4.96</td><td>—</td><td>XP_001703564</td><td>182</td></tr>
<tr><td>11</td><td>jgi|Chlre4|521856| au5.g11476_t1:1355-1480</td><td>−4.87</td><td>—</td><td>XP_001691165</td><td>516</td></tr>
<tr><td>12</td><td>jgi|Chlre4|512501| au5.g2756_t1:79-213</td><td>−4.85</td><td>—</td><td>—</td><td>—</td></tr>
<tr><td>13</td><td>jgi|Chlre4|516261| au5.g6278_t1:87-255</td><td>−4.82</td><td></td><td>XP_001697937</td><td>590</td></tr>
<tr><td>14</td><td>jgi|Chlre4|517935| au5.g7833_t1:73-154</td><td>−4.80</td><td>—</td><td>—</td><td>—</td></tr>
<tr><td>15</td><td>jgi|Chlre4|521621| au5.g11252_t1:1529-1690</td><td>−4.78</td><td>—</td><td>—</td><td>—</td></tr>
<tr><td>16</td><td>jgi|Chlre4|510735| au5.g1093_t1:2936-3258</td><td>−4.68</td><td>—</td><td>XP_001702142</td><td>268</td></tr>
<tr><td>17</td><td>jgi|Chlre4|519614| au5.g9382_t1:52-2262</td><td>−4.68</td><td>VIG1</td><td>XP_001694669</td><td>361</td></tr>
<tr><td>18</td><td>jgi|Chlre4|520495| au5.g10220_t1:53-192</td><td>−4.65</td><td>—</td><td>XP_001697557</td><td>91</td></tr>
<tr><td>19</td><td>jgi|Chlre4|519116| au5.g8918_t1:1732-2084</td><td>−4.64</td><td>—</td><td>XP_001699975</td><td>185</td></tr>
<tr><td>20</td><td>jgi|Chlre4|521566| au5.g11198_t1:0-150</td><td>−4.63</td><td>—</td><td>XP_001693207</td><td>5234</td></tr>
</table>

| No. | Function | Closest Hit for Hypotheticals | Category |
|---|---|---|---|
| 1 | Predicted protein | Snurportin-1 (nuclear import) (Monoraphidium) | Regulation/Localization |
| 2 | Predicted protein | Serine/threonine protein kinase (Microcystis) | Signaling/Cell cycle |
| 3 | Predicted protein | Hypotheticals | — |
| 4 | Predicted protein | Transmembrane E3 ubiquitin-protein ligase 1-like (Zn-finger) (Camelina) | Localization/Regulation |
| 5 | Peptide methionine-S-sulfoxide reductase | — | Metabolism/Redox |
| 6 | Predicted protein | Inositol oxygenase (Monoraphidium) | Metabolism/Redox |
| 7 | Predicted protein | Hypotheticals | — |
| 8 | Hypothetical protein | T-complex protein 10 (chaperone) domain-containing protein (Rozella) | Protein stability |
| 9 | Hypothetical protein | None | — |
| 10 | Predicted protein | DNA-directed RNA polymerase (Ostreococcus) | Regulation |
| 11 | Hypothetical protein | ATP-dependent DNA helicase (Rhizoctonia) | Regulation |
| 12 | — | — | — |
| 13 | Hypothetical protein | Kinesin-like protein (Oxytricha) | Localization |
| 14 | — | — | — |
| 15 | — | Dicer-like protein (*Chlamydomonas reinhardtii*) | Regulation |

TABLE 11b-continued

| Identification of TF64-regulated genes. | | | |
|---|---|---|---|
| 16 | Hypothetical protein | Hypotheticals (*Chlamydomonas reinhardtii*) | — |
| 17 | Vasa intronic gene (putative RISC associated factor) | — | Regulation |
| 18 | Predicted protein | Calcium/calmodulin-dependent protein kinase (Cladophialophora) | Signaling/Cell cycle |
| 19 | Hypothetical protein | Carboxylesterase (Chrondromyces) | Metabolism |
| 20 | Predicted protein | None | — |

Top 20 Up-Regulated Genes in *C. reinhardtii* TF64-9

| No. | Gene ID | Log2 Fold Change | Gene Symbol | Accession No. | Protein Length |
|---|---|---|---|---|---|
| 1 | jgi\|Chlre4\|523567\| au5.g13085_t1:285-1460 | 5.88 | LHCBM8 | XP_001695467 | 254 |
| 2 | jgi\|Chlre4\|521087\| au5.g10761_t1:39-2944 | 5.86 | METE | XP_001702934 | 815 |
| 3 | jgi\|Chlre4\|512084\| au5.g2359_t1:10431-10587 | 5.51 | DCL2 | XP_001698921 | 5684 |
| 4 | jgi\|Chlre4\|512529\| au5.g2782_t1:35-1932 | 5.47 | GAP1 | XP_001703199 | 371 |
| 5 | jgi\|Chlre4\|521595\| au5.g11226_t1:266-2760 | 5.16 | SAH1 | XP_001693339 | 483 |
| 6 | jgi\|Chlre4\|523561\| au5.g13079_t1:149-1280 | 4.98 | LHCBM4 | XP_001695344 | 254 |
| 7 | jgi\|Chlre4\|518569\| au5.g8417_t1:356-3190 | 4.95 | BIP2 | XP_001701884 | 662 |
| 8 | jgi\|Chlre4\|526287\| au5.g15661_t1:0-160 | 4.91 | — | XP_001696684 | 577 |
| 9 | jgi\|Chlre4\|522775\| au5.g12346_t1:17-1931 | 4.82 | — | XP_001697724 | 262 |
| 10 | jgi\|Chlre4\|514561\| au5.g4680_t1:249-354 | 4.56 | — | — | — |
| 11 | jgi\|Chlre4\|518501\| au5.g8356_t1:6-97 | 4.51 | — | XP_001701651 | 825 |
| 12 | jgi\|Chlre4\|520083\| au5.g9823_t1:3664-4112 | 4.50 | GCP3 | XP_001699475 | 930 |
| 13 | jgi\|Chlre4\|515402\| au5.g5474_t1:537-2854 | 4.47 | PHC13 | XP_001690309 | 506 |
| 14 | jgi\|Chlre4\|522427\| au5.g12017_t1:8-1276 | 4.46 | — | XP_001702210 | 320 |
| 15 | jgi\|Chlre4\|524246\| au5.g13735_t1:144-263 | 4.42 | GGH1 | XP_001700978 | 395 |
| 16 | jgi\|Chlre4\|518951\| au5.g8765_t1:2102-2222 | 4.41 | — | XP_001699834 | 565 |
| 17 | jgi\|Chlre4\|524734\| au5.g14197_t1:2040-2317 | 4.32 | — | XP_001700124 | 124 |
| 18 | jgi\|Chlre4\|520302\| au5.g10033_t1:278-1558 | 4.29 | TEF13 | XP_001703033 | 150 |
| 19 | jgi\|Chlre4\|524988\| au5.g14435_t1:1814-1954 | 4.27 | — | XP_001692594 | 241 |
| 20 | jgi\|Chlre4\|513993\| au5.g4144_t1:98-242 | 4.12 | — | — | — |

| No. | Function | Closest Hit for Hypotheticals | Category |
|---|---|---|---|
| 1 | Chlorophylla-b binding protein of LHCII | — | Photosynthesis |
| 2 | Cobalamin-independent methionine synthasae | — | Metabolism |
| 3 | Dicer-like protein | — | Regulation |
| 4 | Glyceraldehyde 3-phosphate dehydrogenase | — | Metabolism |
| 5 | S-Adenosyl homocysteine hydrolase | — | Metabolism |
| 6 | Chlorophylla-b binding protein of LHCII | — | Photosynthesis |
| 7 | Binding protein 2 (HSP70-like) | — | Regulation |
| 8 | Cell wall protein | — | Cell structure |

TABLE 11b-continued

| Identification of TF64-regulated genes. | | | |
|---|---|---|---|
| 9 | Hypothetical protein | Hypotheticals | — |
| 10 | — | — | — |
| 11 | Predicted protein (Pherophorin) | Hypotheticals | Cell structure |
| 12 | Gamma tubulin interacting protein | — | Cell structure/Localization |
| 13 | Cell wall protein pherophorin-C13 | — | Cell structure |
| 14 | Hypothetical protein | None | — |
| 15 | Gamma-glutamyl hydrolase | — | Metabolism |
| 16 | Predicted protein | Kinetochore protein (Monoraphidium) | Cell cycle |
| 17 | Predicted protein | None | — |
| 18 | Predicted protein | Aminoacyl-tRNA synthase CAAD domain, Curvature thylakoid | Localization |
| 19 | Predicted protein | Hypotheticals | — |
| 20 | — | — | — |

TABLE 11c

Identification of TF64-regulated genes.

Top 20 Down-Regulated Genes in *C. reinhardtii* TF64-9

| No. | Gene ID | Log2 Fold Change | Gene Symbol | Acession No. | Protein Length |
|---|---|---|---|---|---|
| 1 | jgi\|Chlre4\|516390\| au5.g6397_t1:9021-11277 | −8.08 | — | XP_001701467 | 415 |
| 2 | jgi\|Chlre4\|526060\| au5.g15439_t1:1-1486 | −7.81 | — | XP_001694632 | 205 |
| 3 | jgi\|Chlre4\|515007\| au5.g5104_t1:7-111 | −6.22 | — | — | — |
| 4 | jgi\|Chlre4\|515035\| au5.g5129_t1:1-2180 | −6.16 | — | XP_001699067 | 202 |
| 5 | jgi\|Chlre4\|525250\| au5.g14686_t1:1808-1933 | −5.62 | CNX3 | XP_001696086 | 158 |
| 6 | jgi\|Chlre4\|519344\| au5.g9128_t1:1286-1407 | −5.54 | — | XP_001699873 | 285 |
| 7 | jgi\|Chlre4\|519746\| au5.g9511_t1:3078-3200 | −5.34 | — | XP_001694814 | 849 |
| 8 | jgi\|Chlre4\|519781\| au5.g9545_t1:8-295 | −5.32 | — | — | — |
| 9 | jgi\|Chlre4\|525292\| au5.g14727_t1:6992-7141 | −4.89 | — | XP_001696021 | 509 |
| 10 | jgi\|Chlre4\|515252\| au5.g5337_t1:24-2393 | −4.85 | — | XP_001699041 | 368 |
| 11 | jgi\|Chlre4\|524801\| au5.g14261_t1:85-214 | −4.83 | — | XP_001692414 | 358 |
| 12 | jgi\|Chlre4\|509820\| au5.g239_t1:3263-3428 | −4.76 | — | XP_001702523 | 249 |
| 13 | jgi\|Chlre4\|517501\| au5.g7428_t1:0-158 | −4.70 | ZYS1a | XP_001703789 | 183 |
| 14 | jgi\|Chlre4\|518295\| au5.g8166_t1:3257-3355 | −4.69 | — | XP_001699461 | 454 |
| 15 | jgi\|Chlre4\|522765\| au5.g12336_t1:12-248 | −4.66 | — | XP_001702143 | 345 |
| 16 | jgi\|Chlre4\|512725\| au5.g2956_t1:743-841 | −4.65 | — | XP_001700531 | 139 |
| 17 | jgi\|Chlre4\|522065\| au5.g11678_t1:3348-3418 | −4.63 | — | — | — |
| 18 | jgi\|Chlre4\|523269\| au5.g12806_t1:2071-2239 | −4.61 | — | XP_001696499 | 500 |
| 19 | jgi\|Chlre4\|512204\| au5.g2477_t1:657-808 | −4.54 | — | — | — |
| 20 | jgi\|Chlre4\|512657\| au5.g2894_t1:3901-4046 | −4.53 | — | — | — |

| No. | Function | Closest Hit for Hypotheticals | Category |
|---|---|---|---|
| 1 | Predicted protein | Snurportin-1 (nuclear import) (Monoraphidium) | Regulation/Localization |

TABLE 11c-continued

Identification of TF64-regulated genes.

| | | | |
|---|---|---|---|
| 2 | Hypothetical protein | Hypotheticals | — |
| 3 | — | — | — |
| 4 | Hypothetical protein | None | — |
| 5 | Molybdenum cofactor synthesis-step 1 protein | — | Metabolism/Redox |
| 6 | Hypothetical protein | Antibiotic biosynthesis monooxygenase (Acidovorax), Negative regulatory factor (HIV) | Metabolism/Redox |
| 7 | Predicted protein | GRIP (glutamate receptor-interacting protein) (Auxenochlorella) | Metabolism |
| 8 | — | Putative ribonuclease H protein | Regulation |
| 9 | Hypothetical protein | Chitin binding domain-containing protein (Strongyloides) | Metabolism |
| 10 | Hypothetical protein | Hypotheticals | — |
| 11 | Predicted protein | Hypotheticals | — |
| 12 | Predicted protein | Hypotheticals | — |
| 13 | Transcription factor, zygote-specific | — | Regulation |
| 14 | Hypothetical protein | AP2 family transcription factor (Volvox) | Regulation |
| 15 | Hypothetical protein | Reverse transcriptase (Chlorella) | Regulation |
| 16 | Predicted protein | Hypotheticals | — |
| 17 | — | — | — |
| 18 | Hypothetical protein | KDEL motif-containing protein 1 (Chlamydotis) | Localization |
| 19 | — | — | — |
| 20 | — | Hypotheticals | — |

TF64-7 RNA-Seq data for Yeast One-Hybrid Assayed Genes

| No. | Gene ID | Log2 Fold Change | Gene Symbol | Acession No. | Protein Length |
|---|---|---|---|---|---|
| 1a | jgi\|Chlre4\|516524\|au5.g6524_t1:5-1994 | 2.10 | LHCBM5 | XP_001695927 | 289 |
| 1b | jgi\|Chlre4\|516524\|au5.g6524_t1:5-1994 | 1.56 | LHCBM5 | | |
| 2a | jgi\|Chlre4\|509966\|au5.g377_t1:5-1831 | −0.47 | LCI5 | XP_001690584 | 235 |
| 2b | jgi\|Chlre4\|509966\|au5.g377_t1:5-1831 | −0.85 | LCI5 | | |
| 2c | jgi\|Chlre4\|509966\|au5.g377_t1:5-1831 | −1.52 | LCI5 | | |
| 3a | jgi\|Chlre4\|521190\|au5.g10858_t1:251-1857 | −0.40 | SEBP1 | XP_001691997 | 389 |
| 4a | jgi\|Chlre4\|524083\|au5.g13574_t1:501-1961 | −0.61 | Nar1.2 | XP_001691213 | 336 |
| 5a | jgi\|Chlre4\|524053\|au5.g13545_t1:9-2267 | −1.57 | LCIC | XP_001691223 | 443 |

| No. | Function | Closest Hit for Hypotheticals | Category |
|---|---|---|---|
| 1a | Minor chlorophyll a-b binding protein of photosystem II | — | Photosynthesis |
| 1b | | | |
| 2a | Low-CO2-inducible protein | — | |
| 2b | | | |
| 2c | | | |
| 3a | Sedoheptulose-1,7-bisphosphatase | — | Metabolism |
| 4a | Anion transporter | — | Metabolism/Redox |
| 5a | Low-CO2 inducible protein | — | Carbon-concentrating mechanism |

TABLE 11c-continued

Identification of TF64-regulated genes.

TF64-9 RNA-Seq data for Yeast One-Hybrid Assayed Genes

| No. | Gene ID | Log2 Fold Change | Gene Symbol | Acession No. | Protein Length |
|---|---|---|---|---|---|
| 1a | jgi\|Chlre4\|516524\| au5.g6524_t1:5-1994 | 0.92 | LHCBM5 | XP_001695927 | 289 |
| 1b | jgi\|Chlre4\|516524\| au5.g6524_t1:5-1994 | 1.04 | LHCBM5 | | |
| 2a | jgi\|Chlre4\|509966\| au5.g377_t1:5-1831 | −3.66 | LCI5 | XP_001690584 | 235 |
| 2b | jgi\|Chlre4\|509966\| au5.g377_t1:5-1831 | 1.43 | LCI5 | | |
| 2c | jgi\|Chlre4\|509966\| au5.g377_t1:5-1831 | −1.77 | LCI5 | | |
| 2d | jgi\|Chlre4\|509966\| au5.g377_t1:5-1831 | −1.82 | LCI5 | | |
| 3a | jgi\|Chlre4\|521190\| au5.g10858_t1:251-1857 | −0.62 | SEBP1 | XP_001691997 | 389 |
| 5a | jgi\|Chlre4\|524053\| au5.g13545_t1:9-2267 | −2.33 | LCIC | XP_001691223 | 443 |

| No. | Function | Closest Hit for Hypotheticals | Category |
|---|---|---|---|
| 1a | Minor chlorophyll a-b binding protein of photosystem II | — | Photosynthesis |
| 1b | | | |
| 2a | Low-CO2-inducible protein | — | |
| 2b | | | |
| 2c | | | |
| 2d | | | |
| 3a | Sedoheptulose-1,7-bisphosphatase | — | Metabolism |
| 5a | Low-CO2 inducible protein | — | Carbon-concentrating mechanism |

TABLE 12

Top 20 up-regulated genes in *C. reinhardtii* cc1010::TF64-7.

| No. | Gene ID | Log2 Fold Change | Gene Symbol | Function | Category |
|---|---|---|---|---|---|
| 1 | jgi\|Chlre4\|513883\| au5.g4042_t1:0-146 | 7.58 | LHCBM7 | Chlorophylla-b binding protein of LHCII | Photosynthesis |
| 2 | jgi\|Chlre4\|523567\| au5.g13085_t1:285-1460 | 7.09 | LHCBM8 | Chlorophylla-b binding protein of LHCII | Photosynthesis |
| 3 | jgi\|Chlre4\|523561\| au5.g13079_t1:149-1280 | 6.81 | LHCBM4 | Chlorophylla-b binding protein of LHCII | Photosynthesis |
| 4 | jgi\|Chlre4\|518507\| au5.g8360_t1:204-4111 | 6.80 | FAP211 | Flagellar associated protein | Motility |
| 5 | jgi\|Chlre4\|521087\| au5.g10761_t1:39-2944 | 6.66 | METE | Cobalamin-independent methionine synthase | Metabolism |
| 6 | jgi\|Chlre4\|521595\| au5.g11226_t1:266-2760 | 6.09 | SAH1 | S-Adenosyl homocysteine hydrolase | Metabolism |
| 7 | jgi\|Chlre4\|515402\| au5.g5474_t1:537-2854 | 5.79 | PHC13 | Cell wall protein pherophorin-C13 | Cell structure |
| 8 | jgi\|Chlre4\|520083\| au5.g9823_t1:3664-4112 | 5.77 | GCP3 | Gamma tubulin interacting protein | Cell structure |
| 9 | jgi\|Chlre4\|520120\| au5.g9859_t1:2-129 | 5.39 | LHCBM1 | Chlorophylla-b binding protein of LHCII | Photosynthesis |
| 10 | jgi\|Chlre4\|524285\| au5.g13771_t1:3002-3795 | 5.34 | MCM4 | Minichromosome maintenance protein 4 | Cell cycle |

TABLE 12-continued

Top 20 up-regulated genes in *C. reinhardtii* cc1010::TF64-7.

| No. | Gene ID | Log2 Fold Change | Gene Symbol | Function | Category |
|---|---|---|---|---|---|
| 11 | jgi\|Chlre4\|512084\| au5.g2359_t1:10431-10587 | 5.15 | DCL2 | Dicer-like protein | Regulation |
| 12 | jgi\|Chlre4\|512529\| au5.g2782_t1:35-1932 | 5.11 | GAP1 | Glyceraldehyde 3-phosphate dehydrogenase | Metabolism |
| 13 | jgi\|Chlre4\|518966\| au5.g8779_t1:1773-1883 | 5.09 | SYP72 | Qc-SNARE protein, SYP7-family | Localization |
| 14 | jgi\|Chlre4\|519390 au5.g9173_t1:283-2258 | 5.07 | FTSZ1 | Plastid division protein | Cell cycle |
| 15 | jgi\|Chlre4\|515943\| au5.g5981_t1:176-2507 | 4.99 | FTSZ2 | Plastid division protein | Cell cycle |
| 16 | jgi\|Chlre4\|520083\| au5.g9823_t1:4197-4255 | 4.79 | GCP3 | Gamma tubulin interacting protein | Cell structure/ Localization |
| 17 | jgi\|Chlre4\|523024\| au5.g12580_t1:45-2087 | 4 75 | EFG8 | Mitochondrial translation factor Tu | Translation |
| 18 | jgi\|Chlre4\|513496\| au5.g3676_t1:1531-1934 | 4.73 | GLN3 | Glutamine synthetase | Metabolism |
| 19 | jgi\|Chlre4\|513333\| au5.g3525_t1:167-1848 | 4.69 | MIND1 | Chloroplast septum site-determining protein | Cell cycle |
| 20 | jgi\|Chlre4\|520302\| au5.g10033_t1:278-1558 | 4.66 | TEF13 | Aminoacyl-tRNA synthase CAAD domain | Localization |

Bioinformatic analysis of promoters of genes regulated by TF64. We chose three sets of promoters, TF64-activated, TF64-inhibited, and TF64-non-regulated, from the low-constitutive TF64-7 RNA-Seq dataset to analyze for common motifs. Promoters included 1,000 bps 5' to the ATG translation start site of the 30 top activated, inhibited, and non-regulated (log 2=0) genes. Most genes did not have annotated 5' UTRs. Promoters from each regulatory category were analyzed by MEME to identify any common motifs, however no statistically significant sequences were found for any group. Additionally, we used the program AME (Analysis of Motif Enrichment) [34] to determine if the bHLH canonical binding site, CANNTG, was present with statistical significance, and it was not for any of the three promoter categories.

We further analyzed the promoter groups using the alignment software Jalview [35]. Promoters were aligned without gaps and all CANNTG sequences were identified for each group. Analysis of CANNTG composition as well as relative location within the promoter did not reveal significant differences among the three promoter groups analyzed. These data suggest that the CANNTG sequence is ubiquitous throughout the *C. reinhardtii* genome. While this motif may play a role in TF64-DNA binding, it is not solely responsible for the gene regulation observed in the TF64-constitutive expression strains¬. It is likely that other co-factors and/or regulatory elements are important for transcription of the genes we identified to be regulated by TF64, further underscoring the complex nature of nuclear gene regulation in eukaryotic microalgae.

Figure 15:
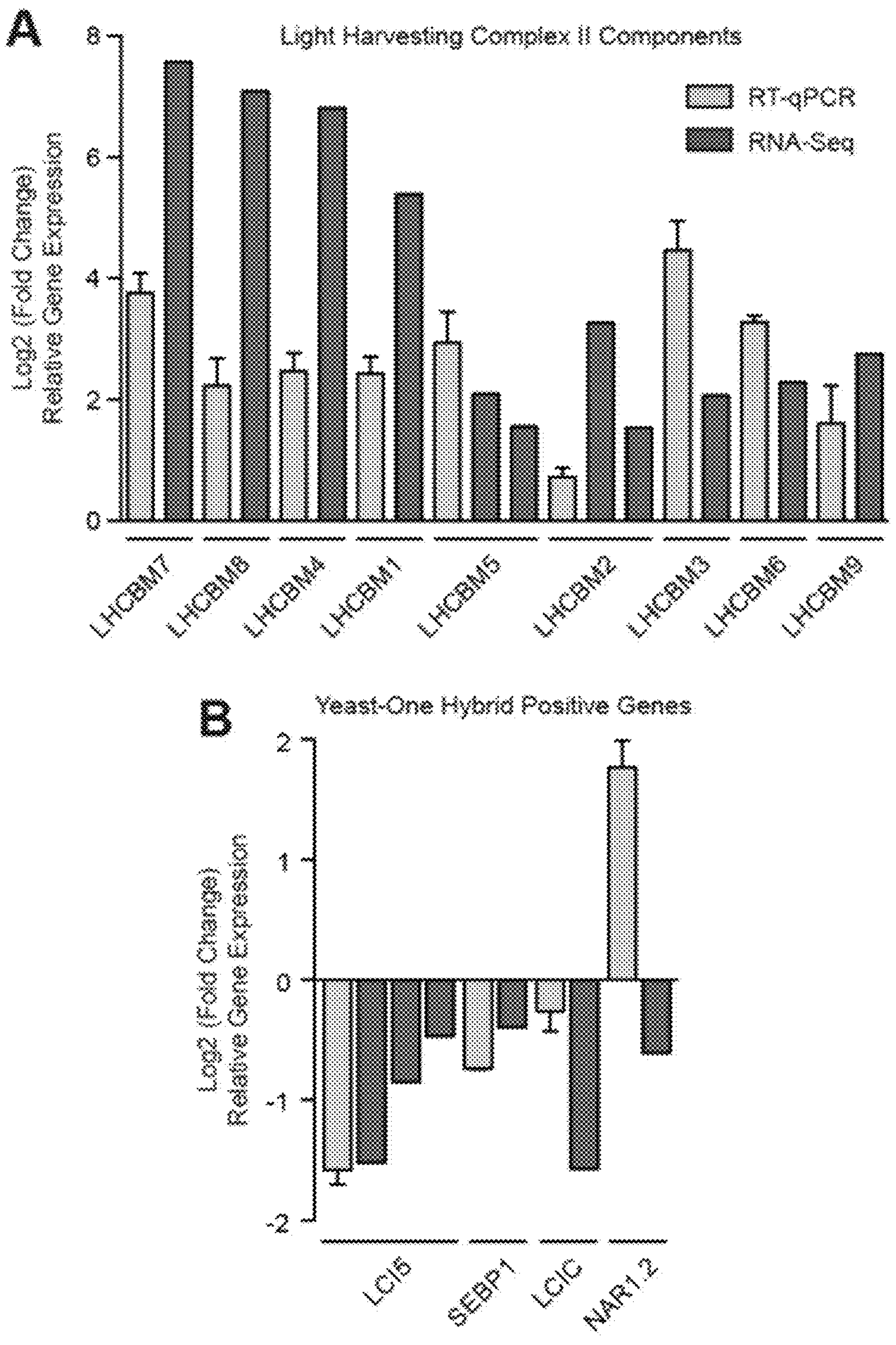
FIG. 15, panels A-B, illustrates transcription regulation of light harvesting complex II components and Yeast One-Hybrid-assayed genes by TF64. Expression data for A) genes LHCBM1-9 and B) genes LCI5, SEBP1, LCIC, NAR1.2 from strain cc1010::TF64-7 compared to cc1010::GFP analyzed by RT-qPCR and RNA-Seq. The log 2 (fold change) was plotted. RT-qPCR data is from two biological replicates with SEM. RNA-Seq data is the average of three biological replicates. Note that there were multiple unique reads for certain genes.

TF64 activates transcription of light harvesting complex II components. To validate our RNA-Seq analysis, we performed reverse transcriptase quantitative PCR (RT-qPCR) on selected genes. Strains cc1010::TF64-7 and cc1010::GFP were cultured in TAP medium under constant light for three days until mid-log phase growth was reached. RNA was isolated from cells and cDNA was synthesized for RT-qPCR analysis. Among the top activated genes from the TF64-7 RNA-Seq dataset were LHCBM7, LHCBM8, LHCBM4, and LHCBM1 (Table 10) of light harvesting complex II (PSII) [44]. We were able to confirm that transcripts from these genes were approximately 16 times (for LHCBM7), four times (for LHCBM8 and LHCBM4), and eight times (for LHCBM1) more abundant in the TF64-producing strain compared to the GFP-producing strain by RT-qPCR (FIG. 15, panel A). Furthermore, genes LHCBM5, LHCBM2, LHCBM3, LHCBM6, and LHCBM5 also of PSII [44] were additionally analyzed and found to be activated in the TF64-producing strain (FIG. 15, panel A). Interestingly, the promoter of gene LHCBM5 was assayed in our Y1H screen but was not detected to activate transcription with TF64 in yeast. FIG. 15, panel A shows transcript abundance data for each of these genes by RNA-Seq and RT-qPCR. These data indicate TF64 plays a role in activating PSII components and possibly regulation of photosynthesis. The nine PSII promoters were analyzed similarly to those previously discussed. Again, MEME did not identify any new motifs, CANNTG was not present with statistical significance determined by AME (data not shown), and CANNTG composition and location were not different from any group of promoters analyzed from the RNA-Seq selected promoters.

Transcription analysis of Y1H-assayed genes. We also investigated transcription of the genes whose promoters were found to activate transcription with TF64 by Y1H (i.e., LCI5, SEBP1, LCIC, and Nar1.2). RNA-Seq data indicated that each of these genes were down-regulated in *C. reinhardtii* cells constitutively expressing the gene encoding TF64 (FIG. 15, panel B, Table 11). By RT-qPCR, we confirmed that transcription of the genes LCI5, SEBP1, and LCIC were in fact inhibited by constitutive expression of the gene encoding of TF64. Nar1.2, however, was activated in our RT-qPCR analysis (FIG. 15, panel B). Overall, these data support our RNA-Seq analysis.

Collectively, these results highlight the nature of high-throughput screens, like the Y1H, and high-throughput sequencing data, as generated here by RNA-sequencing: they produce large amounts of data that can serve as an excellent starting point for narrowing down potential molecular interactions of interest. Here, we successfully used these two screens to identify potential TF-promoter binding partners in *C. reinhardtii.*

Conclusions.

In this study, we successfully constructed a recombinant transcription factor library that includes 92 (nearly one third of the putative) transcription factors (TFs) encoded by the nuclear genome of *C. reinhardtii*. To date, very few TFs have actually been characterized from this species of microalgae [20]. We analyzed the 92 TFs' ability to activate transcription via a yeast one-hybrid screen, studied the TFs' abilities to be constitutively expressed in their native organism *C. reinhardtii*, and finally assessed transcription profiles by RNA-Seq from two independent strains constitutively expressing one specific TF (TF64). These high-throughput studies were designed to narrow down the vast amount of hypothetical transcription factor-promoter binding pairs in *C. reinhardtii* (~350 TFs×15,000 nuclear genes=5,250,000 potential interactions). Our results establish a clear direction for investigation of direct binding partners that could be used in an engineered synthetic nuclear transcription system in green algae.

Using a yeast one-hybrid assay [37], we were able to analyze 4,508 potential binding interactions between TFs and promoter fragments. Sixty-five of these were found to be positive hits correlating with 28 TFs with potential DNA binding activity. We assayed five promoters (LCIC, LCI5, SEBP1, Nar1.2, and LHCBM5) in different combinations from *C. reinhardtii, V. carteri, C. vulgaris, A. thaliana*, and *Z. mays*. The ability to activate transcription from unique DNA sequences by a number of the putative TFs analyzed support the bioinformatic data [24] suggesting these proteins are in fact functional transcription factors, capable of regulating transcription in *C. reinhardtii.*

Compiling the yeast one-hybrid data, we sought to identify common motifs among promoter fragments found to activate transcription in combination with an individual TF. The promoters, however, proved to be more cryptic than anticipated. We studied TF64-associated promoters, 13 sequences in total, and were unable to identify commonalities by bioinformatics. It may be that a larger number of promoters need to be analyzed before such a characterization is possible. In the future, it would be interesting to compare DNA sequences from a larger dataset of *C. reinhardtii* promoters and also determine if identified motifs were conserved in the promoters of other closely or distantly related species.

Our TF library was cloned into a *C. reinhardtii* constitutive expression vector for production in *C. reinhardtii*. To our knowledge, this was the first attempt to constitutively produce a recombinant library of native TFs in *C. reinhardtii*. Of the 92 TF-encoding vectors that were transformed, only eight resulted in successful production of protein under the conditions attempted. As almost all of the TFs produced protein in *S. cerevisiae*, the algae expression data suggest that the failure for most TFs to produce protein in *C. reinhardtii* is possibly due to adverse effects of constitutively expressing their genes. It is possible these TFs could be produced under more tightly controlled experimental conditions, or when placed under inducible or conditional expression systems.

TF64 was our most successful TF in that it was able to be produced in multiple strains of *C. reinhardtii* and it was the most active TF in the yeast one-hybrid assay. From RNA-sequencing data on strains constitutively producing TF64, compared to a GFP-constitutive strain, we were able to determine that TF64 likely plays a role in regulating transcription of genes involved in multiple cellular and developmental processes in wild type *C. reinhardtii*. Constitutive production of TF64 led to an increase in transcript levels of genes functioning in photosynthesis and the cell cycle, as well as many others. Follow-up studies on the biological role of TF64 should prove to be interesting from a basic science perspective, leading to greater insights into the *C. reinhardtii* lifecycle.

Our goal with this study was to identify potential cognate transcription factor-promoter pairs from *C. reinhardtii* that, once validated, could be used in a synthetic nuclear transcription system. From our yeast one-hybrid data, we identified 28 TFs with possible DNA binding activity. Further studies are required to confirm these interactions in vivo in *C. reinhardtii*. Specifically focusing on TF64, we were able to verify the activation of transcription of nine genes, LHCBM1-9, by both RNA-Seq and RT-qPCR. It is yet to be determined if this gene activation is in fact due to a direct TF-promoter binding interaction.

These data lay the groundwork for the construction of a synthetic transcription system. This line of work provides the scientific community the necessary tools for sophisticated and robust genetic engineering in microalgae.

References for Example 2

1. Blunt J W, Copp B R, Keyzers R A, Munro M H, Prinsep M R Marine natural products. Nat Prod Rep 29: 144-222.
2. Dufresne A, Ostrowski M, Scanlan D J, Garczarek L, Mazard S, et al. (2008) Unraveling the genomic mosaic of a ubiquitous genus of marine cyanobacteria. Genome Biol 9: R90.
3. Parker M S, Mock T, Armbrust E V (2008) Genomic insights into marine microalgae. Annu Rev Genet 42: 619-645.
4. Gimpel J A, Specht E A, Georgianna D R, Mayfield S P Advances in microalgae engineering and synthetic biology applications for biofuel production. Curr Opin Chem Biol 17: 489-495.
5. Cardozo K H, Guaratini T, Barros M P, Falcao V R, Tonon A P, et al. (2007) Metabolites from algae with economical impact. Comp Biochem Physiol C Toxicol Pharmacol 146: 60-78.
6. Rosales-Mendoza S, Paz-Maldonado L M, Soria-Guerra R E *Chlamydomonas reinhardtii* as a viable platform for the production of recombinant proteins: current status and perspectives. Plant Cell Rep 31: 479-494.
7. Specht E, Miyake-Stoner S, Mayfield S Micro-algae come of age as a platform for recombinant protein production. Biotechnol Lett 32: 1373-1383.
8. Jones C S, Mayfield S P Algae biofuels: versatility for the future of bioenergy. Curr Opin Biotechnol 23: 346-351.
9. Stephens E, Ross I L, King Z, Mussgnug R I, Kruse O, et al. An economic and technical evaluation of microalgal biofuels. Nat Biotechnol 28: 126-128.
10. Georgianna D R, Mayfield S P Exploiting diversity and synthetic biology for the production of algal biofuels. Nature 488: 329-335.
11. Merchant S S, Prochnik S E, Vallon O, Harris E H, Karpowicz S J, et al. (2007) The *Chlamydomonas* genome reveals the evolution of key animal and plant functions. Science 318: 245-250.

12. Tran M, Van C, Barrera D J, Pettersson P L, Peinado C D, et al. Production of unique immunotoxin cancer therapeutics in algal chloroplasts. Proc Natl Acad Sci USA 110: E15-22.
13. Gregory J A, Li F, Tomosada L M, Cox C J, Topol A B, et al. Algae-produced Pfs25 elicits antibodies that inhibit malaria transmission. PLoS One 7: e37179.
14. Gimpel J A, Hyun J S, Schoepp N G, Mayfield S P Production of recombinant proteins in microalgae at pilot greenhouse scale. Biotechnol Bioeng 112: 339-345.
15. Lingg N, Zhang P, Song Z, Bardor M The sweet tooth of biopharmaceuticals: importance of recombinant protein glycosylation analysis. Biotechnol J 7: 1462-1472.
16. Corchero J L, Gasser B, Resina D, Smith W, Parrilli E, et al. Unconventional microbial systems for the cost-efficient production of high-quality protein therapeutics. Biotechnol Adv 31: 140-153.
17. Rasala B A, Chao S S, Pier M, Barrera D J, Mayfield S P Enhanced genetic tools for engineering multigene traits into green algae. PLoS One 9: e94028.
18. Neupert J, Karcher D, Bock R (2009) Generation of *Chlamydomonas* strains that efficiently express nuclear transgenes. Plant J 57: 1140-1150.
19. Rasala B A, Lee P A, Shen Z, Briggs S P, Mendez M, et al. Robust expression and secretion of Xylanase1 in *Chlamydomonas reinhardtii* by fusion to a selection gene and processing with the FMDV 2A peptide. PLoS One 7: e43349.
20. Riano-Pachon D M, Correa L G, Trejos-Espinosa R, Mueller-Roeber B (2008) Green transcription factors: a *chlamydomonas* overview. Genetics 179: 31-39.
21. Yoshioka S, Taniguchi F, Miura K, Inoue T, Yamano T, et al. (2004) The novel Myb transcription factor LCR1 regulates the CO2-responsive gene Cah1, encoding a periplasmic carbonic anhydrase in *Chlamydomonas reinhardtii*. Plant Cell 16: 1466-1477.
22. Ibanez-Salazar A, Rosales-Mendoza S, Rocha-Uribe A, Ramirez-Alonso J I, Lara-Hernandez I, et al. Over-expression of Dof-type transcription factor increases lipid production in *Chlamydomonas reinhardtii*. J Biotechnol 184: 27-38.
23. Tsai C H, Warakanont J, Takeuchi T, Sears B B, Moellering E R, et al. The protein Compromised Hydrolysis of Triacylglycerols 7 (CHT7) acts as a repressor of cellular quiescence in *Chlamydomonas*. Proc Natl Acad Sci USA 111: 15833-15838.
24. Riano-Pachon D M, Ruzicic S, Dreyer I, Mueller-Roeber B (2007) PlnTFDB: an integrative plant transcription factor database. BMC Bioinformatics 8: 42.
25. Gorman D S, Levine R P (1965) Cytochrome f and plastocyanin: their sequence in the photosynthetic electron transport chain of *Chlamydomonas reinhardi*. Proc Natl Acad Sci USA 54: 1665-1669.
26. Perez-Rodriguez P, Riano-Pachon D M, Correa L G, Rensing S A, Kersten B, et al. PlnTFDB: updated content and new features of the plant transcription factor database. Nucleic Acids Res 38: D822-827.
27. Korbie D J, Mattick J S (2008) Touchdown PCR for increased specificity and sensitivity in PCR amplification. Nat Protoc 3: 1452-1456.
28. Goecks J, Nekrutenko A, Taylor J Galaxy: a comprehensive approach for supporting accessible, reproducible, and transparent computational research in the life sciences. Genome Biol 11: R86.
29. Blankenberg D, Von Kuster G, Coraor N, Ananda G, Lazarus R, et al. Galaxy: a web-based genome analysis tool for experimentalists. Curr Protoc Mol Biol Chapter 19: Unit 19 10 11-21.
30. Giardine B, Riemer C, Hardison R C, Burhans R, Elnitski L, et al. (2005) Galaxy: a platform for interactive large-scale genome analysis. Genome Res 15: 1451-1455.
31. Livak K J, Schmittgen T D (2001) Analysis of relative gene expression data using real-time quantitative PCR and the 2(−Delta Delta C(T)) Method. Methods 25: 402-408.
32. Bailey T L, Boden M, Buske F A, Frith M, Grant C E, et al. (2009) MEME SUITE: tools for motif discovery and searching. Nucleic Acids Res 37: W202-208.
33. Bailey T L, Elkan C (1994) Fitting a mixture model by expectation maximization to discover motifs in biopolymers. Proc Int Conf Intell Syst Mol Biol 2: 28-36.
34. McLeay R C, Bailey T L Motif Enrichment Analysis: a unified framework and an evaluation on ChIP data. BMC Bioinformatics 11: 165.
35. Waterhouse A M, Procter J B, Martin D M, Clamp M, Barton G J (2009) Jalview Version 2—a multiple sequence alignment editor and analysis workbench. Bioinformatics 25: 1189-1191.
36. Reece-Hoyes J S, Marian Walhout A J Yeast one-hybrid assays: a historical and technical perspective. Methods 57: 441-447.
37. Gaudinier A, Zhang L, Reece-Hoyes J S, Taylor-Teeples M, Pu L, et al. Enhanced Y1H assays for *Arabidopsis*. Nat Methods 8: 1053-1055.
38. Wilson T E, Fahrner T J, Johnston M, Milbrandt J (1991) Identification of the DNA binding site for NGFI-B by genetic selection in yeast. Science 252: 1296-1300.
39. Verhaegent M, Christopoulos T K (2002) Recombinant *Gaussia* luciferase. Overexpression, purification, and analytical application of a bioluminescent reporter for DNA hybridization. Anal Chem 74: 4378-4385.
40. Yamano T, Tsujikawa T, Hatano K, Ozawa S, Takahashi Y, et al. Light and low-CO2-dependent LCIB-LCIC complex localization in the chloroplast supports the carbon-concentrating mechanism in *Chlamydomonas reinhardtii*. Plant Cell Physiol 51: 1453-1468.
41. Turkina M V, Blanco-Rivero A, Vainonen J P, Vener A V, Villarejo A (2006) CO2 limitation induces specific redox-dependent protein phosphorylation in *Chlamydomonas reinhardtii*. Proteomics 6: 2693-2704.
42. Mariscal V, Moulin P, Orsel M, Miller A J, Fernandez E, et al. (2006) Differential regulation of the *Chlamydomonas* Nar1 gene family by carbon and nitrogen. Protist 157: 421-433.
43. Hahn D, Kaltenbach C, Kuck U (1998) The Calvin cycle enzyme sedoheptulose-1,7-bisphosphatase is encoded by a light-regulated gene in *Chlamydomonas reinhardtii*. Plant Mol Biol 36: 929-934.
44. Stauber E J, Fink A, Markert C, Kruse O, Johanningmeier U, et al. (2003) Proteomics of *Chlamydomonas reinhardtii* light-harvesting proteins. Eukaryot Cell 2: 978-994.
45. Fang W, Si Y, Douglass S, Casero D, Merchant S S, et al. Transcriptome-wide changes in *Chlamydomonas reinhardtii* gene expression regulated by carbon dioxide and the CO2-concentrating mechanism regulator CIA5/CCM1. Plant Cell 24: 1876-1893.
46. Pireyre M, Burow M Regulation of MYB and bHLH transcription factors: a glance at the protein level. Mol Plant 8: 378-388.

47. Robinson K A, Lopes J M (2000) SURVEY AND SUMMARY: *Saccharomyces cerevisiae* basic helix-loop-helix proteins regulate diverse biological processes. Nucleic Acids Res 28: 1499-1505.

48. Feller A, Machemer K, Braun E L, Grotewold E Evolutionary and comparative analysis of MYB and bHLH plant transcription factors. Plant J 66: 94-116.

49. Kewley R J, Whitelaw M L, Chapman-Smith A (2004) The mammalian basic helix-loop-helix/PAS family of transcriptional regulators. Int J Biochem Cell Biol 36: 189-204.

50. Lang E J, Cross P J, Mittelstadt G, Jameson G B, Parker E J Allosteric ACTion: the varied ACT domains regulating enzymes of amino-acid metabolism. Curr Opin Struct Biol 29: 102-111.

51. Zhao H, Li X, Ma L Basic helix-loop-helix transcription factors and epidermal cell fate determination in *Arabidopsis*. Plant Signal Behav 7: 1556-1560.

52. Castilhos G, Lazzarotto F, Spagnolo-Fonini L, Bodanese-Zanettini Margis-Pinheiro M Possible roles of basic helix-loop-helix transcription factors in adaptation to drought. Plant Sci 223: 1-7.

53. Curtis D J, Salmon J M, Pimanda J E Concise review: Blood relatives: formation and regulation of hematopoietic stem cells by the basic helix-loop-helix transcription factors stem cell leukemia and lymphoblastic leukemia-derived sequence 1. Stem Cells 30: 1053-1058.

54. Fritzsch B, Eberl D F, Beisel K W The role of bHLH genes in ear development and evolution: revisiting a 10-year-old hypothesis. Cell Mol Life Sci 67: 3089-3099.

55. Powell L M, Jarman A P (2008) Context dependence of proneural bHLH proteins. Curr Opin Genet Dev 18: 411-417.

Example 3

Identifying Conditional Regulatory Elements in *C. reinhardtii* Nuclear Genome For photosynthetic organisms, light and dark cycles act as major drivers of metabolism and gene expression pattern variation. During day time, green algae can utilize photosynthesis to drive the production of sugars that are then used for energy in a myriad of metabolic processes including the production of starches and sugars. During the night the cells must utilize stored energy in the form of sugars, starches, or lipids to continue metabolic activity. The switching from phototrophic to hetrotropic metabolism requires large sets of genes to be switched on or off. In *Chlamydomonas* ~80% of the genome displays detectable periodic gene expression changes throughout a 24 hour day/night cycle (Zones et al., 2015). We therefore predicted that unique regulatory motifs may be used to regulate these light-induced or dark-induced genes in response to light intensity. If identified, these motifs can then be utilized to drive transgene expression specifically in response to light or dark conditions. Since light is one of the easiest variables to control in commercial scale cultivation of algae, design and production of light/dark-responsive synthetic promoters would be highly useful for inducing or silencing transgene expression.

Using high resolution RNA-seq data taken from *Chlamydomonas reinhardtii* on a 12 hour light-12 hour dark cycle (Zones et al., 2015, supra) we identified genes that were differentially expressed by at least two fold between the middle of the light-period (day) and the middle of the dark-period (night) while displaying moderate to high expression levels overall during their upregulated time period. Specifically, we averaged the Reads Per Kilobase of transcript per Million mapped reads (RPKM) for each transcript during the middle 4 hours of the 12-hour light period and the middle 4 hours of the 12-hour dark period. Genes with at least a 2-fold increase in averaged read count during the light phase compared to the dark phase and an average RPKM of more than 100 were determined to be light-upregulated strong expressers. Similarly genes with at least a 2-fold increase in average read count during the dark phase compared to the light and an average RPKM of more than 100 were determined to be dark-upregulated strong expressers. Collectively this represented 255 light-upregulated genes and 248 dark-upregulated genes. The 1000 bp region 5' from the transcriptional start site of these genes was retrieved (Phytozome 12, *Chlamydomonas reinhardtii* genome v5.5) and analyzed using the POWRS motif identification program (Davis et al., 2012). All default settings on POWRS were used and −1000 bp regions from all 17737 annotated genes in the whole genome used as the background control data set. POWRS identified 31 and 32 enriched motif clusters in the light-upregulated and dark-upregulated promoter datasets, respectively compared to promoters in the rest of the genome. Motifs enriched in the light-upregulated or dark-upregulated data sets were compared each other using the Tomtom motif comparison tool (Gupta, et al., (2007) Genome Biol. 8(2):R24). FIGS. 16A and 16B identify motifs unique to either the light up-regulated (FIG. 16A) or dark-upregulated (FIG. 16B) data sets. Many of the light/dark-regulated motifs are different from the motifs identified from simply looking at the highest expressed genes during logarithmic growth in the previous example. Taken together this shows that comparison of promoters from genes up or down regulated in unique abiotic contexts can be used to identify unique motifs that may regulate those genes in a specific context for selective expression or repression of a transgene construct. These motifs can then be assembled in to synthetic algae promoters as was shown in the first example.

References for Example 3

Crooks G. E., Hon G., Chandonia J. M., Brenner S. E. WebLogo: A sequence logo generator, Genome Research. 2004. 14:1188-1190.

Zones J. M., Blaby I. K., Merchant S. S., Umen J. G. High-Resolution Profiling of a Synchronized Diurnal Transcriptome from *Chlamydomonas reinhardtii* Reveals Continuous Cell and Metabolic Differentiation. Plant Cell. 2015. 27(10):2743-69.

Davis I. W., Benninger C., Benfey P. N., Elich T. POWRS: position-sensitive motif discovery. PLoS One. 2012. 7(7): e40373.

Gupta S., Stamatoyannopoulos J. A., Bailey T. L., Noble W. S. Quantifying similarity between motifs. Genome Biol. 2007. 8(2):R24.

Example 4

Other Systems for Regulatory Elements

Statistical analyses as those presented above serve as an unbiased method for identifying conserved nucleotide motifs which correlate with increased transcription levels. This strategy alleviates the necessity for understanding the mechanism of action of the associated sequence. For an organism like *Chlamydomonas reinhardtii*, it is favorable to use this approach due to large gaps in the understanding of regulatory elements in the species. However, a wealth of knowledge is available across the kingdom Plantae which serve as a guide to understanding the complex transcriptional regulation found in *C. reinhardtii*. One of the best-understood aspects of the regulatory system is that by encouraging an activating transcription factor to bind in a regulatory region associated with a transgene, one can increase transcript abundance and subsequent protein accumulation. Systems have been derived in *S. cerevisiae* and *E. coli* which take advantage of known DNA-binding proteins to engineer complex circuits of protein expression for a wide variety of purposes (Wang et al. 2011, Ellis et al. 2009, Kotula et al. 2014).

Transcription factor families are easily identifiable in silico and homology analysis to better-understood systems can provide a groundwork for understanding in *C. reinhardtii*. The Plant Transcription Factor Database (PTFDB) (//planttfdb.cbi.pku.edu.cn/) has identified each family of transcription factor found in *C. reinhardtii* based on sequence homology to other plants. The PTFDB has also compiled data from across the literature to provide putative binding sites for those families of transcription factors. Transcription factor (TF) binding sites have been studied across plants through one of the following processes: amp-DAP, ChIP/ChIP-seq, DAP, PBM, or SELEX. TF binding sites found in the literature that are associated with a given TF family are projected to other species to help characterize binding in a virgin system. The sequence motifs attributed to TF families found in *C. reinhardtii* are provided as position-weight matrices in FIGS. 17A-C. These serve as a promising set of sequences for synthetic promoter engineering. By integrating these sequences into a novel synthetic promoter, we can project the regulation of the transgene onto one or many specific transcription factor. We know that certain transcription factors have variable function based on external stimuli (Riano-Pachon et al. 2008), and as such these sequences are clear candidates for inducible promoter engineering.

In an effort to better characterize the in vivo TF/sequence cognate pairs for *C. reinhardtii,* 90 predicted transcription factors were cloned from *C. reinhardtii* cDNA into a constitutive nuclear expression construct (Andersen et a 2017). Upon characterization of their binding in a Y1H assay, a bHLH-family transcription factor (Cre02.g109700.t1.2, will be referred to as TF64) was selected for further analysis. Three strains were designed to determine if constitutive expression of a transgenic transcription factor can increase recombinant protein abundance in *C. reinhardtii*. We generated a strain which expressed high levels of TF64, one which expressed low levels of TF64, and a control strain which used the same construct to express GFP, a non-DNA binding protein. These three strains in addition to an untransformed wild-type strain were transformed with an expression cassette which drives OFP expression, which is easily detected by a fluorescent plate reader. The promoter associated with the OFP gene must contain binding site(s) associated with the bHLH transcription factor family (CANNTG). Conveniently, the AR1 promoter that is well-established in the field has three putative bHLH binding sites, identified in FIG. 18. The AR1 promoter was used to drive the expression of OFP in the TF64 expression strains, shown in FIG. 19. These data indicate that presence of putative TF-binding site motifs in an expression construct when combined with their associated transcription factors can help drive recombinant protein accumulation. The generation of more in vivo cognate TF/site pairs based on the putative TF binding sites shown in FIGS. 17A-C will facilitate the development of more advanced promoters with the added functionality of orthogonal regulation.

References for Example 4

Wang B., Kitney R I., Joly N., Buck M. Engineering modular and orthogonal genetic logic gates for robust digital-like synthetic biology. Nat Commun. 2011 Oct. 18; 2:508.

Ellis T., Wang X., Collins J. J. Diversity-based, model-guided construction of synthetic gene networks with predicted functions. Nat Biotechnol. 2009 May; 27(5): 465-71.

Kotula J. W., Kerns S. J., Shaket L. A., Siraj L., Collins J. J., Way J. C., Silver P. A. Programmable bacteria detect and record an environmental signal in the mammalian gut. Proc. Natl. Acad. Sci. U.S.A. 2014 Apr. 1; 111(13):4838-4843.

M S Anderson, T J Muff, D R Georgianna, S P Mayfield. Towards a synthetic nuclear transcription system in green algae: Characterization of *Chlamydomonas reinhardtii* nuclear transcription factors and identification of targeted promoters, Algal Research (2017) 22: 47-55.

Riaño-Pachón DM, Corrêa LGG, Trejos-Espinosa R, Mueller-Roeber B. Green Transcription Factors: A *Chlamydomonas* Overview. Genetics. 2008; 179(1): 31-39.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A synthetic promoter capable of promoting and/or initiating transcription of a polynucleotide in an algal cell, the synthetic promoter comprising the nucleotide sequence of SAP11 of SEQ ID NO: 39.

2. The synthetic promoter I am usually not so download of yes of claim 1, wherein the algal cell is a green algal cell.

3. An expression cassette comprising the synthetic promoter of claim 1.

4. A vector comprising the expression cassette of claim 3.

5. A cell comprising the synthetic promoter of claim 1.

6. The cell of claim 5, wherein the cell is a *Chlamydomonas reinhardtii* cell.

7. A kit comprising the synthetic promoter of claim 1.

8. The promoter of claim 1, wherein said promoter is operably linked to a polynucleotide of interest, and one or more transcription factors encoded by a polynucleotide comprising at least about 60% sequence identity to SEQ ID NOs:87-178.

9. A cell comprising the promoter of claim 1.

10. The synthetic promoter of claim 2, wherein the green algal cell is a *Chlamydomonas* cell.

11. The synthetic promoter of claim 10, wherein the green algal cell is a *Chlamydomonas reinhardtii* cell.

12. The vector of claim 4, wherein the vector is a plasmid vector.

13. The cell of claim 5, wherein said cell comprises a heterologous expression cassette comprising said promoter.

14. The cell of claim 5, wherein said cell comprises a vector comprising an expression cassette that comprises said promoter.

15. The cell of claim 5, wherein the cell is a green algal cell.

16. The cell of claim 15, wherein said cell is a *Chlamydomonas* cell.

17. The cell of claim 16, wherein said cell is a *Chlamydomonas reinhardtii* cell.

* * * * *